US012697350B2

(12) United States Patent
McFarland et al.

(10) Patent No.: US 12,697,350 B2
(45) Date of Patent: Aug. 4, 2026

(54) METHODS AND COMPOSITIONS FOR TREATING A PREMATURE TERMINATION CODON-MEDIATED DISORDER

(71) Applicant: Tevard Biosciences, Inc., Boston, MA (US)

(72) Inventors: Sean McFarland, Dorchester Center, MA (US); Ying-Hsin Chen, Ashland, MA (US); Peter M. Eimon, Brighton, MA (US)

(73) Assignee: Tevard Biosciences, Inc., Boston, MA (US)

( * ) Notice: Subject to any disclaimer, the term of this patent is extended or adjusted under 35 U.S.C. 154(b) by 497 days.

(21) Appl. No.: 17/773,112

(22) PCT Filed: Oct. 30, 2020

(86) PCT No.: PCT/US2020/058415
§ 371 (c)(1),
(2) Date: Apr. 29, 2022

(87) PCT Pub. No.: WO2021/087401
PCT Pub. Date: May 6, 2021

(65) Prior Publication Data
US 2024/0148772 A1 May 9, 2024

Related U.S. Application Data

(60) Provisional application No. 62/929,428, filed on Nov. 1, 2019.

(51) Int. Cl.
| | |
|---|---|
| *C07H 21/04* | (2006.01) |
| *A61K 31/70* | (2006.01) |
| *A61K 31/7115* | (2006.01) |
| *A61K 48/00* | (2006.01) |
| *C12N 15/63* | (2006.01) |
| *C12N 15/86* | (2006.01) |
| *A01K 67/00* | (2006.01) |

(52) U.S. Cl.
CPC .......... *A61K 31/7115* (2013.01); *C12N 15/86* (2013.01); *C12N 2750/14143* (2013.01)

(58) Field of Classification Search
CPC ................ A61K 31/7115; C12N 15/86; C12N 2750/14143
See application file for complete search history.

(56) References Cited

U.S. PATENT DOCUMENTS

| | | |
|---|---|---|
| 4,687,737 A | 8/1987 | Sharp et al. |
| 5,840,702 A | 11/1998 | Bedwell |
| 6,309,830 B1 | 10/2001 | Panchal et al. |
| 6,964,859 B2 | 11/2005 | Rajbhandary et al. |
| 7,029,665 B2 | 4/2006 | Panchal et al. |
| 8,338,386 B2 | 12/2012 | McLean et al. |
| 10,513,699 B2 | 12/2019 | Short |
| 10,905,778 B2 | 2/2021 | Coller et al. |
| 10,982,209 B2 | 4/2021 | Xia et al. |
| 11,661,600 B2 | 5/2023 | Ahern et al. |
| 2004/0219516 A1 | 11/2004 | Bennett et al. |
| 2005/0014835 A1 | 1/2005 | Arakawa et al. |
| 2009/0298920 A1 | 12/2009 | Dardel et al. |
| 2012/0077186 A1 | 3/2012 | Skach et al. |
| 2012/0117673 A1 | 5/2012 | Ardell |
| 2016/0222379 A1 | 8/2016 | Brasch et al. |
| 2017/0342422 A1 | 11/2017 | Holzmann et al. |
| 2017/0354672 A1 | 12/2017 | Siegwart et al. |
| 2018/0171321 A1 | 6/2018 | Mureev et al. |
| 2018/0320175 A1 | 11/2018 | Lee et al. |
| 2020/0101174 A1 | 4/2020 | Coller et al. |
| 2020/0263180 A1 | 8/2020 | Mali et al. |
| 2020/0277607 A1 | 9/2020 | Mali et al. |
| 2020/0291401 A1 | 9/2020 | Ahern et al. |
| 2020/0407714 A1 | 12/2020 | Ignatova et al. |
| 2021/0023120 A1 | 1/2021 | Siegwart et al. |
| 2021/0163948 A1 | 6/2021 | Mali et al. |
| 2021/0198673 A1 | 7/2021 | Mali et al. |
| 2023/0203482 A1 | 6/2023 | Puchalt et al. |
| 2023/0407300 A1 | 12/2023 | Ahern et al. |

FOREIGN PATENT DOCUMENTS

| | | |
|---|---|---|
| CN | 107177592 A | 9/2017 |
| WO | WO-1999036519 A1 | 7/1999 |
| WO | WO-2007070659 A2 | 6/2007 |
| WO | WO-2017049409 A1 | 3/2017 |
| WO | WO-2017152809 A1 | 9/2017 |
| WO | WO-2017201091 A1 | 11/2017 |
| WO | WO-2018031531 A4 | 4/2018 |
| WO | WO-2018161032 A1 | 9/2018 |
| WO | WO-2019090154 A1 | 5/2019 |
| WO | WO-2019090169 A1 | 5/2019 |
| WO | WO-2020069194 A1 | 4/2020 |
| WO | WO-2020069199 A1 | 4/2020 |

(Continued)

OTHER PUBLICATIONS

Albers, et al. (2021) "Repurposing tRNAs for nonsense suppression", Nature Communications 12(3850): 1-10.
Andersen, et al. (2003) "Elongation factors in protein biosynthesis," Trends in Biochemical Sci., 28(8): 434-441.
Atkinson, et al. (1994) "Mutations to nonsense codons in human genetic disease: implications for gene therapy by nonsense suppressor tRNAs", Nucleic Acids Research 22(8): 1327-1334.
Bednarova, et al. (2017) "Lost in Translation: Defects in Transfer RNA Modifications and Neurological Disorders," Front Mol Neurosci, 10: 135.
Biddle, et al. (2016) "Modification of orthogonal tRNAs: unexpected consequences for sense codon reassignment," Nucleic Acids Res, 44(21): 10042-10050.

(Continued)

*Primary Examiner* — Quang Nguyen
(74) *Attorney, Agent, or Firm* — Goodwin Procter LLP

(57) ABSTRACT

The invention relates generally to modified tRNAs and the use of modified tRNAs to express in a mammalian cell a functional gene product encoded by a gene containing a premature termination codon and/or to treat a disease mediated by a premature termination codon, e.g., Dravet syndrome.

19 Claims, 49 Drawing Sheets

Specification includes a Sequence Listing.

(56) References Cited

FOREIGN PATENT DOCUMENTS

| WO | WO-2020208169 A1 | 10/2020 |
| WO | WO-2021072201 A1 | 4/2021 |
| WO | WO-2021087401 A1 | 5/2021 |
| WO | WO-2021092064 A1 | 5/2021 |
| WO | WO-2021113218 A1 | 6/2021 |
| WO | WO-2022235861 A1 | 11/2022 |

OTHER PUBLICATIONS

Bordeira-Carrico, et al. (2014) "Rescue of wild-type E-cadherin expression from nonsense-mutated cancer cells by a suppressor-tRNA," Eur J Hum Genet, 22(9): 1085-1092.

Capone, et al. (1985) "Amber, ochre and opal suppressor tRNA genes derived from a human serine tRNA gene", The EMBO Journal 4(1): 213-221.

Chan, et al. (2023) TPA: Mus musculus tRNA-Arg-TCT-3-1 gene, GenBank: HG984234.1, Submitted May 13, 2014; downloaded from the internet <https://www.ncbi.nlm.nih.gov/nucleotide/HG984234.1?report=genbank&log$=nuclalign&blast_rank=1&RID=CPUPP058016on> Aug. 3, 2023, pp. 1-2.

Dreher, et al. (1999) "Quantitative Assessment of EF-1?GTP Binding to Aminoacyl-tRNAs, Aminoacyl-viral RNA, and tRNA Shows Close Correspondence to the RNA Binding Properties of EF-Tu," The Journal of Biochemistry, 274(2): 666-672.

Forster, et al. (1993) "Discrimination between initiation and elongation of protein biosynthesis in yeast: identity assured by a nucleotide modification in the initiator tRNA," Nucleic Acids Research, 21(24): 5679-5683.

Gatti (2012) "SMRT compounds correct nonsense mutations in primary immunodeficiency and other genetic models", Am N Y Acad Sci 1250: 33-40.

Geiduschek, et al. (1988) "Transcription by RNA Polymerase III", Annu Rev Biochem 57, 873-914.

Guy, et al. (2014) "Identification of the determinants of tRNA function and susceptibility to rapid tRNA decay by high-throughput in vivo analysis", Genes & Development 28, 1721-1732.

Huang, et al. (2012) "In vivo identification of essential nucleotides in tRNA Leu to its functions by using a constructed yeast tRNA Leu knockout strain," Nucleic Acids Research 40(20), 10463-10477.

International Search Report for PCT/US2018/059065, mailed Apr. 15, 2019 (5 pages).

International Search Report for PCT/US2018/059085, mailed Feb. 21, 2019 (5 pages).

International Search Report for PCT/US2020/058415, mailed Apr. 9, 2021 (5 pages).

International Search Report for PCT/US2022/027765, mailed Oct. 13, 2022 (7 pages).

Katrekar, et al. (2017) "In vivo RNA targeting of point mutations via suppressor tRNAs and adenosine deaminases", URL:https://www.biorxiv.org/content/biorxiv/early/2017/10/28/210278.full.pdf, doi:http://dx.doi.org/10.1101/210278, 25 pages.

Keeling, et al. (2014) "Therapeutics based on stop codon readthrough", Annual Review of Genomics and Human Genetics 15(1), 371-394.

Klassen, et al. (2018) "Collaboration of tRNA modifications and elongation factor eEF1A in decoding and nonsense suppression," Scientific Reports, 8(12749): 1-12.

Kleina, et al. (1990) "Construction of Escherichia coli Amber Suppressor tRNA Genes," J Mol Biol 213, 705-717.

Koukuntla, et al. (2013) "U6 promoter-enhanced GlnUAG suppressor tRNA has higher suppression efficacy and can be stably expressed in 293 cells," Journal of Gene Medicine 15, 93-101.

Lueck, et al. (2016) "Engineered tRNA suppression of a CFTR nonsense mutation," bioRxiv, Nov. 20, pp. 1-9.

Lueck, et al. (2018) "Engineered transfer RNAs for suppression of premature termination codons," bioRxiv preprint first posted online Aug. 27, 2018. [online].

Lueck, et al. (2019) "Engineered transfer RNAs for suppression of premature termination codons", Nature Communications 10(822), 1-11.

Muller, et al. (2008) "Spliceosomal Peptide P140 for Immunotherapy of Systemic Lupus Erythematosus Results of an Early Phase II Clinical Trial," Arthritis & Rheumatism 58 (12), 3873-3883.

Olejniczak, et al. (2005) "Idiosyncratic tuning of tRNAs to achieve uniform ribosome binding," Nature Structural & Molecular Biology 12(9), 788-793.

Panchal, et al. (1999) "Partial functional correction of xeroderma pigmentosum group A cells by suppressor tRNA," Hum Gene Ther, 10: 2209-2219.

Raftery, et al. (1987) "Systematic alterations in the anticodon arm make tRNA Glu-Suoc a more efficient suppressor," EMBO Journal 6(5), 1499-1506.

Roy, et al. (2016) "Ataluren stimulates ribosomal selection of near-cognate tRNAs to promote nonsense suppression," Proc Natl Acad Sci USA, 113: 12508-12513.

Russian Office Action for RU Application No. 2020117787, 6 pages, dated Nov. 1, 2022. [English Translation].

Saks, et al. (2011) "Functional consequences of T-stem mutations in E. coli tRNA$^{Thr}_{UGU}$ in vitro and in vivo," RNA, 17: 1038-1047.

Schmid, et al. (2014) "A Versatile RNA Vector for Delivery of Coding and Noncoding RNAs," J Virol, 88(4): 2333-2336.

Schrader, et al. (2009) "Understanding the Sequence Specificity of tRNA Binding to Elongation Factor Tu using tRNA Mutagenesis," J Mol Biol 386, 1255-1264.

Schrader, et al. (2011) "Tuning the affinity of aminoacyl-tRNA to elongation factor Tu for optimal decoding," PNAS 108(13), 5215-5220.

Sharp, et al. (1985) "Structure and transcription of eukaryotic tRNA genes," Crit Rev Biochem 19(2), 107-144.

Singer, et al. (1998) "Genes and genomes," Moscow, "Mir" 1: 52, Table 1.5. [Non-English].

Sissler, et al. (1996) "Arginine aminoacylation identity is context-dependent and ensured by alternate recognition sets in the anticodon loop of accepting tRNA transcripts", The EMBO Journal 15(18), 5069-5076.

Temple, et al. (1982) "Construction of a functional human suppressor tRNA gene: an approach to gene therapy for beta-thalassaemia," Nature, 296: 537-540.

Tuorto, et al. (2016) "Genome recoding by tRNA modifications," Open Biol., 6(12): 160287.

Vasil'eva, et al. (2004) "Influence of Nucleotide Changes in tRNA $^{Phe}$ on the Acceptor End Positioning in the Complex With Phenylalanyl-tRNA Synthetase," Biochemistry, 69: 192-203. [English Abstract].

Written Opinion for PCT/US2018/059065, mailed Apr. 15, 2019 (6 pages).

Written Opinion for PCT/US2018/059085, mailed Feb. 21, 2019 (6 pages).

Written Opinion for PCT/US2020/058415, mailed Apr. 9, 2021 (6 pages).

Written Opinion for PCT/US2022/027765, mailed Oct. 13, 2022 (13 pages).

U.S. Appl. No. 18/558,926, Methods and Compositions for Treating a Premature Termination Codon-Mediated Disorder, filed Nov. 3, 2023.

U.S. Appl. No. 16/761,205, Methods of Rescuing Stop Codons via Genetic Reassignment With ACE-tRNA, filed May 1, 2020.

U.S. Appl. No. 18/137,931, Methods of Rescuing Stop Codons via Genetic Reassignment With ACE-tRNA, filed Apr. 21, 2023.

U.S. Appl. No. 18/137,942, Methods of Rescuing Stop Codons via Genetic Reassignment With ACE-tRNA, filed Apr. 21, 2023.

U.S. Appl. No. 16/760,932, Methods of Rescuing Stop Codons via Genetic Reassignment With ACE-tRNA, filed May 1, 2020.

U.S. Appl. No. 18/430,760, Methods of Rescuing Stop Codons via Genetic Reassignment With ACE-tRNA, filed Feb. 2, 2024.

| position | residues | ratios |
|---|---|---|
| 0 | Gm/G | 1/4 |
| 1 | Ψ/U | 3/14 |
| 4 | Am/A | 2/28 |
| 4 | Um/U | 5/45 |
| 4 | Cm/C | 4/51 |
| 4 | Gm/G | 2/41 |
| 6 | $m^2$G/G | 20/36 |
| 7 | $m^2$G/G | 1/69 |
| 9 | $m^1$A/A | 1/69 |
| 9 | $m^1$G/xG/G | 56/1/43 |
| 10 | $m^2$G/G | 103/70 |
| 12 | $ac^4$C/C | 32/21 |
| 13 | Ψ/U | 47/8 |
| 13 | Cm/C | 1/83 |
| 14 | $m^1$A/xA/A | 9/1/165 |
| 16 | D/U | 123/25 |
| 17 | D/U | 39/0 |
| 18 | Gm/G | 40/138 |
| 20 | $acp^3$U/D/U | 4/118/11 |
| 20a | $acp^3$U/D/Ψ/xU/U | 6/64/2/2/2 |
| 20b | D/Ψ/U | 8/6/2 |
| 25 | Ψ/U | 1/28 |
| 26 | Ψ/U | 1/24 |
| 26 | $m^{22}$G/$m^2$G/xG/G | 90/16/2/8 |
| 27 | Ψ/U | 70/10 |
| 27 | $m^{22}$G/G | 3/14 |
| 28 | Ψ/U | 37/38 |
| 30 | Ψ/U | 1/4 |
| 31 | Ψ/U | 4/2 |
| 32 | Ψm/Um/Ψ/U | 2/6/24/8 |
| 32 | Cm/$m^3$C/xC/C | 40/16/2/80 |
| 34 | I/A | 32/0 |
| 34 | $s^2$U/Um/$mchm^5$U/ $ncm^5$U/$cmnm^5$Um/ $mcm^5s^2$U/$mcm^5$U/ ψ/xU/U | 1/3/1/ 3/1/ 7/4/ 1/11/5 |
| 34 | Cm/$f^5$Cm/$m^5$C/xC/C | 8/1/1/2/44 |
| 34 | QtRNA/manQtRNA/ galQtRNA/GmG | 5/4/ 3/17/20 |

| position | residues | ratios |
|---|---|---|
| 35 | Ψ/U | 7/50 |
| 36 | Ψ/xU/U | 2/3/50 |
| 37 | $m^1$I/$ms^2t^5$A/$i^6$A/ $m^6t^6$A/$t^6$A/xA/A | 6/2/22/ 2/48/4/45 |
| 37 | $m^1$G/$02yW$/xG/ yW/G | 33/6/2/ 7/1 |
| 38 | Ψ/U | 17/1 |
| 38 | $m^5$C/xC/C | 10/1/26 |
| 39 | $m^7$Ψ/Ψm/ Um/Ψ/U | 2/6/ 1/79/2 |
| 39 | Gm/G | 4/32 |
| 40 | Ψ/U | 6/1 |
| 40 | $m^5$C/C | 3/139 |
| 44 | Um/xU/U | 20/2/18 |
| e11 | Ψ/U | 2/4 |
| e12 | Ψ/U | 6/11 |
| e14 | Ψ/U | 2/6 |
| e2 | $m^3$C/C | 7/7 |
| 46 | $m^7$G/G | 86/39 |
| 47 | D/xU/U | 83/1/16 |
| 48 | D/U | 1/25 |
| 48 | $m^5$C/xC/C | 95/1/46 |
| 49 | xA/A | 1/19 |
| 49 | $m^5$C/xC/C | 64/1/13 |
| 50 | Ψ/U | 4/45 |
| 50 | $m^5$C/C | 15/71 |
| 54 | $m^5$Um/$m^5$U/Ψ/U | 16/111/11/17 |
| 55 | Ψ/U | 166/12 |
| 58 | $m^7$A/xA/A | 151/1/26 |
| 64 | Ar(p)/A | 2/43 |
| 64 | Gr(p)/xG/G | 1/1/87 |
| 65 | Ψ/U | 1/32 |
| 67 | Ψ/U | 2/63 |
| 67 | $m^2$G/G | 2/64 |
| 68 | Ψ/U | 1/37 |
| 72 | Ψ/U | 1/16 |
| 72 | $m^5$C/C | 5/132 |

| SEQ ID NO | Leader Name | GlnTTA (%GFP+) | GlnTTA (Mean Intensity) | ArgTCA (%GFP+) | ArgTCA (Mean Intensity) |
|---|---|---|---|---|---|
| 869 | Ser-TGA-4-1 | 62.74% | 57.40% | 30.23% | 32.20% |
| 870 | Ser-CGA-4-1 | 53.60% | 56.87% | 50.97% | 58.31% |
| 871 | Arg-TCG-5-1 | 57.64% | 55.07% | 49.56% | 56.87% |
| 872 | Ser-GCT-2-1 | 57.47% | 53.97% | 48.68% | 47.35% |
| 873 | Ile-AAT-4-1 | 54.66% | 53.13% | 56.41% | 59.93% |
| 874 | Ala-AGC-4-1 | 59.93% | 50.78% | 48.51% | 53.57% |
| 875 | Arg-TCT-1-1 | 50.09% | 50.22% | 49.74% | 53.58% |
| 876 | Leu-TAA-1-1 | 56.41% | 49.91% | 57.82% | 58.29% |
| 877 | Arg-CCG-2-1 | 55.71% | 48.81% | 54.13% | 59.05% |
| 878 | Ser-GCT-3-1 | 47.45% | 45.48% | 55.54% | 62.93% |
| 879 | Ser-TGA-1-1 | 47.10% | 45.46% | 49.03% | 60.64% |
| 880 | Asn-GTT-1-1 | 50.97% | 43.37% | 44.64% | 55.25% |
| 881 | Arg-TCT-2-1 | 52.37% | 40.67% | 57.64% | 59.76% |
| 882 | Asn-GTT-3-1 | 52.02% | 40.28% | 52.55% | 55.95% |
| 883 | Tyr-GTA-5-1 | 51.14% | 38.55% | 42.53% | 35.75% |
| 884 | Val-CAC-2-1 | 44.11% | 37.73% | 51.67% | 53.84% |
| 885 | Thr-TGT-1-1 | 46.75% | 36.77% | 49.56% | 56.01% |
| 886 | Arg-TCG-1-1 | 46.40% | 36.14% | 39.72% | 52.06% |
| 887 | Lys-TTT-6-1 | 45.69% | 35.77% | 52.02% | 57.66% |
| 888 | Arg-TCG-3-1 | 37.61% | 27.54% | 52.20% | 61.17% |

FIGURE 32

SEQUENCE LISTING

```
<160> NUMBER OF SEQ ID NOS: 902

<210> SEQ ID NO 1
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggccagtgg cgcaatggat aacgcgtctg acttcagatc agaagattcc aggttcgact      60
cctggctggc tcg                                                         73

<210> SEQ ID NO 2
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggccagtgg cgcaatggat aacgcgtctg acttcagatc agaagattgt aggttcgact      60
cctacctggc tcg                                                         73

<210> SEQ ID NO 3
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggccagtgg cgcaatggat aacgcgtctg acttcagatc agaagattct aggttcgact      60
cctggctggc tcg                                                         73

<210> SEQ ID NO 4
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccgcgtgg cctaatggat aaggcgtctg atttcagatc agaagattga gggttcgagt      60
cccttcgtgg tcg                                                         73

<210> SEQ ID NO 5
```

```
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggccgcgtgg cctaatggat aaggcgtctg atttcagatc agaagattgg gggttcgagt       60
cccttcgtgg tcg                                                          73

<210> SEQ ID NO 6
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gacccagtgg cctaatggat aaggcatcag ccttcagagc tggggattgt gggttcgagt       60
cccatctggg tcg                                                          73

<210> SEQ ID NO 7
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gccccagtgg cctaatggat aaggcactgg ccttcaaagc cagggattgt gggttcgagt       60
cccacctggg gta                                                          73

<210> SEQ ID NO 8
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gccccagtgg cctaatggat aaggcactgg ccttcaaagc cagggattgt gggttcgagt       60
cccacctggg gtg                                                          73

<210> SEQ ID NO 9
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gccccggtgg cctaatggat aaggcattgg ccttcaaagc cagggattgt gggttcgagt       60
cccacccggg gta                                                          73

<210> SEQ ID NO 10
<211> LENGTH: 73
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 10
gccccagtgg cctaatggat aaggcattgg ccttcaaagc cagggattgt gggttcgagt        60
cccatctggg gtg                                                           73

<210> SEQ ID NO 11
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggccgcgtgg cctaatggat aaggcgtctg acttcagatc agaagattgc aggttcgagt        60
cctgccgcgg tcg                                                           73

<210> SEQ ID NO 12
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaccgcgtgg cctaatggat aaggcgtctg acttcagatc agaagattga gggttcgagt        60
cccttcgtgg tcg                                                           73

<210> SEQ ID NO 13
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaccacgtgg cctaatggat aaggcgtctg acttcagatc agaagattga gggttcgaat        60
cccttcgtgg ttg                                                           73

<210> SEQ ID NO 14
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gaccacgtgg cctaacggat aaggcgtctg acttcagatc agaagattga gggttcgaat        60
cccttcgtgg tta                                                           73

<210> SEQ ID NO 15
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

-continued

```
ggctctgtgg cgcaatggat agcgcattgg acttcaagtg acgagaaagc gattcaaagg      60
ttgtgggttc gaatcccacc agagtcg                                          87

<210> SEQ ID NO 16
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggctctgtgg cgcaatggat agcgcattgg acttcaaatt caaaggttgt gggttcgaat      60
cccaccagag tcg                                                         73

<210> SEQ ID NO 17
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggctccgtgg cgcaatggat agcgcattgg acttcaagag gctgaaggca ttcaaaggtt      60
ccgggttcga gtcccggcgg agtcg                                            85

<210> SEQ ID NO 18
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggctccgtgg cgcaatggat agcgcattgg acttcaaatt caaaggttcc gggttcgagt      60
cccggcggag tcg                                                         73

<210> SEQ ID NO 19
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggctctgtgg cgcaatggat agcgcattgg acttcaagca tgattgagag attcaaaggt      60
tgcgggttcg agtcccgcca gagtcg                                           86

<210> SEQ ID NO 20
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggctctgtgg cgcaatggat agcgcattgg acttcaaatt caaaggttgc gggttcgagt      60
cccgccagag tcg                                                         73
```

<210> SEQ ID NO 21
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggctctgtgg cgcaatggat agcgcattgg acttcaagac aaatggaggc attcaaaggt      60
tgtgggttcg agtcccacca gagtcg                                           86

<210> SEQ ID NO 22
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggctctgtgg cgcaatggat agcgcattgg acttcaaatt caaaggttgt gggttcgagt      60
cccaccagag tcg                                                         73

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtctctgtgg cgcaatggac gagcgcgctg gacttcaaat ccagaggttc tgggttcgag      60
tcccggcaga gatg                                                        74

<210> SEQ ID NO 24
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggctctgtgg agcaatggat agcacattgg acttcaagca tgaccgagag attcaaaggt      60
tgcgggttcg agtcccacca gagttg                                           86

<210> SEQ ID NO 25
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggctctgtgg agcaatggat agcacattgg acttcaaatt caaaggttgc gggttcgagt      60
cccaccagag ttg                                                         73

<210> SEQ ID NO 26
<211> LENGTH: 200

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ctacccagag gcaggcggga gactcccccg agcgtccaat aagagcgccg ccaatggagc      60
cgcccgcccg cgggggtgca gagggacttc cgggtgaggt cctccgctac ttccctcccc     120
acggaaaaga tagaccagtc tgacgcgagc ctgaaggcgg ctacacgctt taagctaagt     180
aaaggcacct tctcgctggc                                                 200

<210> SEQ ID NO 27
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
acttgtatgt tgtttttatc tgtcagtttg ttaatcccaa gattcccttt ggaaataaag      60
cgaaattgac cgtagtggtt atgaccaact tctagtctaa acttaattct tggaactcaa     120
ggatctgagc aaacaactgt cagggtgaca cattgcttaa acggtgacag cggtcgagag     180
ccttgtcccg gatggagagt                                                 200

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctgagacctc taagagcctt atcttgattt gaagggatga gggtggttgt g              51

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acaagccttt tcagctttag agggtgagca aaggatgtgg gatctgagaa c              51

<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctaatagaaa gaaatgagac cgcctgatgg aaaaatgtga aagtaaactt t              51

<210> SEQ ID NO 31
<211> LENGTH: 1854
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 31
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtcgag gtgagcccca cgttctgctt cactctcccc atctcccccc cctccccacc     360
cccaattttg tatttattta ttttttaatt attttgtgca gcgatggggg cggggggggg     420
gggggggcgc gcgccaggcg gggcggggcg gggcgagggg cggggcgggg cgaggcggag     480
aggtgcggcg gcagccaatc agagcggcgc gctccgaaag tttccttta tggcgaggcg     540 gcggcggcgg cggccctata aaaagcgaag cgcgcggcgg gcgggagtcg ctgcgcgctg     600
ccttcgcccc gtgccccgct ccgccgccgc ctcgcgccgc ccgccccggc tctgactgac     660
cgcgttactc ccacaggtga gcgggcggga cggcccttct cctccgggct gtaattagcg     720
cttggtttaa tgacggcttg tttcttttct gtggctgcgt gaaagccttg aggggctccg     780
ggagcgccag caggaaggaa atgggcgggg agggccttcg tgcgtcgccg cgccgccgtc     840
cccttctccc tctccagcct cggggctgtc cgcgggggga cggctgcctt cggggggggac     900 ggggcagggc ggggttcggc ttctggcgtg tgaccggcgg ctctagagcc tctgctaacc     960
atgttcatgc cttcttcttt ttcctacagc tcctgggcaa cgtgctggtt attgtgctgt    1020
ctcatcattt tggcaaagaa ttgcggccca acggtaccgg atccaccggc cgccaccatg    1080
ggaagcccaa agaagaagcg taaggtaatg gtgagcaagg gcgaggagct gttcaccggg    1140
gtggtgccca tcctggtcga gctggacggc gacgtaaacg gccacaagtt cagcgtgtcc    1200
ggcgagggcg agggcgatgc cacctacggc aagctgaccc tgaagttcat ctgcaccacc    1260
ggcaagctgc ccgtgccctg gcccaccctc gtgaccaccc tgacctacgg cgtgcagtgc    1320
ttcagccgct accccgacca catgaagcag cacgacttct tcaagtccgc catgcccgaa    1380
ggctacgtcc aggagtgaac catcttcttc aaggacgacg gcaactacaa gacccgcgcc    1440
gaggtgaagt tcgagggcga caccctggtg aaccgcatcg agctgaaggg catcgacttc    1500
aaggaggacg gcaacatcct ggggcacaag ctggagtaca actacaacag ccacaacgtc    1560
tatatcatgg ccgacaagca gaagaacggc atcaaggtga acttcaagat ccgccacaac    1620
atcgaggacg gcagcgtgca gctcgccgac cactaccagc agaacacccc catcggcgac    1680
ggccccgtgc tgctgcccga caaccactac ctgagcaccc agtccgccct gagcaaagac    1740
cccaacgaga agcgcgatca catggtcctg ctggagttcg tgaccgccgc cgggatcact    1800
ctcggcatgg acgagctgta caaggggagc cccaagaaaa agcggaaggt gtaa          1854

<210> SEQ ID NO 32
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
acttgtatgt tgtttttatc tgtcagtttg ttaatcccaa gattcccttt ggaaataaag        60
cgaaattgac cgtagtggtt atgaccaact tctagtctaa actt                        104
```

<210> SEQ ID NO 33
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gagggcctat ttcccatgat tccttcatat ttgcatatac gatacaaggc tgttagagag        60
ataattagaa ttaatttgac tgtaaacaca aagatattag tacaaaatac gtgacgtaga       120
aagtaataat ttcttgggta gtttgcagtt ttaaaattat gttttaaaat ggactatcat       180
atgcttaccg taacttgaaa gtatttcgat ttcttggctt tatatatctt gtggaaagga       240
cgggcggagg aaggcacctt ctcgctggc                                        269
```

<210> SEQ ID NO 34
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
acttgtatgt tgtttttatc tgtcagtttg ttaatcccaa gattcc                       46
```

<210> SEQ ID NO 35
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
gtctctgtgg cgcaatggac gagcgcgctg gacttcaaat ccagaggttc cgggttcgag        60
tcccggcaga gatg                                                          74
```

<210> SEQ ID NO 36
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
ggtcccatgg tgtaatggtt agcactctgg actttaaatc cagcgatccg agttcaaatc        60
tcggtgggac ct                                                            72
```

<210> SEQ ID NO 37
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

-continued

```
ggttccatgg tgtaatggtt agcactctgg actttaaatc cagcgacccg agttcaaatc      60
tcggtgggac ct                                                         72

<210> SEQ ID NO 38
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggttccatgg tgtaatggtt agcactctgg actttaaatc cagcgatccg agttcaaatc      60
tcggtggaac ct                                                         72

<210> SEQ ID NO 39
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggttccatgg tgtaatggtt agcactctgg actttaaatc cagcgatccg agttcaaatc      60
tcggtgggac ct                                                         72

<210> SEQ ID NO 40
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggttccatgg tgtaatggtg agcactctgg actttaaatc cagcgatccg agttcaaatc      60
tcggtgggac ct                                                         72

<210> SEQ ID NO 41
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggttccatgg tgtaatggct agcactctgg actttaaatc cagcgatccg agttcaaatc      60
tcggtgggat tt                                                         72

<210> SEQ ID NO 42
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggttccatgg tgtaatggtt agcactctgg actttaaatc cagccataca agttcaaatc      60
tcagtggaac ct                                                         72
```

```
<210> SEQ ID NO 43
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggttccttgg tgtaagatga gcactctgga ttttaaatcc agcgatcaga gttcaaatct      60
cggtgggacc t                                                          71

<210> SEQ ID NO 44
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggtcccatgg tgtaatggtt agcactctgg actttaaatc cagcaatctg agttcaaatc      60
tcggtgggac ct                                                         72

<210> SEQ ID NO 45
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggccccatgg tgtaatggtt agcactctgg actttaaatc cagcgatccg agttcaaatc      60
tcggtgggac ct                                                         72

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggtctcatgg tgtaatggtt agcacactgg actttaagtc cagcaatccg agttcgagtc      60
ttggtgagac ca                                                         72

<210> SEQ ID NO 47
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggacccatgg tgtaatggtt agcactctgg actttaaatc cagcaatcca agttcaaatc      60
tcggtgggac ct                                                         72

<210> SEQ ID NO 48
<211> LENGTH: 72
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 48
gtttccatgg tgtaatggtt ggcactctgg actttaaatc cagcaatcca agttcaagtc      60
tctgtgggac ct                                                          72

<210> SEQ ID NO 49
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gtcaggatgg ccgagtggtc taaggcgcca gactctagct atggcttcct cgctctgagg      60
gttctggtct cccctggagg cgtgggttcg aatcccactt ctgaca                     106

<210> SEQ ID NO 50
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gtcaggatgg ccgagtggtc taaggcgcca gactctagct tagcttccct gtctggggat      60
tctggtctcc gtatggaggc gtgggttcga atcccacttc tgaca                      105

<210> SEQ ID NO 51
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gtcaggatgg ccgagtggtc taaggcgcca gactctaggt gacaagcctt acctacgggt      60
gttctggtct ccgaatggag gcgtgggttc gaatcccact tctgaca                    107

<210> SEQ ID NO 52
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gtcaggatgg ccgagtggtc taaggcgcca gactctagcg ttcgcttcct ctactgaggg      60
ttctggtctc cgtgtggagg cgtgggttcg aatcccactt ctgaca                     106

<210> SEQ ID NO 53
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 53
gtcaggatgg ccgagtggtc taaggcgcca gacttcagct atggcttcct cgctctgagg      60
gttctggtct cccctggagg cgtgggttcg aatcccactt ctgaca                    106

<210> SEQ ID NO 54
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gtcaggatgg ccgagtggtc taaggcgcca gacttcagct tagcttccct gtctggggat      60
tctggtctcc gtatggaggc gtgggttcga atcccacttc tgaca                     105

<210> SEQ ID NO 55
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gtcaggatgg ccgagtggtc taaggcgcca gacttcaggt gacaagcctt acctacgggt      60
gttctggtct ccgaatggag gcgtgggttc gaatcccact tctgaca                   107

<210> SEQ ID NO 56
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gtcaggatgg ccgagtggtc taaggcgcca gacttcagcg ttcgcttcct ctactgaggg      60
ttctggtctc cgtgtggagg cgtgggttcg aatcccactt ctgaca                    106

<210> SEQ ID NO 57
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gtcaggatgg ccgagtggtc taaggcgcca gactttagct atggcttcct cgctctgagg      60
gttctggtct cccctggagg cgtgggttcg aatcccactt ctgaca                    106

<210> SEQ ID NO 58
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gtcaggatgg ccgagtggtc taaggcgcca gactttagct tagcttccct gtctggggat      60

-continued

```
tctggtctcc gtatggaggc gtgggttcga atcccacttc tgaca                        105

<210> SEQ ID NO 59
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gtcaggatgg ccgagtggtc taaggcgcca gactttaggt gacaagcctt acctacgggt       60
gttctggtct ccgaatggag gcgtgggttc gaatcccact tctgaca                    107

<210> SEQ ID NO 60
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gtcaggatgg ccgagtggtc taaggcgcca gactttagcg ttcgcttcct ctactgaggg       60
ttctggtctc cgtgtggagg cgtgggttcg aatcccactt ctgaca                     106

<210> SEQ ID NO 61
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccttcgatag ctcagttggt agagcggagg actctagagt tactagaata gtgatcctta       60
ggtcgctggt tcgaatccgg ctcgaagga                                         89

<210> SEQ ID NO 62
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccttcgatag ctcagttggt agagcggagg actctagtca gtacaatatg gtaatcctta       60
ggtcgctggt tcgattccgg ctcgaagga                                         89

<210> SEQ ID NO 63
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccttcgatag ctcagctggt agagcggagg actctaggct tgtggctgtg gacatcctta       60
ggtcgctggt tcgattccgg ctcgaagga                                         89
```

```
<210> SEQ ID NO 64
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccttcgatag ctcagctggt agagcggagg actctagcta actccccgtt agaagacatc      60
cttaggtcgc tggttcgact ccggctcgaa gga                                   93

<210> SEQ ID NO 65
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctttcgatag ttcagttggt agagcggagg actctagagt attaacgttg gtgatcctta      60
ggtcgctggt tcgagtccgg ctcgaagga                                        89

<210> SEQ ID NO 66
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccttcgatag ctcagttggt agagcggagg actttagagt tactagaata gtgatcctta      60
ggtcgctggt tcgaatccgg ctcgaagga                                        89

<210> SEQ ID NO 67
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccttcgatag ctcagttggt agagcggagg actttagtca gtacaatatg gtaatcctta      60
ggtcgctggt tcgattccgg ctcgaagga                                        89

<210> SEQ ID NO 68
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccttcgatag ctcagctggt agagcggagg actttaggct tgtggctgtg gacatcctta      60
ggtcgctggt tcgattccgg ctcgaagga                                        89

<210> SEQ ID NO 69
<211> LENGTH: 93
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 69
ccttcgatag ctcagctggt agagcggagg actttagcta actccccgtt agaagacatc      60
cttaggtcgc tggttcgact ccggctcgaa gga                                   93

<210> SEQ ID NO 70
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctttcgatag ttcagttggt agagcggagg actttagagt attaacgttg gtgatcctta      60
ggtcgctggt tcgagtccgg ctcgaagga                                        89

<210> SEQ ID NO 71
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gggggtatag ctcagtggta gagcatttga cttcagatca agaggtccct ggttcaaatc      60
caggtgcccc ct                                                          72

<210> SEQ ID NO 72
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gggggtatag ctcaggggta gagcatttga cttcagatca agaggtccct ggttcaaatc      60
cagatgcccc ct                                                          72

<210> SEQ ID NO 73
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gggggtatag ctcaggggta gagtatttgg cttcagatca agaggtccct ggttcaaatc      60
caggtgcccc ct                                                          72

<210> SEQ ID NO 74
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 74
gggggtatag ctcagggta gagcatttga cttcagatca agaggtcctt ggttcaaatc      60
caggtgtccc ct                                                        72

<210> SEQ ID NO 75
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gggggtatag ctcagaggta gagcatttga cttcagatca agagatctct ggttcaaatc      60
caggtgcccc ct                                                        72

<210> SEQ ID NO 76
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gggggtatag ctcaggggta gagcatttga cttcagatca agaggtccct agttcaaatc      60
caggtgcccc ct                                                        72

<210> SEQ ID NO 77
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggtggtatag ctcaggggta gagcatttga cttcagatca agagatccct ggttcgaatc      60
caggtgcccc ct                                                        72

<210> SEQ ID NO 78
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gggggtataa ctcaggggta gagcatttga cttcagatca agaggtccct ggttcaaatc      60
caggtgcccc ct                                                        72

<210> SEQ ID NO 79
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tggggtatag ctcaggggta gagcatttga cttcagatca agaggtccct ggttcaaatc      60

-continued

```
caggtgcccc ct                                                              72

<210> SEQ ID NO 80
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gggggtatag ctcagaggaa gagcatttga cttcagatca agaggtccct gattcaaatc         60
caggtgcccc ct                                                              72

<210> SEQ ID NO 81
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gggggtaaag ctcaggggta gagcatttga cttcagatta agaggtccct ggttcaaatc         60
caggtacccc ct                                                              72

<210> SEQ ID NO 82
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gggggtatag ctcagtggta gagcatttga cttcagatca agaggtccct ggttcaaatc         60
cgggtgcccc ct                                                              72

<210> SEQ ID NO 83
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggggttatag ctcaggtgta gagcatttga cttcagatca agaggtccct ggttcaaatc         60
caggtgcccc ct                                                              72

<210> SEQ ID NO 84
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gggggtatag ctcaggggta gagcatttga cttcagatca cgaggtccct ggttcaaatc         60
gaggtgcccc ct                                                              72

<210> SEQ ID NO 85
```

```
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggggtatag ctcaggggtg gagcatttga cttcagatca aggggtccct gtttcaaatc      60
caggtgcccc ct                                                          72

<210> SEQ ID NO 86
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gggggtatag ctcagtggta gagcatttga cttcagatca agaggtcccc ggttcaaatc      60
cgggtgcccc ct                                                          72

<210> SEQ ID NO 87
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gggggtatag ctcaggggta gagcatttga cttcagatca agaggtccct ggttcaaatc      60
caggtgcccc ct                                                          72

<210> SEQ ID NO 88
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gggggtatag ctcaggggta gagcatttga cttcagatca agaggtccct ggttcaaatc      60
cgggtgcccc ct                                                          72

<210> SEQ ID NO 89
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggggtatag ctcaggggta gagcatttga cttcagatca agaggtccct ggttcaaatc      60
caggtacccc ct                                                          72

<210> SEQ ID NO 90
<211> LENGTH: 72
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 90
gggggtatag ctcaggggta gagcatttga cttcagatca agaggtcccc ggttcaaatc        60
cgggtgcccc ct                                                             72

<210> SEQ ID NO 91
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gggggcatag ctcaggggta gagcatttga cttcagatca agaggtcccc ggttcaaatc        60
cgggtgctcc ct                                                             72

<210> SEQ ID NO 92
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gggggtatag ctcaggggta gagcatttga cttcagatta agaggtccct ggttcaaatc        60
caggtgcccc ct                                                             72

<210> SEQ ID NO 93
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tccctggtgg tctagtggtt aggattcggc gctctaaccg ccgcggcccg ggttcgattc        60
ccggtcaggg aa                                                             72

<210> SEQ ID NO 94
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tccctggtgg tctagtggtt aggatttggc gctctaaccg ccgcggcctg ggttcgattc        60
ccggtcaggg aa                                                             72

<210> SEQ ID NO 95
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95

-continued

```
tccctggtgg tctagtggtt aggctttggt gctctaacct ccatggccca ggtttgattc      60
ctggtcaggg aa                                                          72

<210> SEQ ID NO 96
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tccctggtgg tctagtggtt aggattcggc gctttaaccg ccgcggcccg ggttcgattc      60
ccggtcaggg aa                                                          72

<210> SEQ ID NO 97
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tccctggtgg tctagtggtt aggatttggc gctttaaccg ccgcggcctg ggttcgattc      60
ccggtcaggg aa                                                          72

<210> SEQ ID NO 98
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tccctggtgg tctagtggtt aggctttggt gctttaacct ccatggccca ggtttgattc      60
ctggtcaggg aa                                                          72

<210> SEQ ID NO 99
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tcccacatgg tctagcggtt aggattcctg gttctaaccc aggcggcccg ggttcgactc      60
ccggtgtggg aa                                                          72

<210> SEQ ID NO 100
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcccatatgg tctagcggtt aggattcctg gttctaaccc aggcggcccg ggttcgactc      60
ccggtatggg aa                                                          72
```

-continued

<210> SEQ ID NO 101
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tccctggtgg tctagtggct aggattcggc gctctaaccg ccgcggcccg ggttcgattc        60
ccggtcaggg aa                                                            72

<210> SEQ ID NO 102
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tcccacatgg tctagcggtt aggattcctg gttttaaccc aggcggcccg ggttcgactc        60
ccggtgtggg aa                                                            72

<210> SEQ ID NO 103
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tcccatatgg tctagcggtt aggattcctg gttttaaccc aggcggcccg ggttcgactc        60
ccggtatggg aa                                                            72

<210> SEQ ID NO 104
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tccctggtgg tctagtggct aggattcggc gctttaaccg ccgcggcccg ggttcgattc        60
ccggtcaggg aa                                                            72

<210> SEQ ID NO 105
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtttccgtag tgtagtggtt agcgcgttcg ccttcaaaag cgaaaggtcc ccggttcgaa        60
accgggcgga aaca                                                          74

<210> SEQ ID NO 106
<211> LENGTH: 71

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcgccgctgg tgtagtggta tcatgcaaga tttcaattct tgcgacccgg gttcgattcc      60
cgggcggcgc a                                                           71

<210> SEQ ID NO 107
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcattggtag ttcaatggta gaattctcgc cttcaacgcg ggtgacccgg gttcgattcc      60
cggccaatgc a                                                           71

<210> SEQ ID NO 108
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcattggtgg ttcaatggta gaattctcgc cttcaacgcg ggtgacccgg gttcgattcc      60
cggccaatgc a                                                           71

<210> SEQ ID NO 109
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gcattggtgg ttcaatggta gaattctcgc cttcaactcg ggtgacccgg gttcgattcc      60
cggccaatgc a                                                           71

<210> SEQ ID NO 110
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcatgggtgg ttcagtggta gaattctcgc cttcaacgcg ggaggcccgg gttcgattcc      60
cggcccatgc a                                                           71

<210> SEQ ID NO 111
<211> LENGTH: 71
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 111
gcattggtgg ttcagtggta gaattctcgc cttcaacgcg ggaggcccgg gttcgattcc          60
cggccaatgc a                                                               71

<210> SEQ ID NO 112
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcattggtgg ttcagtggta gaattctcgc cttcaacgcg ggaggcccgg gtttgattcc          60
cggccaatgc a                                                               71

<210> SEQ ID NO 113
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcattggtgg ttcagtggta gaattctcgc cttcaacgcg ggaggcccgg gttcggttcc          60
cggccaatgc a                                                               71

<210> SEQ ID NO 114
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gcgttggtgg tatagtggtg agcatagctg ccttcaaagc agttgacccg ggttcgattc          60
ccggccaacg ca                                                              72

<210> SEQ ID NO 115
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggtagcgtgg ccgagcggtc taaggcgctg gattctagct ccagtctctt cggggggcgtg          60 ggttcgaatc ccaccgctgc ca                                                   82

<210> SEQ ID NO 116
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggtagtgtgg ccgagcggtc taaggcgctg gattctagct ccagtctctt cggggcgtg        60 ggttcgaatc ccaccgctgc ca                                                82

<210> SEQ ID NO 117
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ggtagtgtgg ccgagcggtc taaggcgctg gattctagct ccagtctctt cggggcgtg        60 ggttcgaatc ccaccactgc ca                                                82

<210> SEQ ID NO 118
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggtagcgtgg ccgagcggtc taaggcgctg gatttcagct ccagtctctt cggggcgtg        60 ggttcgaatc ccaccgctgc ca                                                82

<210> SEQ ID NO 119
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggtagtgtgg ccgagcggtc taaggcgctg gatttcagct ccagtctctt cggggcgtg        60 ggttcgaatc ccaccgctgc ca                                                82

<210> SEQ ID NO 120
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggtagtgtgg ccgagcggtc taaggcgctg gatttcagct ccagtctctt cggggcgtg        60 ggttcgaatc ccaccactgc ca                                                82

<210> SEQ ID NO 121
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggtagcgtgg ccgagcggtc taaggcgctg gattttagct ccagtctctt cggggcgtg        60 ggttcgaatc ccaccgctgc ca                                                82

-continued

```
<210> SEQ ID NO 122
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggtagtgtgg ccgagcggtc taaggcgctg gattttagct ccagtctctt cgggggcgtg      60
ggttcgaatc ccaccgctgc ca                                               82

<210> SEQ ID NO 123
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggtagtgtgg ccgagcggtc taaggcgctg gattttagct ccagtctctt cgggggcgtg      60
ggttcgaatc ccaccactgc ca                                               82

<210> SEQ ID NO 124
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gtcaggatgg ccgagtggtc taaggcgcca gactctagtt ctggtctccc ctggaggcgt      60
gggttcgaat cccacttctg aca                                              83

<210> SEQ ID NO 125
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gtcaggatgg ccgagtggtc taaggcgcca gactctagtt ctggtctccg tatggaggcg      60
tgggttcgaa tcccacttct gaca                                             84

<210> SEQ ID NO 126
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtcaggatgg ccgagtggtc taaggcgcca gactctagtt ctggtctccg aatggaggcg      60
tgggttcgaa tcccacttct gaca                                             84

<210> SEQ ID NO 127
<211> LENGTH: 84
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 127
gtcaggatgg ccgagtggtc taaggcgcca gactctagtt ctggtctccg tgtggaggcg      60
tgggttcgaa tcccacttct gaca                                            84

<210> SEQ ID NO 128
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gtcaggatgg ccgagtggtc taaggcgcca gacttcagtt ctggtctccc ctggaggcgt      60
gggttcgaat cccacttctg aca                                             83

<210> SEQ ID NO 129
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gtcaggatgg ccgagtggtc taaggcgcca gacttcagtt ctggtctccg tatggaggcg      60
tgggttcgaa tcccacttct gaca                                            84

<210> SEQ ID NO 130
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gtcaggatgg ccgagtggtc taaggcgcca gacttcagtt ctggtctccg aatggaggcg      60
tgggttcgaa tcccacttct gaca                                            84

<210> SEQ ID NO 131
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gtcaggatgg ccgagtggtc taaggcgcca gacttcagtt ctggtctccg tgtggaggcg      60
tgggttcgaa tcccacttct gaca                                            84

<210> SEQ ID NO 132
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 132
gtcaggatgg ccgagtggtc taaggcgcca gactttagtt ctggtctccc ctggaggcgt      60
gggttcgaat cccacttctg aca      83

<210> SEQ ID NO 133
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtcaggatgg ccgagtggtc taaggcgcca gactttagtt ctggtctccg tatggaggcg      60
tgggttcgaa tcccacttct gaca      84

<210> SEQ ID NO 134
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gtcaggatgg ccgagtggtc taaggcgcca gactttagtt ctggtctccg aatggaggcg      60
tgggttcgaa tcccacttct gaca      84

<210> SEQ ID NO 135
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gtcaggatgg ccgagtggtc taaggcgcca gactttagtt ctggtctccg tgtggaggcg      60
tgggttcgaa tcccacttct gaca      84

<210> SEQ ID NO 136
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gtcaggatgg ccgagcggtc taaggcgctg cgttctagtc gcagtctccc ctggaggcgt      60
gggttcgaat cccactcctg aca      83

<210> SEQ ID NO 137
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtcaggatgg ccgagcggtc taaggcgctg cgttctagtc gcagtctccc ctggaggcgt      60

-continued

```
gggttcgaat cccacttctg aca                                                83

<210> SEQ ID NO 138
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtcaggatgg ccgagtggtc taaggagctg tgttctagtc gcagtctccc ctggaggcgt      60
gggttcgaat cccactcctg aca                                                83

<210> SEQ ID NO 139
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtcaggatgg ccgagcagtc taaggcactg cgttctagtc gcagtctccc ctggaggcgt      60
ggattcgaat cccactcctg aca                                                83

<210> SEQ ID NO 140
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtcaggatgg ccgagcggtc taaggcgctg cgtttcagtc gcagtctccc ctggaggcgt      60
gggttcgaat cccactcctg aca                                                83

<210> SEQ ID NO 141
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gtcaggatgg ccgagcggtc taaggcgctg cgtttcagtc gcagtctccc ctggaggcgt      60
gggttcgaat cccacttctg aca                                                83

<210> SEQ ID NO 142
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gtcaggatgg ccgagtggtc taaggagctg tgtttcagtc gcagtctccc ctggaggcgt      60
gggttcgaat cccactcctg aca                                                83
```

```
<210> SEQ ID NO 143
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gtcaggatgg ccgagcagtc taaggcactg cgtttcagtc gcagtctccc ctggaggcgt      60
ggattcgaat cccactcctg aca                                             83

<210> SEQ ID NO 144
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtcaggatgg ccgagcggtc taaggcgctg cgttttagtc gcagtctccc ctggaggcgt      60
gggttcgaat cccactcctg aca                                             83

<210> SEQ ID NO 145
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gtcaggatgg ccgagcggtc taaggcgctg cgttttagtc gcagtctccc ctggaggcgt      60
gggttcgaat cccacttctg aca                                             83

<210> SEQ ID NO 146
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gtcaggatgg ccgagtggtc taaggagctg tgttttagtc gcagtctccc ctggaggcgt      60
gggttcgaat cccactcctg aca                                             83

<210> SEQ ID NO 147
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gtcaggatgg ccgagcagtc taaggcactg cgttttagtc gcagtctccc ctggaggcgt      60
ggattcgaat cccactcctg aca                                             83

<210> SEQ ID NO 148
<211> LENGTH: 83
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 148
accagaatgg ccgagtggtt aaggcgttgg actctagatc caatggattt atatccgcgt      60
gggttcgaac cccacttctg gta                                              83

<210> SEQ ID NO 149
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
accaggatgg ccgagtggtt aaggcgttgg actctagatc caatggacat atgtctgcgt      60
gggttcgaac cccactcctg gta                                              83

<210> SEQ ID NO 150
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
actgggatgg ctgagtggtt aaggcgttgg actctagatc caatgggcgg ttgcctgcgt      60
gggttcgaac cccactccca gta                                              83

<210> SEQ ID NO 151
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gatgggatgg ctgagaggtt aaggctttgg actctagatc caatgggcag atgcctgcgt      60
gggtttgaac cccactccca ata                                              83

<210> SEQ ID NO 152
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
accagaatgg ccgagtggtt aaggcgttgg acttcagatc caatggattt atatccgcgt      60
gggttcgaac cccacttctg gta                                              83

<210> SEQ ID NO 153
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 153
accaggatgg ccgagtggtt aaggcgttgg acttcagatc caatggacat atgtctgcgt      60
gggttcgaac cccactcctg gta                                            83

<210> SEQ ID NO 154
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
actgggatgg ctgagtggtt aaggcgttgg acttcagatc caatgggcgg ttgcctgcgt      60
gggttcgaac cccactccca gta                                            83

<210> SEQ ID NO 155
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gatgggatgg ctgagaggtt aaggctttgg acttcagatc caatgggcag atgcctgcgt      60
gggtttgaac cccactccca ata                                            83

<210> SEQ ID NO 156
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
accagaatgg ccgagtggtt aaggcgttgg actttagatc caatggattt atatccgcgt      60
gggttcgaac cccacttctg gta                                            83

<210> SEQ ID NO 157
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
accaggatgg ccgagtggtt aaggcgttgg actttagatc caatggacat atgtctgcgt      60
gggttcgaac cccactcctg gta                                            83

<210> SEQ ID NO 158
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
actgggatgg ctgagtggtt aaggcgttgg actttagatc caatgggcgg ttgcctgcgt      60
```

```
gggttcgaac cccactccca gta                                              83
```

```
<210> SEQ ID NO 159
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gatgggatgg ctgagaggtt aaggctttgg actttagatc caatgggcag atgcctgcgt    60
gggtttgaac cccactccca ata                                              83
```

```
<210> SEQ ID NO 160
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggtagcgtgg ccgagcggtc taaggcgctg gattctagct ccagtctctt cggaggcgtg    60
ggttcgaatc ccaccgctgc ca                                               82
```

```
<210> SEQ ID NO 161
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtagtgtgg ccgagcggtc taaggcgctg gattctagct ccagtctctt cggaggcgtg    60
ggttcgaatc ccaccactgc ca                                               82
```

```
<210> SEQ ID NO 162
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggtagcgtgg ccgagtggtc taaggcgctg gattctagct ccagtcattt cgatggcgtg    60
ggttcgaatc ccaccgctgc ca                                               82
```

```
<210> SEQ ID NO 163
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggtagcgtgg ccgagcggtc taaggcgctg gatttcagct ccagtctctt cggaggcgtg    60
ggttcgaatc ccaccgctgc ca                                               82
```

```
<210> SEQ ID NO 164
```

```
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggtagtgtgg ccgagcggtc taaggcgctg gatttcagct ccagtctctt cggaggcgtg       60
ggttcgaatc ccaccactgc ca                                                82

<210> SEQ ID NO 165
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggtagcgtgg ccgagtggtc taaggcgctg gatttcagct ccagtcattt cgatggcgtg       60
ggttcgaatc ccaccgctgc ca                                                82

<210> SEQ ID NO 166
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggtagcgtgg ccgagcggtc taaggcgctg gattttagct ccagtctctt cggaggcgtg       60
ggttcgaatc ccaccgctgc ca                                                82

<210> SEQ ID NO 167
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggtagtgtgg ccgagcggtc taaggcgctg gattttagct ccagtctctt cggaggcgtg       60
ggttcgaatc ccaccactgc ca                                                82

<210> SEQ ID NO 168
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggtagcgtgg ccgagtggtc taaggcgctg gattttagct ccagtcattt cgatggcgtg       60
ggttcgaatc ccaccgctgc ca                                                82

<210> SEQ ID NO 169
<211> LENGTH: 73
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 169
gcccagctag ctcagttggt agagcgtggg actctaaatc ctagggtcgt gggttcgaac        60
cccacgttgg gcg                                                           73

<210> SEQ ID NO 170
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gcccagctag ctcagtctgt agagcatgag actctaagtc tcagggtcat gggttggagc        60
cccatgttgt gca                                                           73

<210> SEQ ID NO 171
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gcctagctag ttcagtcggt agagcatgag actctaaatc tcaggttcat gagtttgagc        60
cccatgttgg tttggca                                                       77

<210> SEQ ID NO 172
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ccccggctag ctcagtcagt agagcttgag aatctaaatc tcagggtcgt gggttggagc        60
cccacgttgg gcg                                                           73

<210> SEQ ID NO 173
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
gatcaccgga agaggtgaca gacacctcgg ggcccatgaa cgtttggaat tcgtaaggac        60
atgagaatct cggtggttcc gtgtctgccc gccatcgcgg ccaccggcca cgggcccaag       120
ccaagtgtag cgaagcttag aaaaggttgc ccaacgtcat gtggcttgag aaggctgccg       180
ggcgccttaa gccgccagca                                                   200

<210> SEQ ID NO 174
<211> LENGTH: 200
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 174

```
cactgaacct ttttttggcc ttagaatccc tgttttgggg cctgcaggaa gtagcaacca      60
acccgagcct ccgcagggaa tgcactgacc tgtagaatgg acgttcagct tccctccctg     120
tgtctcaaca cgattacatt tcaggaacag cctgggctgg gaggcactgc gcacgcgcgc     180
cgagtcgggc ggaaaaataa                                                 200
```

<210> SEQ ID NO 175
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtcgag gtgagcccca cgttctgctt cactctcccc atctcccccc cctccccacc     360
cccaattttg tatttattta tttttttaatt attttgtgca gcgatggggg cggggggggg     420 ggggggggcgc gcgccaggcg gggcggggcg gggcgagggg cggggcgggg cgaggcggag     480
aggtgcggcg gcagccaatc agagcggcgc gctccgaaag tttcctttta tggcgaggcg     540
gcggcggcgg cggccctata aaaagcgaag cgcgcggcgg gcgggagtcg ctgcgcgctg     600
ccttcgcccc gtgccccgct ccgcgccgcc ctcgcgccgc ccgcccccggc tctgactgac     660 cgcgttactc ccacaggtga gcgggcggga cggcccttct cctccgggct gtaattagcg     720
cttggtttaa tgacggcttg tttcttttct gtggctgcgt gaaagccttg aggggctccg     780
ggagcgccgg caggaaggaa atgggcgggg agggccttcg tgcgtcgccg cgccgccgtc     840
cccttctccc tctccagcct cggggctgtc cgcggggggga cggctgcctt cggggggggac     900 ggggcagggc ggggttcggc ttctggcgtg tgaccggcgg ctctagagcc tctgctaacc     960
atgttcatgc cttcttcttt ttcctacagc tcctgggcaa cgtgctggtt attgtgctgt    1020
ctcatcattt tggcaaagaa ttgcggccca acggtaccgg atccaccggc cgccaccatg    1080
ggaagcccaa agaagaagcg taaggtaatg gtgagcaagg gcgaggagct gttcaccggg    1140
gtggtgccca tcctggtcga gctggacggc gacgtaaacg gccacaagtt cagcgtgtcc    1200
ggcgagggcg agggcgatgc cacctacggc aagctgaccc tgaagttcat ctgcaccacc    1260
ggcaagctgc ccgtgccctg gcccaccctc gtgaccaccc tgacctacgg cgtgtaatgc    1320
ttcagccgct accccgacca catgaagcag cacgacttct tcaagtccgc catgcccgaa    1380
ggctacgtcc aggagcgcac catcttcttc aaggacgacg gcaactacaa gacccgcgcc    1440
gaggtgaagt tcgagggcga caccctggtg aaccgcatcg agctgaaggg catcgacttc    1500
aaggaggacg gcaacatcct ggggcacaag ctggagtaca actacaacag ccacaacgtc    1560
tatatcatgg ccgacaagca gaagaacggc atcaaggtga acttcaagat ccgccacaac    1620
atcgaggacg gcagcgtgca gctcgccgac cactaccagc agaacacccc catcggcgac    1680
```

-continued

```
ggccccgtgc tgctgcccga caaccactac ctgagcaccc agtccgccct gagcaaagac   1740
cccaacgaga agcgcgatca catggtcctg ctggagttcg tgaccgccgc cgggatcact   1800
ctcggcatgg acgagctgta caagggaagc cccaagaaaa agcggaaggt gtaa          1854
```

```
<210> SEQ ID NO 176
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 176
```

```
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtcgag gtgagcccca cgttctgctt cactctcccc atctcccccc cctccccacc    360
cccaattttg tatttattta ttttttaatt attttgtgca gcgatggggg cggggggggg    420
gggggggcgc gcgccaggcg gggcggggcg gggcgagggg cggggcgggg cgaggcggag    480
aggtgcggcg gcagccaatc agagcggcgc gctccgaaag tttcctttta tggcgaggcg    540
gcggcggcgc cggccctata aaaagcgaag cgcgcggcgg gcgggagtcg ctgcgcgctg    600
ccttcgcccc gtgccccgct ccgccgccgc ctcgcgccgc ccgccccggc tctgactgac    660
cgcgttactc ccacaggtga gcgggcggga cggcccttct cctccgggct gtaattagcg    720
cttggtttaa tgacggcttg tttcttttct gtggctgcgt gaaagccttg aggggctccg    780
ggagcgccgg caggaaggaa atgggcgggg agggccttcg tgcgtcgccg cgccgccgtc    840
cccttctccc tctccagcct cggggctgtc cgcggggggga cggctgcctt cgggggggac    900
ggggcagggc ggggttcggc ttctggcgtg tgaccggcgg ctctagagcc tctgctaacc    960
atgttcatgc cttcttcttt ttcctacagc tcctgggcaa cgtgctggtt attgtgctgt   1020
ctcatcattt tggcaaagaa ttgcggccca acggtaccgg atccaccggc cgccaccatg   1080
ggaagcccaa agaagaagcg taaggtaatg gtgagcaagg gcgaggagct gttcaccggg   1140
gtggtgccca tcctggtcga gctggacggc gacgtaaacg gccacaagtt cagcgtgtcc   1200
ggcgagggcg agggcgatgc cacctacggc aagctgaccc tgaagttcat ctgcaccacc   1260
ggcaagctgc ccgtgccctg gcccaccctc gtgaccaccc tgacctacgg cgtgcagtgc   1320
ttcagccgct accccgacca catgaagcag cacgacttct tcaagtccgc catgcccgaa   1380
ggctacgtcc aggagcgcac catcttcttc aaggacgacg gcaactacaa gacccgcgcc   1440
gaggtgaagt tcgagggcga caccctggtg aaccgcatcg agctgaaggg catcgacttc   1500
aaggaggacg gcaacatcct ggggcacaag ctggagtaca actacaacag ccacaacgtc   1560
tatatcatgg ccgacaagca gaagaacggc atcaaggtga acttcaagat ccgccacaac   1620
atcgaggacg gcagcgtgca gctcgccgac cactaccagc agaacacccc catcggcgac   1680
ggccccgtgc tgctgcccga caaccactac ctgagcaccc agtccgccct gagcaaagac   1740
cccaacgaga agcgcgatca catggtcctg ctggagttcg tgaccgccgc cgggatcact   1800
ctcggcatgg acgagctgta caagggaagc cccaagaaaa agcggaaggt gtaa          1854
```

-continued

<210> SEQ ID NO 177
<211> LENGTH: 1981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
ggctccggtg cccgtcagtg ggcagagcgc acatcgccca cagtccccga gaagttgggg        60
ggaggggtcg gcaattgaac cggtgcctag agaaggtggc gcggggtaaa ctgggaaagt       120
gatgtcgtgt actggctccg ccttttttccc gagggtgggg gagaaccgta tataagtgca      180
ctagtcgccg tgaacgttct ttttcgcaac gggtttgccg ccagaacaca ggtaagtgcc       240
gtgtgtggtt cccgcgggcc tggcctcttt acgggttatg gcccttgcgt gccttgaatt       300
acttccacct ggctgcagta cgtgattctt gatcccgagc ttcgggttgg aagtgggtgg       360
gagagttcgt ggccttgcgc ttaaggagcc ccttcgcctc gtgcttgagt tgtggcctgg       420
cctgggcgct ggggccgccg cgtgcgaatc tggtggcacc ttcgcgcctg tctcgctgct       480
ttcgataagt ctctagccat ttaaaatttt tgatgacctg ctgcgacgct ttttttctgg       540
caagatagtc ttgtaaatgc gggccaagat cagcacactg gtatttcggt ttttggggcc       600
gcgggcggcg acgggccccg tgcgtcccag cgcacatgtt cggcgaggcg gggcctgcga       660
gcgcggccac cgagaatcgg acggggtag tctcaagctg cccggcctgc tctggtgcct        720
ggcctcgcgc cgccgtgtat cgccccgccc tgggcggcaa ggctggcccg gtcggcacca       780
gttgcgtgag cggaaagatg gccgcttccc ggccctgctg cagggagcac aaaatggagg       840
acgcggcgct cgggagagcg ggcgggtgag tcacccacac aaaggaaaag ggcctttccg       900
tcctcagccg tcgcttcatg tgactccacg gagtaccggg cgccgtccag gcacctcgat       960
tagttctcca gcttttggag tacgtcgtct ttaggttggg gggaggggtt ttatgcgatg      1020
gagtttcccc acactgagtg ggtggagact gaagttaggc cagcttggca cttgatgtaa      1080
ttctccttgg aatttgccct ttttgagttt ggatcttggt tcattctcaa gcctcagaca      1140
gtggttcaaa gttttttttct tccatttcag gtgtcgtgag gtaccggatc caccggccgc      1200
caccatggga agcccaaaga agaagcgtaa ggtaatggtg agcaagggcg aggagctgtt      1260 caccgggggtg gtgcccatcc tggtcgagct ggacggcgac gtaaacggcc acaagttcag      1320
cgtgtccggc gagggcgagg gcgatgccac ctacggcaag ctgaccctga agttcatctg      1380
caccaccggc aagctgcccg tgccctggcc caccctcgtg accaccctga cctacggcgt      1440
gcagtgcttc agccgctacc ccgaccacat gaagcagcac gacttcttca gtccgccat       1500 gcccgaaggc tacgtccagg agtgaaccat cttcttcaag gacgacggca actacaagac      1560
ccgcgccgag gtgaagttcg agggcgacac cctggtgaac cgcatcgagc tgaagggcat      1620
cgacttcaag gaggacggca acatcctggg gcacaagctg gagtacaact acaacagcca      1680
caacgtctat atcatggccg acaagcagaa gaacggcatc aaggtgaact tcaagatccg      1740
ccacaacatc gaggacggca gcgtgcagct cgccgaccac taccagcaga caccccccat      1800
cggcgacggc cccgtgctgc tgcccgacaa ccactacctg agcacccagt ccgccctgag      1860
caaagacccc aacgagaagc gcgatcacat ggtcctgctg gagttcgtga ccgccgccgg      1920
gatcactctc ggcatggacg agctgtacaa gggaagcccc aagaaaaagc ggaaggtgta      1980
a                                                                      1981

-continued

```
<210> SEQ ID NO 178
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggtcccatgg tgtaatggtt agcactctgg actctaaatc cagcgatccg agttcaaatc        60
tcggtgggac ct                                                            72

<210> SEQ ID NO 179
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggttccatgg tgtaatggtt agcactctgg actctaaatc cagcgacccg agttcaaatc        60
tcggtgggac ct                                                            72

<210> SEQ ID NO 180
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ggttccatgg tgtaatggtt agcactctgg actctaaatc cagcgatccg agttcaaatc        60
tcggtggaac ct                                                            72

<210> SEQ ID NO 181
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggttccatgg tgtaatggtt agcactctgg actctaaatc cagcgatccg agttcaaatc        60
tcggtgggac ct                                                            72

<210> SEQ ID NO 182
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggttccatgg tgtaatggtg agcactctgg actctaaatc cagcgatccg agttcaaatc        60
tcggtgggac ct                                                            72

<210> SEQ ID NO 183
<211> LENGTH: 72
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggttccatgg tgtaatggct agcactctgg actctaaatc cagcgatccg agttcaaatc      60
tcggtgggat tt                                                         72

<210> SEQ ID NO 184
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ggttccatgg tgtaatggtt agcactctgg actctaaatc cagccataca agttcaaatc      60
tcagtggaac ct                                                         72

<210> SEQ ID NO 185
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggttccttgg tgtaagatga gcactctgga ttctaaatcc agcgatcaga gttcaaatct      60
cggtgggacc t                                                          71

<210> SEQ ID NO 186
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ggtcccatgg tgtaatggtt agcactctgg actctaaatc cagcaatctg agttcaaatc      60
tcggtgggac ct                                                         72

<210> SEQ ID NO 187
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ggccccatgg tgtaatggtt agcactctgg actctaaatc cagcgatccg agttcaaatc      60
tcggtgggac ct                                                         72

<210> SEQ ID NO 188
<211> LENGTH: 72
<212> TYPE: DNA
<213> ORGANISM: Artificial Sequence
<220> FEATURE:
<223> OTHER INFORMATION: Description of Artificial Sequence: Synthetic
```

-continued

```
          oligonucleotide

<400> SEQUENCE: 188
ggtctcatgg tgtaatggtt agcacactgg actctaagtc cagcaatccg agttcgagtc        60
ttggtgagac ca                                                            72

<210> SEQ ID NO 189
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ggacccatgg tgtaatggtt agcactctgg actctaaatc cagcaatcca agttcaaatc        60
tcggtgggac ct                                                            72

<210> SEQ ID NO 190
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gtttccatgg tgtaatggtt ggcactctgg actctaaatc cagcaatcca agttcaagtc        60
tctgtgggac ct                                                            72

<210> SEQ ID NO 191
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ctgcaaagtt ctttgaaaga gcaacaaaat ggcttcaact atctgagtga c                51

<210> SEQ ID NO 192
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ctgcaaagtt ctttgaaaga gcaataaaat ggcttcaact atctgagtga c                51

<210> SEQ ID NO 193
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctgagacctc taagagcctt atctcgattt gaagggatga gggtggttgt g                51

<210> SEQ ID NO 194
```

<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
acaagccttt tcagctttag agggcgagca aaggatgtgg gatctgagaa c          51

<210> SEQ ID NO 195
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ctaatagaaa gaaatgagac cgcccggtgg aaaaatgtga aagtaaactt t          51

<210> SEQ ID NO 196
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gcccggctag ctcagtcggt agagcatggg actctaaatc ccagggtcgt gggttcgagc      60
cccacgttgg gcg                                                        73

<210> SEQ ID NO 197
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gcccggctag ctcagtcggt agagcatgag actctaaatc tcagggtcgt gggttcgagc      60
cccacgttgg gcg                                                        73

<210> SEQ ID NO 198
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gcccagctag ctcagtctgt agagcatgag actctaaatc tcagggtcgt gagttcgagc      60
cccacgttgg gtg                                                        73

<210> SEQ ID NO 199
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199

```
gcccagatag ctcagtgggt agagcatgag actctaaatc tcagggtcat gggttcatgc      60
cccatgttgg gta                                                        73

<210> SEQ ID NO 200
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gtcctgctgg ctcagtcggt acagcatggg actctaaatc ccagggtcgt gggttcgagc      60
tccacgttgg gta                                                        73

<210> SEQ ID NO 201
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gcctggctag ctcagtccat agagcatggg actctaaatc ccagggtcat gggttcgagc      60
cccatattag gca                                                        73

<210> SEQ ID NO 202
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gcccagctag cttagttggt agagcatgag actctaaatc tcagagtcat gggttcaggc      60
ctcatgtttg gca                                                        73

<210> SEQ ID NO 203
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
aacctggcta ggtcagttgg tagatcatga gactctaaat ctcagggtca tgggttcaag      60
ccccatgttg gttt                                                       74

<210> SEQ ID NO 204
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gcccagctag ctcagttggt agagcgtggg actttaaatc ctagggtcgt gggttcgaac      60
cccacgttgg gcg                                                        73
```

```
<210> SEQ ID NO 205
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gcccagctag ctcagtctgt agagcatgag actttaagtc tcagggtcat gggttggagc      60
cccatgttgt gca                                                         73

<210> SEQ ID NO 206
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gcctagctag ttcagtcggt agagcatgag actttaaatc tcaggttcat gagtttgagc      60
cccatgttgg tttggca                                                     77

<210> SEQ ID NO 207
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ccccggctag ctcagtcagt agagcttgag aatttaaatc tcagggtcgt gggttggagc      60
cccacgttgg gcg                                                         73

<210> SEQ ID NO 208
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gcccggctag ctcagtcggt agagcatggg actttaaatc ccagggtcgt gggttcgagc      60
cccacgttgg gcg                                                         73

<210> SEQ ID NO 209
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gcccggctag ctcagtcggt agagcatgag actttaaatc tcagggtcgt gggttcgagc      60
cccacgttgg gcg                                                         73

<210> SEQ ID NO 210
<211> LENGTH: 73
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gcccagctag ctcagtctgt agagcatgag actttaaatc tcagggtcgt gagttcgagc      60
cccacgttgg gtg                                                         73

<210> SEQ ID NO 211
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gcccagatag ctcagtgggt agagcatgag actttaaatc tcagggtcat gggttcatgc      60
cccatgttgg gta                                                         73

<210> SEQ ID NO 212
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gtcctgctgg ctcagtcggt acagcatggg actttaaatc ccagggtcgt gggttcgagc      60
tccacgttgg gta                                                         73

<210> SEQ ID NO 213
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gcctggctag ctcagtccat agagcatggg actttaaatc ccagggtcat gggttcgagc      60
cccatattag gca                                                         73

<210> SEQ ID NO 214
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gcccagctag cttagttggt agagcatgag actttaaatc tcagagtcat gggttcaggc      60
ctcatgtttg gca                                                         73

<210> SEQ ID NO 215
<211> LENGTH: 74
<212> TYPE: DNA
<213> ORGANISM: Artificial Sequence
<220> FEATURE:
<223> OTHER INFORMATION: Description of Artificial Sequence: Synthetic
```

-continued

```
        oligonucleotide

<400> SEQUENCE: 215
aacctggcta ggtcagttgg tagatcatga gactttaaat ctcagggtca tgggttcaag      60
ccccatgttg gttt                                                        74

<210> SEQ ID NO 216
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gcccggatag ctcagtcggt agagcatcag actctaaatc tgagggtcca gggttcaagt      60
ccctgttcgg gcg                                                         73

<210> SEQ ID NO 217
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcctggatag ctcagtcggt agagcatcag actctaaatc tgagggtcca gggttcaagt      60
ccctgttcag gcg                                                         73

<210> SEQ ID NO 218
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gcctggatag ctcaattggt agagcatcag actctaaatc tgagggttca gggttcaagt      60
ccctgttcag gcg                                                         73

<210> SEQ ID NO 219
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gcccagccag ctcagtaggt agagtatgag actctaaatc tcagggtggt gggttcgagc      60
cccatgttgg ggg                                                         73

<210> SEQ ID NO 220
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
```

-continued

```
tgtggtgtag ctcagtcggt agagcatcag actctaaatc tgagggtcca gggttcaggt      60
ccctgttcgg gtgccaaaa                                                    79
```

```
<210> SEQ ID NO 221
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gcccggatag ctcagtcggt agagcatcag actttaaatc tgagggtcca gggttcaagt      60
ccctgttcgg gcg                                                         73
```

```
<210> SEQ ID NO 222
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gcctggatag ctcagtcggt agagcatcag actttaaatc tgagggtcca gggttcaagt      60
ccctgttcag gcg                                                         73
```

```
<210> SEQ ID NO 223
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gcctggatag ctcaattggt agagcatcag actttaaatc tgagggttca gggttcaagt      60
ccctgttcag gcg                                                         73
```

```
<210> SEQ ID NO 224
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcccagccag ctcagtaggt agagtatgag actttaaatc tcagggtggt gggttcgagc      60
cccatgttgg ggg                                                        73
```

```
<210> SEQ ID NO 225
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tgtggtgtag ctcagtcggt agagcatcag actttaaatc tgagggtcca gggttcaggt      60
ccctgttcgg gtgccaaaa                                                    79
```

```
<210> SEQ ID NO 226
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gtagtcgtgg ccgagtggtt aaggcgatgg actctaaatc cattggggtt tccccgcgca        60
ggttcgaatc ctgccgacta cg                                                  82

<210> SEQ ID NO 227
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gtagtcgtgg ccgagtggtt aaggcgatgg actctaaatc cattggggtc tccccgcgca        60
ggttcgaatc ctgccgacta cg                                                  82

<210> SEQ ID NO 228
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtagtcgtgg ccaagtgagt aaggcaatgg actctaaatc cattggggtc tcccagcaca        60
ggttcaaatc ctgctgacta tg                                                  82

<210> SEQ ID NO 229
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gtagtcgtgg ccgagtggtt aaggcgatgg acttcaaatc cattggggtt tccccgcgca        60
ggttcgaatc ctgccgacta cg                                                  82

<210> SEQ ID NO 230
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gtagtcgtgg ccgagtggtt aaggcgatgg acttcaaatc cattggggtc tccccgcgca        60
ggttcgaatc ctgccgacta cg                                                  82

<210> SEQ ID NO 231
<211> LENGTH: 82
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 231
gtagtcgtgg ccaagtgagt aaggcaatgg acttcaaatc cattggggtc tcccagcaca        60
ggttcaaatc ctgctgacta tg                                                 82

<210> SEQ ID NO 232
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gtagtcgtgg ccgagtggtt aaggcgatgg actttaaatc cattggggtt tccccgcgca        60
ggttcgaatc ctgccgacta cg                                                 82

<210> SEQ ID NO 233
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gtagtcgtgg ccgagtggtt aaggcgatgg actttaaatc cattggggtc tccccgcgca        60
ggttcgaatc ctgccgacta cg                                                 82

<210> SEQ ID NO 234
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gtagtcgtgg ccaagtgagt aaggcaatgg actttaaatc cattggggtc tcccagcaca        60
ggttcaaatc ctgctgacta tg                                                 82

<210> SEQ ID NO 235
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gctgtgatgg ccgagtggtt aaggcgttgg actctaaatc caatggggtc tccccgcgca        60
ggttcgaatc ctgctcacag cg                                                 82

<210> SEQ ID NO 236
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 236
gtcacggtgg ccgagtggtt aaggcgttgg actctaaatc caatggggtt tccccgcaca      60
ggttcgaatc ctgttcgtga cg                                             82

<210> SEQ ID NO 237
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gctgtgatgg ccgagtggtt aaggcgttgg actctaaatc caatgggttc ttcccgcgca      60
ggttcaaatc ctgctcacag cg                                             82

<210> SEQ ID NO 238
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gctgtgatgg ccgagtggtt aaggcgttgg acttcaaatc caatggggtc tccccgcgca      60
ggttcgaatc ctgctcacag cg                                             82

<210> SEQ ID NO 239
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gtcacggtgg ccgagtggtt aaggcgttgg acttcaaatc caatggggtt tccccgcaca      60
ggttcgaatc ctgttcgtga cg                                             82

<210> SEQ ID NO 240
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gctgtgatgg ccgagtggtt aaggcgttgg acttcaaatc caatgggttc ttcccgcgca      60
ggttcaaatc ctgctcacag cg                                             82

<210> SEQ ID NO 241
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gctgtgatgg ccgagtggtt aaggcgttgg actttaaatc caatggggtc tccccgcgca      60
ggttcgaatc ctgctcacag cg                                                      82

<210> SEQ ID NO 242
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gtcacggtgg ccgagtggtt aaggcgttgg actttaaatc caatggggtt tccccgcaca      60
ggttcgaatc ctgttcgtga cg                                                      82

<210> SEQ ID NO 243
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gctgtgatgg ccgagtggtt aaggcgttgg actttaaatc caatgggttc ttcccgcgca      60
ggttcaaatc ctgctcacag cg                                                      82

<210> SEQ ID NO 244
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gacgaggtgg ccgagtggtt aaggcgatgg actctaaatc cattgtgctc tgcacgcgtg      60
ggttcgaatc ccaccttcgt cg                                                      82

<210> SEQ ID NO 245
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gacgaggtgg ccgagtggtt aaggcgatgg actctaaatc cattgtgctc tgcacgcatg      60
ggttcgaatc ccatcctcgt cg                                                      82

<210> SEQ ID NO 246
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gacgaggtgg ccgagtggtt aaggcgatgg actctaaatc cattgtgctt tgcacgcgtg      60
ggttcgaatc ccatcctcgt cg                                                      82

-continued

```
<210> SEQ ID NO 247
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gacgaggtgg ccgagtggtt aaggcgatgg actctaaatc cattgtgctc tgcacgcgtg      60
ggttcgaatc ccatcctcgt cg                                               82

<210> SEQ ID NO 248
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gatgaggtgg ccgagtggtt aaggcgatgg actctaaatc cattgtgctc tgcacgcatg      60
ggttcgaatc ccatcctcat cg                                               82

<210> SEQ ID NO 249
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gacgaggtgg ccgagtggtt aaggcgatgg acttcaaatc cattgtgctc tgcacgcgtg      60
ggttcgaatc ccaccttcgt cg                                               82

<210> SEQ ID NO 250
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gacgaggtgg ccgagtggtt aaggcgatgg acttcaaatc cattgtgctc tgcacgcatg      60
ggttcgaatc ccatcctcgt cg                                               82

<210> SEQ ID NO 251
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gacgaggtgg ccgagtggtt aaggcgatgg acttcaaatc cattgtgctt tgcacgcgtg      60
ggttcgaatc ccatcctcgt cg                                               82

<210> SEQ ID NO 252
<211> LENGTH: 82
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 252
gacgaggtgg ccgagtggtt aaggcgatgg acttcaaatc cattgtgctc tgcacgcgtg      60
ggttcgaatc ccatcctcgt cg                                               82

<210> SEQ ID NO 253
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gatgaggtgg ccgagtggtt aaggcgatgg acttcaaatc cattgtgctc tgcacgcatg      60
ggttcgaatc ccatcctcat cg                                               82

<210> SEQ ID NO 254
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gacgaggtgg ccgagtggtt aaggcgatgg actttaaatc cattgtgctc tgcacgcgtg      60
ggttcgaatc ccaccttcgt cg                                               82

<210> SEQ ID NO 255
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gacgaggtgg ccgagtggtt aaggcgatgg actttaaatc cattgtgctc tgcacgcatg      60
ggttcgaatc ccatcctcgt cg                                               82

<210> SEQ ID NO 256
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gacgaggtgg ccgagtggtt aaggcgatgg actttaaatc cattgtgctt tgcacgcgtg      60
ggttcgaatc ccatcctcgt cg                                               82

<210> SEQ ID NO 257
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 257
gacgaggtgg ccgagtggtt aaggcgatgg actttaaatc cattgtgctc tgcacgcgtg      60
ggttcgaatc ccatcctcgt cg                                               82

<210> SEQ ID NO 258
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gatgaggtgg ccgagtggtt aaggcgatgg actttaaatc cattgtgctc tgcacgcatg      60
ggttcgaatc ccatcctcat cg                                               82

<210> SEQ ID NO 259
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gctgaaatag ctcagttggg agagcattag actctagatc taaaggtccc tggtttgatc      60
ccgggtttcg gca                                                        73

<210> SEQ ID NO 260
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gctgaaatag ctcagttggg agagcattag acttcagatc taaaggtccc tggtttgatc      60
ccgggtttcg gca                                                        73

<210> SEQ ID NO 261
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gctgaaatag ctcagttggg agagcattag actttagatc taaaggtccc tggtttgatc      60
ccgggtttcg gca                                                        73

<210> SEQ ID NO 262
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gcagcgatgg ccgagtggtt aaggcgttgg actctaaatc caatggggtc tccccgcgca      60
```

-continued

```
ggttcgaacc ctgctcgctg cg                                              82

<210> SEQ ID NO 263
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gcagcgatgg ccgagtggtt aaggcgttgg acttcaaatc caatggggtc tccccgcgca      60
ggttcgaacc ctgctcgctg cg                                              82

<210> SEQ ID NO 264
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gcagcgatgg ccgagtggtt aaggcgttgg actttaaatc caatggggtc tccccgcgca      60
ggttcgaacc ctgctcgctg cg                                              82

<210> SEQ ID NO 265
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gacctcgtgg cgcaatggta gcgcgtctga ctctagatca gaaggttgcg tgttcaaatc      60
acgtcggggt ca                                                         72

<210> SEQ ID NO 266
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gacctcgtgg cgcaacggta gcgcgtctga ctctagatca gaaggctgcg tgttcgaatc      60
acgtcggggt ca                                                         72

<210> SEQ ID NO 267
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggcctcgtgg cgcaacggta gcgcgtctga ctctagatca gaaggttgcg tgttcaaatc      60
acgtcggggt ca                                                         72

<210> SEQ ID NO 268
```

-continued

<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gacctcgtgg cgcaacggta gcgcgtctga ctctagatca gaaggttgcg tgttcaaatc      60
acgtcggggt ca                                                          72

<210> SEQ ID NO 269
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gacctcgtgg cgcaatggta gcgcgtctga ctctagatca gaaggttgcg tgttcaagtc      60
acgtcggggt ca                                                          72

<210> SEQ ID NO 270
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gacctcgtgg cacaatggta gcacgtctga ctctagatca gaaggttgcg tgttcaaatc      60
acgtcggggt ca                                                          72

<210> SEQ ID NO 271
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gacctcgtgg cgcaatggta gcgcgtctga cttcagatca gaaggttgcg tgttcaaatc      60
acgtcggggt ca                                                          72

<210> SEQ ID NO 272
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gacctcgtgg cgcaacggta gcgcgtctga cttcagatca gaaggctgcg tgttcgaatc      60
acgtcggggt ca                                                          72

<210> SEQ ID NO 273
<211> LENGTH: 72
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 273
ggcctcgtgg cgcaacggta gcgcgtctga cttcagatca gaaggttgcg tgttcaaatc          60
acgtcggggt ca                                                               72

<210> SEQ ID NO 274
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gacctcgtgg cgcaacggta gcgcgtctga cttcagatca gaaggttgcg tgttcaaatc          60
acgtcggggt ca                                                               72

<210> SEQ ID NO 275
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gacctcgtgg cgcaatggta gcgcgtctga cttcagatca gaaggttgcg tgttcaagtc          60
acgtcggggt ca                                                               72

<210> SEQ ID NO 276
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gacctcgtgg cacaatggta gcacgtctga cttcagatca gaaggttgcg tgttcaaatc          60
acgtcggggt ca                                                               72

<210> SEQ ID NO 277
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ccttcgatag ctcagttggt agagcggagg actctagatc cttaggtcgc tggttcgaat          60
ccggctcgaa gga                                                              73

<210> SEQ ID NO 278
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278

```
ccttcgatag ctcagttggt agagcggagg actctagatc cttaggtcgc tggttcgatt      60
ccggctcgaa gga                                                          73

<210> SEQ ID NO 279
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ccttcgatag ctcagctggt agagcggagg actctagatc cttaggtcgc tggttcgatt      60
ccggctcgaa gga                                                          73

<210> SEQ ID NO 280
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccttcgatag ctcagctggt agagcggagg actctagatc cttaggtcgc tggttcgact      60
ccggctcgaa gga                                                          73

<210> SEQ ID NO 281
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ctttcgatag ttcagttggt agagcggagg actctagatc cttaggtcgc tggttcgagt      60
ccggctcgaa gga                                                          73

<210> SEQ ID NO 282
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ccttcgatag ctcagttggt agagcggagg actttagatc cttaggtcgc tggttcgaat      60
ccggctcgaa gga                                                          73

<210> SEQ ID NO 283
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ccttcgatag ctcagttggt agagcggagg actttagatc cttaggtcgc tggttcgatt      60
ccggctcgaa gga                                                          73
```

```
<210> SEQ ID NO 284
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccttcgatag ctcagctggt agagcggagg actttagatc cttaggtcgc tggttcgatt        60
ccggctcgaa gga                                                           73

<210> SEQ ID NO 285
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccttcgatag ctcagctggt agagcggagg actttagatc cttaggtcgc tggttcgact        60
ccggctcgaa gga                                                           73

<210> SEQ ID NO 286
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ctttcgatag ttcagttggt agagcggagg actttagatc cttaggtcgc tggttcgagt        60
ccggctcgaa gga                                                           73

<210> SEQ ID NO 287
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggcctcgtgg cgcaacggta gcgcgtctga cttcagatca gaaggttgcg ggttcaaatc        60
ccgtcggggt ca                                                            72

<210> SEQ ID NO 288
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ggcctcgtgg cgcaacggta gcgcgtctga cttcagatca gaaggttacg ggttcaaatc        60
ccgtcggggt ca                                                            72

<210> SEQ ID NO 289
<211> LENGTH: 72
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggcctcgtgg cgcaacggta gcgcgtctga cttcagatca gaaggttccg ggttcaaatc      60
ccggcggggt ca                                                          72

<210> SEQ ID NO 290
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cgtcggctct gtggcgcaat ggatagcgca ttggacttca aattcaaagg ttgtgggttc      60
gagtcccaga gtcg                                                        74

<210> SEQ ID NO 291
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
cgtcgcccca gtggcctaat ggataaggca ctggccttca aagccaggga ttgtgggttc      60
gagtcccacc tggggtg                                                     77

<210> SEQ ID NO 292
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cgtcggctcc gtggcgcaat ggatagcgca ttggacttca aattcaaagg ttccgggttc      60
gagtcccggc ggagtcg                                                     77

<210> SEQ ID NO 293
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
cgtcgcccca gtggcctaat ggataaggca ttggccttca aagccaggga ttgtgggttc      60
gagtcccatc tggggtg                                                     77

<210> SEQ ID NO 294
<211> LENGTH: 77
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 294
cgtcggctct gtggcgcaat ggatagcgca ttggacttca aattcaaagg ttgtgggttc        60
gaatcccacc agagtcg                                                       77

<210> SEQ ID NO 295
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
cgtcggctct gtggcgcaat ggatagcgca ttggacttca agctgagcct agtgtggtca        60
ttcaaaggtt gtgggttcga gtcccaccag agtcg                                   95

<210> SEQ ID NO 296
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cgtcgccccg gtggcctaat ggataaggca ttggccttca aagccaggga ttgtgggttc        60
gagtcccacc cggggta                                                       77

<210> SEQ ID NO 297
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cgtcggctcc gtggcgcaat ggatagcgca ttggacttca agaggctgaa ggcattcaaa        60
ggttccgggt tcgagtcccg gcggagtcg                                          89

<210> SEQ ID NO 298
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
cgtcggctct gtggcgcaat ggatagcgca ttggacttca agtgacgaat agagcaattc        60
aaaggttgtg ggttcgaatc ccaccagagt cg                                      92

<210> SEQ ID NO 299
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299

```
cgtcggccgc gtggcctaat ggataaggcg tctgacttca gatcagaaga ttgcaggttc         60
gagtcctgcc gcggtcg                                                         77

<210> SEQ ID NO 300
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cgtcgaccgc gtggcctaat ggataaggcg tctgacttca gatcagaaga ttgagggttc         60
gagtcccttc gtggtcg                                                         77

<210> SEQ ID NO 301
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cgtcggctct gtggcgcaat ggatagcgca ttggacttca agatagttag agaaattcaa         60
aggttgtggg ttcgagtccc accagagtcg                                           90

<210> SEQ ID NO 302
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
cgtcggttcc atggtgtaat ggtgagcact ctggactcta aatccagcga tccgagttcg         60
agtctcggtg gaacct                                                          76

<210> SEQ ID NO 303
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cgtcggcccc atggtgtaat ggttagcact ctggactcta aatccagcga tccgagttca         60
aatctcggtg ggacct                                                          76

<210> SEQ ID NO 304
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
cgtcggtccc atggtgtaat ggttagcact ctggactcta aatccagcaa tccgagttcg         60
aatctcggtg ggacct                                                          76
```

-continued

```
<210> SEQ ID NO 305
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
cgtcggtccc atggtgtaat ggttagcact ctggactcta aatccagcga tccgagttca      60
aatctcggtg ggacct                                                       76

<210> SEQ ID NO 306
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
cgtcggcccc atggtgtaat ggtcagcact ctggactcta aatccagcga tccgagttca      60
aatctcggtg ggaccc                                                       76

<210> SEQ ID NO 307
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cgtcggttcc atggtgtaat ggtaagcact ctggactcta aatccagcga tccgagttcg      60
agtctcggtg gaacct                                                       76

<210> SEQ ID NO 308
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
cgtcggttcc atggtgtaat ggttagcact ctggactcta aatccggtaa tccgagttca      60
aatctcggtg gaacct                                                       76

<210> SEQ ID NO 309
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
cgtcggttcc atggtgtaat ggttagcact ctggactcta aatccagcga tccgagttca      60
agtctcggtg gaacct                                                       76

<210> SEQ ID NO 310
<211> LENGTH: 76
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 310
cgtcggttcc atggtgtaat ggtaagcact ctggacttta aatccagcga tccgagttcg      60
agtctcggtg gaacct                                                      76

<210> SEQ ID NO 311
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
cgtcggcccc atggtgtaat ggttagcact ctggacttta aatccagcga tccgagttca      60
aatctcggtg ggacct                                                      76

<210> SEQ ID NO 312
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
cgtcggttcc atggtgtaat ggtgagcact ctggacttta aatccagcga tccgagttcg      60
agtctcggtg gaacct                                                      76

<210> SEQ ID NO 313
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cgtcggttcc atggtgtaat ggttagcact ctggacttta aatccagcga tccgagttca      60
aatctcggtg gaacct                                                      76

<210> SEQ ID NO 314
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
cgtcggtccc atggtgtaat ggttagcact ctggacttta aatccagcga tccgagttca      60
aatctcggtg ggacct                                                      76

<210> SEQ ID NO 315
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 315
cgtcggtccc atggtgtaat ggttagcact ctggacttta aatccagcaa tccgagttcg        60
aatctcggtg ggacct                                                       76

<210> SEQ ID NO 316
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cgtcggttcc atggtgtaat ggttagcact ctggacttta aatccggtaa tccgagttca        60
aatctcggtg gaacct                                                       76

<210> SEQ ID NO 317
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
cgtcggcccc atggtgtaat ggtcagcact ctggacttta aatccagcga tccgagttca        60
aatctcggtg ggaccc                                                       76

<210> SEQ ID NO 318
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
cgtcggttcc atggtgtaat ggttagcact ctggacttta aatccagcga tccgagttca        60
agtctcggtg gaacct                                                       76

<210> SEQ ID NO 319
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
cgtcgacctc gtggcgcaat ggtagcgcgt ctgactctag atcagaaggt tgcgtgttca        60
agtcacgtcg gggtca                                                       76

<210> SEQ ID NO 320
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cgtcgacctc gtggcgcaac ggtagcgcgt ctgactctag atcagaaggt tgcgtgttca        60
```

```
aatcacgtcg gggtca                                                    76

<210> SEQ ID NO 321
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cgtcggcctc gtggcgcaac ggtagcgcgt ctgactctag atcagaaggt tgcgtgttca    60
aatcacgtcg gggtca                                                    76

<210> SEQ ID NO 322
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cgtcgacctc gtggcgcaac ggtagcgcgt ctgactctag atcagaaggc tgcgtgttcg    60
aatcacgtcg gggtca                                                    76

<210> SEQ ID NO 323
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
cgtcgacctc gtggcgcaac ggcagcgcgt ctgactctag atcagaaggt tgcgtgttca    60
aatcacgtcg gggtca                                                    76

<210> SEQ ID NO 324
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
cgtctcccac atggtctagc ggttaggatt cctggttcta acccaggcgg cccgggttcg    60
actcccggtg tgggaa                                                    76

<210> SEQ ID NO 325
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
cgtctcccat atggtctagc ggttaggatt cctggttcta acccaggtgg cccgggttcg    60
actcccggta tgggaa                                                    76
```

```
<210> SEQ ID NO 326
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
cgtctccctg gtggtctagt ggctaggatt cggcgctcta accgccgcgg cccgggttcg      60
attcccggtc agggaa                                                       76

<210> SEQ ID NO 327
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
cgtctccctg gtggtctagt ggttaggatt cggcgctcta accgccgcgg cccgggttcg      60
attcccggtc agggaa                                                       76

<210> SEQ ID NO 328
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cgtctccctg gtctagtggc taggattcgg cgctctaacc gccgcggccc gggttcgatt      60
cccggccagg gaa                                                          73

<210> SEQ ID NO 329
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
cgtctcccac atggtctagc ggttaggatt cctggttcta acccaggcgg cccgggttcg      60
actcccggtg tgggaa                                                       76

<210> SEQ ID NO 330
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
cgtctcccat atggtctagc ggttaggatt cctggttcta acccaggtgg cccgggttcg      60
actcccggta tgggaa                                                       76

<210> SEQ ID NO 331
<211> LENGTH: 76
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 331
cgtctccctg gtggtctagt ggttaggatt cggcgctcta accgccgcgg cccgggttcg      60
attcccggtc agggaa                                                      76

<210> SEQ ID NO 332
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
cgtctccctg gtggtctagt ggttaggatt cggcgctcta accgccgcgg cccgggttcg      60
attcccggtc aggaaa                                                      76

<210> SEQ ID NO 333
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
cgtctccctg gtggtctagt ggctaggatt cggcgctcta accgccgcgg cccgggttcg      60
attcccggcc agggaa                                                      76

<210> SEQ ID NO 334
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ggcctcgtgg cgcaacggta gcgcgtctga cttcagatca gaaggttgcg tgttcaaatc      60
acgtcggggt ca                                                          72

<210> SEQ ID NO 335
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gacctcgtgg cgcaatggta gcgcgtctga cttcagatca gaaggttgcg tgttcaagtc      60
acgtcggggt ca                                                          72

<210> SEQ ID NO 336
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 336
gacctcgtgg cgcaacggta gcgcgtctga cttcagatca gaaggttgcg tgttcaaatc      60
acgtcggggt ca                                                         72

<210> SEQ ID NO 337
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gacctcgtgg cgcaacggta gcgcgtctga cttcagatca gaaggctgcg tgttcgaatc      60
acgtcggggt ca                                                         72

<210> SEQ ID NO 338
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gacctcgtgg cgcaacggca gcgcgtctga cttcagatca gaaggttgcg tgttcaaatc      60
acgtcggggt ca                                                         72

<210> SEQ ID NO 339
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gcgttggtgg tatagtggtt agcatagctg ccttcaaagc agttgacccg ggttcgattc      60
ccggccaacg ca                                                         72

<210> SEQ ID NO 340
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gcgttggtgg tatagtggtg agcatagctg ccttcaaagc agttgacccg ggttcgattc      60
ccggccaacg ca                                                         72

<210> SEQ ID NO 341
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gcgttggtgg tatagtggta agcatagctg ccttcaaagc agttgacccg ggttcgattc      60
```

-continued

```
ccggccaacg ca                                                                72

<210> SEQ ID NO 342
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
ggcctcgtgg cgcaacggta gcgcgtctga cttcagatca gaaggttgcg tgttcaaatc       60
acgtcggggt ca                                                                72

<210> SEQ ID NO 343
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gacctcgtgg cgcaatggta gcgcgtctga cttcagatca gaaggttgcg tgttcaagtc       60
acgtcggggt ca                                                                72

<210> SEQ ID NO 344
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gacctcgtgg cgcaacggta gcgcgtctga cttcagatca gaaggttgcg tgttcaaatc       60
acgtcggggt ca                                                                72

<210> SEQ ID NO 345
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gacctcgtgg cgcaacggta gcgcgtctga cttcagatca gaaggctgcg tgttcgaatc       60
acgtcggggt ca                                                                72

<210> SEQ ID NO 346
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gacctcgtgg cgcaacggca gcgcgtctga cttcagatca gaaggttgcg tgttcaaatc       60
acgtcggggt ca                                                                72

<210> SEQ ID NO 347
```

-continued

```
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ggcctcatgg tgcaacagta gtgtgtctga cttcagatca gaaggttgta tgttcaaatc      60
acgtaggggt ca                                                          72

<210> SEQ ID NO 348
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
ggcctcgtgg cgcaacggta gcgcgtctga ctctagatca gaaggttgcg tgttcaaatc      60
acgtcggggt ca                                                          72

<210> SEQ ID NO 349
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gacctcgtgg cgcaatggta gcgcgtctga ctctagatca gaaggttgcg tgttcaagtc      60
acgtcggggt ca                                                          72

<210> SEQ ID NO 350
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gacctcgtgg cgcaacggta gcgcgtctga ctctagatca gaaggttgcg tgttcaaatc      60
acgtcggggt ca                                                          72

<210> SEQ ID NO 351
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gacctcgtgg cgcaacggta gcgcgtctga ctctagatca gaaggctgcg tgttcgaatc      60
acgtcggggt ca                                                          72

<210> SEQ ID NO 352
<211> LENGTH: 72
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 352
gacctcgtgg cgcaacggca gcgcgtctga ctctagatca gaaggttgcg tgttcaaatc        60
acgtcggggt ca                                                            72

<210> SEQ ID NO 353
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ggcctcatgg tgcaacagta gtgtgtctga ctctagatca gaaggttgta tgttcaaatc        60
acgtaggggt ca                                                            72

<210> SEQ ID NO 354
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gcattggtgg ttcagtggta gaattctcgc cttcaacgcg ggagacccgg gttcaattcc        60
cggccaatgc a                                                             71

<210> SEQ ID NO 355
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gcgccgctgg tgtagtggta tcatgcaaga tttcaattct tgcgacccgg gttcgattcc        60
cgggcggcgc a                                                             71

<210> SEQ ID NO 356
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gcattggtgg ttcaatggta gaattctcgc cttcaacgca ggagacccag gttcgattcc        60
tggccaatgc a                                                             71

<210> SEQ ID NO 357
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357

-continued

```
gcgttggtgg tttagtggta gaattctcgc cttcaatgcg ggagacccgg gttcaattcc      60
cggccactgc a                                                           71

<210> SEQ ID NO 358
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gccttggtgg tgcagtggta gaattctcgc cttcaacgtg ggagacccgg gttcaattcc      60
cggccaatgc a                                                           71

<210> SEQ ID NO 359
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ggtggttcag tggtagaatt ctcgccttca acgcgggaga cccgggttta attcccggtc      60
a                                                                      61

<210> SEQ ID NO 360
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gtggtctagt ggttaggatt cagcgcttca accgccgcag cccgggttcg attcccggtc      60
a                                                                      61

<210> SEQ ID NO 361
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gcgtcagtgg tttagtggtg gaattcctgc cttcaatgca cgagatccgt gttcaactcc      60
tggttggtgc a                                                           71

<210> SEQ ID NO 362
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gcgtcagtgg ttttagtggt ggaattcctg ccttcaatgc acgagatccg tgttcaactc      60
ctggttggtg ca                                                          72
```

-continued

```
<210> SEQ ID NO 363
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gcgttggcag ttcagtggta gaattctcgc cttcaacccg ggagacctgg attccatttc      60
cggcaaatgc a                                                           71

<210> SEQ ID NO 364
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gcatgggtgg ttcagtggta gaattctcgc cttcaacgcg ggaggcccgg gttcgattcc      60
cggcccatgc a                                                           71

<210> SEQ ID NO 365
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gcattggtgg ttcagtggta gaattctcgc cttcaacgcg ggaggcccgg gttcgattcc      60
cggccaatgc a                                                           71

<210> SEQ ID NO 366
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gcattggtgg ttcagtggta gaattctcgc cttcaacgcg ggaggcccgg gtttgattcc      60
cggccagtgc a                                                           71

<210> SEQ ID NO 367
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gcataggtgg ttcagtggta gaattcttgc cttcaacgca ggaggcccag gtttgattcc      60
tggcccatgc a                                                           71

<210> SEQ ID NO 368
<211> LENGTH: 71
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gcattggtgg ttcagtggta gaattctcgc cttcaatgcg ggcggccggg cttcgattcc      60
tggccaatgc a                                                          71

<210> SEQ ID NO 369
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gcatgggtga ttcagtggta gaattttcac cttcaatgca ggaggtccag gttcatttcc      60
tggcctatgc a                                                          71

<210> SEQ ID NO 370
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gcgttggtgg tatagtggtt agcatagctg ccttcaaagc agttgacccg ggttcgattc      60
ccggccaacg ca                                                         72

<210> SEQ ID NO 371
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gcgttggtgg tatagtggtg agcatagctg ccttcaaagc agttgacccg ggttcgattc      60
ccggccaacg ca                                                         72

<210> SEQ ID NO 372
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gcgttggtgg tatagtggta agcatagctg ccttcaaagc agttgacccg ggttcgattc      60
ccggccaacg ca                                                         72

<210> SEQ ID NO 373
<211> LENGTH: 72
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 373
gcgttggtgg tatagtggtg agcatagttg ccttcaaagc agttgacccg ggctcgattc      60
ccgcccaacg ca                                                            72

<210> SEQ ID NO 374
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcgttggtgg tatagtggtg agcatagttg ccttcaaagc agttgacccg ggctcgattc      60
ccggccaacg ca                                                            72

<210> SEQ ID NO 375
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gggccagtgg cgcaatggat aacgcgtctg acttcagatc agaagattcc aggttcgact      60
cctggctggc tcg                                                           73

<210> SEQ ID NO 376
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gggccagtgg cgcaatggat aacgcgtctg acttcagatc agaagattct aggttcgact      60
cctggctggc tcg                                                           73

<210> SEQ ID NO 377
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggccgcgtgg cctaatggat aaggcgtctg atttcagatc agaagattga gggttcgagt      60
cccttcgtgg tcg                                                           73

<210> SEQ ID NO 378
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
```

-continued

```
gacccagtgg cctaatggat aaggcatcag ccttcagagc tggggattgt gggttcgagt      60
cccatctggg tcg                                                          73

<210> SEQ ID NO 379
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gccccagtgg cctaatggat aaggcactgg ccttcaaagc cagggattgt gggttcgagt      60
cccacctggg gta                                                          73

<210> SEQ ID NO 380
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gccccagtgg cctaatggat aaggcactgg ccttcaaagc cagggattgt gggttcgagt      60
cccacctggg gtg                                                          73

<210> SEQ ID NO 381
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gccccggtgg cctaatggat aaggcattgg ccttcaaagc cagggattgt gggttcgagt      60
cccacccggg gta                                                          73

<210> SEQ ID NO 382
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
gccccagtgg cctaatggat aaggcattgg ccttcaaagc cagggattgt gggttcgagt      60
cccatctggg gtg                                                          73

<210> SEQ ID NO 383
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
gccccagtgg cctgatggat aaggtactgg ccttcaaagc cagggattgt gggttcgagt      60
tccacctggg gta                                                          73
```

-continued

```
<210> SEQ ID NO 384
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ggccgcgtgg cctaatggat aaggcgtctg acttcagatc agaagattgc aggttcgagt      60
cctgccgcgg tcg                                                          73

<210> SEQ ID NO 385
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
gaccacgtgg cctaatggat aaggcgtctg acttcagatc agaagattga gggttcgaat      60
ccctccgtgg tta                                                         73

<210> SEQ ID NO 386
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gaccgcgtgg cctaatggat aaggcgtctg acttcagatc agaagattga gggttcgagt      60
cccttcgtgg tcg                                                         73

<210> SEQ ID NO 387
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gaccacgtgg cctaatggat aaggcgtctg acttcagatc agaagattga gggttcgaat      60
cccttcgtgg tta                                                         73

<210> SEQ ID NO 388
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
gaccacgtgg cctaatggat aaggcgtctg acttcagatc agaagattga gggttcgaat      60
cccttcgtgg ttg                                                         73

<210> SEQ ID NO 389
<211> LENGTH: 73
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 389
ggccgtgtgg cctaatggat aaggcgtctg acttcagatc aaaagattgc aggtttgagt      60
tctgccacgg tcg                                                          73

<210> SEQ ID NO 390
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
ggctccgtgg cgcaatggat agcgcattgg acttcaagag gctgaaggca ttcaaaggtt      60
ccgggttcga gtcccggcgg agtcg                                             85

<210> SEQ ID NO 391
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ggctccgtgg cgcaatggat agcgcattgg acttcaaatt caaaggttcc gggttcgagt      60
cccggcggag tcg                                                          73

<210> SEQ ID NO 392
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ggctctgtgg cgcaatggat agcgcattgg acttcaagtg acgaatagag caattcaaag      60
gttgtgggtt cgaatcccac cagagtcg                                          88

<210> SEQ ID NO 393
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
ggctctgtgg cgcaatggat agcgcattgg acttcaaatt caaaggttgt gggttcgaat      60
cccaccagag tcg                                                          73

<210> SEQ ID NO 394
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 394
ggctctgtgg cgcaatggat agcgcattgg acttcaagct gagcctagtg tggtcattca      60
aaggttgtgg gttcgagtcc caccagagtc g                                     91

<210> SEQ ID NO 395
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ggctctgtgg cgcaatggat agcgcattgg acttcaaatt caaaggttgt gggttcgagt      60
cccaccagag tcg                                                         73

<210> SEQ ID NO 396
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
ggctctgtgg cgcaatggat agcgcattgg acttcaagat agttagagaa attcaaaggt      60
tgtgggttcg agtcccacca gagtcg                                           86

<210> SEQ ID NO 397
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gtctctgtgg cgcaatggac gagcgcgctg gacttcaaat ccagaggttc cgggttcgag      60
tcccggcaga gatg                                                        74

<210> SEQ ID NO 398
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
ggctctgtgg cgcaatggat agcgcattgg acttcaagcc taaatcaaga gattcaaagg      60
ttgcgggttc gagtccctcc agagtcg                                          87

<210> SEQ ID NO 399
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ggctctgtgg cgcaatggat agcgcattgg acttcaaatt caaaggttgc gggttcgagt      60

-continued

```
ccctccagag tcg                                                          73

<210> SEQ ID NO 400
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ggcagcatag cagagtggtt caggttacag gttcaagatg taaactgagt tcaaatccca    60
gttctgcca                                                             69

<210> SEQ ID NO 401
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tggtgtaata ggtagcacag agaattctag attctcaggg gtaggttcaa ttcctat       57

<210> SEQ ID NO 402
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
taggacatgg tgtgataggt agcatggaga attctagatt ctcaggggta ggttcaattc    60
ctacagttct ag                                                         72

<210> SEQ ID NO 403
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
taggacgtgg tgtgataggt agcatgggga attctagatt ctcaggggtg ggttcaattc    60
ctatagttct ag                                                         72

<210> SEQ ID NO 404
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
taggacgtgg tgtagtaggt agcatggaga atgctaaatt ctcaggggta ggttcaattc    60
ctatagttct ag                                                         72

<210> SEQ ID NO 405
<211> LENGTH: 72
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
taggacatgg tgtaataggt agaatggaga attctaaatt ctcaggggta ggttcaattc        60
ctatagttct ag                                                            72

<210> SEQ ID NO 406
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
taggatgtgg tgtattaggt agcacagaga attctagatt ctcaggggta ggttcgattc        60
ctataattct ac                                                            72

<210> SEQ ID NO 407
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
taggacttgg tgtaatgggt agcacagaga attctagatt ctcaggggtg ggttcaattc        60
ctttcgtcct ag                                                            72

<210> SEQ ID NO 408
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
tctaggatgt ggtgtgatag gtagcatgga gaattctaga ttctcagggg taggttcaat        60
tcctatattc tagaa                                                         75

<210> SEQ ID NO 409
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
taggacgtgg tgtgataggt agcatggaga attctagatt ctcagggatg ggttcaattc        60
ctatagtcct ag                                                            72

<210> SEQ ID NO 410
<211> LENGTH: 72
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 410
taggacgtgg tgtgataggt agcacggaga attctagatt ctcagggatg ggttcaattc        60
ctgtagttct ag                                                            72

<210> SEQ ID NO 411
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ggttccatgg tgtaatggtt agcactctgg actctaaatc cagcgatccg agttcaaatc        60
tcggtggaac ct                                                            72

<210> SEQ ID NO 412
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ggttccatgg tgtaatggtg accactttgg actctaaata cagtgatcag agttcaagtc        60
tcactggaac ct                                                            72

<210> SEQ ID NO 413
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ggttccatgg tgtaatggtg agggctttgg actctaacta cagtgatcag agttcaagtc        60
tcagtgggac ct                                                            72

<210> SEQ ID NO 414
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ggttccatgg tgtaatggta agcaccctgg actctaaatc cagcaaccag agttccagtc        60
tcagcgtgga cct                                                           73

<210> SEQ ID NO 415
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415

```
ggtagtgtag tctactggtt aaacgcttgg gctctaacat taacgtcctg ggttcaaatc      60
ccagctttgt ca                                                          72

<210> SEQ ID NO 416
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
ggttccatgg tgtaatggtt agcactctgg actctaaatc cagcgatccg agttcaagtc      60
tcggtggaac ct                                                          72

<210> SEQ ID NO 417
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ggttccatgg tgtaatggtg agcactctgg actctaaatc cagcgatccg agttcgagtc      60
tcggtggaac ct                                                          72

<210> SEQ ID NO 418
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ggttccatgg tgtaatggta agcactctgg actctaaatc cagcgatccg agttcgagtc      60
tcggtggaac ct                                                          72

<210> SEQ ID NO 419
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ggttccatgg tgtaatggtt agcactctgg actctaaatc cggtaatccg agttcaaatc      60
tcggtggaac ct                                                          72

<210> SEQ ID NO 420
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
ggccccatgg tgtaatggtc agcactctgg actctaaatc cagcgatccg agttcaaatc      60
tcggtgggac cc                                                          72
```

```
<210> SEQ ID NO 421
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
ggttccatgg tgtaatggta agcactctgg actctaaatc cagccatctg agttcgagtc      60
tctgtggaac ct                                                          72

<210> SEQ ID NO 422
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ggttccatgg tgtaatggtg agcactttgg actctaaata cagtgatcag agttcaagtc      60
tcactgggac ct                                                          72

<210> SEQ ID NO 423
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
ggttccatgg gttaatggtg agcaccctgg actctaaatc aagcgatccg agttcaaatc      60
tcggtggtac ct                                                          72

<210> SEQ ID NO 424
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gtttccatgg tgtaatggtg agcactctgg actctaaatc cagaaataca ttcaaagaat      60
taagaaca                                                              68

<210> SEQ ID NO 425
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
ggtcccatgg tgtaatggtt agcactctgg actctaaatc cagcgatccg agttcaaatc      60
tcggtgggac ct                                                          72

<210> SEQ ID NO 426
<211> LENGTH: 72
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 426
ggtcccatgg tgtaatggtt agcactctgg actctaaatc cagcaatccg agttcgaatc     60
tcggtgggac ct                                                        72

<210> SEQ ID NO 427
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ggccccatgg tgtaatggtt agcactctgg actctaaatc cagcgatccg agttcaaatc     60
tcggtgggac ct                                                        72

<210> SEQ ID NO 428
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
ggtcccatgg tgtaatggtt agcactctgg gctctaaatc cagcaatccg agttcgaatc     60
ttggtgggac ct                                                        72

<210> SEQ ID NO 429
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ggctgtgtac ctcagtgggc aagggtatgg actctaaagc cagactattt gggttcaaat     60
cccagcttgg cct                                                       73

<210> SEQ ID NO 430
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gaccatgtgg cctaagggaa aagacatctc actctaggtc agaagattga gggttcaagt     60
cctttcatgg tca                                                       73

<210> SEQ ID NO 431
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 431
ggtacagtgt taaaggggag aaaaattgct gactctaaat acagtagacc taggtttgaa      60
tcctggcttt acca                                                        74

<210> SEQ ID NO 432
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
tggtgtaata ggtagcacag agaattttag attctcaggg gtaggttcaa ttcctat       57

<210> SEQ ID NO 433
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
taggacatgg tgtgataggt agcatggaga attttagatt ctcaggggta ggttcaattc      60
ctacagttct ag                                                          72

<210> SEQ ID NO 434
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
taggacgtgg tgtgataggt agcatgggga attttagatt ctcaggggtg ggttcaattc      60
ctatagttct ag                                                          72

<210> SEQ ID NO 435
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
taggacgtgg tgtagtaggt agcatggaga atgttaaatt ctcaggggta ggttcaattc      60
ctatagttct ag                                                          72

<210> SEQ ID NO 436
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
taggacatgg tgtaataggt agaatggaga attttaaatt ctcaggggta ggttcaattc      60
ctatagttct ag                                                          72
```

```
<210> SEQ ID NO 437
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
taggatgtgg tgtattaggt agcacagaga attttagatt ctcaggggta ggttcgattc      60
ctataattct ac                                                          72

<210> SEQ ID NO 438
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
taggacttgg tgtaatgggt agcacagaga attttagatt ctcaggggtg ggttcaattc      60
ctttcgtcct ag                                                          72

<210> SEQ ID NO 439
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tctaggatgt ggtgtgatag gtagcatgga gaattttaga ttctcagggg taggttcaat      60
tcctatattc tagaa                                                       75

<210> SEQ ID NO 440
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
taggacgtgg tgtgataggt agcatggaga attttagatt ctcagggatg ggttcaattc      60
ctatagtcct ag                                                          72

<210> SEQ ID NO 441
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
taggacgtgg tgtgataggt agcacggaga attttagatt ctcagggatg ggttcaattc      60
ctgtagttct ag                                                          72

<210> SEQ ID NO 442
<211> LENGTH: 72
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ggttccatgg tgtaatggtt agcactctgg actttaaatc cagcgatccg agttcaaatc      60
tcggtggaac ct                                                          72

<210> SEQ ID NO 443
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
ggttccatgg tgtaatggtg accactttgg actttaaata cagtgatcag agttcaagtc      60
tcactggaac ct                                                          72

<210> SEQ ID NO 444
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
ggttccatgg tgtaatggtg agggctttgg actttaacta cagtgatcag agttcaagtc      60
tcagtgggac ct                                                          72

<210> SEQ ID NO 445
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
ggttccatgg tgtaatggta agcaccctgg actttaaatc cagcaaccag agttccagtc      60
tcagcgtgga cct                                                         73

<210> SEQ ID NO 446
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ggtagtgtag tctactggtt aaacgcttgg gctttaacat taacgtcctg ggttcaaatc      60
ccagctttgt ca                                                          72

<210> SEQ ID NO 447
<211> LENGTH: 72
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 447
ggttccatgg tgtaatggtt agcactctgg actttaaatc cagcgatccg agttcaagtc      60
tcggtggaac ct                                                           72

<210> SEQ ID NO 448
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
ggttccatgg tgtaatggtg agcactctgg actttaaatc cagcgatccg agttcgagtc      60
tcggtggaac ct                                                           72

<210> SEQ ID NO 449
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ggttccatgg tgtaatggta agcactctgg actttaaatc cagcgatccg agttcgagtc      60
tcggtggaac ct                                                           72

<210> SEQ ID NO 450
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ggttccatgg tgtaatggtt agcactctgg actttaaatc cggtaatccg agttcaaatc      60
tcggtggaac ct                                                           72

<210> SEQ ID NO 451
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ggccccatgg tgtaatggtc agcactctgg actttaaatc cagcgatccg agttcaaatc      60
tcggtgggac cc                                                           72

<210> SEQ ID NO 452
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
```

```
ggttccatgg tgtaatggta agcactctgg actttaaatc cagccatctg agttcgagtc      60
tctgtggaac ct                                                          72

<210> SEQ ID NO 453
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
ggttccatgg tgtaatggtg agcactttgg actttaaata cagtgatcag agttcaagtc      60
tcactgggac ct                                                          72

<210> SEQ ID NO 454
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
ggttccatgg gttaatggtg agcaccctgg actttaaatc aagcgatccg agttcaaatc      60
tcggtggtac ct                                                          72

<210> SEQ ID NO 455
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
gtttccatgg tgtaatggtg agcactctgg actttaaatc cagaaataca ttcaaagaat      60
taagaaca                                                               68

<210> SEQ ID NO 456
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ggtcccatgg tgtaatggtt agcactctgg actttaaatc cagcgatccg agttcaaatc      60
tcggtgggac ct                                                          72

<210> SEQ ID NO 457
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
ggtcccatgg tgtaatggtt agcactctgg actttaaatc cagcaatccg agttcgaatc      60
tcggtgggac ct                                                          72
```

<210> SEQ ID NO 458
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
ggccccatgg tgtaatggtt agcactctgg actttaaatc cagcgatccg agttcaaatc      60
tcggtgggac ct                                                          72

<210> SEQ ID NO 459
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
ggtcccatgg tgtaatggtt agcactctgg gctttaaatc cagcaatccg agttcgaatc      60
ttggtgggac ct                                                          72

<210> SEQ ID NO 460
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ggctgtgtac ctcagtgggc aagggtatgg actttaaagc cagactattt gggttcaaat      60
cccagcttgg cct                                                         73

<210> SEQ ID NO 461
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
gaccatgtgg cctaagggaa aagacatctc actttaggtc agaagattga gggttcaagt      60
cctttcatgg tca                                                         73

<210> SEQ ID NO 462
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
ggtacagtgt taaaggggag aaaaattgct gactttaaat acagtagacc taggtttgaa      60
tcctggcttt acca                                                        74

<210> SEQ ID NO 463
<211> LENGTH: 72
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 463
tccctggtgg tctagtggtt aggattcggc gctttaaccg ccgcggcccg ggttcgattc      60
ccggtcaggg aa                                                          72

<210> SEQ ID NO 464
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tccctggtgg tctagtggtt aggattcggc gctttaaccg ccgcggcccg ggttcgattc      60
ccggtcagga aa                                                          72

<210> SEQ ID NO 465
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
cccctggtgg tctagtgctt aggattcggt gctttaaccg ctgctgcctg cgttcgattc      60
ccggtcaggg aa                                                          72

<210> SEQ ID NO 466
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tccttgatgt ctagtggtta ggatttggtg ctttaactgc agcagcctgg gttcatttct      60
cagtcaggga a                                                           71

<210> SEQ ID NO 467
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tcccatatgg tctagcggtt aggattcctg gttttaaccc aggtggcccg ggttcgactc      60
ccggtatggg aa                                                          72

<210> SEQ ID NO 468
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 468
tccgtggtgg tctagtggct aggattcggc gctttaaccg cctgcagctc gagttcgatt      60
cctggtcagg gaa                                                        73

<210> SEQ ID NO 469
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ccctgtggtc tagtggctaa gactttgtgc tttaattgct gcatcctagg ttcaattccc      60
agtcaggga                                                            69

<210> SEQ ID NO 470
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tcccacatgg tctagcggtt aggattcctg gttttaaccc aggcggcccg ggttcgactc      60
ccggtgtggg aa                                                        72

<210> SEQ ID NO 471
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tccctggtgg tctagtggct aggattcggc gctttaaccg ccgcggcccg ggttcgattc      60
ccggccaggg aa                                                        72

<210> SEQ ID NO 472
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tccctggtgg tctagtggct aggattcggc gctttaaccg ccgcggcccg ggttcgattc      60
ccggtcaggg aa                                                        72

<210> SEQ ID NO 473
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gcgttggtgg tgtagtggtg agcacagctg cctttaaagc agttaacgcg ggttcgattc      60

-continued

```
ccgggtaacg aa                                                              72

<210> SEQ ID NO 474
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
tccttggtgg tctagtggct aggattcggt gctttaacct gtgcggcccg ggttcaattc         60
ccgatgaagg aa                                                              72

<210> SEQ ID NO 475
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tgtctggtgg tcaagtggct aggatttggc gctttaactg ccgcggcccg cgttcgattc         60
ccggtcaggg aa                                                              72

<210> SEQ ID NO 476
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tccctggtgg tctagtggct aggattcggc gctttaaccg cctgcagctc gagttcgatt         60
cctggtcagg gaa                                                             73

<210> SEQ ID NO 477
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gcaatggtgg ttcagtggta gaattctcgc ctttaacaca ggagacccgg gttcaattcc         60
tgacccatgt a                                                               71

<210> SEQ ID NO 478
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tccctggtgg tctagtggtt aggattcggc gctctaaccg ccgcggcccg ggttcgattc         60
ccggtcaggg aa                                                              72
```

-continued

```
<210> SEQ ID NO 479
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
tccctggtgg tctagtggtt aggattcggc gctctaaccg ccgcggcccg ggttcgattc      60
ccggtcagga aa                                                          72

<210> SEQ ID NO 480
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
cccctggtgg tctagtgctt aggattcggt gctctaaccg ctgctgcctg cgttcgattc      60
ccggtcaggg aa                                                          72

<210> SEQ ID NO 481
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tccttgatgt ctagtggtta ggatttggtg ctctaactgc agcagcctgg gttcatttct      60
cagtcaggga a                                                           71

<210> SEQ ID NO 482
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
tcccatatgg tctagcggtt aggattcctg gttctaaccc aggtggcccg ggttcgactc      60
ccggtatggg aa                                                          72

<210> SEQ ID NO 483
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tccgtggtgg tctagtggct aggattcggc gctctaaccg cctgcagctc gagttcgatt      60
cctggtcagg gaa                                                         73

<210> SEQ ID NO 484
<211> LENGTH: 69
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 484
ccctgtggtc tagtggctaa gactttgtgc tctaattgct gcatcctagg ttcaattccc      60
agtcaggga                                                              69

<210> SEQ ID NO 485
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
tcccacatgg tctagcggtt aggattcctg gttctaaccc aggcggcccg ggttcgactc      60
ccggtgtggg aa                                                          72

<210> SEQ ID NO 486
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
tccctggtgg tctagtggct aggattcggc gctctaaccg ccgcggcccg ggttcgattc      60
ccggccaggg aa                                                          72

<210> SEQ ID NO 487
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tccctggtgg tctagtggct aggattcggc gctctaaccg ccgcggcccg ggttcgattc      60
ccggtcaggg aa                                                          72

<210> SEQ ID NO 488
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gcgttggtgg tgtagtggtg agcacagctg cctctaaagc agttaacgcg ggttcgattc      60
ccgggtaacg aa                                                          72

<210> SEQ ID NO 489
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 489
tccttggtgg tctagtggct aggattcggt gctctaacct gtgcggcccg ggttcaattc      60
ccgatgaagg aa                                                         72

<210> SEQ ID NO 490
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
tgtctggtgg tcaagtggct aggatttggc gctctaactg ccgcggcccg cgttcgattc      60
ccggtcaggg aa                                                         72

<210> SEQ ID NO 491
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tccctggtgg tctagtggct aggattcggc gctctaaccg cctgcagctc gagttcgatt      60
cctggtcagg gaa                                                        73

<210> SEQ ID NO 492
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
gcaatggtgg ttcagtggta gaattctcgc ctctaacaca ggagacccgg gttcaattcc      60
tgacccatgt a                                                          71

<210> SEQ ID NO 493
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
ccttcaatag ttcagctggt agagcagagg actttagcta cttcctcagt aggagacgtc      60
cttaggttgc tggttcgatt ccagcttgaa gga                                  93

<210> SEQ ID NO 494
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
ccttcaatag ttcagctggt agagcagagg actttaggtc cttaggttgc tggttcgatt      60
```

-continued

```
ccagcttgaa gga                                                      73

<210> SEQ ID NO 495
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
ggtaaaatgg ctgagtaagc tttagacttt aaatctaaag agagattgag ctctcttttt    60
acca                                                                64

<210> SEQ ID NO 496
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
ggtaaaatga ctgagtaagc attagacttt aaatctaaag acagaggtca agacctcttt    60
ttacca                                                              66

<210> SEQ ID NO 497
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
ggtaaaatgg ctgagtaagc attagacttt aaatctaaag acagaggtca aggcctcttt    60
ttacca                                                              66

<210> SEQ ID NO 498
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
ggtaaaatgg ctgagtaagc attagacttt aaatctaaag acagaggtca aggccttttt    60
acca                                                                64

<210> SEQ ID NO 499
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ccttcgatag ctcagttggt agagcggagg actttagttg gctgtgtcct tagacatcct    60
taggtcgctg gttcgaatcc ggctcgaagg a                                  91

<210> SEQ ID NO 500
```

-continued

```
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ccttcgatag ctcagttggt agagcggagg actttagatc cttaggtcgc tggttcgaat      60
ccggctcgaa gga                                                         73

<210> SEQ ID NO 501
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
gggggtatag ctcagggcta gagctttttg actttagagc aagaggtccc tggttcaaat      60
ccaggttctc cct                                                         73

<210> SEQ ID NO 502
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
tatagctcag tggtagagca tttaacttta gatcaagagg tccctggatc aactctgggt      60
g                                                                      61

<210> SEQ ID NO 503
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gtcagtgttg cacaacggtt aagtgaagag gctttaaacc cagactggat gggttcaatt      60
cccatctctg ccg                                                         73

<210> SEQ ID NO 504
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ccttcgatag ctcagttggt agagcggagg actttagtgg atagggcgtg gcaatcctta      60
ggtcgctggt tcgattccgg ctcgaagga                                        89

<210> SEQ ID NO 505
<211> LENGTH: 73
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 505
ccttcgatag ctcagttggt agagcggagg actttagatc cttaggtcgc tggttcgatt       60
ccggctcgaa gga                                                          73

<210> SEQ ID NO 506
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
ccttcgatag ctcagttggt agagcggagg actttaggct cattaagcaa ggtatcctta       60
ggtcgctggt tcgaatccgg ctcggagga                                         89

<210> SEQ ID NO 507
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ccttcgatag ctcagttggt agagcggagg actttagatc cttaggtcgc tggttcgaat       60
ccggctcgga gga                                                          73

<210> SEQ ID NO 508
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ccttcgatag ctcagctggt agagcggagg actttagatt gtatagacat ttgcggacat       60
ccttaggtcg ctggttcgat tccagctcga agga                                   94

<210> SEQ ID NO 509
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
ccttcgatag ctcagctggt agagcggagg actttagatc cttaggtcgc tggttcgatt       60
ccagctcgaa gga                                                          73

<210> SEQ ID NO 510
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510

```
ccttcgatag ctcagctggt agagcggagg actttagcta cttcctcagc aggagacatc        60
cttaggtcgc tggttcgatt ccggctcgaa gga                                      93

<210> SEQ ID NO 511
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
ccttcgatag ctcagctggt agagcggagg actttagatc cttaggtcgc tggttcgatt        60
ccggctcgaa gga                                                            73

<210> SEQ ID NO 512
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
ccttcgatag ctcagctggt agagcggagg actttaggcg cgcgcccgtg gccatcctta        60
ggtcgctggt tcgattccgg ctcgaagga                                          89

<210> SEQ ID NO 513
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
ccttcgatag ctcagctggt agagcggagg actttagatc cttaggtcgc tggttcgatt        60
ccggctcgaa gga                                                            73

<210> SEQ ID NO 514
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
ccttcgatag ctcagctggt agagcggagg actttagcct gtagaaacat ttgtggacat        60
ccttaggtcg ctggttcgat tccggctcga agga                                    94

<210> SEQ ID NO 515
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
ccttcgatag ctcagctggt agagcggagg actttagatc cttaggtcgc tggttcgatt        60
ccggctcgaa gga                                                            73
```

-continued

<210> SEQ ID NO 516
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ccttcgatag ctcagctggt agagcggagg actttagatt gtacagacat ttgcggacat      60
ccttaggtcg ctggttcgat tccggctcga agga                                 94

<210> SEQ ID NO 517
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
ccttcgatag ctcagctggt agagcggagg actttagatc cttaggtcgc tggttcgatt      60
ccggctcgaa gga                                                        73

<210> SEQ ID NO 518
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ccttcgatag ctcagctggt agagcggagg actttagtac ttaatgtgtg gtcatcctta      60
ggtcgctggt tcgattccgg ctcgaagga                                       89

<210> SEQ ID NO 519
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
ccttcgatag ctcagctggt agagcggagg actttagatc cttaggtcgc tggttcgatt      60
ccggctcgaa gga                                                        73

<210> SEQ ID NO 520
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ccttcgatag ctcagctggt agagcggagg actttagggg tttgaatgtg gtcatcctta      60
ggtcgctggt tcgaatccgg ctcggagga                                       89

<210> SEQ ID NO 521
<211> LENGTH: 73

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
ccttcgatag ctcagctggt agagcggagg actttagatc cttaggtcgc tggttcgaat        60
ccggctcgga gga                                                           73

<210> SEQ ID NO 522
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ccttcgatag ctcagctggt agagcggagg actttagact gcggaaacgt ttgtggacat        60
ccttaggtcg ctggttcaat tccggctcga agga                                    94

<210> SEQ ID NO 523
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
ccttcgatag ctcagctggt agagcggagg actttagatc cttaggtcgc tggttcaatt        60
ccggctcgaa gga                                                           73

<210> SEQ ID NO 524
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ctttcgatag ctcagttggt agagcggagg actttaggtt cattaaacta aggcatcctt        60
aggtcgctgg ttcgaatccg gctcgaagga                                         90

<210> SEQ ID NO 525
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ctttcgatag ctcagttggt agagcggagg actttagatc cttaggtcgc tggttcgaat        60
ccggctcgaa gga                                                           73

<210> SEQ ID NO 526
<211> LENGTH: 88
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 526
tcttcaatag ctcagctggt agagcggagg actttaggtg cacgcccgtg gccattctta      60
ggtgctggtt tgattccgac ttggagag                                         88

<210> SEQ ID NO 527
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcttcaatag ctcagctggt agagcggagg actttagatt cttaggtgct ggtttgattc      60
cgacttggag ag                                                          72

<210> SEQ ID NO 528
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
ggtaaaatgg ctgagtgaag cattggactt taaatctaaa gacaggggtt aagcctcttt      60
ttacca                                                                 66

<210> SEQ ID NO 529
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
ggtaaaatgg ctgagcaagc attggacttt aaatctaaag acagatgttg agccatcttt      60
ttagca                                                                 66

<210> SEQ ID NO 530
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ggtaaaatgg ctgagtgaag cattggactt taaatctaaa gacaggggct aagcctcttt      60
ttacca                                                                 66

<210> SEQ ID NO 531
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531

-continued

```
ggtaaaatgg ctgagcaagc attagacttt aaatctaaag acagaggtta aggcctcttt      60
ttacca                                                                  66
```

```
<210> SEQ ID NO 532
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
ggtaaaatgg ctgagtaagc attagacttt aaatctaaag acagaggtca aggcctcttt      60
tttcct                                                                  66
```

```
<210> SEQ ID NO 533
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
ggtaaaatgg ctgagcaagc attagacttt aaatctgaaa acagaggtca aaggtctctt      60
tttacca                                                                 67
```

```
<210> SEQ ID NO 534
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ggtaaaatgg ctgagtaagc attagacttt aaatctaaag acagaggtca aggcctcttt      60
ttacca                                                                  66
```

```
<210> SEQ ID NO 535
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
ggtaaaatga ctgaataagc cttagacttt aaatctgaag acagaggtca aggcctcttt      60
ttacca                                                                  66
```

```
<210> SEQ ID NO 536
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
ggtaaaatgg ctgagtaagc attggacttt aaatctaaag acagaggtca agacctcttt      60
ttacca                                                                  66
```

<210> SEQ ID NO 537
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ggtaaaatgg ctgagtaaag cattagactt taaatctaag gacagaggct aaacctcttt        60
ttacca                                                                     66

<210> SEQ ID NO 538
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ccttcaatag ttcagctggt agagcagagg actctagcta cttcctcagt aggagacgtc        60
cttaggttgc tggttcgatt ccagcttgaa gga                                      93

<210> SEQ ID NO 539
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ccttcaatag ttcagctggt agagcagagg actctaggtc cttaggttgc tggttcgatt        60
ccagcttgaa gga                                                             73

<210> SEQ ID NO 540
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ggtaaaatgg ctgagtaagc tttagactct aaatctaaag agagattgag ctctcttttt        60
acca                                                                       64

<210> SEQ ID NO 541
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
ggtaaaatga ctgagtaagc attagactct aaatctaaag acagaggtca agacctcttt        60
ttacca                                                                     66

<210> SEQ ID NO 542
<211> LENGTH: 66
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 542
ggtaaaatgg ctgagtaagc attagactct aaatctaaag acagaggtca aggcctcttt      60
ttacca                                                               66

<210> SEQ ID NO 543
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ggtaaaatgg ctgagtaagc attagactct aaatctaaag acagaggtca aggccttttt      60
acca                                                                 64

<210> SEQ ID NO 544
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ccttcgatag ctcagttggt agagcggagg actctagttg gctgtgtcct tagacatcct      60
taggtcgctg gttcgaatcc ggctcgaagg a                                   91

<210> SEQ ID NO 545
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
ccttcgatag ctcagttggt agagcggagg actctagatc cttaggtcgc tggttcgaat      60
ccggctcgaa gga                                                       73

<210> SEQ ID NO 546
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
gggggtatag ctcagggcta gagctttttg actctagagc aagaggtccc tggttcaaat      60
ccaggttctc cct                                                       73

<210> SEQ ID NO 547
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 547
tatagctcag tggtagagca tttaactcta gatcaagagg tccctggatc aactctgggt          60
g                                                                          61

<210> SEQ ID NO 548
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gtcagtgttg cacaacggtt aagtgaagag gctctaaacc cagactggat gggttcaatt          60
cccatctctg ccg                                                             73

<210> SEQ ID NO 549
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
ccttcgatag ctcagttggt agagcggagg actctagtgg atagggcgtg gcaatcctta          60
ggtcgctggt tcgattccgg ctcgaagga                                            89

<210> SEQ ID NO 550
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
ccttcgatag ctcagttggt agagcggagg actctagatc cttaggtcgc tggttcgatt          60
ccggctcgaa gga                                                             73

<210> SEQ ID NO 551
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
ccttcgatag ctcagttggt agagcggagg actctaggct cattaagcaa ggtatcctta          60
ggtcgctggt tcgaatccgg ctcggagga                                            89

<210> SEQ ID NO 552
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
ccttcgatag ctcagttggt agagcggagg actctagatc cttaggtcgc tggttcgaat          60

-continued

```
ccggctcgga gga                                                73

<210> SEQ ID NO 553
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
ccttcgatag ctcagctggt agagcggagg actctagatt gtatagacat ttgcggacat    60
ccttaggtcg ctggttcgat tccagctcga agga                                94

<210> SEQ ID NO 554
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ccttcgatag ctcagctggt agagcggagg actctagatc cttaggtcgc tggttcgatt    60
ccagctcgaa gga                                                73

<210> SEQ ID NO 555
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
ccttcgatag ctcagctggt agagcggagg actctagcta cttcctcagc aggagacatc    60
cttaggtcgc tggttcgatt ccggctcgaa gga                                 93

<210> SEQ ID NO 556
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
ccttcgatag ctcagctggt agagcggagg actctagatc cttaggtcgc tggttcgatt    60
ccggctcgaa gga                                                73

<210> SEQ ID NO 557
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
ccttcgatag ctcagctggt agagcggagg actctaggcg cgcgcccgtg gccatcctta    60
ggtcgctggt tcgattccgg ctcgaagga                                      89
```

-continued

```
<210> SEQ ID NO 558
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
ccttcgatag ctcagctggt agagcggagg actctagatc cttaggtcgc tggttcgatt      60
ccggctcgaa gga                                                        73

<210> SEQ ID NO 559
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
ccttcgatag ctcagctggt agagcggagg actctagcct gtagaaacat ttgtggacat      60
ccttaggtcg ctggttcgat tccggctcga agga                                 94

<210> SEQ ID NO 560
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ccttcgatag ctcagctggt agagcggagg actctagatc cttaggtcgc tggttcgatt      60
ccggctcgaa gga                                                        73

<210> SEQ ID NO 561
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
ccttcgatag ctcagctggt agagcggagg actctagatt gtacagacat ttgcggacat      60
ccttaggtcg ctggttcgat tccggctcga agga                                 94

<210> SEQ ID NO 562
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
ccttcgatag ctcagctggt agagcggagg actctagatc cttaggtcgc tggttcgatt      60
ccggctcgaa gga                                                        73

<210> SEQ ID NO 563
<211> LENGTH: 89
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 563
ccttcgatag ctcagctggt agagcggagg actctagtac ttaatgtgtg gtcatcctta     60
ggtcgctggt tcgattccgg ctcgaagga                                       89

<210> SEQ ID NO 564
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
ccttcgatag ctcagctggt agagcggagg actctagatc cttaggtcgc tggttcgatt     60
ccggctcgaa gga                                                        73

<210> SEQ ID NO 565
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ccttcgatag ctcagctggt agagcggagg actctagggg tttgaatgtg gtcatcctta     60
ggtcgctggt tcgaatccgg ctcggagga                                       89

<210> SEQ ID NO 566
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
ccttcgatag ctcagctggt agagcggagg actctagatc cttaggtcgc tggttcgaat     60
ccggctcgga gga                                                        73

<210> SEQ ID NO 567
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
ccttcgatag ctcagctggt agagcggagg actctagact gcggaaacgt ttgtggacat     60
ccttaggtcg ctggttcaat tccggctcga agga                                 94

<210> SEQ ID NO 568
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 568
ccttcgatag ctcagctggt agagcggagg actctagatc cttaggtcgc tggttcaatt      60
ccggctcgaa gga                                                         73

<210> SEQ ID NO 569
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
ctttcgatag ctcagttggt agagcggagg actctaggtt cattaaacta aggcatcctt      60
aggtcgctgg ttcgaatccg gctcgaagga                                       90

<210> SEQ ID NO 570
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
ctttcgatag ctcagttggt agagcggagg actctagatc cttaggtcgc tggttcgaat      60
ccggctcgaa gga                                                         73

<210> SEQ ID NO 571
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
tcttcaatag ctcagctggt agagcggagg actctaggtg cacgcccgtg gccattctta      60
ggtgctggtt tgattccgac ttggagag                                         88

<210> SEQ ID NO 572
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
tcttcaatag ctcagctggt agagcggagg actctagatt cttaggtgct ggtttgattc      60
cgacttggag ag                                                          72

<210> SEQ ID NO 573
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
ggtaaaatgg ctgagtgaag cattggactc taaatctaaa gacaggggtt aagcctcttt      60
```

-continued

```
ttacca                                                              66

<210> SEQ ID NO 574
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
ggtaaaatgg ctgagcaagc attggactct aaatctaaag acagatgttg agccatcttt      60
ttagca                                                              66

<210> SEQ ID NO 575
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
ggtaaaatgg ctgagtgaag cattggactc taaatctaaa gacaggggct aagcctcttt      60
ttacca                                                              66

<210> SEQ ID NO 576
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
ggtaaaatgg ctgagcaagc attagactct aaatctaaag acagaggtta aggcctcttt      60
ttacca                                                              66

<210> SEQ ID NO 577
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ggtaaaatgg ctgagtaagc attagactct aaatctaaag acagaggtca aggcctcttt      60
tttcct                                                              66

<210> SEQ ID NO 578
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
ggtaaaatgg ctgagcaagc attagactct aaatctgaaa acagaggtca aaggtctctt      60
tttacca                                                             67

<210> SEQ ID NO 579
```

```
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
ggtaaaatgg ctgagtaagc attagactct aaatctaaag acagaggtca aggcctcttt      60
ttacca                                                                 66

<210> SEQ ID NO 580
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ggtaaaatga ctgaataagc cttagactct aaatctgaag acagaggtca aggcctcttt      60
ttacca                                                                 66

<210> SEQ ID NO 581
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
ggtaaaatgg ctgagtaagc attggactct aaatctaaag acagaggtca agacctcttt      60
ttacca                                                                 66

<210> SEQ ID NO 582
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
ggtaaaatgg ctgagtaaag cattagactc taaatctaag gacagaggct aaacctcttt      60
ttacca                                                                 66

<210> SEQ ID NO 583
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
gttaagatgg cagagcctgg taattgcatt aaacttaaaa ttttataatc agaggttcaa      60
ctcctcttct taaca                                                       75

<210> SEQ ID NO 584
<211> LENGTH: 75
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 584
gttaagatgg cagagcccgg caattgcatt agacttaaaa ctttataatc agaggttcaa      60
ctcctctcat taaca                                                       75

<210> SEQ ID NO 585
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
ggtagcgtgg ccgagcggtc taaggcgctg gattttagct ccagtctctt cgggggcgtg      60
ggttcaaatc ccaccgctgc ca                                               82

<210> SEQ ID NO 586
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ggtagcgtgg ccgagtggtc taagacgctg gattttagct ccagtctctt cgggggcgtg      60
ggtttgaatc ccaccgctgc ca                                               82

<210> SEQ ID NO 587
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
gggccagtgg ctcaatggat aatgcgtctg actttaaatc agaagattcc agccttgact      60
cctggctggc tca                                                         73

<210> SEQ ID NO 588
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
ggtagggtgg ccgagcggtc taaggcactg tattttaact ccagtctctt cagaggcatg      60
ggtttgaatc ccactgctgc ca                                               82

<210> SEQ ID NO 589
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
```

-continued

```
gccgagcggt ctaaggctcc ggattttagc gccggtgtct tcggaggcat gggttcgaat        60
tccac                                                                      65

<210> SEQ ID NO 590
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 590
gtcaggatgg ccgagtggtc taaggcgcca gactttagct aagcttcctc cgcggtgggg        60
attctggtct ccaatggagg cgtgggttcg aatcccactt ctgaca                      106

<210> SEQ ID NO 591
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
gtcaggatgg ccgagtggtc taaggcgcca gactttagtt ctggtctcca atggaggcgt        60
gggttcgaat cccacttctg aca                                                 83

<210> SEQ ID NO 592
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 592
gtcaggatgg ccgagtggtc taaggcgcca gactttagct tggcttcctc gtgttgagga        60
ttctggtctc caatggaggc gtgggttcga atcccacttc tgaca                       105

<210> SEQ ID NO 593
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
gtcaggatgg ccgagtggtc taaggcgcca gactttagtt ctggtctcca atggaggcgt        60
gggttcgaat cccacttctg aca                                                 83

<210> SEQ ID NO 594
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 594
gtcaggatgg ccgagtggtc taaggcgcca gactttagct tactgcttcc tgtgttcggg        60
tcttctggtc tccgtatgga ggcgtgggtt cgaatcccac ttctgaca                    108
```

-continued

```
<210> SEQ ID NO 595
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
gtcaggatgg ccgagtggtc taaggcgcca gactttagtt ctggtctccg tatggaggcg      60
tgggttcgaa tcccacttct gaca                                            84

<210> SEQ ID NO 596
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 596
gtcaggatgg ccgagtggtc taaggcgcca gactttagtt gctacttccc aggtttgggg      60
cttctggtct ccgcatggag gcgtgggttc gaatcccact tctgaca                  107

<210> SEQ ID NO 597
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
gtcaggatgg ccgagtggtc taaggcgcca gactttagtt ctggtctccg catggaggcg      60
tgggttcgaa tcccacttct gaca                                            84

<210> SEQ ID NO 598
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 598
gtcaggatgg ccgagtggtc taaggcgcca gactttaggt aagcaccttg cctgcgggct      60
ttctggtctc cggatggagg cgtgggttcg aatcccactt ctgaca                   106

<210> SEQ ID NO 599
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
gtcaggatgg ccgagtggtc taaggcgcca gactttagtt tctggtctcc ggatggaggc      60
gtgggttcga atcccacttc tgaca                                           85

<210> SEQ ID NO 600
<211> LENGTH: 74
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
gcctccttag tgcagtaggt agcgcatcag tctttaaatc tgaatggtcc tgagttcaag        60
cctcagaggg ggca                                                          74

<210> SEQ ID NO 601
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
gtcaggatgg ccgagcagtc ttaaggcgct gcgttttaat cgcaccctcc gctggaggcg        60
tgggttcgaa tcccactttt gaca                                               84

<210> SEQ ID NO 602
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
ggttccatgg tgtaatggtg agcactctgg actttaaatc cagaagtagt gctggaacaa        60

<210> SEQ ID NO 603
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
gtcagggtgg ctgagcagtc tgaggggctg cgttttagtc gcagtctgcc ctggaggcgt        60
gggttcgaat cccactcctg aaa                                                83

<210> SEQ ID NO 604
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
accaggatgg ccgagtggtt aaggcgttgg actttagatc caatggacat atgtccgcgt        60
gggttcgaac cccactcctg gta                                                83

<210> SEQ ID NO 605
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
accgggatgg ccgagtggtt aaggcgttgg actttagatc caatgggctg gtgcccgcgt        60
gggttcgaac cccactctcg gta                                               83

<210> SEQ ID NO 606
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
accagaatgg ccgagtggtt aaggcgttgg actttagatc caatggattc atatccgcgt        60
gggttcgaac cccacttctg gta                                               83

<210> SEQ ID NO 607
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
accgggatgg ctgagtggtt aaggcgttgg actttagatc caatggacag gtgtccgcgt        60
gggttcgagc cccactcccg gta                                               83

<210> SEQ ID NO 608
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
actcatttgg ctgagtggtt aaggcattgg actttagatc caatggagta gtggctgtgt        60
gggtttaaac cccactactg gta                                               83

<210> SEQ ID NO 609
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
gagaaagtca tcgtagttac gaagttggct ttaacccagt tttgggaggt tcaattcctt        60
cctttctct                                                              69

<210> SEQ ID NO 610
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
accaggatgg ccaagtagtt aaaggcactg gactttagag ccaatggaca tatgtctgtg        60

```
tgggtttgaa ccccactcct ggtg                                          84

<210> SEQ ID NO 611
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ggtagcgtgg ccgagcggtc taaggcgctg gattttagct ccagtctctt cggaggcgtg       60
ggttcgaatc ccaccgctgc ca                                             82

<210> SEQ ID NO 612
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
ggtagtgtgg ccgagcggtc taaggcgctg gattttagct ccagtctctt cgggggcgtg       60
ggttcgaatc ccaccactgc ca                                             82

<210> SEQ ID NO 613
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ggtagcgtgg ccgagtggtc taaggcgctg gattttagct ccagtcattt cgatggcgtg       60
ggttcgaatc ccaccgctgc ca                                             82

<210> SEQ ID NO 614
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
ggtagtgtgg ttgaatggtc taaggcactg aattttagct ccagtctctt tggggacgtg       60
ggtttaaatc ccactgctgc aa                                             82

<210> SEQ ID NO 615
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
gttaagatgg cagagcctgg taattgcact aaacttaaaa ttttataatc agaggttcaa       60
ctcctcttct taaca                                                    75

<210> SEQ ID NO 616
```

```
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
gttaagatgg cagagcccgg caattgcact agacttaaaa ctttataatc agaggttcaa      60
ctcctctcat taaca                                                       75

<210> SEQ ID NO 617
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ggtagcgtgg ccgagcggtc taaggcgctg gattctagct ccagtctctt cggggggcgtg    60 ggttcaaatc ccaccgctgc ca                                               82

<210> SEQ ID NO 618
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
ggtagcgtgg ccgagtggtc taagacgctg gattctagct ccagtctctt cggggggcgtg    60 ggtttgaatc ccaccgctgc ca                                               82

<210> SEQ ID NO 619
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
gggccagtgg ctcaatggat aatgcgtctg actctaaatc agaagattcc agccttgact      60
cctggctggc tca                                                         73

<210> SEQ ID NO 620
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
ggtagggtgg ccgagcggtc taaggcactg tattctaact ccagtctctt cagaggcatg      60
ggtttgaatc ccactgctgc ca                                               82

<210> SEQ ID NO 621
<211> LENGTH: 65
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 621
gccgagcggt ctaaggctcc ggattctagc gccggtgtct cggaggcat gggttcgaat          60 tccac                                                                     65

<210> SEQ ID NO 622
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 622
gtcaggatgg ccgagtggtc taaggcgcca gactctagct aagcttcctc cgcggtgggg         60
attctggtct ccaatggagg cgtgggttcg aatcccactt ctgaca                       106

<210> SEQ ID NO 623
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
gtcaggatgg ccgagtggtc taaggcgcca gactctagtt ctggtctcca atggaggcgt         60
gggttcgaat cccacttctg aca                                                 83

<210> SEQ ID NO 624
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 624
gtcaggatgg ccgagtggtc taaggcgcca gactctagct tggcttcctc gtgttgagga         60
ttctggtctc caatggaggc gtgggttcga atcccacttc tgaca                        105

<210> SEQ ID NO 625
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
gtcaggatgg ccgagtggtc taaggcgcca gactctagtt ctggtctcca atggaggcgt         60
gggttcgaat cccacttctg aca                                                 83

<210> SEQ ID NO 626
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 626
gtcaggatgg ccgagtggtc taaggcgcca gactctagct tactgcttcc tgtgttcggg          60
tcttctggtc tccgtatgga ggcgtgggtt cgaatcccac ttctgaca                      108

<210> SEQ ID NO 627
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
gtcaggatgg ccgagtggtc taaggcgcca gactctagtt ctggtctccg tatggaggcg          60
tgggttcgaa tcccacttct gaca                                                 84

<210> SEQ ID NO 628
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 628
gtcaggatgg ccgagtggtc taaggcgcca gactctagtt gctacttccc aggtttgggg          60
cttctggtct ccgcatggag gcgtgggttc gaatcccact tctgaca                       107

<210> SEQ ID NO 629
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gtcaggatgg ccgagtggtc taaggcgcca gactctagtt ctggtctccg catggaggcg          60
tgggttcgaa tcccacttct gaca                                                 84

<210> SEQ ID NO 630
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 630
gtcaggatgg ccgagtggtc taaggcgcca gactctaggt aagcaccttg cctgcgggct          60
ttctggtctc cggatggagg cgtgggttcg aatcccactt ctgaca                        106

<210> SEQ ID NO 631
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
gtcaggatgg ccgagtggtc taaggcgcca gactctagtt tctggtctcc ggatggaggc          60
gtgggttcga atcccacttc tgaca                                                85

<210> SEQ ID NO 632
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gcctccttag tgcagtaggt agcgcatcag tctctaaatc tgaatggtcc tgagttcaag      60
cctcagaggg ggca                                                       74

<210> SEQ ID NO 633
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
gtcaggatgg ccgagcagtc ttaaggcgct gcgttctaat cgcaccctcc gctggaggcg      60
tgggttcgaa tcccactttt gaca                                            84

<210> SEQ ID NO 634
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
ggttccatgg tgtaatggtg agcactctgg actctaaatc cagaagtagt gctggaacaa      60

<210> SEQ ID NO 635
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
gtcagggtgg ctgagcagtc tgaggggctg cgttctagtc gcagtctgcc ctggaggcgt      60
gggttcgaat cccactcctg aaa                                             83

<210> SEQ ID NO 636
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
accaggatgg ccgagtggtt aaggcgttgg actctagatc caatggacat atgtccgcgt      60
gggttcgaac cccactcctg gta                                             83

<210> SEQ ID NO 637
<211> LENGTH: 83
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 637
accgggatgg ccgagtggtt aaggcgttgg actctagatc caatgggctg gtgcccgcgt      60
gggttcgaac cccactctcg gta                                              83

<210> SEQ ID NO 638
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
accagaatgg ccgagtggtt aaggcgttgg actctagatc caatggattc atatccgcgt      60
gggttcgaac cccacttctg gta                                              83

<210> SEQ ID NO 639
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
accgggatgg ctgagtggtt aaggcgttgg actctagatc caatggacag gtgtccgcgt      60
gggttcgagc cccactcccg gta                                              83

<210> SEQ ID NO 640
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
actcatttgg ctgagtggtt aaggcattgg actctagatc caatggagta gtggctgtgt      60
gggtttaaac cccactactg gta                                              83

<210> SEQ ID NO 641
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
gagaaagtca tcgtagttac gaagttggct ctaacccagt tttgggaggt tcaattcctt      60
cctttctct                                                              69

<210> SEQ ID NO 642
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 642
accaggatgg ccaagtagtt aaaggcactg gactctagag ccaatggaca tatgtctgtg    60
tgggtttgaa ccccactcct ggtg                                          84

<210> SEQ ID NO 643
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ggtagcgtgg ccgagcggtc taaggcgctg gattctagct ccagtctctt cggaggcgtg    60
ggttcgaatc ccaccgctgc ca                                            82

<210> SEQ ID NO 644
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
ggtagtgtgg ccgagcggtc taaggcgctg gattctagct ccagtctctt cgggggcgtg    60
ggttcgaatc ccaccactgc ca                                            82

<210> SEQ ID NO 645
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ggtagcgtgg ccgagtggtc taaggcgctg gattctagct ccagtcattt cgatggcgtg    60
ggttcgaatc ccaccgctgc ca                                            82

<210> SEQ ID NO 646
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
ggtagtgtgg ttgaatggtc taaggcactg aattctagct ccagtctctt tggggacgtg    60
ggtttaaatc ccactgctgc aa                                            82

<210> SEQ ID NO 647
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
gttaagatgg cagagcctgg taattgcatc aaacttaaaa ttttataatc agaggttcaa    60

-continued ctcctcttct taaca                                                              75

<210> SEQ ID NO 648
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
gttaagatgg cagagcccgg caattgcatc agacttaaaa ctttataatc agaggttcaa        60
ctcctctcat taaca                                                              75

<210> SEQ ID NO 649
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
ggtagcgtgg ccgagcggtc taaggcgctg gatttcagct ccagtctctt cgggggcgtg        60
ggttcaaatc ccaccgctgc ca                                                      82

<210> SEQ ID NO 650
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
ggtagcgtgg ccgagtggtc taagacgctg gatttcagct ccagtctctt cgggggcgtg        60
ggtttgaatc ccaccgctgc ca                                                      82

<210> SEQ ID NO 651
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
gggccagtgg ctcaatggat aatgcgtctg acttcaaatc agaagattcc agccttgact        60
cctggctggc tca                                                                73

<210> SEQ ID NO 652
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ggtagggtgg ccgagcggtc taaggcactg tatttcaact ccagtctctt cagaggcatg        60
ggtttgaatc ccactgctgc ca                                                      82

<210> SEQ ID NO 653

```
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
gccgagcggt ctaaggctcc ggatttcagc gccggtgtct tcggaggcat gggttcgaat      60
tccac                                                                  65

<210> SEQ ID NO 654
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 654
gtcaggatgg ccgagtggtc taaggcgcca gacttcagct aagcttcctc cgcggtgggg      60
attctggtct ccaatggagg cgtgggttcg aatcccactt ctgaca                   106

<210> SEQ ID NO 655
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
gtcaggatgg ccgagtggtc taaggcgcca gacttcagtt ctggtctcca atggaggcgt      60
gggttcgaat cccacttctg aca                                              83

<210> SEQ ID NO 656
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 656
gtcaggatgg ccgagtggtc taaggcgcca gacttcagct tggcttcctc gtgttgagga      60
ttctggtctc caatggaggc gtgggttcga atcccacttc tgaca                    105

<210> SEQ ID NO 657
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
gtcaggatgg ccgagtggtc taaggcgcca gacttcagtt ctggtctcca atggaggcgt      60
gggttcgaat cccacttctg aca                                              83

<210> SEQ ID NO 658
<211> LENGTH: 108
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 658
gtcaggatgg ccgagtggtc taaggcgcca gacttcagct tactgcttcc tgtgttcggg      60
tcttctggtc tccgtatgga ggcgtgggtt cgaatcccac ttctgaca                  108

<210> SEQ ID NO 659
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
gtcaggatgg ccgagtggtc taaggcgcca gacttcagtt ctggtctccg tatggaggcg      60
tgggttcgaa tcccacttct gaca                                             84

<210> SEQ ID NO 660
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 660
gtcaggatgg ccgagtggtc taaggcgcca gacttcagtt gctacttccc aggtttgggg      60
cttctggtct ccgcatggag gcgtgggttc gaatcccact tctgaca                   107

<210> SEQ ID NO 661
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
gtcaggatgg ccgagtggtc taaggcgcca gacttcagtt ctggtctccg catggaggcg      60
tgggttcgaa tcccacttct gaca                                             84

<210> SEQ ID NO 662
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 662
gtcaggatgg ccgagtggtc taaggcgcca gacttcaggt aagcaccttg cctgcgggct      60
ttctggtctc cggatggagg cgtgggttcg aatcccactt ctgaca                    106

<210> SEQ ID NO 663
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663

-continued

```
gtcaggatgg ccgagtggtc taaggcgcca gacttcagtt tctggtctcc ggatggaggc       60
gtgggttcga atcccacttc tgaca                                              85

<210> SEQ ID NO 664
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
gcctccttag tgcagtaggt agcgcatcag tcttcaaatc tgaatggtcc tgagttcaag       60
cctcagaggg ggca                                                         74

<210> SEQ ID NO 665
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
gtcaggatgg ccgagcagtc ttaaggcgct gcgtttcaat cgcaccctcc gctggaggcg       60
tgggttcgaa tcccactttt gaca                                              84

<210> SEQ ID NO 666
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ggttccatgg tgtaatggtg agcactctgg acttcaaatc cagaagtagt gctggaacaa       60

<210> SEQ ID NO 667
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
gtcagggtgg ctgagcagtc tgaggggctg cgtttcagtc gcagtctgcc ctggaggcgt       60
gggttcgaat cccactcctg aaa                                               83

<210> SEQ ID NO 668
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
accaggatgg ccgagtggtt aaggcgttgg acttcagatc caatggacat atgtccgcgt       60
gggttcgaac cccactcctg gta                                               83
```

```
<210> SEQ ID NO 669
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
accgggatgg ccgagtggtt aaggcgttgg acttcagatc caatgggctg gtgcccgcgt      60
gggttcgaac cccactctcg gta                                              83

<210> SEQ ID NO 670
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
accagaatgg ccgagtggtt aaggcgttgg acttcagatc caatggattc atatccgcgt      60
gggttcgaac cccacttctg gta                                              83

<210> SEQ ID NO 671
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
accgggatgg ctgagtggtt aaggcgttgg acttcagatc caatggacag gtgtccgcgt      60
gggttcgagc cccactcccg gta                                              83

<210> SEQ ID NO 672
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
actcatttgg ctgagtggtt aaggcattgg acttcagatc caatggagta gtggctgtgt      60
gggtttaaac cccactactg gta                                              83

<210> SEQ ID NO 673
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
gagaaagtca tcgtagttac gaagttggct tcaacccagt tttgggaggt tcaattcctt      60
cctttctct                                                             69

<210> SEQ ID NO 674
<211> LENGTH: 84
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 674
accaggatgg ccaagtagtt aaaggcactg gacttcagag ccaatggaca tatgtctgtg       60
tgggtttgaa ccccactcct ggtg                                             84

<210> SEQ ID NO 675
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
ggtagcgtgg ccgagcggtc taaggcgctg gatttcagct ccagtctctt cggaggcgtg       60
ggttcgaatc ccaccgctgc ca                                               82

<210> SEQ ID NO 676
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
ggtagtgtgg ccgagcggtc taaggcgctg gatttcagct ccagtctctt cggggcgtg        60 ggttcgaatc ccaccactgc ca                                               82

<210> SEQ ID NO 677
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
ggtagcgtgg ccgagtggtc taaggcgctg gatttcagct ccagtcattt cgatggcgtg       60
ggttcgaatc ccaccgctgc ca                                               82

<210> SEQ ID NO 678
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
ggtagtgtgg ttgaatggtc taaggcactg aatttcagct ccagtctctt tggggacgtg       60
ggtttaaatc ccactgctgc aa                                               82

<210> SEQ ID NO 679
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 679
gagaaggtca cagaggttat gggattggct ttaaaccagt ctgtggggggg ttcgattccc      60 tccttttttca                                                             70

<210> SEQ ID NO 680
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
gagaaggtca tagaggttat gggattggct ttaaaccagt ctctggggggg ttcgattccc      60 tccttttttca                                                             70

<210> SEQ ID NO 681
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
gaaaaagtca taggggttat gaggctggct ttaaaccagc cttaggaggt tcaattcctt      60 ccttttttttg                                                             69

<210> SEQ ID NO 682
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
ggccggttag ctcagttggt tagagcgtgc tgctttaaat gccagggtcg aggtttcgat      60
ccccgtacgg gcct                                                         74

<210> SEQ ID NO 683
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gtagtcgtgg ccgagtggtt aaggcgatgg actttaaatc cattggggtt tccccgcgca      60
ggttcgaatc ctgccgacta cg                                                82

<210> SEQ ID NO 684
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gtagtcgtgg ccgagtggtt aaggcgatgg actttaaatc cattggggtt tccccacgca      60
```

-continued ggttcgaatc ctgccgacta cg                                                82

<210> SEQ ID NO 685
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
gtagtcgtgg ccgagtggtt aaggtgatgg actttaaacc cattggggtc tccccgcgca        60
ggttcgaatc ctgccgacta cg                                                82

<210> SEQ ID NO 686
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
gggtgtatgg ctcaggggta gagaatttga ctttagatca agaggtccct ggttcaaatc        60
caggtgcccc ct                                                           72

<210> SEQ ID NO 687
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
agttgtagct gagtggttaa ggcaacgagc tttaaattcg ttggtttctc tctgtgcagg        60
tttgaatcct gctaatta                                                     78

<210> SEQ ID NO 688
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
caagaaattc atagaggtta tgggattggc tttaaaccag tttcaggagg ttcgattcct        60
tcctttttgg                                                              70

<210> SEQ ID NO 689
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gctgtgatgg ccgagtggtt aaggcgttgg actttaaatc caatggggtc tccccgcgca        60
ggttcgaatc ctgctcacag cg                                                82

<210> SEQ ID NO 690

-continued

```
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
gctgtgatgg ccgagtggtt aaggcgttgg actttaaatc caatggggtc tccccgcgca      60
ggttcaaatc ctgctcacag cg                                                82

<210> SEQ ID NO 691
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
gctgtgatgg ccgagtggtt aaggtgttgg actttaaatc caatgggggt tccccgcgca      60
ggttcaaatc ctgctcacag cg                                                82

<210> SEQ ID NO 692
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
gtcacggtgg ccgagtggtt aaggcgttgg actttaaatc caatggggtt tccccgcaca      60
ggttcgaatc ctgttcgtga cg                                                82

<210> SEQ ID NO 693
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
gacgaggtgg ccgagtggtt aaggcgatgg actttaaatc cattgtgctc tgcacgcgtg      60
ggttcgaatc ccaccctcgt cg                                                82

<210> SEQ ID NO 694
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
gacgaggtgg ccgagtggtt aaggcgatgg actttaaatc cattgtgctc tgcacgcgtg      60
ggttcgaatc ccaccttcgt cg                                                82

<210> SEQ ID NO 695
<211> LENGTH: 74
<212> TYPE: DNA
<213> ORGANISM: Artificial Sequence
<220> FEATURE:
```

449                                                                                                                        450

<223> OTHER INFORMATION: Description of Artificial Sequence: Synthetic
      oligonucleotide

<400> SEQUENCE: 695
ggccggttag ctcagttggt tagagcgtgc tttaactaat gccagggtcg aggtttcgat          60
ccccgtacgg gcct                                                            74

<210> SEQ ID NO 696
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
gacgaggtgg ccgagtggtt aaggcgatgg actttaaatc cattgtgctc tgcacacgtg          60
ggttcgaatc ccatcctcgt cg                                                   82

<210> SEQ ID NO 697
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
gaggcctggc cgagtggtta aggcgatgga ctttaaatcc attgtgctct gcacgcgtgg          60
gttcgaatcc catcctcg                                                        78

<210> SEQ ID NO 698
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
gcagcgatgg ccgagtggtt aaggcgttgg actttaaatc caatggggtc tccccgcgca          60
ggttcgaacc ctgctcgctg cg                                                   82

<210> SEQ ID NO 699
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
gtagtcgtgg ccgagtggtt aaggcgatgg actttaaatc cattggggtt tccccgcgca          60
ggttcgaatc ctgccgacta cg                                                   82

<210> SEQ ID NO 700
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700

```
gtagtcgtgg ccgagtggtt aaggcgatgg actttaaatc cattggggtc tccccgcgca      60
ggttcgaatc ctgccgacta cg                                              82

<210> SEQ ID NO 701
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
gtagtcgtgg ccgagtggtt aaggcgatgg actttaaatc cattggggtt tccccgcgca      60
ggttcgaatc ctgtcggcta cg                                              82

<210> SEQ ID NO 702
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gagaaggtca cagaggttat gggattggct ctaaaccagt ctgtgggggg ttcgattccc      60
tcctttttca                                                            70

<210> SEQ ID NO 703
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
gagaaggtca tagaggttat gggattggct ctaaaccagt ctctgggggg ttcgattccc      60
tcctttttca                                                            70

<210> SEQ ID NO 704
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
gaaaaagtca taggggttat gaggctggct ctaaaccagc cttaggaggt tcaattcctt      60
ccttttttg                                                             69

<210> SEQ ID NO 705
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ggccggttag ctcagttggt tagagcgtgc tgctctaaat gccagggtcg aggtttcgat      60
ccccgtacgg gcct                                                        74
```

```
<210> SEQ ID NO 706
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
gtagtcgtgg ccgagtggtt aaggcgatgg actctaaatc cattggggtt tccccgcgca      60
ggttcgaatc ctgccgacta cg                                              82

<210> SEQ ID NO 707
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
gtagtcgtgg ccgagtggtt aaggcgatgg actctaaatc cattggggtt tccccacgca      60
ggttcgaatc ctgccgacta cg                                              82

<210> SEQ ID NO 708
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
gtagtcgtgg ccgagtggtt aaggtgatgg actctaaacc cattggggtc tccccgcgca      60
ggttcgaatc ctgccgacta cg                                              82

<210> SEQ ID NO 709
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
gggtgtatgg ctcaggggta gagaatttga ctctagatca agaggtccct ggttcaaatc      60
caggtgcccc ct                                                         72

<210> SEQ ID NO 710
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
agttgtagct gagtggttaa ggcaacgagc tctaaattcg ttggtttctc tctgtgcagg      60
tttgaatcct gctaatta                                                   78

<210> SEQ ID NO 711
<211> LENGTH: 70
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
caagaaattc atagaggtta tgggattggc tctaaaccag tttcaggagg ttcgattcct       60
tcctttttgg                                                              70

<210> SEQ ID NO 712
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
gctgtgatgg ccgagtggtt aaggcgttgg actctaaatc caatggggtc tccccgcgca       60
ggttcgaatc ctgctcacag cg                                                82

<210> SEQ ID NO 713
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
gctgtgatgg ccgagtggtt aaggcgttgg actctaaatc caatggggtc tccccgcgca       60
ggttcaaatc ctgctcacag cg                                                82

<210> SEQ ID NO 714
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
gctgtgatgg ccgagtggtt aaggtgttgg actctaaatc caatgggggt tccccgcgca       60
ggttcaaatc ctgctcacag cg                                                82

<210> SEQ ID NO 715
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
gtcacggtgg ccgagtggtt aaggcgttgg actctaaatc caatgggtt tccccgcaca       60 ggttcgaatc ctgttcgtga cg                                                82

<210> SEQ ID NO 716
<211> LENGTH: 82
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 716
gacgaggtgg ccgagtggtt aaggcgatgg actctaaatc cattgtgctc tgcacgcgtg      60
ggttcgaatc ccaccctcgt cg                                               82

<210> SEQ ID NO 717
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
gacgaggtgg ccgagtggtt aaggcgatgg actctaaatc cattgtgctc tgcacgcgtg      60
ggttcgaatc ccaccttcgt cg                                               82

<210> SEQ ID NO 718
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
ggccggttag ctcagttggt tagagcgtgc tctaactaat gccagggtcg aggtttcgat      60
ccccgtacgg gcct                                                        74

<210> SEQ ID NO 719
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
gacgaggtgg ccgagtggtt aaggcgatgg actctaaatc cattgtgctc tgcacacgtg      60
ggttcgaatc ccatcctcgt cg                                               82

<210> SEQ ID NO 720
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
gaggcctggc cgagtggtta aggcgatgga ctctaaatcc attgtgctct gcacgcgtgg      60
gttcgaatcc catcctcg                                                    78

<210> SEQ ID NO 721
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721

-continued

```
gcagcgatgg ccgagtggtt aaggcgttgg actctaaatc caatggggtc tccccgcgca          60
ggttcgaacc ctgctcgctg cg                                                    82

<210> SEQ ID NO 722
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
gtagtcgtgg ccgagtggtt aaggcgatgg actctaaatc cattggggtt tccccgcgca          60
ggttcgaatc ctgccgacta cg                                                    82

<210> SEQ ID NO 723
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
gtagtcgtgg ccgagtggtt aaggcgatgg actctaaatc cattggggtc tccccgcgca          60
ggttcgaatc ctgccgacta cg                                                    82

<210> SEQ ID NO 724
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
gtagtcgtgg ccgagtggtt aaggcgatgg actctaaatc cattggggtt tccccgcgca          60
ggttcgaatc ctgtcggcta cg                                                    82

<210> SEQ ID NO 725
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
gagaaggtca cagaggttat gggattggct tcaaaccagt ctgtgggggg ttcgattccc          60 tccttttttca                                                                 70

<210> SEQ ID NO 726
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
gagaaggtca tagaggttat gggattggct tcaaaccagt ctctgggggg ttcgattccc          60 tccttttttca                                                                 70
```

```
<210> SEQ ID NO 727
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
gaaaaagtca taggggttat gaggctggct tcaaaccagc cttaggaggt tcaattcctt      60
ccttttttg                                                             69

<210> SEQ ID NO 728
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
ggccggttag ctcagttggt tagagcgtgc tgcttcaaat gccagggtcg aggtttcgat      60
ccccgtacgg gcct                                                       74

<210> SEQ ID NO 729
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
gtagtcgtgg ccgagtggtt aaggcgatgg acttcaaatc cattggggtt tccccgcgca      60
ggttcgaatc ctgccgacta cg                                              82

<210> SEQ ID NO 730
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gtagtcgtgg ccgagtggtt aaggcgatgg acttcaaatc cattggggtt tccccacgca      60
ggttcgaatc ctgccgacta cg                                              82

<210> SEQ ID NO 731
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
gtagtcgtgg ccgagtggtt aaggtgatgg acttcaaacc cattgggtc tccccgcgca       60 ggttcgaatc ctgccgacta cg                                              82

<210> SEQ ID NO 732
<211> LENGTH: 72
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 732
gggtgtatgg ctcaggggta gagaatttga cttcagatca agaggtccct ggttcaaatc      60
caggtgcccc ct                                                          72

<210> SEQ ID NO 733
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
agttgtagct gagtggttaa ggcaacgagc ttcaaattcg ttggtttctc tctgtgcagg      60
tttgaatcct gctaatta                                                    78

<210> SEQ ID NO 734
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
caagaaattc atagaggtta tgggattggc ttcaaaccag tttcaggagg ttcgattcct      60
tccttttggg                                                             70

<210> SEQ ID NO 735
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
gctgtgatgg ccgagtggtt aaggcgttgg acttcaaatc caatggggtc tccccgcgca      60
ggttcgaatc ctgctcacag cg                                               82

<210> SEQ ID NO 736
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gctgtgatgg ccgagtggtt aaggcgttgg acttcaaatc caatggggtc tccccgcgca      60
ggttcaaatc ctgctcacag cg                                               82

<210> SEQ ID NO 737
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
gctgtgatgg ccgagtggtt aaggtgttgg acttcaaatc caatgggggt tccccgcgca    60
ggttcaaatc ctgctcacag cg    82

<210> SEQ ID NO 738
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
gtcacggtgg ccgagtggtt aaggcgttgg acttcaaatc caatggggtt tccccgcaca    60
ggttcgaatc ctgttcgtga cg    82

<210> SEQ ID NO 739
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
gacgaggtgg ccgagtggtt aaggcgatgg acttcaaatc cattgtgctc tgcacgcgtg    60
ggttcgaatc ccaccctcgt cg    82

<210> SEQ ID NO 740
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gacgaggtgg ccgagtggtt aaggcgatgg acttcaaatc cattgtgctc tgcacgcgtg    60
ggttcgaatc ccaccttcgt cg    82

<210> SEQ ID NO 741
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
ggccggttag ctcagttggt tagagcgtgc ttcaactaat gccagggtcg aggtttcgat    60
ccccgtacgg gcct    74

<210> SEQ ID NO 742
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
gacgaggtgg ccgagtggtt aaggcgatgg acttcaaatc cattgtgctc tgcacacgtg    60

-continued

```
ggttcgaatc ccatcctcgt cg                                          82

<210> SEQ ID NO 743
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
gaggcctggc cgagtggtta aggcgatgga cttcaaatcc attgtgctct gcacgcgtgg     60
gttcgaatcc catcctcg                                               78

<210> SEQ ID NO 744
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
gcagcgatgg ccgagtggtt aaggcgttgg acttcaaatc caatggggtc tccccgcgca     60
ggttcgaacc ctgctcgctg cg                                          82

<210> SEQ ID NO 745
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
gtagtcgtgg ccgagtggtt aaggcgatgg acttcaaatc cattggggtt tccccgcgca     60
ggttcgaatc ctgccgacta cg                                          82

<210> SEQ ID NO 746
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
gtagtcgtgg ccgagtggtt aaggcgatgg acttcaaatc cattggggtc tccccgcgca     60
ggttcgaatc ctgccgacta cg                                          82

<210> SEQ ID NO 747
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
gtagtcgtgg ccgagtggtt aaggcgatgg acttcaaatc cattggggtt tccccgcgca     60
ggttcgaatc ctgtcggcta cg                                          82
```

-continued

```
<210> SEQ ID NO 748
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gcccagctag ctcagtcggt agagcataag actttaaatc tcagggttgt ggattcgtgc        60
cccatgctgg gtg                                                           73

<210> SEQ ID NO 749
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
ctgcagctag ctcagtcggt agagcatgag actttaaatc tcagggtcat gggttcgtgc        60
cccatgttgg g                                                             71

<210> SEQ ID NO 750
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
ccagcatgtc tcagtcggta tagtgtgaga ctttaaatct cagggtcgtg ggttcaagcc        60
ccacattggg                                                               70

<210> SEQ ID NO 751
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
gtctagctag atcagttggt agagcataag actttaaatc tcagggtcat gggtttgagc        60
cctacgttgg gcg                                                           73

<210> SEQ ID NO 752
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gcccagctag ctcagccggt agagcacaag actttaaatc tcagggtcgt gggtttgagc        60
cctgtgttga gca                                                           73

<210> SEQ ID NO 753
<211> LENGTH: 69
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 753
ccgaatagct tagttgatga agcgtgagac tttaaatctc agggtagtgg gttcaagccc      60
cacattgga                                                              69

<210> SEQ ID NO 754
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
gcctggctac ctcagttggt agagcatggg actttaaatc ccagagtcag tgggttcaag      60
cctcacattg agtg                                                        74

<210> SEQ ID NO 755
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
gcccggctag ctcagtcggt agagcatgag accttaaatc tcagggtcgt gggttcgagc      60
cccacgttgg gcg                                                         73

<210> SEQ ID NO 756
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
gcccggctag ctcagtcggt agagcatggg actttaaatc tcagggtcgt gggttcgagc      60
cccacgttgg gcg                                                         73

<210> SEQ ID NO 757
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
gcccggctag ctcagtcgat agagcatgag actttaaatc tcagggtcgt gggttcgagc      60
cgcacgttgg gcg                                                         73

<210> SEQ ID NO 758
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 758
gcccagctag ctcagtcggt agagcatgag actttaaatc tcagggtcat gggtttgagc      60
cccacgtttg gtg                                                         73

<210> SEQ ID NO 759
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
gcctggctag ctcagtcggc aaagcatgag actttaaatc tcagggtcgt gggctcgagc      60
tccatgttgg gcg                                                         73

<210> SEQ ID NO 760
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gcccgactac ctcagtcggt ggagcatggg actttacatc ccagggttgt gggttcgagc      60
cccacattgg gca                                                         73

<210> SEQ ID NO 761
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
ccccggctgg ctcagtcagt agatcatgag actttaaatc tcagggtcgt gggttcacgc      60
cccacactgg gcg                                                         73

<210> SEQ ID NO 762
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
gcgctagtca gtagagcatg agactttaaa tctcagggtc gtgggttcga gccccacatc      60
gggcg                                                                  65

<210> SEQ ID NO 763
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
gcctggatag ctcagttggt agagcatcag actttaaatc tgagggtcca gggttcaagt      60
```

-continued

```
ccctgttcag gca                                                        73

<210> SEQ ID NO 764
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
gccaggatag ttcaggtggt agagcatcag actttaaacc tgagggttca gggttcaagt      60
ctctgtttgg gcg                                                        73

<210> SEQ ID NO 765
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
acccagatag ctcagtcagt agagcatcag actttaaatc tgagggtcca aggttcatgt      60
ccctttttgg gtg                                                        73

<210> SEQ ID NO 766
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
acctgggtag cttagttggt agagcattgg actttaaatt tgagggccca ggtttcaagt      60
ccctgtttgg gtg                                                        73

<210> SEQ ID NO 767
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
gcctgggtag ctcagtcggt agagctatca gactttaagc ctgaggattc agggttcaat      60
cccttgctgg ggcg                                                       74

<210> SEQ ID NO 768
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
gatagctcag ttgatagagc atcagacttt aaatctgagg gtccagggtt catgtccctg      60
tt                                                                    62

<210> SEQ ID NO 769
```

-continued

```
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
gttggggtaa ctcagttggt agagtagcag actttacatc tgagggtcca gggtttaagt        60
ccatgtccag gca                                                          73

<210> SEQ ID NO 770
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
gcctggatag ctcagttggt agagcatcag actttaaatc tgagggtcca gggttcaagt        60
ccctgttcag gcg                                                          73

<210> SEQ ID NO 771
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
gcctggatag ctcagtcggt agagcatcag actttaaatc tgagggtcca gggttcaagt        60
ccctgttcag gcg                                                          73

<210> SEQ ID NO 772
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
gcccggatag ctcagtcggt agagcatcag actttaaatc tgagggtccg gggttcaagt        60
ccctgttcgg gcg                                                          73

<210> SEQ ID NO 773
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
gcctgggtag ctcagtcggt agagcatcag actttaaatc tgagggtcca gggttcaagt        60
ccctgtccag gcg                                                          73

<210> SEQ ID NO 774
<211> LENGTH: 73
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 774
gcctggatag ctcagttggt agaacatcag actttaaatc tgacggtgca gggttcaagt      60
ccctgttcag gcg                                                         73

<210> SEQ ID NO 775
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
gcccggagag ctcagtgggt agagcatcag actttaaatc tgagggtcca gggttcaagt      60
cctcgttcgg gca                                                         73

<210> SEQ ID NO 776
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
acctgggtag ctcagtaggt agaacatcag actttaaatc tgagggtcta gggttcaagt      60
ccctgtccag gcg                                                         73

<210> SEQ ID NO 777
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
gcctggatag ctccttcggt agagcatcat cagactttaa atgtgagggt ccagggttca      60
agttcctgtt tgggcg                                                      76

<210> SEQ ID NO 778
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
gcccagctag ctcagtcggt agagcataag actctaaatc tcagggttgt ggattcgtgc      60
cccatgctgg gtg                                                         73

<210> SEQ ID NO 779
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779

-continued

```
ctgcagctag ctcagtcggt agagcatgag actctaaatc tcagggtcat gggttcgtgc     60
cccatgttgg g                                                           71

<210> SEQ ID NO 780
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
ccagcatgtc tcagtcggta tagtgtgaga ctctaaatct cagggtcgtg ggttcaagcc     60
ccacattggg                                                             70

<210> SEQ ID NO 781
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
gtctagctag atcagttggt agagcataag actctaaatc tcagggtcat gggtttgagc     60
cctacgttgg gcg                                                         73

<210> SEQ ID NO 782
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
gcccagctag ctcagccggt agagcacaag actctaaatc tcagggtcgt gggtttgagc     60
cctgtgttga gca                                                         73

<210> SEQ ID NO 783
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
ccgaatagct tagttgatga agcgtgagac tctaaatctc agggtagtgg gttcaagccc     60
cacattgga                                                              69

<210> SEQ ID NO 784
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
gcctggctac ctcagttggt agagcatggg actctaaatc ccagagtcag tgggttcaag     60
cctcacattg agtg                                                        74
```

```
<210> SEQ ID NO 785
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
gcccggctag ctcagtcggt agagcatgag accctaaatc tcagggtcgt gggttcgagc      60
cccacgttgg gcg                                                        73

<210> SEQ ID NO 786
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
gcccggctag ctcagtcggt agagcatggg actctaaatc tcagggtcgt gggttcgagc      60
cccacgttgg gcg                                                        73

<210> SEQ ID NO 787
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
gcccggctag ctcagtcgat agagcatgag actctaaatc tcagggtcgt gggttcgagc      60
cgcacgttgg gcg                                                        73

<210> SEQ ID NO 788
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
gcccagctag ctcagtcggt agagcatgag actctaaatc tcagggtcat gggtttgagc      60
cccacgtttg gtg                                                        73

<210> SEQ ID NO 789
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
gcctggctag ctcagtcggc aaagcatgag actctaaatc tcagggtcgt gggctcgagc      60
tccatgttgg gcg                                                        73

<210> SEQ ID NO 790
<211> LENGTH: 73
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
gcccgactac ctcagtcggt ggagcatggg actctacatc ccagggttgt gggttcgagc      60
cccacattgg gca                                                        73

<210> SEQ ID NO 791
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
ccccggctgg ctcagtcagt agatcatgag actctaaatc tcagggtcgt gggttcacgc      60
cccacactgg gcg                                                        73

<210> SEQ ID NO 792
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
gcgctagtca gtagagcatg agactctaaa tctcagggtc gtgggttcga gccccacatc      60
gggcg                                                                65

<210> SEQ ID NO 793
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
gcctggatag ctcagttggt agagcatcag actctaaatc tgagggtcca gggttcaagt      60
ccctgttcag gca                                                        73

<210> SEQ ID NO 794
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
gccaggatag ttcaggtggt agagcatcag actctaaacc tgagggttca gggttcaagt      60
ctctgtttgg gcg                                                        73

<210> SEQ ID NO 795
<211> LENGTH: 73
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 795
acccagatag ctcagtcagt agagcatcag actctaaatc tgagggtcca aggttcatgt    60
cccttttggg gtg    73

<210> SEQ ID NO 796
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
acctgggtag cttagttggt agagcattgg actctaaatt tgagggccca ggtttcaagt    60
ccctgtttgg gtg    73

<210> SEQ ID NO 797
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
gcctgggtag ctcagtcggt agagctatca gactctaagc ctgaggattc agggttcaat    60
cccttgctgg ggcg    74

<210> SEQ ID NO 798
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
gatagctcag ttgatagagc atcagactct aaatctgagg gtccagggtt catgtccctg    60
tt    62

<210> SEQ ID NO 799
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799 gttgggghtaa ctcagttggt agagtagcag actctacatc tgagggtcca gggtttaagt    60
ccatgtccag gca    73

<210> SEQ ID NO 800
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800

-continued

```
gcctggatag ctcagttggt agagcatcag actctaaatc tgagggtcca gggttcaagt          60
ccctgttcag gcg                                                              73

<210> SEQ ID NO 801
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
gcctggatag ctcagtcggt agagcatcag actctaaatc tgagggtcca gggttcaagt          60
ccctgttcag gcg                                                              73

<210> SEQ ID NO 802
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
gcccggatag ctcagtcggt agagcatcag actctaaatc tgagggtccg gggttcaagt          60
ccctgttcgg gcg                                                              73

<210> SEQ ID NO 803
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
gcctgggtag ctcagtcggt agagcatcag actctaaatc tgagggtcca gggttcaagt          60
ccctgtccag gcg                                                              73

<210> SEQ ID NO 804
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
gcctggatag ctcagttggt agaacatcag actctaaatc tgacggtgca gggttcaagt          60
ccctgttcag gcg                                                              73

<210> SEQ ID NO 805
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
gcccggagag ctcagtgggt agagcatcag actctaaatc tgagggtcca gggttcaagt          60
cctcgttcgg gca                                                              73
```

-continued

<210> SEQ ID NO 806
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
acctgggtag ctcagtaggt agaacatcag actctaaatc tgagggtcta gggttcaagt          60
ccctgtccag gcg                                                             73

<210> SEQ ID NO 807
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
gcctggatag ctccttcggt agagcatcat cagactctaa atgtgagggt ccagggttca          60
agttcctgtt tgggcg                                                          76

<210> SEQ ID NO 808
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
ggcagaatgg tgcagcggtt cagcacccag gctcttcagc cagctgttgc ctgggctcaa          60
atcccagctc tgcca                                                           75

<210> SEQ ID NO 809
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 809
ggctgtatag ctcagtggta gagcatttga cttcagaatc ctatactcag gggaaggaga          60
actgggggtt tctcagtggg tcaaaggact tgtagtggta aatcaaaagc aactctataa         120
gctatgtaac aaactttaaa gtcatatgta gctgggttca aatcctgttt ctgcca            176

<210> SEQ ID NO 810
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
ggctgtatag ctcagtggta gagcatttga cttcagcttt aaagtcatat gtagctgggt          60
tcaaatcctg tttctgcca                                                       79

<210> SEQ ID NO 811

-continued

```
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
gggggcatag ctcagtggta gagcatttga cttcagatca agaggtccct ggttcaaatc    60
caggtgcccc ct                                                        72

<210> SEQ ID NO 812
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
gggggtatag ctcaggggta gagcatttga cttcagatca agaggtccct ggttcaaatc    60
caggtgcccc cc                                                        72

<210> SEQ ID NO 813
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
gggggtatag cttagcggta gagcatttga cttcagatca agaggtcccc ggttcaaatc    60
cgggtgcccc ct                                                        72

<210> SEQ ID NO 814
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
gggggtatag cttaggggta gagcatttga cttcagatca aaaggtccct ggttcaaatc    60
caggtgcccc tt                                                        72

<210> SEQ ID NO 815
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
gggggtatag ctcaggggta gagcatttga cttcagatca agaggtcccc agttcaaatc    60
tgggtgcccc ct                                                        72

<210> SEQ ID NO 816
<211> LENGTH: 72
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 816
gggggtatag ctcaggggta gagcatttga cttcagatca agaagtcccc ggttcaaatc      60
cgggtgcccc ct                                                          72

<210> SEQ ID NO 817
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
gggggtatag ctcaggggta gagcatttga cttcagatca agaggtctct ggttcaaatc      60
caggtgcccc ct                                                          72

<210> SEQ ID NO 818
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
gggggtatag ctcaggggta gagcacttga cttcagatca agaagtcctt ggttcaaatc      60
caggtgcccc ct                                                          72

<210> SEQ ID NO 819
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
ggggatatag ctcaggggta gagcatttga cttcagatca agaggtcccc ggttcaaatc      60
cgggtgcccc cc                                                          72

<210> SEQ ID NO 820
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
gggggtatag ttcaggggta gagcatttga cttcagatca agaggtccct ggttcaaatc      60
caggtgcccc ct                                                          72

<210> SEQ ID NO 821
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821

-continued

```
gggggtatag ctcaggggta gagcatttga cttcaaatca agaggtccct gattcaaatc      60
caggtgcccc ct                                                          72

<210> SEQ ID NO 822
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
gggcgtatag ctcaggggta gagcatttga cttcagatca agaggtcccc agttcaaatc      60
tgggtgcccc ct                                                          72

<210> SEQ ID NO 823
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
gggggtatag ctcacaggta gagcatttga cttcagatca agaggtcccc ggttcaaatc      60
tgggtgcccc ct                                                          72

<210> SEQ ID NO 824
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
gggcgtatag ctcaggggta gagcatttga cttcagatca agaggtcccc agttcaaatc      60
tgggtgccca                                                             70

<210> SEQ ID NO 825
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
gggggtatag ctcacaggta gagcatttga cttcagatca agaggtcccc ggttcaaatc      60
cggttactcc ct                                                          72

<210> SEQ ID NO 826
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
gggggtaggg ctcagggata gagcatttga cttcagatca agaggtcccc ggttcgaatc      60
taggtgcccc ct                                                          72
```

```
<210> SEQ ID NO 827
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
ggtatatctc aggggggcaga gcatttgact tcagatcaag aggtccccgg ttgaaatccg        60
ggtgct                                                                   66

<210> SEQ ID NO 828
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
gggggtatag ctcaggggta gagcacttga cttcagatca agaggtccct ggttcaaatc        60
caggtgcccc ct                                                            72

<210> SEQ ID NO 829
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
gggggtatag ctcagtggta gagcatttga cttcagatca agaggtccct ggttcaaatc        60
cgggtgcccc ct                                                            72

<210> SEQ ID NO 830
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
gggggtatag ctcagtgggt agagcatttg acttcagatc aagaggtccc cggttcaaat        60
ccgggtgccc cct                                                           73

<210> SEQ ID NO 831
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
gggggtgtag ctcagtggta gagcatttga cttcagatca agaggtccct ggttcaaatc        60
caggtgcccc ct                                                            72

<210> SEQ ID NO 832
<211> LENGTH: 72
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
gggggtatag ctcaggggta gagcatttga cttcagatca agaggtcccc ggttcaaatc      60
cgggtgcccc ct                                                          72

<210> SEQ ID NO 833
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
gggggtatag ctcaggggta gagcatttga cttcagatca agaggtccct ggttcaaatc      60
caggtgcccc ct                                                          72

<210> SEQ ID NO 834
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
gacctcgtgg cgcaatggta gcgcgtctga cttcagatca gaaggttgcg tgttcaaatc      60
acgtcggggt ca                                                          72

<210> SEQ ID NO 835
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
gacctcgtgg cacaatggta gcacgtctga cttcagatca gaaggttgcg tgttcaaatc      60
acgtcggggt ca                                                          72

<210> SEQ ID NO 836
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 836
gaagcggtgg ctcaatggta gagctttcga cttcaattaa atcttggaaa ttccacggaa      60
taagattgca atcgaagggt tgcaggttca attcctgtcc gtttca                     106

<210> SEQ ID NO 837
<211> LENGTH: 72
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 837
gaagcggtgg ctcaatggta gagctttcga cttcaaatcg aagggttgca ggttcaattc    60
ctgtccgttt ca    72

<210> SEQ ID NO 838
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
ggcctcatgg tgcaacagta gtgtgtctga cttcagatca gaaggttgta tgttcaaatc    60
acatagtggt ca    72

<210> SEQ ID NO 839
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
gacctcgtgg tgaaatggta gcatgtttga cttcaaatca ggaggttgtg tgttcaagtc    60
acatcagggt ca    72

<210> SEQ ID NO 840
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
gaccttgtgg cgcaatggta gcatgtttga cttcaaatca ggaggttgtg tgttcaagtc    60
acatcagggt ca    72

<210> SEQ ID NO 841
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
gacctcgtgg cgcaacggta gcgcgtctga cttcagatca gaaggctgcg tgttcgaatc    60
acgccggggt ca    72

<210> SEQ ID NO 842
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842

-continued

```
gaccttgtgg ctcaatggta gcgcatctga cttcagatca ggaggttgca cgttcaaatc      60
atgccggggt ca                                                           72

<210> SEQ ID NO 843
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
gaccttgtgg cgcaacggta gcgcgtctga cttcagatca gaaggttgcg tgttcaaatc      60
acgtcggggt ca                                                           72

<210> SEQ ID NO 844
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
gacctcgtgg cgcaacggta gcgcgtctga cttcagatca gaaggttgcg tattcaaatc      60
acgtcggggt ca                                                           72

<210> SEQ ID NO 845
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
gacctcgtgg cgcaacggca gcgcgtctga cttcacatta gaaggttgcg tgttcaaatc      60
acgtcggggt ca                                                           72

<210> SEQ ID NO 846
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
gacctcatgg cgcaacggta gcgcgtctga cttcagatca gaaggttgcg tgttcaaatc      60
acatcggggt ca                                                           72

<210> SEQ ID NO 847
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
gacctcgtgg tgcaacggta gcgcgtatga tttcagatca gaaggttgcg tgttcaaatc      60
acgtcggggt ca                                                           72
```

```
<210> SEQ ID NO 848
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
gacctcgtag cgcaacggta gcgcgtctga cttcagatca gaaggttgcg tgttcaaatc      60
acgtcggggt ca                                                          72

<210> SEQ ID NO 849
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
aggggtatag ctcaattggc agagcgtcgg tcttcaaaac cgaaggttgt aggttcgatt      60
cctactgccc ctgcca                                                      76

<210> SEQ ID NO 850
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
gacctcatgg cgcaacggta gcgcgtctga cttcagatca gaaggttgcg tgttcaaatc      60
acgtcggggt ca                                                          72

<210> SEQ ID NO 851
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
gacctcgtgg cgcaacggta gcgcgtctaa cttcagatca gaaggttgcg tgttcaaatc      60
acgtcggggt ca                                                          72

<210> SEQ ID NO 852
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
acgggagtag ctcagttggt agagcaccgg tcttcaaaac cgggtgtcgg gagttcgagc      60
ctctcctccc gtg                                                         73

<210> SEQ ID NO 853
<211> LENGTH: 72
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 853
gacctcgtgg cgcaacggta gcgcgtctga cttcagatca gaaggttgca tgttcaaatc      60
acgtcggggt ca                                                          72

<210> SEQ ID NO 854
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
gactccgtgg cgcaacggta gcgcgtccga cttcagatcg gaaggttgcg tgttcaaatc      60
acgtcggggt ca                                                          72

<210> SEQ ID NO 855
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
gactccgtgg cgcaacggta gcgcgtctga cttcagatca gaaggttgcg tgttcaaatc      60
acgtcggggt ca                                                          72

<210> SEQ ID NO 856
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
ggcctcgtgg cgcaacggta gcgcgtctga ctccagatca gaaggttgcg tgttcaaatc      60
acgtcggggt ca                                                          72

<210> SEQ ID NO 857
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
ggcctcgtgg cgcaacggta gcacgtctga ctccagatca gaaggttgcg tgttcaaatc      60
acgtcggggt ca                                                          72

<210> SEQ ID NO 858
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 858
cggcctcgtg gcgcaacggt agcacgtctg acttcagatc agaaggttgc gtgttcaaat        60
cacgtcgggg tca                                                          73

<210> SEQ ID NO 859
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
ggcctcgtcg cgcaacggta gcgcgtctga ctccagatca gaaggttgcg tgttcaaatc        60
acgtcggggt ca                                                           72

<210> SEQ ID NO 860
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
ggcctcgtcg cgcaacggta gcgcgtctga cttcagatca gaaggttgcg tgttcaaatc        60
acgtcggggt ca                                                           72

<210> SEQ ID NO 861
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
ggcctcgtcg cgcaacggta gcacgtctga ctccagatca gaaggttgcg tgttcaaatc        60
acgtcggggt ca                                                           72

<210> SEQ ID NO 862
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 862
ggcctcgtcg cgcaacggta gcacgtctga cttcagatca gaaggttgcg tgttcaaatc        60
acgtcggggt ca                                                           72

<210> SEQ ID NO 863
<211> LENGTH: 2009
<212> TYPE: PRT
<213> ORGANISM: Homo sapiens

<400> SEQUENCE: 863

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu

-continued

```
               20                25                30

Lys Ala Lys Asn Pro Lys Pro Asp Lys Lys Asp Asp Asp Glu Asn Gly
            35                40                45

Pro Lys Pro Asn Ser Asp Leu Glu Ala Gly Lys Asn Leu Pro Phe Ile
        50                55                60

Tyr Gly Asp Ile Pro Pro Glu Met Val Ser Glu Pro Leu Glu Asp Leu
65                70                75                80

Asp Pro Tyr Tyr Ile Asn Lys Lys Thr Phe Ile Val Leu Asn Lys Gly
                85                90                95

Lys Ala Ile Phe Arg Phe Ser Ala Thr Ser Ala Leu Tyr Ile Leu Thr
            100               105               110

Pro Phe Asn Pro Leu Arg Lys Ile Ala Ile Lys Ile Leu Val His Ser
        115               120               125

Leu Phe Ser Met Leu Ile Met Cys Thr Ile Leu Thr Asn Cys Val Phe
    130               135               140

Met Thr Met Ser Asn Pro Pro Asp Trp Thr Lys Asn Val Glu Tyr Thr
145               150               155               160

Phe Thr Gly Ile Tyr Thr Phe Glu Ser Leu Ile Lys Ile Ile Ala Arg
                165               170               175

Gly Phe Cys Leu Glu Asp Phe Thr Phe Leu Arg Asp Pro Trp Asn Trp
            180               185               190

Leu Asp Phe Thr Val Ile Thr Phe Ala Tyr Val Thr Glu Phe Val Asp
            195               200               205

Leu Gly Asn Val Ser Ala Leu Arg Thr Phe Arg Val Leu Arg Ala Leu
    210               215               220

Lys Thr Ile Ser Val Ile Pro Gly Leu Lys Thr Ile Val Gly Ala Leu
225               230               235               240

Ile Gln Ser Val Lys Lys Leu Ser Asp Val Met Ile Leu Thr Val Phe
            245               250               255

Cys Leu Ser Val Phe Ala Leu Ile Gly Leu Gln Leu Phe Met Gly Asn
            260               265               270

Leu Arg Asn Lys Cys Ile Gln Trp Pro Pro Thr Asn Ala Ser Leu Glu
        275               280               285

Glu His Ser Ile Glu Lys Asn Ile Thr Val Asn Tyr Asn Gly Thr Leu
    290               295               300

Ile Asn Glu Thr Val Phe Glu Phe Asp Trp Lys Ser Tyr Ile Gln Asp
305               310               315               320

Ser Arg Tyr His Tyr Phe Leu Glu Gly Phe Leu Asp Ala Leu Leu Cys
            325               330               335

Gly Asn Ser Ser Asp Ala Gly Gln Cys Pro Glu Gly Tyr Met Cys Val
            340               345               350

Lys Ala Gly Arg Asn Pro Asn Tyr Gly Tyr Thr Ser Phe Asp Thr Phe
            355               360               365

Ser Trp Ala Phe Leu Ser Leu Phe Arg Leu Met Thr Gln Asp Phe Trp
    370               375               380

Glu Asn Leu Tyr Gln Leu Thr Leu Arg Ala Ala Gly Lys Thr Tyr Met
385               390               395               400

Ile Phe Phe Val Leu Val Ile Phe Leu Gly Ser Phe Tyr Leu Ile Asn
            405               410               415

Leu Ile Leu Ala Val Val Ala Met Ala Tyr Glu Glu Gln Asn Gln Ala
            420               425               430

Thr Leu Glu Glu Ala Glu Gln Lys Glu Ala Glu Phe Gln Gln Met Ile
        435               440               445
```

-continued

```
Glu Gln Leu Lys Lys Gln Gln Glu Ala Ala Gln Gln Ala Ala Thr Ala
    450             455             460

Thr Ala Ser Glu His Ser Arg Glu Pro Ser Ala Ala Gly Arg Leu Ser
465             470             475             480

Asp Ser Ser Ser Glu Ala Ser Lys Leu Ser Ser Lys Ser Ala Lys Glu
            485             490             495

Arg Arg Asn Arg Arg Lys Lys Arg Lys Gln Lys Glu Gln Ser Gly Gly
            500             505             510

Glu Glu Lys Asp Glu Asp Glu Phe Gln Lys Ser Glu Ser Glu Asp Ser
    515             520             525

Ile Arg Arg Lys Gly Phe Arg Phe Ser Ile Glu Gly Asn Arg Leu Thr
    530             535             540

Tyr Glu Lys Arg Tyr Ser Ser Pro His Gln Ser Leu Leu Ser Ile Arg
545             550             555             560

Gly Ser Leu Phe Ser Pro Arg Arg Asn Ser Arg Thr Ser Leu Phe Ser
            565             570             575

Phe Arg Gly Arg Ala Lys Asp Val Gly Ser Glu Asn Asp Phe Ala Asp
            580             585             590

Asp Glu His Ser Thr Phe Glu Asp Asn Glu Ser Arg Arg Asp Ser Leu
    595             600             605

Phe Val Pro Arg Arg His Gly Glu Arg Arg Asn Ser Asn Leu Ser Gln
    610             615             620

Thr Ser Arg Ser Ser Arg Met Leu Ala Val Phe Pro Ala Asn Gly Lys
625             630             635             640

Met His Ser Thr Val Asp Cys Asn Gly Val Val Ser Leu Val Gly Gly
            645             650             655

Pro Ser Val Pro Thr Ser Pro Val Gly Gln Leu Leu Pro Glu Val Ile
            660             665             670

Ile Asp Lys Pro Ala Thr Asp Asp Asn Gly Thr Thr Thr Glu Thr Glu
    675             680             685

Met Arg Lys Arg Arg Ser Ser Ser Phe His Val Ser Met Asp Phe Leu
    690             695             700

Glu Asp Pro Ser Gln Arg Gln Arg Ala Met Ser Ile Ala Ser Ile Leu
705             710             715             720

Thr Asn Thr Val Glu Glu Leu Glu Glu Ser Arg Gln Lys Cys Pro Pro
            725             730             735

Cys Trp Tyr Lys Phe Ser Asn Ile Phe Leu Ile Trp Asp Cys Ser Pro
            740             745             750

Tyr Trp Leu Lys Val Lys His Val Val Asn Leu Val Val Met Asp Pro
            755             760             765

Phe Val Asp Leu Ala Ile Thr Ile Cys Ile Val Leu Asn Thr Leu Phe
    770             775             780

Met Ala Met Glu His Tyr Pro Met Thr Asp His Phe Asn Asn Val Leu
785             790             795             800

Thr Val Gly Asn Leu Val Phe Thr Gly Ile Phe Thr Ala Glu Met Phe
            805             810             815

Leu Lys Ile Ile Ala Met Asp Pro Tyr Tyr Tyr Phe Gln Glu Gly Trp
            820             825             830

Asn Ile Phe Asp Gly Phe Ile Val Thr Leu Ser Leu Val Glu Leu Gly
            835             840             845

Leu Ala Asn Val Glu Gly Leu Ser Val Leu Arg Ser Phe Arg Leu Leu
    850             855             860
```

-continued

```
Arg Val Phe Lys Leu Ala Lys Ser Trp Pro Thr Leu Asn Met Leu Ile
865             870             875             880

Lys Ile Ile Gly Asn Ser Val Gly Ala Leu Gly Asn Leu Thr Leu Val
                885             890             895

Leu Ala Ile Ile Val Phe Ile Phe Ala Val Val Gly Met Gln Leu Phe
                900             905             910

Gly Lys Ser Tyr Lys Asp Cys Val Cys Lys Ile Ala Ser Asp Cys Gln
            915             920             925

Leu Pro Arg Trp His Met Asn Asp Phe Phe His Ser Phe Leu Ile Val
            930             935             940

Phe Arg Val Leu Cys Gly Glu Trp Ile Glu Thr Met Trp Asp Cys Met
945             950             955             960

Glu Val Ala Gly Gln Ala Met Cys Leu Thr Val Phe Met Met Val Met
                965             970             975

Val Ile Gly Asn Leu Val Val Leu Asn Leu Phe Leu Ala Leu Leu Leu
                980             985             990

Ser Ser Phe Ser Ala Asp Asn Leu  Ala Ala Thr Asp Asp  Asp Asn Glu
            995             1000            1005

Met Asn  Asn Leu Gln Ile Ala  Val Asp Arg Met His  Lys Gly Val
    1010            1015            1020

Ala Tyr  Val Lys Arg Lys Ile  Tyr Glu Phe Ile Gln  Gln Ser Phe
    1025            1030            1035

Ile Arg  Lys Gln Lys Ile Leu  Asp Glu Ile Lys Pro  Leu Asp Asp
    1040            1045            1050

Leu Asn  Asn Lys Lys Asp Ser  Cys Met Ser Asn His  Thr Ala Glu
    1055            1060            1065

Ile Gly  Lys Asp Leu Asp Tyr  Leu Lys Asp Val Asn  Gly Thr Thr
    1070            1075            1080

Ser Gly  Ile Gly Thr Gly Ser  Ser Val Glu Lys Tyr  Ile Ile Asp
    1085            1090            1095

Glu Ser  Asp Tyr Met Ser Phe  Ile Asn Asn Pro Ser  Leu Thr Val
    1100            1105            1110

Thr Val  Pro Ile Ala Val Gly  Glu Ser Asp Phe Glu  Asn Leu Asn
    1115            1120            1125

Thr Glu  Asp Phe Ser Ser Glu  Ser Asp Leu Glu Glu  Ser Lys Glu
    1130            1135            1140

Lys Leu  Asn Glu Ser Ser Ser  Ser Ser Glu Gly Ser  Thr Val Asp
    1145            1150            1155

Ile Gly  Ala Pro Val Glu Glu  Gln Pro Val Val Glu  Pro Glu Glu
    1160            1165            1170

Thr Leu  Glu Pro Glu Ala Cys  Phe Thr Glu Gly Cys  Val Gln Arg
    1175            1180            1185

Phe Lys  Cys Cys Gln Ile Asn  Val Glu Glu Gly Arg  Gly Lys Gln
    1190            1195            1200

Trp Trp  Asn Leu Arg Arg Thr  Cys Phe Arg Ile Val  Glu His Asn
    1205            1210            1215

Trp Phe  Glu Thr Phe Ile Val  Phe Met Ile Leu Leu  Ser Ser Gly
    1220            1225            1230

Ala Leu  Ala Phe Glu Asp Ile  Tyr Ile Asp Gln Arg  Lys Thr Ile
    1235            1240            1245

Lys Thr  Met Leu Glu Tyr Ala  Asp Lys Val Phe Thr  Tyr Ile Phe
    1250            1255            1260

Ile Leu  Glu Met Leu Leu Lys  Trp Val Ala Tyr Gly  Tyr Gln Thr
```

-continued

|      |      |      |      |      |      |      |      |      |      |      |      |      |
|------|------|------|------|------|------|------|------|------|------|------|------|------|
|      | 1265 |      |      |      | 1270 |      |      |      | 1275 |      |      |      |

Tyr Phe Thr Asn Ala Trp Cys Trp Leu Asp Phe Leu Ile Val Asp
    1280              1285              1290

Val Ser Leu Val Ser Leu Thr Ala Asn Ala Leu Gly Tyr Ser Glu
    1295              1300              1305

Leu Gly Ala Ile Lys Ser Leu Arg Thr Leu Arg Ala Leu Arg Pro
    1310              1315              1320

Leu Arg Ala Leu Ser Arg Phe Glu Gly Met Arg Val Val Val Asn
    1325              1330              1335

Ala Leu Leu Gly Ala Ile Pro Ser Ile Met Asn Val Leu Leu Val
    1340              1345              1350

Cys Leu Ile Phe Trp Leu Ile Phe Ser Ile Met Gly Val Asn Leu
    1355              1360              1365

Phe Ala Gly Lys Phe Tyr His Cys Ile Asn Thr Thr Thr Gly Asp
    1370              1375              1380

Arg Phe Asp Ile Glu Asp Val Asn Asn His Thr Asp Cys Leu Lys
    1385              1390              1395

Leu Ile Glu Arg Asn Glu Thr Ala Arg Trp Lys Asn Val Lys Val
    1400              1405              1410

Asn Phe Asp Asn Val Gly Phe Gly Tyr Leu Ser Leu Leu Gln Val
    1415              1420              1425

Ala Thr Phe Lys Gly Trp Met Asp Ile Met Tyr Ala Ala Val Asp
    1430              1435              1440

Ser Arg Asn Val Glu Leu Gln Pro Lys Tyr Glu Glu Ser Leu Tyr
    1445              1450              1455

Met Tyr Leu Tyr Phe Val Ile Phe Ile Ile Phe Gly Ser Phe Phe
    1460              1465              1470

Thr Leu Asn Leu Phe Ile Gly Val Ile Ile Asp Asn Phe Asn Gln
    1475              1480              1485

Gln Lys Lys Lys Phe Gly Gly Gln Asp Ile Phe Met Thr Glu Glu
    1490              1495              1500

Gln Lys Lys Tyr Tyr Asn Ala Met Lys Lys Leu Gly Ser Lys Lys
    1505              1510              1515

Pro Gln Lys Pro Ile Pro Arg Pro Gly Asn Lys Phe Gln Gly Met
    1520              1525              1530

Val Phe Asp Phe Val Thr Arg Gln Val Phe Asp Ile Ser Ile Met
    1535              1540              1545

Ile Leu Ile Cys Leu Asn Met Val Thr Met Met Val Glu Thr Asp
    1550              1555              1560

Asp Gln Ser Glu Tyr Val Thr Thr Ile Leu Ser Arg Ile Asn Leu
    1565              1570              1575

Val Phe Ile Val Leu Phe Thr Gly Glu Cys Val Leu Lys Leu Ile
    1580              1585              1590

Ser Leu Arg His Tyr Tyr Phe Thr Ile Gly Trp Asn Ile Phe Asp
    1595              1600              1605

Phe Val Val Val Ile Leu Ser Ile Val Gly Met Phe Leu Ala Glu
    1610              1615              1620

Leu Ile Glu Lys Tyr Phe Val Ser Pro Thr Leu Phe Arg Val Ile
    1625              1630              1635

Arg Leu Ala Arg Ile Gly Arg Ile Leu Arg Leu Ile Lys Gly Ala
    1640              1645              1650

Lys Gly Ile Arg Thr Leu Leu Phe Ala Leu Met Met Ser Leu Pro
    1655              1660              1665

-continued

```
Ala Leu Phe Asn Ile Gly Leu  Leu Leu Phe Leu Val  Met Phe Ile
    1670            1675           1680

Tyr Ala Ile Phe Gly Met Ser  Asn Phe Ala Tyr Val  Lys Arg Glu
    1685            1690           1695

Val Gly Ile Asp Asp Met Phe  Asn Phe Glu Thr Phe  Gly Asn Ser
    1700            1705           1710

Met Ile Cys Leu Phe Gln Ile  Thr Thr Ser Ala Gly  Trp Asp Gly
    1715            1720           1725

Leu Leu Ala Pro Ile Leu Asn  Ser Lys Pro Pro Asp  Cys Asp Pro
    1730            1735           1740

Asn Lys Val Asn Pro Gly Ser  Ser Val Lys Gly Asp  Cys Gly Asn
    1745            1750           1755

Pro Ser Val Gly Ile Phe Phe  Phe Val Ser Tyr Ile  Ile Ile Ser
    1760            1765           1770

Phe Leu Val Val Val Asn Met  Tyr Ile Ala Val Ile  Leu Glu Asn
    1775            1780           1785

Phe Ser Val Ala Thr Glu Glu  Ser Ala Glu Pro Leu  Ser Glu Asp
    1790            1795           1800

Asp Phe Glu Met Phe Tyr Glu  Val Trp Glu Lys Phe  Asp Pro Asp
    1805            1810           1815

Ala Thr Gln Phe Met Glu Phe  Glu Lys Leu Ser Gln  Phe Ala Ala
    1820            1825           1830

Ala Leu Glu Pro Pro Leu Asn  Leu Pro Gln Pro Asn  Lys Leu Gln
    1835            1840           1845

Leu Ile Ala Met Asp Leu Pro  Met Val Ser Gly Asp  Arg Ile His
    1850            1855           1860

Cys Leu Asp Ile Leu Phe Ala  Phe Thr Lys Arg Val  Leu Gly Glu
    1865            1870           1875

Ser Gly Glu Met Asp Ala Leu  Arg Ile Gln Met Glu  Glu Arg Phe
    1880            1885           1890

Met Ala Ser Asn Pro Ser Lys  Val Ser Tyr Gln Pro  Ile Thr Thr
    1895            1900           1905

Thr Leu Lys Arg Lys Gln Glu  Glu Val Ser Ala Val  Ile Ile Gln
    1910            1915           1920

Arg Ala Tyr Arg Arg His Leu  Leu Lys Arg Thr Val  Lys Gln Ala
    1925            1930           1935

Ser Phe Thr Tyr Asn Lys Asn  Lys Ile Lys Gly Gly  Ala Asn Leu
    1940            1945           1950

Leu Ile Lys Glu Asp Met Ile  Ile Asp Arg Ile Asn  Glu Asn Ser
    1955            1960           1965

Ile Thr Glu Lys Thr Asp Leu  Thr Met Ser Thr Ala  Ala Cys Pro
    1970            1975           1980

Pro Ser Tyr Asp Arg Val Thr  Lys Pro Ile Val Glu  Lys His Glu
    1985            1990           1995

Gln Glu Gly Lys Asp Glu Lys  Ala Lys Gly Lys
    2000            2005
```

```
<210> SEQ ID NO 864
<211> LENGTH: 1998
<212> TYPE: PRT
<213> ORGANISM: Homo sapiens

<400> SEQUENCE: 864

Met Glu Gln Thr Val Leu Val Pro Pro Gly Pro Asp Ser Phe Asn Phe
```

-continued

```
1               5                    10                   15

Phe Thr Arg Glu Ser Leu Ala Ala Ile Glu Arg Arg Ile Ala Glu Glu
            20                   25                   30

Lys Ala Lys Asn Pro Lys Pro Asp Lys Lys Asp Asp Asp Glu Asn Gly
            35                   40                   45

Pro Lys Pro Asn Ser Asp Leu Glu Ala Gly Lys Asn Leu Pro Phe Ile
        50                   55                   60

Tyr Gly Asp Ile Pro Pro Glu Met Val Ser Glu Pro Leu Glu Asp Leu
65                   70                   75                   80

Asp Pro Tyr Tyr Ile Asn Lys Lys Thr Phe Ile Val Leu Asn Lys Gly
            85                   90                   95

Lys Ala Ile Phe Arg Phe Ser Ala Thr Ser Ala Leu Tyr Ile Leu Thr
            100                  105                  110

Pro Phe Asn Pro Leu Arg Lys Ile Ala Ile Lys Ile Leu Val His Ser
            115                  120                  125

Leu Phe Ser Met Leu Ile Met Cys Thr Ile Leu Thr Asn Cys Val Phe
            130                  135                  140

Met Thr Met Ser Asn Pro Pro Asp Trp Thr Lys Asn Val Glu Tyr Thr
145                  150                  155                  160

Phe Thr Gly Ile Tyr Thr Phe Glu Ser Leu Ile Lys Ile Ile Ala Arg
                165                  170                  175

Gly Phe Cys Leu Glu Asp Phe Thr Phe Leu Arg Asp Pro Trp Asn Trp
            180                  185                  190

Leu Asp Phe Thr Val Ile Thr Phe Ala Tyr Val Thr Glu Phe Val Asp
            195                  200                  205

Leu Gly Asn Val Ser Ala Leu Arg Thr Phe Arg Val Leu Arg Ala Leu
        210                  215                  220

Lys Thr Ile Ser Val Ile Pro Gly Leu Lys Thr Ile Val Gly Ala Leu
225                  230                  235                  240

Ile Gln Ser Val Lys Lys Leu Ser Asp Val Met Ile Leu Thr Val Phe
                245                  250                  255

Cys Leu Ser Val Phe Ala Leu Ile Gly Leu Gln Leu Phe Met Gly Asn
            260                  265                  270

Leu Arg Asn Lys Cys Ile Gln Trp Pro Pro Thr Asn Ala Ser Leu Glu
        275                  280                  285

Glu His Ser Ile Glu Lys Asn Ile Thr Val Asn Tyr Asn Gly Thr Leu
        290                  295                  300

Ile Asn Glu Thr Val Phe Glu Phe Asp Trp Lys Ser Tyr Ile Gln Asp
305                  310                  315                  320

Ser Arg Tyr His Tyr Phe Leu Glu Gly Phe Leu Asp Ala Leu Leu Cys
                325                  330                  335

Gly Asn Ser Ser Asp Ala Gly Gln Cys Pro Glu Gly Tyr Met Cys Val
            340                  345                  350

Lys Ala Gly Arg Asn Pro Asn Tyr Gly Tyr Thr Ser Phe Asp Thr Phe
            355                  360                  365

Ser Trp Ala Phe Leu Ser Leu Phe Arg Leu Met Thr Gln Asp Phe Trp
        370                  375                  380

Glu Asn Leu Tyr Gln Leu Thr Leu Arg Ala Ala Gly Lys Thr Tyr Met
385                  390                  395                  400

Ile Phe Phe Val Leu Val Ile Phe Leu Gly Ser Phe Tyr Leu Ile Asn
                405                  410                  415

Leu Ile Leu Ala Val Val Ala Met Ala Tyr Glu Glu Gln Asn Gln Ala
            420                  425                  430
```

-continued

```
Thr Leu Glu Glu Ala Glu Gln Lys Glu Ala Glu Phe Gln Gln Met Ile
        435             440             445

Glu Gln Leu Lys Lys Gln Gln Glu Ala Ala Gln Gln Ala Ala Thr Ala
    450             455             460

Thr Ala Ser Glu His Ser Arg Glu Pro Ser Ala Ala Gly Arg Leu Ser
465             470             475             480

Asp Ser Ser Ser Glu Ala Ser Lys Leu Ser Ser Lys Ser Ala Lys Glu
                485             490             495

Arg Arg Asn Arg Arg Lys Lys Arg Lys Gln Lys Glu Gln Ser Gly Gly
            500             505             510

Glu Glu Lys Asp Glu Asp Glu Phe Gln Lys Ser Glu Ser Glu Asp Ser
        515             520             525

Ile Arg Arg Lys Gly Phe Arg Phe Ser Ile Glu Gly Asn Arg Leu Thr
    530             535             540

Tyr Glu Lys Arg Tyr Ser Ser Pro His Gln Ser Leu Leu Ser Ile Arg
545             550             555             560

Gly Ser Leu Phe Ser Pro Arg Arg Asn Ser Arg Thr Ser Leu Phe Ser
            565             570             575

Phe Arg Gly Arg Ala Lys Asp Val Gly Ser Glu Asn Asp Phe Ala Asp
            580             585             590

Asp Glu His Ser Thr Phe Glu Asp Asn Glu Ser Arg Arg Asp Ser Leu
        595             600             605

Phe Val Pro Arg Arg His Gly Glu Arg Arg Asn Ser Asn Leu Ser Gln
    610             615             620

Thr Ser Arg Ser Ser Arg Met Leu Ala Val Phe Pro Ala Asn Gly Lys
625             630             635             640

Met His Ser Thr Val Asp Cys Asn Gly Val Val Ser Leu Val Gly Gly
            645             650             655

Pro Ser Val Pro Thr Ser Pro Val Gly Gln Leu Leu Pro Glu Gly Thr
            660             665             670

Thr Thr Glu Thr Glu Met Arg Lys Arg Arg Ser Ser Ser Phe His Val
        675             680             685

Ser Met Asp Phe Leu Glu Asp Pro Ser Gln Arg Gln Arg Ala Met Ser
    690             695             700

Ile Ala Ser Ile Leu Thr Asn Thr Val Glu Glu Leu Glu Glu Ser Arg
705             710             715             720

Gln Lys Cys Pro Pro Cys Trp Tyr Lys Phe Ser Asn Ile Phe Leu Ile
            725             730             735

Trp Asp Cys Ser Pro Tyr Trp Leu Lys Val Lys His Val Val Asn Leu
            740             745             750

Val Val Met Asp Pro Phe Val Asp Leu Ala Ile Thr Ile Cys Ile Val
    755             760             765

Leu Asn Thr Leu Phe Met Ala Met Glu His Tyr Pro Met Thr Asp His
    770             775             780

Phe Asn Asn Val Leu Thr Val Gly Asn Leu Val Phe Thr Gly Ile Phe
785             790             795             800

Thr Ala Glu Met Phe Leu Lys Ile Ile Ala Met Asp Pro Tyr Tyr Tyr
            805             810             815

Phe Gln Glu Gly Trp Asn Ile Phe Asp Gly Phe Ile Val Thr Leu Ser
            820             825             830

Leu Val Glu Leu Gly Leu Ala Asn Val Glu Gly Leu Ser Val Leu Arg
        835             840             845
```

-continued

```
Ser Phe Arg Leu Leu Arg Val Phe Lys Leu Ala Lys Ser Trp Pro Thr
850                 855                 860

Leu Asn Met Leu Ile Lys Ile Ile Gly Asn Ser Val Gly Ala Leu Gly
865                 870                 875                 880

Asn Leu Thr Leu Val Leu Ala Ile Ile Val Phe Ile Phe Ala Val Val
            885                 890                 895

Gly Met Gln Leu Phe Gly Lys Ser Tyr Lys Asp Cys Val Cys Lys Ile
            900                 905                 910

Ala Ser Asp Cys Gln Leu Pro Arg Trp His Met Asn Asp Phe Phe His
            915                 920                 925

Ser Phe Leu Ile Val Phe Arg Val Leu Cys Gly Glu Trp Ile Glu Thr
930                 935                 940

Met Trp Asp Cys Met Glu Val Ala Gly Gln Ala Met Cys Leu Thr Val
945                 950                 955                 960

Phe Met Met Val Met Val Ile Gly Asn Leu Val Val Leu Asn Leu Phe
            965                 970                 975

Leu Ala Leu Leu Leu Ser Ser Phe Ser Ala Asp Asn Leu Ala Ala Thr
            980                 985                 990

Asp Asp Asp Asn Glu Met Asn Asn  Leu Gln Ile Ala Val  Asp Arg Met
            995                 1000                1005

His Lys  Gly Val Ala Tyr Val  Lys Arg Lys Ile Tyr  Glu Phe Ile
    1010                1015                1020

Gln Gln  Ser Phe Ile Arg Lys  Gln Lys Ile Leu Asp  Glu Ile Lys
    1025                1030                1035

Pro Leu  Asp Asp Leu Asn Asn  Lys Lys Asp Ser Cys  Met Ser Asn
    1040                1045                1050

His Thr  Ala Glu Ile Gly Lys  Asp Leu Asp Tyr Leu  Lys Asp Val
    1055                1060                1065

Asn Gly  Thr Thr Ser Gly Ile  Gly Thr Gly Ser Ser  Val Glu Lys
    1070                1075                1080

Tyr Ile  Ile Asp Glu Ser Asp  Tyr Met Ser Phe Ile  Asn Asn Pro
    1085                1090                1095

Ser Leu  Thr Val Thr Val Pro  Ile Ala Val Gly Glu  Ser Asp Phe
    1100                1105                1110

Glu Asn  Leu Asn Thr Glu Asp  Phe Ser Ser Glu Ser  Asp Leu Glu
    1115                1120                1125

Glu Ser  Lys Glu Lys Leu Asn  Glu Ser Ser Ser Ser  Ser Glu Gly
    1130                1135                1140

Ser Thr  Val Asp Ile Gly Ala  Pro Val Glu Glu Gln  Pro Val Val
    1145                1150                1155

Glu Pro  Glu Glu Thr Leu Glu  Pro Glu Ala Cys Phe  Thr Glu Gly
    1160                1165                1170

Cys Val  Gln Arg Phe Lys Cys  Cys Gln Ile Asn Val  Glu Glu Gly
    1175                1180                1185

Arg Gly  Lys Gln Trp Trp Asn  Leu Arg Arg Thr Cys  Phe Arg Ile
    1190                1195                1200

Val Glu  His Asn Trp Phe Glu  Thr Phe Ile Val Phe  Met Ile Leu
    1205                1210                1215

Leu Ser  Ser Gly Ala Leu Ala  Phe Glu Asp Ile Tyr  Ile Asp Gln
    1220                1225                1230

Arg Lys  Thr Ile Lys Thr Met  Leu Glu Tyr Ala Asp  Lys Val Phe
    1235                1240                1245

Thr Tyr  Ile Phe Ile Leu Glu  Met Leu Leu Lys Trp  Val Ala Tyr
```

-continued

```
        1250               1255               1260

Gly Tyr Gln Thr Tyr Phe Thr  Asn Ala Trp Cys Trp  Leu Asp Phe
    1265               1270               1275

Leu Ile Val Asp Val Ser Leu  Val Ser Leu Thr Ala  Asn Ala Leu
    1280               1285               1290

Gly Tyr Ser Glu Leu Gly Ala  Ile Lys Ser Leu Arg  Thr Leu Arg
    1295               1300               1305

Ala Leu Arg Pro Leu Arg Ala  Leu Ser Arg Phe Glu  Gly Met Arg
    1310               1315               1320

Val Val Val Asn Ala Leu Leu  Gly Ala Ile Pro Ser  Ile Met Asn
    1325               1330               1335

Val Leu Leu Val Cys Leu Ile  Phe Trp Leu Ile Phe  Ser Ile Met
    1340               1345               1350

Gly Val Asn Leu Phe Ala Gly  Lys Phe Tyr His Cys  Ile Asn Thr
    1355               1360               1365

Thr Thr Gly Asp Arg Phe Asp  Ile Glu Asp Val Asn  Asn His Thr
    1370               1375               1380

Asp Cys Leu Lys Leu Ile Glu  Arg Asn Glu Thr Ala  Arg Trp Lys
    1385               1390               1395

Asn Val Lys Val Asn Phe Asp  Asn Val Gly Phe Gly  Tyr Leu Ser
    1400               1405               1410

Leu Leu Gln Val Ala Thr Phe  Lys Gly Trp Met Asp  Ile Met Tyr
    1415               1420               1425

Ala Ala Val Asp Ser Arg Asn  Val Glu Leu Gln Pro  Lys Tyr Glu
    1430               1435               1440

Glu Ser Leu Tyr Met Tyr Leu  Tyr Phe Val Ile Phe  Ile Ile Phe
    1445               1450               1455

Gly Ser Phe Phe Thr Leu Asn  Leu Phe Ile Gly Val  Ile Ile Asp
    1460               1465               1470

Asn Phe Asn Gln Gln Lys Lys  Lys Phe Gly Gly Gln  Asp Ile Phe
    1475               1480               1485

Met Thr Glu Glu Gln Lys Lys  Tyr Tyr Asn Ala Met  Lys Lys Leu
    1490               1495               1500

Gly Ser Lys Lys Pro Gln Lys  Pro Ile Pro Arg Pro  Gly Asn Lys
    1505               1510               1515

Phe Gln Gly Met Val Phe Asp  Phe Val Thr Arg Gln  Val Phe Asp
    1520               1525               1530

Ile Ser Ile Met Ile Leu Ile  Cys Leu Asn Met Val  Thr Met Met
    1535               1540               1545

Val Glu Thr Asp Asp Gln Ser  Glu Tyr Val Thr Thr  Ile Leu Ser
    1550               1555               1560

Arg Ile Asn Leu Val Phe Ile  Val Leu Phe Thr Gly  Glu Cys Val
    1565               1570               1575

Leu Lys Leu Ile Ser Leu Arg  His Tyr Tyr Phe Thr  Ile Gly Trp
    1580               1585               1590

Asn Ile Phe Asp Phe Val Val  Val Ile Leu Ser Ile  Val Gly Met
    1595               1600               1605

Phe Leu Ala Glu Leu Ile Glu  Lys Tyr Phe Val Ser  Pro Thr Leu
    1610               1615               1620

Phe Arg Val Ile Arg Leu Ala  Arg Ile Gly Arg Ile  Leu Arg Leu
    1625               1630               1635

Ile Lys Gly Ala Lys Gly Ile  Arg Thr Leu Leu Phe  Ala Leu Met
    1640               1645               1650
```

-continued

```
Met Ser Leu Pro Ala Leu Phe Asn Ile Gly Leu Leu Leu Phe Leu
    1655             1660             1665

Val Met Phe Ile Tyr Ala Ile Phe Gly Met Ser Asn Phe Ala Tyr
    1670             1675             1680

Val Lys Arg Glu Val Gly Ile Asp Asp Met Phe Asn Phe Glu Thr
    1685             1690             1695

Phe Gly Asn Ser Met Ile Cys Leu Phe Gln Ile Thr Thr Ser Ala
    1700             1705             1710

Gly Trp Asp Gly Leu Leu Ala Pro Ile Leu Asn Ser Lys Pro Pro
    1715             1720             1725

Asp Cys Asp Pro Asn Lys Val Asn Pro Gly Ser Ser Val Lys Gly
    1730             1735             1740

Asp Cys Gly Asn Pro Ser Val Gly Ile Phe Phe Phe Val Ser Tyr
    1745             1750             1755

Ile Ile Ile Ser Phe Leu Val Val Val Asn Met Tyr Ile Ala Val
    1760             1765             1770

Ile Leu Glu Asn Phe Ser Val Ala Thr Glu Glu Ser Ala Glu Pro
    1775             1780             1785

Leu Ser Glu Asp Asp Phe Glu Met Phe Tyr Glu Val Trp Glu Lys
    1790             1795             1800

Phe Asp Pro Asp Ala Thr Gln Phe Met Glu Phe Glu Lys Leu Ser
    1805             1810             1815

Gln Phe Ala Ala Ala Leu Glu Pro Pro Leu Asn Leu Pro Gln Pro
    1820             1825             1830

Asn Lys Leu Gln Leu Ile Ala Met Asp Leu Pro Met Val Ser Gly
    1835             1840             1845

Asp Arg Ile His Cys Leu Asp Ile Leu Phe Ala Phe Thr Lys Arg
    1850             1855             1860

Val Leu Gly Glu Ser Gly Glu Met Asp Ala Leu Arg Ile Gln Met
    1865             1870             1875

Glu Glu Arg Phe Met Ala Ser Asn Pro Ser Lys Val Ser Tyr Gln
    1880             1885             1890

Pro Ile Thr Thr Thr Leu Lys Arg Lys Gln Glu Glu Val Ser Ala
    1895             1900             1905

Val Ile Ile Gln Arg Ala Tyr Arg Arg His Leu Leu Lys Arg Thr
    1910             1915             1920

Val Lys Gln Ala Ser Phe Thr Tyr Asn Lys Asn Lys Ile Lys Gly
    1925             1930             1935

Gly Ala Asn Leu Leu Ile Lys Glu Asp Met Ile Ile Asp Arg Ile
    1940             1945             1950

Asn Glu Asn Ser Ile Thr Glu Lys Thr Asp Leu Thr Met Ser Thr
    1955             1960             1965

Ala Ala Cys Pro Pro Ser Tyr Asp Arg Val Thr Lys Pro Ile Val
    1970             1975             1980

Glu Lys His Glu Gln Glu Gly Lys Asp Glu Lys Ala Lys Gly Lys
    1985             1990             1995
```

```
<210> SEQ ID NO 865
<211> LENGTH: 1981
<212> TYPE: PRT
<213> ORGANISM: Homo sapiens

<400> SEQUENCE: 865

Met Glu Gln Thr Val Leu Val Pro Pro Gly Pro Asp Ser Phe Asn Phe
```

-continued

```
1            5              10             15

Phe Thr Arg Glu Ser Leu Ala Ala Ile Glu Arg Arg Ile Ala Glu Glu
            20             25             30

Lys Ala Lys Asn Pro Lys Pro Asp Lys Lys Asp Asp Asp Glu Asn Gly
            35             40             45

Pro Lys Pro Asn Ser Asp Leu Glu Ala Gly Lys Asn Leu Pro Phe Ile
        50             55             60

Tyr Gly Asp Ile Pro Pro Glu Met Val Ser Glu Pro Leu Glu Asp Leu
65             70             75             80

Asp Pro Tyr Tyr Ile Asn Lys Lys Thr Phe Ile Val Leu Asn Lys Gly
            85             90             95

Lys Ala Ile Phe Arg Phe Ser Ala Thr Ser Ala Leu Tyr Ile Leu Thr
            100            105            110

Pro Phe Asn Pro Leu Arg Lys Ile Ala Ile Lys Ile Leu Val His Ser
            115            120            125

Leu Phe Ser Met Leu Ile Met Cys Thr Ile Leu Thr Asn Cys Val Phe
        130            135            140

Met Thr Met Ser Asn Pro Pro Asp Trp Thr Lys Asn Val Glu Tyr Thr
145            150            155            160

Phe Thr Gly Ile Tyr Thr Phe Glu Ser Leu Ile Lys Ile Ile Ala Arg
            165            170            175

Gly Phe Cys Leu Glu Asp Phe Thr Phe Leu Arg Asp Pro Trp Asn Trp
            180            185            190

Leu Asp Phe Thr Val Ile Thr Phe Ala Tyr Val Thr Glu Phe Val Asp
        195            200            205

Leu Gly Asn Val Ser Ala Leu Arg Thr Phe Arg Val Leu Arg Ala Leu
        210            215            220

Lys Thr Ile Ser Val Ile Pro Gly Leu Lys Thr Ile Val Gly Ala Leu
225            230            235            240

Ile Gln Ser Val Lys Lys Leu Ser Asp Val Met Ile Leu Thr Val Phe
            245            250            255

Cys Leu Ser Val Phe Ala Leu Ile Gly Leu Gln Leu Phe Met Gly Asn
            260            265            270

Leu Arg Asn Lys Cys Ile Gln Trp Pro Pro Thr Asn Ala Ser Leu Glu
        275            280            285

Glu His Ser Ile Glu Lys Asn Ile Thr Val Asn Tyr Asn Gly Thr Leu
        290            295            300

Ile Asn Glu Thr Val Phe Glu Phe Asp Trp Lys Ser Tyr Ile Gln Asp
305            310            315            320

Ser Arg Tyr His Tyr Phe Leu Glu Gly Phe Leu Asp Ala Leu Leu Cys
            325            330            335

Gly Asn Ser Ser Asp Ala Gly Gln Cys Pro Glu Gly Tyr Met Cys Val
        340            345            350

Lys Ala Gly Arg Asn Pro Asn Tyr Gly Tyr Thr Ser Phe Asp Thr Phe
        355            360            365

Ser Trp Ala Phe Leu Ser Leu Phe Arg Leu Met Thr Gln Asp Phe Trp
    370            375            380

Glu Asn Leu Tyr Gln Leu Thr Leu Arg Ala Ala Gly Lys Thr Tyr Met
385            390            395            400

Ile Phe Phe Val Leu Val Ile Phe Leu Gly Ser Phe Tyr Leu Ile Asn
            405            410            415

Leu Ile Leu Ala Val Val Ala Met Ala Tyr Glu Glu Gln Asn Gln Ala
        420            425            430
```

-continued

```
Thr Leu Glu Glu Ala Glu Gln Lys Glu Ala Glu Phe Gln Gln Met Ile
        435             440             445

Glu Gln Leu Lys Lys Gln Gln Glu Ala Ala Gln Gln Ala Ala Thr Ala
    450             455             460

Thr Ala Ser Glu His Ser Arg Glu Pro Ser Ala Ala Gly Arg Leu Ser
465             470             475             480

Asp Ser Ser Ser Glu Ala Ser Lys Leu Ser Ser Lys Ser Ala Lys Glu
            485             490             495

Arg Arg Asn Arg Arg Lys Lys Arg Lys Gln Lys Glu Gln Ser Gly Gly
            500             505             510

Glu Glu Lys Asp Glu Asp Glu Phe Gln Lys Ser Glu Ser Glu Asp Ser
    515             520             525

Ile Arg Arg Lys Gly Phe Arg Phe Ser Ile Glu Gly Asn Arg Leu Thr
    530             535             540

Tyr Glu Lys Arg Tyr Ser Ser Pro His Gln Ser Leu Leu Ser Ile Arg
545             550             555             560

Gly Ser Leu Phe Ser Pro Arg Arg Asn Ser Arg Thr Ser Leu Phe Ser
            565             570             575

Phe Arg Gly Arg Ala Lys Asp Val Gly Ser Glu Asn Asp Phe Ala Asp
            580             585             590

Asp Glu His Ser Thr Phe Glu Asp Asn Glu Ser Arg Arg Asp Ser Leu
            595             600             605

Phe Val Pro Arg Arg His Gly Glu Arg Arg Asn Ser Asn Leu Ser Gln
            610             615             620

Thr Ser Arg Ser Ser Arg Met Leu Ala Val Phe Pro Ala Asn Gly Lys
625             630             635             640

Met His Ser Thr Val Asp Cys Asn Gly Val Val Ser Leu Gly Thr Thr
            645             650             655

Thr Glu Thr Glu Met Arg Lys Arg Arg Ser Ser Ser Phe His Val Ser
            660             665             670

Met Asp Phe Leu Glu Asp Pro Ser Gln Arg Gln Arg Ala Met Ser Ile
            675             680             685

Ala Ser Ile Leu Thr Asn Thr Val Glu Glu Leu Glu Glu Ser Arg Gln
            690             695             700

Lys Cys Pro Pro Cys Trp Tyr Lys Phe Ser Asn Ile Phe Leu Ile Trp
705             710             715             720

Asp Cys Ser Pro Tyr Trp Leu Lys Val Lys His Val Val Asn Leu Val
            725             730             735

Val Met Asp Pro Phe Val Asp Leu Ala Ile Thr Ile Cys Ile Val Leu
            740             745             750

Asn Thr Leu Phe Met Ala Met Glu His Tyr Pro Met Thr Asp His Phe
            755             760             765

Asn Asn Val Leu Thr Val Gly Asn Leu Val Phe Thr Gly Ile Phe Thr
    770             775             780

Ala Glu Met Phe Leu Lys Ile Ile Ala Met Asp Pro Tyr Tyr Tyr Phe
785             790             795             800

Gln Glu Gly Trp Asn Ile Phe Asp Gly Phe Ile Val Thr Leu Ser Leu
            805             810             815

Val Glu Leu Gly Leu Ala Asn Val Glu Gly Leu Ser Val Leu Arg Ser
            820             825             830

Phe Arg Leu Leu Arg Val Phe Lys Leu Ala Lys Ser Trp Pro Thr Leu
            835             840             845
```

-continued

```
Asn Met Leu Ile Lys Ile Ile Gly Asn Ser Val Gly Ala Leu Gly Asn
    850                 855                 860

Leu Thr Leu Val Leu Ala Ile Ile Val Phe Ile Phe Ala Val Val Gly
865                 870                 875                 880

Met Gln Leu Phe Gly Lys Ser Tyr Lys Asp Cys Val Cys Lys Ile Ala
                885                 890                 895

Ser Asp Cys Gln Leu Pro Arg Trp His Met Asn Asp Phe Phe His Ser
            900                 905                 910

Phe Leu Ile Val Phe Arg Val Leu Cys Gly Glu Trp Ile Glu Thr Met
        915                 920                 925

Trp Asp Cys Met Glu Val Ala Gly Gln Ala Met Cys Leu Thr Val Phe
    930                 935                 940

Met Met Val Met Val Ile Gly Asn Leu Val Val Leu Asn Leu Phe Leu
945                 950                 955                 960

Ala Leu Leu Leu Ser Ser Phe Ser Ala Asp Asn Leu Ala Ala Thr Asp
                965                 970                 975

Asp Asp Asn Glu Met Asn Asn Leu Gln Ile Ala Val Asp Arg Met His
            980                 985                 990

Lys Gly Val Ala Tyr Val Lys Arg  Lys Ile Tyr Glu Phe  Ile Gln Gln
        995                 1000                 1005

Ser Phe  Ile Arg Lys Gln Lys  Ile Leu Asp Glu Ile  Lys Pro Leu
    1010                 1015                 1020

Asp Asp  Leu Asn Asn Lys Lys  Asp Ser Cys Met Ser  Asn His Thr
    1025                 1030                 1035

Ala Glu  Ile Gly Lys Asp Leu  Asp Tyr Leu Lys Asp  Val Asn Gly
    1040                 1045                 1050

Thr Thr  Ser Gly Ile Gly Thr  Gly Ser Ser Val Glu  Lys Tyr Ile
    1055                 1060                 1065

Ile Asp  Glu Ser Asp Tyr Met  Ser Phe Ile Asn Asn  Pro Ser Leu
    1070                 1075                 1080

Thr Val  Thr Val Pro Ile Ala  Val Gly Glu Ser Asp  Phe Glu Asn
    1085                 1090                 1095

Leu Asn  Thr Glu Asp Phe Ser  Ser Glu Ser Asp Leu  Glu Glu Ser
    1100                 1105                 1110

Lys Glu  Lys Leu Asn Glu Ser  Ser Ser Ser Ser Glu  Gly Ser Thr
    1115                 1120                 1125

Val Asp  Ile Gly Ala Pro Val  Glu Glu Gln Pro Val  Val Glu Pro
    1130                 1135                 1140

Glu Glu  Thr Leu Glu Pro Glu  Ala Cys Phe Thr Glu  Gly Cys Val
    1145                 1150                 1155

Gln Arg  Phe Lys Cys Cys Gln  Ile Asn Val Glu Glu  Gly Arg Gly
    1160                 1165                 1170

Lys Gln  Trp Trp Asn Leu Arg  Arg Thr Cys Phe Arg  Ile Val Glu
    1175                 1180                 1185

His Asn  Trp Phe Glu Thr Phe  Ile Val Phe Met Ile  Leu Leu Ser
    1190                 1195                 1200

Ser Gly  Ala Leu Ala Phe Glu  Asp Ile Tyr Ile Asp  Gln Arg Lys
    1205                 1210                 1215

Thr Ile  Lys Thr Met Leu Glu  Tyr Ala Asp Lys Val  Phe Thr Tyr
    1220                 1225                 1230

Ile Phe  Ile Leu Glu Met Leu  Leu Lys Trp Val Ala  Tyr Gly Tyr
    1235                 1240                 1245

Gln Thr  Tyr Phe Thr Asn Ala  Trp Cys Trp Leu Asp  Phe Leu Ile
```

-continued

```
        1250              1255              1260

Val Asp Val Ser Leu Val Ser  Leu Thr Ala Asn Ala  Leu Gly Tyr
    1265              1270              1275

Ser Glu Leu Gly Ala Ile Lys  Ser Leu Arg Thr Leu  Arg Ala Leu
    1280              1285              1290

Arg Pro Leu Arg Ala Leu Ser  Arg Phe Glu Gly Met  Arg Val Val
    1295              1300              1305

Val Asn Ala Leu Leu Gly Ala  Ile Pro Ser Ile Met  Asn Val Leu
    1310              1315              1320

Leu Val Cys Leu Ile Phe Trp  Leu Ile Phe Ser Ile  Met Gly Val
    1325              1330              1335

Asn Leu Phe Ala Gly Lys Phe  Tyr His Cys Ile Asn  Thr Thr Thr
    1340              1345              1350

Gly Asp Arg Phe Asp Ile Glu  Asp Val Asn Asn His  Thr Asp Cys
    1355              1360              1365

Leu Lys Leu Ile Glu Arg Asn  Glu Thr Ala Arg Trp  Lys Asn Val
    1370              1375              1380

Lys Val Asn Phe Asp Asn Val  Gly Phe Gly Tyr Leu  Ser Leu Leu
    1385              1390              1395

Gln Val Ala Thr Phe Lys Gly  Trp Met Asp Ile Met  Tyr Ala Ala
    1400              1405              1410

Val Asp Ser Arg Asn Val Glu  Leu Gln Pro Lys Tyr  Glu Glu Ser
    1415              1420              1425

Leu Tyr Met Tyr Leu Tyr Phe  Val Ile Phe Ile Ile  Phe Gly Ser
    1430              1435              1440

Phe Phe Thr Leu Asn Leu Phe  Ile Gly Val Ile Ile  Asp Asn Phe
    1445              1450              1455

Asn Gln Gln Lys Lys Lys Phe  Gly Gly Gln Asp Ile  Phe Met Thr
    1460              1465              1470

Glu Glu Gln Lys Lys Tyr Tyr  Asn Ala Met Lys Lys  Leu Gly Ser
    1475              1480              1485

Lys Lys Pro Gln Lys Pro Ile  Pro Arg Pro Gly Asn  Lys Phe Gln
    1490              1495              1500

Gly Met Val Phe Asp Phe Val  Thr Arg Gln Val Phe  Asp Ile Ser
    1505              1510              1515

Ile Met Ile Leu Ile Cys Leu  Asn Met Val Thr Met  Met Val Glu
    1520              1525              1530

Thr Asp Asp Gln Ser Glu Tyr  Val Thr Thr Ile Leu  Ser Arg Ile
    1535              1540              1545

Asn Leu Val Phe Ile Val Leu  Phe Thr Gly Glu Cys  Val Leu Lys
    1550              1555              1560

Leu Ile Ser Leu Arg His Tyr  Tyr Phe Thr Ile Gly  Trp Asn Ile
    1565              1570              1575

Phe Asp Phe Val Val Val Ile  Leu Ser Ile Val Gly  Met Phe Leu
    1580              1585              1590

Ala Glu Leu Ile Glu Lys Tyr  Phe Val Ser Pro Thr  Leu Phe Arg
    1595              1600              1605

Val Ile Arg Leu Ala Arg Ile  Gly Arg Ile Leu Arg  Leu Ile Lys
    1610              1615              1620

Gly Ala Lys Gly Ile Arg Thr  Leu Leu Phe Ala Leu  Met Met Ser
    1625              1630              1635

Leu Pro Ala Leu Phe Asn Ile  Gly Leu Leu Leu Phe  Leu Val Met
    1640              1645              1650
```

```
Phe Ile Tyr Ala Ile Phe Gly Met Ser Asn Phe Ala Tyr Val Lys
    1655              1660              1665

Arg Glu Val Gly Ile Asp Asp Met Phe Asn Phe Glu Thr Phe Gly
    1670              1675              1680

Asn Ser Met Ile Cys Leu Phe Gln Ile Thr Thr Ser Ala Gly Trp
    1685              1690              1695

Asp Gly Leu Leu Ala Pro Ile Leu Asn Ser Lys Pro Pro Asp Cys
    1700              1705              1710

Asp Pro Asn Lys Val Asn Pro Gly Ser Ser Val Lys Gly Asp Cys
    1715              1720              1725

Gly Asn Pro Ser Val Gly Ile Phe Phe Phe Val Ser Tyr Ile Ile
    1730              1735              1740

Ile Ser Phe Leu Val Val Val Asn Met Tyr Ile Ala Val Ile Leu
    1745              1750              1755

Glu Asn Phe Ser Val Ala Thr Glu Glu Ser Ala Glu Pro Leu Ser
    1760              1765              1770

Glu Asp Asp Phe Glu Met Phe Tyr Glu Val Trp Glu Lys Phe Asp
    1775              1780              1785

Pro Asp Ala Thr Gln Phe Met Glu Phe Glu Lys Leu Ser Gln Phe
    1790              1795              1800

Ala Ala Ala Leu Glu Pro Pro Leu Asn Leu Pro Gln Pro Asn Lys
    1805              1810              1815

Leu Gln Leu Ile Ala Met Asp Leu Pro Met Val Ser Gly Asp Arg
    1820              1825              1830

Ile His Cys Leu Asp Ile Leu Phe Ala Phe Thr Lys Arg Val Leu
    1835              1840              1845

Gly Glu Ser Gly Glu Met Asp Ala Leu Arg Ile Gln Met Glu Glu
    1850              1855              1860

Arg Phe Met Ala Ser Asn Pro Ser Lys Val Ser Tyr Gln Pro Ile
    1865              1870              1875

Thr Thr Thr Leu Lys Arg Lys Gln Glu Glu Val Ser Ala Val Ile
    1880              1885              1890

Ile Gln Arg Ala Tyr Arg Arg His Leu Leu Lys Arg Thr Val Lys
    1895              1900              1905

Gln Ala Ser Phe Thr Tyr Asn Lys Asn Lys Ile Lys Gly Gly Ala
    1910              1915              1920

Asn Leu Leu Ile Lys Glu Asp Met Ile Ile Asp Arg Ile Asn Glu
    1925              1930              1935

Asn Ser Ile Thr Glu Lys Thr Asp Leu Thr Met Ser Thr Ala Ala
    1940              1945              1950

Cys Pro Pro Ser Tyr Asp Arg Val Thr Lys Pro Ile Val Glu Lys
    1955              1960              1965

His Glu Gln Glu Gly Lys Asp Glu Lys Ala Lys Gly Lys
    1970              1975              1980
```

```
<210> SEQ ID NO 866
<211> LENGTH: 1997
<212> TYPE: PRT
<213> ORGANISM: Homo sapiens

<400> SEQUENCE: 866

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
```

-continued

```
          20                25                30
Lys Ala Lys Asn Pro Lys Pro Asp Lys Lys Asp Asp Asp Glu Asn Gly
        35                40                45

Pro Lys Pro Asn Ser Asp Leu Glu Ala Gly Lys Asn Leu Pro Phe Ile
        50                55                60

Tyr Gly Asp Ile Pro Pro Glu Met Val Ser Glu Pro Leu Glu Asp Leu
65                70                75                80

Asp Pro Tyr Tyr Ile Asn Lys Lys Thr Phe Ile Val Leu Asn Lys Gly
                85                90                95

Lys Ala Ile Phe Arg Phe Ser Ala Thr Ser Ala Leu Tyr Ile Leu Thr
                100               105               110

Pro Phe Asn Pro Leu Arg Lys Ile Ala Ile Lys Ile Leu Val His Ser
        115               120               125

Leu Phe Ser Met Leu Ile Met Cys Thr Ile Leu Thr Asn Cys Val Phe
        130               135               140

Met Thr Met Ser Asn Pro Pro Asp Trp Thr Lys Asn Val Glu Tyr Thr
145               150               155               160

Phe Thr Gly Ile Tyr Thr Phe Glu Ser Leu Ile Lys Ile Ile Ala Arg
                165               170               175

Gly Phe Cys Leu Glu Asp Phe Thr Phe Leu Arg Asp Pro Trp Asn Trp
                180               185               190

Leu Asp Phe Thr Val Ile Thr Phe Ala Tyr Val Thr Glu Phe Val Asp
                195               200               205

Leu Gly Asn Val Ser Ala Leu Arg Thr Phe Arg Val Leu Arg Ala Leu
        210               215               220

Lys Thr Ile Ser Val Ile Pro Gly Leu Lys Thr Ile Val Gly Ala Leu
225               230               235               240

Ile Gln Ser Val Lys Lys Leu Ser Asp Val Met Ile Leu Thr Val Phe
                245               250               255

Cys Leu Ser Val Phe Ala Leu Ile Gly Leu Gln Leu Phe Met Gly Asn
                260               265               270

Leu Arg Asn Lys Cys Ile Gln Trp Pro Pro Thr Asn Ala Ser Leu Glu
        275               280               285

Glu His Ser Ile Glu Lys Asn Ile Thr Val Asn Tyr Asn Gly Thr Leu
        290               295               300

Ile Asn Glu Thr Val Phe Glu Phe Asp Trp Lys Ser Tyr Ile Gln Asp
305               310               315               320

Ser Arg Tyr His Tyr Phe Leu Glu Gly Phe Leu Asp Ala Leu Leu Cys
                325               330               335

Gly Asn Ser Ser Asp Ala Gly Gln Cys Pro Glu Gly Tyr Met Cys Val
        340               345               350

Lys Ala Gly Arg Asn Pro Asn Tyr Gly Tyr Thr Ser Phe Asp Thr Phe
        355               360               365

Ser Trp Ala Phe Leu Ser Leu Phe Arg Leu Met Thr Gln Asp Phe Trp
        370               375               380

Glu Asn Leu Tyr Gln Leu Thr Leu Arg Ala Ala Gly Lys Thr Tyr Met
385               390               395               400

Ile Phe Phe Val Leu Val Ile Phe Leu Gly Ser Phe Tyr Leu Ile Asn
                405               410               415

Leu Ile Leu Ala Val Val Ala Met Ala Tyr Glu Glu Gln Asn Gln Ala
        420               425               430

Thr Leu Glu Glu Ala Glu Gln Lys Glu Ala Glu Phe Gln Gln Met Ile
        435               440               445
```

-continued

```
Glu Gln Leu Lys Lys Gln Gln Glu Ala Ala Gln Ala Ala Thr Ala Thr
    450             455             460

Ala Ser Glu His Ser Arg Glu Pro Ser Ala Ala Gly Arg Leu Ser Asp
465             470             475             480

Ser Ser Ser Glu Ala Ser Lys Leu Ser Ser Lys Ser Ala Lys Glu Arg
            485             490             495

Arg Asn Arg Arg Lys Lys Arg Lys Gln Lys Glu Gln Ser Gly Gly Glu
            500             505             510

Glu Lys Asp Glu Asp Glu Phe Gln Lys Ser Glu Ser Glu Asp Ser Ile
            515             520             525

Arg Arg Lys Gly Phe Arg Phe Ser Ile Glu Gly Asn Arg Leu Thr Tyr
            530             535             540

Glu Lys Arg Tyr Ser Ser Pro His Gln Ser Leu Leu Ser Ile Arg Gly
545             550             555             560

Ser Leu Phe Ser Pro Arg Arg Asn Ser Arg Thr Ser Leu Phe Ser Phe
            565             570             575

Arg Gly Arg Ala Lys Asp Val Gly Ser Glu Asn Asp Phe Ala Asp Asp
            580             585             590

Glu His Ser Thr Phe Glu Asp Asn Glu Ser Arg Arg Asp Ser Leu Phe
            595             600             605

Val Pro Arg Arg His Gly Glu Arg Arg Asn Ser Asn Leu Ser Gln Thr
    610             615             620

Ser Arg Ser Ser Arg Met Leu Ala Val Phe Pro Ala Asn Gly Lys Met
625             630             635             640

His Ser Thr Val Asp Cys Asn Gly Val Val Ser Leu Val Gly Gly Pro
            645             650             655

Ser Val Pro Thr Ser Pro Val Gly Gln Leu Leu Pro Glu Gly Thr Thr
            660             665             670

Thr Glu Thr Glu Met Arg Lys Arg Arg Ser Ser Ser Phe His Val Ser
            675             680             685

Met Asp Phe Leu Glu Asp Pro Ser Gln Arg Gln Arg Ala Met Ser Ile
    690             695             700

Ala Ser Ile Leu Thr Asn Thr Val Glu Glu Leu Glu Glu Ser Arg Gln
705             710             715             720

Lys Cys Pro Pro Cys Trp Tyr Lys Phe Ser Asn Ile Phe Leu Ile Trp
            725             730             735

Asp Cys Ser Pro Tyr Trp Leu Lys Val Lys His Val Val Asn Leu Val
            740             745             750

Val Met Asp Pro Phe Val Asp Leu Ala Ile Thr Ile Cys Ile Val Leu
            755             760             765

Asn Thr Leu Phe Met Ala Met Glu His Tyr Pro Met Thr Asp His Phe
    770             775             780

Asn Asn Val Leu Thr Val Gly Asn Leu Val Phe Thr Gly Ile Phe Thr
785             790             795             800

Ala Glu Met Phe Leu Lys Ile Ile Ala Met Asp Pro Tyr Tyr Tyr Phe
            805             810             815

Gln Glu Gly Trp Asn Ile Phe Asp Gly Phe Ile Val Thr Leu Ser Leu
            820             825             830

Val Glu Leu Gly Leu Ala Asn Val Glu Gly Leu Ser Val Leu Arg Ser
            835             840             845

Phe Arg Leu Leu Arg Val Phe Lys Leu Ala Lys Ser Trp Pro Thr Leu
    850             855             860
```

-continued

```
Asn Met Leu Ile Lys Ile Ile Gly Asn Ser Val Gly Ala Leu Gly Asn
865             870             875             880

Leu Thr Leu Val Leu Ala Ile Ile Val Phe Ile Phe Ala Val Val Gly
                885             890             895

Met Gln Leu Phe Gly Lys Ser Tyr Lys Asp Cys Val Cys Lys Ile Ala
            900             905             910

Ser Asp Cys Gln Leu Pro Arg Trp His Met Asn Asp Phe Phe His Ser
            915             920             925

Phe Leu Ile Val Phe Arg Val Leu Cys Gly Glu Trp Ile Glu Thr Met
        930             935             940

Trp Asp Cys Met Glu Val Ala Gly Gln Ala Met Cys Leu Thr Val Phe
945             950             955             960

Met Met Val Met Val Ile Gly Asn Leu Val Val Leu Asn Leu Phe Leu
            965             970             975

Ala Leu Leu Leu Ser Ser Phe Ser Ala Asp Asn Leu Ala Ala Thr Asp
            980             985             990

Asp Asp Asn Glu Met Asn Asn Leu  Gln Ile Ala Val Asp  Arg Met His
        995             1000            1005

Lys Gly  Val Ala Tyr Val Lys  Arg Lys Ile Tyr Glu  Phe Ile Gln
    1010            1015            1020

Gln Ser  Phe Ile Arg Lys Gln  Lys Ile Leu Asp Glu  Ile Lys Pro
    1025            1030            1035

Leu Asp  Asp Leu Asn Asn Lys  Lys Asp Ser Cys Met  Ser Asn His
    1040            1045            1050

Thr Ala  Glu Ile Gly Lys Asp  Leu Asp Tyr Leu Lys  Asp Val Asn
    1055            1060            1065

Gly Thr  Thr Ser Gly Ile Gly  Thr Gly Ser Ser Val  Glu Lys Tyr
    1070            1075            1080

Ile Ile  Asp Glu Ser Asp Tyr  Met Ser Phe Ile Asn  Asn Pro Ser
    1085            1090            1095

Leu Thr  Val Thr Val Pro Ile  Ala Val Gly Glu Ser  Asp Phe Glu
    1100            1105            1110

Asn Leu  Asn Thr Glu Asp Phe  Ser Ser Glu Ser Asp  Leu Glu Glu
    1115            1120            1125

Ser Lys  Glu Lys Leu Asn Glu  Ser Ser Ser Ser Ser  Glu Gly Ser
    1130            1135            1140

Thr Val  Asp Ile Gly Ala Pro  Val Glu Glu Gln Pro  Val Val Glu
    1145            1150            1155

Pro Glu  Glu Thr Leu Glu Pro  Glu Ala Cys Phe Thr  Glu Gly Cys
    1160            1165            1170

Val Gln  Arg Phe Lys Cys Cys  Gln Ile Asn Val Glu  Glu Gly Arg
    1175            1180            1185

Gly Lys  Gln Trp Trp Asn Leu  Arg Arg Thr Cys Phe  Arg Ile Val
    1190            1195            1200

Glu His  Asn Trp Phe Glu Thr  Phe Ile Val Phe Met  Ile Leu Leu
    1205            1210            1215

Ser Ser  Gly Ala Leu Ala Phe  Glu Asp Ile Tyr Ile  Asp Gln Arg
    1220            1225            1230

Lys Thr  Ile Lys Thr Met Leu  Glu Tyr Ala Asp Lys  Val Phe Thr
    1235            1240            1245

Tyr Ile  Phe Ile Leu Glu Met  Leu Leu Lys Trp Val  Ala Tyr Gly
    1250            1255            1260

Tyr Gln  Thr Tyr Phe Thr Asn  Ala Trp Cys Trp Leu  Asp Phe Leu
```

-continued

```
        1265                    1270                    1275

Ile Val  Asp Val Ser Leu Val  Ser Leu Thr Ala Asn  Ala Leu Gly
        1280                    1285                    1290

Tyr Ser  Glu Leu Gly Ala Ile  Lys Ser Leu Arg Thr  Leu Arg Ala
        1295                    1300                    1305

Leu Arg  Pro Leu Arg Ala Leu  Ser Arg Phe Glu Gly  Met Arg Val
        1310                    1315                    1320

Val Val  Asn Ala Leu Leu Gly  Ala Ile Pro Ser Ile  Met Asn Val
        1325                    1330                    1335

Leu Leu  Val Cys Leu Ile Phe  Trp Leu Ile Phe Ser  Ile Met Gly
        1340                    1345                    1350

Val Asn  Leu Phe Ala Gly Lys  Phe Tyr His Cys Ile  Asn Thr Thr
        1355                    1360                    1365

Thr Gly  Asp Arg Phe Asp Ile  Glu Asp Val Asn Asn  His Thr Asp
        1370                    1375                    1380

Cys Leu  Lys Leu Ile Glu Arg  Asn Glu Thr Ala Arg  Trp Lys Asn
        1385                    1390                    1395

Val Lys  Val Asn Phe Asp Asn  Val Gly Phe Gly Tyr  Leu Ser Leu
        1400                    1405                    1410

Leu Gln  Val Ala Thr Phe Lys  Gly Trp Met Asp Ile  Met Tyr Ala
        1415                    1420                    1425

Ala Val  Asp Ser Arg Asn Val  Glu Leu Gln Pro Lys  Tyr Glu Glu
        1430                    1435                    1440

Ser Leu  Tyr Met Tyr Leu Tyr  Phe Val Ile Phe Ile  Ile Phe Gly
        1445                    1450                    1455

Ser Phe  Phe Thr Leu Asn Leu  Phe Ile Gly Val Ile  Ile Asp Asn
        1460                    1465                    1470

Phe Asn  Gln Gln Lys Lys Lys  Phe Gly Gly Gln Asp  Ile Phe Met
        1475                    1480                    1485

Thr Glu  Glu Gln Lys Lys Tyr  Tyr Asn Ala Met Lys  Lys Leu Gly
        1490                    1495                    1500

Ser Lys  Lys Pro Gln Lys Pro  Ile Pro Arg Pro Gly  Asn Lys Phe
        1505                    1510                    1515

Gln Gly  Met Val Phe Asp Phe  Val Thr Arg Gln Val  Phe Asp Ile
        1520                    1525                    1530

Ser Ile  Met Ile Leu Ile Cys  Leu Asn Met Val Thr  Met Met Val
        1535                    1540                    1545

Glu Thr  Asp Asp Gln Ser Glu  Tyr Val Thr Thr Ile  Leu Ser Arg
        1550                    1555                    1560

Ile Asn  Leu Val Phe Ile Val  Leu Phe Thr Gly Glu  Cys Val Leu
        1565                    1570                    1575

Lys Leu  Ile Ser Leu Arg His  Tyr Tyr Phe Thr Ile  Gly Trp Asn
        1580                    1585                    1590

Ile Phe  Asp Phe Val Val Val  Ile Leu Ser Ile Val  Gly Met Phe
        1595                    1600                    1605

Leu Ala  Glu Leu Ile Glu Lys  Tyr Phe Val Ser Pro  Thr Leu Phe
        1610                    1615                    1620

Arg Val  Ile Arg Leu Ala Arg  Ile Gly Arg Ile Leu  Arg Leu Ile
        1625                    1630                    1635

Lys Gly  Ala Lys Gly Ile Arg  Thr Leu Leu Phe Ala  Leu Met Met
        1640                    1645                    1650

Ser Leu  Pro Ala Leu Phe Asn  Ile Gly Leu Leu Leu  Phe Leu Val
        1655                    1660                    1665
```

```
Met Phe  Ile Tyr Ala Ile Phe  Gly Met Ser Asn Phe  Ala Tyr Val
    1670             1675             1680

Lys Arg  Glu Val Gly Ile Asp  Asp Met Phe Asn Phe  Glu Thr Phe
    1685             1690             1695

Gly Asn  Ser Met Ile Cys Leu  Phe Gln Ile Thr Thr  Ser Ala Gly
    1700             1705             1710

Trp Asp  Gly Leu Leu Ala Pro  Ile Leu Asn Ser Lys  Pro Pro Asp
    1715             1720             1725

Cys Asp  Pro Asn Lys Val Asn  Pro Gly Ser Ser Val  Lys Gly Asp
    1730             1735             1740

Cys Gly  Asn Pro Ser Val Gly  Ile Phe Phe Phe Val  Ser Tyr Ile
    1745             1750             1755

Ile Ile  Ser Phe Leu Val Val  Val Asn Met Tyr Ile  Ala Val Ile
    1760             1765             1770

Leu Glu  Asn Phe Ser Val Ala  Thr Glu Glu Ser Ala  Glu Pro Leu
    1775             1780             1785

Ser Glu  Asp Asp Phe Glu Met  Phe Tyr Glu Val Trp  Glu Lys Phe
    1790             1795             1800

Asp Pro  Asp Ala Thr Gln Phe  Met Glu Phe Glu Lys  Leu Ser Gln
    1805             1810             1815

Phe Ala  Ala Ala Leu Glu Pro  Pro Leu Asn Leu Pro  Gln Pro Asn
    1820             1825             1830

Lys Leu  Gln Leu Ile Ala Met  Asp Leu Pro Met Val  Ser Gly Asp
    1835             1840             1845

Arg Ile  His Cys Leu Asp Ile  Leu Phe Ala Phe Thr  Lys Arg Val
    1850             1855             1860

Leu Gly  Glu Ser Gly Glu Met  Asp Ala Leu Arg Ile  Gln Met Glu
    1865             1870             1875

Glu Arg  Phe Met Ala Ser Asn  Pro Ser Lys Val Ser  Tyr Gln Pro
    1880             1885             1890

Ile Thr  Thr Thr Leu Lys Arg  Lys Gln Glu Glu Val  Ser Ala Val
    1895             1900             1905

Ile Ile  Gln Arg Ala Tyr Arg  Arg His Leu Leu Lys  Arg Thr Val
    1910             1915             1920

Lys Gln  Ala Ser Phe Thr Tyr  Asn Lys Asn Lys Ile  Lys Gly Gly
    1925             1930             1935

Ala Asn  Leu Leu Ile Lys Glu  Asp Met Ile Ile Asp  Arg Ile Asn
    1940             1945             1950

Glu Asn  Ser Ile Thr Glu Lys  Thr Asp Leu Thr Met  Ser Thr Ala
    1955             1960             1965

Ala Cys  Pro Pro Ser Tyr Asp  Arg Val Thr Lys Pro  Ile Val Glu
    1970             1975             1980

Lys His  Glu Gln Glu Gly Lys  Asp Glu Lys Ala Lys  Gly Lys
    1985             1990             1995
```

```
<210> SEQ ID NO 867
<211> LENGTH: 1980
<212> TYPE: PRT
<213> ORGANISM: Homo sapiens

<400> SEQUENCE: 867

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
```

-continued

```
               20                    25                    30

Lys Ala Lys Asn Pro Lys Pro Asp Lys Lys Asp Asp Asp Glu Asn Gly
            35                    40                    45

Pro Lys Pro Asn Ser Asp Leu Glu Ala Gly Lys Asn Leu Pro Phe Ile
       50                    55                    60

Tyr Gly Asp Ile Pro Pro Glu Met Val Ser Glu Pro Leu Glu Asp Leu
65                    70                    75                    80

Asp Pro Tyr Tyr Ile Asn Lys Lys Thr Phe Ile Val Leu Asn Lys Gly
                 85                    90                    95

Lys Ala Ile Phe Arg Phe Ser Ala Thr Ser Ala Leu Tyr Ile Leu Thr
            100                   105                   110

Pro Phe Asn Pro Leu Arg Lys Ile Ala Ile Lys Ile Leu Val His Ser
            115                   120                   125

Leu Phe Ser Met Leu Ile Met Cys Thr Ile Leu Thr Asn Cys Val Phe
       130                   135                   140

Met Thr Met Ser Asn Pro Pro Asp Trp Thr Lys Asn Val Glu Tyr Thr
145                   150                   155                   160

Phe Thr Gly Ile Tyr Thr Phe Glu Ser Leu Ile Lys Ile Ile Ala Arg
                 165                   170                   175

Gly Phe Cys Leu Glu Asp Phe Thr Phe Leu Arg Asp Pro Trp Asn Trp
            180                   185                   190

Leu Asp Phe Thr Val Ile Thr Phe Ala Tyr Val Thr Glu Phe Val Asp
            195                   200                   205

Leu Gly Asn Val Ser Ala Leu Arg Thr Phe Arg Val Leu Arg Ala Leu
       210                   215                   220

Lys Thr Ile Ser Val Ile Pro Gly Leu Lys Thr Ile Val Gly Ala Leu
225                   230                   235                   240

Ile Gln Ser Val Lys Lys Leu Ser Asp Val Met Ile Leu Thr Val Phe
                 245                   250                   255

Cys Leu Ser Val Phe Ala Leu Ile Gly Leu Gln Leu Phe Met Gly Asn
            260                   265                   270

Leu Arg Asn Lys Cys Ile Gln Trp Pro Pro Thr Asn Ala Ser Leu Glu
            275                   280                   285

Glu His Ser Ile Glu Lys Asn Ile Thr Val Asn Tyr Asn Gly Thr Leu
       290                   295                   300

Ile Asn Glu Thr Val Phe Glu Phe Asp Trp Lys Ser Tyr Ile Gln Asp
305                   310                   315                   320

Ser Arg Tyr His Tyr Phe Leu Glu Gly Phe Leu Asp Ala Leu Leu Cys
            325                   330                   335

Gly Asn Ser Ser Asp Ala Gly Gln Cys Pro Glu Gly Tyr Met Cys Val
            340                   345                   350

Lys Ala Gly Arg Asn Pro Asn Tyr Gly Tyr Thr Ser Phe Asp Thr Phe
            355                   360                   365

Ser Trp Ala Phe Leu Ser Leu Phe Arg Leu Met Thr Gln Asp Phe Trp
       370                   375                   380

Glu Asn Leu Tyr Gln Leu Thr Leu Arg Ala Ala Gly Lys Thr Tyr Met
385                   390                   395                   400

Ile Phe Phe Val Leu Val Ile Phe Leu Gly Ser Phe Tyr Leu Ile Asn
                 405                   410                   415

Leu Ile Leu Ala Val Val Ala Met Ala Tyr Glu Glu Gln Asn Gln Ala
            420                   425                   430

Thr Leu Glu Glu Ala Glu Gln Lys Glu Ala Glu Phe Gln Gln Met Ile
            435                   440                   445
```

-continued

```
Glu Gln Leu Lys Lys Gln Gln Glu Ala Ala Gln Ala Ala Thr Ala Thr
    450             455             460

Ala Ser Glu His Ser Arg Glu Pro Ser Ala Ala Gly Arg Leu Ser Asp
465             470             475             480

Ser Ser Ser Glu Ala Ser Lys Leu Ser Ser Lys Ser Ala Lys Glu Arg
            485             490             495

Arg Asn Arg Arg Lys Lys Arg Lys Gln Lys Glu Gln Ser Gly Gly Glu
            500             505             510

Glu Lys Asp Glu Asp Glu Phe Gln Lys Ser Glu Ser Glu Asp Ser Ile
            515             520             525

Arg Arg Lys Gly Phe Arg Phe Ser Ile Glu Gly Asn Arg Leu Thr Tyr
    530             535             540

Glu Lys Arg Tyr Ser Ser Pro His Gln Ser Leu Leu Ser Ile Arg Gly
545             550             555             560

Ser Leu Phe Ser Pro Arg Arg Asn Ser Arg Thr Ser Leu Phe Ser Phe
            565             570             575

Arg Gly Arg Ala Lys Asp Val Gly Ser Glu Asn Asp Phe Ala Asp Asp
            580             585             590

Glu His Ser Thr Phe Glu Asp Asn Glu Ser Arg Arg Asp Ser Leu Phe
            595             600             605

Val Pro Arg Arg His Gly Glu Arg Arg Asn Ser Asn Leu Ser Gln Thr
    610             615             620

Ser Arg Ser Ser Arg Met Leu Ala Val Phe Pro Ala Asn Gly Lys Met
625             630             635             640

His Ser Thr Val Asp Cys Asn Gly Val Val Ser Leu Gly Thr Thr Thr
            645             650             655

Glu Thr Glu Met Arg Lys Arg Arg Ser Ser Ser Phe His Val Ser Met
            660             665             670

Asp Phe Leu Glu Asp Pro Ser Gln Arg Gln Arg Ala Met Ser Ile Ala
            675             680             685

Ser Ile Leu Thr Asn Thr Val Glu Glu Leu Glu Glu Ser Arg Gln Lys
    690             695             700

Cys Pro Pro Cys Trp Tyr Lys Phe Ser Asn Ile Phe Leu Ile Trp Asp
705             710             715             720

Cys Ser Pro Tyr Trp Leu Lys Val Lys His Val Val Asn Leu Val Val
            725             730             735

Met Asp Pro Phe Val Asp Leu Ala Ile Thr Ile Cys Ile Val Leu Asn
            740             745             750

Thr Leu Phe Met Ala Met Glu His Tyr Pro Met Thr Asp His Phe Asn
            755             760             765

Asn Val Leu Thr Val Gly Asn Leu Val Phe Thr Gly Ile Phe Thr Ala
    770             775             780

Glu Met Phe Leu Lys Ile Ile Ala Met Asp Pro Tyr Tyr Tyr Phe Gln
785             790             795             800

Glu Gly Trp Asn Ile Phe Asp Gly Phe Ile Val Thr Leu Ser Leu Val
            805             810             815

Glu Leu Gly Leu Ala Asn Val Glu Gly Leu Ser Val Leu Arg Ser Phe
            820             825             830

Arg Leu Leu Arg Val Phe Lys Leu Ala Lys Ser Trp Pro Thr Leu Asn
            835             840             845

Met Leu Ile Lys Ile Ile Gly Asn Ser Val Gly Ala Leu Gly Asn Leu
    850             855             860
```

-continued

```
Thr Leu Val Leu Ala Ile Ile Val Phe Ile Phe Ala Val Val Gly Met
865             870             875             880

Gln Leu Phe Gly Lys Ser Tyr Lys Asp Cys Val Cys Lys Ile Ala Ser
            885             890             895

Asp Cys Gln Leu Pro Arg Trp His Met Asn Asp Phe Phe His Ser Phe
            900             905             910

Leu Ile Val Phe Arg Val Leu Cys Gly Glu Trp Ile Glu Thr Met Trp
        915             920             925

Asp Cys Met Glu Val Ala Gly Gln Ala Met Cys Leu Thr Val Phe Met
        930             935             940

Met Val Met Val Ile Gly Asn Leu Val Val Leu Asn Leu Phe Leu Ala
945             950             955             960

Leu Leu Leu Ser Ser Phe Ser Ala Asp Asn Leu Ala Ala Thr Asp Asp
            965             970             975

Asp Asn Glu Met Asn Asn Leu Gln Ile Ala Val Asp Arg Met His Lys
            980             985             990

Gly Val Ala Tyr Val Lys Arg Lys  Ile Tyr Glu Phe Ile  Gln Gln Ser
        995             1000            1005

Phe Ile Arg Lys Gln Lys Ile  Leu Asp Glu Ile Lys  Pro Leu Asp
    1010            1015            1020

Asp Leu Asn Asn Lys Lys Asp  Ser Cys Met Ser Asn  His Thr Ala
    1025            1030            1035

Glu Ile Gly Lys Asp Leu Asp  Tyr Leu Lys Asp Val  Asn Gly Thr
    1040            1045            1050

Thr Ser Gly Ile Gly Thr Gly  Ser Ser Val Glu Lys  Tyr Ile Ile
    1055            1060            1065

Asp Glu Ser Asp Tyr Met Ser  Phe Ile Asn Asn Pro  Ser Leu Thr
    1070            1075            1080

Val Thr Val Pro Ile Ala Val  Gly Glu Ser Asp Phe  Glu Asn Leu
    1085            1090            1095

Asn Thr Glu Asp Phe Ser Ser  Glu Ser Asp Leu Glu  Glu Ser Lys
    1100            1105            1110

Glu Lys Leu Asn Glu Ser Ser  Ser Ser Ser Glu Gly  Ser Thr Val
    1115            1120            1125

Asp Ile Gly Ala Pro Val Glu  Glu Gln Pro Val Val  Glu Pro Glu
    1130            1135            1140

Glu Thr Leu Glu Pro Glu Ala  Cys Phe Thr Glu Gly  Cys Val Gln
    1145            1150            1155

Arg Phe Lys Cys Cys Gln Ile  Asn Val Glu Glu Gly  Arg Gly Lys
    1160            1165            1170

Gln Trp Trp Asn Leu Arg Arg  Thr Cys Phe Arg Ile  Val Glu His
    1175            1180            1185

Asn Trp Phe Glu Thr Phe Ile  Val Phe Met Ile Leu  Leu Ser Ser
    1190            1195            1200

Gly Ala Leu Ala Phe Glu Asp  Ile Tyr Ile Asp Gln  Arg Lys Thr
    1205            1210            1215

Ile Lys Thr Met Leu Glu Tyr  Ala Asp Lys Val Phe  Thr Tyr Ile
    1220            1225            1230

Phe Ile Leu Glu Met Leu Leu  Lys Trp Val Ala Tyr  Gly Tyr Gln
    1235            1240            1245

Thr Tyr Phe Thr Asn Ala Trp  Cys Trp Leu Asp Phe  Leu Ile Val
    1250            1255            1260

Asp Val Ser Leu Val Ser Leu  Thr Ala Asn Ala Leu  Gly Tyr Ser
```

-continued

```
    1265                1270                1275

Glu Leu  Gly Ala Ile Lys Ser  Leu Arg Thr Leu Arg  Ala Leu Arg
    1280                1285                1290

Pro Leu  Arg Ala Leu Ser Arg  Phe Glu Gly Met Arg  Val Val Val
    1295                1300                1305

Asn Ala  Leu Leu Gly Ala Ile  Pro Ser Ile Met Asn  Val Leu Leu
    1310                1315                1320

Val Cys  Leu Ile Phe Trp Leu  Ile Phe Ser Ile Met  Gly Val Asn
    1325                1330                1335

Leu Phe  Ala Gly Lys Phe Tyr  His Cys Ile Asn Thr  Thr Thr Gly
    1340                1345                1350

Asp Arg  Phe Asp Ile Glu Asp  Val Asn Asn His Thr  Asp Cys Leu
    1355                1360                1365

Lys Leu  Ile Glu Arg Asn Glu  Thr Ala Arg Trp Lys  Asn Val Lys
    1370                1375                1380

Val Asn  Phe Asp Asn Val Gly  Phe Gly Tyr Leu Ser  Leu Leu Gln
    1385                1390                1395

Val Ala  Thr Phe Lys Gly Trp  Met Asp Ile Met Tyr  Ala Ala Val
    1400                1405                1410

Asp Ser  Arg Asn Val Glu Leu  Gln Pro Lys Tyr Glu  Glu Ser Leu
    1415                1420                1425

Tyr Met  Tyr Leu Tyr Phe Val  Ile Phe Ile Ile Phe  Gly Ser Phe
    1430                1435                1440

Phe Thr  Leu Asn Leu Phe Ile  Gly Val Ile Ile Asp  Asn Phe Asn
    1445                1450                1455

Gln Gln  Lys Lys Lys Phe Gly  Gly Gln Asp Ile Phe  Met Thr Glu
    1460                1465                1470

Glu Gln  Lys Lys Tyr Tyr Asn  Ala Met Lys Lys Leu  Gly Ser Lys
    1475                1480                1485

Lys Pro  Gln Lys Pro Ile Pro  Arg Pro Gly Asn Lys  Phe Gln Gly
    1490                1495                1500

Met Val  Phe Asp Phe Val Thr  Arg Gln Val Phe Asp  Ile Ser Ile
    1505                1510                1515

Met Ile  Leu Ile Cys Leu Asn  Met Val Thr Met Met  Val Glu Thr
    1520                1525                1530

Asp Asp  Gln Ser Glu Tyr Val  Thr Thr Ile Leu Ser  Arg Ile Asn
    1535                1540                1545

Leu Val  Phe Ile Val Leu Phe  Thr Gly Glu Cys Val  Leu Lys Leu
    1550                1555                1560

Ile Ser  Leu Arg His Tyr Tyr  Phe Thr Ile Gly Trp  Asn Ile Phe
    1565                1570                1575

Asp Phe  Val Val Val Ile Leu  Ser Ile Val Gly Met  Phe Leu Ala
    1580                1585                1590

Glu Leu  Ile Glu Lys Tyr Phe  Val Ser Pro Thr Leu  Phe Arg Val
    1595                1600                1605

Ile Arg  Leu Ala Arg Ile Gly  Arg Ile Leu Arg Leu  Ile Lys Gly
    1610                1615                1620

Ala Lys  Gly Ile Arg Thr Leu  Leu Phe Ala Leu Met  Met Ser Leu
    1625                1630                1635

Pro Ala  Leu Phe Asn Ile Gly  Leu Leu Leu Phe Leu  Val Met Phe
    1640                1645                1650

Ile Tyr  Ala Ile Phe Gly Met  Ser Asn Phe Ala Tyr  Val Lys Arg
    1655                1660                1665
```

```
Glu Val Gly Ile Asp Asp Met  Phe Asn Phe Glu Thr  Phe Gly Asn
    1670            1675            1680

Ser Met  Ile Cys Leu Phe Gln  Ile Thr Thr Ser Ala  Gly Trp Asp
    1685            1690            1695

Gly Leu  Leu Ala Pro Ile Leu  Asn Ser Lys Pro Pro  Asp Cys Asp
    1700            1705            1710

Pro Asn  Lys Val Asn Pro Gly  Ser Ser Val Lys Gly  Asp Cys Gly
    1715            1720            1725

Asn Pro  Ser Val Gly Ile Phe  Phe Phe Val Ser Tyr  Ile Ile Ile
    1730            1735            1740

Ser Phe  Leu Val Val Val Asn  Met Tyr Ile Ala Val  Ile Leu Glu
    1745            1750            1755

Asn Phe  Ser Val Ala Thr Glu  Glu Ser Ala Glu Pro  Leu Ser Glu
    1760            1765            1770

Asp Asp  Phe Glu Met Phe Tyr  Glu Val Trp Glu Lys  Phe Asp Pro
    1775            1780            1785

Asp Ala  Thr Gln Phe Met Glu  Phe Glu Lys Leu Ser  Gln Phe Ala
    1790            1795            1800

Ala Ala  Leu Glu Pro Pro Leu  Asn Leu Pro Gln Pro  Asn Lys Leu
    1805            1810            1815

Gln Leu  Ile Ala Met Asp Leu  Pro Met Val Ser Gly  Asp Arg Ile
    1820            1825            1830

His Cys  Leu Asp Ile Leu Phe  Ala Phe Thr Lys Arg  Val Leu Gly
    1835            1840            1845

Glu Ser  Gly Glu Met Asp Ala  Leu Arg Ile Gln Met  Glu Glu Arg
    1850            1855            1860

Phe Met  Ala Ser Asn Pro Ser  Lys Val Ser Tyr Gln  Pro Ile Thr
    1865            1870            1875

Thr Thr  Leu Lys Arg Lys Gln  Glu Glu Val Ser Ala  Val Ile Ile
    1880            1885            1890

Gln Arg  Ala Tyr Arg Arg His  Leu Leu Lys Arg Thr  Val Lys Gln
    1895            1900            1905

Ala Ser  Phe Thr Tyr Asn Lys  Asn Lys Ile Lys Gly  Gly Ala Asn
    1910            1915            1920

Leu Leu  Ile Lys Glu Asp Met  Ile Ile Asp Arg Ile  Asn Glu Asn
    1925            1930            1935

Ser Ile  Thr Glu Lys Thr Asp  Leu Thr Met Ser Thr  Ala Ala Cys
    1940            1945            1950

Pro Pro  Ser Tyr Asp Arg Val  Thr Lys Pro Ile Val  Glu Lys His
    1955            1960            1965

Glu Gln  Glu Gly Lys Asp Glu  Lys Ala Lys Gly Lys
    1970            1975            1980
```

<210> SEQ ID NO 868
<211> LENGTH: 1195
<212> TYPE: PRT
<213> ORGANISM: Homo sapiens

<400> SEQUENCE: 868

```
Met Phe Leu Lys Ile Ile Ala Met Asp Pro Tyr Tyr Tyr Phe Gln Glu
1               5               10              15

Gly Trp Asn Ile Phe Asp Gly Phe Ile Val Thr Leu Ser Leu Val Glu
            20              25              30

Leu Gly Leu Ala Asn Val Glu Gly Leu Ser Val Leu Arg Ser Phe Arg
```

-continued

```
              35                  40                  45
Leu Leu Arg Val Phe Lys Leu Ala Lys Ser Trp Pro Thr Leu Asn Met
    50                  55                  60

Leu Ile Lys Ile Ile Gly Asn Ser Val Gly Ala Leu Gly Asn Leu Thr
65                  70                  75                  80

Leu Val Leu Ala Ile Ile Val Phe Ile Phe Ala Val Val Gly Met Gln
                85                  90                  95

Leu Phe Gly Lys Ser Tyr Lys Asp Cys Val Cys Lys Ile Ala Ser Asp
            100                 105                 110

Cys Gln Leu Pro Arg Trp His Met Asn Asp Phe Phe His Ser Phe Leu
            115                 120                 125

Ile Val Phe Arg Val Leu Cys Gly Glu Trp Ile Glu Thr Met Trp Asp
    130                 135                 140

Cys Met Glu Val Ala Gly Gln Ala Met Cys Leu Thr Val Phe Met Met
145                 150                 155                 160

Val Met Val Ile Gly Asn Leu Val Val Leu Asn Leu Phe Leu Ala Leu
                165                 170                 175

Leu Leu Ser Ser Phe Ser Ala Asp Asn Leu Ala Ala Thr Asp Asp Asp
            180                 185                 190

Asn Glu Met Asn Asn Leu Gln Ile Ala Val Asp Arg Met His Lys Gly
            195                 200                 205

Val Ala Tyr Val Lys Arg Lys Ile Tyr Glu Phe Ile Gln Gln Ser Phe
    210                 215                 220

Ile Arg Lys Gln Lys Ile Leu Asp Glu Ile Lys Pro Leu Asp Asp Leu
225                 230                 235                 240

Asn Asn Lys Lys Asp Ser Cys Met Ser Asn His Thr Ala Glu Ile Gly
            245                 250                 255

Lys Asp Leu Asp Tyr Leu Lys Asp Val Asn Gly Thr Thr Ser Gly Ile
            260                 265                 270

Gly Thr Gly Ser Ser Val Glu Lys Tyr Ile Ile Asp Glu Ser Asp Tyr
            275                 280                 285

Met Ser Phe Ile Asn Asn Pro Ser Leu Thr Val Thr Val Pro Ile Ala
    290                 295                 300

Val Gly Glu Ser Asp Phe Glu Asn Leu Asn Thr Glu Asp Phe Ser Ser
305                 310                 315                 320

Glu Ser Asp Leu Glu Glu Ser Lys Glu Lys Leu Asn Glu Ser Ser Ser
            325                 330                 335

Ser Ser Glu Gly Ser Thr Val Asp Ile Gly Ala Pro Val Glu Glu Gln
            340                 345                 350

Pro Val Val Glu Pro Glu Glu Thr Leu Glu Pro Glu Ala Cys Phe Thr
            355                 360                 365

Glu Gly Cys Val Gln Arg Phe Lys Cys Cys Gln Ile Asn Val Glu Glu
            370                 375                 380

Gly Arg Gly Lys Gln Trp Trp Asn Leu Arg Arg Thr Cys Phe Arg Ile
385                 390                 395                 400

Val Glu His Asn Trp Phe Glu Thr Phe Ile Val Phe Met Ile Leu Leu
                405                 410                 415

Ser Ser Gly Ala Leu Ala Phe Glu Asp Ile Tyr Ile Asp Gln Arg Lys
            420                 425                 430

Thr Ile Lys Thr Met Leu Glu Tyr Ala Asp Lys Val Phe Thr Tyr Ile
            435                 440                 445

Phe Ile Leu Glu Met Leu Leu Lys Trp Val Ala Tyr Gly Tyr Gln Thr
    450                 455                 460
```

-continued

```
Tyr Phe Thr Asn Ala Trp Cys Trp Leu Asp Phe Leu Ile Val Asp Val
465                 470                 475                 480

Ser Leu Val Ser Leu Thr Ala Asn Ala Leu Gly Tyr Ser Glu Leu Gly
                485                 490                 495

Ala Ile Lys Ser Leu Arg Thr Leu Arg Ala Leu Arg Pro Leu Arg Ala
                500                 505                 510

Leu Ser Arg Phe Glu Gly Met Arg Val Val Val Asn Ala Leu Leu Gly
            515                 520                 525

Ala Ile Pro Ser Ile Met Asn Val Leu Leu Val Cys Leu Ile Phe Trp
        530                 535                 540

Leu Ile Phe Ser Ile Met Gly Val Asn Leu Phe Ala Gly Lys Phe Tyr
545                 550                 555                 560

His Cys Ile Asn Thr Thr Thr Gly Asp Arg Phe Asp Ile Glu Asp Val
            565                 570                 575

Asn Asn His Thr Asp Cys Leu Lys Leu Ile Glu Arg Asn Glu Thr Ala
            580                 585                 590

Arg Trp Lys Asn Val Lys Val Asn Phe Asp Asn Val Gly Phe Gly Tyr
        595                 600                 605

Leu Ser Leu Leu Gln Val Ala Thr Phe Lys Gly Trp Met Asp Ile Met
        610                 615                 620

Tyr Ala Ala Val Asp Ser Arg Asn Val Glu Leu Gln Pro Lys Tyr Glu
625                 630                 635                 640

Glu Ser Leu Tyr Met Tyr Leu Tyr Phe Val Ile Phe Ile Ile Phe Gly
            645                 650                 655

Ser Phe Phe Thr Leu Asn Leu Phe Ile Gly Val Ile Ile Asp Asn Phe
            660                 665                 670

Asn Gln Gln Lys Lys Lys Phe Gly Gly Gln Asp Ile Phe Met Thr Glu
            675                 680                 685

Glu Gln Lys Lys Tyr Tyr Asn Ala Met Lys Lys Leu Gly Ser Lys Lys
        690                 695                 700

Pro Gln Lys Pro Ile Pro Arg Pro Gly Asn Lys Phe Gln Gly Met Val
705                 710                 715                 720

Phe Asp Phe Val Thr Arg Gln Val Phe Asp Ile Ser Ile Met Ile Leu
            725                 730                 735

Ile Cys Leu Asn Met Val Thr Met Met Val Glu Thr Asp Asp Gln Ser
            740                 745                 750

Glu Tyr Val Thr Thr Ile Leu Ser Arg Ile Asn Leu Val Phe Ile Val
            755                 760                 765

Leu Phe Thr Gly Glu Cys Val Leu Lys Leu Ile Ser Leu Arg His Tyr
        770                 775                 780

Tyr Phe Thr Ile Gly Trp Asn Ile Phe Asp Phe Val Val Val Ile Leu
785                 790                 795                 800

Ser Ile Val Gly Met Phe Leu Ala Glu Leu Ile Glu Lys Tyr Phe Val
                805                 810                 815

Ser Pro Thr Leu Phe Arg Val Ile Arg Leu Ala Arg Ile Gly Arg Ile
            820                 825                 830

Leu Arg Leu Ile Lys Gly Ala Lys Gly Ile Arg Thr Leu Leu Phe Ala
        835                 840                 845

Leu Met Met Ser Leu Pro Ala Leu Phe Asn Ile Gly Leu Leu Leu Phe
        850                 855                 860

Leu Val Met Phe Ile Tyr Ala Ile Phe Gly Met Ser Asn Phe Ala Tyr
865                 870                 875                 880
```

```
Val Lys Arg Glu Val Gly Ile Asp Asp Met Phe Asn Phe Glu Thr Phe
                885                 890                 895

Gly Asn Ser Met Ile Cys Leu Phe Gln Ile Thr Thr Ser Ala Gly Trp
            900                 905                 910

Asp Gly Leu Leu Ala Pro Ile Leu Asn Ser Lys Pro Pro Asp Cys Asp
        915                 920                 925

Pro Asn Lys Val Asn Pro Gly Ser Ser Val Lys Gly Asp Cys Gly Asn
    930                 935                 940

Pro Ser Val Gly Ile Phe Phe Phe Val Ser Tyr Ile Ile Ile Ser Phe
945                 950                 955                 960

Leu Val Val Val Asn Met Tyr Ile Ala Val Ile Leu Glu Asn Phe Ser
                965                 970                 975

Val Ala Thr Glu Glu Ser Ala Glu Pro Leu Ser Glu Asp Asp Phe Glu
                980                 985                 990

Met Phe Tyr Glu Val Trp Glu Lys  Phe Asp Pro Asp Ala  Thr Gln Phe
            995                 1000                1005

Met Glu  Phe Glu Lys Leu Ser  Gln Phe Ala Ala Ala  Leu Glu Pro
    1010                1015                1020

Pro Leu  Asn Leu Pro Gln Pro  Asn Lys Leu Gln Leu  Ile Ala Met
    1025                1030                1035

Asp Leu  Pro Met Val Ser Gly  Asp Arg Ile His Cys  Leu Asp Ile
    1040                1045                1050

Leu Phe  Ala Phe Thr Lys Arg  Val Leu Gly Glu Ser  Gly Glu Met
    1055                1060                1065

Asp Ala  Leu Arg Ile Gln Met  Glu Glu Arg Phe Met  Ala Ser Asn
    1070                1075                1080

Pro Ser  Lys Val Ser Tyr Gln  Pro Ile Thr Thr Thr  Leu Lys Arg
    1085                1090                1095

Lys Gln  Glu Glu Val Ser Ala  Val Ile Ile Gln Arg  Ala Tyr Arg
    1100                1105                1110

Arg His  Leu Leu Lys Arg Thr  Val Lys Gln Ala Ser  Phe Thr Tyr
    1115                1120                1125

Asn Lys  Asn Lys Ile Lys Gly  Gly Ala Asn Leu Leu  Ile Lys Glu
    1130                1135                1140

Asp Met  Ile Ile Asp Arg Ile  Asn Glu Asn Ser Ile  Thr Glu Lys
    1145                1150                1155

Thr Asp  Leu Thr Met Ser Thr  Ala Ala Cys Pro Pro  Ser Tyr Asp
    1160                1165                1170

Arg Val  Thr Lys Pro Ile Val  Glu Lys His Glu Gln  Glu Gly Lys
    1175                1180                1185

Asp Glu  Lys Ala Lys Gly Lys
    1190                1195
```

<210> SEQ ID NO 869
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 869
ccaaaacatc ttttactgta gtatctactt accatactac ccaagaatgg cacactgctc      60
acatcttcaa aagcttaaac caagagcact acacaggtgc                           100

-continued

```
<210> SEQ ID NO 870
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 870
tgtgtgtcgg ggccggtacc ctgcttccgg ttcccgcacg cattcccgga ttgcagtgcg        60
gaccccttct gtaagcgcgc gataaagcgc ggttttggaa                              100

<210> SEQ ID NO 871
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 871
tcatgtcata taagtagaac catacaatat atatataaaa tccaggttaa tagccaatct        60
tacaacattt ctcatatttt ttgcagttgc taagccatgg                              100

<210> SEQ ID NO 872
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 872
acattacaat acatatcaac atatcaccat aattaaattg caagtcttcg tcaaaagcaa        60
gccttaaagg agtatcccaa aaacacattt tccccagaag                              100

<210> SEQ ID NO 873
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 873
agacctttag agcgtggtta aacccatatg ttgggattta tgctgctttt atggtagcaa        60
taccctatat taagatttga agtagacccg gaaagttagt                              100

<210> SEQ ID NO 874
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 874
gttcatgaaa gaataaataa atgtttaaaa aaaaaaaaaa ctgaggtaaa tttctatatt        60
ctttcataaa agcagtttaa agacgaacgt ttttcgaggt                              100

<210> SEQ ID NO 875
<211> LENGTH: 100
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 875
gctgggtctc ggtgacactg acgacgggag gcgcggtcgg aagagcgcgg ggccgtcgcc       60
tctggcttaa catagcagat gcgctgagac tccaacaggt                            100

<210> SEQ ID NO 876
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 876
cagtggcggc gaaaactctc tgcgttctgg agggagggtg cgggcaggag gaggtagagg       60
atgccttgta agcggagcaa aaacaaggtt caacgtctgc                            100

<210> SEQ ID NO 877
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 877
caaatcactt gcctctcggc gcgagaccgc gatgcgcggg ggcgggagcg tgatgatggc       60
atcgcgtaag gagagggtgt gagaagccgg atcctgtggt                            100

<210> SEQ ID NO 878
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 878
ccctgtgtcc gaagaggtct gcgttgcgac ttacgtggta gtgcttggaa ggtgcggagt       60
agatgagaga taagtgaatg tggacaaacc tgtcacgtag                            100

<210> SEQ ID NO 879
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 879
gagcggagct cagagggtgc gcgctccgcc ctttcgcggg cctggcatga gcgcagtggt       60
tgttacacta aagtgtctcc gcctgtcgaa tattctcgtg                            100

<210> SEQ ID NO 880
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 880
gtgtcactgg tttcaaatca acctcaattt ttttggagac gtgagtgctg agcatttttt      60
cttcagtgaa gtgacttggc agccaaaatc gccaacgccc                          100

<210> SEQ ID NO 881
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 881
tcctggcatg tcccgcccaa gtcccttagc cccgctcccc aaccctgccc cattcccact      60
ctagtacccg taagctacaa gacgccgccg ttcgtcgggt                          100

<210> SEQ ID NO 882
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 882
tgctcagtcg tcctgccggg cgggccctga ggttgcaagg gacggaggaa gtttcgtgcg      60
tgcgcccttc ctatagcgcc cagtagaact gacagtacct                          100

<210> SEQ ID NO 883
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 883
tcctcggatt acgcatgctc agtgcaatct tcggttgcct ggactagcgc tccggttttt      60
ctgtgctgaa cctcagggga cgccgacaca cgtacacgtc                          100

<210> SEQ ID NO 884
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 884
gataatttcc tgaaagaaaa gatcaattcg atgttaccaa atctgggata tccagaaaaa      60
ttttcttctt ctcctaggag aaaaactatc aaatgtcagg                          100

<210> SEQ ID NO 885
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 885
tctctcacgg caaactgttg cagactgtag agacgctatg ccaagaatct tttacttaaa      60
```

-continued agcaggaata gattcaatag gcaacttcac tgcacatgta                             100

<210> SEQ ID NO 886
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 886
caacctcccc ttctcaagga gcaggtggat tggtcccgag ctagctggtg ggcggaggtg     60 acgttttttat aagttgctca agagacggta acaaccgacg                          100

<210> SEQ ID NO 887
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 887
gtggaacttc cactgaatta ctcttttcgc atgtaagatc actgaaccgt gataatcatt     60
gatcctattt gtagaactgt atgaaacagt tccctaagga                           100

<210> SEQ ID NO 888
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 888
tcgctcaaca ggcggccagg gtgcgagcag tgaagctgcg gcacgccgga gcgtttaatg     60
gccatcaaat tggcctctct aggaggtagc tgcagccgga                           100

<210> SEQ ID NO 889
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
atagaaagaa atgagactgc tcgatagaaa aatgtgaaag taaactttga t             51

<210> SEQ ID NO 890
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
atagaaagaa atgagactgc tcgacagaaa aatgtgaaag taaactttga t             51

<210> SEQ ID NO 891
<211> LENGTH: 51
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 891
tataatgcaa tgaaaaaatt aggatagaaa aaaccgcaaa agcctatacc t                51

<210> SEQ ID NO 892
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
tataatgcaa tgaaaaaatt aggacagaaa aaaccgcaaa agcctatacc t                51

<210> SEQ ID NO 893
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
gagaagtttg atcccgatgc aacttagttc atggaatttg aaaaattatc t                51

<210> SEQ ID NO 894
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
gagaagtttg atcccgatgc aactcagttc atggaatttg aaaaattatc t                51

<210> SEQ ID NO 895
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
aaaggcacct tctcgctggc                                                   20

<210> SEQ ID NO 896
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
acttgtatgt tgttttt                                                      17

<210> SEQ ID NO 897
<211> LENGTH: 10
<212> TYPE: DNA
<213> ORGANISM: Artificial Sequence
<220> FEATURE:
<223> OTHER INFORMATION: Description of Artificial Sequence: Synthetic

___ oligonucleotide

<400> SEQUENCE: 897
tctcgctggc                                                           10

<210> SEQ ID NO 898
<211> LENGTH: 6063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 898
atggagcaaa cagtgcttgt accaccagga cctgacagct tcaacttctt caccagagaa        60
tcccttgcag ctattgaaag gcgcattgca gaagagaagg ctaagaatcc caagccagac       120
aaaaaagatg atgatgaaaa tggcccaaag ccaaacagtg acttggaagc tgggaagaac       180
cttccattta tctatggaga cattcctcca gagatggtgt cggagcctct ggaggacctg       240
gacccctact atatcaataa gaagactttt atagtattga ataaagggaa ggccatcttc       300
cggttcagtg ccacctccgc cctgtacatt ttaacaccct tcaatcctct taggaaaata       360
gctattaaga ttttggtaca ctcattattc agcatgttaa tcatgtgcac tattttgaca       420
aactgtgtat ttatgacaat gagtaaccct cccgactgga caaagaatgt ggagtacacc       480
ttcacaggaa tatatacttt tgaatcacta ataaaaatta ttgcaagggg cttctgttta       540
gaagatttta ctttccttcg cgacccatgg aactggctgg acttcactgt cattacattc       600
gcatatgtga cggagtttgt ggacctgggc aatgtctcag cattgagaac attcagagtt       660
cttcgagcat tgaaaactat ttcagtcatt ccaggcctga agaccatcgt gggggccctg       720
atccagtcgg tgaagaagct gtctgacgtc atgatactca ctgtgttctg tctcagtgtg       780
ttcgcactca tcgggttgca gctcttcatg ggcaacctga ggaataaatg tgtacagtgg       840
cctcccacca acgcttccct tgaggaacat agcatagaga agaatataac tatggattac       900
aatggcacac ttgtaaatga aaccgtgttc gagtttgact ggaaatcata cattcaagac       960
tcaagatatc attatttcct ggagggtgtt ttagatgcac tgctgtgtgg aaatagctct      1020
gatgcaggcc aatgtccaga aggatatatg tgtgtaaaag ctggtagaaa ccctaattat      1080
ggttacacaa gctttgatac cttcagttgg gcattttttgt ccctgtttcg actgatgact      1140
caggacttct gggaaaatct ataccaactg acattgcgtg ctgctggcaa aacctacatg      1200 atatttttttg tgctggtcat tttcttgggc tcattctacc tgataaactt gatcctggct      1260
gtggtggcca tggcctatga ggagcagaat caggccacac tggaggaggc tgaacagaaa      1320
gaggcagaat ttcagcagat gttggagcaa cttaagaagc agcaagaggc tgcacagcag      1380
gcagcggcta caacagcctc agaacattcc agggagccca gtgcagcagg caggctctca      1440
gatagctctt cagaagcctc taagttgagt tcgaagagtg ctaaagaaag acgaaatcgg      1500
aggaaaaaaa ggaaacagaa agagcagtct ggaggagaag agaaagatga tgatgaattc      1560
cacaagtctg agtctgaaga cagcatcagg aggaaggggt ttcgcttctc catagaaggg      1620
aatagactga catatgaaaa gaggtactct tcccccgcatc agtctctgtt aagcattcgt      1680
ggttccctgt ctcccccaag acgcaatagc agaacaagtc ttttcagctt tagagggcga      1740 gccaaggat gtggggtctga gaatgacttt gctgatgatg aacacagcac ctttgaggat      1800
aatgagagcc gtagagactc actgttcgtt ccccgaagac acggagagcg acgcaacagt      1860

```
aacctgagcc agaccagcag gtcctcccga atgctggcgg tgtttccagc caatgggaag    1920
atgcacagca cggtggattg caatggtgtg gtttccttgg ttggtggacc ctcagttccc    1980
acatcgccag ttggacagct tctgccagag ggaacaacca ctgaaactga gatgagaaag    2040
aggaggtcga gctctttcca tgtttccatg gactttctag aagatccttc ccagaggcaa    2100
agggcaatga gcatagccag catcttaaca aatacagtag aagaactaga agaatccagg    2160
cagaaatgtc caccctgttg gtataaattt tccaacatat tcttaatttg ggactgttct    2220
ccatattggc tgaaagttaa acatattgtc aacctggtgg tgatggaccc atttgttgat    2280
ctggccatta ccatctgcat tgtgttaaat acgctcttca tggctatgga gcactacccc    2340
atgactgaac atttcaacca tgttcttaca gtgggaaact tggtcttcac tgggattttc    2400
acagcagaaa tgttcctgaa aatcatcgca atggatcctt actattactt ccaagaaggc    2460
tggaatatct ttgatggttt cattgtgaca ctcagcctgg tagaacttgg ccttgccaat    2520
gtggaaggat tgtcagttct ccgttcattt cgactgctcc gagtgttcaa gttggcaaag    2580
tcttggccca cactgaatat gctcattaag atcattggta actcggtggg agcactgggc    2640
aacctgactc tggtgttggc catcattgtc tttatttttg ccgtggttgg catgcagctg    2700
tttgaaaaaa gttacaaaga ttgtgtctgc aaaaattgcca ctgactgcaa actcccacgt    2760
tggcacatga acgacttctt ccactcgttc ctgatcgtgt tccgcgtgct gtgtgggag    2820 tggatagaga ccatgtggga ctgcatggag gtggcaggac aagctatgtg ccttactgtc    2880
ttcatgatgg tcatggtgat tgggaacctt gtggtcttga acctctttct ggccttgctt    2940
ctgagctcat ttagtgcaga caaccttgca gccactgatg atgacaatga gatgaacaac    3000
ctgcagattg ctgtggacag gatgcacaaa ggaatagctt atgtaaaaag aaaaatatat    3060
gaattcattc aacaatcctt tgttaagaaa cagaagattc tagatgaaat taagccactt    3120
gatgatctaa acaacagaaa agacaattgt atctctaacc acacaacaga aattgggaaa    3180
gatctggact gtctgaaaga tgtgaatgga accacaagtg gcatagggac gggcagcagt    3240
gtggagaagt acatcattga tgagagtgat tatatgtcat tcataaacaa ccccagcctc    3300
actgtgactg tgcccattgc tgtgggagag tctgactttg agaacttaaa cacagaagac    3360
tttagcagtg aatcagatct agaagaaagc aaagagaaac tcaacgaaag cagtagctcc    3420
tcagagggaa gcacagtaga cattggggcg cctgcagagg aacagcctgt cattgaacca    3480
gaagaaaccc ttgagcccga agcttgcttc actgaaggct gtgtccagag attcaagtgc    3540
tgtcaaatca gcgtggaaga aggaagaggg aaacagtggt ggaacctacg gaggacgtgc    3600
ttccgaatag ttgaacacaa ctggtttgag accttcattg tgttcatgat tctcctgagt    3660
agtggtgccc tggcctttga ggatatatat attgatcagc gaaagacgat caaaaccatg    3720
ctggagtatg ctgacaaagt cttcacttac attttcatcc tggagatgct cctcaaatgg    3780
gtggcctatg ctatcaaac atacttcacc aatgcctggt gttggctaga cttcttaatt    3840
gttgatgttt cattggtcag tttaacagca aatgccttgg gttactctga actcggggcc    3900
atcaaatccc taaggacact aagagctctg agacccctaa gagccttatc acgatttgaa    3960
gggatgaggg tggttgtgaa tgccctgtta ggagcaattc catccatcat gaatgtgctt    4020
ctggtttgcc ttatattctg gctaattttc agcatcatgg gcgtaaattt gtttgctggc    4080
aaattctacc actgtgttaa caccacaact ggtgacatat ttgagatcag cgaagtcaat    4140
aatcattctg attgcctaaa actaatagaa agaaatgaga ccgcccggtg gaaaaatgtg    4200
aaagtaaact ttgataatgt aggatttggg tatctttctt tgcttcaagt tgccacattt    4260
```

-continued

```
aagggctgga tggatatcat gtatgctgca gttgattcca gaaatgttga actacagcct      4320
aagtatgagg aaagcctgta catgtatttg tacttcgtca tcttcatcat cttcgggtcc      4380
ttctttaccc tgaacctgtt tattggtgtc attatcgaca atttcaacca gcaaaagaag      4440
aagtttggag gtcaagacat ctttatgaca gaagaacaga agaaatacta taatgcaatg      4500
aagaaattag gatcaaaaaa gccacaaaag cctatccctc gacctggaaa caaatttcaa      4560
ggaatggttt ttgactttgt aaccagacaa gtgtttgata tcagcatcat gatcctcatc      4620
tgtctgaaca tggtgaccat gatggtggaa acggatgacc agagcgatta tgtgacaagc      4680
attttgtcac gcatcaacct ggtgttcatc gtcctgttca ccggcgagtg tgtgctcaag      4740
ctcatctcgc tccgccatta ttatttcacc attggatgga acattttcga ttttgtggtg      4800
gtcatcctct ccattgtagg gatgtttctt gcggagctaa tagaaaagta ttttgtgtct      4860
cctaccctgt tccgagtcat ccgcctggcc aggattggac gaatcctacg cctgatcaaa      4920
ggtgccaagg ggatccgcac gctgctcttt gctctgatga tgtcccttcc tgcgctgttt      4980
aacatcggcc tcctgctttt tctcgtcatg ttcatctacg ccatctttgg gatgtccaac      5040
tttgcctatg ttaagaggga agttgggatt gatgacatgt tcaactttga gaccttcggc      5100
aacagcatga tctgcctgtt ccaaatcacc acctctgcgg gctgggatgg actgctggcc      5160
cccatcctca acagcaaacc ccctgactgt gaccctaata aagttaaccc tggaagctcg      5220
gtgaagggag actgtgggaa cccatctgtg gggattttct tttttgtcag ctacatcatc      5280
atatccttcc tggttgtggt gaacatgtac attgctgtca tcctggagaa cttcagcgtt      5340
gccacagaag aaagtgcaga gcctctgagt gaggacgact ttgagatgtt ctacgaggtc      5400
tgggagaagt cgaccctga cgccacccag ttcatggaat ttgaaaaatt atctcagttt      5460
gcagctgctc tagaaccccc tctcaatttg ccacaaccaa acaaacttca gctcattgcc      5520
atggacctgc ccatggtgag tggagaccgc atccactgcc tggacatctt atttgctttt      5580
acaaagcggg tgttgggtga gagtggagag atggatgctc ttcgaatcca gatggaagag      5640
cggttcatgg cttccaaccc ctccaaggtc tcttatcagc ccatcactac tacattaaaa      5700
cgcaaacaag aggaggtgtc agctgttatc attcagcgag cttataggcg ccacctttg      5760 aagcgaacag taaaacaagc ttcattcaca tacaataaga acaaactcaa aggtggggct      5820
aatcttcttg taaaagaaga catgctcatt gacagaataa acgaaaactc tattacggag      5880
aaaactgacc tgacaatgtc cacagcagct tgtccgccct cctacgatcg ggtgacaaag      5940
ccaatcgtgg agaaacacga gcaggaaggg aaggatgaaa aagccaaagg gaaagactac      6000
aaagaccatg acggtgatta taaagatcat gacatcgatt acaaggatga cgatgacaag      6060
taa                                                                       6063
```

<210> SEQ ID NO 899
<211> LENGTH: 6063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 899

```
atggagcaaa cagtgcttgt accaccagga cctgacagct tcaacttctt caccagagaa       60
tcccttgcag ctattgaaag gcgcattgca gaagagaagg ctaagaatcc caagccagac      120
aaaaaagatg atgatgaaaa tggcccaaag ccaaacagtg acttggaagc tgggaagaac      180
```

-continued

```
cttccattta tctatggaga cattcctcca gagatggtgt cggagcctct ggaggacctg     240
gacccctact atatcaataa gaagactttt atagtattga ataaagggaa ggccatcttc     300
cggttcagtg ccacctccgc cctgtacatt ttaacaccct tcaatcctct taggaaaata     360
gctattaaga tttttggtaca ctcattattc agcatgttaa tcatgtgcac tattttgaca     420
aactgtgtat ttatgacaat gagtaaccct cccgactgga caaagaatgt ggagtacacc     480
ttcacaggaa tatatacttt tgaatcacta ataaaaatta ttgcaagggg cttctgttta     540
gaagatttta ctttccttcg cgacccatgg aactggctgg acttcactgt cattacattc     600
gcatatgtga cggagtttgt ggacctgggc aatgtctcag cattgagaac attcagagtt     660
cttcgagcat tgaaaactat ttcagtcatt ccaggcctga agaccatcgt gggggccctg     720
atccagtcgg tgaagaagct gtctgacgtc atgatactca ctgtgttctg tctcagtgtg     780
ttcgcactca tcgggttgca gctcttcatg ggcaacctga ggaataaatg tgtacagtgg     840
cctcccacca acgcttccct tgaggaacat agcatagaga agaatataac tatggattac     900
aatggcacac ttgtaaatga aaccgtgttc gagtttgact ggaaatcata cattcaagac     960
tcaagatatc attatttcct ggagggtgtt ttagatgcac tgctgtgtgg aaatagctct    1020
gatgcaggcc aatgtccaga aggatatatg tgtgtaaaag ctggtagaaa ccctaattat    1080
ggttacacaa gctttgatac cttcagttgg gcattttgt ccctgtttcg actgatgact    1140
caggacttct gggaaaatct ataccaactg acattgcgtg ctgctggcaa aacctacatg    1200 atatttttg tgctggtcat tttcttgggc tcattctacc tgataaactt gatcctggct    1260
gtggtggcca tggcctatga ggagcagaat caggccacac tggaggaggc tgaacagaaa    1320
gaggcagaat ttcagcagat gttggagcaa cttaagaagc agcaagaggc tgcacagcag    1380
gcagcggcta caacagcctc agaacattcc agggagccca gtgcagcagg caggctctca    1440
gatagctctt cagaagcctc taagttgagt tcgaagagtg ctaaagaaag acgaaatcgg    1500 aggaaaaaa ggaaacagaa agagcagtct ggaggagaag agaaagatga tgatgaattc    1560
cacaagtctg agtctgaaga cagcatcagg aggaaggggt ttcgcttctc catagaaggg    1620
aatagactga catatgaaaa gaggtactct tccccgcatc agtctctgtt aagcattcgt    1680
ggttccctgt tctccccaag acgcaatagc agaacaagtc ttttcagctt tagagggcga    1740
gccaaggatg tggggtctga gaatgacttt gctgatgatg aacacagcac ctttgaggat    1800
aatgagagcc gtagagactc actgttcgtt ccccgaagac acggagagcg acgcaacagt    1860
aacctgagcc agaccagcag gtcctcccga atgctggcgg tgtttccagc caatgggaag    1920
atgcacagca cggtggattg caatggtgtg gtttccttgg ttggtggacc ctcagttccc    1980
acatcgccag ttggacagct tctgccagag ggaacaacca ctgaaactga gatgagaaag    2040
aggaggtcga gctctttcca tgtttccatg gactttctag aagatccttc ccagaggcaa    2100
agggcaatga gcatagccag catcttaaca aatacagtag aagaactaga agaatccagg    2160
cagaaatgtc caccctgttg gtataaattt tccaacatat tcttaatttg ggactgttct    2220
ccatattggc tgaaagttaa acatattgtc aacctggtgg tgatggaccc atttgttgat    2280
ctggccatta ccatctgcat tgtgttaaat acgctcttca tggctatgga gcactacccc    2340
atgactgaac atttcaacca tgttcttaca gtgggaaact tggtcttcac tgggattttc    2400
acagcagaaa tgtccctgaa aatcatcgca atggatcctt actattactt ccaagaaggc    2460
tggaatatct ttgatggttt cattgtgaca ctcagcctgg tagaacttgg ccttgccaat    2520
```

-continued

```
gtggaaggat tgtcagttct ccgttcattt cgactgctcc gagtgttcaa gttggcaaag    2580
tcttggccca cactgaatat gctcattaag atcattggta actcggtggg agcactgggc    2640
aacctgactc tggtgttggc catcattgtc tttatttttg ccgtggttgg catgcagctg    2700
tttgaaaaaa gttacaaaga ttgtgtctgc aaaattgcca ctgactgcaa actcccacgt    2760
tggcacatga acgacttctt ccactcgttc ctgatcgtgt tccgcgtgct gtgtggggag    2820
tggatagaga ccatgtggga ctgcatggag gtggcaggac aagctatgtg ccttactgtc    2880
ttcatgatgg tcatggtgat tgggaacctt gtggtcttga acctctttct ggccttgctt    2940
ctgagctcat ttagtgcaga caaccttgca gccactgatg atgacaatga gatgaacaac    3000
ctgcagattg ctgtggacag gatgcacaaa ggaatagctt atgtaaaaag aaaaatatat    3060
gaattcattc aacaatcctt tgttaagaaa cagaagattc tagatgaaat taagccactt    3120
gatgatctaa acaacagaaa agacaattgt atctctaacc acacaacaga aattgggaaa    3180
gatctggact gtctgaaaga tgtgaatgga accacaagtg gcatagggac gggcagcagt    3240
gtggagaagt acatcattga tgagagtgat tatatgtcat tcataaacaa ccccagcctc    3300
actgtgactg tgcccattgc tgtgggagag tctgactttg agaacttaaa cacagaagac    3360
tttagcagtg aatcagatct agaagaaagc aaagagaaac tcaacgaaag cagtagctcc    3420
tcagagggaa gcacagtaga cattgggggcg cctgcagagg aacagcctgt cattgaacca    3480
gaagaaaccc ttgagcccga agcttgcttc actgaaggct gtgtccagag attcaagtgc    3540
tgtcaaatca gcgtggaaga aggaagaggg aaacagtggt ggaacctacg gaggacgtgc    3600
ttccgaatag ttgaacacaa ctggtttgag accttcattg tgttcatgat tctcctgagt    3660
agtggtgccc tggcctttga ggatatatat attgatcagc gaaagacgat caaaaccatg    3720
ctggagtatg ctgacaaagt cttcacttac attttcatcc tggagatgct cctcaaatgg    3780
gtggcctatg gctatcaaac atacttcacc aatgcctggt gttggctaga cttcttaatt    3840
gttgatgttt cattggtcag tttaacagca aatgccttgg gttactctga actcggggcc    3900
atcaaatccc taaggacact aagagctctg agacccctaa gagccttatc acgatttgaa    3960
gggatgaggt tggttgtgaa tgccctgtta ggagcaattc catccatcat gaatgtgctt    4020
ctggtttgcc ttatattctg gctaattttc agcatcatgg gcgtaaattt gtttgctggc    4080
aaattctacc actgtgttaa caccacaact ggtgacatat ttgagatcag cgaagtcaat    4140
aatcattctg attgcctaaa actaatagaa agaaatgaga ccgcctgatg gaaaaatgtg    4200
aaagtaaact ttgataatgt aggatttggg tatctttctt tgcttcaagt tgccacattt    4260
aagggctgga tggatatcat gtatgctgca gttgattcca gaaatgttga actacagcct    4320
aagtatgagg aaagcctgta catgtatttg tacttcgtca tcttcatcat cttcgggtcc    4380
ttctttaccc tgaacctgtt tattggtgtc attatcgaca atttcaacca gcaaaagaag    4440
aagtttggag gtcaagacat ctttatgaca gaagaacaga gaaatacta taatgcaatg    4500 aagaaattag gatcaaaaaa gccacaaaag cctatccctc gacctggaaa caaatttcaa    4560
ggaatggttt ttgactttgt aaccagacaa gtgtttgata tcagcatcat gatcctcatc    4620
tgtctgaaca tggtgaccat gatggtggaa acggatgacc agagcgatta tgtgacaagc    4680
attttgtcac gcatcaacct ggtgttcatc gtcctgttca ccggcgagtg tgtgctcaag    4740
ctcatctcgc tccgccatta ttatttcacc attggatgga acatttttcga ttttgtggtg    4800 gtcatcctct ccattgtagg gatgtttctt gcggagctaa tagaaaagta ttttgtgtct    4860
cctaccctgt tccgagtcat ccgcctggcc aggattggac gaatcctacg cctgatcaaa    4920
```

-continued

```
ggtgccaagg ggatccgcac gctgctcttt gctctgatga tgtcccttcc tgcgctgttt      4980
aacatcggcc tcctgctttt tctcgtcatg ttcatctacg ccatctttgg gatgtccaac      5040
tttgcctatg ttaagaggga agttgggatt gatgacatgt tcaactttga gaccttcggc      5100
aacagcatga tctgcctgtt ccaaatcacc acctctgcgg gctgggatgg actgctggcc      5160
cccatcctca acagcaaacc ccctgactgt gaccctaata aagttaaccc tggaagctcg      5220
gtgaagggag actgtgggaa cccatctgtg gggattttct tttttgtcag ctacatcatc      5280
atatccttcc tggttgtggt gaacatgtac attgctgtca tcctggagaa cttcagcgtt      5340
gccacagaag aaagtgcaga gcctctgagt gaggacgact ttgagatgtt ctacgaggtc      5400
tgggagaagt tcgaccctga cgccacccag ttcatggaat ttgaaaaatt atctcagttt      5460
gcagctgctc tagaacccccc tctcaatttg ccacaaccaa acaaacttca gctcattgcc      5520
atggacctgc ccatggtgag tggagaccgc atccactgcc tggacatctt atttgctttt      5580
acaaagcggg tgttgggtga gagtggagag atggatgctc ttcgaatcca gatggaagag      5640
cggttcatgg cttccaaccc ctccaaggtc tcttatcagc ccatcactac tacattaaaa      5700
cgcaaacaag aggaggtgtc agctgttatc attcagcgag cttataggcg ccacctttg      5760 aagcgaacag taaaacaagc ttcattcaca tacaataaga acaaactcaa aggtggggct      5820
aatcttcttg taaaagaaga catgctcatt gacagaataa acgaaaactc tattacggag      5880
aaaactgacc tgacaatgtc cacagcagct tgtccgccct cctacgatcg ggtgacaaag      5940
ccaatcgtgg agaaacacga gcaggaaggg aaggatgaaa aagccaaagg gaaagactac      6000
aaagaccatg acggtgatta taaagatcat gacatcgatt acaaggatga cgatgacaag      6060
taa                                                                    6063
```

```
<210> SEQ ID NO 900
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
agcgctccgg tttttctgtg ctgaacctca ggggacgccg acacacgtac acgtc              55

<210> SEQ ID NO 901
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 902
<211> LENGTH: 7
<212> TYPE: PRT
<213> ORGANISM: Tobacco etch virus
<220> FEATURE:
<221> NAME/KEY: MOD_RES
<222> LOCATION: (7)..(7)
```

-continued

```
<223> OTHER INFORMATION: Gly or Ser

<400> SEQUENCE: 902

Glu Asn Leu Tyr Phe Gln Xaa
1               5
```

METHODS AND COMPOSITIONS FOR TREATING A PREMATURE TERMINATION CODON-MEDIATED DISORDER

CROSS-REFERENCE TO RELATED APPLICATIONS

This application is a § 371 National Stage of International (PCT) Application No. PCT/US2020/058415, filed on Oct. 30, 2020, which claims the benefit of, and priority to, U.S. Provisional Patent Application No. 62/929,428, filed Nov. 1, 2019, the entire contents of each of which are hereby incorporated by reference in their entirety for all purposes.

FIELD OF THE INVENTION

The invention relates generally to methods and compositions for expressing a gene product encoded by a gene containing a premature termination codon and/or treating a disorder mediated by a premature termination codon.

BACKGROUND

Protein synthesis is directed by a genetic code that includes 61 three-base-pair codons encoding amino acids that are incorporated into the protein being synthesized and 3 three-base-pair codons (referred to as stop or termination codons) that terminate the synthesis of a protein. When a nucleic acid sequence encoding a protein is mutated to contain a premature termination codon rather than a codon for the next amino acid, the resulting protein is prematurely terminated, which is often nonfunctional or less functional than the untruncated or full length protein. Such mutations, termed nonsense mutations, are often associated with, or are a causative agent in numerous different genetic diseases.

A number of disorders are associated with, or are caused by nonsense mutations. These include epilepsies, for example, Dravet Syndrome, Genetic Epilepsy with Febrile Seizures (GEFS), Benign Familial Infantile Epilepsy (BFIE), Early Infantile Epileptic Encephalopathy (EIEE), Lennox-Gastaut Syndrome, Rett Syndrome, PPM-X Syndrome, Ohtahara Syndrome, Episodic Ataxia, Hemiplegic Migraine, Iditiopathic Generalized Epilepsy, FOXG1 Syndrome, Familial Focal Epilepsy with Variable Foci (FFEVF), Childhood-Onset Epileptic Encephalopathy, SYNGAP1-Related Intellectual Disability, Pyridoxine-Dependent Epilepsy, Familial Infantile Myoclonic Epilepsy (FIME), Myoclonic Astatic Epilepsy, X-Linked Intellectual Disability, Partial Epilepsy and Episodic Ataxia, Febrile Seizures, Autosomal Dominant Partial Epilepsy with Auditory Features (ADPEAF), PNPO-Deficiency, Progressive Myoclonus Epilepsy, Action Myoclonus—Renal Failure (AMRF), CDKL5 deficiency disorder, and Benign Familial Infantile Seizures (BFIS).

By way of example, Dravet Syndrome is a rare and catastrophic form of intractable epilepsy that begins in infancy Initially, patients experience prolonged seizures. In their second year, additional types of seizure begin to occur, which typically coincide with a developmental decline, possibly due to repeated cerebral hypoxia. This leads to poor development of language and motor skills. Mutations in SCN1A (encoding the voltage-gated sodium channel a subunit Nav1.1), SCN1B (encoding the voltage-gated sodium channel (31 subunit), SCN2A (encoding Nav1.2), SCN3A (encoding Nav1.3), SCN9A (encoding Nav1.7), GABRG2 (encoding the γ-aminobutyric acid receptor γ2 subunit), GABRD (encoding the γ-aminobutyric acid receptor A subunit) and/or PCDH19 (encoding Protocadherin-19) genes have been linked to Dravet Syndrome.

Dravet syndrome may be caused by a nonsense mutation in, for example, the SCN1A gene resulting in a premature termination codon and a lack of or reduced amount of untruncated or functional protein. The SCN1A gene normally codes for the neuronal voltage-gated sodium channel α subunit, Na(V)1.1. In mouse models, loss-of-function mutations in SCN1A have been observed to result in a decrease in sodium currents and impaired excitability of GABAergic interneurons of the hippocampus.

Despite the efforts made to date, there is a need in the art for improved compositions and methods for treating diseases mediated by premature termination codons, including Dravet syndrome.

SUMMARY OF THE INVENTION

The invention is based, in part, upon the discovery of tRNAs (e.g., suppressor tRNAs), that permit an amino acid to be incorporated into a gene product encoded by a gene in a mammalian cell at a position that would otherwise result in a truncated gene product caused by a premature termination codon (PTC) in the gene. The invention is further based, in part, upon the discovery that a tRNA that permits an amino acid to be incorporated into a gene product encoded by a gene at a position that would otherwise result in a truncated gene product caused by a PTC in the gene, e.g., a tRNA described herein, can be used to treat a disease mediated by a PTC in a gene in a subject.

Accordingly, in one aspect, the invention provides a tRNA comprising a nucleotide sequence set forth in TABLE 2. In certain embodiments, the tRNA comprises a nucleotide sequence selected from SEQ ID NOs: 19-21, 37, 39, 40, 44, 179, 181, 182, and 186.

In certain embodiments, the tRNA comprises one or more naturally occurring nucleotide modifications, e.g., selected from 5-methyl uridine, 5-carbamoylmethyluridine, 5-carbamoyl-methyl-2-O-methyluridine, 5-methoxy-carbonylm-ethyluridine, 5-methoxycarbonylmethyl-2-thiouridine, pseudouridine, dihydrouridine, 1-methyladenosine, and inosine.

In another aspect, the invention provides an expression vector comprising a nucleotide sequence encoding any of the foregoing tRNAs. In certain embodiments, the expression vector comprises 1, 2, 3, 4, or more than 4 copy numbers of the nucleotide sequence encoding the tRNA. In certain embodiments, the expression vector comprises a nucleotide sequence corresponding to a genomic DNA sequence flanking a wild-type tRNA gene. For example, in certain embodiments, the expression vector comprises a nucleotide sequence set forth in TABLE 4. In certain embodiments, the nucleotide sequence set forth in TABLE 4 is selected from SEQ ID NOs: 869-888. In certain embodiments, the nucleotide sequence set forth in TABLE 4 is operably linked to the nucleotide sequence encoding the tRNA. In certain embodiments, in the expression vector, the nucleotide sequence set forth in TABLE 4 is 5' to the nucleotide sequence encoding the tRNA. In certain embodiments, in the expression vector, the nucleotide sequence set forth in TABLE 4 is immediately 5' to (i.e., adjacent) the nucleotide sequence encoding the tRNA.

In another aspect, the invention provides an expression vector comprising a nucleotide sequence encoding a tRNA set forth in TABLE 3, wherein the expression vector comprises 1, 2, 3, 4, or more than 4 copy numbers of the nucleotide sequence encoding the tRNA. In certain embodiments, the tRNA comprises a nucleotide sequence selected from SEQ ID NOs: 6-9, 11, 16-18, 22, 35, 36, 38, 45, 178, 180, and 187.

In another aspect, the invention provides an expression vector comprising a nucleotide sequence encoding a tRNA set forth in TABLE 3, wherein the expression vector further comprises a nucleotide sequence set forth in TABLE 4. In certain embodiments, the tRNA comprises a nucleotide sequence selected from SEQ ID NOs: 6-9, 11, 16-18, 22, 35, 36, 38, 45, 178, 180, and 187. In certain embodiments, the nucleotide sequence set forth in TABLE 4 is selected from SEQ ID NOs: 869-888. In certain embodiments, the nucleotide sequence set forth in TABLE 4 is operably linked to the nucleotide sequence encoding the tRNA. In certain embodiments, in the expression vector, the nucleotide sequence set forth in TABLE 4 is 5' to the nucleotide sequence encoding the tRNA. In certain embodiments, in the expression vector, the nucleotide sequence set forth in TABLE 4 is immediately 5' to (i.e., adjacent) the nucleotide sequence encoding the tRNA.

In certain embodiments of any of the foregoing expression vectors, the expression vector is a viral vector, e.g., a DNA virus vector, e.g., an adeno-associated virus (AAV) vector.

In another aspect, the invention provides a pharmaceutical composition comprising any of the foregoing tRNAs or any of the foregoing expression vectors and a pharmaceutically acceptable excipient. In certain embodiments, the tRNA or expression vector is not conjugated to, or associated with, another moiety, e.g., a carrier particle, e.g., an aminolipid particle. In certain embodiments, the composition does not comprise a nanoparticle and/or an aminolipid delivery compound.

In another aspect, the invention provides a method of expressing in a mammalian cell a functional gene product encoded by a gene containing a premature termination codon, the method comprising introducing into the cell an effective amount of any of the foregoing tRNAs or expression vectors, thereby permitting an amino acid to be incorporated into the gene product at a position that would otherwise result in a truncated gene product caused by the premature termination codon. In certain embodiments of any of the foregoing methods, the gene is selected from a gene set forth in TABLE 5 or TABLE 6. In certain embodiments, the gene is a SCN1A gene.

In another aspect, the invention provides a method of expressing in a mammalian cell a functional gene product encoded by a gene containing a premature termination codon, the method comprising introducing into the cell an effective amount of a tRNA set forth in TABLE 3 (e.g., a tRNA comprising a nucleotide sequence selected from SEQ ID NOs: 6-9, 11, 16-18, 22, 35, 36, 38, 45, 178, 180, and 187), or an expression vector comprising a nucleotide sequence encoding the tRNA, thereby permitting an amino acid to be incorporated into the gene product at a position that would otherwise result in a truncated gene product caused by the premature termination codon, wherein the gene is a gene set forth in TABLE 5. In certain embodiments, the gene is a SCN1A gene.

In certain embodiments of any of the foregoing methods, the cell contains less truncated gene product than a cell without the tRNA. In certain embodiments, the cell contains a greater amount of functional gene product than a cell without the tRNA.

In another aspect, the invention provides a method of increasing in a cell voltage-gated sodium channel activity encoded by a SCN1A gene containing a premature termination codon, the method comprising introducing into the cell an effective amount of any of the foregoing tRNAs or any of the foregoing expression vectors, thereby permitting an amino acid to be incorporated into the SCN1A gene product at a position that would otherwise result in a truncated SCN1A gene product caused by the premature termination codon.

In another aspect, the invention provides a method of increasing in a cell voltage-gated sodium channel activity encoded by a SCN1A gene containing a premature termination codon, the method comprising introducing into the cell an effective amount of a tRNA set forth in TABLE 3 (e.g., a tRNA comprising a nucleotide sequence selected from SEQ ID NOs: 6-9, 11, 16-18, 22, 35, 36, 38, 45, 178, 180, and 187), or an expression vector comprising a nucleotide sequence encoding the tRNA, thereby permitting an amino acid to be incorporated into the SCN1A gene product at a position that would otherwise result in a truncated SCN1A gene product caused by the premature termination codon.

In certain embodiments of any of the foregoing methods, wherein the gene is a SCN1A gene, the SCN1A gene product produced with the tRNA is a functional SCN1A gene product. In certain embodiments, the functional SCN1A gene product has greater activity than the truncated SCN1A gene product. In certain embodiments, the functional SCN1A gene product is the Nav1.1 protein. In certain embodiments, the functional SCN1A gene product comprises the amino acid sequence of any one of SEQ ID NOs: 863-868.

In certain embodiments of any of the foregoing methods, the cell is a human cell. In certain embodiments, the cell is a central nervous system cell, e.g., a neuron. In certain embodiments, the tRNA becomes aminoacylated in the cell.

In another aspect, the invention provides a method of treating a premature termination codon-mediated disorder in a subject in need thereof, wherein the subject has a gene with a premature termination codon, the method comprising administering to the subject an effective amount of any of the foregoing tRNAs or any of the foregoing expression vectors, thereby to treat the disorder in the subject. In certain embodiments, the disorder is selected from a disorder set forth in TABLE 5 or TABLE 6.

In another aspect, the invention provides a method of treating a premature termination codon-mediated disorder in a subject in need thereof, wherein the subject has a gene with a premature termination codon, the method comprising administering to the subject an effective amount of a tRNA set forth in TABLE 3 (e.g., a tRNA comprising a nucleotide sequence selected from SEQ ID NOs: 6-9, 11, 16-18, 22, 35, 36, 38, 45, 178, 180, and 187), or an expression vector comprising a nucleotide sequence encoding the tRNA, thereby to treat the disorder in the subject, wherein the disorder is a disorder set forth in TABLE 5.

In certain embodiments of any of the foregoing methods of treatment, the disorder is an epilepsy, e.g., Dravet syndrome. In certain embodiments, the subject is human. In certain embodiments, the method further comprises administering an effective amount of another agent, e.g., DIACOMIT® (stiripentol), EPIODOLEX® (cannabidiol), a ketogenic diet, ONFI® (clobazam), TOPAMAX® (topiramate), fenfluramine, or valproic acid, to the subject.

In certain embodiments of any of the foregoing methods, wherein the gene is a SCN1A gene, the premature termination codon in the SCN1A gene is caused by a mutation, or a combination of mutations, selected from c.664C>T, c.1129C>T, c.1492A>T, c.1624C>T, c.1738C>T, c.1837C>T, c.2134C>T, c.2593C>T, c.3637C>T, c.3733C>T, c.3985C>T, c.4573C>T, c.5656C>T, and c.5734C>T. In certain embodiments, the premature termination codon is caused by a mutation selected from c.1738C>T and c.3985C>T.

These and other aspects and features of the invention are described in the following detailed description and claims.

DESCRIPTION OF THE DRAWINGS

The invention can be more completely understood with reference to the following drawings.

FIG. 2B is a table showing the modification profile for tRNA sequences from the cytosol of certain eukaryotic organisms. The ratios in the table indicate the frequency of occurrence of listed nucleotide at the numbered position shown in FIG. 2A. The abbreviations for the modified residues are defined in Motorin et al. (2005) "Transfer RNA Modification," ENCYCLOPEDIA OF LIFE SCIENCES, John Wily & Sons, Inc.

FIG. 8A is a depiction of an experimental approach to measure suppressor tRNA activity using a construct which contains an EGFP reporter with a PTC and a suppressor tRNA. Native termination codons are indicated as shaded circles, and premature termination codons are indicated as unshaded circles. A standard Arg-tRNA (with an anticodon that binds CGA) will result in no read-through of the PTC in EGFP, and a non-functional truncated EGFP protein. A suppressor tRNA (with an anticodon that binds UGA) allows for read-through the PTC in EGFP resulting in full-length, functional EGFP protein.

7

Figure 9:
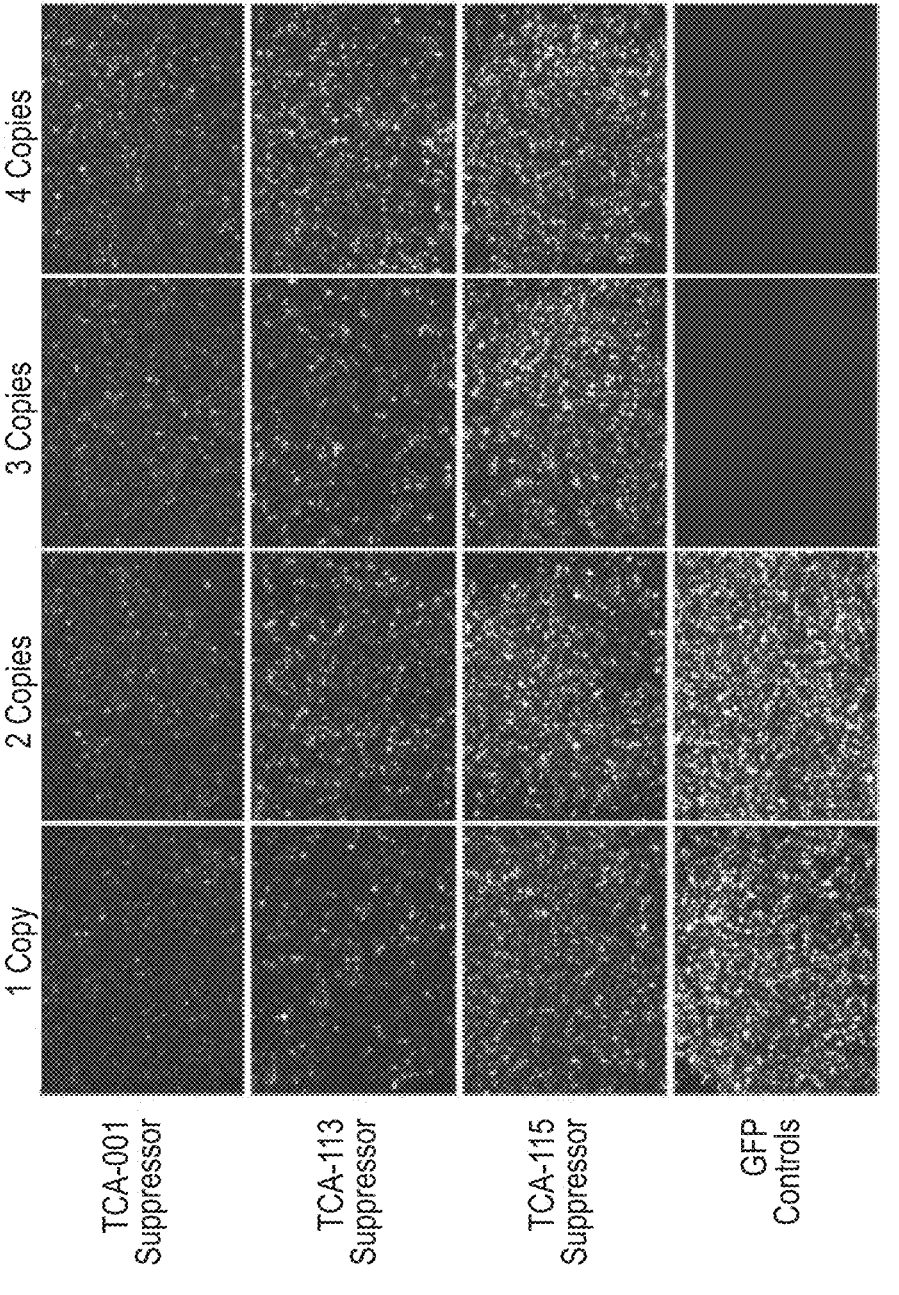

FIG. 9 depicts fluorescent images of Neuro-2a cells transfected with an expression construct containing an EGFP-R96X-TGA reporter (SEQ ID NO: 31) and the indicated Arg$_{TCA}$ suppressor tRNA at the indicated copy number. Suppressor tRNAs are TCA-001 (SEQ ID NO: 11), TCA-113 (SEQ ID NO: 16), and TCA-115 (SEQ ID NO: 18). Each copy of the suppressor tRNA also contains 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32). Images were taken ~24 hours post transfection. From left to right, the GFP controls are 1) wild-type EGFP alone, 2) wild-type EGFP on an expression construct including a single copy of the Arg$_{TCA}$ suppressor tRNA #001 (SEQ ID NO: 11), 3) the EGFP-R96X-TGA reporter alone, and 4) the EGFP-R96X-TGA reporter on an expression construct including four copies of a wild-type Arg-tRNA with an unmodified TCG anticodon.

Figure 10:
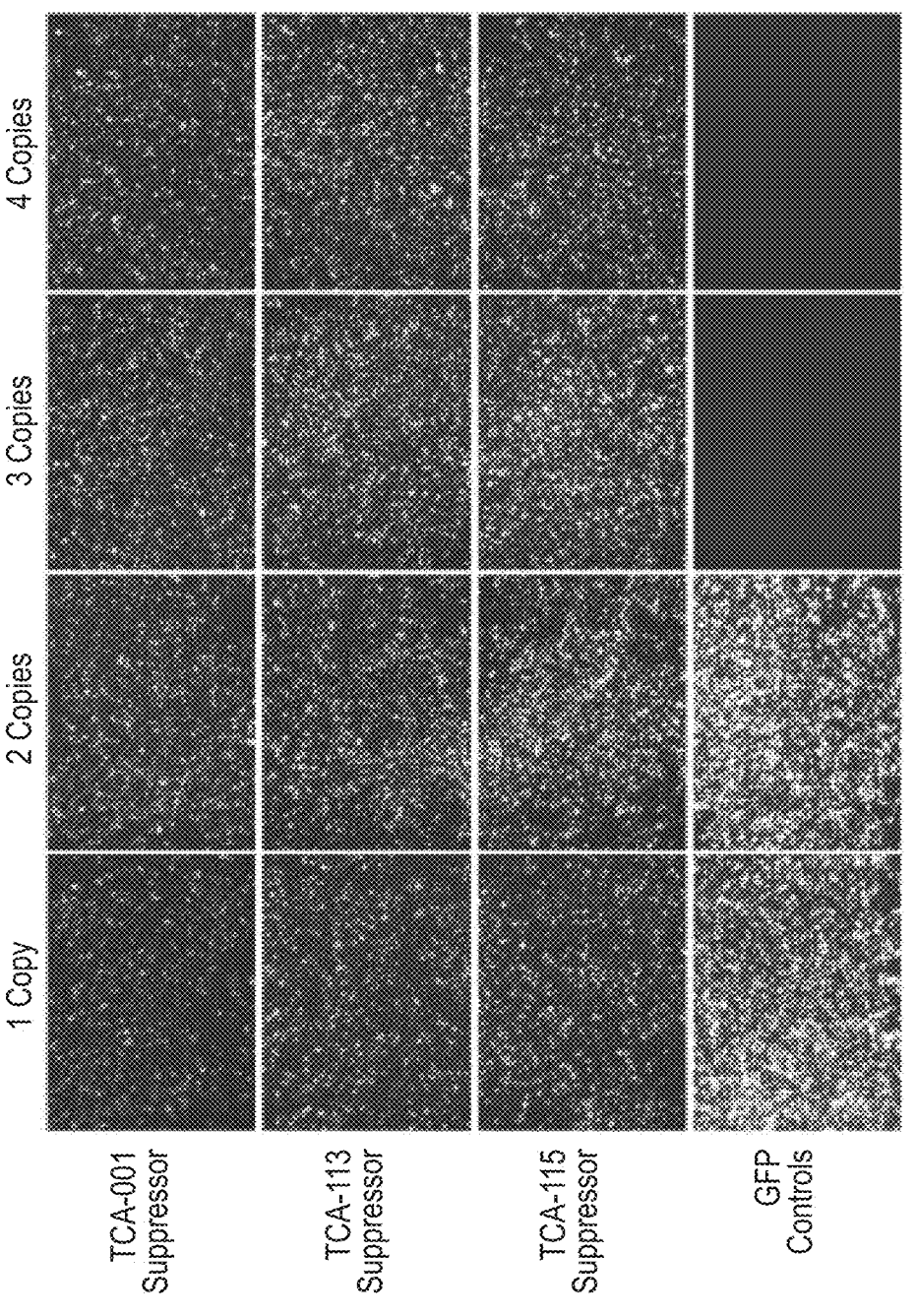

FIG. 10 depicts fluorescent images of Flp-In-293 cells transfected with an expression construct containing an EGFP-R96X-TGA reporter (SEQ ID NO: 31) and the indicated Arg$_{TCA}$ suppressor tRNA at the indicated copy number. Suppressor tRNAs are TCA-001 (SEQ ID NO: 11), TCA-113 (SEQ ID NO: 16), and TCA-115 (SEQ ID NO: 18). Each copy of the suppressor tRNA also contained 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32). Images were taken ~48 hours post transfection. From left to right, the GFP controls are 1) wild-type EGFP alone, 2) wild-type EGFP on an expression construct including a single copy of the Arg$_{TCA}$ suppressor tRNA #001 (SEQ ID NO: 11), 3) the EGFP-R96X-TGA reporter alone, and 4) the EGFP-R96X-TGA reporter on an expression construct including four copies of a wild-type Arg-tRNA with an unmodified TCG anticodon.

Figure 11:
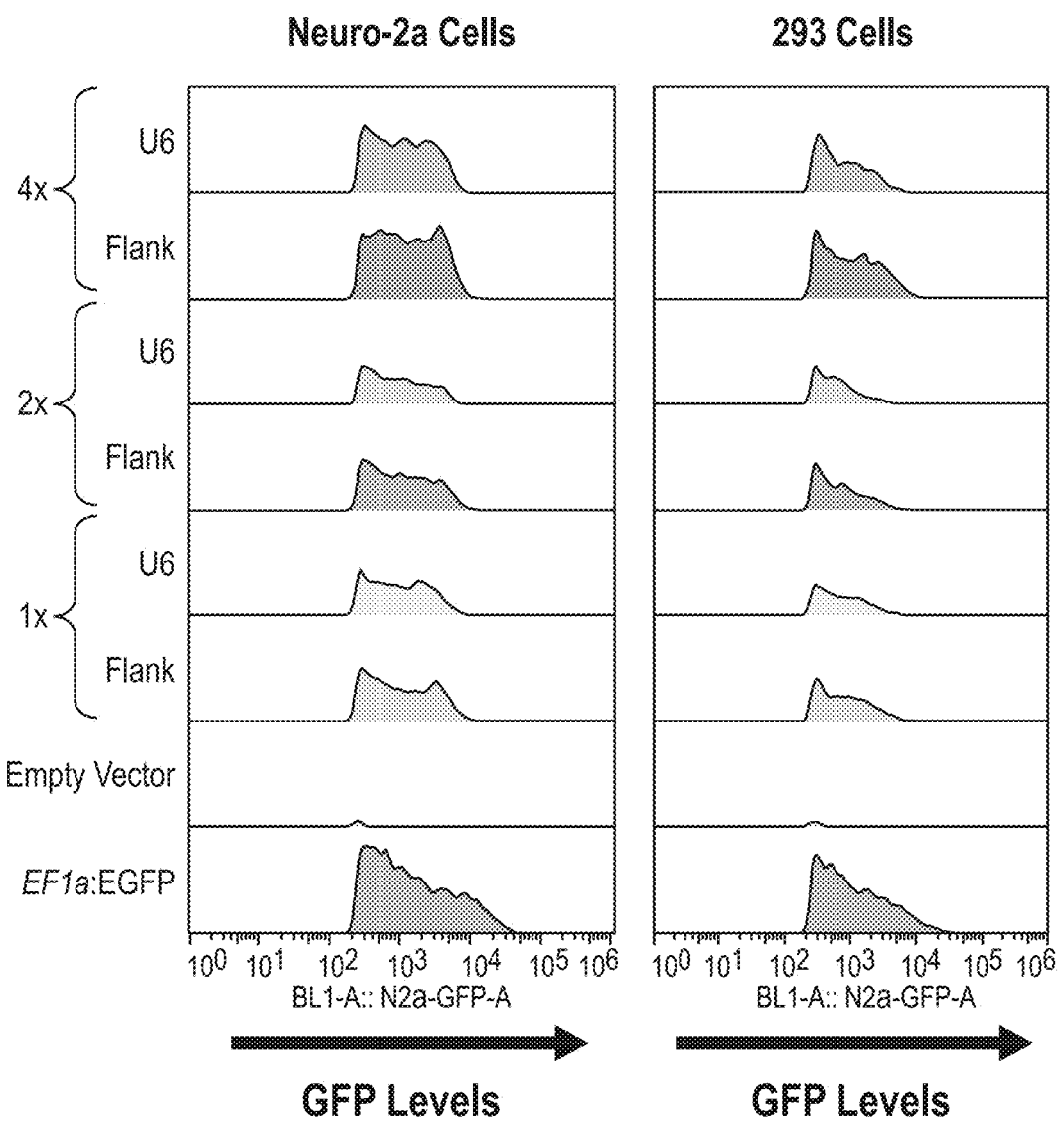

FIG. 11 shows fluorescence as measured by flow cytometry for Neuro-2a and Flp-In-293 cells transfected with an expression construct containing an EGFP-R96X-TGA reporter (SEQ ID NO: 177) and the Arg$_{TCA}$ suppressor tRNA #001 (SEQ ID NO: 11). Expression constructs included one (1×), two (2×), or four (4×) copies of the suppressor tRNA in the context of either (i) a U6 promoter including 19 bps of upstream flanking genomic DNA from tRNA-Arg-TCG-1-1 (SEQ ID NO: 33) and 46 bps of downstream flanking genomic DNA from tRNA-Arg-TCG-1-1 (SEQ ID NO: 34) ("U6"), or (ii) 200 bps upstream flanking genomic DNA from tRNA-Arg-TCG-1-1 (SEQ ID NO: 26) and 200 bps of downstream flanking genomic DNA from tRNA-Arg-TCG-1-1 (SEQ ID NO: 27) ("Flank"). "Empty vector" indicates cells transfected with an expression construct that does not contain a tRNA or an EGFP reporter, "EF1a:EGFP" indicates cells transfected with a version of the EGFP reporter that lacks a PTC. Analysis was carried out ~48 hours post transfection. Data are presented as histograms displaying the frequency distribution of the data versus fluorescence intensity for viable cells expressing EGFP above background.

Figure 12:
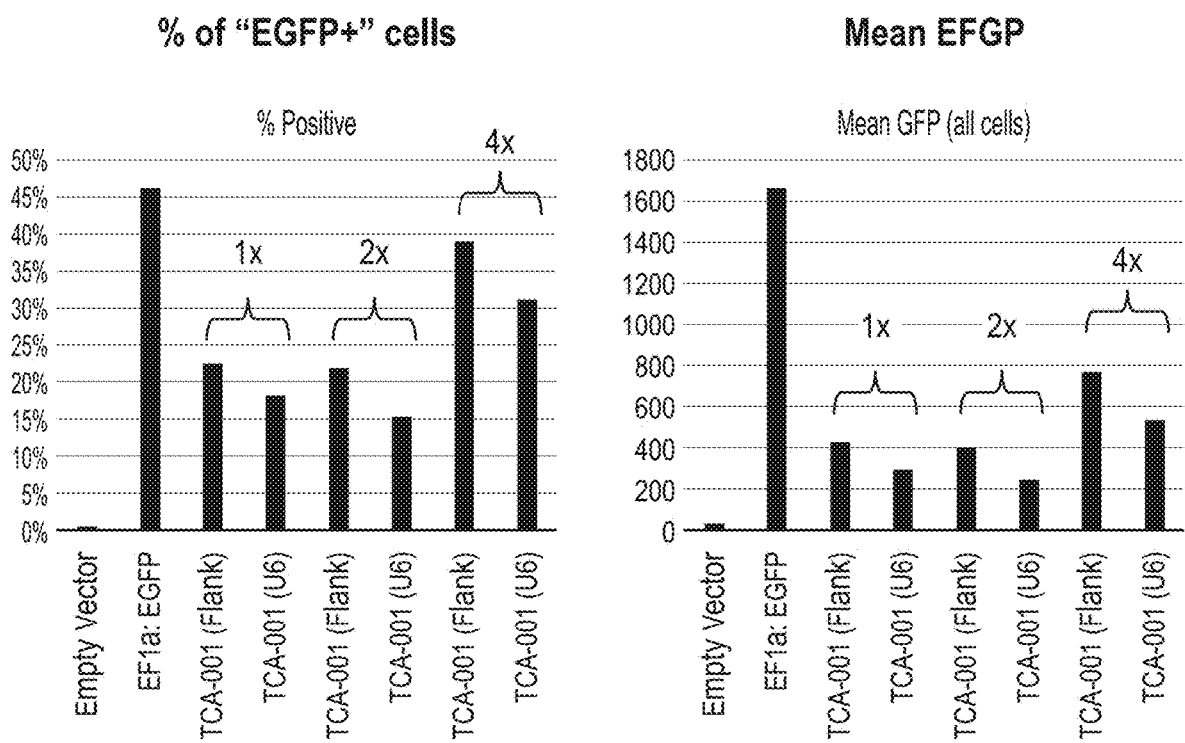

FIG. 12 depicts percentage of EGFP positive cells and mean EGFP intensity in all viable cells as measured by flow cytometry for Neuro-2a cells transfected with an expression construct containing an EGFP-R96X-TGA reporter (SEQ ID NO: 177) and the Arg$_{TCA}$ suppressor tRNA #001 (SEQ ID NO: 11) with the indicated copy number, in the context of either (i) a U6 promoter including 19 bps of upstream flanking genomic DNA from tRNA-Arg-TCG-1-1 (SEQ ID NO: 33) and 46 bps of downstream flanking genomic DNA from tRNA-Arg-TCG-1-1 (SEQ ID NO: 34) ("U6"), or (ii) 200 bps upstream flanking genomic DNA from tRNA-Arg-TCG-1-1 (SEQ ID NO: 26) and 200 bps of downstream flanking genomic DNA from tRNA-Arg-TCG-1-1 (SEQ ID NO: 27) ("Flank"). "Empty vector" indicates cells transfected with an expression construct that does not contain a tRNA or an EGFP reporter, "EF1a:EGFP" indicates cells transfected with a version of the EGFP reporter that lacks a PTC. Analysis was carried out ~48 hours post transfection. These plots summarize data from Neuro-2a cells in FIG. 11.

Figure 13:
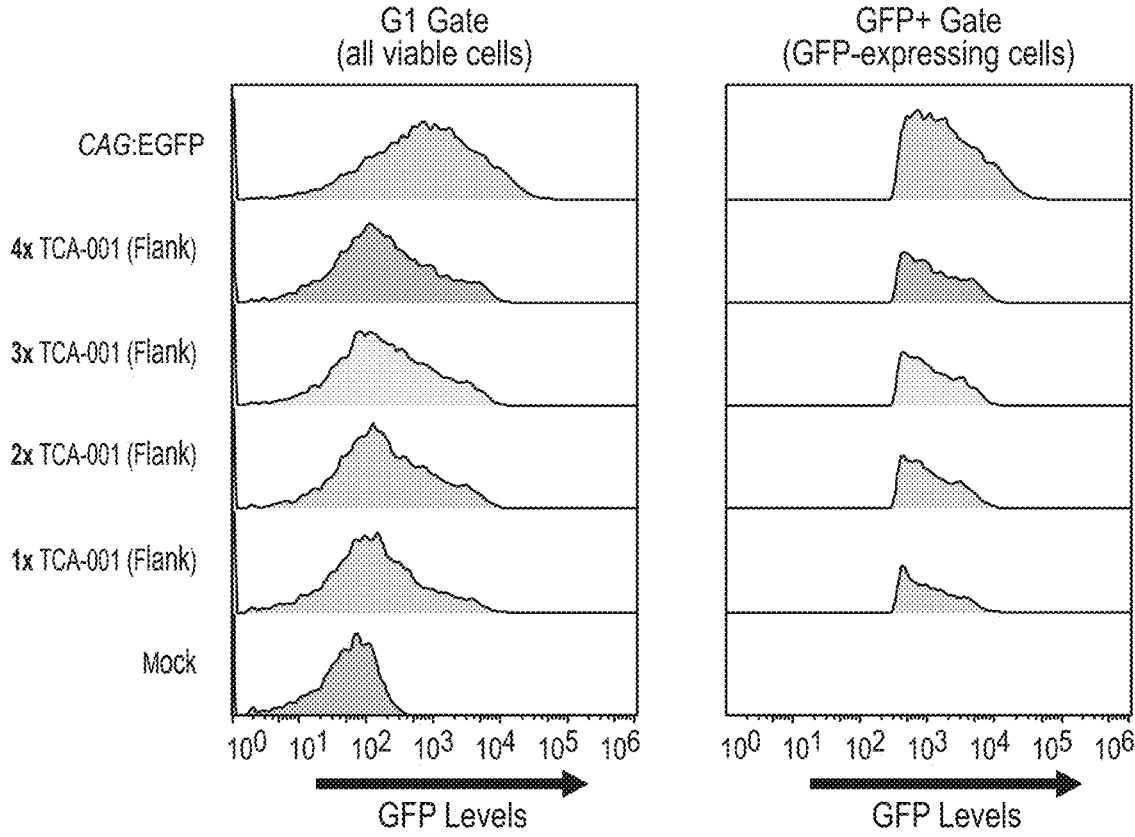

FIG. 13 shows fluorescence as measured by flow cytometry for Neuro-2a cells transfected with an expression construct containing an EGFP-R96X-TGA reporter (SEQ ID NO: 31) and the Arg$_{TCA}$ suppressor tRNA #001 (SEQ ID NO: 11). Expression constructs included one (1×), two (2×), three (3×), or four (4×) copies of the suppressor tRNA. Each copy of the suppressor tRNA also contains 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32) ("Flank"). "CAG:EGFP" indicates cells transfected with a version of the EGFP reporter that lacks a PTC, "Mock" indicates cells transfected with the EGFP-R96X-TGA reporter alone. Analysis was carried out ~48 hours post transfection. Data are presented as histograms displaying the frequency distribution of the data versus fluorescence intensity for all viable cells ("G1 Gate") and for viable cells expressing EGFP above background ("GFP+Gate").

Figure 14:
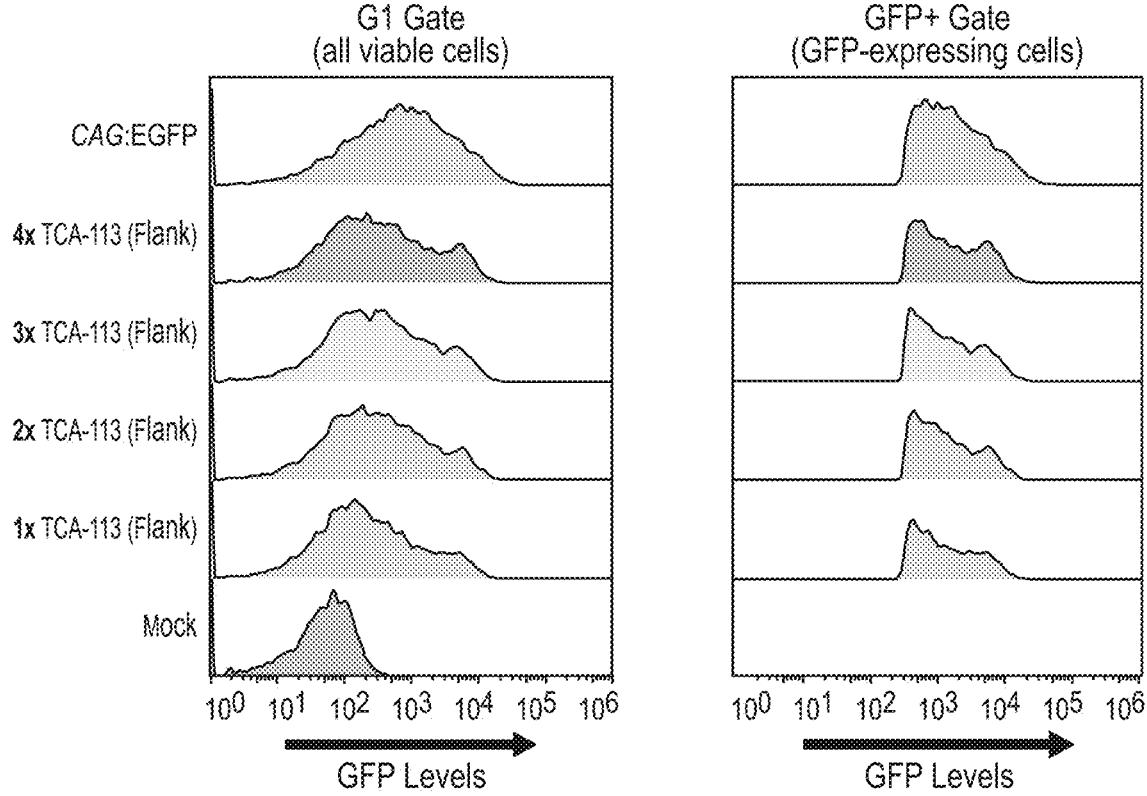

FIG. 14 shows fluorescence as measured by flow cytometry for Neuro-2a cells transfected with an expression construct containing an EGFP-R96X-TGA reporter (SEQ ID NO: 31) and the Arg$_{TCA}$ suppressor tRNA #113 (SEQ ID NO: 16). Expression constructs included one (1×), two (2×), three (3×), or four (4×) copies of the suppressor tRNA. Each copy of the suppressor tRNA also contained 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32) ("Flank"). "CAG:EGFP" indicates cells transfected with a version of the EGFP reporter that lacks a PTC, "Mock" indicates cells transfected with the EGFP-PTC reporter alone. Analysis was carried out ~48 hours post transfection. Data are presented as histograms displaying the frequency distribution of the data versus fluorescence intensity for all viable cells ("G1 Gate") and for viable cells expressing EGFP above background ("GFP+Gate").

Figure 15:
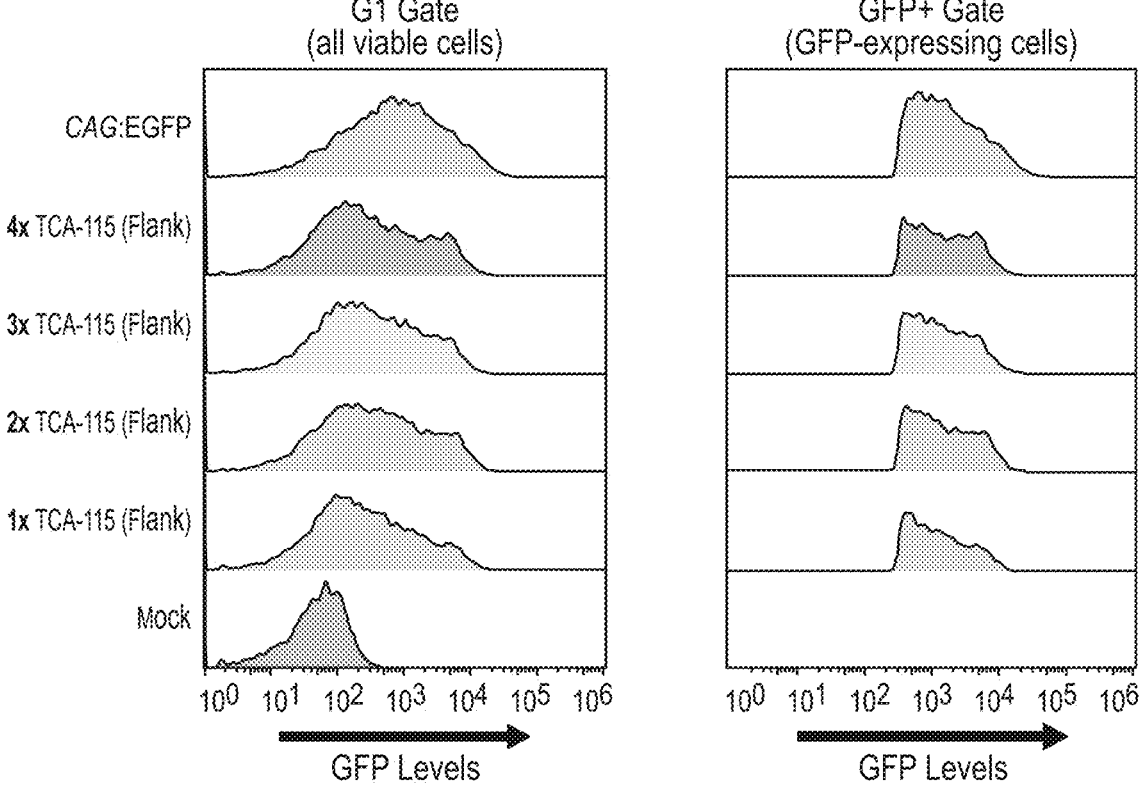

FIG. 15 shows fluorescence as measured by flow cytometry for Neuro-2a cells transfected with an expression construct containing an EGFP-R96X-TGA reporter (SEQ ID NO: 31) and the Arg$_{TCA}$ suppressor tRNA #115 (SEQ ID NO: 18). Expression constructs included one (1×), two (2×), three (3×), or four (4×) copies of the suppressor tRNA. Each copy of the suppressor tRNA also contained 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32) ("Flank"). "CAG:EGFP" indicates cells transfected with a version of the EGFP reporter that lacks a PTC, "Mock" indicates cells transfected with the EGFP-R96X-TGA reporter alone. Analysis was carried out ~48 hours post transfection. Data are presented as histograms displaying the frequency distribution of the data versus fluorescence intensity for all viable cells ("G1 Gate") and for viable cells expressing EGFP above background ("GFP+Gate").

Figure 16:
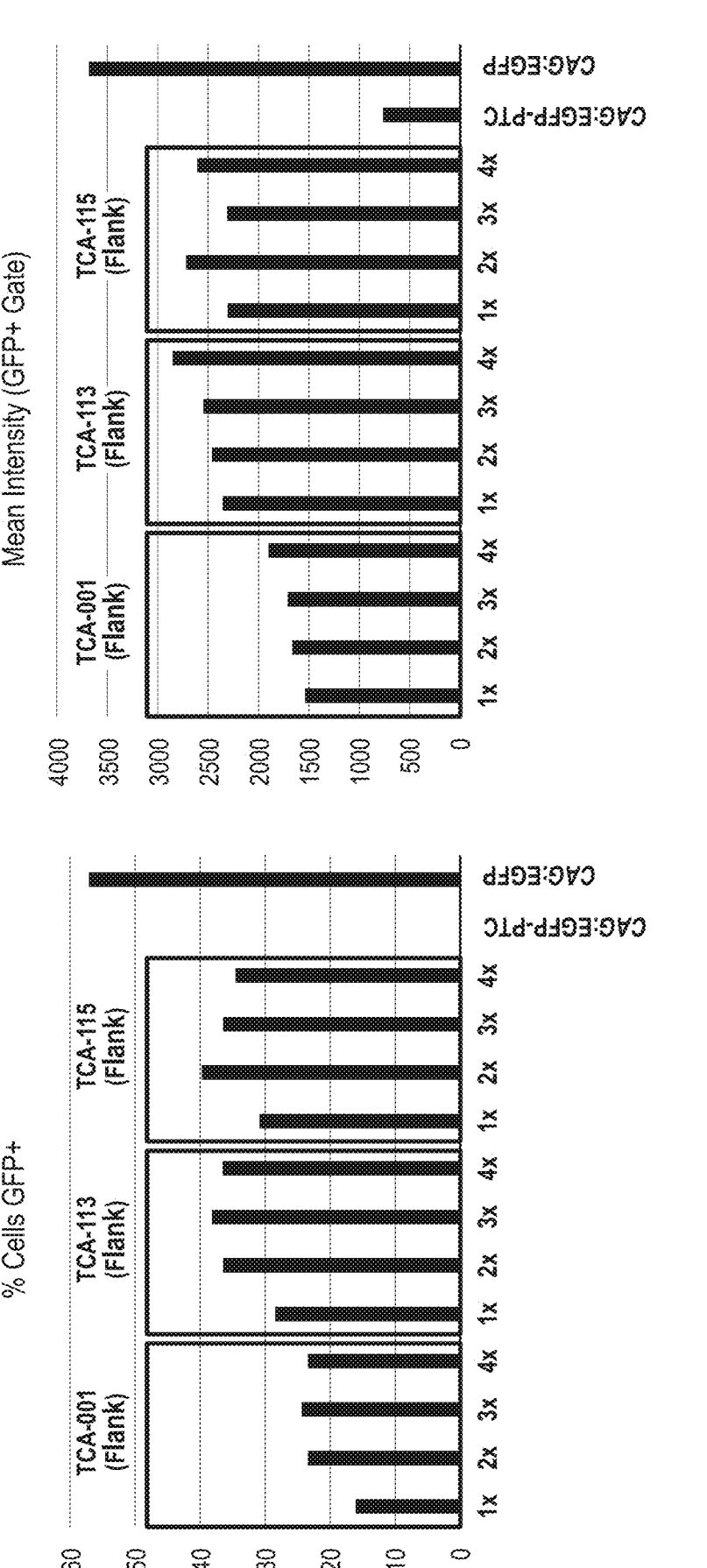

FIG. 16 depicts percentage of EGFP positive cells in all viable cells ("% Cells GFP+") and mean EGFP intensity in EGFP positive cells ("GFP+Gate") as measured by flow cytometry for Neuro-2a cells transfected with an expression construct containing an EGFP-R96X-TGA reporter (SEQ ID NO: 31) and the indicated suppressor tRNA at the indicated copy number. Suppressor tRNAs are TCA-001 (SEQ ID NO: 11), TCA-113 (SEQ ID NO: 16), and TCA-115 (SEQ ID NO: 18). "CAG:EGFP" indicates cells transfected with a version of the EGFP reporter that lacks a PTC, "CAG:EGFP-PTC" indicates cells transfected with the EGFP-R96X-TGA reporter alone. These plots summarize data from FIGS. 13-15.

Figure 17:
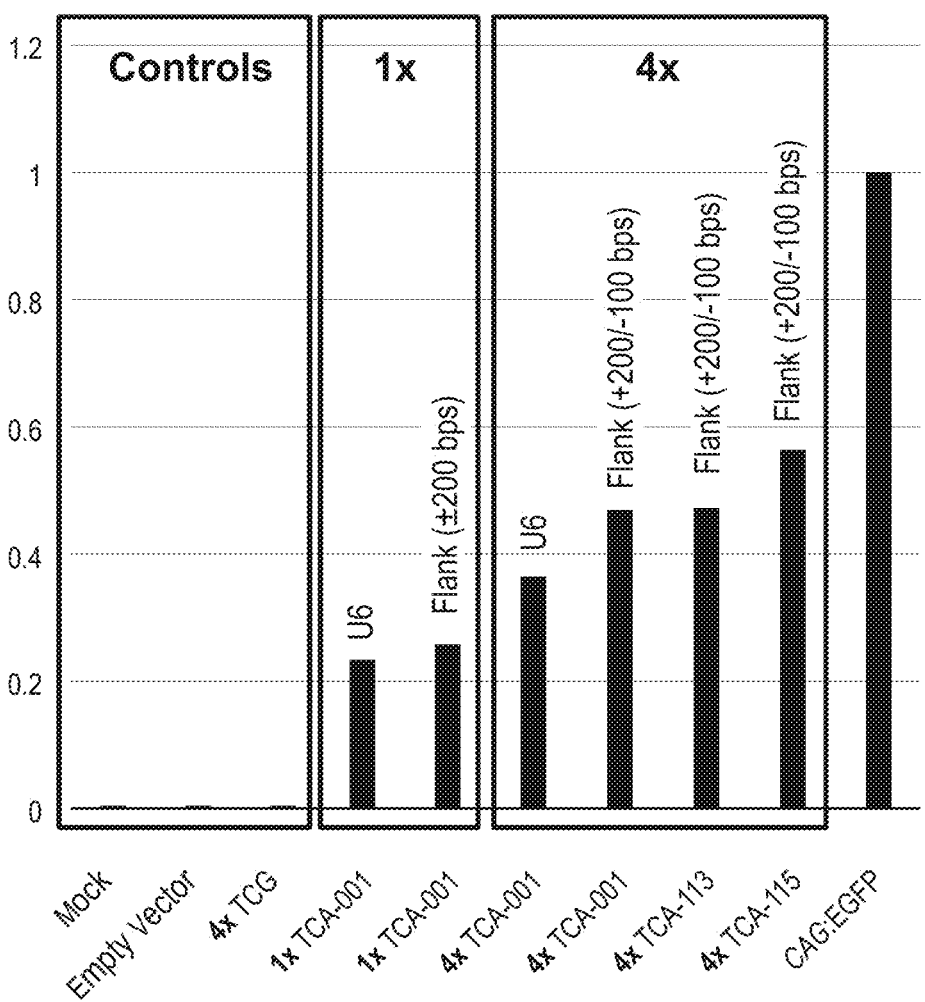

FIG. 17 depicts the percentage of EGFP positive cells as measured by flow cytometry for Neuro-2a cells transfected with an expression construct containing an EGFP-R96X-TGA reporter (SEQ ID NO: 31) and the indicated $Arg_{TCA}$ suppressor tRNA with the indicated copy number and flanking sequence. Suppressor tRNAs are TCA-001 (SEQ ID NO: 11), TCA-113 (SEQ ID NO: 16), and TCA-115 (SEQ ID NO: 18). "U6" indicates a U6 promoter including 19 bps of upstream flanking genomic DNA from tRNA-Arg-TCG-1-1 (SEQ ID NO: 33) and 46 bps of downstream flanking genomic DNA from tRNA-Arg-TCG-1-1 (SEQ ID NO: 34), "Flank (±200 bps)" indicates 200 bps upstream flanking genomic DNA from tRNA-Arg-TCG-1-1 (SEQ ID NO: 26) and 200 bps of downstream flanking genomic DNA from tRNA-Arg-TCG-1-1 (SEQ ID NO: 27), "Flank (+200/−100 bps)" indicates 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32) ("Flank"). "Mock" indicates mock transfected cells, "Empty Vector" indicates cells transfected with an expression construct that does not contain a tRNA or an EGFP reporter, "4×TCG" indicates cells transfected with an expression construct that contains an EGFP-R96X-TGA reporter and 4 copies of a wild-type Arg-tRNA with a TCG anticodon, "CAG:EGFP" indicates cells transfected with a version of the EGFP reporter that lacks a PTC. All data are normalized to positive control (CAG:EGFP). Plots show the percentage of viable cells that express GFP above background.

Figure 18:
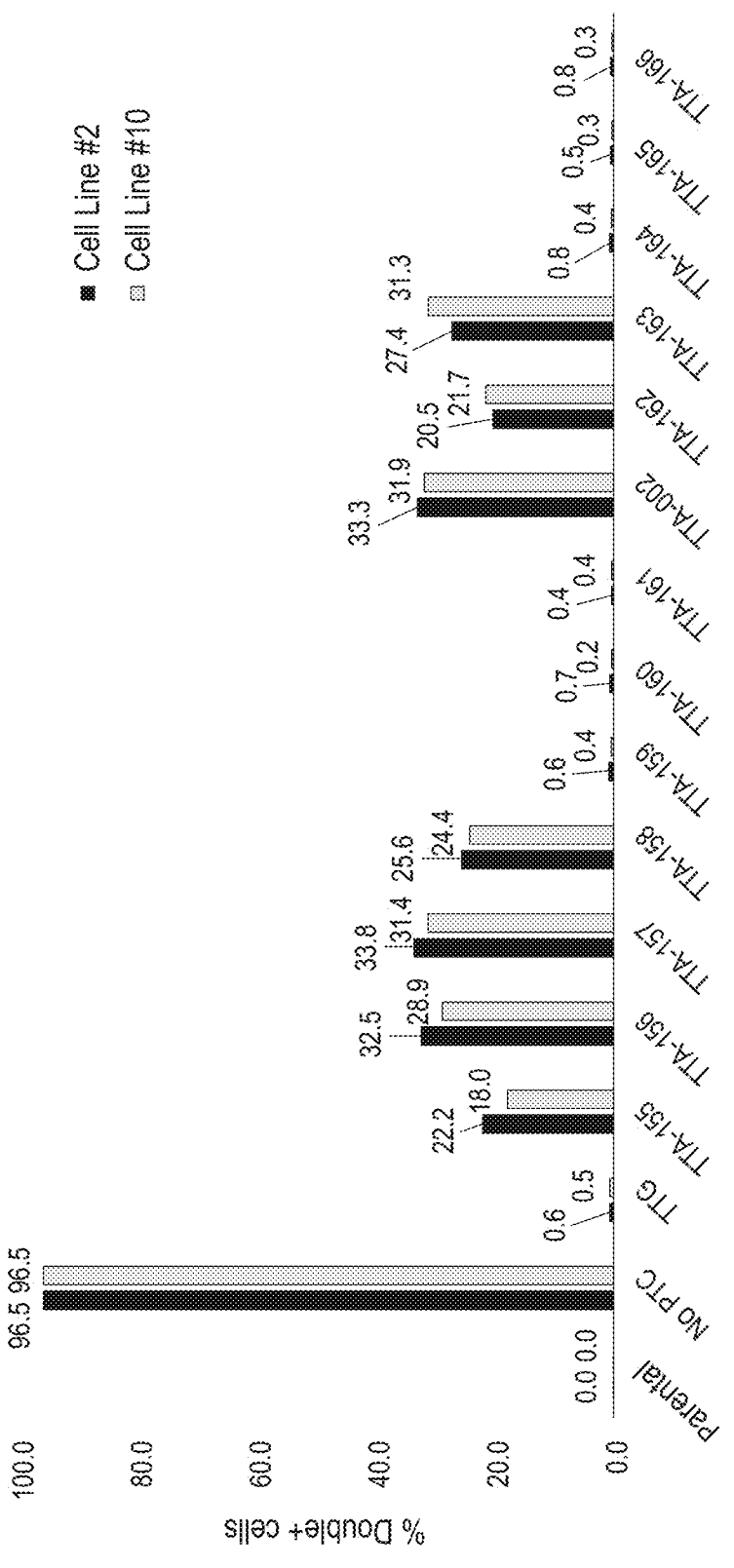

FIG. 18 is a graph depicting readthrough activity of $Gln_{TTA}$ suppressor tRNAs in two independently derived Flp-In-293 cell lines (#2 and #10) stably expressing a dual fluorescent reporter with the $Dmd^{mdx}$-PTC linker region (SEQ ID NO: 192), which is derived from a clinically relevant DMD nonsense mutation linked to Duchenne muscular dystrophy. Cells were transfected with the indicated $Gln_{TTA}$ suppressor tRNAs (SEQ ID NOs: 36-48) and readthrough activity was measured by flow cytometry at 24 hours post transfection. "Parental" indicates the original Flp-In-293 cell line without a fluorescent reporter, "no PTC" indicates a Flp-In-293 cell line stably expressing a dual fluorescent reporter with a version of the $Dmd^{mdx}$-PTC linker region that lacks a PTC (SEQ ID NO: 191), "TTG" indicates cells transfected with an expression construct that contains a wild-type Gln-tRNA with a TTG anticodon. Readthrough activity was measured by flow cytometry and is presented as the percentage of viable cells that that express both tdTomato and EGFP above baseline ("% Double+ cells").

Figure 19:
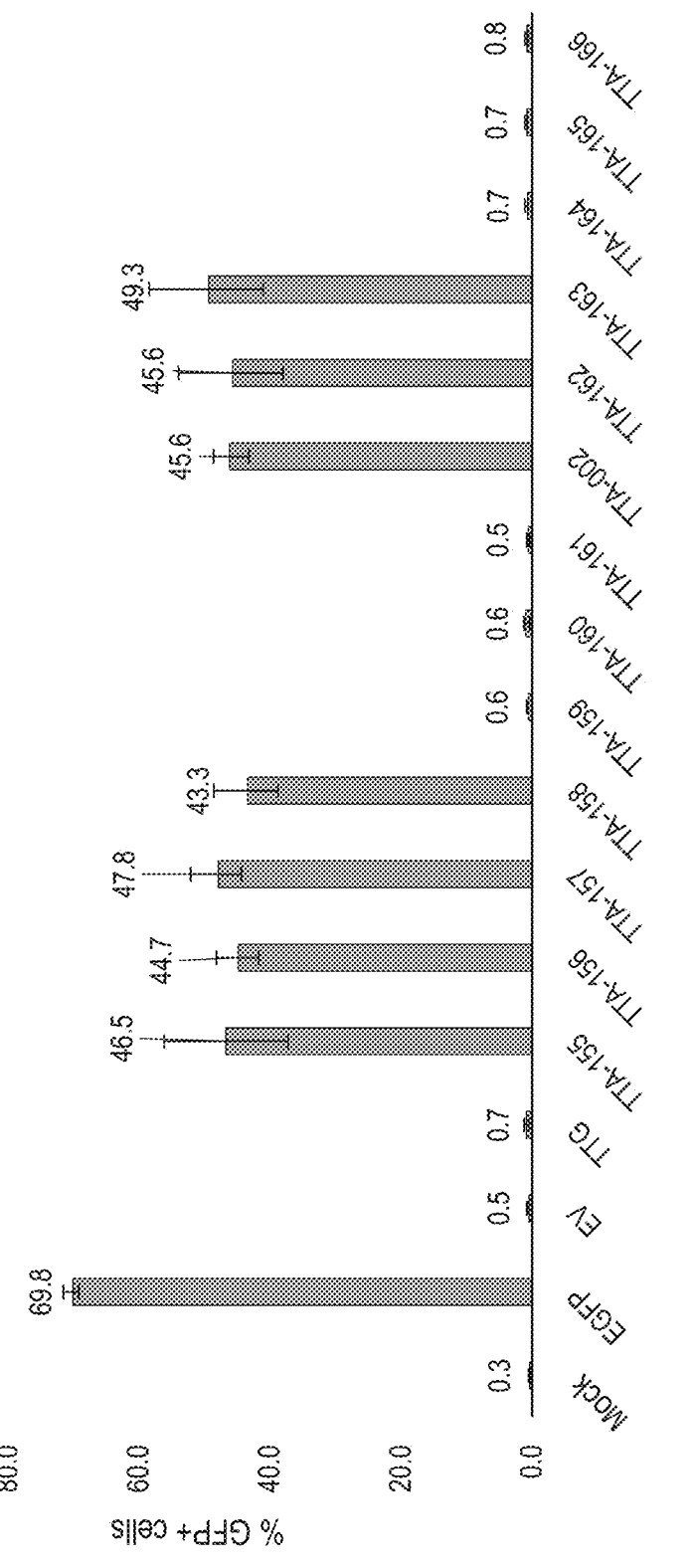

FIG. 19 is a graph depicting readthrough activity of the indicated $Gln_{TTA}$ suppressor tRNAs (SEQ ID NOs: 36-48) in Neuro-2a cells co-transfected with an expression construct containing an EGFP-Q69X-TAA reporter (SEQ ID NO: 175). "Mock" indicates mock-transfected cells, "EGFP" indicates cells transfected with a version of the EGFP reporter that lacks a PTC, "EV" (empty vector) indicates cells transfected with an expression construct that does not contain a tRNA or an EGFP reporter, "TTG" indicates cells co-transfected with the EGFP-Q69X-TAA reporter and an expression construct that contains a wild-type Gln-tRNA with a TTG anticodon. Readthrough activity was measured by flow cytometry and is presented as the percentage of viable cells that express GFP above background. Error bars represent the standard deviation of the data.

Figure 20:
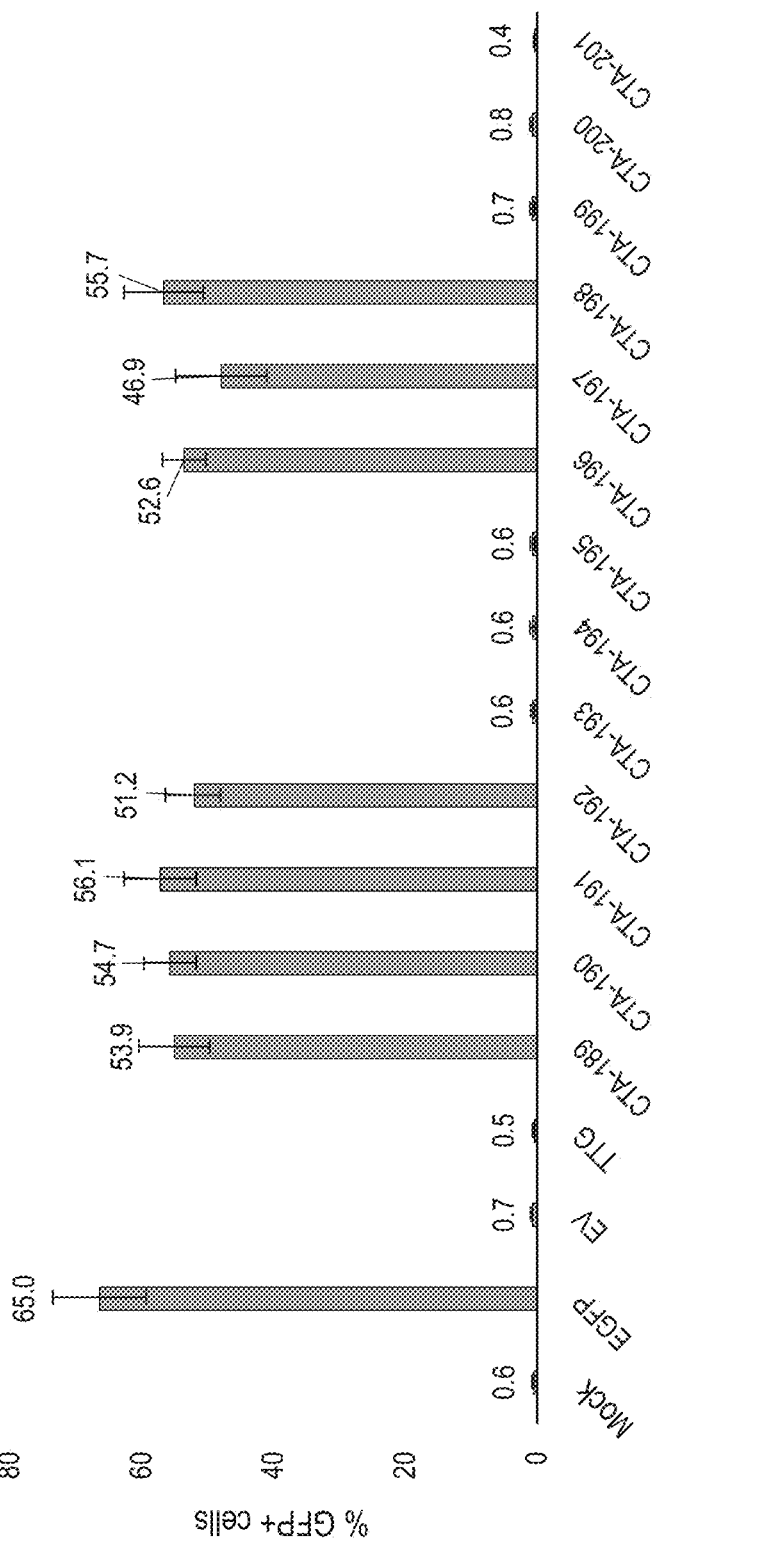

FIG. 20 is a graph depicting readthrough activity of the indicated GlncTA suppressor tRNAs (SEQ ID NOs: 78-90) in Neuro-2a cells co-transfected with an expression construct containing an EGFP-Q69X-TAG reporter (SEQ ID NO: 176). "Mock" indicates mock-transfected cells, "EGFP" indicated cells transfected with a version of the EGFP reporter that lacks a PTC, "EV" (empty vector) indicates cells transfected with an expression construct that does not contain a tRNA or an EGFP reporter, "TTG" indicates cells co-transfected with the EGFP-Q69X-TAG reporter and an expression construct that contains a wild-type Gln-tRNA with a TTG anticodon. Readthrough activity was measured by flow cytometry and is presented as the percentage of viable cells that express GFP above background. Error bars represent the standard deviation of the data.

Figure 21:
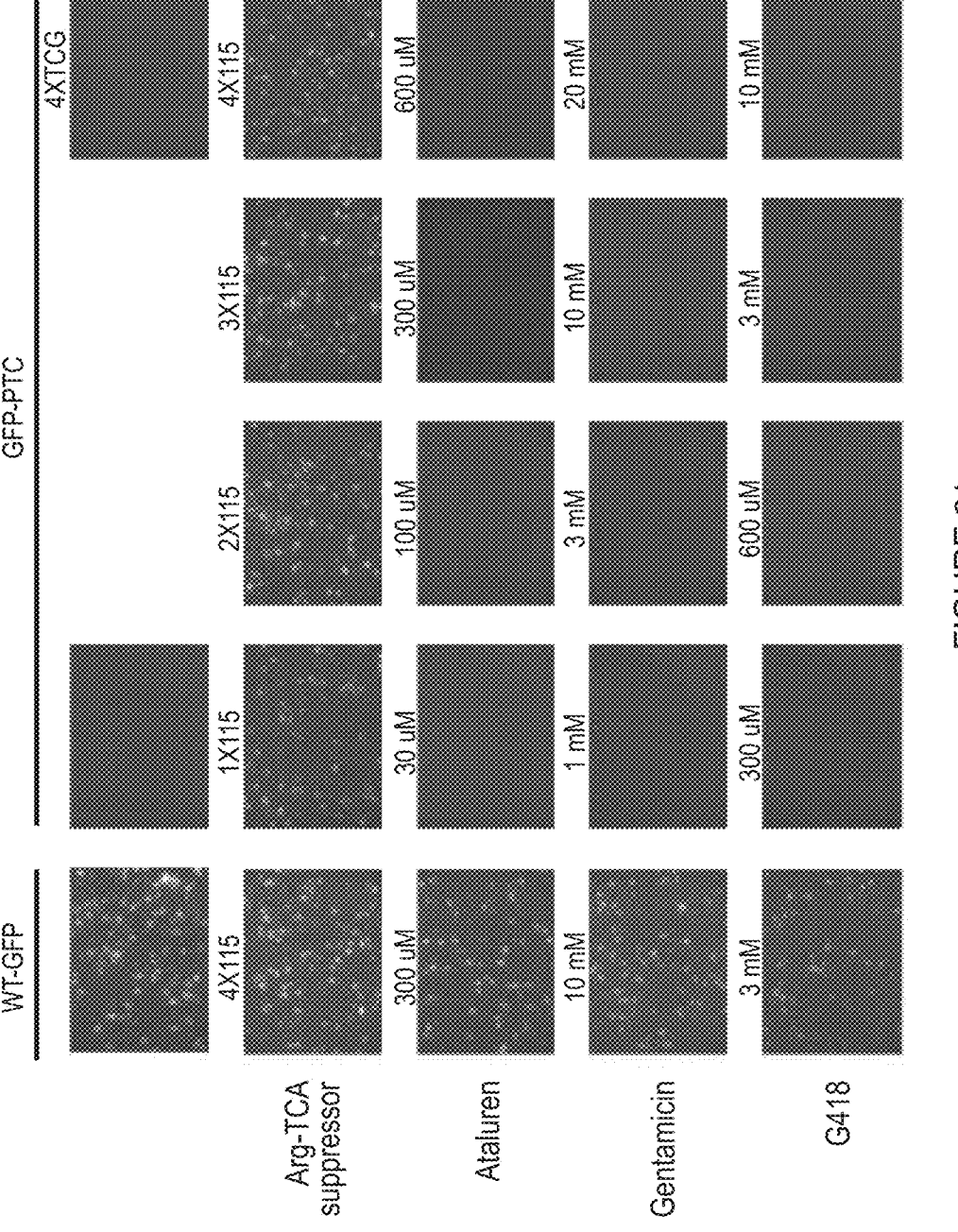

FIG. 21 depicts fluorescent images of Neuro-2a cells ~24 hours after transfection with an expression construct containing an EGFP-R96X-TGA reporter ("GFP-PTC") and either (i) including the $Arg_{TCA}$ suppressor tRNA #115 (SEQ ID NO: 18) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hours after transfection and the indicated drugs at the indicated concentrations were added at this point. Controls in the left column were transfected with an expression construct containing wild-type EGFP ("WT-GFP") and the indicated drug or $Arg_{TCA}$ suppressor tRNA at the indicated copy number.

Figure 22:
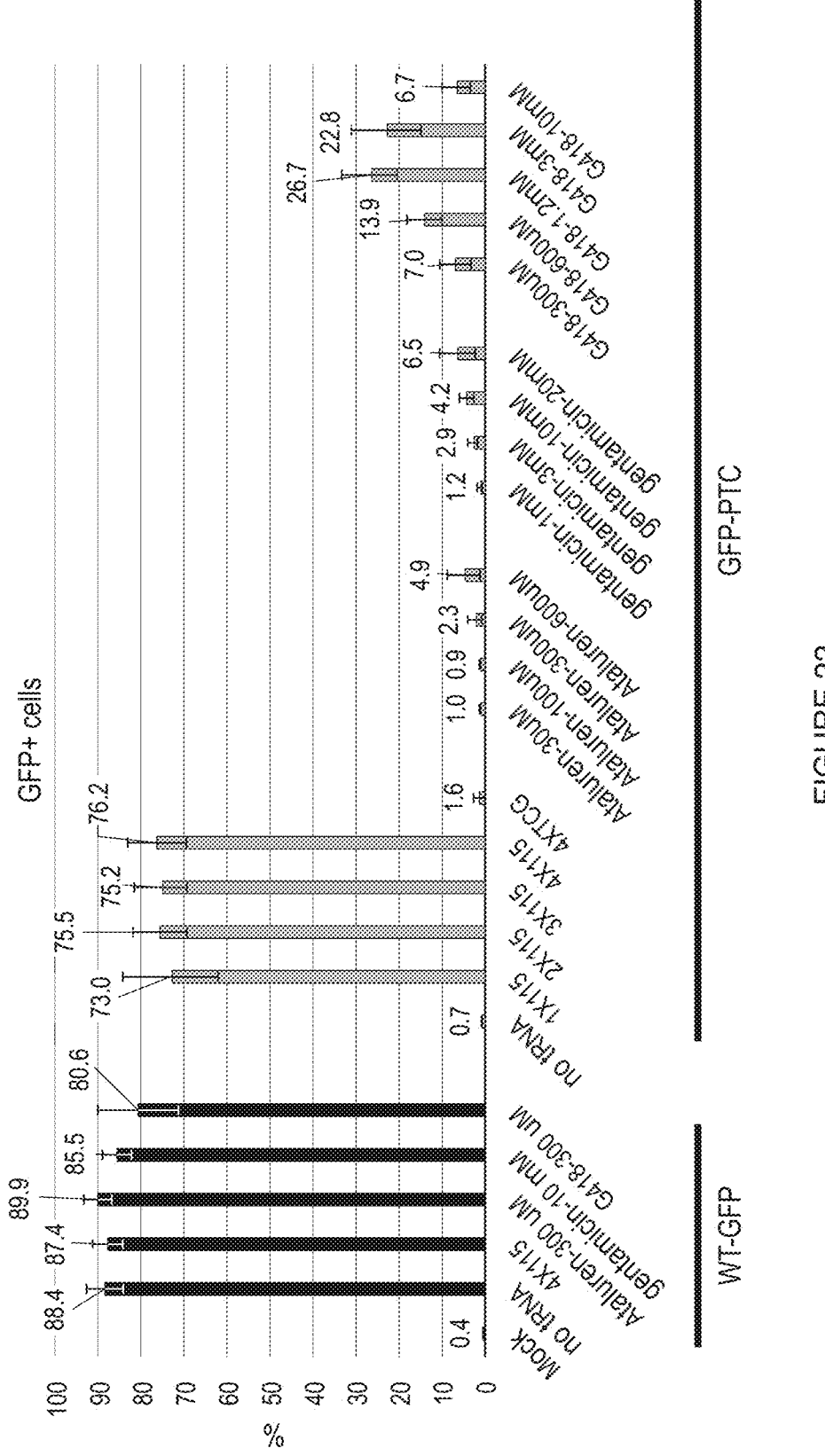

FIG. 22 is a graph depicting percentage of GFP positive cells as measured by flow cytometry at ~48 hours post transfection. Neuro-2a cells were transfected with an expression construct containing an EGFP-R96X-TGA reporter ("GFP-PTC") and either (i) including the $Arg_{TCA}$ suppressor tRNA #115 (SEQ ID NO: 18) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hours after transfection and the indicated drugs at the indicated concentrations were added at this point. A reporter containing wildtype EGFP without a PTC ("WT-GFP") was used as a control. "Mock" indicates mock transfected cells. "4×TCG" indicates cells transfected with an expression construct that contains four copies of a wild-type Arg-tRNA with a TCG anticodon and the EGFP-R96X-TGA reporter. Plot shows the percentage of viable cells that express EGFP above background. The percentage of cells that expressed GFP ranged from 73.0 to 76.2% for the cells expressing the $Arg_{TCA}$ suppressor, relative to 0.7 to 1.6% for negative controls, 0.9 to 4.9% for cells treated with ataluren, 1.2 to 6.5% for cells treated with gentamicin, and 6.7% to 26.7% for cells treated with G418.

Figure 23:
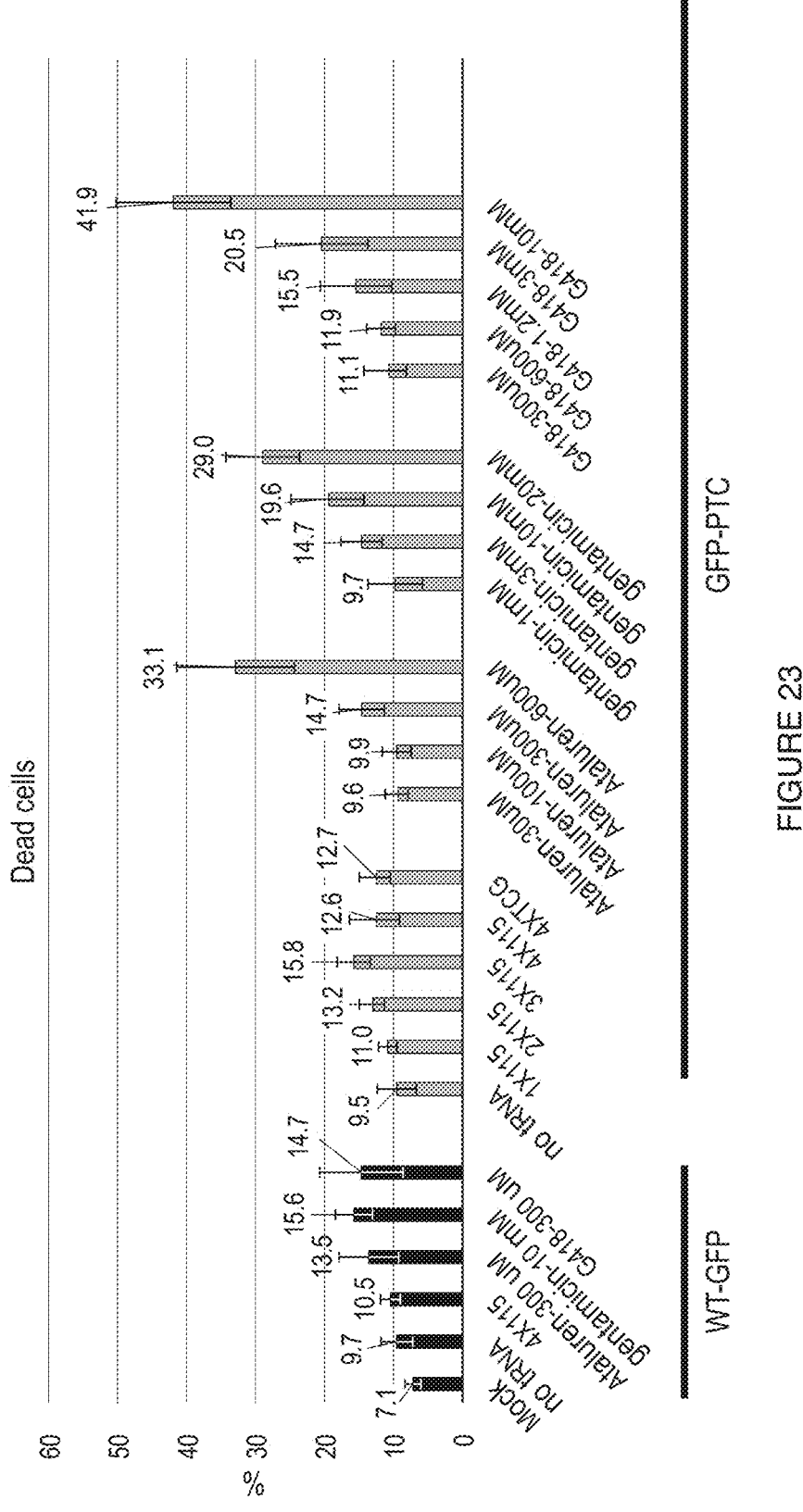

FIG. 23 is a graph depicting cell viability from FIG. 22 as measured by flow cytometry at ~48 hours post transfection. Neuro-2a cells were transfected with an expression construct containing the EGFP-R96X-TGA reporter ("GFP-PTC") and either (i) transfected with an expression construct including the $Arg_{TCA}$ suppressor tRNA #115 (SEQ ID NO: 18) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hour after transfection and the indicated drugs at the indicated concentrations were added at this point. A reporter containing wildtype GFP without a PTC ("WT-GFP") was used as a control. "Mock" indicates mock transfected cells. "4×TCG" indicates cells transfected with an expression construct that contains four copies of a wild-type Arg-tRNA with a TCG anticodon and the EGFP-R96X-TGA reporter. Cell viability was assessed by flow cytometry using 7-Amino Actinomycin D (7-AAD), a membrane impermeant dye that is generally excluded from viable cells.

Figure 24:
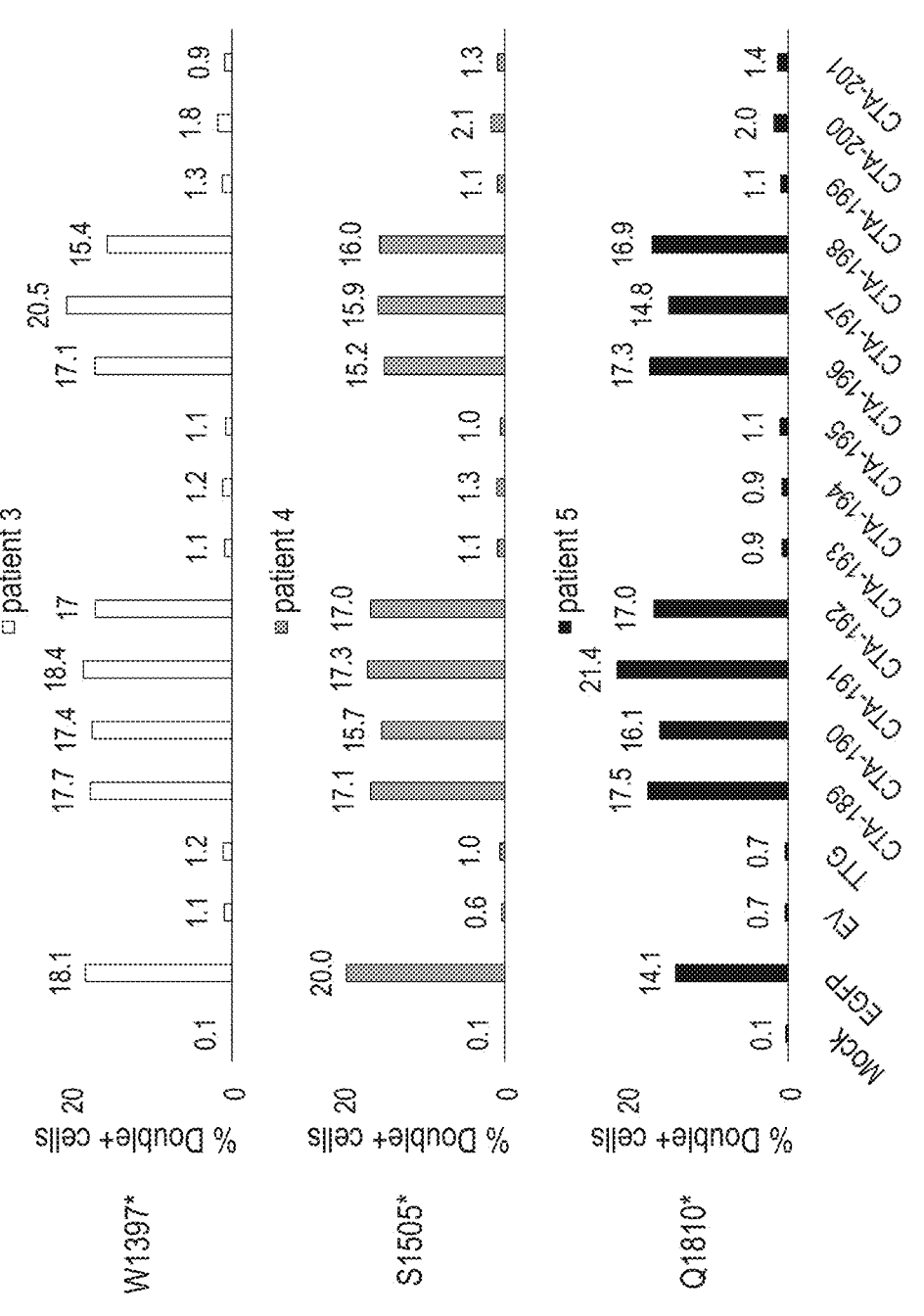

FIG. 24 is a graph depicting readthrough activity of the indicated GlncTA suppressor tRNAs (SEQ ID NOs: 178-190) in Flp-In-293 cells transiently co-transfected with the indicated dual fluorescent reporter constructs that contain linker regions (SEQ ID NOs: 889, 891, and 893) derived from three clinically relevant Gln(Q)-to-TAG PTC mutations in SCN1A (W1397*, S1505*, and Q1810*) that are linked to Dravet syndrome. "Mock" indicates mock-transfected cells, "No PTC" indicates cells transfected with versions of the dual fluorescent reporter constructs lacking a PTC (SEQ ID Nos: 890, 892, and 894), "EV" (empty vector) indicates cells transfected with an expression construct that does not contain a tRNA or a fluorescent reporter, "TTG" indicates cells co-transfected with the indicated dual fluorescent reporter construct and an expression construct that contains a wild-type Gln-tRNA with a TTG anticodon. Readthrough activity was measured by flow cytometry at ~24 hours post-transfection and is presented as the percentage of viable cells that that express both tdTomato and EGFP above baseline ("% Double+ cells").

Figure 25:
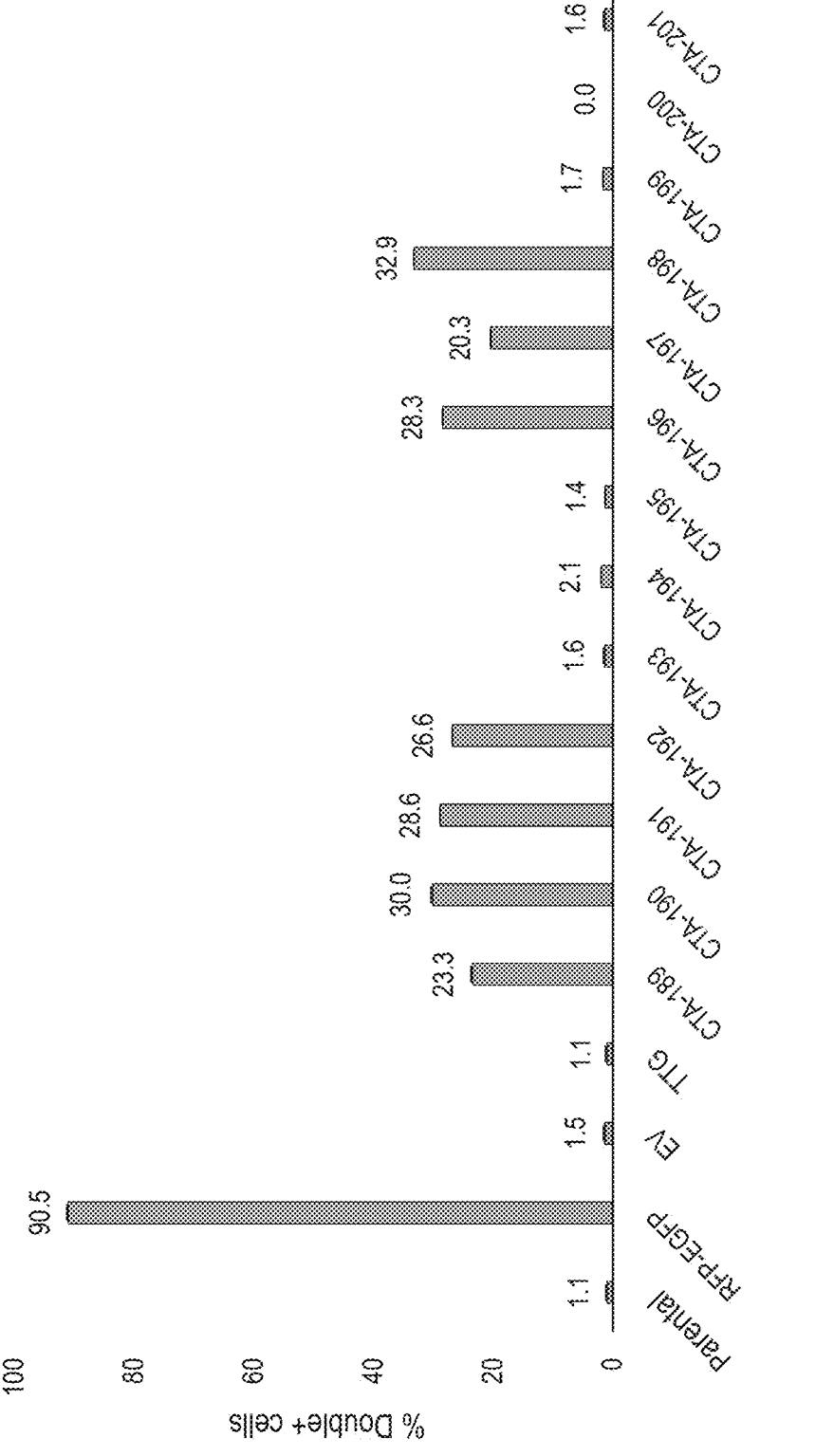

FIG. 25 is a graph depicting readthrough activity of the indicated GlncTA suppressor tRNAs (SEQ ID NOs: 178-190) in a Flp-In-293 cell line containing an integrated dual fluorescent reporter construct that contains a linker region (SEQ ID NO: 889) which is derived from a clinically relevant PTC mutation in SCN1A (W1397*) that is linked to Dravet syndrome. "Mock" indicates mock-transfected cells, "RFP-EGFP" indicates a Flp-In-293 cell line containing an integrated version of the dual fluorescent reporter construct lacking a PTC (SEQ ID NO: 890), "EV" (empty vector) indicates cells transfected with an expression construct that does not contain a tRNA or an EGFP reporter, "TTG" indicates cells transfected with a wild-type Gln-tRNA with a TTG anticodon. Readthrough activity was measured by flow cytometry at ~24 hours post transfection and is presented as the percentage of cells that that express both tdTomato and EGFP above background ("% Double+ cells").

Figure 26A:
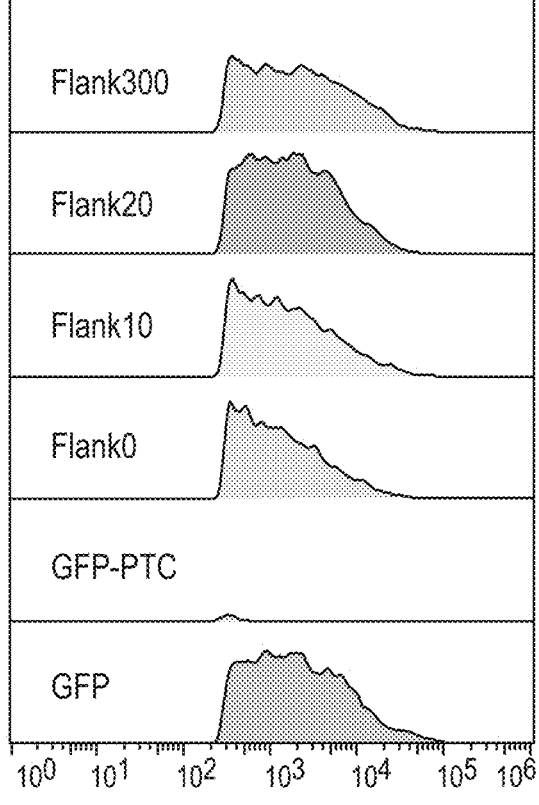
Figure 26B:
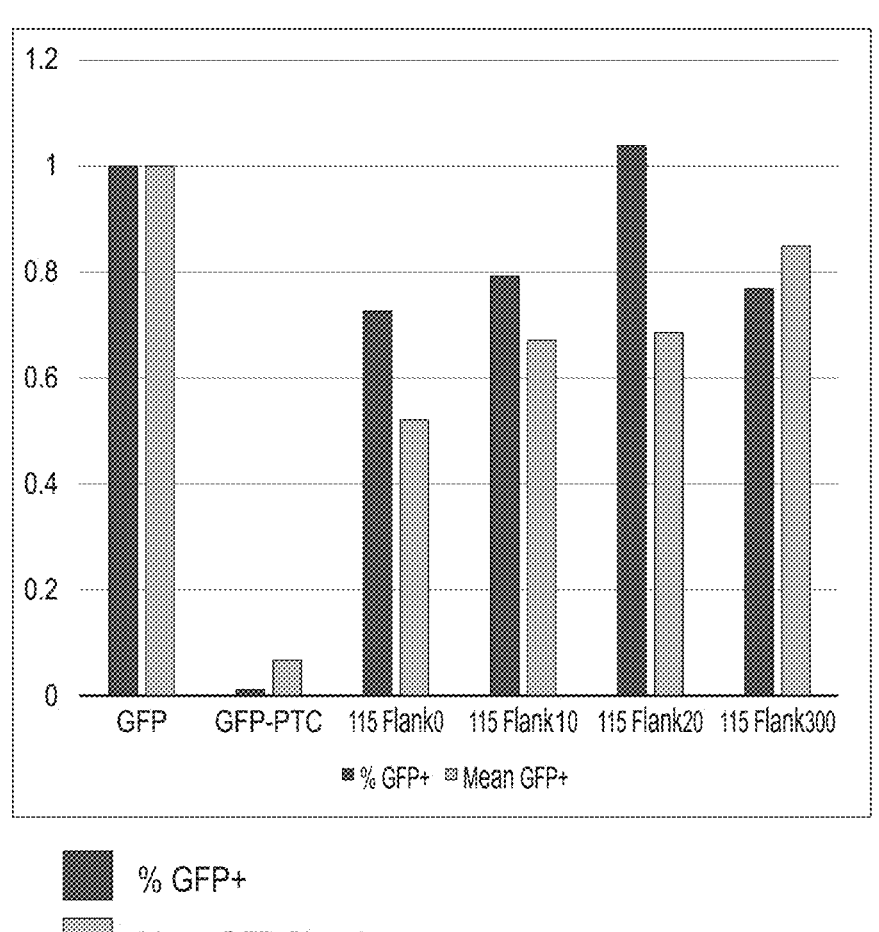

FIG. 26A shows fluorescence as measured by flow cytometry for Neuro-2a cells transfected with an expression construct containing an EGFP-R96X-TGA reporter (SEQ ID NO: 31) and a single copy of the $Arg_{TCA}$ suppressor tRNA #115 (SEQ ID NO: 18), in the context of either (i) 200 bps upstream flanking genomic DNA from tRNA-Arg-TCG-1-1 (SEQ ID NO: 26) and 104 bps of downstream flanking genomic DNA from tRNA-Arg-TCG-1-1 (SEQ ID NO: 32) ("Flank300"), (ii) 20 bps upstream flanking genomic DNA from tRNA-Arg-TCG-1-1 (SEQ ID NO: 895) and 17 bps of downstream flanking genomic DNA from tRNA-Arg-TCG-1-1 (SEQ ID NO: 896) ("Flank20"), (iii) 10 bps upstream flanking genomic DNA from tRNA-Arg-TCG-1-1 (SEQ ID NO: 897) and 17 bps of downstream flanking genomic DNA from tRNA-Arg-TCG-1-1 (SEQ ID NO: 896) ("Flank10"), or (iv) 0 bps upstream flanking genomic DNA from tRNA-Arg-TCG-1-1 and 17 bps of downstream flanking genomic DNA from tRNA-Arg-TCG-1-1 (SEQ ID NO: 896) ("Flank0"). Details of the expression vectors are shown in TABLE 11. "GFP-PTC" indicates cells transfected with the EGFP-R96X-TGA reporter alone (SEQ ID NO: 31), "GFP" indicates cells transfected with a version of the EGFP reporter that lacks a PTC. Readthrough activity was measured by flow cytometry at ~24 hours post transfection. Data are presented as histograms displaying the frequency distribution of the data versus fluorescence intensity for cells expressing EGFP above background. FIG. 26B shows the percentage of EGFP positive cells in all viable cells ("% GFP+") and mean EGFP intensity in viable cells expressing EGFP above background ("Mean GFP Signal") for the cells depicted in FIG. 26A.

Figure 27:
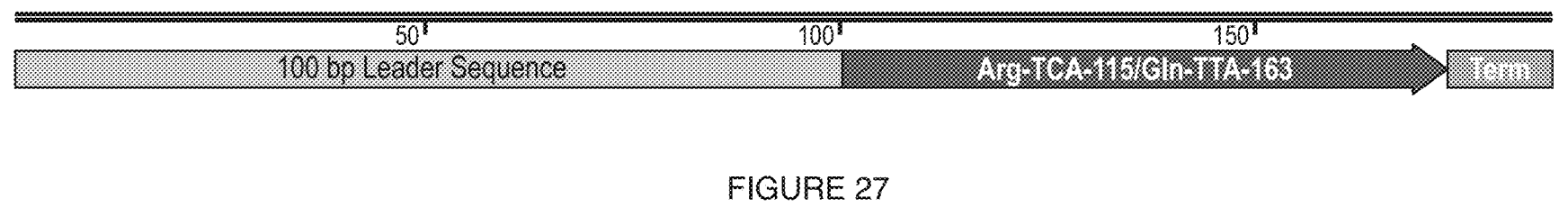

FIG. 27 is a schematic representation of the constructs used to test the impact of a 5' leader sequence on the read-through of a premature termination codon (PTC) by a suppressor tRNA. Constructs contain (i) a 100 bp 5' leader sequence derived from genomic DNA located upstream of tRNA genes that are highly expressed in HEK293 cells, (ii) a single copy of either the $Arg_{TCA}$ suppressor tRNA #115 (SEQ ID NO: 18) or the $Gln_{TTA}$ suppressor tRNA #163 (SEQ ID NO: 45), and (iii) an RNA polymerase III termination signal ("Term").

Figure 28:
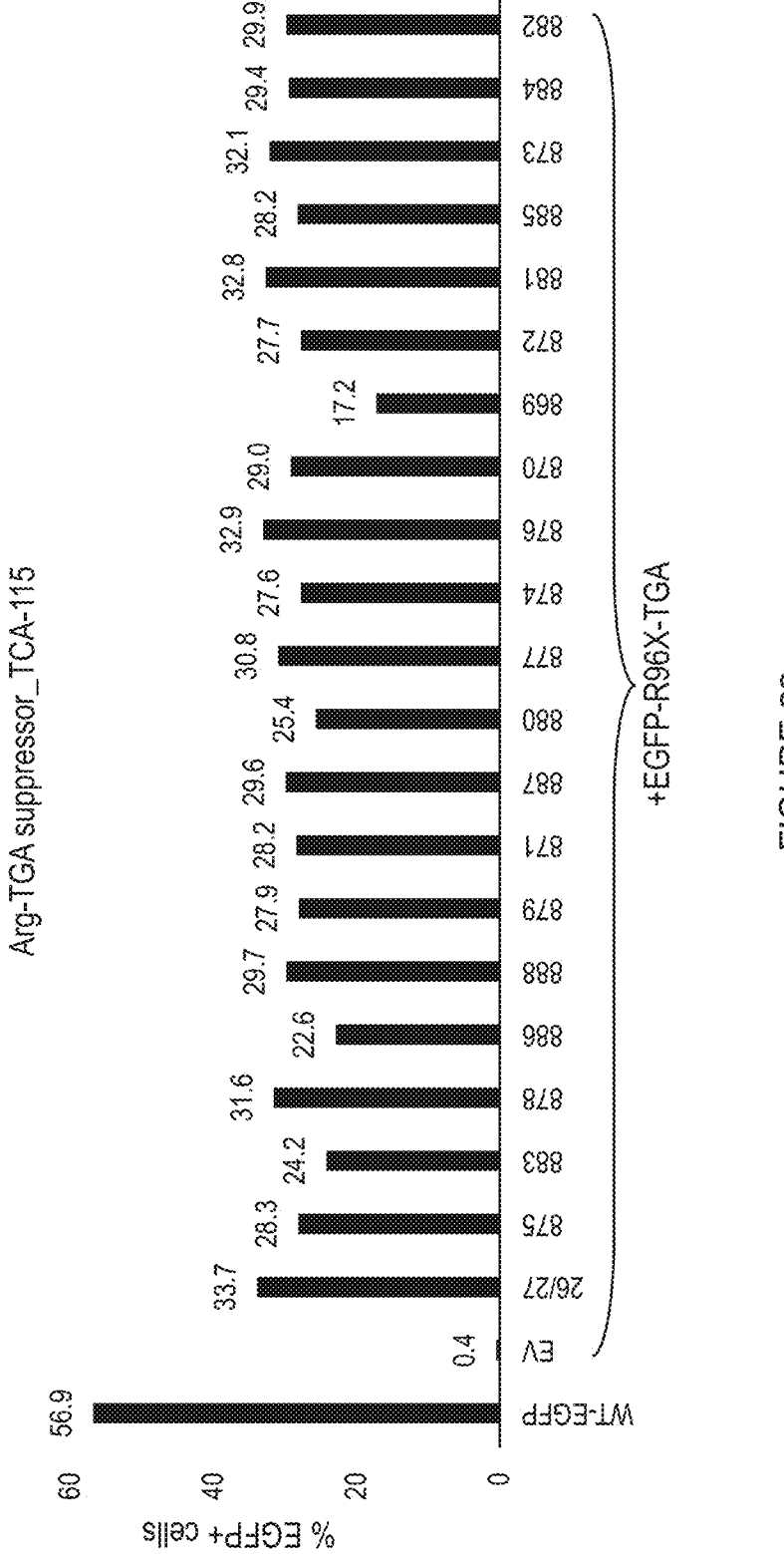

FIG. 28 is a graph depicting the readthrough activity of the indicated $Arg_{TCA}$ suppressor tRNA expression constructs as measured by flow cytometry in Flp-In-293 cells at ~24 hours post transfection. Cells were co-transfected with constructs containing (i) an EGFP-R96X-TGA reporter (SEQ ID NO: 31) and (ii) the $Arg_{TCA}$ suppressor tRNA #115 (SEQ ID NO: 18) in the context of the indicated 100 bps upstream genomic DNA leader sequences (SEQ ID NOs: 869-888). "WT-EGFP" indicates cells transfected with a reporter containing wild-type GFP without a PTC, "EV" (empty vector) indicates cells co-transfected with an expression construct that does not contain a tRNA or an EGFP reporter, and "26/27" indicates cells co-transfected with the $Arg_{TCA}$ suppressor tRNA #115 (SEQ ID NO: 18) in the context of 200 bps upstream flanking genomic DNA from tRNA-Arg-TCG-1-1 (SEQ ID NO: 26) and 200 bps of downstream flanking genomic DNA from tRNA-Arg-TCG-1-1 (SEQ ID NO: 27). The plot shows the percentage of viable cells that express EGFP above background. The percentage of cells that expressed EGFP ranged from 17.2 to 33.7% for the cells expressing the $Arg_{TCA}$ suppressor, relative to 0.4% for the empty vector control.

Figure 29:
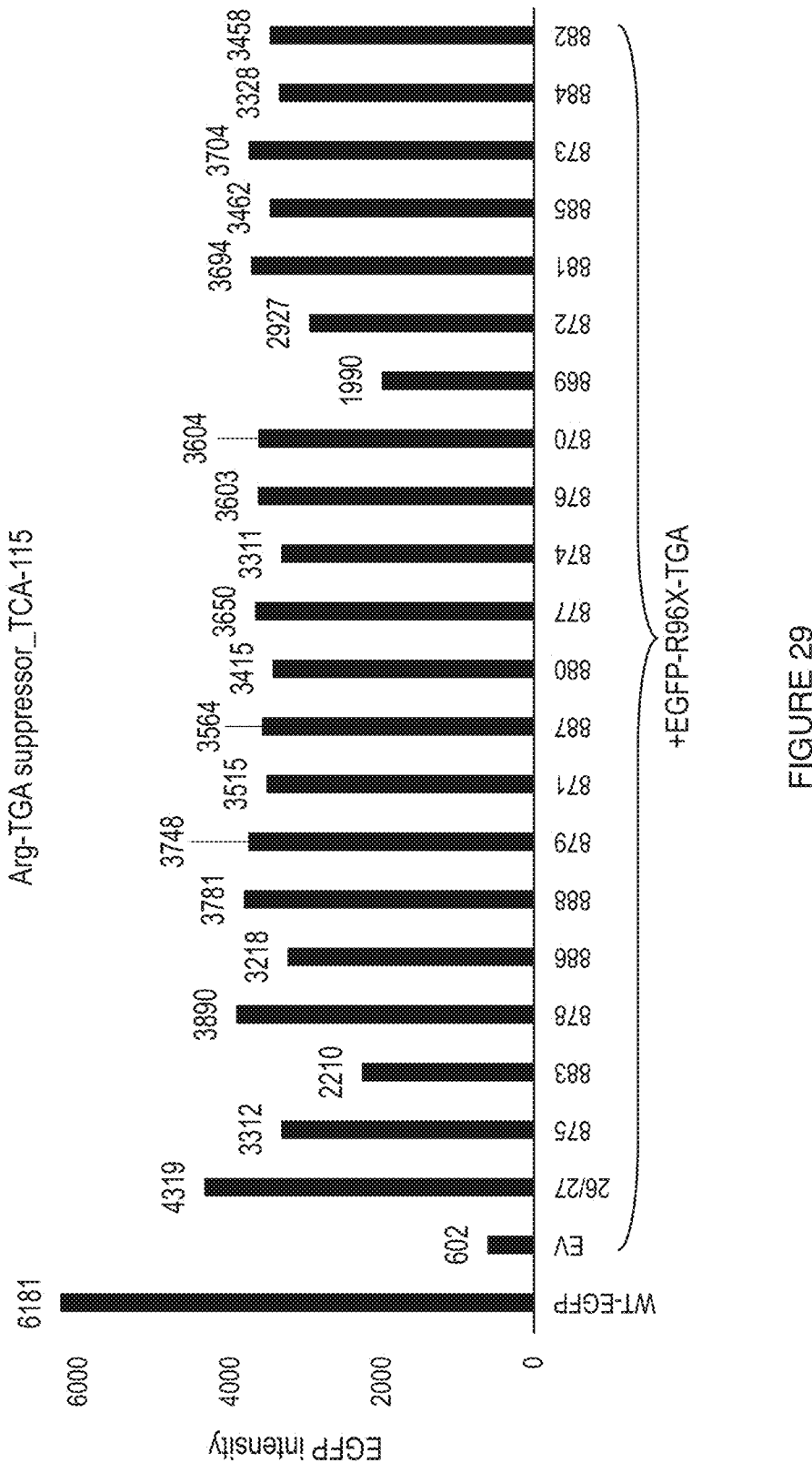

FIG. 29 is a graph depicting the readthrough activity of the indicated $Arg_{TCA}$ suppressor tRNA expression constructs as measured by flow cytometry in Flp-In-293 cells at ~24 hours post transfection. Cells were co-transfected with constructs containing (i) an EGFP-R96X-TGA reporter (SEQ ID NO: 31) and (ii) the $Arg_{TCA}$ suppressor tRNA #115 (SEQ ID NO: 18) in the context of the indicated 100 bps upstream genomic DNA leader sequences (SEQ ID NOs: 869-888). "WT-EGFP" indicates cells transfected with a reporter containing wild-type GFP without a PTC, "EV" (empty vector) indicates cells co-transfected with an expression construct that does not contain a tRNA or an EGFP reporter, and "26/27" indicates cells co-transfected with the $Arg_{TCA}$ suppressor tRNA #115 (SEQ ID NO: 18) in the context of 200 bps upstream flanking genomic DNA from tRNA-Arg-TCG-1-1 (SEQ ID NO: 26) and 200 bps of downstream flanking genomic DNA from tRNA-Arg-TCG-1-1 (SEQ ID NO: 27). The plot shows mean EGFP intensity in cells expressing EGFP above background. The mean EGFP intensity ranged from 1990 to 4319 for the cells expressing the $Arg_{TCA}$ suppressor, relative to 602 for the empty vector control.

Figure 30:
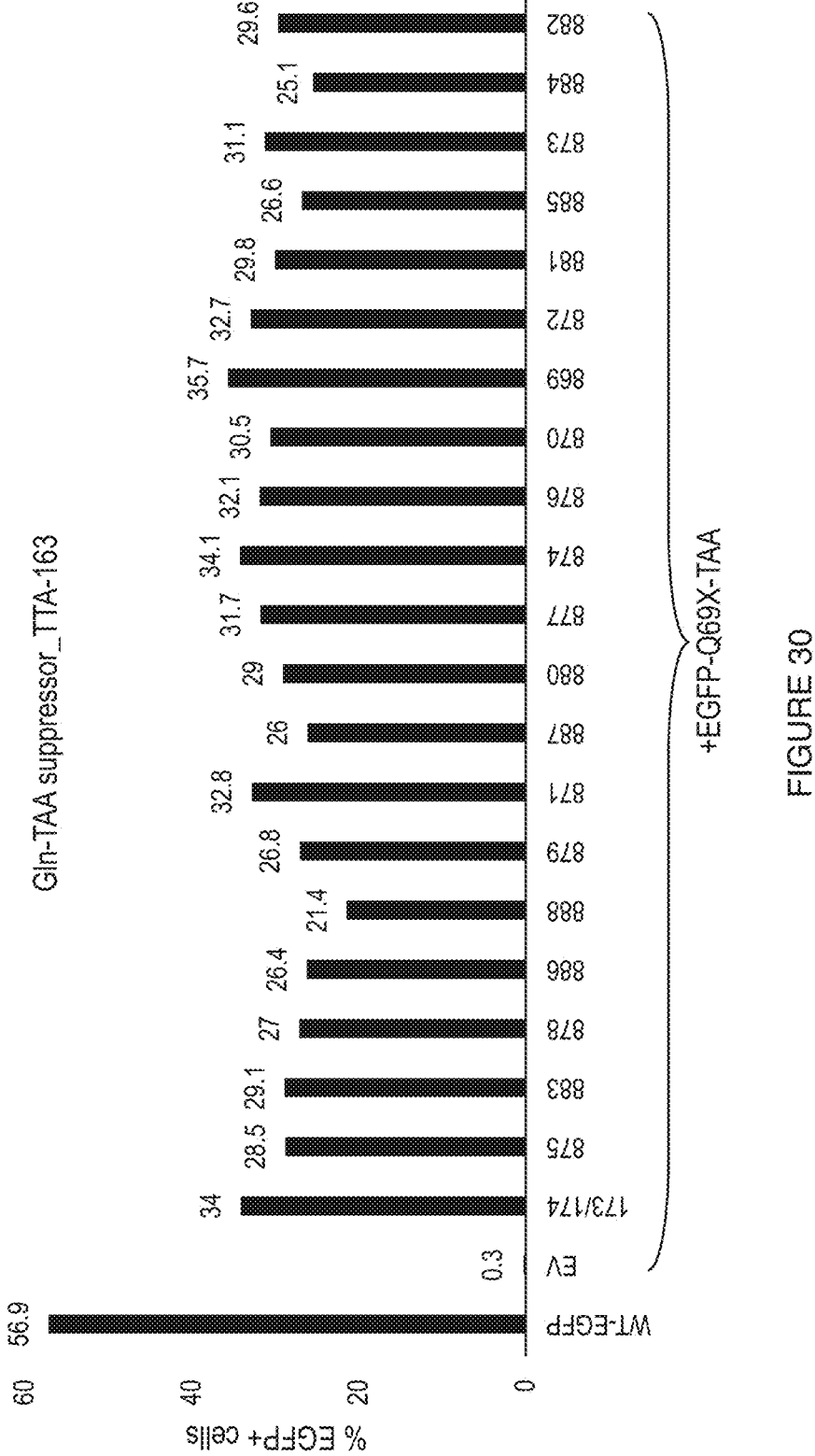

FIG. 30 is a graph depicting the readthrough activity of the indicated $Gln_{TTA}$ suppressor tRNA expression constructs as measured by flow cytometry in Flp-In-293 cells at ~24 hours post transfection. Cells were co-transfected with constructs containing (i) an EGFP-Q69X-TAA reporter (SEQ ID NO: 175) and (ii) the $Gln_{TTA}$ suppressor tRNA #163 (SEQ ID NO: 45) in the context of the indicated 100 bps upstream genomic DNA leader sequences (SEQ ID NOs: 869-888). "WT-EGFP" indicates cells transfected with a reporter containing wild-type GFP without a PTC, "EV" (empty vector) indicates cells co-transfected with an expression construct that does not contain a tRNA or an EGFP reporter, and "173/174" indicates cells co-transfected with the $Gln_{TTA}$ suppressor tRNA #163 (SEQ ID NO: 45) in the context of 200 bps upstream flanking genomic DNA from tRNA-Gln-TTG-1-1 (SEQ ID NO: 173) and 200 bps of downstream flanking genomic DNA from tRNA-Gln-TTG-1-1 (SEQ ID NO: 174). The plot shows the percentage of viable cells that express EGFP above background. The percentage of cells that expressed EGFP ranged from 21.4 to 35.7% for the cells expressing the $Gln_{TTA}$ suppressor, relative to 0.3% for the empty vector control.

Figure 31:
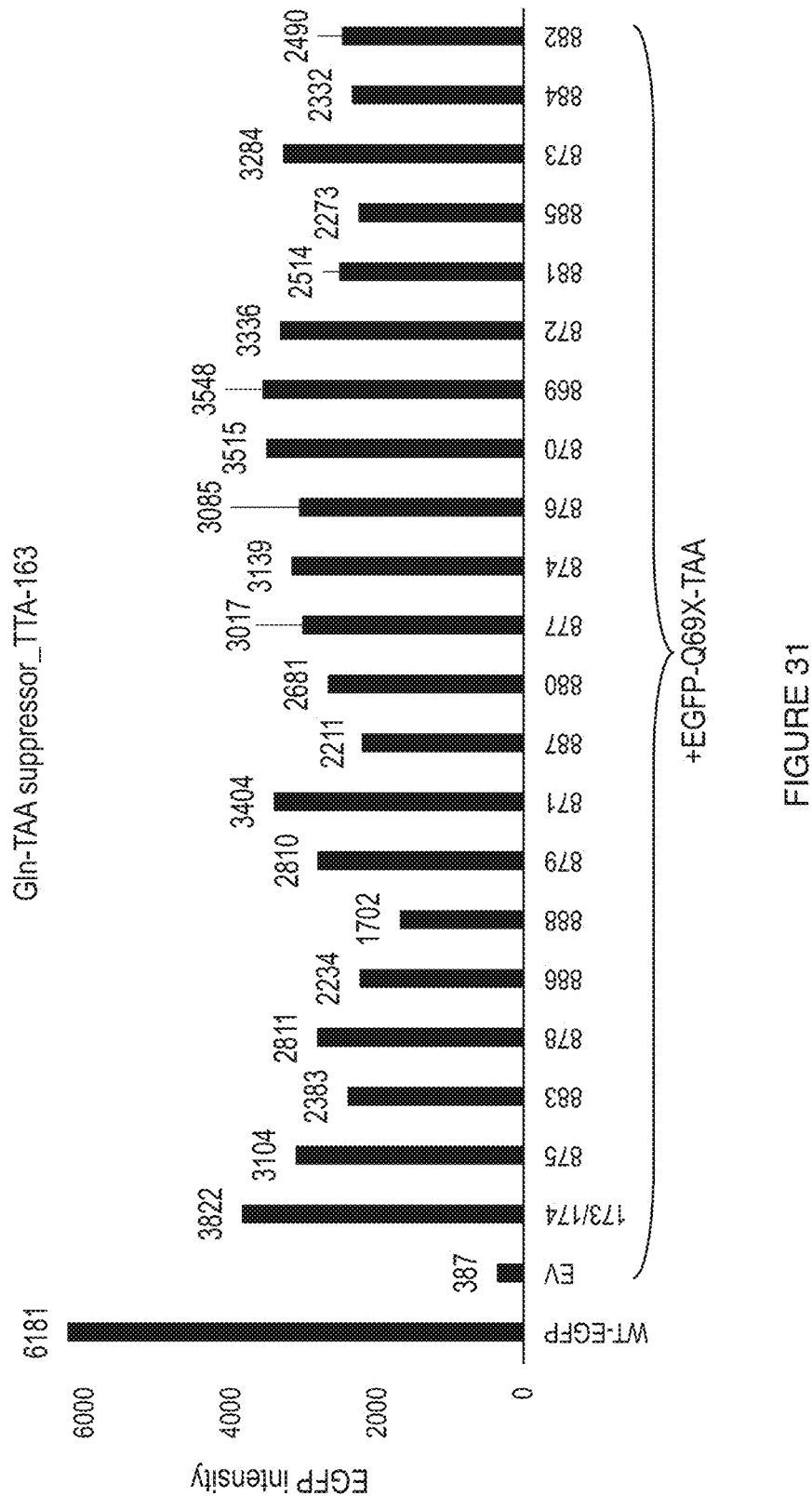

FIG. 31 is a graph depicting the readthrough activity of the indicated $Gln_{TTA}$ suppressor tRNA expression constructs as measured by flow cytometry in Flp-In-293 cells at ~24 hours post transfection. Cells were co-transfected with constructs containing (i) an EGFP-Q69X-TAA reporter (SEQ ID NO: 175) and (ii) the $Gln_{TTA}$ suppressor tRNA #163 (SEQ ID NO: 45) in the context of the indicated 100 bps upstream genomic DNA leader sequences (SEQ ID NOs: 869-888). "WT-EGFP" indicates cells transfected with a reporter containing wild-type GFP without a PTC, "EV" (empty vector) indicates cells co-transfected with an expression construct that does not contain a tRNA or an EGFP reporter, and "173/174" indicates cells co-transfected with the $Gln_{TTA}$ suppressor tRNA #163 (SEQ ID NO: 45) in the context of 200 bps upstream flanking genomic DNA from tRNA-Gln-TTG-1-1 (SEQ ID NO: 173) and 200 bps of downstream flanking genomic DNA from tRNA-Gln-TTG-1-1 (SEQ ID NO: 174). The plot shows mean EGFP intensity in cells expressing EGFP above background. The mean EGFP intensity ranged from 1702 to 3822 for the cells expressing the $Gln_{TTA}$ suppressor, relative to 387 for the empty vector control.

FIG. 32 is table summarizing the results of FIGS. 28-31, where the values have been normalized to cells transfected with wild-type GFP without a PTC.

Figure 33:
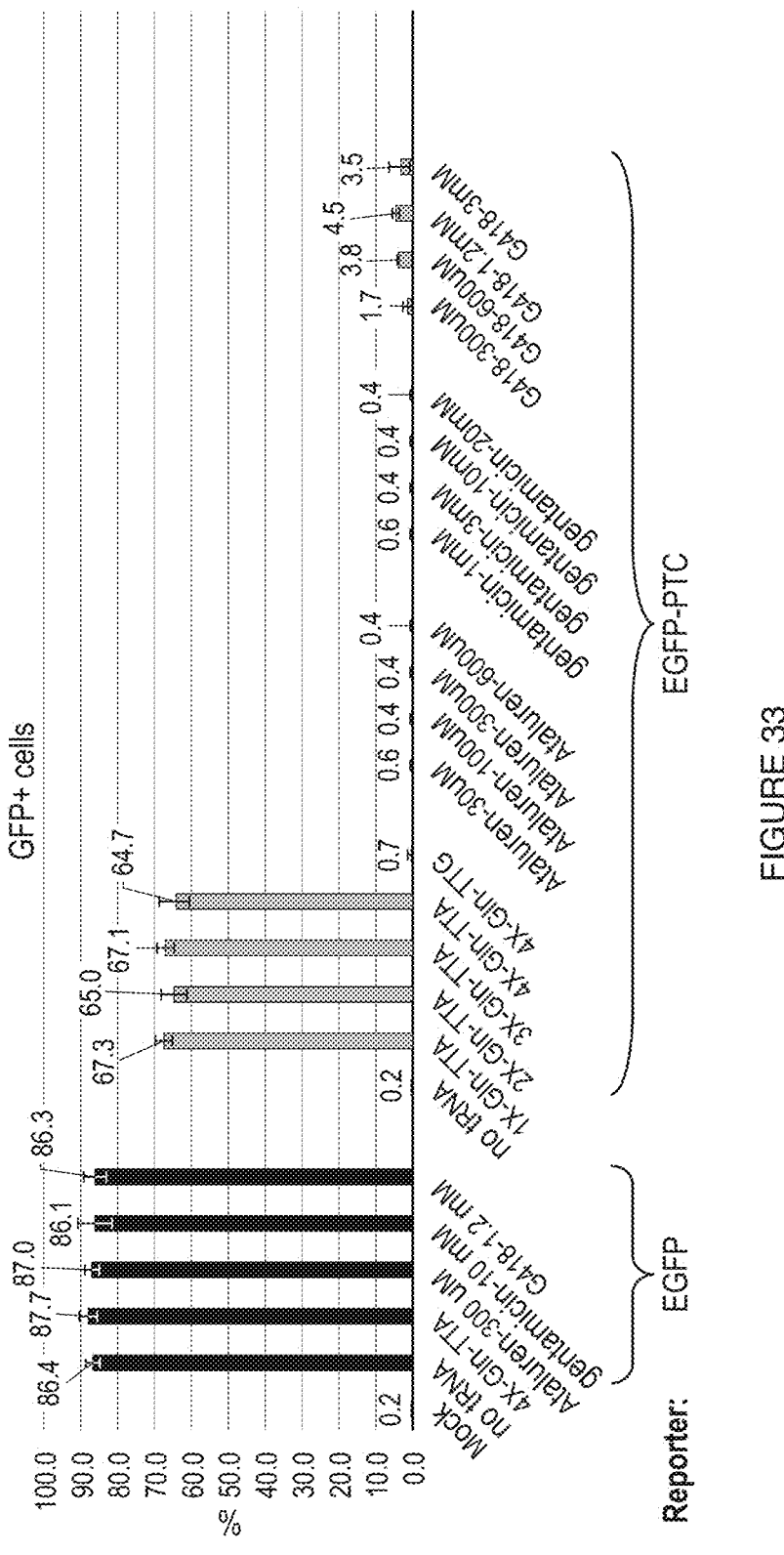

FIG. 33 is a graph depicting the percentage of EGFP positive cells as measured by flow cytometry in three independent experiments at ~48 hours post transfection. Neuro-2a cells were transfected with an expression construct containing the EGFP-Q69X-TAA reporter ("EGFP-PTC") (SEQ ID NO: 175) and either (i) including the $Gln_{TTA}$ suppressor tRNA #002 (SEQ ID NO: 36) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hours after transfection and the indicated drugs at the indicated concentrations were added at this point. A reporter containing wildtype EGFP without a PTC ("EGFP") was used as a control. "Mock" indicates mock transfected cells, "no tRNA" indicates cells transfected with the indicated EGFP expression construct alone, "4X-Gln-TTG" indicates cells transfected with an expression construct that contains four copies of a wild-type Gln-tRNA with a TTG anticodon and the EGFP-Q69X-TAA reporter. The plot shows the percentage of viable cells that express GFP above background. Error bars represent the standard deviation of the data. The percentage of cells that expressed GFP ranged from 64.7 to 67.3% for the cells expressing the $Gln_{TTA}$ suppressor, relative to 0.2 to 0.7% for negative controls, 0.4 to 0.6% for cells treated with ataluren, 0.4% for cells treated with gentamicin, and 1.7% to 4.5% for cells treated with G418.

Figure 34:
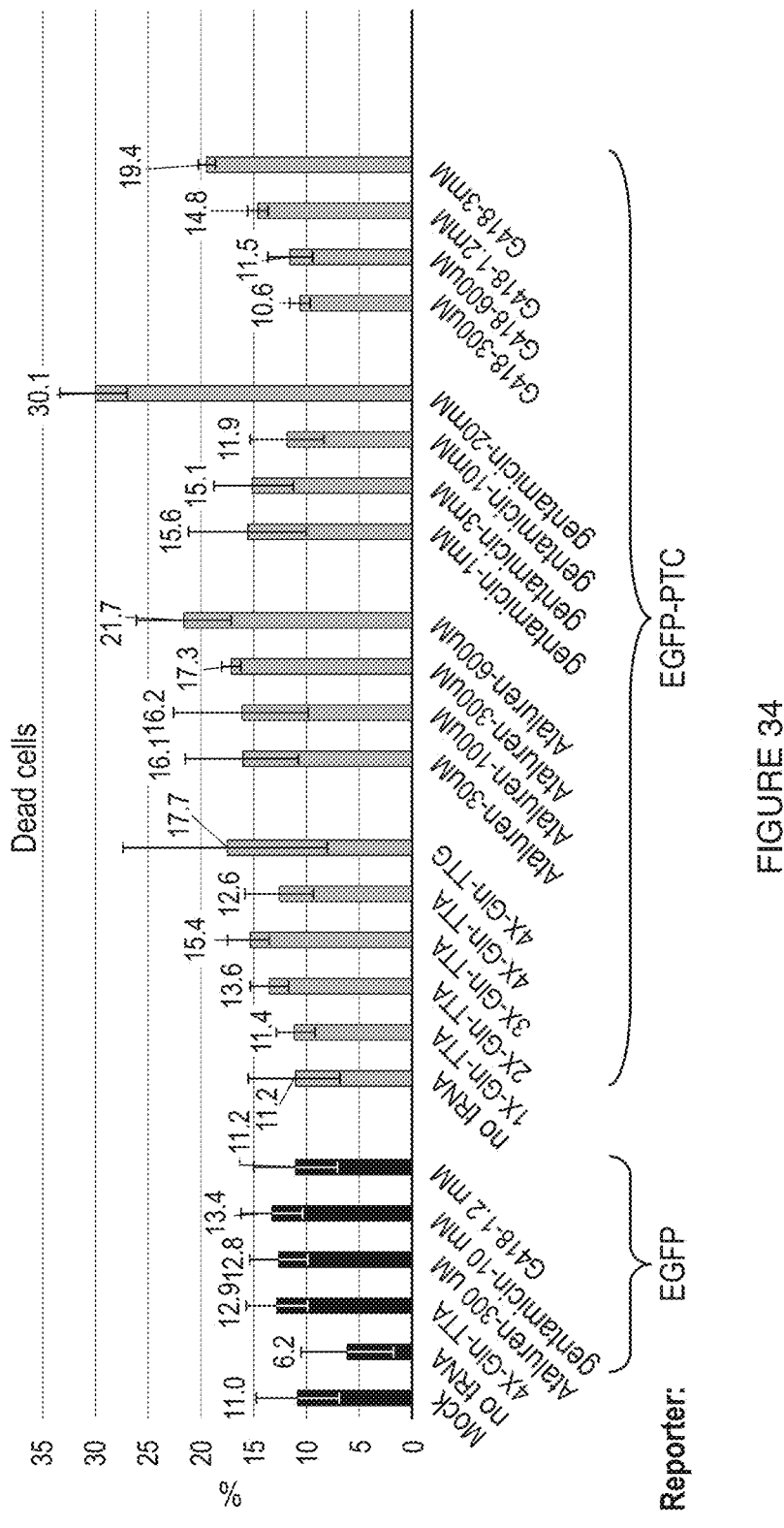

FIG. 34 is a graph depicting cell viability from FIG. 33 as measured by flow cytometry at ~48 hours post transfection. Neuro-2a cells were transfected with an expression construct containing the EGFP-Q69X-TAA reporter ("EGFP-PTC") (SEQ ID NO: 175) and either (i) including the $Gln_{TTA}$ suppressor tRNA #002 (SEQ ID NO: 36) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hours after transfection and the indicated drugs at the indicated concentrations were added at this point. A reporter containing wildtype EGFP without a PTC ("EGFP") was used as a control. "Mock" indicates mock transfected cells, "no tRNA" indicates cells transfected with the indicated EGFP expression construct alone, "4X-Gln-TTG" indicates cells transfected with an expression construct that contains four copies of a wild-type Gln-tRNA with a TTG anticodon and the EGFP-Q69X-TAA reporter. Cell viability was assessed by flow cytometry using 7-Amino Actinomycin D (7-AAD), a membrane impermeant dye that is generally excluded from viable cells.

Figure 35:
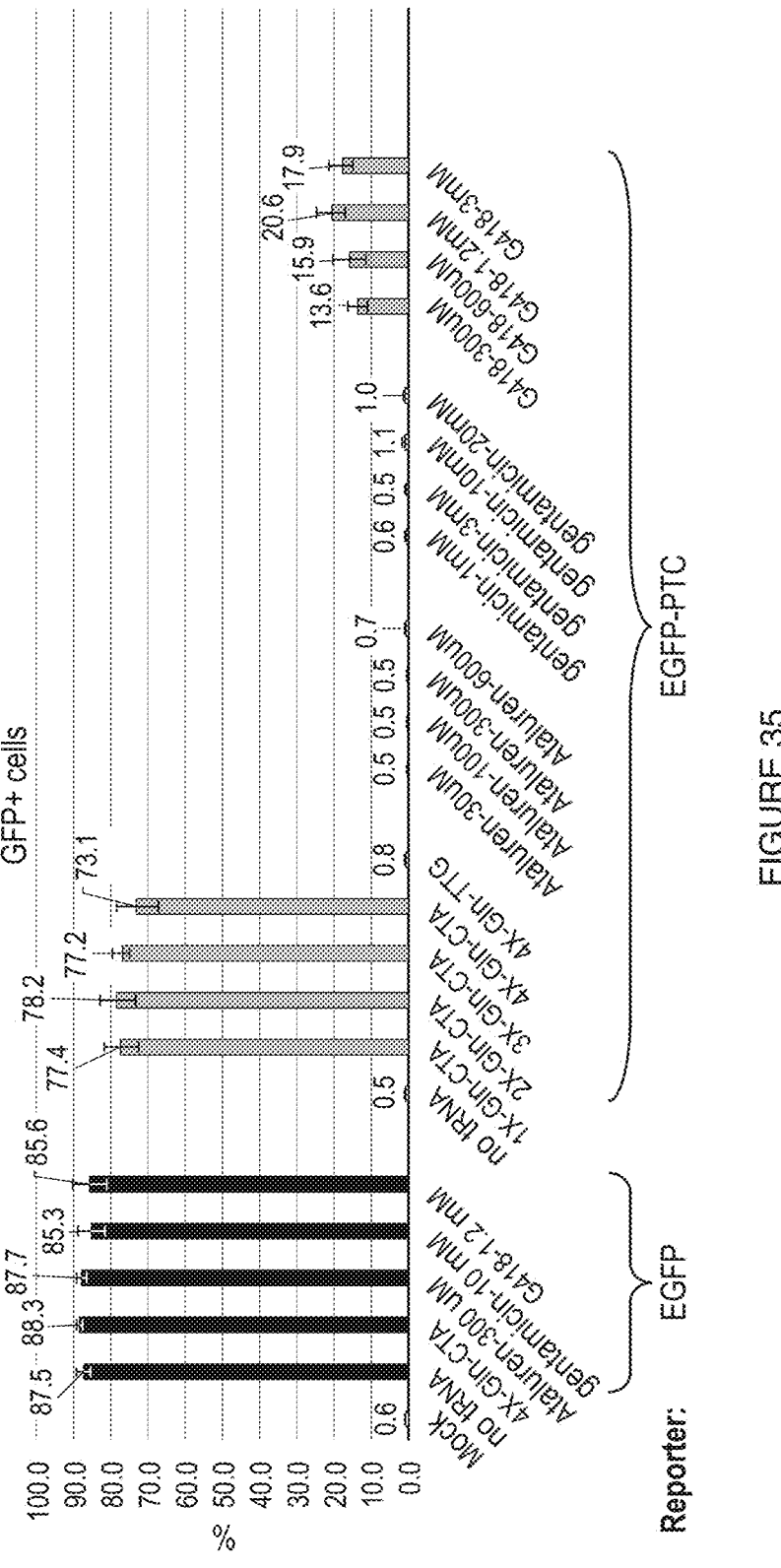

FIG. 35 is a graph depicting the percentage of EGFP positive cells as measured by flow cytometry in three independent experiments at ~48 hours post transfection. Neuro-2a cells were transfected with an expression construct containing the EGFP-Q69X-TAG reporter ("EGFP-PTC") (SEQ ID NO: 176) and either (i) including the GlncTA suppressor tRNA #196 (SEQ ID NO: 178) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hour after transfection and the indicated drugs at the indicated concentrations were added at this point. A reporter containing wildtype EGFP without a PTC ("EGFP") was used as a control. "Mock" indicates mock transfected cells, "no tRNA" indicates cells transfected with the indicated EGFP expression construct alone, "4X-Gln-TTG" indicates cells transfected with an expression construct that contains four copies of a wild-type Gln-tRNA with a TTG anticodon and the EGFP-Q69X-TAA reporter. Plot shows the percentage of viable cells that express GFP above background. The percentage of cells that expressed GFP ranged from 73.1 to 78.2% for the cells expressing the GlncTA suppressor, relative to 0.5 to 0.8% for negative controls, 0.5 to 0.7% for cells treated with ataluren, 0.5 to 1.1% for cells treated with gentamicin, and 13.6% to 20.6% for cells treated with G418.

Figure 36:
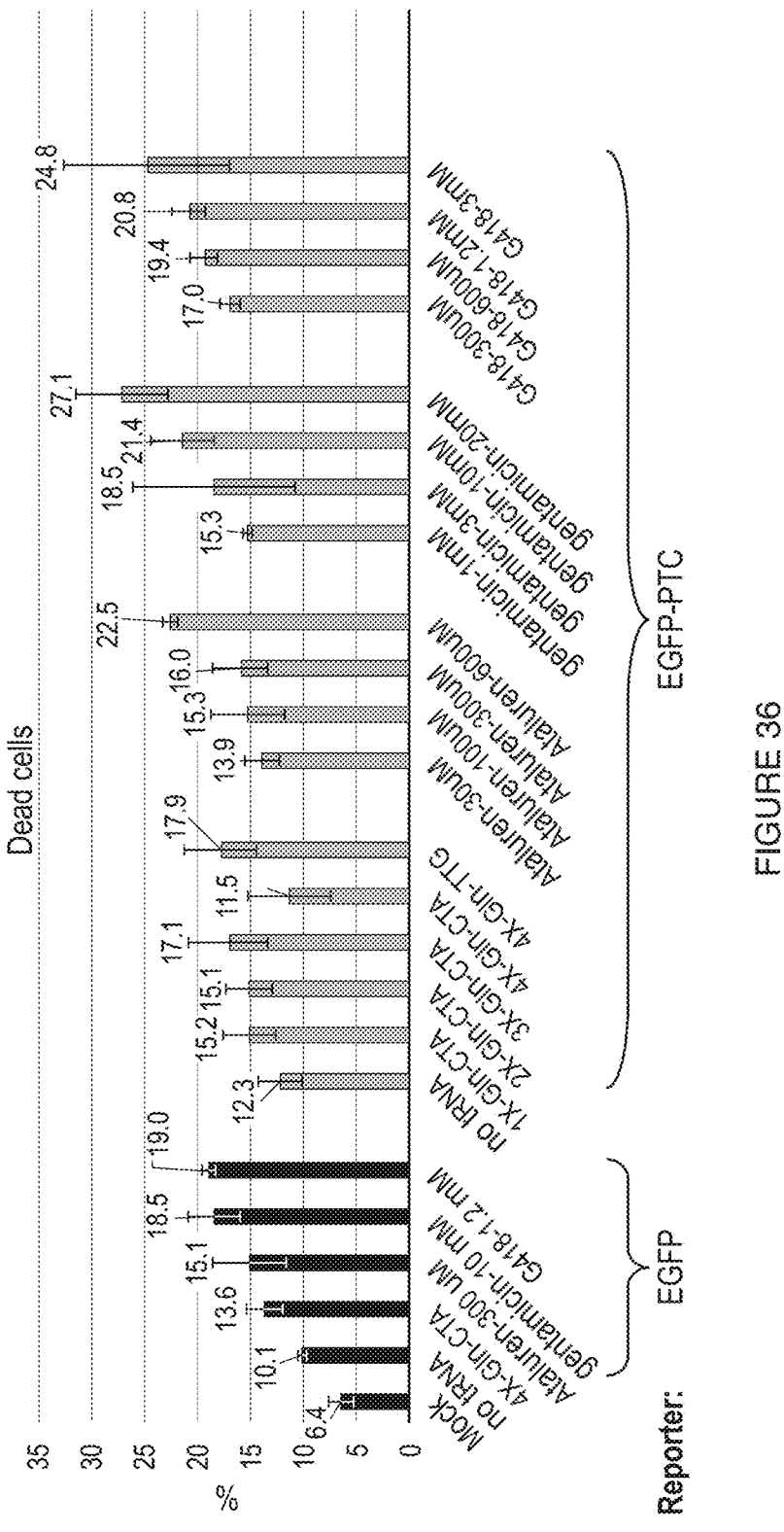

FIG. 36 is a graph depicting cell viability from FIG. 35 as measured by flow cytometry at ~48 hours post transfection.

Neuro-2a cells were transfected with an expression construct containing the EGFP-Q69X-TAG reporter ("EGFP-PTC") (SEQ ID NO: 176) and either (i) including the GlncTA suppressor tRNA #196 (SEQ ID NO: 178) at the indicated copy number on the same construct, or (ii) treated with ataluren at the indicated concentration, (iii) treated with gentamicin at the indication concentration, or (iv) treated with G418 at the indicated concentration. For all experimental conditions, cell culture medium was replaced with fresh medium ~6 hour after transfection and the indicated drugs at the indicated concentrations were added at this point. A reporter containing wildtype EGFP without a PTC ("EGFP") was used as a control. "Mock" indicates mock transfected cells, "no tRNA" indicates cells transfected with the indicated EGFP expression construct alone, "4X-Gln-TTG" indicates cells transfected with an expression construct that contains four copies of a wild-type Gln-tRNA with a TTG anticodon and the EGFP-Q69X-TAA reporter. Cell viability was assessed by flow cytometry using 7-Amino Actinomycin D (7-AAD), a membrane impermeant dye that is generally excluded from viable cells.

Figure 37A:
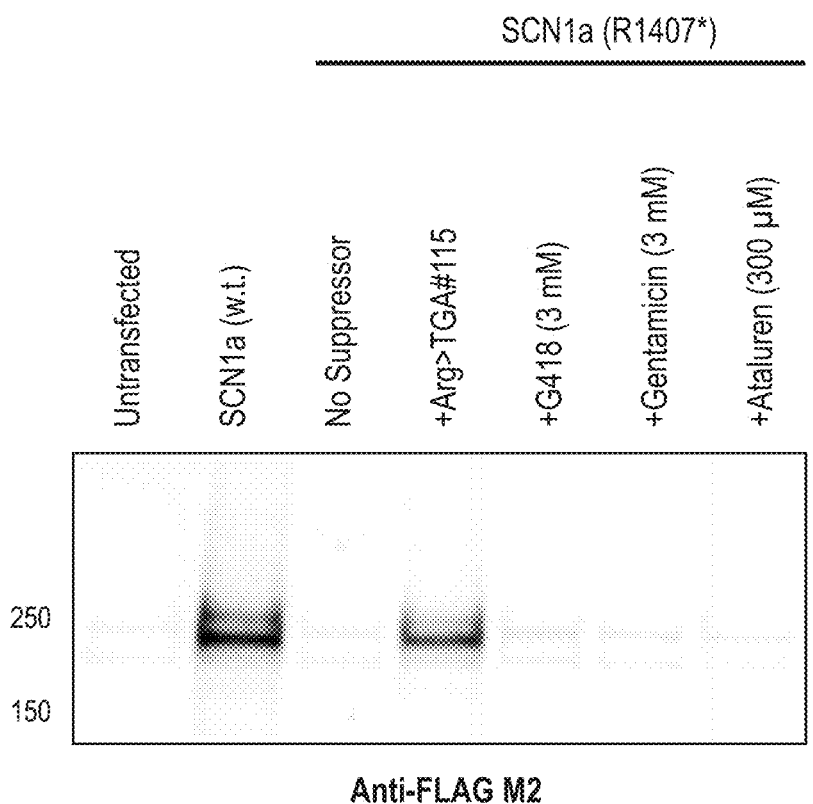
Figure 37B:
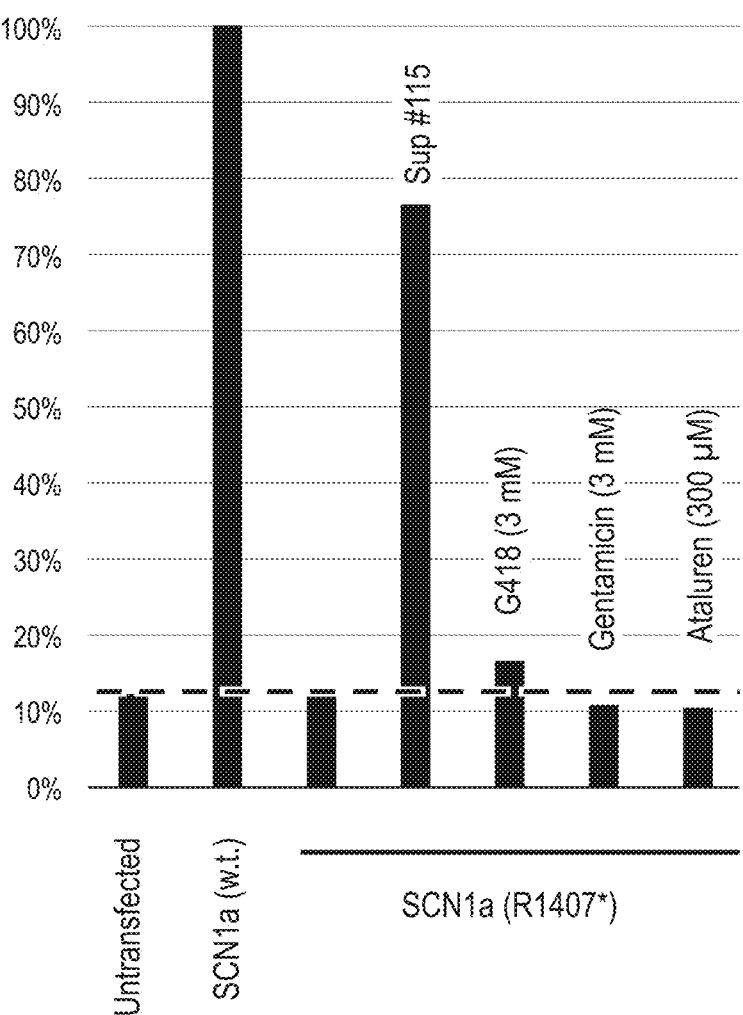

FIG. 37A is a Western blot depicting rescue of full-length SCN1A protein expression by a suppressor tRNA. Flp-In-293 cells were transfected with an expression construct containing mouse SCN1A with an Arg(R)-to-TGA PTC (R1407X) and a 3×FLAG tag peptide (DYKDHD-G-DYKDHD-I-DYKDDDDK) at the C-terminus (SEQ ID NO: 899) ("SCN1a (R1407*)") and either (i) co-transfected with an expression construct containing the $\text{Arg}_{TCA}$ suppressor tRNA #115 (SEQ ID NO: 18) ("Arg>TGA #115"), or (ii) treated with ataluren at the indicated concentration, (iii) treated with gentamicin at the indication concentration, or (iv) treated with G418 at the indicated concentration. "SCN1a (w.t.)" indicates cells transfected with an expression construct containing wild-type mouse SCN1A and a 3×FLAG tag peptide at the C-terminus (SEQ ID NO: 898). Protein was isolated at 24 hours post transfection and SCN1A was detected using a monoclonal anti-FLAG M2 antibody. Molecular weights based on protein molecular weight markers are indicated to the left of the gel. FIG. 37B is a quantification of the Western blot shown in FIG. 37A. The intensity of bands corresponding to the size of full-length SCN1A protein was measured using ImageJ and all intensity values were normalized to wild-type SCN1A protein ("SCN1a (w.t.)" lane). Cells co-transfected with expression vectors containing mutant SCN1A and the $\text{Arg}_{TCA}$ suppressor tRNA expressed greater than 70% of the full-length SCN1A expressed by cells transfected with an expression construct containing wild-type SCN1A.

Figure 38A:
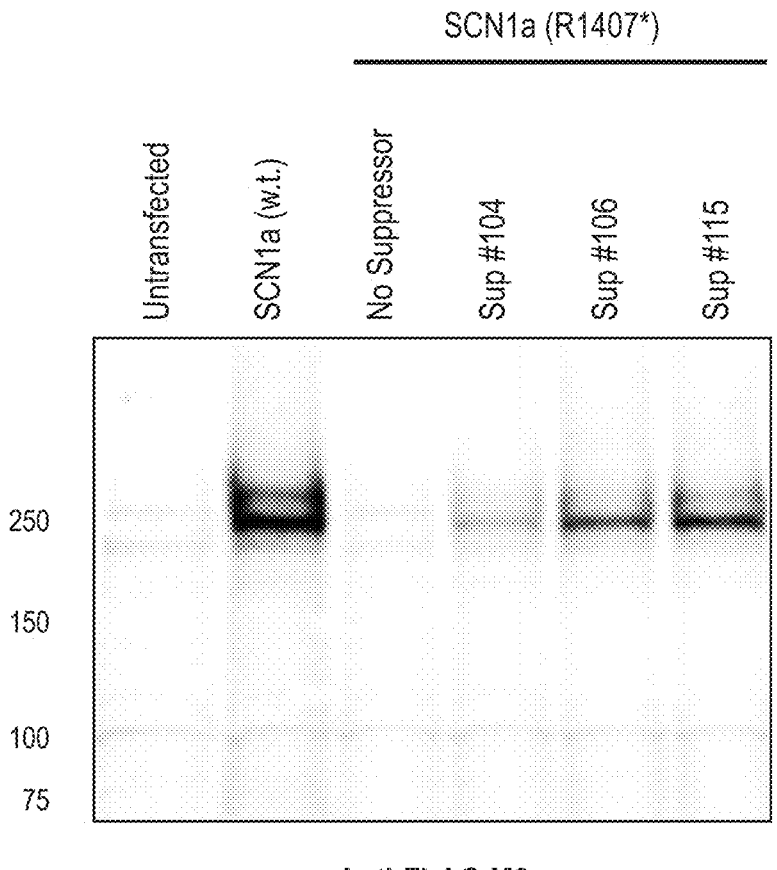
Figure 38B:
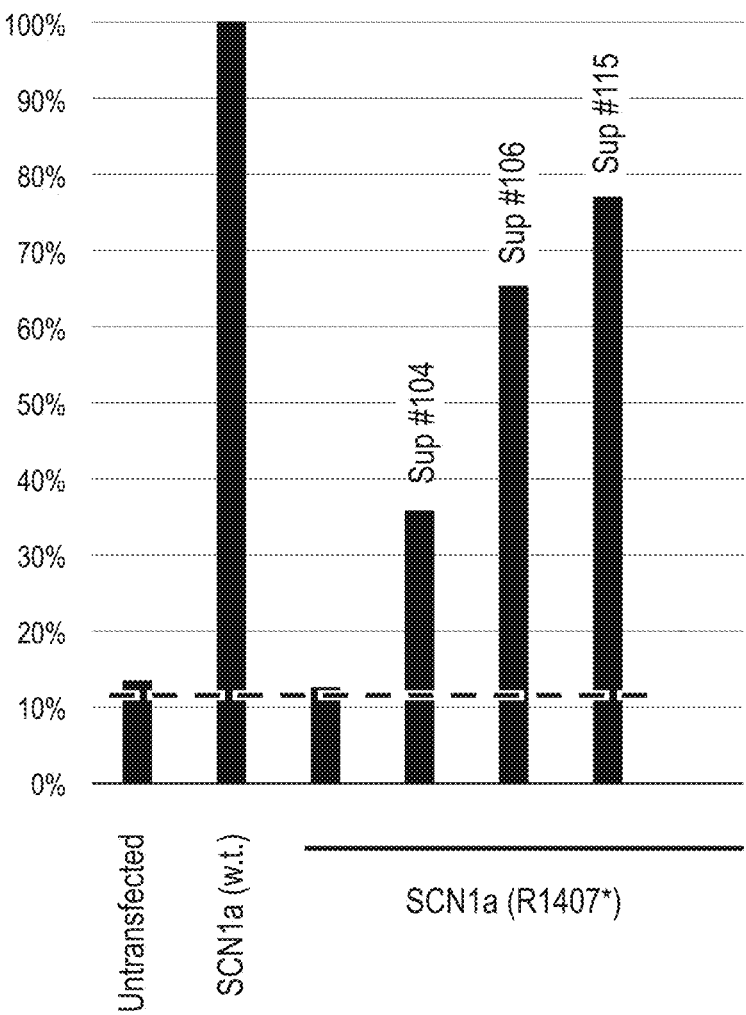

FIG. 38A is a Western blot depicting rescue of full-length SCN1A protein expression by suppressor tRNAs. Flp-In-293 cells were co-transfected with (i) an expression construct containing mouse SCN1A with an Arginine-to-TGA PTC (R1407X) and a 3×FLAG tag peptide (DYKDHD-G-DYKDHD-I-DYKDDDDK) at the C-terminus (SEQ ID NO: 899) ("SCN1a (R1407*)") and (ii) either the #104 $\text{Arg}_{TCA}$ suppressor tRNA (SEQ ID NO: 6) ("Sup #104"), the #106 $\text{Arg}_{TCA}$ suppressor tRNA (SEQ ID NO: 8) ("Sup #106"), or the $\text{Arg}_{TCA}$ suppressor tRNA #115 (SEQ ID NO: 18) ("Sup #115"). "SCN1a (w.t.)" indicates cells transfected with an expression construct containing wild-type mouse SCN1A and a 3×FLAG tag peptide at the C-terminus (SEQ ID NO: 898). Protein was isolated at 24 hours post transfection and SCN1A was detected using a monoclonal anti-FLAG M2 antibody. Molecular weights based on protein molecular weight markers are indicated to the left of the gel. FIG. 38B is a quantification of the Western blot shown in FIG. 38A. The intensity of bands corresponding to the size of full-length SCN1A protein was measured using ImageJ and all intensity values were normalized to wild-type SCN1A protein ("SCN1a (w.t.)" lane). Cells co-transfected with expression vectors containing mutant SCN1A and the $\text{Arg}_{TCA}$ suppressor tRNA expressed greater than 30% (Sup #104), greater than 60% (Sup #106), or greater than 70% (Sup #115) of the full-length SCN1A expressed by cells transfected with an expression construct containing wild-type SCN1A.

Figure 39A:
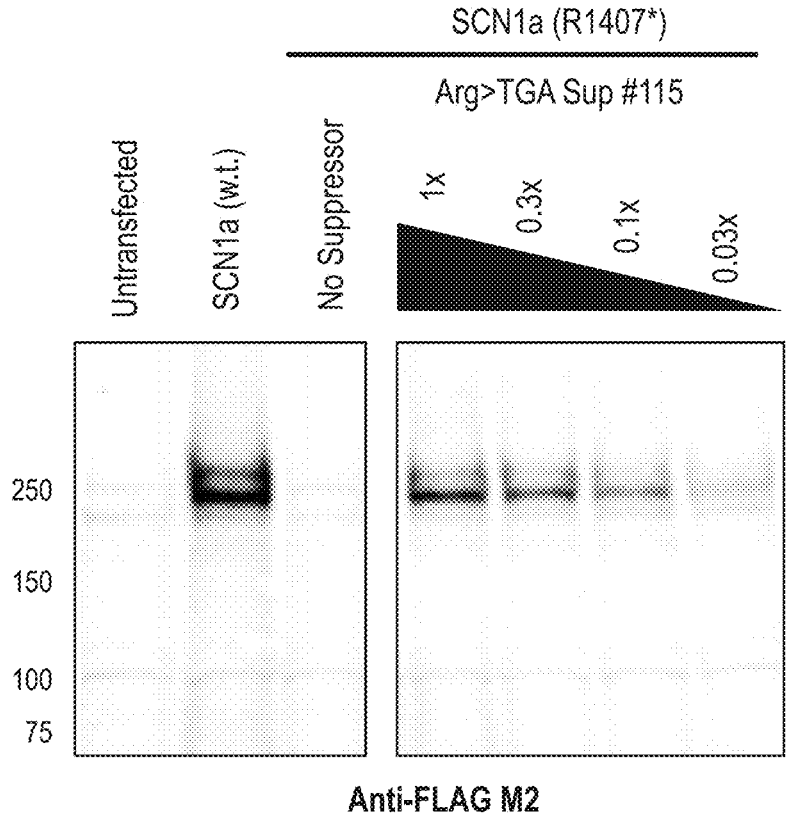
Figure 39B:
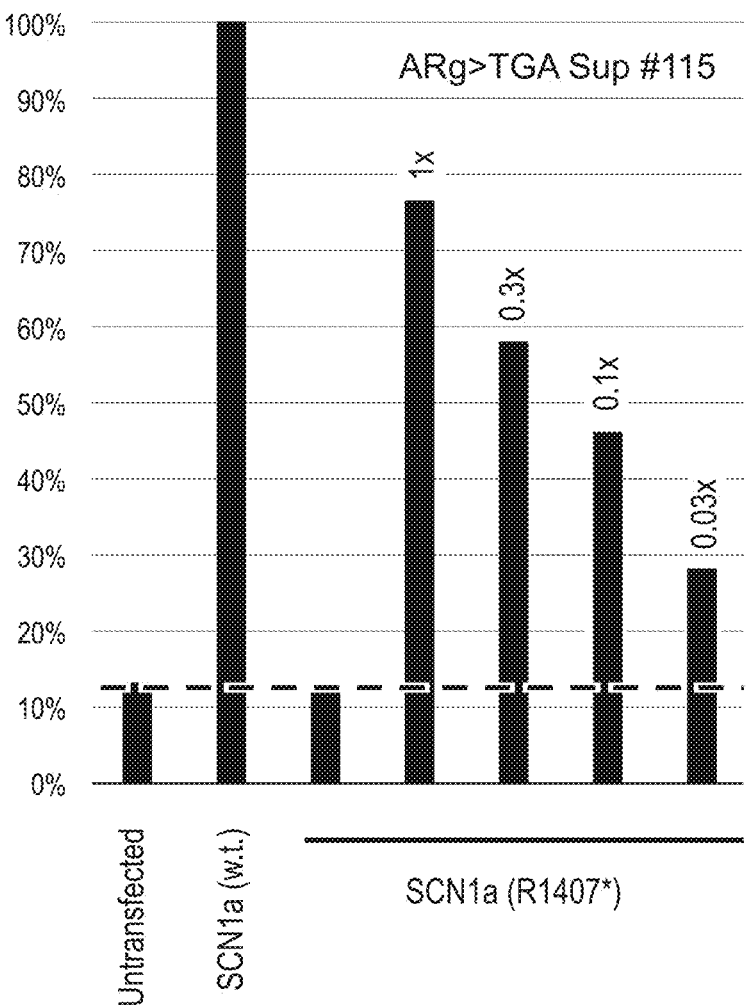

FIG. 39A is a Western blot depicting rescue of full-length SCN1A protein expression by a suppressor tRNA. Flp-In-293 cells were cultured in 6-well cell culture plates and co-transfected with (i) an expression construct containing mouse SCN1A with an Arginine-to-TGA PTC (R1407X) and a 3×FLAG tag peptide (DYKDHD-G-DYKDHD-I-DYKDDDDK) at the C-terminus (SEQ ID NO: 899) ("SCN1a (R1407*)") and (ii) the $\text{Arg}_{TCA}$ suppressor tRNA #115 (SEQ ID NO: 18) ("Arg>TGA #115") at the indicated concentrations. 1× indicates 400 ng of the $\text{Arg}_{TCA}$ suppressor tRNA construct per well, 0.3× indicates 133 ng of the $\text{Arg}_{TCA}$ suppressor tRNA construct per well, 0.1× indicates 40 ng of the $\text{Arg}_{TCA}$ suppressor tRNA construct per well, and 0.03× indicates 13 ng of the $\text{Arg}_{TCA}$ suppressor tRNA construct per well. "SCN1a (w.t.)" indicates cells transfected with an expression construct containing wild-type mouse SCN1A and a 3×FLAG tag peptide at the C-terminus (SEQ ID NO: 898). Protein was isolated at 24 hours post transfection and SCN1A was detected using a monoclonal anti-FLAG M2 antibody. Molecular weights based on protein molecular weight markers are indicated to the left of the gel. FIG. 39B is a quantification of the Western blot shown in FIG. 39A. The intensity of bands corresponding to the size of full-length SCN1A protein was measured using ImageJ and all intensity values were normalized to wild-type SCN1A protein ("SCN1a (w.t.)" lane).

Figure 40:
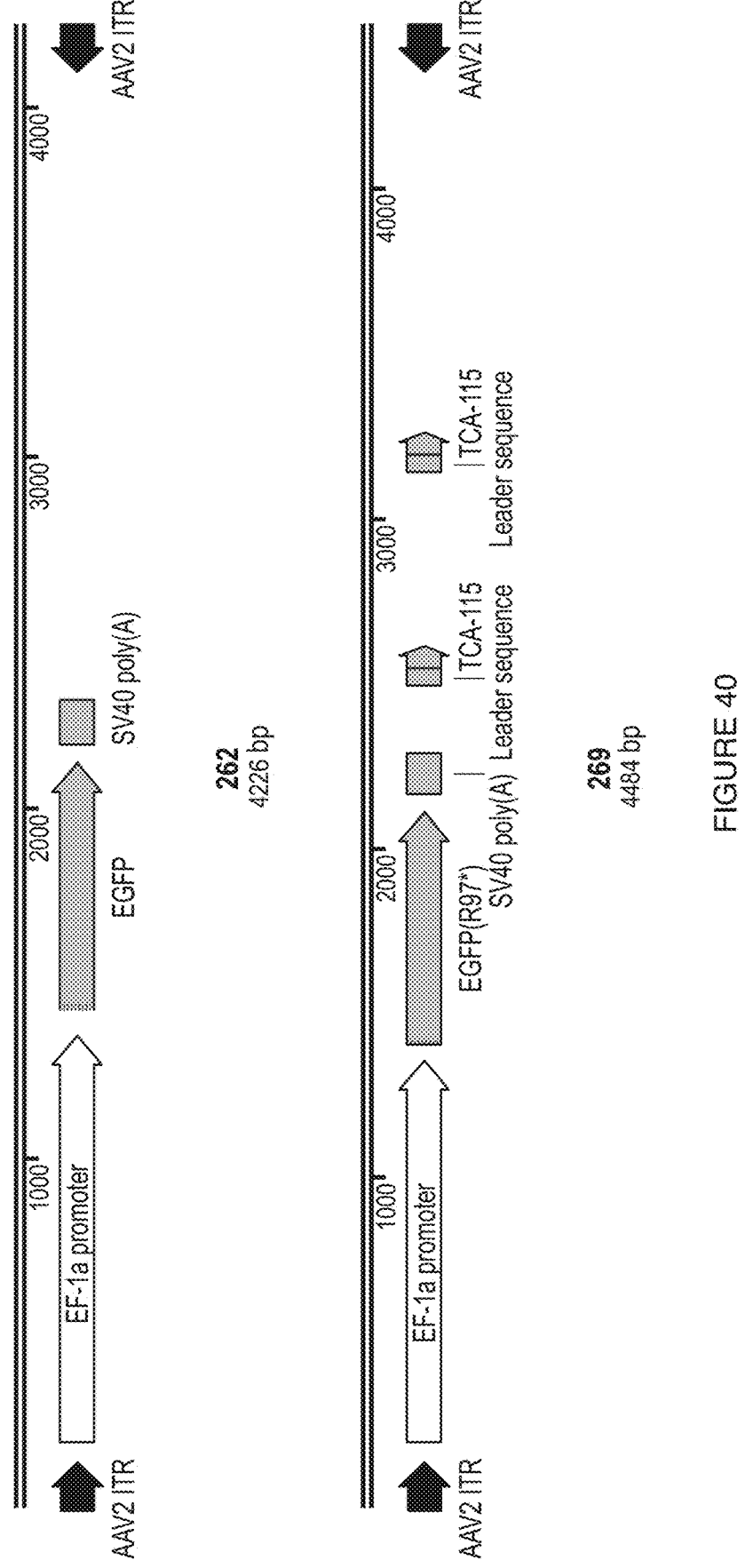

FIG. 40 is a schematic representation of constructs that were packaged into AAV-PHP.eB capsids. Construct 262 contains wild-type EGFP driven by an EF1a promoter. Construct 269 contains EGFP-R96X-TGA driven by an EF1a promoter (SEQ ID NO: 177) and two copies of the $\text{Arg}_{TCA}$ suppressor tRNA #115 (SEQ ID NO: 18) ("TCA-115") in the context of 55 bps upstream flanking genomic DNA from tRNA-Tyr-GTA-5-1 (SEQ ID NO: 900). Both constructs contain 5' and 3' ITR sequences from AAV2, which provide cis-acting elements for AAV replication and packaging.

Figure 41:
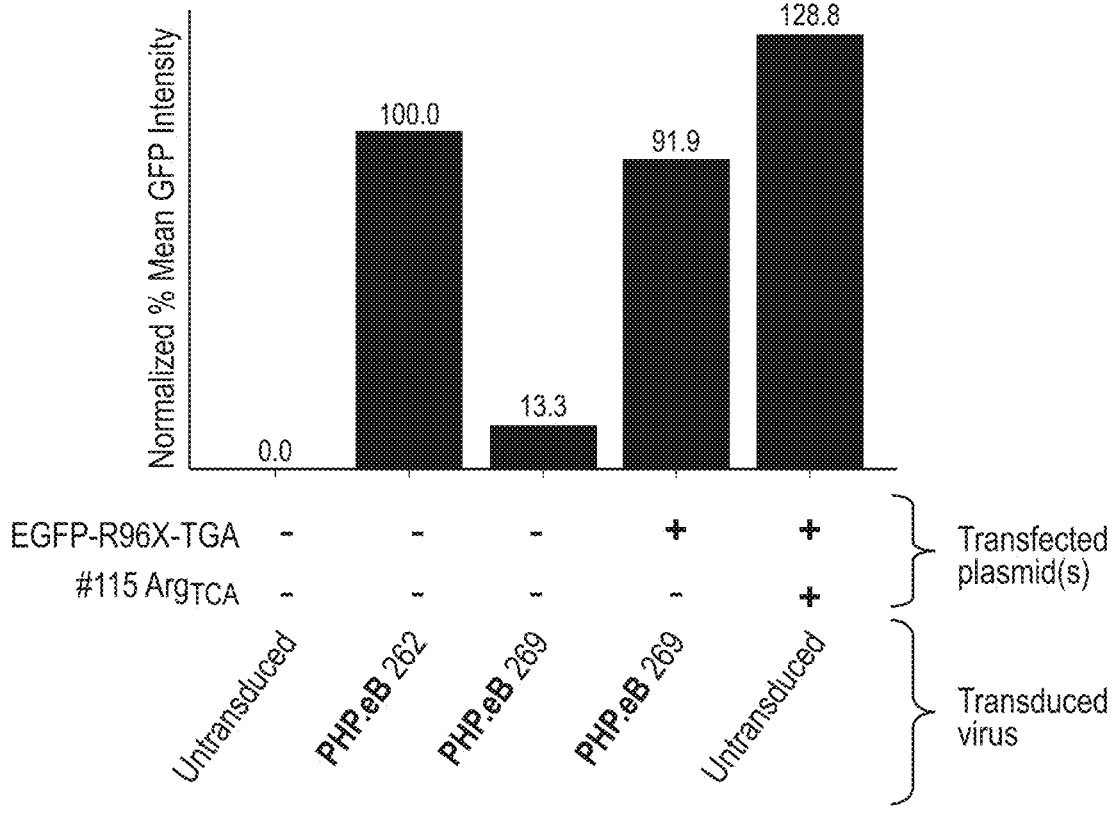

FIG. 41 depicts readthrough activity of suppressor tRNAs delivered by AAV. AAV-PHP.eB containing the constructs shown in FIG. 40 was produced by Vigene Biosciences. 48 hours prior to AAV transduction, 293 cells were pre-transfected with an expression construct containing the LY6A gene, which is required for robust transduction by AAV-PHP.eB. Cells were transduced at an MOI of 1E5 vg/cell. Where indicated, cells were also transfected with an expression construct containing the EGFP-R96X-TGA reporter (SEQ ID NO: 31) and an expression construct containing the $\text{Arg}_{TCA}$ suppressor tRNA #115 (SEQ ID NO: 18). At 72 hours post transduction, the EGFP signal was quantified by immunofluorescence. Live cell images were captured on an EVOS FL Auto 2 imaging system. CellProfiler software was used to segment and extract the integrated EGFP intensity for nuclei in each image. These values were averaged across all nuclei in each condition. Background average integrated EGFP intensity from the negative control condition was subtracted from each of these averages, and all values were normalized. The plot depicts the normalized % GFP intensity with all values normalized to cells transduced with AAV-PHP.eB containing construct 262.

Figure 42:
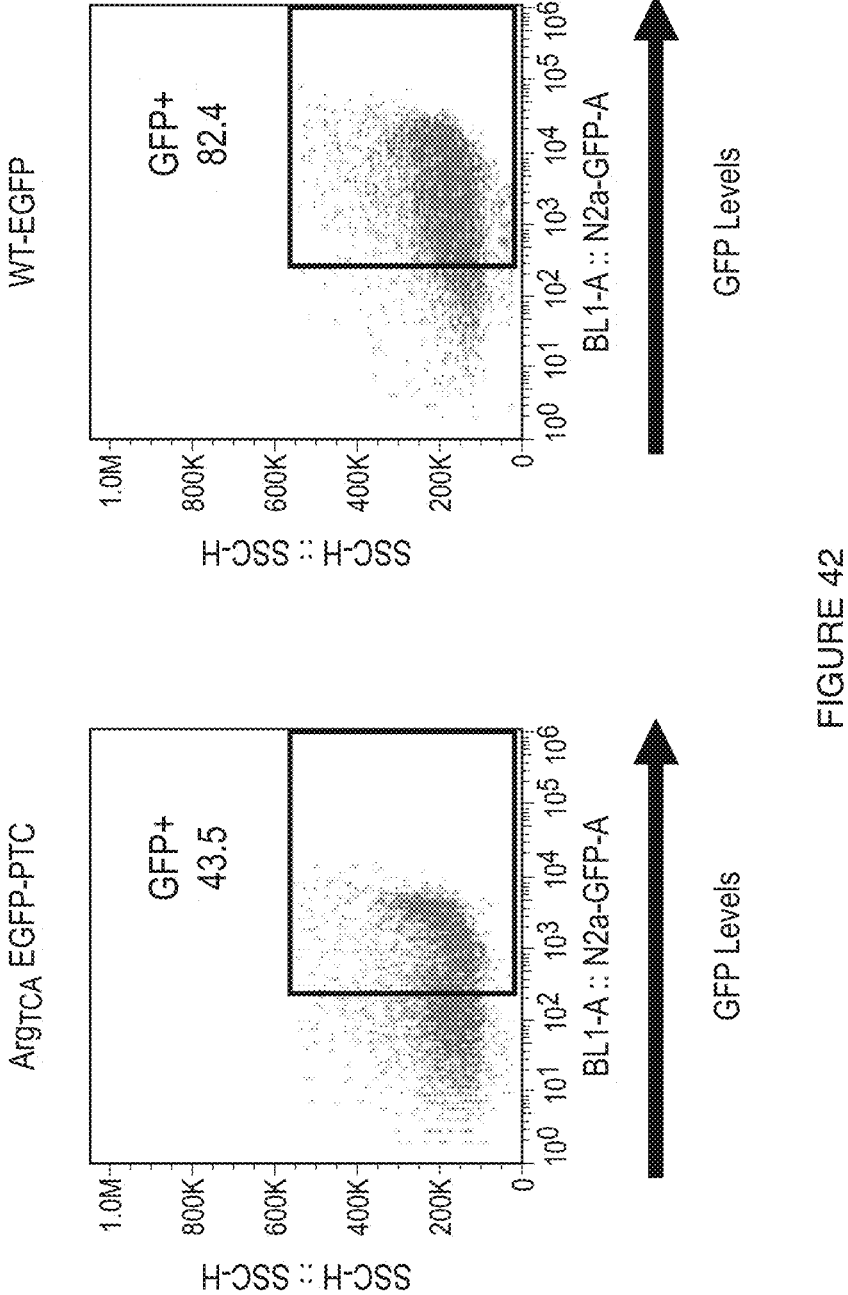

FIG. 42 shows fluorescence as measured by flow cytometry for Neuro-2a cells used in ribosome footprint profiling analysis. Cells were transfected with either (i) an expression construct containing an EGFP-R96X-TGA reporter (SEQ ID NO: 177) and the Arg$_{TCA}$ suppressor tRNA #001 (SEQ ID NO: 11) on the same construct ("Arg$_{TCA}$ EGFP-PTC") or (ii) an expression construct containing a version of the EGFP reporter that lacks a PTC ("WT-EGFP").

Figure 43:
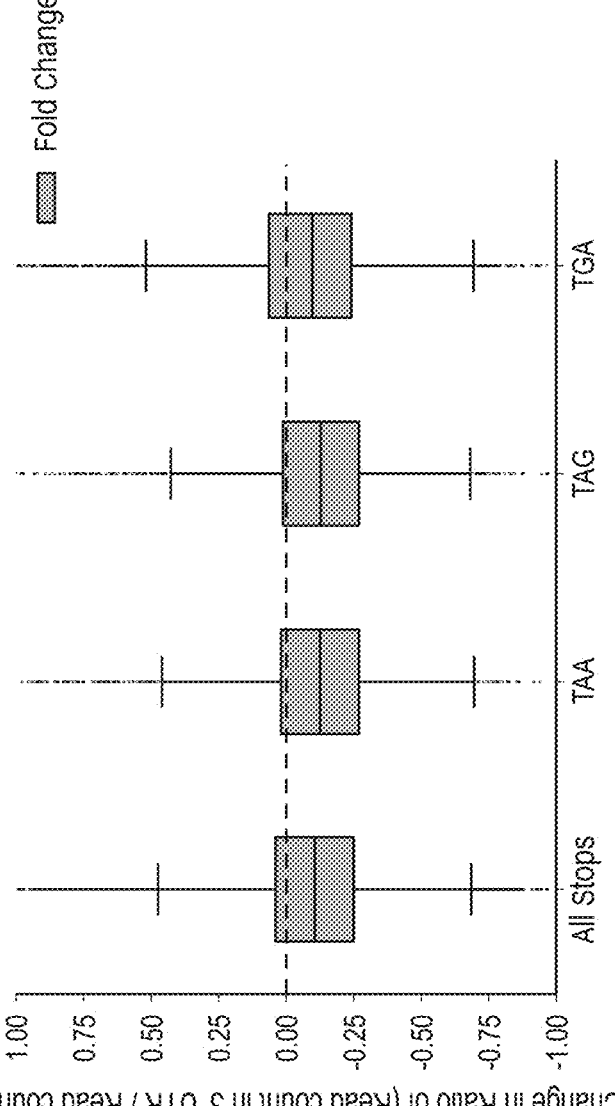

FIG. 43 depicts fold change in 3' UTR read density distributions (as determined by ribosome profiling) between the two Neuro-2a cells populations shown in FIG. 42. Cells were transfected with either (i) an expression construct containing an EGFP-R96X-TGA reporter (SEQ ID NO: 177) and the Arg$_{TCA}$ suppressor tRNA #001 (SEQ ID NO: 11) on the same construct ("Arg$_{TCA}$ EGFP-PTC") or (ii) an expression construct containing a version of the EGFP reporter that lacks a PTC ("WT-EGFP"). Cells were lysed at ~48 hours post transfection and subjected to ribosome footprint profiling. Raw reads were trimmed of adapters using Trimmomatic then depleted for non-coding RNA by aligning against Ensembl's mouse mm10 ncRNA reference using bowtie2. Remaining reads were aligned against UCSC's mm10 mouse reference assembly, again using bowtie2. Multi-mapping reads were discarded. The resulting final set of aligned reads was quantified using the RiboProfiling package in R and custom Python scripting. Python was used to generate plots examining 3' UTR occupancy and fold change for each gene with 20 or more uniquely mapping reads, and the distributions for genes with each native stop codon were compared using the 2 sample Kolmogorov-Smirnov test.

DETAILED DESCRIPTION

The invention is based, in part, upon the discovery of tRNAs (e.g., suppressor tRNAs), that permit an amino acid to be incorporated into a gene product encoded by a gene in a mammalian cell at a position that would otherwise result in a truncated gene product caused by a premature termination codon (PTC) in the gene. The invention is further based, in part, upon the discovery that a tRNA that permits an amino acid to be incorporated into a gene product encoded by a gene at a position that would otherwise result in a truncated gene product caused by a PTC in the gene can be used to treat a disease mediated by a PTC in a gene in a subject.

Accordingly, in one aspect, the invention provides a tRNA (e.g., an isolated tRNA) comprising a nucleotide sequence set forth in TABLE 2.

In another aspect, the invention provides an expression vector comprising a nucleotide sequence encoding a tRNA, e.g., as shown in TABLEs 1-3. In certain embodiments, the expression vector comprises 1, 2, 3, 4, or more than 4 copy numbers of the nucleotide sequence encoding the tRNA. In certain embodiments, the expression vector comprises a nucleotide sequence corresponding to a genomic DNA sequence flanking a wild-type tRNA gene. For example, in certain embodiments, the expression vector comprises a nucleotide sequence set forth in TABLE 4.

In another aspect, the invention provides a pharmaceutical composition comprising any of the foregoing tRNAs or any of the foregoing expression vectors and a pharmaceutically acceptable excipient.

In another aspect, the invention provides a method of expressing in a mammalian cell a functional gene product encoded by a gene containing a premature termination codon, the method comprising introducing into the cell an effective amount of a tRNA (e.g., as shown in TABLEs 1-3 below, e.g., comprising SEQ ID NO: 6-9, 11, 16-22, 35-40, 44, 45, 178-182, 186, or 187), or an expression vector comprising a nucleotide sequence encoding the tRNA, thereby permitting an amino acid to be incorporated into the gene product at a position that would otherwise result in a truncated gene product caused by the premature termination codon.

In certain embodiments of any of the foregoing methods, the cell contains less truncated gene product than a cell without the tRNA. For example, in certain embodiments, the cell contains less than about 5%, about 10%, about 20%, about 30%, about 40%, about 50%, about 60%, about 70%, about 80%, or about 90% of the truncated gene product relative to a cell without the tRNA. In certain embodiments, the cell contains from about 5% to about 80%, about 5% to about 60%, about 5% to about 40%, about 5% to about 20%, about 5% to about 10%, about 10% to about 80%, about 10% to about 60%, about 10% to about 40%, about 10% to about 20%, about 20% to about 80%, about 20% to about 60%, about 20% to about 40%, about 40% to about 80%, about 40% to about 60%, or about 60% to about 80% of the truncated gene product relative to a cell without the tRNA. In certain embodiments, there is no detectable truncated gene product in the cell. Truncated gene product amount or expression may be measured by any method known in the art, for example, Western blot or ELISA.

In certain embodiments, the cell contains a greater amount of functional gene product than a cell without the tRNA. For example, in certain embodiments, the method increases the amount of functional gene product in a cell, tissue, or subject by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, or about 500% relative to a cell, tissue, or subject without the tRNA. In certain embodiments, the method increases the amount of functional gene product in a cell, tissue, or subject, by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject without the tRNA. Functional gene product amount or expression may be measured by any method known in the art, for example, Western blot or ELISA.

In certain embodiments, the tRNA permits an amino acid to be incorporated into the gene product at a position corresponding to a premature termination codon (i.e. the tRNA permits read-through of the premature termination codon), but the tRNA does not permit a substantial amount of amino acid to be incorporated into a gene product at a position corresponding to a native stop codon (i.e., the tRNA does not permit read-through of a native stop codon). For example, in certain embodiments, a disclosed tRNA does not increase read-through of a native stop codon (or all native stop codons) in a cell, tissue, or subject, or increases read-through by less than about 1%, about 2%, about 3%, about 4%, about 5%, about 10%, about 20%, about 30%, about 40%, or about 50%, relative to a cell, tissue, or subject that has not been contacted with the tRNA. Read-through of a native stop codon may be measured by any method known in the art, for example, ribosome profiling as described in Example 13 herein.

In certain embodiments of any of the foregoing methods, the gene is selected from a gene set forth in TABLE 5 or TABLE 6. In certain embodiments, the gene is a SCN1A gene.

In another aspect, the invention provides a method of expressing in a cell a functional SCN1A gene product encoded by a SCN1A gene containing a premature termination codon, the method comprising introducing into the cell an effective amount of a tRNA (e.g., as shown in TABLEs 1-3 below, e.g., comprising SEQ ID NO: 6-9, 11, 16-22, 35-40, 44, 45, 178-182, 186, or 187), or an expression vector comprising a nucleotide sequence encoding the tRNA, thereby permitting an amino acid to be incorporated into the SCN1A gene product at a position that would otherwise result in a truncated SCN1A gene product caused by the premature termination codon.

In another aspect, the invention provides a method of increasing in a cell voltage-gated sodium channel activity encoded by a SCN1A gene containing a premature termination codon, the method comprising introducing into the cell an effective amount of a tRNA (e.g., as shown in TABLEs 1-3 below, e.g., comprising SEQ ID NO: 6-9, 11, 16-22, 35-40, 44, 45, 178-182, 186, or 187), or an expression vector comprising a nucleotide sequence encoding the tRNA, thereby permitting an amino acid to be incorporated into the SCN1A gene product at a position that would otherwise result in a truncated SCN1A gene product caused by the premature termination codon.

In another aspect, the invention provides a method of treating a premature termination codon-mediated disorder in a subject in need thereof wherein the subject has a gene with a premature termination codon, the method comprising administering to the subject an effective amount of a tRNA (e.g., as shown in TABLEs 1-3 below, e.g., comprising SEQ ID NO: 6-9, 11, 16-22, 35-40, 44, 45, 178-182, 186, or 187), or an expression vector comprising a nucleotide sequence encoding the tRNA, thereby to treat the disorder in the subject. In certain embodiments, the disorder is selected from a disorder set forth in TABLE 5 or TABLE 6.

In another aspect, the invention provides a method of treating Dravet syndrome in a subject in need thereof wherein the subject has a SCN1A gene with a premature termination codon, the method comprising administering to the subject an effective amount of a tRNA (e.g., as shown in TABLEs 1-3 below, e.g., comprising SEQ ID NO: 6-9, 11, 16-22, 35-40, 44, 45, 178-182, 186, or 187), or an expression vector comprising a nucleotide sequence encoding the tRNA, thereby to treat Dravet syndrome in the subject.

I. tRNAs and Suppressor tRNAs

During protein synthesis, a transfer RNA (tRNA) delivers an amino acid to a ribosome for incorporation into a growing protein (polypeptide) chain. tRNAs typically are about 70 to 100 nucleotides in length, and active tRNAs contain a 3' CCA sequence that may be transcribed into the tRNA during its synthesis or may be added later during post-transcriptional processing. During aminoacylation, the amino acid that is attached to a given tRNA molecule is covalently attached to the 2' or 3' hydroxyl group of the 3'-terminal ribose to form an aminoacyl-tRNA (aa-tRNA). It is understood that an amino acid can spontaneously migrate from the 2'-hydroxyl group to the 3'-hydroxyl group and vice versa, but it is incorporated into a growing protein chain at the ribosome from the 3'-OH position. A loop at the other end of the folded aa-tRNA molecule contains a sequence of three bases known as the anticodon. When this anticodon sequence hybridizes or base-pairs with a complementary three-base codon sequence in a ribosome-bound messenger RNA (mRNA), the aa-tRNA binds to the ribosome and its amino acid is incorporated into the polypeptide chain being synthesized by the ribosome. Because all tRNAs that base-pair with a specific codon are aminoacylated with a single specific amino acid, the translation of the genetic code is effected by tRNAs. Each of the 61 non-termination codons in an mRNA directs the binding of its cognate aa-tRNA and the addition of a single specific amino acid to the growing polypeptide chain being synthesized by the ribosome.

tRNAs are generally highly conserved and are often functional across species. Accordingly, a tRNA derived from a bacterial tRNA, a non-mammalian eukaryotic tRNA, or a mammalian (e.g., human) tRNA may be useful in the practice of the invention. Nucleotide sequences encoding naturally occurring human tRNAs are known and generally available to those of skill in the art through sources such as Genbank. See also Sprinzl et al. (2005) NUCLEIC ACIDS RES. 33: D139-40; Buckland et al. (1996) GENOMICS 35(1):164-71; Schimmel et al. (Eds.) (1979) "Transfer-RNA: Structure, Properties, and Recognition," Cold Spring Harbor Laboratory; Agris (1983) "The Modified Nucleosides of Transfer RNA, II," Alan R. Liss Inc. tRNAs are generally highly conserved and are often functional across species.

Suppressor tRNAs are modified tRNAs that insert a suitable amino acid at a mutant site, e.g., a PTC, in protein encoding gene. The use of the word in suppressor is based on the fact, that under certain circumstance, the modified tRNA "suppresses" the phenotypic effect of the coding mutation. Suppressor tRNAs typically contain a mutation (modification) in either the anticodon, changing codon specificity, or at some position that alters the aminoacylation identity of the tRNA.

In certain embodiments, a tRNA (e.g., a suppressor tRNA) contains a modified anticodon region, such that the modified anticodon hybridizes with a different codon than the corresponding naturally occurring anticodon. In certain embodiments, the modified anticodon hybridizes with a termination codon, e.g., a PTC, and as a result, the tRNA incorporates an amino acid into a gene product rather than terminating protein synthesis. In certain embodiments, the modified anticodon hybridizes with a premature termination codon and, and as a result, the tRNA incorporates an amino acid into a gene product at a position that would otherwise result in a truncated gene product caused by the premature termination codon.

In certain embodiments, a tRNA comprises an anticodon that hybridizes to a codon selected from UAG (i.e., an "amber" termination codon), UGA (i.e., an "opal" termination codon), and UAA (i.e., an "ochre" termination codon). In certain embodiments, the anticodon hybridizes to a codon selected from UGA to UAA. In certain embodiments, the anticodon hybridizes to UGA. In certain embodiments, a tRNA comprises an anticodon that hybridizes to a non-standard termination codon, e.g., a 4-nucleotide codon (See, for example, Moore et al. (2000) J. Mol. Biol. 298:195, and Hohsaka et al. (1999) J. Am. Chem. Soc. 121:12194).

In certain embodiments, the tRNA is aminoacylated or is capable of being aminoacylated with any natural amino acid. For example, a tRNA may be capable of being aminoacylated with alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In certain embodiments the tRNA is capable of being aminoacylated with serine, leucine, glutamine, or arginine. In certain embodiments the tRNA is capable of being aminoacylated with glutamine or arginine. In certain embodiments the tRNA is capable of being aminoacylated with arginine.

In certain embodiments, the tRNA (i) comprises an anticodon that hybridizes to a codon as indicated in TABLE 1, and (ii) is aminoacylated or is capable of being aminoacylated with an amino acid as indicated in TABLE 1.

In certain embodiments, the tRNA comprises, consists essentially of, or consists of a nucleotide sequence shown in TABLE 2. In certain embodiments, the tRNA comprises, consists essentially of, or consists of a nucleotide sequence having 80%, 85%, 86%, 87%, 88%, 89%, 90%, 91%, 92%, 93%, 94%, 95%, 96%, 97%, 98%, or 99% sequence identity to a nucleotide sequence shown in TABLE 2. In certain embodiments, the tRNA comprises, consists essentially of, or consists of a nucleotide sequence selected from SEQ ID NOs: 19-21, 37, 39, 40, 44, 179, 181, 182, and 186, or a nucleotide sequence having 80%, 85%, 86%, 87%, 88%, 89%, 90%, 91%, 92%, 93%, 94%, 95%, 96%, 97%, 98%, or 99% sequence identity to a nucleotide sequence selected from SEQ ID NOs: 19-21, 37, 39, 40, 44, 179, 181, 182, and 186. It is understood that, throughout the description, in each instance where a tRNA comprises, consists essentially of, or consists of a nucleotide sequence including one or more thymines (T), a tRNA is also contemplated that comprises, consists essentially of, or consists of the same nucleotide sequence including a uracil (U) in place of one or more of the thymines (T), or a uracil (U) in place of all the thymines (T). Similarly, in each instance where a tRNA comprises, consists essentially of, or consists of a nucleotide sequence including one or more uracils (U), a tRNA is also contemplated that comprises, consists essentially of, or consists of a nucleotide sequence including a thymine (T) in place of the one or more of the uracils (U), or a thymine (T) in place of all the uracils (U).

TABLE 1

| codon: UAG | codon: UGA | codon: UAA |
|---|---|---|
| amino acid: alanine | amino acid: alanine | amino acid: alanine |
| codon: UAG | codon: UGA | codon: UAA |
| amino acid: arginine | amino acid: arginine | amino acid: arginine |
| codon: UAG | codon: UGA | codon: UAA |
| amino acid: asparagine | amino acid: asparagine | amino acid: asparagine |
| codon: UAG | codon: UGA | codon: UAA |
| amino acid: aspartic acid | amino acid: aspartic acid | amino acid: aspartic acid |
| codon: UAG | codon: UGA | codon: UAA |
| amino acid: cysteine | amino acid: cysteine | amino acid: cysteine |
| codon: UAG | codon: UGA | codon: UAA |
| amino acid: glutamine | amino acid: glutamine | amino acid: glutamine |
| codon: UAG | codon: UGA | codon: UAA |
| amino acid: glutamic acid | amino acid: glutamic acid | amino acid: glutamic acid |
| codon: UAG | codon: UGA | codon: UAA |
| amino acid: glycine | amino acid: glycine | amino acid: glycine |
| codon: UAG | codon: UGA | codon: UAA |
| amino acid: histidine | amino acid: histidine | amino acid: histidine |
| codon: UAG | codon: UGA | codon: UAA |
| amino acid: isoleucine | amino acid: isoleucine | amino acid: isoleucine |
| codon: UAG | codon: UGA | codon: UAA |
| amino acid: leucine | amino acid: leucine | amino acid: leucine |
| codon: UAG | codon: UGA | codon: UAA |
| amino acid: lysine | amino acid: lysine | amino acid: lysine |
| codon: UAG | codon: UGA | codon: UAA |
| amino acid: methionine | amino acid: methionine | amino acid: methionine |
| codon: UAG | codon: UGA | codon: UAA |
| amino acid: phenylalanine | amino acid: phenylalanine | amino acid: phenylalanine |
| codon: UAG | codon: UGA | codon: UAA |
| amino acid: proline | amino acid: proline | amino acid: proline |
| codon: UAG | codon: UGA | codon: UAA |
| amino acid: serine | amino acid: serine | amino acid: serine |
| codon: UAG | codon: UGA | codon: UAA |
| amino acid: threonine | amino acid: threonine | amino acid: threonine |
| codon: UAG | codon: UGA | codon: UAA |
| amino acid: tryptophan | amino acid: tryptophan | amino acid: tryptophan |
| codon: UAG | codon: UGA | codon: UAA |
| amino acid: tyrosine | amino acid: tyrosine | amino acid: tyrosine |
| codon: UAG | codon: UGA | codon: UAA |
| amino acid: valine | amino acid: valine | amino acid: valine |

TABLE 2

| SEQ ID NO | Suppressor tRNA Sequence (anticodon lowercase) |
|---|---|
| 2 | GGGCCAGTGGCGCAATGGATAACGCGTCTGACTtcaGATCAGAAGATTGTAG<br>GTTCGACTCCTACCTGGCTCG |
| 5 | GGCCGCGTGGCCTAATGGATAAGGCGTCTGATTtcaGATCAGAAGATTGGGG<br>GTTCGAGTCCCTTCGTGGTCG |
| 14 | GACCACGTGGCCTAACGGATAAGGCGTCTGACTtcaGATCAGAAGATTGAGG<br>GTTCGAATCCCTTCGTGGTTA |
| 15 | GGCTCTGTGGCGCAATGGATAGCGCATTGGACTtcaAGTGACGAGAAAGCGA<br>TTCAAAGGTTGTGGGTTCGAATCCCACCAGAGTCG |
| 19 | GGCTCTGTGGCGCAATGGATAGCGCATTGGACTtcaAGCATGATTGAGAGAT<br>TCAAAGGTTGCGGGTTCGAGTCCCGCCAGAGTCG |
| 20 | GGCTCTGTGGCGCAATGGATAGCGCATTGGACTtcaAATTCAAAGGTTGCGG<br>GTTCGAGTCCCGCCAGAGTCG |
| 21 | GGCTCTGTGGCGCAATGGATAGCGCATTGGACTtcaAGACAAATGGAGGCAT<br>TCAAAGGTTGTGGGTTCGAGTCCCACCAGAGTCG |
| 23 | GTCTCTGTGGCGCAATGGACGAGCGCGCTGGACTtcaAATCCAGAGGTTCTG<br>GGTTCGAGTCCCGGCAGAGATG |
| 24 | GGCTCTGTGGAGCAATGGATAGCACATTGGACTtcaAGCATGACCGAGAGAT<br>TCAAAGGTTGCGGGTTCGAGTCCCACCAGAGTTG |
| 25 | GGCTCTGTGGAGCAATGGATAGCACATTGGACTtcaAATTCAAAGGTTGCGG<br>GTTCGAGTCCCACCAGAGTTG |
| 37 | GGTCCCATGGTGTAATGGTTAGCACTCTGGACTttaAATCCAGCGATCCGAG<br>TTCAAATCTCGGTGGGACCT |
| 39 | GGTTCCATGGTGTAATGGTTAGCACTCTGGACTttaAATCCAGCGATCCGAG<br>TTCAAATCTCGGTGGAACCT |
| 40 | GGTTCCATGGTGTAATGGTTAGCACTCTGGACTttaAATCCAGCGATCCGAG<br>TTCAAATCTCGGTGGGACCT |
| 41 | GGTTCCATGGTGTAATGGTGAGCACTCTGGACTttaAATCCAGCGATCCGAG<br>TTCAAATCTCGGTGGGACCT |
| 42 | GGTTCCATGGTGTAATGGCTAGCACTCTGGACTttaAATCCAGCGATCCGAG<br>TTCAAATCTCGGTGGGATTT |
| 43 | GGTTCCATGGTGTAATGGTTAGCACTCTGGACTttaAATCCAGCCATACAAG<br>TTCAAATCTCAGTGGAACCT |
| 44 | GGTTCCTTGGTGTAAGATGAGCACTCTGGATTtttaAATCCAGCGATCAGAGT<br>TCAAATCTCGGTGGGACCT |
| 46 | GGCCCCATGGTGTAATGGTTAGCACTCTGGACTttaAATCCAGCGATCCGAG<br>TTCAAATCTCGGTGGGACCT |
| 47 | GGTCTCATGGTGTAATGGTTAGCACACTGGACTttaAGTCCAGCAATCCGAG<br>TTCGAGTCTTGGTGAGACCA |
| 48 | GGACCCATGGTGTAATGGTTAGCACTCTGGACTttaAATCCAGCAATCCAAG<br>TTCAAATCTCGGTGGGACCT |
| 49 | GTCAGGATGGCCGAGTGGTCTAAGGCGCCAGACTctaGCTATGGCTTCCTCG<br>CTCTGAGGGTTCTGGTCTCCCCTGGAGGCGTGGGTTCGAATCCCACTTCTGA<br>CA |
| 50 | GTCAGGATGGCCGAGTGGTCTAAGGCGCCAGACTctaGCTTAGCTTCCCTGT<br>CTGGGGATTCTGGTCTCCGTATGGAGGCGTGGGTTCGAATCCCACTTCTGAC<br>A |
| 51 | GTCAGGATGGCCGAGTGGTCTAAGGCGCCAGACTctaGGTGACAAGCCTTAC<br>CTACGGGTGTTCTGGTCTCCGAATGGAGGCGTGGGTTCGAATCCCACTTCTG<br>ACA |
| 52 | GTCAGGATGGCCGAGTGGTCTAAGGCGCCAGACTctaGCGTTCGCTTCCTCT<br>ACTGAGGGTTCTGGTCTCCGTGTGGAGGCGTGGGTTCGAATCCCACTTCTGA<br>CA |

TABLE 2-continued

| SEQ ID NO | Suppressor tRNA Sequence (anticodon lowercase) |
|---|---|
| 53 | GTCAGGATGGCCGAGTGGTCTAAGGCGCCAGACTtcaGCTATGGCTTCCTCG<br>CTCTGAGGGTTCTGGTCTCCCCTGGAGGCGTGGGTTCGAATCCCACTTCTGA<br>CA |
| 54 | GTCAGGATGGCCGAGTGGTCTAAGGCGCCAGACTtcaGCTTAGCTTCCCTGT<br>CTGGGGATTCTGGTCTCCGTATGGAGGCGTGGGTTCGAATCCCACTTCTGAC<br>A |
| 55 | GTCAGGATGGCCGAGTGGTCTAAGGCGCCAGACTtcaGGTGACAAGCCTTAC<br>CTACGGGTGTTCTGGTCTCCGAATGGAGGCGTGGGTTCGAATCCCACTTCTG<br>ACA |
| 56 | GTCAGGATGGCCGAGTGGTCTAAGGCGCCAGACTtcaGCGTTCGCTTCCTCT<br>ACTGAGGGTTCTGGTCTCCGTGTGGAGGCGTGGGTTCGAATCCCACTTCTGA<br>CA |
| 57 | GTCAGGATGGCCGAGTGGTCTAAGGCGCCAGACTttaGCTATGGCTTCCTCG<br>CTCTGAGGGTTCTGGTCTCCCCTGGAGGCGTGGGTTCGAATCCCACTTCTGA<br>CA |
| 58 | GTCAGGATGGCCGAGTGGTCTAAGGCGCCAGACTttaGCTTAGCTTCCCTGT<br>CTGGGGATTCTGGTCTCCGTATGGAGGCGTGGGTTCGAATCCCACTTCTGAC<br>A |
| 59 | GTCAGGATGGCCGAGTGGTCTAAGGCGCCAGACTttaGGTGACAAGCCTTAC<br>CTACGGGTGTTCTGGTCTCCGAATGGAGGCGTGGGTTCGAATCCCACTTCTG<br>ACA |
| 60 | GTCAGGATGGCCGAGTGGTCTAAGGCGCCAGACTttaGCGTTCGCTTCCTCT<br>ACTGAGGGTTCTGGTCTCCGTGTGGAGGCGTGGGTTCGAATCCCACTTCTGA<br>CA |
| 61 | CCTTCGATAGCTCAGTTGGTAGAGCGGAGGACTctaGAGTTACTAGAATAGT<br>GATCCTTAGGTCGCTGGTTCGAATCCGGCTCGAAGGA |
| 62 | CCTTCGATAGCTCAGTTGGTAGAGCGGAGGACTctaGTCAGTACAATATGGT<br>AATCCTTAGGTCGCTGGTTCGATTCCGGCTCGAAGGA |
| 63 | CCTTCGATAGCTCAGCTGGTAGAGCGGAGGACTctaGGCTTGTGGCTGTGGA<br>CATCCTTAGGTCGCTGGTTCGATTCCGGCTCGAAGGA |
| 64 | CCTTCGATAGCTCAGCTGGTAGAGCGGAGGACTctaGCTAACTCCCCGTTAG<br>AAGACATCCTTAGGTCGCTGGTTCGACTCCGGCTCGAAGGA |
| 65 | CTTTCGATAGTTCAGTTGGTAGAGCGGAGGACTctaGAGTATTAACGTTGGT<br>GATCCTTAGGTCGCTGGTTCGAGTCCGGCTCGAAGGA |
| 66 | CCTTCGATAGCTCAGTTGGTAGAGCGGAGGACTttaGAGTTACTAGAATAGT<br>GATCCTTAGGTCGCTGGTTCGAATCCGGCTCGAAGGA |
| 67 | CCTTCGATAGCTCAGTTGGTAGAGCGGAGGACTttaGTCAGTACAATATGGT<br>AATCCTTAGGTCGCTGGTTCGATTCCGGCTCGAAGGA |
| 68 | CCTTCGATAGCTCAGCTGGTAGAGCGGAGGACTttaGGCTTGTGGCTGTGGA<br>CATCCTTAGGTCGCTGGTTCGATTCCGGCTCGAAGGA |
| 69 | CCTTCGATAGCTCAGCTGGTAGAGCGGAGGACTttaGCTAACTCCCCGTTAG<br>AAGACATCCTTAGGTCGCTGGTTCGACTCCGGCTCGAAGGA |
| 70 | CTTTCGATAGTTCAGTTGGTAGAGCGGAGGACTttaGAGTATTAACGTTGGT<br>GATCCTTAGGTCGCTGGTTCGAGTCCGGCTCGAAGGA |
| 71 | GGGGGTATAGCTCAGTGGTAGAGCATTTGACTtcaGATCAAGAGGTCCCTGG<br>TTCAAATCCAGGTGCCCCCT |
| 72 | GGGGGTATAGCTCAGGGGTAGAGCATTTGACTtcaGATCAAGAGGTCCCTGG<br>TTCAAATCCAGATGCCCCCT |
| 73 | GGGGGTATAGCTCAGGGGTAGAGTATTTGGCTtcaGATCAAGAGGTCCCTGG<br>TTCAAATCCAGGTGCCCCCT |
| 74 | GGGGGTATAGCTCAGGGGTAGAGCATTTGACTtcaGATCAAGAGGTCCTTGG<br>TTCAAATCCAGGTGTCCCCT |
| 75 | GGGGGTATAGCTCAGAGGTAGAGCATTTGACTtcaGATCAAGAGATCTCTGG<br>TTCAAATCCAGGTGCCCCCT |

TABLE 2-continued

| SEQ ID NO | Suppressor tRNA Sequence (anticodon lowercase) |
|---|---|
| 76 | GGGGGTATAGCTCAGGGGTAGAGCATTTGACTtcaGATCAAGAGGTCCCTAG<br>TTCAAATCCAGGTGCCCCCT |
| 77 | GGTGGTATAGCTCAGGGGTAGAGCATTTGACTtcaGATCAAGAGATCCCTGG<br>TTCGAATCCAGGTGCCCCCT |
| 78 | GGGGGTATAACTCAGGGGTAGAGCATTTGACTtcaGATCAAGAGGTCCCTGG<br>TTCAAATCCAGGTGCCCCCT |
| 79 | TGGGGTATAGCTCAGGGGTAGAGCATTTGACTtcaGATCAAGAGGTCCCTGG<br>TTCAAATCCAGGTGCCCCCT |
| 80 | GGGGGTATAGCTCAGAGGAAGAGCATTTGACTtcaGATCAAGAGGTCCCTGA<br>TTCAAATCCAGGTGCCCCCT |
| 81 | GGGGGTAAAGCTCAGGGGTAGAGCATTTGACTtcaGATTAAGAGGTCCCTGG<br>TTCAAATCCAGGTACCCCCT |
| 83 | GGGGTTATAGCTCAGGTGTAGAGCATTTGACTtcaGATCAAGAGGTCCCTGG<br>TTCAAATCCAGGTGCCCCCT |
| 84 | GGGGGTATAGCTCAGGGGTAGAGCATTTGACTtcaGATCACGAGGTCCCTGG<br>TTCAAATCGAGGTGCCCCCT |
| 85 | GGGGGTATAGCTCAGGGGTGGAGCATTTGACTtcaGATCAAGGGGTCCCTGT<br>TTCAAATCCAGGTGCCCCCT |
| 86 | GGGGGTATAGCTCAGTGGTAGAGCATTTGACTtcaGATCAAGAGGTCCCCGG<br>TTCAAATCCGGGTGCCCCCT |
| 88 | GGGGGTATAGCTCAGGGGTAGAGCATTTGACTtcaGATCAAGAGGTCCCTGG<br>TTCAAATCCGGGTGCCCCCT |
| 89 | GGGGGTATAGCTCAGGGGTAGAGCATTTGACTtcaGATCAAGAGGTCCCTGG<br>TTCAAATCCAGGTACCCCCT |
| 91 | GGGGGCATAGCTCAGGGGTAGAGCATTTGACTtcaGATCAAGAGGTCCCCGG<br>TTCAAATCCGGGTGCTCCCT |
| 92 | GGGGGTATAGCTCAGGGGTAGAGCATTTGACTtcaGATTAAGAGGTCCCTGG<br>TTCAAATCCAGGTGCCCCCT |
| 94 | TCCCTGGTGGTCTAGTGGTTAGGATTTGGCGCTctaACCGCCGCGGCCTGGG<br>TTCGATTCCCGGTCAGGGAA |
| 95 | TCCCTGGTGGTCTAGTGGTTAGGCTTTGGTGCTctaACCTCCATGGCCCAGG<br>TTTGATTCCTGGTCAGGGAA |
| 97 | TCCCTGGTGGTCTAGTGGTTAGGATTTGGCGCTttaACCGCCGCGGCCTGGG<br>TTCGATTCCCGGTCAGGGAA |
| 98 | TCCCTGGTGGTCTAGTGGTTAGGCTTTGGTGCTttaACCTCCATGGCCCAGG<br>TTTGATTCCTGGTCAGGGAA |
| 100 | TCCCATATGGTCTAGCGGTTAGGATTCCTGGTTctaACCCAGGCGGCCCGGG<br>TTCGACTCCCGGTATGGGAA |
| 103 | TCCCATATGGTCTAGCGGTTAGGATTCCTGGTTttaACCCAGGCGGCCCGGG<br>TTCGACTCCCGGTATGGGAA |
| 105 | GTTTCCGTAGTGTAGTGGTTAGCGCGTTCGCCTtcaAAAGCGAAAGGTCCCC<br>GGTTCGAAACCGGGCGGAAACA |
| 107 | GCATTGGTAGTTCAATGGTAGAATTCTCGCCTtcaACGCGGGTGACCCGGGT<br>TCGATTCCCGGCCAATGCA |
| 108 | GCATTGGTGGTTCAATGGTAGAATTCTCGCCTtcaACGCGGGTGACCCGGGT<br>TCGATTCCCGGCCAATGCA |
| 109 | GCATTGGTGGTTCAATGGTAGAATTCTCGCCTtcaACTCGGGTGACCCGGGT<br>TCGATTCCCGGCCAATGCA |
| 112 | GCATTGGTGGTTCAGTGGTAGAATTCTCGCCTtcaACGCGGGAGGCCCGGGT<br>TTGATTCCCGGCCAATGCA |
| 113 | GCATTGGTGGTTCAGTGGTAGAATTCTCGCCTtcaACGCGGGAGGCCCGGGT<br>TCGGTTCCCGGCCAATGCA |

TABLE 2-continued

| SEQ ID NO | Suppressor tRNA Sequence (anticodon lowercase) |
|---|---|
| 115 | GGTAGCGTGGCCGAGCGGTCTAAGGCGCTGGATTctaGCTCCAGTCTCTTCG<br>GGGGCGTGGGTTCGAATCCCACCGCTGCCA |
| 116 | GGTAGTGTGGCCGAGCGGTCTAAGGCGCTGGATTctaGCTCCAGTCTCTTCG<br>GGGGCGTGGGTTCGAATCCCACCGCTGCCA |
| 118 | GGTAGCGTGGCCGAGCGGTCTAAGGCGCTGGATTtcaGCTCCAGTCTCTTCG<br>GGGGCGTGGGTTCGAATCCCACCGCTGCCA |
| 119 | GGTAGTGTGGCCGAGCGGTCTAAGGCGCTGGATTtcaGCTCCAGTCTCTTCG<br>GGGGCGTGGGTTCGAATCCCACCGCTGCCA |
| 121 | GGTAGCGTGGCCGAGCGGTCTAAGGCGCTGGATTttaGCTCCAGTCTCTTCG<br>GGGGCGTGGGTTCGAATCCCACCGCTGCCA |
| 122 | GGTAGTGTGGCCGAGCGGTCTAAGGCGCTGGATTttaGCTCCAGTCTCTTCG<br>GGGGCGTGGGTTCGAATCCCACCGCTGCCA |
| 124 | GTCAGGATGGCCGAGTGGTCTAAGGCGCCAGACTctaGTTCTGGTCTCCCCT<br>GGAGGCGTGGGTTCGAATCCCACTTCTGACA |
| 126 | GTCAGGATGGCCGAGTGGTCTAAGGCGCCAGACTctaGTTCTGGTCTCCGAA<br>TGGAGGCGTGGGTTCGAATCCCACTTCTGACA |
| 127 | GTCAGGATGGCCGAGTGGTCTAAGGCGCCAGACTctaGTTCTGGTCTCCGTG<br>TGGAGGCGTGGGTTCGAATCCCACTTCTGACA |
| 128 | GTCAGGATGGCCGAGTGGTCTAAGGCGCCAGACTtcaGTTCTGGTCTCCCCT<br>GGAGGCGTGGGTTCGAATCCCACTTCTGACA |
| 130 | GTCAGGATGGCCGAGTGGTCTAAGGCGCCAGACTtcaGTTCTGGTCTCCGAA<br>TGGAGGCGTGGGTTCGAATCCCACTTCTGACA |
| 131 | GTCAGGATGGCCGAGTGGTCTAAGGCGCCAGACTtcaGTTCTGGTCTCCGTG<br>TGGAGGCGTGGGTTCGAATCCCACTTCTGACA |
| 132 | GTCAGGATGGCCGAGTGGTCTAAGGCGCCAGACTttaGTTCTGGTCTCCCCT<br>GGAGGCGTGGGTTCGAATCCCACTTCTGACA |
| 134 | GTCAGGATGGCCGAGTGGTCTAAGGCGCCAGACTttaGTTCTGGTCTCCGAA<br>TGGAGGCGTGGGTTCGAATCCCACTTCTGACA |
| 135 | GTCAGGATGGCCGAGTGGTCTAAGGCGCCAGACTttaGTTCTGGTCTCCGTG<br>TGGAGGCGTGGGTTCGAATCCCACTTCTGACA |
| 136 | GTCAGGATGGCCGAGCGGTCTAAGGCGCTGCGTTctaGTCGCAGTCTCCCCT<br>GGAGGCGTGGGTTCGAATCCCACTCCTGACA |
| 137 | GTCAGGATGGCCGAGCGGTCTAAGGCGCTGCGTTctaGTCGCAGTCTCCCCT<br>GGAGGCGTGGGTTCGAATCCCACTTCTGACA |
| 138 | GTCAGGATGGCCGAGTGGTCTAAGGAGCTGTGTTctaGTCGCAGTCTCCCCT<br>GGAGGCGTGGGTTCGAATCCCACTCCTGACA |
| 139 | GTCAGGATGGCCGAGCAGTCTAAGGCACTGCGTTctaGTCGCAGTCTCCCCT<br>GGAGGCGTGGATTCGAATCCCACTCCTGACA |
| 140 | GTCAGGATGGCCGAGCGGTCTAAGGCGCTGCGTTtcaGTCGCAGTCTCCCCT<br>GGAGGCGTGGGTTCGAATCCCACTCCTGACA |
| 141 | GTCAGGATGGCCGAGCGGTCTAAGGCGCTGCGTTtcaGTCGCAGTCTCCCCT<br>GGAGGCGTGGGTTCGAATCCCACTTCTGACA |
| 142 | GTCAGGATGGCCGAGTGGTCTAAGGAGCTGTGTTtcaGTCGCAGTCTCCCCT<br>GGAGGCGTGGGTTCGAATCCCACTCCTGACA |
| 143 | GTCAGGATGGCCGAGCAGTCTAAGGCACTGCGTTtcaGTCGCAGTCTCCCCT<br>GGAGGCGTGGATTCGAATCCCACTCCTGACA |
| 144 | GTCAGGATGGCCGAGCGGTCTAAGGCGCTGCGTTttaGTCGCAGTCTCCCCT<br>GGAGGCGTGGGTTCGAATCCCACTCCTGACA |
| 145 | GTCAGGATGGCCGAGCGGTCTAAGGCGCTGCGTTttaGTCGCAGTCTCCCCT<br>GGAGGCGTGGGTTCGAATCCCACTTCTGACA |
| 146 | GTCAGGATGGCCGAGTGGTCTAAGGAGCTGTGTTttaGTCGCAGTCTCCCCT<br>GGAGGCGTGGGTTCGAATCCCACTCCTGACA |

TABLE 2-continued

| SEQ ID NO | Suppressor tRNA Sequence (anticodon lowercase) |
| --- | --- |
| 147 | GTCAGGATGGCCGAGCAGTCTAAGGCACTGCGTTttaGTCGCAGTCTCCCCT<br>GGAGGCGTGGATTCGAATCCCACTCCTGACA |
| 148 | ACCAGAATGGCCGAGTGGTTAAGGCGTTGGACTctaGATCCAATGGATTTAT<br>ATCCGCGTGGGTTCGAACCCCACTTCTGGTA |
| 149 | ACCAGGATGGCCGAGTGGTTAAGGCGTTGGACTctaGATCCAATGGACATAT<br>GTCTGCGTGGGTTCGAACCCCACTCCTGGTA |
| 150 | ACTGGGATGGCTGAGTGGTTAAGGCGTTGGACTctaGATCCAATGGGCGGTT<br>GCCTGCGTGGGTTCGAACCCCACTCCCAGTA |
| 151 | GATGGGATGGCTGAGAGGTTAAGGCTTTGGACTctaGATCCAATGGGCAGAT<br>GCCTGCGTGGGTTTGAACCCCACTCCCAATA |
| 152 | ACCAGAATGGCCGAGTGGTTAAGGCGTTGGACTtcaGATCCAATGGATTTAT<br>ATCCGCGTGGGTTCGAACCCCACTTCTGGTA |
| 153 | ACCAGGATGGCCGAGTGGTTAAGGCGTTGGACTtcaGATCCAATGGACATAT<br>GTCTGCGTGGGTTCGAACCCCACTCCTGGTA |
| 154 | ACTGGGATGGCTGAGTGGTTAAGGCGTTGGACTtcaGATCCAATGGGCGGTT<br>GCCTGCGTGGGTTCGAACCCCACTCCCAGTA |
| 155 | GATGGGATGGCTGAGAGGTTAAGGCTTTGGACTtcaGATCCAATGGGCAGAT<br>GCCTGCGTGGGTTTGAACCCCACTCCCAATA |
| 156 | ACCAGAATGGCCGAGTGGTTAAGGCGTTGGACTtttaGATCCAATGGATTTAT<br>ATCCGCGTGGGTTCGAACCCCACTTCTGGTA |
| 157 | ACCAGGATGGCCGAGTGGTTAAGGCGTTGGACTtttaGATCCAATGGACATAT<br>GTCTGCGTGGGTTCGAACCCCACTCCTGGTA |
| 158 | ACTGGGATGGCTGAGTGGTTAAGGCGTTGGACTtttaGATCCAATGGGCGGTT<br>GCCTGCGTGGGTTCGAACCCCACTCCCAGTA |
| 159 | GATGGGATGGCTGAGAGGTTAAGGCTTTGGACTtttaGATCCAATGGGCAGAT<br>GCCTGCGTGGGTTTGAACCCCACTCCCAATA |
| 161 | GGTAGTGTGGCCGAGCGGTCTAAGGCGCTGGATTctaGCTCCAGTCTCTTCG<br>GAGGCGTGGGTTCGAATCCCACCACTGCCA |
| 164 | GGTAGTGTGGCCGAGCGGTCTAAGGCGCTGGATTtcaGCTCCAGTCTCTTCG<br>GAGGCGTGGGTTCGAATCCCACCACTGCCA |
| 167 | GGTAGTGTGGCCGAGCGGTCTAAGGCGCTGGATTttaGCTCCAGTCTCTTCG<br>GAGGCGTGGGTTCGAATCCCACCACTGCCA |
| 169 | GCCCAGCTAGCTCAGTTGGTAGAGCGTGGGACTctaAATCCTAGGGTCGTGG<br>GTTCGAACCCCACGTTGGGCG |
| 170 | GCCCAGCTAGCTCAGTCTGTAGAGCATGAGACTctaAGTCTCAGGGTCATGG<br>GTTGGAGCCCCATGTTGTGCA |
| 171 | GCCTAGCTAGTTCAGTCGGTAGAGCATGAGACTctaAATCTCAGGTTCATGA<br>GTTTGAGCCCCATGTTGGTTTGGCA |
| 172 | CCCCGGCTAGCTCAGTCAGTAGAGCTTGAGAATctaAATCTCAGGGTCGTGG<br>GTTGGAGCCCCACGTTGGGCG |
| 179 | GGTTCCATGGTGTAATGGTTAGCACTCTGGACTctaAATCCAGCGACCCGAG<br>TTCAAATCTCGGTGGGACCT |
| 181 | GGTTCCATGGTGTAATGGTTAGCACTCTGGACTctaAATCCAGCGATCCGAG<br>TTCAAATCTCGGTGGGACCT |
| 182 | GGTTCCATGGTGTAATGGTGAGCACTCTGGACTctaAATCCAGCGATCCGAG<br>TTCAAATCTCGGTGGGACCT |
| 183 | GGTTCCATGGTGTAATGGCTAGCACTCTGGACTctaAATCCAGCGATCCGAG<br>TTCAAATCTCGGTGGGATTT |
| 184 | GGTTCCATGGTGTAATGGTTAGCACTCTGGACTctaAATCCAGCCATACAAG<br>TTCAAATCTCAGTGGAACCT |
| 185 | GGTTCCTTGGTGTAAGATGAGCACTCTGGATTctaAATCCAGCGATCAGAGT<br>TCAAATCTCGGTGGGACCT |

TABLE 2-continued

| SEQ ID NO | Suppressor tRNA Sequence (anticodon lowercase) |
|---|---|
| 186 | GGTCCCATGGTGTAATGGTTAGCACTCTGGACTctaAATCCAGCAATCTGAG<br>TTCAAATCTCGGTGGGACCT |
| 188 | GGTCTCATGGTGTAATGGTTAGCACACTGGACTctaAGTCCAGCAATCCGAG<br>TTCGAGTCTTGGTGAGACCA |
| 189 | GGACCCATGGTGTAATGGTTAGCACTCTGGACTctaAATCCAGCAATCCAAG<br>TTCAAATCTCGGTGGGACCT |
| 190 | GTTTCCATGGTGTAATGGTTGGCACTCTGGACTctaAATCCAGCAATCCAAG<br>TTCAAGTCTCTGTGGGACCT |
| 196 | GCCCGGCTAGCTCAGTCGGTAGAGCATGGGACTctaAATCCCAGGGTCGTGG<br>GTTCGAGCCCCACGTTGGGCG |
| 197 | GCCCGGCTAGCTCAGTCGGTAGAGCATGAGACTctaAATCTCAGGGTCGTGG<br>GTTCGAGCCCCACGTTGGGCG |
| 198 | GCCCAGCTAGCTCAGTCTGTAGAGCATGAGACTctaAATCTCAGGGTCGTGA<br>GTTCGAGCCCCACGTTGGGTG |
| 199 | GCCCAGATAGCTCAGTGGGTAGAGCATGAGACTctaAATCTCAGGGTCATGG<br>GTTCATGCCCCATGTTGGGTA |
| 200 | GTCCTGCTGGCTCAGTCGGTACAGCATGGGACTctaAATCCCAGGGTCGTGG<br>GTTCGAGCTCCACGTTGGGTA |
| 201 | GCCTGGCTAGCTCAGTCCATAGAGCATGGGACTctaAATCCCAGGGTCATGG<br>GTTCGAGCCCCATATTAGGCA |
| 202 | GCCCAGCTAGCTTAGTTGGTAGAGCATGAGACTctaAATCTCAGAGTCATGG<br>GTTCAGGCCTCATGTTTGGCA |
| 203 | AACCTGGCTAGGTCAGTTGGTAGATCATGAGACTctaAATCTCAGGGTCATG<br>GGTTCAAGCCCCATGTTGGTTT |
| 204 | GCCCAGCTAGCTCAGTTGGTAGAGCGTGGGACTttaAATCCTAGGGTCGTGG<br>GTTCGAACCCCACGTTGGGCG |
| 205 | GCCCAGCTAGCTCAGTCTGTAGAGCATGAGACTttaAGTCTCAGGGTCATGG<br>GTTGGAGCCCCATGTTGTGCA |
| 206 | GCCTAGCTAGTTCAGTCGGTAGAGCATGAGACTttaAATCTCAGGTTCATGA<br>GTTTGAGCCCCATGTTGGTTTGGCA |
| 207 | CCCCGGCTAGCTCAGTCAGTAGAGCTTGAGAATttaAATCTCAGGGTCGTGG<br>GTTGGAGCCCCACGTTGGGCG |
| 208 | GCCCGGCTAGCTCAGTCGGTAGAGCATGGGACTttaAATCCCAGGGTCGTGG<br>GTTCGAGCCCCACGTTGGGCG |
| 209 | GCCCGGCTAGCTCAGTCGGTAGAGCATGAGACTttaAATCTCAGGGTCGTGG<br>GTTCGAGCCCCACGTTGGGCG |
| 210 | GCCCAGCTAGCTCAGTCTGTAGAGCATGAGACTttaAATCTCAGGGTCGTGA<br>GTTCGAGCCCCACGTTGGGTG |
| 211 | GCCCAGATAGCTCAGTGGGTAGAGCATGAGACTttaAATCTCAGGGTCATGG<br>GTTCATGCCCCATGTTGGGTA |
| 212 | GTCCTGCTGGCTCAGTCGGTACAGCATGGGACTttaAATCCCAGGGTCGTGG<br>GTTCGAGCTCCACGTTGGGTA |
| 213 | GCCTGGCTAGCTCAGTCCATAGAGCATGGGACTttaAATCCCAGGGTCATGG<br>GTTCGAGCCCCATATTAGGCA |
| 214 | GCCCAGCTAGCTTAGTTGGTAGAGCATGAGACTttaAATCTCAGAGTCATGG<br>GTTCAGGCCTCATGTTTGGCA |
| 215 | AACCTGGCTAGGTCAGTTGGTAGATCATGAGACTttaAATCTCAGGGTCATG<br>GGTTCAAGCCCCATGTTGGTTT |
| 216 | GCCCGGATAGCTCAGTCGGTAGAGCATCAGACTctaAATCTGAGGGTCCAGG<br>GTTCAAGTCCCTGTTCGGGCG |
| 218 | GCCTGGATAGCTCAATTGGTAGAGCATCAGACTctaAATCTGAGGGTTCAGG<br>GTTCAAGTCCCTGTTCAGGCG |

TABLE 2-continued

| SEQ ID NO | Suppressor tRNA Sequence (anticodon lowercase) |
|---|---|
| 219 | GCCCAGCCAGCTCAGTAGGTAGAGTATGAGACTctaAATCTCAGGGTGGTGG GTTCGAGCCCCATGTTGGGGG |
| 220 | TGTGGTGTAGCTCAGTCGGTAGAGCATCAGACTctaAATCTGAGGGTCCAGG GTTCAGGTCCCTGTTCGGGTGCCAAAA |
| 221 | GCCCGGATAGCTCAGTCGGTAGAGCATCAGACTtttAATCTGAGGGTCCAGG GTTCAAGTCCCTGTTCGGGCG |
| 223 | GCCTGGATAGCTCAATTGGTAGAGCATCAGACTtttAATCTGAGGGTTCAGG GTTCAAGTCCCTGTTCAGGCG |
| 224 | GCCCAGCCAGCTCAGTAGGTAGAGTATGAGACTtttAATCTCAGGGTGGTGG GTTCGAGCCCCATGTTGGGGG |
| 225 | TGTGGTGTAGCTCAGTCGGTAGAGCATCAGACTtttAATCTGAGGGTCCAGG GTTCAGGTCCCTGTTCGGGTGCCAAAA |
| 228 | GTAGTCGTGGCCAAGTGAGTAAGGCAATGGACTctaAATCCATTGGGGTCTC CCAGCACAGGTTCAAATCCTGCTGACTATG |
| 231 | GTAGTCGTGGCCAAGTGAGTAAGGCAATGGACTtcaAATCCATTGGGGTCTC CCAGCACAGGTTCAAATCCTGCTGACTATG |
| 234 | GTAGTCGTGGCCAAGTGAGTAAGGCAATGGACTtttAATCCATTGGGGTCTC CCAGCACAGGTTCAAATCCTGCTGACTATG |
| 237 | GCTGTGATGGCCGAGTGGTTAAGGCGTTGGACTctaAATCCAATGGGTTCTT CCCGCGCAGGTTCAAATCCTGCTCACAGCG |
| 240 | GCTGTGATGGCCGAGTGGTTAAGGCGTTGGACTtcaAATCCAATGGGTTCTT CCCGCGCAGGTTCAAATCCTGCTCACAGCG |
| 243 | GCTGTGATGGCCGAGTGGTTAAGGCGTTGGACTtttAATCCAATGGGTTCTT CCCGCGCAGGTTCAAATCCTGCTCACAGCG |
| 245 | GACGAGGTGGCCGAGTGGTTAAGGCGATGGACTctaAATCCATTGTGCTCTG CACGCATGGGTTCGAATCCCATCCTCGTCG |
| 246 | GACGAGGTGGCCGAGTGGTTAAGGCGATGGACTctaAATCCATTGTGCTTTG CACGCGTGGGTTCGAATCCCATCCTCGTCG |
| 247 | GACGAGGTGGCCGAGTGGTTAAGGCGATGGACTctaAATCCATTGTGCTCTG CACGCGTGGGTTCGAATCCCATCCTCGTCG |
| 248 | GATGAGGTGGCCGAGTGGTTAAGGCGATGGACTctaAATCCATTGTGCTCTG CACGCATGGGTTCGAATCCCATCCTCATCG |
| 250 | GACGAGGTGGCCGAGTGGTTAAGGCGATGGACTtcaAATCCATTGTGCTCTG CACGCATGGGTTCGAATCCCATCCTCGTCG |
| 251 | GACGAGGTGGCCGAGTGGTTAAGGCGATGGACTtcaAATCCATTGTGCTTTG CACGCGTGGGTTCGAATCCCATCCTCGTCG |
| 252 | GACGAGGTGGCCGAGTGGTTAAGGCGATGGACTtcaAATCCATTGTGCTCTG CACGCGTGGGTTCGAATCCCATCCTCGTCG |
| 253 | GATGAGGTGGCCGAGTGGTTAAGGCGATGGACTtcaAATCCATTGTGCTCTG CACGCATGGGTTCGAATCCCATCCTCATCG |
| 255 | GACGAGGTGGCCGAGTGGTTAAGGCGATGGACTtttAATCCATTGTGCTCTG CACGCATGGGTTCGAATCCCATCCTCGTCG |
| 256 | GACGAGGTGGCCGAGTGGTTAAGGCGATGGACTtttAATCCATTGTGCTTTG CACGCGTGGGTTCGAATCCCATCCTCGTCG |
| 257 | GACGAGGTGGCCGAGTGGTTAAGGCGATGGACTtttAATCCATTGTGCTCTG CACGCGTGGGTTCGAATCCCATCCTCGTCG |
| 258 | GATGAGGTGGCCGAGTGGTTAAGGCGATGGACTtttAATCCATTGTGCTCTG CACGCATGGGTTCGAATCCCATCCTCATCG |
| 259 | GCTGAAATAGCTCAGTTGGGAGAGCATTAGACTctaGATCTAAAGGTCCCTG GTTTGATCCCGGGTTTCGGCA |
| 260 | GCTGAAATAGCTCAGTTGGGAGAGCATTAGACTtcaGATCTAAAGGTCCCTG GTTTGATCCCGGGTTTCGGCA |

TABLE 2-continued

| SEQ ID NO | Suppressor tRNA Sequence (anticodon lowercase) |
|---|---|
| 261 | GCTGAAATAGCTCAGTTGGGAGAGCATTAGACTttaGATCTAAAGGTCCCTG<br>GTTTGATCCCGGGTTTCGGCA |
| 265 | GACCTCGTGGCGCAATGGTAGCGCGTCTGACTctaGATCAGAAGGTTGCGTG<br>TTCAAATCACGTCGGGGTCA |
| 270 | GACCTCGTGGCACAATGGTAGCACGTCTGACTctaGATCAGAAGGTTGCGTG<br>TTCAAATCACGTCGGGGTCA |
| 280 | CCTTCGATAGCTCAGCTGGTAGAGCGGAGGACTctaGATCCTTAGGTCGCTG<br>GTTCGACTCCGGCTCGAAGGA |
| 281 | CTTTCGATAGTTCAGTTGGTAGAGCGGAGGACTctaGATCCTTAGGTCGCTG<br>GTTCGAGTCCGGCTCGAAGGA |
| 285 | CCTTCGATAGCTCAGCTGGTAGAGCGGAGGACTttaGATCCTTAGGTCGCTG<br>GTTCGACTCCGGCTCGAAGGA |
| 286 | CTTTCGATAGTTCAGTTGGTAGAGCGGAGGACTttaGATCCTTAGGTCGCTG<br>GTTCGAGTCCGGCTCGAAGGA |

In certain embodiments, the tRNA comprises, consists essentially of, or consists of a nucleotide sequence shown in TABLE 3. In certain embodiments, the tRNA comprises, consists essentially of, or consists of a nucleotide sequence having 80%, 85%, 86%, 87%, 88%, 89%, 90%, 91%, 92%, 93%, 94%, 95%, 96%, 97%, 98%, or 99% sequence identity to a nucleotide sequence shown in TABLE 3. In certain embodiments, the tRNA comprises, consists essentially of, or consists of a nucleotide sequence selected from SEQ ID NOs: 6-9, 11, 16-18, 22, 35, 36, 38, 45, 178, 180, and 187, or a nucleotide sequence having 80%, 85%, 86%, 87%, 88%, 89%, 90%, 91%, 92%, 93%, 94%, 95%, 96%, 97%, 98%, or 99% sequence identity to a nucleotide sequence selected from SEQ ID NOs: 6-9, 11, 16-18, 22, 35, 36, 38, 45, 178, 180, and 187.

TABLE 3

| SEQ ID NO | Suppressor tRNA Sequence |
|---|---|
| 1 | GGGCCAGTGGCGCAATGGATAACGCGTCTGACTtcaGATCAGAAGATTCCAG<br>GTTCGACTCCTGGCTGGCTCG |
| 3 | GGGCCAGTGGCGCAATGGATAACGCGTCTGACTtcaGATCAGAAGATTCTAG<br>GTTCGACTCCTGGCTGGCTCG |
| 4 | GGCCGCGTGGCCTAATGGATAAGGCGTCTGATTtcaGATCAGAAGATTGAGG<br>GTTCGAGTCCCTTCGTGGTCG |
| 6 | GACCCAGTGGCCTAATGGATAAGGCATCAGCCTtcaGAGCTGGGGATTGTGG<br>GTTCGAGTCCCATCTGGGTCG |
| 7 | GCCCCAGTGGCCTAATGGATAAGGCACTGGCCTtcaAAGCCAGGGATTGTGG<br>GTTCGAGTCCCACCTGGGGTA |
| 8 | GCCCCAGTGGCCTAATGGATAAGGCACTGGCCTtcaAAGCCAGGGATTGTGG<br>GTTCGAGTCCCACCTGGGGTG |
| 9 | GCCCCGGTGGCCTAATGGATAAGGCATTGGCCTtcaAAGCCAGGGATTGTGG<br>GTTCGAGTCCCACCCGGGGTA |
| 10 | GCCCCAGTGGCCTAATGGATAAGGCATTGGCCTtcaAAGCCAGGGATTGTGG<br>GTTCGAGTCCCATCTGGGGTG |
| 11 | GGCCGCGTGGCCTAATGGATAAGGCGTCTGACTtcaGATCAGAAGATTGCAG<br>GTTCGAGTCCTGCCGCGGTCG |
| 12 | GACCGCGTGGCCTAATGGATAAGGCGTCTGACTtcaGATCAGAAGATTGAGG<br>GTTCGAGTCCCTTCGTGGTCG |
| 13 | GACCACGTGGCCTAATGGATAAGGCGTCTGACTtcaGATCAGAAGATTGAGG<br>GTTCGAATCCCTTCGTGGTTG |
| 16 | GGCTCTGTGGCGCAATGGATAGCGCATTGGACTtcaAATTCAAAGGTTGTGG<br>GTTCGAATCCCACCAGAGTCG |
| 17 | GGCTCCGTGGCGCAATGGATAGCGCATTGGACTtcaAGAGGCTGAAGGCATT<br>CAAAGGTTCCGGGTTCGAGTCCCGGCGGAGTCG |

TABLE 3-continued

| SEQ ID NO | Suppressor tRNA Sequence |
|---|---|
| 18 | GGCTCCGTGGCGCAATGGATAGCGCATTGGACTtcaAATTCAAAGGTTCCGG<br>GTTCGAGTCCCGGCGGAGTCG |
| 22 | GGCTCTGTGGCGCAATGGATAGCGCATTGGACTtcaAATTCAAAGGTTGTGG<br>GTTCGAGTCCCACCAGAGTCG |
| 35 | GTCTCTGTGGCGCAATGGACGAGCGCGCTGGACTtcaAATCCAGAGGTTCCG<br>GGTTCGAGTCCCGGCAGAGATG |
| 36 | GGTCCCATGGTGTAATGGTTAGCACTCTGGACTttaAATCCAGCGATCCGAG<br>TTCAAATCTCGGTGGGACCT |
| 38 | GGTTCCATGGTGTAATGGTTAGCACTCTGGACTttaAATCCAGCGATCCGAG<br>TTCAAATCTCGGTGGAACCT |
| 45 | GGCCCCATGGTGTAATGGTTAGCACTCTGGACTttaAATCCAGCGATCCGAG<br>TTCAAATCTCGGTGGGACCT |
| 178 | GGTCCCATGGTGTAATGGTTAGCACTCTGGACTctaAATCCAGCGATCCGAG<br>TTCAAATCTCGGTGGGACCT |
| 180 | GGTTCCATGGTGTAATGGTTAGCACTCTGGACTctaAATCCAGCGATCCGAG<br>TTCAAATCTCGGTGGAACCT |
| 187 | GGCCCCATGGTGTAATGGTTAGCACTCTGGACTctaAATCCAGCGATCCGAG<br>TTCAAATCTCGGTGGGACCT |
| 287 | GGCCTCGTGGCGCAACGGTAGCGCGTCTGACTTCAGATCAGAAGGTTGCGGG<br>TTCAAATCCCGTCGGGGTCA |
| 288 | GGCCTCGTGGCGCAACGGTAGCGCGTCTGACTTCAGATCAGAAGGTTACGGG<br>TTCAAATCCCGTCGGGGTCA |
| 289 | GGCCTCGTGGCGCAACGGTAGCGCGTCTGACTTCAGATCAGAAGGTTCCGGG<br>TTCAAATCCCGGCGGGGTCA |
| 290 | CGTCGGCTCTGTGGCGCAATGGATAGCGCATTGGACTTCAAATTCAAAGGTT<br>GTGGGTTCGAGTCCCAGAGTCG |
| 291 | CGTCGCCCCAGTGGCCTAATGGATAAGGCACTGGCCTTCAAAGCCAGGGATT<br>GTGGGTTCGAGTCCCACCTGGGGTG |
| 292 | CGTCGGCTCCGTGGCGCAATGGATAGCGCATTGGACTTCAAATTCAAAGGTT<br>CCGGGTTCGAGTCCCGGCGGAGTCG |
| 293 | CGTCGCCCCAGTGGCCTAATGGATAAGGCATTGGCCTTCAAAGCCAGGGATT<br>GTGGGTTCGAGTCCCATCTGGGGTG |
| 294 | CGTCGGCTCTGTGGCGCAATGGATAGCGCATTGGACTTCAAATTCAAAGGTT<br>GTGGGTTCGAATCCCACCAGAGTCG |
| 295 | CGTCGGCTCTGTGGCGCAATGGATAGCGCATTGGACTTCAAGCTGAGCCTAG<br>TGTGGTCATTCAAAGGTTGTGGGTTCGAGTCCCACCAGAGTCG |
| 296 | CGTCGCCCCGGTGGCCTAATGGATAAGGCATTGGCCTTCAAAGCCAGGGATT<br>GTGGGTTCGAGTCCCACCCGGGGTA |
| 297 | CGTCGGCTCCGTGGCGCAATGGATAGCGCATTGGACTTCAAGAGGCTGAAGG<br>CATTCAAAGGTTCCGGGTTCGAGTCCCGGCGGAGTCG |
| 298 | CGTCGGCTCTGTGGCGCAATGGATAGCGCATTGGACTTCAAGTGACGAATAG<br>AGCAATTCAAAGGTTGTGGGTTCGAATCCCACCAGAGTCG |
| 299 | CGTCGGCCGCGTGGCCTAATGGATAAGGCGTCTGACTTCAGATCAGAAGATT<br>GCAGGTTCGAGTCCTGCCGCGGTCG |
| 300 | CGTCGACCGCGTGGCCTAATGGATAAGGCGTCTGACTTCAGATCAGAAGATT<br>GAGGGTTCGAGTCCCTTCGTGGTCG |
| 301 | CGTCGGCTCTGTGGCGCAATGGATAGCGCATTGGACTTCAAGATAGTTAGAG<br>AAATTCAAAGGTTGTGGGTTCGAGTCCCACCAGAGTCG |
| 302 | CGTCGGTTCCATGGTGTAATGGTGAGCACTCTGGACTCTAAATCCAGCGATC<br>CGAGTTCGAGTCTCGGTGGAACCT |
| 303 | CGTCGGCCCCATGGTGTAATGGTTAGCACTCTGGACTCTAAATCCAGCGATC<br>CGAGTTCAAATCTCGGTGGGACCT |

TABLE 3-continued

| SEQ ID NO | Suppressor tRNA Sequence |
|---|---|
| 304 | CGTCGGTCCCATGGTGTAATGGTTAGCACTCTGGACTCTAAATCCAGCAATC<br>CGAGTTCGAATCTCGGTGGGACCT |
| 305 | CGTCGGTCCCATGGTGTAATGGTTAGCACTCTGGACTCTAAATCCAGCGATC<br>CGAGTTCAAATCTCGGTGGGACCT |
| 306 | CGTCGGCCCCATGGTGTAATGGTCAGCACTCTGGACTCTAAATCCAGCGATC<br>CGAGTTCAAATCTCGGTGGGACCC |
| 307 | CGTCGGTTCCATGGTGTAATGGTAAGCACTCTGGACTCTAAATCCAGCGATC<br>CGAGTTCGAGTCTCGGTGGAACCT |
| 308 | CGTCGGTTCCATGGTGTAATGGTTAGCACTCTGGACTCTAAATCCGGTAATC<br>CGAGTTCAAATCTCGGTGGAACCT |
| 309 | CGTCGGTTCCATGGTGTAATGGTTAGCACTCTGGACTCTAAATCCAGCGATC<br>CGAGTTCAAGTCTCGGTGGAACCT |
| 310 | CGTCGGTTCCATGGTGTAATGGTAAGCACTCTGGACTTTAAATCCAGCGATC<br>CGAGTTCGAGTCTCGGTGGAACCT |
| 311 | CGTCGGCCCCATGGTGTAATGGTTAGCACTCTGGACTTTAAATCCAGCGATC<br>CGAGTTCAAATCTCGGTGGGACCT |
| 312 | CGTCGGTTCCATGGTGTAATGGTGAGCACTCTGGACTTTAAATCCAGCGATC<br>CGAGTTCGAGTCTCGGTGGAACCT |
| 313 | CGTCGGTTCCATGGTGTAATGGTTAGCACTCTGGACTTTAAATCCAGCGATC<br>CGAGTTCAAATCTCGGTGGAACCT |
| 314 | CGTCGGTCCCATGGTGTAATGGTTAGCACTCTGGACTTTAAATCCAGCGATC<br>CGAGTTCAAATCTCGGTGGGACCT |
| 315 | CGTCGGTCCCATGGTGTAATGGTTAGCACTCTGGACTTTAAATCCAGCAATC<br>CGAGTTCGAATCTCGGTGGGACCT |
| 316 | CGTCGGTTCCATGGTGTAATGGTTAGCACTCTGGACTTTAAATCCGGTAATC<br>CGAGTTCAAATCTCGGTGGAACCT |
| 317 | CGTCGGCCCCATGGTGTAATGGTCAGCACTCTGGACTTTAAATCCAGCGATC<br>CGAGTTCAAATCTCGGTGGGACCC |
| 318 | CGTCGGTTCCATGGTGTAATGGTTAGCACTCTGGACTTTAAATCCAGCGATC<br>CGAGTTCAAGTCTCGGTGGAACCT |
| 319 | CGTCGACCTCGTGGCGCAATGGTAGCGCGTCTGACTCTAGATCAGAAGGTTG<br>CGTGTTCAAGTCACGTCGGGGTCA |
| 320 | CGTCGACCTCGTGGCGCAACGGTAGCGCGTCTGACTCTAGATCAGAAGGTTG<br>CGTGTTCAAATCACGTCGGGGTCA |
| 321 | CGTCGGCCTCGTGGCGCAACGGTAGCGCGTCTGACTCTAGATCAGAAGGTTG<br>CGTGTTCAAATCACGTCGGGGTCA |
| 322 | CGTCGACCTCGTGGCGCAACGGTAGCGCGTCTGACTCTAGATCAGAAGGCTG<br>CGTGTTCGAATCACGTCGGGGTCA |
| 323 | CGTCGACCTCGTGGCGCAACGGCAGCGCGTCTGACTCTAGATCAGAAGGTTG<br>CGTGTTCAAATCACGTCGGGGTCA |
| 324 | CGTCTCCCACATGGTCTAGCGGTTAGGATTCCTGGTTCTAACCCAGGCGGCC<br>CGGGTTCGACTCCCGGTGTGGGAA |
| 325 | CGTCTCCCATATGGTCTAGCGGTTAGGATTCCTGGTTCTAACCCAGGTGGCC<br>CGGGTTCGACTCCCGGTATGGGAA |
| 326 | CGTCTCCCTGGTGGTCTAGTGGCTAGGATTCGGCGCTCTAACCGCCGCGGCC<br>CGGGTTCGATTCCCGGTCAGGGAA |
| 327 | CGTCTCCCTGGTGGTCTAGTGGTTAGGATTCGGCGCTCTAACCGCCGCGGCC<br>CGGGTTCGATTCCCGGTCAGGGAA |
| 328 | CGTCTCCCTGGTCTAGTGGCTAGGATTCGGCGCTCTAACCGCCGCGGCCCGG<br>GTTCGATTCCCGGCCAGGGAA |
| 329 | CGTCTCCCACATGGTCTAGCGGTTAGGATTCCTGGTTCTAACCCAGGCGGCC<br>CGGGTTCGACTCCCGGTGTGGGAA |

TABLE 3-continued

| SEQ ID NO | Suppressor tRNA Sequence |
| --- | --- |
| 330 | CGTCTCCCATATGGTCTAGCGGTTAGGATTCCTGGTTCTAACCCAGGTGGCC<br>CGGGTTCGACTCCCGGTATGGGAA |
| 331 | CGTCTCCCTGGTGGTCTAGTGGTTAGGATTCGGCGCTCTAACCGCCGCGGCC<br>CGGGTTCGATTCCCGGTCAGGGAA |
| 332 | CGTCTCCCTGGTGGTCTAGTGGTTAGGATTCGGCGCTCTAACCGCCGCGGCC<br>CGGGTTCGATTCCCGGTCAGGAAA |
| 333 | CGTCTCCCTGGTGGTCTAGTGGCTAGGATTCGGCGCTCTAACCGCCGCGGCC<br>CGGGTTCGATTCCCGGCCAGGGAA |
| 334 | GGCCTCGTGGCGCAACGGTAGCGCGTCTGACTTCAGATCAGAAGGTTGCGTG<br>TTCAAATCACGTCGGGGTCA |
| 335 | GACCTCGTGGCGCAATGGTAGCGCGTCTGACTTCAGATCAGAAGGTTGCGTG<br>TTCAAGTCACGTCGGGGTCA |
| 336 | GACCTCGTGGCGCAACGGTAGCGCGTCTGACTTCAGATCAGAAGGTTGCGTG<br>TTCAAATCACGTCGGGGTCA |
| 337 | GACCTCGTGGCGCAACGGTAGCGCGTCTGACTTCAGATCAGAAGGCTGCGTG<br>TTCGAATCACGTCGGGGTCA |
| 338 | GACCTCGTGGCGCAACGGCAGCGCGTCTGACTTCAGATCAGAAGGTTGCGTG<br>TTCAAATCACGTCGGGGTCA |
| 339 | GCGTTGGTGGTATAGTGGTTAGCATAGCTGCCTTCAAAGCAGTTGACCCGGG<br>TTCGATTCCCGGCCAACGCA |
| 340 | GCGTTGGTGGTATAGTGGTGAGCATAGCTGCCTTCAAAGCAGTTGACCCGGG<br>TTCGATTCCCGGCCAACGCA |
| 341 | GCGTTGGTGGTATAGTGGTAAGCATAGCTGCCTTCAAAGCAGTTGACCCGGG<br>TTCGATTCCCGGCCAACGCA |
| 342 | GGCCTCGTGGCGCAACGGTAGCGCGTCTGACTTCAGATCAGAAGGTTGCGTG<br>TTCAAATCACGTCGGGGTCA |
| 343 | GACCTCGTGGCGCAATGGTAGCGCGTCTGACTTCAGATCAGAAGGTTGCGTG<br>TTCAAGTCACGTCGGGGTCA |
| 344 | GACCTCGTGGCGCAACGGTAGCGCGTCTGACTTCAGATCAGAAGGTTGCGTG<br>TTCAAATCACGTCGGGGTCA |
| 345 | GACCTCGTGGCGCAACGGTAGCGCGTCTGACTTCAGATCAGAAGGCTGCGTG<br>TTCGAATCACGTCGGGGTCA |
| 346 | GACCTCGTGGCGCAACGGCAGCGCGTCTGACTTCAGATCAGAAGGTTGCGTG<br>TTCAAATCACGTCGGGGTCA |
| 347 | GGCCTCATGGTGCAACAGTAGTGTGTCTGACTTCAGATCAGAAGGTTGTATG<br>TTCAAATCACGTAGGGGTCA |
| 348 | GGCCTCGTGGCGCAACGGTAGCGCGTCTGACTCTAGATCAGAAGGTTGCGTG<br>TTCAAATCACGTCGGGGTCA |
| 349 | GACCTCGTGGCGCAATGGTAGCGCGTCTGACTCTAGATCAGAAGGTTGCGTG<br>TTCAAGTCACGTCGGGGTCA |
| 350 | GACCTCGTGGCGCAACGGTAGCGCGTCTGACTCTAGATCAGAAGGTTGCGTG<br>TTCAAATCACGTCGGGGTCA |
| 351 | GACCTCGTGGCGCAACGGTAGCGCGTCTGACTCTAGATCAGAAGGCTGCGTG<br>TTCGAATCACGTCGGGGTCA |
| 352 | GACCTCGTGGCGCAACGGCAGCGCGTCTGACTCTAGATCAGAAGGTTGCGTG<br>TTCAAATCACGTCGGGGTCA |
| 353 | GGCCTCATGGTGCAACAGTAGTGTGTCTGACTCTAGATCAGAAGGTTGTATG<br>TTCAAATCACGTAGGGGTCA |
| 354 | GCATTGGTGGTTCAGTGGTAGAATTCTCGCCTTCAACGCGGGAGACCCGGGT<br>TCAATTCCCGGCCAATGCA |
| 355 | GCGCCGCTGGTGTAGTGGTATCATGCAAGATTTCAATTCTTGCGACCCGGGT<br>TCGATTCCCGGGCGGCGCA |

TABLE 3-continued

| SEQ ID NO | Suppressor tRNA Sequence |
|---|---|
| 356 | GCATTGGTGGTTCAATGGTAGAATTCTCGCCTTCAACGCAGGAGACCCAGGT<br>TCGATTCCTGGCCAATGCA |
| 357 | GCGTTGGTGGTTTAGTGGTAGAATTCTCGCCTTCAATGCGGGAGACCCGGGT<br>TCAATTCCCGGCCACTGCA |
| 358 | GCCTTGGTGGTGCAGTGGTAGAATTCTCGCCTTCAACGTGGGAGACCCGGGT<br>TCAATTCCCGGCCAATGCA |
| 359 | GGTGGTTCAGTGGTAGAATTCTCGCCTTCAACGCGGGAGACCCGGGTTTAAT<br>TCCCGGTCA |
| 360 | GTGGTCTAGTGGTTAGGATTCAGCGCTTCAACCGCCGCAGCCCGGGTTCGAT<br>TCCCGGTCA |
| 361 | GCGTCAGTGGTTTAGTGGTGGAATTCCTGCCTTCAATGCACGAGATCCGTGT<br>TCAACTCCTGGTTGGTGCA |
| 362 | GCGTCAGTGGTTTTAGTGGTGGAATTCCTGCCTTCAATGCACGAGATCCGTG<br>TTCAACTCCTGGTTGGTGCA |
| 363 | GCGTTGGCAGTTCAGTGGTAGAATTCTCGCCTTCAACCCGGGAGACCTGGAT<br>TCCATTTCCGGCAAATGCA |
| 364 | GCATGGGTGGTTCAGTGGTAGAATTCTCGCCTTCAACGCGGGAGGCCCGGGT<br>TCGATTCCCGGCCCATGCA |
| 365 | GCATTGGTGGTTCAGTGGTAGAATTCTCGCCTTCAACGCGGGAGGCCCGGGT<br>TCGATTCCCGGCCAATGCA |
| 366 | GCATTGGTGGTTCAGTGGTAGAATTCTCGCCTTCAACGCGGGAGGCCCGGGT<br>TTGATTCCCGGCCAGTGCA |
| 367 | GCATAGGTGGTTCAGTGGTAGAATTCTTGCCTTCAACGCAGGAGGCCCAGGT<br>TTGATTCCTGGCCCATGCA |
| 368 | GCATTGGTGGTTCAGTGGTAGAATTCTCGCCTTCAATGCGGGCGGCCGGGCT<br>TCGATTCCTGGCCAATGCA |
| 369 | GCATGGGTGATTCAGTGGTAGAATTTTCACCTTCAATGCAGGAGGTCCAGGT<br>TCATTTCCTGGCCTATGCA |
| 370 | GCGTTGGTGGTATAGTGGTTAGCATAGCTGCCTTCAAAGCAGTTGACCCGGG<br>TTCGATTCCCGGCCAACGCA |
| 371 | GCGTTGGTGGTATAGTGGTGAGCATAGCTGCCTTCAAAGCAGTTGACCCGGG<br>TTCGATTCCCGGCCAACGCA |
| 372 | GCGTTGGTGGTATAGTGGTAAGCATAGCTGCCTTCAAAGCAGTTGACCCGGG<br>TTCGATTCCCGGCCAACGCA |
| 373 | GCGTTGGTGGTATAGTGGTGAGCATAGTTGCCTTCAAAGCAGTTGACCCGGG<br>CTCGATTCCCGCCCAACGCA |
| 374 | GCGTTGGTGGTATAGTGGTGAGCATAGTTGCCTTCAAAGCAGTTGACCCGGG<br>CTCGATTCCCGGCCAACGCA |
| 375 | GGGCCAGTGGCGCAATGGATAACGCGTCTGACTTCAGATCAGAAGATTCCAG<br>GTTCGACTCCTGGCTGGCTCG |
| 376 | GGGCCAGTGGCGCAATGGATAACGCGTCTGACTTCAGATCAGAAGATTCTAG<br>GTTCGACTCCTGGCTGGCTCG |
| 377 | GGCCGCGTGGCCTAATGGATAAGGCGTCTGATTTCAGATCAGAAGATTGAGG<br>GTTCGAGTCCCTTCGTGGTCG |
| 378 | GACCCAGTGGCCTAATGGATAAGGCATCAGCCTTCAGAGCTGGGGATTGTGG<br>GTTCGAGTCCCATCTGGGTCG |
| 379 | GCCCCAGTGGCCTAATGGATAAGGCACTGGCCTTCAAAGCCAGGGATTGTGG<br>GTTCGAGTCCCACCTGGGGTA |
| 380 | GCCCCAGTGGCCTAATGGATAAGGCACTGGCCTTCAAAGCCAGGGATTGTGG<br>GTTCGAGTCCCACCTGGGGTG |
| 381 | GCCCCGGTGGCCTAATGGATAAGGCATTGGCCTTCAAAGCCAGGGATTGTGG<br>GTTCGAGTCCCACCCGGGGTA |

TABLE 3-continued

| SEQ ID NO | Suppressor tRNA Sequence |
|---|---|
| 382 | GCCCCAGTGGCCTAATGGATAAGGCATTGGCCTTCAAAGCCAGGGATTGTGG GTTCGAGTCCCATCTGGGGTG |
| 383 | GCCCCAGTGGCCTGATGGATAAGGTACTGGCCTTCAAAGCCAGGGATTGTGG GTTCGAGTTCCACCTGGGGTA |
| 384 | GGCCGCGTGGCCTAATGGATAAGGCGTCTGACTTCAGATCAGAAGATTGCAG GTTCGAGTCCTGCCGCGGTCG |
| 385 | GACCACGTGGCCTAATGGATAAGGCGTCTGACTTCAGATCAGAAGATTGAGG GTTCGAATCCCTCCGTGGTTA |
| 386 | GACCGCGTGGCCTAATGGATAAGGCGTCTGACTTCAGATCAGAAGATTGAGG GTTCGAGTCCCTTCGTGGTCG |
| 387 | GACCACGTGGCCTAATGGATAAGGCGTCTGACTTCAGATCAGAAGATTGAGG GTTCGAATCCCTTCGTGGTTA |
| 388 | GACCACGTGGCCTAATGGATAAGGCGTCTGACTTCAGATCAGAAGATTGAGG GTTCGAATCCCTTCGTGGTTG |
| 389 | GGCCGTGTGGCCTAATGGATAAGGCGTCTGACTTCAGATCAAAGATTGCAG GTTTGAGTTCTGCCACGGTCG |
| 390 | GGCTCCGTGGCGCAATGGATAGCGCATTGGACTTCAAGAGGCTGAAGGCATT CAAAGGTTCCGGGTTCGAGTCCCGGCGGAGTCG |
| 391 | GGCTCCGTGGCGCAATGGATAGCGCATTGGACTTCAAATTCAAAGGTTCCGG GTTCGAGTCCCGGCGGAGTCG |
| 392 | GGCTCTGTGGCGCAATGGATAGCGCATTGGACTTCAAGTGACGAATAGAGCA ATTCAAAGGTTGTGGGTTCGAATCCCACCAGAGTCG |
| 393 | GGCTCTGTGGCGCAATGGATAGCGCATTGGACTTCAAATTCAAAGGTTGTGG GTTCGAATCCCACCAGAGTCG |
| 394 | GGCTCTGTGGCGCAATGGATAGCGCATTGGACTTCAAGCTGAGCCTAGTGTG GTCATTCAAAGGTTGTGGGTTCGAGTCCCACCAGAGTCG |
| 395 | GGCTCTGTGGCGCAATGGATAGCGCATTGGACTTCAAATTCAAAGGTTGTGG GTTCGAGTCCCACCAGAGTCG |
| 396 | GGCTCTGTGGCGCAATGGATAGCGCATTGGACTTCAAGATAGTTAGAGAAAT TCAAAGGTTGTGGGTTCGAGTCCCACCAGAGTCG |
| 397 | GTCTCTGTGGCGCAATGGACGAGCGCGCTGGACTTCAAATCCAGAGGTTCCG GGTTCGAGTCCCGGCAGAGATG |
| 398 | GGCTCTGTGGCGCAATGGATAGCGCATTGGACTTCAAGCCTAAATCAAGAGA TTCAAAGGTTGCGGGTTCGAGTCCCTCCAGAGTCG |
| 399 | GGCTCTGTGGCGCAATGGATAGCGCATTGGACTTCAAATTCAAAGGTTGCGG GTTCGAGTCCCTCCAGAGTCG |
| 400 | GGCAGCATAGCAGAGTGGTTCAGGTTACAGGTTCAAGATGTAAACTGAGTTC AAATCCCAGTTCTGCCA |
| 401 | TGGTGTAATAGGTAGCACAGAGAATTCTAGATTCTCAGGGGTAGGTTCAATT CCTAT |
| 402 | TAGGACATGGTGTGATAGGTAGCATGGAGAATTCTAGATTCTCAGGGGTAGG TTCAATTCCTACAGTTCTAG |
| 403 | TAGGACGTGGTGTGATAGGTAGCATGGGGAATTCTAGATTCTCAGGGGTGGG TTCAATTCCTATAGTTCTAG |
| 404 | TAGGACGTGGTGTAGTAGGTAGCATGGAGAATGCTAAATTCTCAGGGGTAGG TTCAATTCCTATAGTTCTAG |
| 405 | TAGGACATGGTGTAATAGGTAGAATGGAGAATTCTAAATTCTCAGGGGTAGG TTCAATTCCTATAGTTCTAG |
| 406 | TAGGATGTGGTGTATTAGGTAGCACAGAGAATTCTAGATTCTCAGGGGTAGG TTCGATTCCTATAATTCTAC |
| 407 | TAGGACTTGGTGTAATGGGTAGCACAGAGAATTCTAGATTCTCAGGGGTGGG TTCAATTCCTTTCGTCCTAG |

TABLE 3-continued

| SEQ ID NO | Suppressor tRNA Sequence |
|---|---|
| 408 | TCTAGGATGTGGTGTGATAGGTAGCATGGAGAATTCTAGATTCTCAGGGGTA<br>GGTTCAATTCCTATATTCTAGAA |
| 409 | TAGGACGTGGTGTGATAGGTAGCATGGAGAATTCTAGATTCTCAGGGATGGG<br>TTCAATTCCTATAGTCCTAG |
| 410 | TAGGACGTGGTGTGATAGGTAGCACGGAGAATTCTAGATTCTCAGGGATGGG<br>TTCAATTCCTGTAGTTCTAG |
| 411 | GGTTCCATGGTGTAATGGTTAGCACTCTGGACTCTAAATCCAGCGATCCGAG<br>TTCAAATCTCGGTGGAACCT |
| 412 | GGTTCCATGGTGTAATGGTGACCACTTTGGACTCTAAATACAGTGATCAGAG<br>TTCAAGTCTCACTGGAACCT |
| 413 | GGTTCCATGGTGTAATGGTGAGGGCTTTGGACTCTAACTACAGTGATCAGAG<br>TTCAAGTCTCAGTGGGACCT |
| 414 | GGTTCCATGGTGTAATGGTAAGCACCCTGGACTCTAAATCCAGCAACCAGAG<br>TTCCAGTCTCAGCGTGGACCT |
| 415 | GGTAGTGTAGTCTACTGGTTAAACGCTTGGGCTCTAACATTAACGTCCTGGG<br>TTCAAATCCCAGCTTTGTCA |
| 416 | GGTTCCATGGTGTAATGGTTAGCACTCTGGACTCTAAATCCAGCGATCCGAG<br>TTCAAGTCTCGGTGGAACCT |
| 417 | GGTTCCATGGTGTAATGGTGAGCACTCTGGACTCTAAATCCAGCGATCCGAG<br>TTCGAGTCTCGGTGGAACCT |
| 418 | GGTTCCATGGTGTAATGGTAAGCACTCTGGACTCTAAATCCAGCGATCCGAG<br>TTCGAGTCTCGGTGGAACCT |
| 419 | GGTTCCATGGTGTAATGGTTAGCACTCTGGACTCTAAATCCGGTAATCCGAG<br>TTCAAATCTCGGTGGAACCT |
| 420 | GGCCCCATGGTGTAATGGTCAGCACTCTGGACTCTAAATCCAGCGATCCGAG<br>TTCAAATCTCGGTGGGACCC |
| 421 | GGTTCCATGGTGTAATGGTAAGCACTCTGGACTCTAAATCCAGCCATCTGAG<br>TTCGAGTCTCTGTGGAACCT |
| 422 | GGTTCCATGGTGTAATGGTGAGCACTTTGGACTCTAAATACAGTGATCAGAG<br>TTCAAGTCTCACTGGGACCT |
| 423 | GGTTCCATGGGTTAATGGTGAGCACCCTGGACTCTAAATCAAGCGATCCGAG<br>TTCAAATCTCGGTGGTACCT |
| 424 | GTTTCCATGGTGTAATGGTGAGCACTCTGGACTCTAAATCCAGAAATACATT<br>CAAAGAATTAAGAACA |
| 425 | GGTCCCATGGTGTAATGGTTAGCACTCTGGACTCTAAATCCAGCGATCCGAG<br>TTCAAATCTCGGTGGGACCT |
| 426 | GGTCCCATGGTGTAATGGTTAGCACTCTGGACTCTAAATCCAGCAATCCGAG<br>TTCGAATCTCGGTGGGACCT |
| 427 | GGCCCCATGGTGTAATGGTTAGCACTCTGGACTCTAAATCCAGCGATCCGAG<br>TTCAAATCTCGGTGGGACCT |
| 428 | GGTCCCATGGTGTAATGGTTAGCACTCTGGGCTCTAAATCCAGCAATCCGAG<br>TTCGAATCTTGGTGGGACCT |
| 429 | GGCTGTGTACCTCAGTGGGCAAGGGTATGGACTCTAAAGCCAGACTATTTGG<br>GTTCAAATCCCAGCTTGGCCT |
| 430 | GACCATGTGGCCTAAGGGAAAAGACATCTCACTCTAGGTCAGAAGATTGAGG<br>GTTCAAGTCCTTTCATGGTCA |
| 431 | GGTACAGTGTTAAAGGGGAGAAAAATTGCTGACTCTAAATACAGTAGACCTA<br>GGTTTGAATCCTGGCTTTACCA |
| 432 | TGGTGTAATAGGTAGCACAGAGAATTTTAGATTCTCAGGGGTAGGTTCAATT<br>CCTAT |
| 433 | TAGGACATGGTGTGATAGGTAGCATGGAGAATTTTAGATTCTCAGGGGTAGG<br>TTCAATTCCTACAGTTCTAG |

TABLE 3-continued

| SEQ ID NO | Suppressor tRNA Sequence |
| --- | --- |
| 434 | TAGGACGTGGTGTGATAGGTAGCATGGGGAATTTTAGATTCTCAGGGGTGGG<br>TTCAATTCCTATAGTTCTAG |
| 435 | TAGGACGTGGTGTAGTAGGTAGCATGGAGAATGTTAAATTCTCAGGGGTAGG<br>TTCAATTCCTATAGTTCTAG |
| 436 | TAGGACATGGTGTAATAGGTAGAATGGAGAATTTTAAATTCTCAGGGGTAGG<br>TTCAATTCCTATAGTTCTAG |
| 437 | TAGGATGTGGTGTATTAGGTAGCACAGAGAATTTTAGATTCTCAGGGGTAGG<br>TTCGATTCCTATAATTCTAC |
| 438 | TAGGACTTGGTGTAATGGGTAGCACAGAGAATTTTAGATTCTCAGGGGTGGG<br>TTCAATTCCTTTCGTCCTAG |
| 439 | TCTAGGATGTGGTGTGATAGGTAGCATGGAGAATTTTAGATTCTCAGGGGTA<br>GGTTCAATTCCTATATTCTAGAA |
| 440 | TAGGACGTGGTGTGATAGGTAGCATGGAGAATTTTAGATTCTCAGGGATGGG<br>TTCAATTCCTATAGTCCTAG |
| 441 | TAGGACGTGGTGTGATAGGTAGCACGGAGAATTTTAGATTCTCAGGGATGGG<br>TTCAATTCCTGTAGTTCTAG |
| 442 | GGTTCCATGGTGTAATGGTTAGCACTCTGGACTTTAAATCCAGCGATCCGAG<br>TTCAAATCTCGGTGGAACCT |
| 443 | GGTTCCATGGTGTAATGGTGACCACTTTGGACTTTAAATACAGTGATCAGAG<br>TTCAAGTCTCACTGGAACCT |
| 444 | GGTTCCATGGTGTAATGGTGAGGGCTTTGGACTTTAACTACAGTGATCAGAG<br>TTCAAGTCTCAGTGGGACCT |
| 445 | GGTTCCATGGTGTAATGGTAAGCACCCTGGACTTTAAATCCAGCAACCAGAG<br>TTCCAGTCTCAGCGTGGACCT |
| 446 | GGTAGTGTAGTCTACTGGTTAAACGCTTGGGCTTTAACATTAACGTCCTGGG<br>TTCAAATCCCAGCTTTGTCA |
| 447 | GGTTCCATGGTGTAATGGTTAGCACTCTGGACTTTAAATCCAGCGATCCGAG<br>TTCAAGTCTCGGTGGAACCT |
| 448 | GGTTCCATGGTGTAATGGTGAGCACTCTGGACTTTAAATCCAGCGATCCGAG<br>TTCGAGTCTCGGTGGAACCT |
| 449 | GGTTCCATGGTGTAATGGTAAGCACTCTGGACTTTAAATCCAGCGATCCGAG<br>TTCGAGTCTCGGTGGAACCT |
| 450 | GGTTCCATGGTGTAATGGTTAGCACTCTGGACTTTAAATCCGGTAATCCGAG<br>TTCAAATCTCGGTGGAACCT |
| 451 | GGCCCCATGGTGTAATGGTCAGCACTCTGGACTTTAAATCCAGCGATCCGAG<br>TTCAAATCTCGGTGGGACCC |
| 452 | GGTTCCATGGTGTAATGGTAAGCACTCTGGACTTTAAATCCAGCCATCTGAG<br>TTCGAGTCTCTGTGGAACCT |
| 453 | GGTTCCATGGTGTAATGGTGAGCACTTTGGACTTTAAATACAGTGATCAGAG<br>TTCAAGTCTCACTGGGACCT |
| 454 | GGTTCCATGGGTTAATGGTGAGCACCCTGGACTTTAAATCAAGCGATCCGAG<br>TTCAAATCTCGGTGGTACCT |
| 455 | GTTTCCATGGTGTAATGGTGAGCACTCTGGACTTTAAATCCAGAAATACATT<br>CAAAGAATTAAGAACA |
| 456 | GGTCCCATGGTGTAATGGTTAGCACTCTGGACTTTAAATCCAGCGATCCGAG<br>TTCAAATCTCGGTGGGACCT |
| 457 | GGTCCCATGGTGTAATGGTTAGCACTCTGGACTTTAAATCCAGCAATCCGAG<br>TTCGAATCTCGGTGGGACCT |
| 458 | GGCCCCATGGTGTAATGGTTAGCACTCTGGACTTTAAATCCAGCGATCCGAG<br>TTCAAATCTCGGTGGGACCT |
| 459 | GGTCCCATGGTGTAATGGTTAGCACTCTGGGCTTTAAATCCAGCAATCCGAG<br>TTCGAATCTTGGTGGGACCT |

TABLE 3-continued

| SEQ ID NO | Suppressor tRNA Sequence |
|---|---|
| 460 | GGCTGTGTACCTCAGTGGGCAAGGGTATGGACTTTAAAGCCAGACTATTTGG<br>GTTCAAATCCCAGCTTGGCCT |
| 461 | GACCATGTGGCCTAAGGGAAAAGACATCTCACTTTAGGTCAGAAGATTGAGG<br>GTTCAAGTCCTTTCATGGTCA |
| 462 | GGTACAGTGTTAAAGGGGAGAAAAATTGCTGACTTTAAATACAGTAGACCTA<br>GGTTTGAATCCTGGCTTTACCA |
| 463 | TCCCTGGTGGTCTAGTGGTTAGGATTCGGCGCTTTAACCGCCGCGGCCCGGG<br>TTCGATTCCCGGTCAGGGAA |
| 464 | TCCCTGGTGGTCTAGTGGTTAGGATTCGGCGCTTTAACCGCCGCGGCCCGGG<br>TTCGATTCCCGGTCAGGAAA |
| 465 | CCCCTGGTGGTCTAGTGCTTAGGATTCGGTGCTTTAACCGCTGCTGCCTGCG<br>TTCGATTCCCGGTCAGGGAA |
| 466 | TCCTTGATGTCTAGTGGTTAGGATTTGGTGCTTTAACTGCAGCAGCCTGGGT<br>TCATTTCTCAGTCAGGGAA |
| 467 | TCCCATATGGTCTAGCGGTTAGGATTCCTGGTTTTAACCCAGGTGGCCCGGG<br>TTCGACTCCCGGTATGGGAA |
| 468 | TCCGTGGTGGTCTAGTGGCTAGGATTCGGCGCTTTAACCGCCTGCAGCTCGA<br>GTTCGATTCCTGGTCAGGGAA |
| 469 | CCCTGTGGTCTAGTGGCTAAGACTTTGTGCTTTAATTGCTGCATCCTAGGTT<br>CAATTCCCAGTCAGGGA |
| 470 | TCCCACATGGTCTAGCGGTTAGGATTCCTGGTTTTAACCCAGGCGGCCCGGG<br>TTCGACTCCCGGTGTGGGAA |
| 471 | TCCCTGGTGGTCTAGTGGCTAGGATTCGGCGCTTTAACCGCCGCGGCCCGGG<br>TTCGATTCCCGGCCAGGGAA |
| 472 | TCCCTGGTGGTCTAGTGGCTAGGATTCGGCGCTTTAACCGCCGCGGCCCGGG<br>TTCGATTCCCGGTCAGGGAA |
| 473 | GCGTTGGTGGTGTAGTGGTGAGCACAGCTGCCTTTAAAGCAGTTAACGCGGG<br>TTCGATTCCCGGGTAACGAA |
| 474 | TCCTTGGTGGTCTAGTGGCTAGGATTCGGTGCTTTAACCTGTGCGGCCCGGG<br>TTCAATTCCCGATGAAGGAA |
| 475 | TGTCTGGTGGTCAAGTGGCTAGGATTTGGCGCTTTAACTGCCGCGGCCCGCG<br>TTCGATTCCCGGTCAGGGAA |
| 476 | TCCCTGGTGGTCTAGTGGCTAGGATTCGGCGCTTTAACCGCCTGCAGCTCGA<br>GTTCGATTCCTGGTCAGGGAA |
| 477 | GCAATGGTGGTTCAGTGGTAGAATTCTCGCCTTTAACACAGGAGACCCGGGT<br>TCAATTCCTGACCCATGTA |
| 478 | TCCCTGGTGGTCTAGTGGTTAGGATTCGGCGCTCTAACCGCCGCGGCCCGGG<br>TTCGATTCCCGGTCAGGGAA |
| 479 | TCCCTGGTGGTCTAGTGGTTAGGATTCGGCGCTCTAACCGCCGCGGCCCGGG<br>TTCGATTCCCGGTCAGGAAA |
| 480 | CCCCTGGTGGTCTAGTGCTTAGGATTCGGTGCTCTAACCGCTGCTGCCTGCG<br>TTCGATTCCCGGTCAGGGAA |
| 481 | TCCTTGATGTCTAGTGGTTAGGATTTGGTGCTCTAACTGCAGCAGCCTGGGT<br>TCATTTCTCAGTCAGGGAA |
| 482 | TCCCATATGGTCTAGCGGTTAGGATTCCTGGTTCTAACCCAGGTGGCCCGGG<br>TTCGACTCCCGGTATGGGAA |
| 483 | TCCGTGGTGGTCTAGTGGCTAGGATTCGGCGCTCTAACCGCCTGCAGCTCGA<br>GTTCGATTCCTGGTCAGGGAA |
| 484 | CCCTGTGGTCTAGTGGCTAAGACTTTGTGCTCTAATTGCTGCATCCTAGGTT<br>CAATTCCCAGTCAGGGA |
| 485 | TCCCACATGGTCTAGCGGTTAGGATTCCTGGTTCTAACCCAGGCGGCCCGGG<br>TTCGACTCCCGGTGTGGGAA |

TABLE 3-continued

| SEQ ID NO | Suppressor tRNA Sequence |
|---|---|
| 486 | TCCCTGGTGGTCTAGTGGCTAGGATTCGGCGCTCTAACCGCCGCGGCCCGGG<br>TTCGATTCCCGGCCAGGGAA |
| 487 | TCCCTGGTGGTCTAGTGGCTAGGATTCGGCGCTCTAACCGCCGCGGCCCGGG<br>TTCGATTCCCGGTCAGGGAA |
| 488 | GCGTTGGTGGTGTAGTGGTGAGCACAGCTGCCTCTAAAGCAGTTAACGCGGG<br>TTCGATTCCCGGGTAACGAA |
| 489 | TCCTTGGTGGTCTAGTGGCTAGGATTCGGTGCTCTAACCTGTGCGGCCCGGG<br>TTCAATTCCCGATGAAGGAA |
| 490 | TGTCTGGTGGTCAAGTGGCTAGGATTTGGCGCTCTAACTGCCGCGGCCCGCG<br>TTCGATTCCCGGTCAGGGAA |
| 491 | TCCCTGGTGGTCTAGTGGCTAGGATTCGGCGCTCTAACCGCCTGCAGCTCGA<br>GTTCGATTCCTGGTCAGGGAA |
| 492 | GCAATGGTGGTTCAGTGGTAGAATTCTCGCCTCTAACACAGGAGACCCGGGT<br>TCAATTCCTGACCCATGTA |
| 493 | CCTTCAATAGTTCAGCTGGTAGAGCAGAGGACTTTAGCTACTTCCTCAGTAG<br>GAGACGTCCTTAGGTTGCTGGTTCGATTCCAGCTTGAAGGA |
| 494 | CCTTCAATAGTTCAGCTGGTAGAGCAGAGGACTTTAGGTCCTTAGGTTGCTG<br>GTTCGATTCCAGCTTGAAGGA |
| 495 | GGTAAAATGGCTGAGTAAGCTTTAGACTTTAAATCTAAAGAGAGATTGAGCT<br>CTCTTTTTACCA |
| 496 | GGTAAAATGACTGAGTAAGCATTAGACTTTAAATCTAAAGACAGAGGTCAAG<br>ACCTCTTTTTACCA |
| 497 | GGTAAAATGGCTGAGTAAGCATTAGACTTTAAATCTAAAGACAGAGGTCAAG<br>GCCTCTTTTTACCA |
| 498 | GGTAAAATGGCTGAGTAAGCATTAGACTTTAAATCTAAAGACAGAGGTCAAG<br>GCCTTTTTACCA |
| 499 | CCTTCGATAGCTCAGTTGGTAGAGCGGAGGACTTTAGTTGGCTGTGTCCTTA<br>GACATCCTTAGGTCGCTGGTTCGAATCCGGCTCGAAGGA |
| 500 | CCTTCGATAGCTCAGTTGGTAGAGCGGAGGACTTTAGATCCTTAGGTCGCTG<br>GTTCGAATCCGGCTCGAAGGA |
| 501 | GGGGGTATAGCTCAGGGCTAGAGCTTTTTGACTTTAGAGCAAGAGGTCCCTG<br>GTTCAAATCCAGGTTCTCCCT |
| 502 | TATAGCTCAGTGGTAGAGCATTTAACTTTAGATCAAGAGGTCCCTGGATCAA<br>CTCTGGGTG |
| 503 | GTCAGTGTTGCACAACGGTTAAGTGAAGAGGCTTTAAACCCAGACTGGATGG<br>GTTCAATTCCCATCTCTGCCG |
| 504 | CCTTCGATAGCTCAGTTGGTAGAGCGGAGGACTTTAGTGGATAGGGCGTGGC<br>AATCCTTAGGTCGCTGGTTCGATTCCGGCTCGAAGGA |
| 505 | CCTTCGATAGCTCAGTTGGTAGAGCGGAGGACTTTAGATCCTTAGGTCGCTG<br>GTTCGATTCCGGCTCGAAGGA |
| 506 | CCTTCGATAGCTCAGTTGGTAGAGCGGAGGACTTTAGGCTCATTAAGCAAGG<br>TATCCTTAGGTCGCTGGTTCGAATCCGGCTCGGAGGA |
| 507 | CCTTCGATAGCTCAGTTGGTAGAGCGGAGGACTTTAGATCCTTAGGTCGCTG<br>GTTCGAATCCGGCTCGGAGGA |
| 508 | CCTTCGATAGCTCAGCTGGTAGAGCGGAGGACTTTAGATTGTATAGACATTT<br>GCGGACATCCTTAGGTCGCTGGTTCGATTCCAGCTCGAAGGA |
| 509 | CCTTCGATAGCTCAGCTGGTAGAGCGGAGGACTTTAGATCCTTAGGTCGCTG<br>GTTCGATTCCAGCTCGAAGGA |
| 510 | CCTTCGATAGCTCAGCTGGTAGAGCGGAGGACTTTAGCTACTTCCTCAGCAG<br>GAGACATCCTTAGGTCGCTGGTTCGATTCCGGCTCGAAGGA |
| 511 | CCTTCGATAGCTCAGCTGGTAGAGCGGAGGACTTTAGATCCTTAGGTCGCTG<br>GTTCGATTCCGGCTCGAAGGA |

TABLE 3-continued

| SEQ ID NO | Suppressor tRNA Sequence |
|---|---|
| 512 | CCTTCGATAGCTCAGCTGGTAGAGCGGAGGACTTTAGGCGCGCGCCCGTGGC<br>CATCCTTAGGTCGCTGGTTCGATTCCGGCTCGAAGGA |
| 513 | CCTTCGATAGCTCAGCTGGTAGAGCGGAGGACTTTAGATCCTTAGGTCGCTG<br>GTTCGATTCCGGCTCGAAGGA |
| 514 | CCTTCGATAGCTCAGCTGGTAGAGCGGAGGACTTTAGCCTGTAGAAACATTT<br>GTGGACATCCTTAGGTCGCTGGTTCGATTCCGGCTCGAAGGA |
| 515 | CCTTCGATAGCTCAGCTGGTAGAGCGGAGGACTTTAGATCCTTAGGTCGCTG<br>GTTCGATTCCGGCTCGAAGGA |
| 516 | CCTTCGATAGCTCAGCTGGTAGAGCGGAGGACTTTAGATTGTACAGACATTT<br>GCGGACATCCTTAGGTCGCTGGTTCGATTCCGGCTCGAAGGA |
| 517 | CCTTCGATAGCTCAGCTGGTAGAGCGGAGGACTTTAGATCCTTAGGTCGCTG<br>GTTCGATTCCGGCTCGAAGGA |
| 518 | CCTTCGATAGCTCAGCTGGTAGAGCGGAGGACTTTAGTACTTAATGTGTGGT<br>CATCCTTAGGTCGCTGGTTCGATTCCGGCTCGAAGGA |
| 519 | CCTTCGATAGCTCAGCTGGTAGAGCGGAGGACTTTAGATCCTTAGGTCGCTG<br>GTTCGATTCCGGCTCGAAGGA |
| 520 | CCTTCGATAGCTCAGCTGGTAGAGCGGAGGACTTTAGGGGTTTGAATGTGGT<br>CATCCTTAGGTCGCTGGTTCGAATCCGGCTCGGAGGA |
| 521 | CCTTCGATAGCTCAGCTGGTAGAGCGGAGGACTTTAGATCCTTAGGTCGCTG<br>GTTCGAATCCGGCTCGGAGGA |
| 522 | CCTTCGATAGCTCAGCTGGTAGAGCGGAGGACTTTAGACTGCGGAAACGTTT<br>GTGGACATCCTTAGGTCGCTGGTTCAATTCCGGCTCGAAGGA |
| 523 | CCTTCGATAGCTCAGCTGGTAGAGCGGAGGACTTTAGATCCTTAGGTCGCTG<br>GTTCAATTCCGGCTCGAAGGA |
| 524 | CTTTCGATAGCTCAGTTGGTAGAGCGGAGGACTTTAGGTTCATTAAACTAAG<br>GCATCCTTAGGTCGCTGGTTCGAATCCGGCTCGAAGGA |
| 525 | CTTTCGATAGCTCAGTTGGTAGAGCGGAGGACTTTAGATCCTTAGGTCGCTG<br>GTTCGAATCCGGCTCGAAGGA |
| 526 | TCTTCAATAGCTCAGCTGGTAGAGCGGAGGACTTTAGGTGCACGCCCGTGGC<br>CATTCTTAGGTGCTGGTTTGATTCCGACTTGGAGAG |
| 527 | TCTTCAATAGCTCAGCTGGTAGAGCGGAGGACTTTAGATTCTTAGGTGCTGG<br>TTTGATTCCGACTTGGAGAG |
| 528 | GGTAAAATGGCTGAGTGAAGCATTGGACTTTAAATCTAAAGACAGGGGTTAA<br>GCCTCTTTTTACCA |
| 529 | GGTAAAATGGCTGAGCAAGCATTGGACTTTAAATCTAAAGACAGATGTTGAG<br>CCATCTTTTTAGCA |
| 530 | GGTAAAATGGCTGAGTGAAGCATTGGACTTTAAATCTAAAGACAGGGGCTAA<br>GCCTCTTTTTACCA |
| 531 | GGTAAAATGGCTGAGCAAGCATTAGACTTTAAATCTAAAGACAGAGGTTAAG<br>GCCTCTTTTTACCA |
| 532 | GGTAAAATGGCTGAGTAAGCATTAGACTTTAAATCTAAAGACAGAGGTCAAG<br>GCCTCTTTTTTCCT |
| 533 | GGTAAAATGGCTGAGCAAGCATTAGACTTTAAATCTGAAAACAGAGGTCAAA<br>GGTCTCTTTTTACCA |
| 534 | GGTAAAATGGCTGAGTAAGCATTAGACTTTAAATCTAAAGACAGAGGTCAAG<br>GCCTCTTTTTACCA |
| 535 | GGTAAAATGACTGAATAAGCCTTAGACTTTAAATCTGAAGACAGAGGTCAAG<br>GCCTCTTTTTACCA |
| 536 | GGTAAAATGGCTGAGTAAGCATTGGACTTTAAATCTAAAGACAGAGGTCAAG<br>ACCTCTTTTTACCA |
| 537 | GGTAAAATGGCTGAGTAAAGCATTAGACTTTAAATCTAAGGACAGAGGCTAA<br>ACCTCTTTTTACCA |

TABLE 3-continued

| SEQ ID NO | Suppressor tRNA Sequence |
| --- | --- |
| 538 | CCTTCAATAGTTCAGCTGGTAGAGCAGAGGACTCTAGCTACTTCCTCAGTAG<br>GAGACGTCCTTAGGTTGCTGGTTCGATTCCAGCTTGAAGGA |
| 539 | CCTTCAATAGTTCAGCTGGTAGAGCAGAGGACTCTAGGTCCTTAGGTTGCTG<br>GTTCGATTCCAGCTTGAAGGA |
| 540 | GGTAAAATGGCTGAGTAAGCTTTAGACTCTAAATCTAAAGAGAGATTGAGCT<br>CTCTTTTTACCA |
| 541 | GGTAAAATGACTGAGTAAGCATTAGACTCTAAATCTAAAGACAGAGGTCAAG<br>ACCTCTTTTTACCA |
| 542 | GGTAAAATGGCTGAGTAAGCATTAGACTCTAAATCTAAAGACAGAGGTCAAG<br>GCCTCTTTTTACCA |
| 543 | GGTAAAATGGCTGAGTAAGCATTAGACTCTAAATCTAAAGACAGAGGTCAAG<br>GCCTTTTTACCA |
| 544 | CCTTCGATAGCTCAGTTGGTAGAGCGGAGGACTCTAGTTGGCTGTGTCCTTA<br>GACATCCTTAGGTCGCTGGTTCGAATCCGGCTCGAAGGA |
| 545 | CCTTCGATAGCTCAGTTGGTAGAGCGGAGGACTCTAGATCCTTAGGTCGCTG<br>GTTCGAATCCGGCTCGAAGGA |
| 546 | GGGGGTATAGCTCAGGGCTAGAGCTTTTTGACTCTAGAGCAAGAGGTCCCTG<br>GTTCAAATCCAGGTTCTCCCT |
| 547 | TATAGCTCAGTGGTAGAGCATTTAACTCTAGATCAAGAGGTCCCTGGATCAA<br>CTCTGGGTG |
| 548 | GTCAGTGTTGCACAACGGTTAAGTGAAGAGGCTCTAAACCCAGACTGGATGG<br>GTTCAATTCCCATCTCTGCCG |
| 549 | CCTTCGATAGCTCAGTTGGTAGAGCGGAGGACTCTAGTGGATAGGGCGTGGC<br>AATCCTTAGGTCGCTGGTTCGATTCCGGCTCGAAGGA |
| 550 | CCTTCGATAGCTCAGTTGGTAGAGCGGAGGACTCTAGATCCTTAGGTCGCTG<br>GTTCGATTCCGGCTCGAAGGA |
| 551 | CCTTCGATAGCTCAGTTGGTAGAGCGGAGGACTCTAGGCTCATTAAGCAAGG<br>TATCCTTAGGTCGCTGGTTCGAATCCGGCTCGGAGGA |
| 552 | CCTTCGATAGCTCAGTTGGTAGAGCGGAGGACTCTAGATCCTTAGGTCGCTG<br>GTTCGAATCCGGCTCGGAGGA |
| 553 | CCTTCGATAGCTCAGCTGGTAGAGCGGAGGACTCTAGATTGTATAGACATTT<br>GCGGACATCCTTAGGTCGCTGGTTCGATTCCAGCTCGAAGGA |
| 554 | CCTTCGATAGCTCAGCTGGTAGAGCGGAGGACTCTAGATCCTTAGGTCGCTG<br>GTTCGATTCCAGCTCGAAGGA |
| 555 | CCTTCGATAGCTCAGCTGGTAGAGCGGAGGACTCTAGCTACTTCCTCAGCAG<br>GAGACATCCTTAGGTCGCTGGTTCGATTCCGGCTCGAAGGA |
| 556 | CCTTCGATAGCTCAGCTGGTAGAGCGGAGGACTCTAGATCCTTAGGTCGCTG<br>GTTCGATTCCGGCTCGAAGGA |
| 557 | CCTTCGATAGCTCAGCTGGTAGAGCGGAGGACTCTAGGCGCGCGCCCGTGGC<br>CATCCTTAGGTCGCTGGTTCGATTCCGGCTCGAAGGA |
| 558 | CCTTCGATAGCTCAGCTGGTAGAGCGGAGGACTCTAGATCCTTAGGTCGCTG<br>GTTCGATTCCGGCTCGAAGGA |
| 559 | CCTTCGATAGCTCAGCTGGTAGAGCGGAGGACTCTAGCCTGTAGAAACATTT<br>GTGGACATCCTTAGGTCGCTGGTTCGATTCCGGCTCGAAGGA |
| 560 | CCTTCGATAGCTCAGCTGGTAGAGCGGAGGACTCTAGATCCTTAGGTCGCTG<br>GTTCGATTCCGGCTCGAAGGA |
| 561 | CCTTCGATAGCTCAGCTGGTAGAGCGGAGGACTCTAGATTGTACAGACATTT<br>GCGGACATCCTTAGGTCGCTGGTTCGATTCCGGCTCGAAGGA |
| 562 | CCTTCGATAGCTCAGCTGGTAGAGCGGAGGACTCTAGATCCTTAGGTCGCTG<br>GTTCGATTCCGGCTCGAAGGA |
| 563 | CCTTCGATAGCTCAGCTGGTAGAGCGGAGGACTCTAGTACTTAATGTGTGGT<br>CATCCTTAGGTCGCTGGTTCGATTCCGGCTCGAAGGA |

TABLE 3-continued

| SEQ ID NO | Suppressor tRNA Sequence |
| --- | --- |
| 564 | CCTTCGATAGCTCAGCTGGTAGAGCGGAGGACTCTAGATCCTTAGGTCGCTG<br>GTTCGATTCCGGCTCGAAGGA |
| 565 | CCTTCGATAGCTCAGCTGGTAGAGCGGAGGACTCTAGGGGTTTGAATGTGGT<br>CATCCTTAGGTCGCTGGTTCGAATCCGGCTCGGAGGA |
| 566 | CCTTCGATAGCTCAGCTGGTAGAGCGGAGGACTCTAGATCCTTAGGTCGCTG<br>GTTCGAATCCGGCTCGGAGGA |
| 567 | CCTTCGATAGCTCAGCTGGTAGAGCGGAGGACTCTAGACTGCGGAAACGTTT<br>GTGGACATCCTTAGGTCGCTGGTTCAATTCCGGCTCGAAGGA |
| 568 | CCTTCGATAGCTCAGCTGGTAGAGCGGAGGACTCTAGATCCTTAGGTCGCTG<br>GTTCAATTCCGGCTCGAAGGA |
| 569 | CTTTCGATAGCTCAGTTGGTAGAGCGGAGGACTCTAGGTTCATTAAACTAAG<br>GCATCCTTAGGTCGCTGGTTCGAATCCGGCTCGAAGGA |
| 570 | CTTTCGATAGCTCAGTTGGTAGAGCGGAGGACTCTAGATCCTTAGGTCGCTG<br>GTTCGAATCCGGCTCGAAGGA |
| 571 | TCTTCAATAGCTCAGCTGGTAGAGCGGAGGACTCTAGGTGCACGCCCGTGGC<br>CATTCTTAGGTGCTGGTTTGATTCCGACTTGGAGAG |
| 572 | TCTTCAATAGCTCAGCTGGTAGAGCGGAGGACTCTAGATTCTTAGGTGCTGG<br>TTTGATTCCGACTTGGAGAG |
| 573 | GGTAAAATGGCTGAGTGAAGCATTGGACTCTAAATCTAAAGACAGGGGTTAA<br>GCCTCTTTTTACCA |
| 574 | GGTAAAATGGCTGAGCAAGCATTGGACTCTAAATCTAAAGACAGATGTTGAG<br>CCATCTTTTTAGCA |
| 575 | GGTAAAATGGCTGAGTGAAGCATTGGACTCTAAATCTAAAGACAGGGGCTAA<br>GCCTCTTTTTACCA |
| 576 | GGTAAAATGGCTGAGCAAGCATTAGACTCTAAATCTAAAGACAGAGGTTAAG<br>GCCTCTTTTTACCA |
| 577 | GGTAAAATGGCTGAGTAAGCATTAGACTCTAAATCTAAAGACAGAGGTCAAG<br>GCCTCTTTTTTCCT |
| 578 | GGTAAAATGGCTGAGCAAGCATTAGACTCTAAATCTGAAAACAGAGGTCAAA<br>GGTCTCTTTTTACCA |
| 579 | GGTAAAATGGCTGAGTAAGCATTAGACTCTAAATCTAAAGACAGAGGTCAAG<br>GCCTCTTTTTACCA |
| 580 | GGTAAAATGACTGAATAAGCCTTAGACTCTAAATCTGAAGACAGAGGTCAAG<br>GCCTCTTTTTACCA |
| 581 | GGTAAAATGGCTGAGTAAGCATTGGACTCTAAATCTAAAGACAGAGGTCAAG<br>ACCTCTTTTTACCA |
| 582 | GGTAAAATGGCTGAGTAAAGCATTAGACTCTAAATCTAAGGACAGAGGCTAA<br>ACCTCTTTTTACCA |
| 583 | GTTAAGATGGCAGAGCCTGGTAATTGCATTAAACTTAAAATTTTATAATCAG<br>AGGTTCAACTCCTCTTCTTAACA |
| 584 | GTTAAGATGGCAGAGCCCGGCAATTGCATTAGACTTAAAACTTTATAATCAG<br>AGGTTCAACTCCTCTCATTAACA |
| 585 | GGTAGCGTGGCCGAGCGGTCTAAGGCGCTGGATTTTAGCTCCAGTCTCTTCG<br>GGGGCGTGGGTTCAAATCCCACCGCTGCCA |
| 586 | GGTAGCGTGGCCGAGTGGTCTAAGACGCTGGATTTTAGCTCCAGTCTCTTCG<br>GGGGCGTGGGTTTGAATCCCACCGCTGCCA |
| 587 | GGGCCAGTGGCTCAATGGATAATGCGTCTGACTTTAAATCAGAAGATTCCAG<br>CCTTGACTCCTGGCTGGCTCA |
| 588 | GGTAGGGTGGCCGAGCGGTCTAAGGCACTGTATTTTAACTCCAGTCTCTTCA<br>GAGGCATGGGTTTGAATCCCACTGCTGCCA |
| 589 | GCCGAGCGGTCTAAGGCTCCGGATTTTAGCGCCGGTGTCTTCGGAGGCATGG<br>GTTCGAATTCCAC |

TABLE 3-continued

| SEQ ID NO | Suppressor tRNA Sequence |
|---|---|
| 590 | GTCAGGATGGCCGAGTGGTCTAAGGCGCCAGACTTTAGCTAAGCTTCCTCCG CGGTGGGGATTCTGGTCTCCAATGGAGGCGTGGGTTCGAATCCCACTTCTGA CA |
| 591 | GTCAGGATGGCCGAGTGGTCTAAGGCGCCAGACTTTAGTTCTGGTCTCCAAT GGAGGCGTGGGTTCGAATCCCACTTCTGACA |
| 592 | GTCAGGATGGCCGAGTGGTCTAAGGCGCCAGACTTTAGCTTGGCTTCCTCGT GTTGAGGATTCTGGTCTCCAATGGAGGCGTGGGTTCGAATCCCACTTCTGAC A |
| 593 | GTCAGGATGGCCGAGTGGTCTAAGGCGCCAGACTTTAGTTCTGGTCTCCAAT GGAGGCGTGGGTTCGAATCCCACTTCTGACA |
| 594 | GTCAGGATGGCCGAGTGGTCTAAGGCGCCAGACTTTAGCTTACTGCTTCCTG TGTTCGGGTCTTCTGGTCTCCGTATGGAGGCGTGGGTTCGAATCCCACTTCT GACA |
| 595 | GTCAGGATGGCCGAGTGGTCTAAGGCGCCAGACTTTAGTTCTGGTCTCCGTA TGGAGGCGTGGGTTCGAATCCCACTTCTGACA |
| 596 | GTCAGGATGGCCGAGTGGTCTAAGGCGCCAGACTTTAGTTGCTACTTCCCAG GTTTGGGGCTTCTGGTCTCCGCATGGAGGCGTGGGTTCGAATCCCACTTCTG ACA |
| 597 | GTCAGGATGGCCGAGTGGTCTAAGGCGCCAGACTTTAGTTCTGGTCTCCGCA TGGAGGCGTGGGTTCGAATCCCACTTCTGACA |
| 598 | GTCAGGATGGCCGAGTGGTCTAAGGCGCCAGACTTTAGGTAAGCACCTTGCC TGCGGGCTTTCTGGTCTCCGGATGGAGGCGTGGGTTCGAATCCCACTTCTGA CA |
| 599 | GTCAGGATGGCCGAGTGGTCTAAGGCGCCAGACTTTAGTTTCTGGTCTCCGG ATGGAGGCGTGGGTTCGAATCCCACTTCTGACA |
| 600 | GCCTCCTTAGTGCAGTAGGTAGCGCATCAGTCTTTAAATCTGAATGGTCCTG AGTTCAAGCCTCAGAGGGGGCA |
| 601 | GTCAGGATGGCCGAGCAGTCTTAAGGCGCTGCGTTTTAATCGCACCCTCCGC TGGAGGCGTGGGTTCGAATCCCACTTTTGACA |
| 602 | GGTTCCATGGTGTAATGGTGAGCACTCTGGACTTTAAATCCAGAAGTAGTGC TGGAACAA |
| 603 | GTCAGGGTGGCTGAGCAGTCTGAGGGGCTGCGTTTTAGTCGCAGTCTGCCCT GGAGGCGTGGGTTCGAATCCCACTCCTGAAA |
| 604 | ACCAGGATGGCCGAGTGGTTAAGGCGTTGGACTTTAGATCCAATGGACATAT GTCCGCGTGGGTTCGAACCCCACTCCTGGTA |
| 605 | ACCGGGATGGCCGAGTGGTTAAGGCGTTGGACTTTAGATCCAATGGGCTGGT GCCCGCGTGGGTTCGAACCCCACTCTCGGTA |
| 606 | ACCAGAATGGCCGAGTGGTTAAGGCGTTGGACTTTAGATCCAATGGATTCAT ATCCGCGTGGGTTCGAACCCCACTTCTGGTA |
| 607 | ACCGGGATGGCTGAGTGGTTAAGGCGTTGGACTTTAGATCCAATGGACAGGT GTCCGCGTGGGTTCGAGCCCCACTCCCGGTA |
| 608 | ACTCATTTGGCTGAGTGGTTAAGGCATTGGACTTTAGATCCAATGGAGTAGT GGCTGTGTGGGTTTAAACCCCACTACTGGTA |
| 609 | GAGAAAGTCATCGTAGTTACGAAGTTGGCTTTAACCCAGTTTTGGGAGGTTC AATTCCTTCCTTTCTCT |
| 610 | ACCAGGATGGCCAAGTAGTTAAAGGCACTGGACTTTAGAGCCAATGGACATA TGTCTGTGTGGGTTTGAACCCCACTCCTGGTG |
| 611 | GGTAGCGTGGCCGAGCGGTCTAAGGCGCTGGATTTTAGCTCCAGTCTCTTCG GAGGCGTGGGTTCGAATCCCACCGCTGCCA |
| 612 | GGTAGTGTGGCCGAGCGGTCTAAGGCGCTGGATTTTAGCTCCAGTCTCTTCG GGGGCGTGGGTTCGAATCCCACCACTGCCA |
| 613 | GGTAGCGTGGCCGAGTGGTCTAAGGCGCTGGATTTTAGCTCCAGTCATTTCG ATGGCGTGGGTTCGAATCCCACCGCTGCCA |

TABLE 3-continued

| SEQ ID NO | Suppressor tRNA Sequence |
|---|---|
| 614 | GGTAGTGTGGTTGAATGGTCTAAGGCACTGAATTTTAGCTCCAGTCTCTTTG GGGACGTGGGTTAAATCCCACTGCTGCAA |
| 615 | GTTAAGATGGCAGAGCCTGGTAATTGCACTAAACTTAAAATTTTATAATCAG AGGTTCAACTCCTCTTCTTAACA |
| 616 | GTTAAGATGGCAGAGCCCGGCAATTGCACTAGACTTAAAACTTTATAATCAG AGGTTCAACTCCTCTCATTAACA |
| 617 | GGTAGCGTGGCCGAGCGGTCTAAGGCGCTGGATTCTAGCTCCAGTCTCTTCG GGGGCGTGGGTTCAAATCCCACCGCTGCCA |
| 618 | GGTAGCGTGGCCGAGTGGTCTAAGACGCTGGATTCTAGCTCCAGTCTCTTCG GGGGCGTGGGTTTGAATCCCACCGCTGCCA |
| 619 | GGGCCAGTGGCTCAATGGATAATGCGTCTGACTCTAAATCAGAAGATTCCAG CCTTGACTCCTGGCTGGCTCA |
| 620 | GGTAGGGTGGCCGAGCGGTCTAAGGCACTGTATTCTAACTCCAGTCTCTTCA GAGGCATGGGTTTGAATCCCACTGCTGCCA |
| 621 | GCCGAGCGGTCTAAGGCTCCGGATTCTAGCGCCGGTGTCTTCGGAGGCATGG GTTCGAATTCCAC |
| 622 | GTCAGGATGGCCGAGTGGTCTAAGGCGCCAGACTCTAGCTAAGCTTCCTCCG CGGTGGGGATTCTGGTCTCCAATGGAGGCGTGGGTTCGAATCCCACTTCTGA CA |
| 623 | GTCAGGATGGCCGAGTGGTCTAAGGCGCCAGACTCTAGTTCTGGTCTCCAAT GGAGGCGTGGGTTCGAATCCCACTTCTGACA |
| 624 | GTCAGGATGGCCGAGTGGTCTAAGGCGCCAGACTCTAGCTTGGCTTCCTCGT GTTGAGGATTCTGGTCTCCAATGGAGGCGTGGGTTCGAATCCCACTTCTGAC A |
| 625 | GTCAGGATGGCCGAGTGGTCTAAGGCGCCAGACTCTAGTTCTGGTCTCCAAT GGAGGCGTGGGTTCGAATCCCACTTCTGACA |
| 626 | GTCAGGATGGCCGAGTGGTCTAAGGCGCCAGACTCTAGCTTACTGCTTCCTG TGTTCGGGTCTTCTGGTCTCCGTATGGAGGCGTGGGTTCGAATCCCACTTCT GACA |
| 627 | GTCAGGATGGCCGAGTGGTCTAAGGCGCCAGACTCTAGTTCTGGTCTCCGTA TGGAGGCGTGGGTTCGAATCCCACTTCTGACA |
| 628 | GTCAGGATGGCCGAGTGGTCTAAGGCGCCAGACTCTAGTTGCTACTTCCCAG GTTTGGGGCTTCTGGTCTCCGCATGGAGGCGTGGGTTCGAATCCCACTTCTG ACA |
| 629 | GTCAGGATGGCCGAGTGGTCTAAGGCGCCAGACTCTAGTTCTGGTCTCCGCA TGGAGGCGTGGGTTCGAATCCCACTTCTGACA |
| 630 | GTCAGGATGGCCGAGTGGTCTAAGGCGCCAGACTCTAGGTAAGCACCTTGCC TGCGGGCTTTCTGGTCTCCGGATGGAGGCGTGGGTTCGAATCCCACTTCTGA CA |
| 631 | GTCAGGATGGCCGAGTGGTCTAAGGCGCCAGACTCTAGTTTCTGGTCTCCGG ATGGAGGCGTGGGTTCGAATCCCACTTCTGACA |
| 632 | GCCTCCTTAGTGCAGTAGGTAGCGCATCAGTCTCTAAATCTGAATGGTCCTG AGTTCAAGCCTCAGAGGGGGCA |
| 633 | GTCAGGATGGCCGAGCAGTCTTAAGGCGCTGCGTTCTAATCGCACCCTCCGC TGGAGGCGTGGGTTCGAATCCCACTTTTGACA |
| 634 | GGTTCCATGGTGTAATGGTGAGCACTCTGGACTCTAAATCCAGAAGTAGTGC TGGAACAA |
| 635 | GTCAGGGTGGCTGAGCAGTCTGAGGGGCTGCGTTCTAGTCGCAGTCTGCCCT GGAGGCGTGGGTTCGAATCCCACTCCTGAAA |
| 636 | ACCAGGATGGCCGAGTGGTTAAGGCGTTGGACTCTAGATCCAATGGACATAT GTCCGCGTGGGTTCGAACCCCACTCCTGGTA |
| 637 | ACCGGGATGGCCGAGTGGTTAAGGCGTTGGACTCTAGATCCAATGGGCTGGT GCCCGCGTGGGTTCGAACCCCACTCTCGGTA |

TABLE 3-continued

| SEQ ID NO | Suppressor tRNA Sequence |
|---|---|
| 638 | ACCAGAATGGCCGAGTGGTTAAGGCGTTGGACTCTAGATCCAATGGATTCAT<br>ATCCGCGTGGGTTCGAACCCCACTTCTGGTA |
| 639 | ACCGGGATGGCTGAGTGGTTAAGGCGTTGGACTCTAGATCCAATGGACAGGT<br>GTCCGCGTGGGTTCGAGCCCCACTCCCGGTA |
| 640 | ACTCATTTGGCTGAGTGGTTAAGGCATTGGACTCTAGATCCAATGGAGTAGT<br>GGCTGTGTGGGTTTAAACCCCACTACTGGTA |
| 641 | GAGAAAGTCATCGTAGTTACGAAGTTGGCTCTAACCCAGTTTTGGGAGGTTC<br>AATTCCTTCCTTTCTCT |
| 642 | ACCAGGATGGCCAAGTAGTTAAAGGCACTGGACTCTAGAGCCAATGGACATA<br>TGTCTGTGTGGGTTTGAACCCCACTCCTGGTG |
| 643 | GGTAGCGTGGCCGAGCGGTCTAAGGCGCTGGATTCTAGCTCCAGTCTCTTCG<br>GAGGCGTGGGTTCGAATCCCACCGCTGCCA |
| 644 | GGTAGTGTGGCCGAGCGGTCTAAGGCGCTGGATTCTAGCTCCAGTCTCTTCG<br>GGGGCGTGGGTTCGAATCCCACCACTGCCA |
| 645 | GGTAGCGTGGCCGAGTGGTCTAAGGCGCTGGATTCTAGCTCCAGTCATTTCG<br>ATGGCGTGGGTTCGAATCCCACCGCTGCCA |
| 646 | GGTAGTGTGGTTGAATGGTCTAAGGCACTGAATTCTAGCTCCAGTCTCTTTG<br>GGGACGTGGGTTTAAATCCCACTGCTGCAA |
| 647 | GTTAAGATGGCAGAGCCTGGTAATTGCATCAAACTTAAAATTTTATAATCAG<br>AGGTTCAACTCCTCTTCTTAACA |
| 648 | GTTAAGATGGCAGAGCCCGGCAATTGCATCAGACTTAAAACTTTATAATCAG<br>AGGTTCAACTCCTCTCATTAACA |
| 649 | GGTAGCGTGGCCGAGCGGTCTAAGGCGCTGGATTTCAGCTCCAGTCTCTTCG<br>GGGGCGTGGGTTCAAATCCCACCGCTGCCA |
| 650 | GGTAGCGTGGCCGAGTGGTCTAAGACGCTGGATTTCAGCTCCAGTCTCTTCG<br>GGGGCGTGGGTTTGAATCCCACCGCTGCCA |
| 651 | GGGCCAGTGGCTCAATGGATAATGCGTCTGACTTCAAATCAGAAGATTCCAG<br>CCTTGACTCCTGGCTGGCTCA |
| 652 | GGTAGGGTGGCCGAGCGGTCTAAGGCACTGTATTTCAACTCCAGTCTCTTCA<br>GAGGCATGGGTTTGAATCCCACTGCTGCCA |
| 653 | GCCGAGCGGTCTAAGGCTCCGGATTTCAGCGCCGGTGTCTTCGGAGGCATGG<br>GTTCGAATTCCAC |
| 654 | GTCAGGATGGCCGAGTGGTCTAAGGCGCCAGACTTCAGCTAAGCTTCCTCCG<br>CGGTGGGGATTCTGGTCTCCAATGGAGGCGTGGGTTCGAATCCCACTTCTGA<br>CA |
| 655 | GTCAGGATGGCCGAGTGGTCTAAGGCGCCAGACTTCAGTTCTGGTCTCCAAT<br>GGAGGCGTGGGTTCGAATCCCACTTCTGACA |
| 656 | GTCAGGATGGCCGAGTGGTCTAAGGCGCCAGACTTCAGCTTGGCTTCCTCGT<br>GTTGAGGATTCTGGTCTCCAATGGAGGCGTGGGTTCGAATCCCACTTCTGAC<br>A |
| 657 | GTCAGGATGGCCGAGTGGTCTAAGGCGCCAGACTTCAGTTCTGGTCTCCAAT<br>GGAGGCGTGGGTTCGAATCCCACTTCTGACA |
| 658 | GTCAGGATGGCCGAGTGGTCTAAGGCGCCAGACTTCAGCTTACTGCTTCCTG<br>TGTTCGGGTCTTCTGGTCTCCGTATGGAGGCGTGGGTTCGAATCCCACTTCT<br>GACA |
| 659 | GTCAGGATGGCCGAGTGGTCTAAGGCGCCAGACTTCAGTTCTGGTCTCCGTA<br>TGGAGGCGTGGGTTCGAATCCCACTTCTGACA |
| 660 | GTCAGGATGGCCGAGTGGTCTAAGGCGCCAGACTTCAGTTGCTACTTCCCAG<br>GTTTGGGGCTTCTGGTCTCCGCATGGAGGCGTGGGTTCGAATCCCACTTCTG<br>ACA |
| 661 | GTCAGGATGGCCGAGTGGTCTAAGGCGCCAGACTTCAGTTCTGGTCTCCGCA<br>TGGAGGCGTGGGTTCGAATCCCACTTCTGACA |

TABLE 3-continued

| SEQ ID NO | Suppressor tRNA Sequence |
|---|---|
| 662 | GTCAGGATGGCCGAGTGGTCTAAGGCGCCAGACTTCAGGTAAGCACCTTGCC TGCGGGCTTTCTGGTCTCCGGATGGAGGCGTGGGTTCGAATCCCACTTCTGA CA |
| 663 | GTCAGGATGGCCGAGTGGTCTAAGGCGCCAGACTTCAGTTTCTGGTCTCCGG ATGGAGGCGTGGGTTCGAATCCCACTTCTGACA |
| 664 | GCCTCCTTAGTGCAGTAGGTAGCGCATCAGTCTTCAAATCTGAATGGTCCTG AGTTCAAGCCTCAGAGGGGGCA |
| 665 | GTCAGGATGGCCGAGCAGTCTTAAGGCGCTGCGTTTCAATCGCACCCTCCGC TGGAGGCGTGGGTTCGAATCCCACTTTTGACA |
| 666 | GGTTCCATGGTGTAATGGTGAGCACTCTGGACTTCAAATCCAGAAGTAGTGC TGGAACAA |
| 667 | GTCAGGGTGGCTGAGCAGTCTGAGGGGCTGCGTTTCAGTCGCAGTCTGCCCT GGAGGCGTGGGTTCGAATCCCACTCCTGAAA |
| 668 | ACCAGGATGGCCGAGTGGTTAAGGCGTTGGACTTCAGATCCAATGGACATAT GTCCGCGTGGGTTCGAACCCCACTCCTGGTA |
| 669 | ACCGGGATGGCCGAGTGGTTAAGGCGTTGGACTTCAGATCCAATGGGCTGGT GCCCGCGTGGGTTCGAACCCCACTCTCGGTA |
| 670 | ACCAGAATGGCCGAGTGGTTAAGGCGTTGGACTTCAGATCCAATGGATTCAT ATCCGCGTGGGTTCGAACCCCACTTCTGGTA |
| 671 | ACCGGGATGGCTGAGTGGTTAAGGCGTTGGACTTCAGATCCAATGGACAGGT GTCCGCGTGGGTTCGAGCCCCACTCCCGGTA |
| 672 | ACTCATTTGGCTGAGTGGTTAAGGCATTGGACTTCAGATCCAATGGAGTAGT GGCTGTGTGGGTTTAAACCCCACTACTGGTA |
| 673 | GAGAAAGTCATCGTAGTTACGAAGTTGGCTTCAACCCAGTTTTGGGAGGTTC AATTCCTTCCTTTCTCT |
| 674 | ACCAGGATGGCCAAGTAGTTAAAGGCACTGGACTTCAGAGCCAATGGACATA TGTCTGTGTGGGTTTGAACCCCACTCCTGGTG |
| 675 | GGTAGCGTGGCCGAGCGGTCTAAGGCGCTGGATTTCAGCTCCAGTCTCTTCG GAGGCGTGGGTTCGAATCCCACCGCTGCCA |
| 676 | GGTAGTGTGGCCGAGCGGTCTAAGGCGCTGGATTTCAGCTCCAGTCTCTTCG GGGGCGTGGGTTCGAATCCCACCACTGCCA |
| 677 | GGTAGCGTGGCCGAGTGGTCTAAGGCGCTGGATTTCAGCTCCAGTCATTTCG ATGGCGTGGGTTCGAATCCCACCGCTGCCA |
| 678 | GGTAGTGTGGTTGAATGGTCTAAGGCACTGAATTTCAGCTCCAGTCTCTTTG GGGACGTGGGTTTAAATCCCACTGCTGCAA |
| 679 | GAGAAGGTCACAGAGGTTATGGGATTGGCTTTAAACCAGTCTGTGGGGGGTT CGATTCCCTCCTTTTTCA |
| 680 | GAGAAGGTCATAGAGGTTATGGGATTGGCTTTAAACCAGTCTCTGGGGGGTT CGATTCCCTCCTTTTTCA |
| 681 | GAAAAAGTCATAGGGGTTATGAGGCTGGCTTTAAACCAGCCTTAGGAGGTTC AATTCCTTCCTTTTTTG |
| 682 | GGCCGGTTAGCTCAGTTGGTTAGAGCGTGCTGCTTTAAATGCCAGGGTCGAG GTTTCGATCCCCGTACGGGCCT |
| 683 | GTAGTCGTGGCCGAGTGGTTAAGGCGATGGACTTTAAATCCATTGGGGTTTC CCCGCGCAGGTTCGAATCCTGCCGACTACG |
| 684 | GTAGTCGTGGCCGAGTGGTTAAGGCGATGGACTTTAAATCCATTGGGGTTTC CCCACGCAGGTTCGAATCCTGCCGACTACG |
| 685 | GTAGTCGTGGCCGAGTGGTTAAGGTGATGGACTTTAAACCCATTGGGGTCTC CCCGCGCAGGTTCGAATCCTGCCGACTACG |
| 686 | GGGTGTATGGCTCAGGGGTAGAGAATTTGACTTTAGATCAAGAGGTCCCTGG TTCAAATCCAGGTGCCCCCT |

TABLE 3-continued

| SEQ ID NO | Suppressor tRNA Sequence |
|---|---|
| 687 | AGTTGTAGCTGAGTGGTTAAGGCAACGAGCTTTAAATTCGTTGGTTTCTCTC<br>TGTGCAGGTTTGAATCCTGCTAATTA |
| 688 | CAAGAAATTCATAGAGGTTATGGGATTGGCTTTAAACCAGTTTCAGGAGGTT<br>CGATTCCTTCCTTTTTGG |
| 689 | GCTGTGATGGCCGAGTGGTTAAGGCGTTGGACTTTAAATCCAATGGGGTCTC<br>CCCGCGCAGGTTCGAATCCTGCTCACAGCG |
| 690 | GCTGTGATGGCCGAGTGGTTAAGGCGTTGGACTTTAAATCCAATGGGGTCTC<br>CCCGCGCAGGTTCAAATCCTGCTCACAGCG |
| 691 | GCTGTGATGGCCGAGTGGTTAAGGTGTTGGACTTTAAATCCAATGGGGGTTC<br>CCCGCGCAGGTTCAAATCCTGCTCACAGCG |
| 692 | GTCACGGTGGCCGAGTGGTTAAGGCGTTGGACTTTAAATCCAATGGGGTTTC<br>CCCGCACAGGTTCGAATCCTGTTCGTGACG |
| 693 | GACGAGGTGGCCGAGTGGTTAAGGCGATGGACTTTAAATCCATTGTGCTCTG<br>CACGCGTGGGTTCGAATCCCACCCTCGTCG |
| 694 | GACGAGGTGGCCGAGTGGTTAAGGCGATGGACTTTAAATCCATTGTGCTCTG<br>CACGCGTGGGTTCGAATCCCACCTTCGTCG |
| 695 | GGCCGGTTAGCTCAGTTGGTTAGAGCGTGCTTTAACTAATGCCAGGGTCGAG<br>GTTTCGATCCCCGTACGGGCCT |
| 696 | GACGAGGTGGCCGAGTGGTTAAGGCGATGGACTTTAAATCCATTGTGCTCTG<br>CACACGTGGGTTCGAATCCCATCCTCGTCG |
| 697 | GAGGCCTGGCCGAGTGGTTAAGGCGATGGACTTTAAATCCATTGTGCTCTGC<br>ACGCGTGGGTTCGAATCCCATCCTCG |
| 698 | GCAGCGATGGCCGAGTGGTTAAGGCGTTGGACTTTAAATCCAATGGGGTCTC<br>CCCGCGCAGGTTCGAACCCTGCTCGCTGCG |
| 699 | GTAGTCGTGGCCGAGTGGTTAAGGCGATGGACTTTAAATCCATTGGGGTTTC<br>CCCGCGCAGGTTCGAATCCTGCCGACTACG |
| 700 | GTAGTCGTGGCCGAGTGGTTAAGGCGATGGACTTTAAATCCATTGGGGTCTC<br>CCCGCGCAGGTTCGAATCCTGCCGACTACG |
| 701 | GTAGTCGTGGCCGAGTGGTTAAGGCGATGGACTTTAAATCCATTGGGGTTTC<br>CCCGCGCAGGTTCGAATCCTGTCGGCTACG |
| 702 | GAGAAGGTCACAGAGGTTATGGGATTGGCTCTAAACCAGTCTGTGGGGGGTT<br>CGATTCCCTCCTTTTTCA |
| 703 | GAGAAGGTCATAGAGGTTATGGGATTGGCTCTAAACCAGTCTCTGGGGGGTT<br>CGATTCCCTCCTTTTTCA |
| 704 | GAAAAAGTCATAGGGGTTATGAGGCTGGCTCTAAACCAGCCTTAGGAGGTTC<br>AATTCCTTCCTTTTTTG |
| 705 | GGCCGGTTAGCTCAGTTGGTTAGAGCGTGCTGCTCTAAATGCCAGGGTCGAG<br>GTTTCGATCCCCGTACGGGCCT |
| 706 | GTAGTCGTGGCCGAGTGGTTAAGGCGATGGACTCTAAATCCATTGGGGTTTC<br>CCCGCGCAGGTTCGAATCCTGCCGACTACG |
| 707 | GTAGTCGTGGCCGAGTGGTTAAGGCGATGGACTCTAAATCCATTGGGGTTTC<br>CCCACGCAGGTTCGAATCCTGCCGACTACG |
| 708 | GTAGTCGTGGCCGAGTGGTTAAGGTGATGGACTCTAAACCCATTGGGGTCTC<br>CCCGCGCAGGTTCGAATCCTGCCGACTACG |
| 709 | GGGTGTATGGCTCAGGGGTAGAGAATTTGACTCTAGATCAAGAGGTCCCTGG<br>TTCAAATCCAGGTGCCCCCT |
| 710 | AGTTGTAGCTGAGTGGTTAAGGCAACGAGCTCTAAATTCGTTGGTTTCTCTC<br>TGTGCAGGTTTGAATCCTGCTAATTA |
| 711 | CAAGAAATTCATAGAGGTTATGGGATTGGCTCTAAACCAGTTTCAGGAGGTT<br>CGATTCCTTCCTTTTTGG |
| 712 | GCTGTGATGGCCGAGTGGTTAAGGCGTTGGACTCTAAATCCAATGGGGTCTC<br>CCCGCGCAGGTTCGAATCCTGCTCACAGCG |

TABLE 3-continued

| SEQ ID NO | Suppressor tRNA Sequence |
| --- | --- |
| 713 | GCTGTGATGGCCGAGTGGTTAAGGCGTTGGACTCTAAATCCAATGGGGTCTC CCCGCGCAGGTTCAAATCCTGCTCACAGCG |
| 714 | GCTGTGATGGCCGAGTGGTTAAGGTGTTGGACTCTAAATCCAATGGGGGTTC CCCGCGCAGGTTCAAATCCTGCTCACAGCG |
| 715 | GTCACGGTGGCCGAGTGGTTAAGGCGTTGGACTCTAAATCCAATGGGGTTTC CCCGCACAGGTTCGAATCCTGTTCGTGACG |
| 716 | GACGAGGTGGCCGAGTGGTTAAGGCGATGGACTCTAAATCCATTGTGCTCTG CACGCGTGGGTTCGAATCCCACCCTCGTCG |
| 717 | GACGAGGTGGCCGAGTGGTTAAGGCGATGGACTCTAAATCCATTGTGCTCTG CACGCGTGGGTTCGAATCCCACCTTCGTCG |
| 718 | GGCCGGTTAGCTCAGTTGGTTAGAGCGTGCTCTAACTAATGCCAGGGTCGAG GTTTCGATCCCCGTACGGGCCT |
| 719 | GACGAGGTGGCCGAGTGGTTAAGGCGATGGACTCTAAATCCATTGTGCTCTG CACACGTGGGTTCGAATCCCATCCTCGTCG |
| 720 | GAGGCCTGGCCGAGTGGTTAAGGCGATGGACTCTAAATCCATTGTGCTCTGC ACGCGTGGGTTCGAATCCCATCCTCG |
| 721 | GCAGCGATGGCCGAGTGGTTAAGGCGTTGGACTCTAAATCCAATGGGGTCTC CCCGCGCAGGTTCGAACCCTGCTCGCTGCG |
| 722 | GTAGTCGTGGCCGAGTGGTTAAGGCGATGGACTCTAAATCCATTGGGGTTTC CCCGCGCAGGTTCGAATCCTGCCGACTACG |
| 723 | GTAGTCGTGGCCGAGTGGTTAAGGCGATGGACTCTAAATCCATTGGGGTCTC CCCGCGCAGGTTCGAATCCTGCCGACTACG |
| 724 | GTAGTCGTGGCCGAGTGGTTAAGGCGATGGACTCTAAATCCATTGGGGTTTC CCCGCGCAGGTTCGAATCCTGTCGGCTACG |
| 725 | GAGAAGGTCACAGAGGTTATGGGATTGGCTTCAAACCAGTCTGTGGGGGGTT CGATTCCCTCCTTTTTCA |
| 726 | GAGAAGGTCATAGAGGTTATGGGATTGGCTTCAAACCAGTCTCTGGGGGGTT CGATTCCCTCCTTTTTCA |
| 727 | GAAAAAGTCATAGGGGTTATGAGGCTGGCTTCAAACCAGCCTTAGGAGGTTC AATTCCTTCCTTTTTTG |
| 728 | GGCCGGTTAGCTCAGTTGGTTAGAGCGTGCTGCTTCAAATGCCAGGGTCGAG GTTTCGATCCCCGTACGGGCCT |
| 729 | GTAGTCGTGGCCGAGTGGTTAAGGCGATGGACTTCAAATCCATTGGGGTTTC CCCGCGCAGGTTCGAATCCTGCCGACTACG |
| 730 | GTAGTCGTGGCCGAGTGGTTAAGGCGATGGACTTCAAATCCATTGGGGTTTC CCCACGCAGGTTCGAATCCTGCCGACTACG |
| 731 | GTAGTCGTGGCCGAGTGGTTAAGGTGATGGACTTCAAACCCATTGGGGTCTC CCCGCGCAGGTTCGAATCCTGCCGACTACG |
| 732 | GGGTGTATGGCTCAGGGGTAGAGAATTTGACTTCGATCAAGAGGTCCCTGG TTCAAATCCAGGTGCCCCCT |
| 733 | AGTTGTAGCTGAGTGGTTAAGGCAACGAGCTTCAAATTCGTTGGTTTCTCTC TGTGCAGGTTTGAATCCTGCTAATTA |
| 734 | CAAGAAATTCATAGAGGTTATGGGATTGGCTTCAAACCAGTTTCAGGAGGTT CGATTCCTTCCTTTTTGG |
| 735 | GCTGTGATGGCCGAGTGGTTAAGGCGTTGGACTTCAAATCCAATGGGGTCTC CCCGCGCAGGTTCGAATCCTGCTCACAGCG |
| 736 | GCTGTGATGGCCGAGTGGTTAAGGCGTTGGACTTCAAATCCAATGGGGTCTC CCCGCGCAGGTTCAAATCCTGCTCACAGCG |
| 737 | GCTGTGATGGCCGAGTGGTTAAGGTGTTGGACTTCAAATCCAATGGGGGTTC CCCGCGCAGGTTCAAATCCTGCTCACAGCG |
| 738 | GTCACGGTGGCCGAGTGGTTAAGGCGTTGGACTTCAAATCCAATGGGGTTTC CCCGCACAGGTTCGAATCCTGTTCGTGACG |

TABLE 3-continued

| SEQ ID NO | Suppressor tRNA Sequence |
|---|---|
| 739 | GACGAGGTGGCCGAGTGGTTAAGGCGATGGACTTCAAATCCATTGTGCTCTG<br>CACGCGTGGGTTCGAATCCCACCCTCGTCG |
| 740 | GACGAGGTGGCCGAGTGGTTAAGGCGATGGACTTCAAATCCATTGTGCTCTG<br>CACGCGTGGGTTCGAATCCCACCTTCGTCG |
| 741 | GGCCGGTTAGCTCAGTTGGTTAGAGCGTGCTTCAACTAATGCCAGGGTCGAG<br>GTTTCGATCCCCGTACGGGCCT |
| 742 | GACGAGGTGGCCGAGTGGTTAAGGCGATGGACTTCAAATCCATTGTGCTCTG<br>CACACGTGGGTTCGAATCCCATCCTCGTCG |
| 743 | GAGGCCTGGCCGAGTGGTTAAGGCGATGGACTTCAAATCCATTGTGCTCTGC<br>ACGCGTGGGTTCGAATCCCATCCTCG |
| 744 | GCAGCGATGGCCGAGTGGTTAAGGCGTTGGACTTCAAATCCAATGGGGTCTC<br>CCCGCGCAGGTTCGAACCCTGCTCGCTGCG |
| 745 | GTAGTCGTGGCCGAGTGGTTAAGGCGATGGACTTCAAATCCATTGGGGTTTC<br>CCCGCGCAGGTTCGAATCCTGCCGACTACG |
| 746 | GTAGTCGTGGCCGAGTGGTTAAGGCGATGGACTTCAAATCCATTGGGGTCTC<br>CCCGCGCAGGTTCGAATCCTGCCGACTACG |
| 747 | GTAGTCGTGGCCGAGTGGTTAAGGCGATGGACTTCAAATCCATTGGGGTTTC<br>CCCGCGCAGGTTCGAATCCTGTCGGCTACG |
| 748 | GCCCAGCTAGCTCAGTCGGTAGAGCATAAGACTTTAAATCTCAGGGTTGTGG<br>ATTCGTGCCCCATGCTGGGTG |
| 749 | CTGCAGCTAGCTCAGTCGGTAGAGCATGAGACTTTAAATCTCAGGGTCATGG<br>GTTCGTGCCCCATGTTGGG |
| 750 | CCAGCATGTCTCAGTCGGTATAGTGTGAGACTTTAAATCTCAGGGTCGTGGG<br>TTCAAGCCCCACATTGGG |
| 751 | GTCTAGCTAGATCAGTTGGTAGAGCATAAGACTTTAAATCTCAGGGTCATGG<br>GTTTGAGCCCTACGTTGGGCG |
| 752 | GCCCAGCTAGCTCAGCCGGTAGAGCACAAGACTTTAAATCTCAGGGTCGTGG<br>GTTTGAGCCCTGTGTTGAGCA |
| 753 | CCGAATAGCTTAGTTGATGAAGCGTGAGACTTTAAATCTCAGGGTAGTGGGT<br>TCAAGCCCCACATTGGA |
| 754 | GCCTGGCTACCTCAGTTGGTAGAGCATGGGACTTTAAATCCCAGAGTCAGTG<br>GGTTCAAGCCTCACATTGAGTG |
| 755 | GCCCGGCTAGCTCAGTCGGTAGAGCATGAGACCTTAAATCTCAGGGTCGTGG<br>GTTCGAGCCCCACGTTGGGCG |
| 756 | GCCCGGCTAGCTCAGTCGGTAGAGCATGGGACTTTAAATCTCAGGGTCGTGG<br>GTTCGAGCCCCACGTTGGGCG |
| 757 | GCCCGGCTAGCTCAGTCGATAGAGCATGAGACTTTAAATCTCAGGGTCGTGG<br>GTTCGAGCCGCACGTTGGGCG |
| 758 | GCCCAGCTAGCTCAGTCGGTAGAGCATGAGACTTTAAATCTCAGGGTCATGG<br>GTTTGAGCCCCACGTTTGGTG |
| 759 | GCCTGGCTAGCTCAGTCGGCAAAGCATGAGACTTTAAATCTCAGGGTCGTGG<br>GCTCGAGCTCCATGTTGGGCG |
| 760 | GCCCGACTACCTCAGTCGGTGGAGCATGGGACTTTACATCCCAGGGTTGTGG<br>GTTCGAGCCCCACATTGGGCA |
| 761 | CCCCGGCTGGCTCAGTCAGTAGATCATGAGACTTTAAATCTCAGGGTCGTGG<br>GTTCACGCCCCACACTGGGCG |
| 762 | GCGCTAGTCAGTAGAGCATGAGACTTTAAATCTCAGGGTCGTGGGTTCGAGC<br>CCCACATCGGGCG |
| 763 | GCCTGGATAGCTCAGTTGGTAGAGCATCAGACTTTAAATCTGAGGGTCCAGG<br>GTTCAAGTCCCTGTTCAGGCA |
| 764 | GCCAGGATAGTTCAGGTGGTAGAGCATCAGACTTTAAACCTGAGGGTTCAGG<br>GTTCAAGTCTCTGTTTGGGCG |

TABLE 3-continued

| SEQ ID NO | Suppressor tRNA Sequence |
|---|---|
| 765 | ACCCAGATAGCTCAGTCAGTAGAGCATCAGACTTTAAATCTGAGGGTCCAAG<br>GTTCATGTCCCTTTTTGGGTG |
| 766 | ACCTGGGTAGCTTAGTTGGTAGAGCATTGGACTTTAAATTTGAGGGCCCAGG<br>TTTCAAGTCCCTGTTTGGGTG |
| 767 | GCCTGGGTAGCTCAGTCGGTAGAGCTATCAGACTTTAAGCCTGAGGATTCAG<br>GGTTCAATCCCTTGCTGGGCG |
| 768 | GATAGCTCAGTTGATAGAGCATCAGACTTTAAATCTGAGGGTCCAGGGTTCA<br>TGTCCCTGTT |
| 769 | GTTGGGGTAACTCAGTTGGTAGAGTAGCAGACTTTACATCTGAGGGTCCAGG<br>GTTTAAGTCCATGTCCAGGCA |
| 770 | GCCTGGATAGCTCAGTTGGTAGAGCATCAGACTTTAAATCTGAGGGTCCAGG<br>GTTCAAGTCCCTGTTCAGGCG |
| 771 | GCCTGGATAGCTCAGTCGGTAGAGCATCAGACTTTAAATCTGAGGGTCCAGG<br>GTTCAAGTCCCTGTTCAGGCG |
| 772 | GCCCGGATAGCTCAGTCGGTAGAGCATCAGACTTTAAATCTGAGGGTCCGGG<br>GTTCAAGTCCCTGTTCGGGCG |
| 773 | GCCTGGGTAGCTCAGTCGGTAGAGCATCAGACTTTAAATCTGAGGGTCCAGG<br>GTTCAAGTCCCTGTCCAGGCG |
| 774 | GCCTGGATAGCTCAGTTGGTAGAACATCAGACTTTAAATCTGACGGTGCAGG<br>GTTCAAGTCCCTGTTCAGGCG |
| 775 | GCCCGGAGAGCTCAGTGGGTAGAGCATCAGACTTTAAATCTGAGGGTCCAGG<br>GTTCAAGTCCTCGTTCGGGCA |
| 776 | ACCTGGGTAGCTCAGTAGGTAGAACATCAGACTTTAAATCTGAGGGTCTAGG<br>GTTCAAGTCCCTGTCCAGGCG |
| 777 | GCCTGGATAGCTCCTTCGGTAGAGCATCATCAGACTTTAAATGTGAGGGTCC<br>AGGGTTCAAGTTCCTGTTTGGGCG |
| 778 | GCCCAGCTAGCTCAGTCGGTAGAGCATAAGACTCTAAATCTCAGGGTTGTGG<br>ATTCGTGCCCCATGCTGGGTG |
| 779 | CTGCAGCTAGCTCAGTCGGTAGAGCATGAGACTCTAAATCTCAGGGTCATGG<br>GTTCGTGCCCCATGTTGGG |
| 780 | CCAGCATGTCTCAGTCGGTATAGTGTGAGACTCTAAATCTCAGGGTCGTGGG<br>TTCAAGCCCCACATTGGG |
| 781 | GTCTAGCTAGATCAGTTGGTAGAGCATAAGACTCTAAATCTCAGGGTCATGG<br>GTTTGAGCCCTACGTTGGGCG |
| 782 | GCCCAGCTAGCTCAGCCGGTAGAGCACAAGACTCTAAATCTCAGGGTCGTGG<br>GTTTGAGCCCTGTGTTGAGCA |
| 783 | CCGAATAGCTTAGTTGATGAAGCGTGAGACTCTAAATCTCAGGGTAGTGGGT<br>TCAAGCCCCACATTGGA |
| 784 | GCCTGGCTACCTCAGTTGGTAGAGCATGGGACTCTAAATCCCAGAGTCAGTG<br>GGTTCAAGCCTCACATTGAGTG |
| 785 | GCCCGGCTAGCTCAGTCGGTAGAGCATGAGACCCTAAATCTCAGGGTCGTGG<br>GTTCGAGCCCCACGTTGGGCG |
| 786 | GCCCGGCTAGCTCAGTCGGTAGAGCATGGGACTCTAAATCTCAGGGTCGTGG<br>GTTCGAGCCCCACGTTGGGCG |
| 787 | GCCCGGCTAGCTCAGTCGATAGAGCATGAGACTCTAAATCTCAGGGTCGTGG<br>GTTCGAGCCGCACGTTGGGCG |
| 788 | GCCCAGCTAGCTCAGTCGGTAGAGCATGAGACTCTAAATCTCAGGGTCATGG<br>GTTTGAGCCCCACGTTTGGTG |
| 789 | GCCTGGCTAGCTCAGTCGGCAAAGCATGAGACTCTAAATCTCAGGGTCGTGG<br>GCTCGAGCTCCATGTTGGGCG |
| 790 | GCCCGACTACCTCAGTCGGTGGAGCATGGGACTCTACATCCCAGGGTTGTGG<br>GTTCGAGCCCCACATTGGGCA |

TABLE 3-continued

| SEQ ID NO | Suppressor tRNA Sequence |
|---|---|
| 791 | CCCCGGCTGGCTCAGTCAGTAGATCATGAGACTCTAAATCTCAGGGTCGTGG<br>GTTCACGCCCCACACTGGGCG |
| 792 | GCGCTAGTCAGTAGAGCATGAGACTCTAAATCTCAGGGTCGTGGGTTCGAGC<br>CCCACATCGGGCG |
| 793 | GCCTGGATAGCTCAGTTGGTAGAGCATCAGACTCTAAATCTGAGGGTCCAGG<br>GTTCAAGTCCCTGTTCAGGCA |
| 794 | GCCAGGATAGTTCAGGTGGTAGAGCATCAGACTCTAAACCTGAGGGTTCAGG<br>GTTCAAGTCTCTGTTTGGGCG |
| 795 | ACCCAGATAGCTCAGTCAGTAGAGCATCAGACTCTAAATCTGAGGGTCCAAG<br>GTTCATGTCCCTTTTTGGGTG |
| 796 | ACCTGGGTAGCTTAGTTGGTAGAGCATTGGACTCTAAATTTGAGGGCCCAGG<br>TTTCAAGTCCCTGTTTGGGTG |
| 797 | GCCTGGGTAGCTCAGTCGGTAGAGCTATCAGACTCTAAGCCTGAGGATTCAG<br>GGTTCAATCCCTTGCTGGGGCG |
| 798 | GATAGCTCAGTTGATAGAGCATCAGACTCTAAATCTGAGGGTCCAGGGTTCA<br>TGTCCCTGTT |
| 799 | GTTGGGGTAACTCAGTTGGTAGAGTAGCAGACTCTACATCTGAGGGTCCAGG<br>GTTTAAGTCCATGTCCAGGCA |
| 800 | GCCTGGATAGCTCAGTTGGTAGAGCATCAGACTCTAAATCTGAGGGTCCAGG<br>GTTCAAGTCCCTGTTCAGGCG |
| 801 | GCCTGGATAGCTCAGTCGGTAGAGCATCAGACTCTAAATCTGAGGGTCCAGG<br>GTTCAAGTCCCTGTTCAGGCG |
| 802 | GCCCGGATAGCTCAGTCGGTAGAGCATCAGACTCTAAATCTGAGGGTCCGGG<br>GTTCAAGTCCCTGTTCGGGCG |
| 803 | GCCTGGGTAGCTCAGTCGGTAGAGCATCAGACTCTAAATCTGAGGGTCCAGG<br>GTTCAAGTCCCTGTCCAGGCG |
| 804 | GCCTGGATAGCTCAGTTGGTAGAACATCAGACTCTAAATCTGACGGTGCAGG<br>GTTCAAGTCCCTGTTCAGGCG |
| 805 | GCCCGGAGAGCTCAGTGGGTAGAGCATCAGACTCTAAATCTGAGGGTCCAGG<br>GTTCAAGTCCTCGTTCGGGCA |
| 806 | ACCTGGGTAGCTCAGTAGGTAGAACATCAGACTCTAAATCTGAGGGTCTAGG<br>GTTCAAGTCCCTGTCCAGGCG |
| 807 | GCCTGGATAGCTCCTTCGGTAGAGCATCATCAGACTCTAAATGTGAGGGTCC<br>AGGGTTCAAGTTCCTGTTTGGGCG |
| 808 | GGCAGAATGGTGCAGCGGTTCAGCACCCAGGCTCTTCAGCCAGCTGTTGCCT<br>GGGCTCAAATCCCAGCTCTGCCA |
| 809 | GGCTGTATAGCTCAGTGGTAGAGCATTTGACTTCAGAATCCTATACTCAGGG<br>GAAGGAGAACTGGGGGTTTCTCAGTGGGTCAAAGGACTTGTAGTGGTAAATC<br>AAAAGCAACTCTATAAGCTATGTAACAAACTTTAAAGTCATATGTAGCTGGG<br>TTCAAATCCTGTTTCTGCCA |
| 810 | GGCTGTATAGCTCAGTGGTAGAGCATTTGACTTCAGCTTTAAAGTCATATGT<br>AGCTGGGTTCAAATCCTGTTTCTGCCA |
| 811 | GGGGGCATAGCTCAGTGGTAGAGCATTTGACTTCAGATCAAGAGGTCCCTGG<br>TTCAAATCCAGGTGCCCCCT |
| 812 | GGGGGTATAGCTCAGGGGTAGAGCATTTGACTTCAGATCAAGAGGTCCCTGG<br>TTCAAATCCAGGTGCCCCCC |
| 813 | GGGGGTATAGCTTAGCGGTAGAGCATTTGACTTCAGATCAAGAGGTCCCCGG<br>TTCAAATCCGGGTGCCCCCT |
| 814 | GGGGGTATAGCTTAGGGGTAGAGCATTTGACTTCAGATCAAAAGGTCCCTGG<br>TTCAAATCCAGGTGCCCCTT |
| 815 | GGGGGTATAGCTCAGGGGTAGAGCATTTGACTTCAGATCAAGAGGTCCCCAG<br>TTCAAATCTGGGTGCCCCCT |

TABLE 3-continued

| SEQ ID NO | Suppressor tRNA Sequence |
|---|---|
| 816 | GGGGGTATAGCTCAGGGGTAGAGCATTTGACTTCAGATCAAGAAGTCCCCGG<br>TTCAAATCCGGGTGCCCCCT |
| 817 | GGGGGTATAGCTCAGGGGTAGAGCATTTGACTTCAGATCAAGAGGTCTCTGG<br>TTCAAATCCAGGTGCCCCCT |
| 818 | GGGGGTATAGCTCAGGGGTAGAGCACTTGACTTCAGATCAAGAAGTCCTTGG<br>TTCAAATCCAGGTGCCCCCT |
| 819 | GGGGATATAGCTCAGGGGTAGAGCATTTGACTTCAGATCAAGAGGTCCCCGG<br>TTCAAATCCGGGTGCCCCCC |
| 820 | GGGGGTATAGTTCAGGGGTAGAGCATTTGACTTCAGATCAAGAGGTCCCTGG<br>TTCAAATCCAGGTGCCCCCT |
| 821 | GGGGGTATAGCTCAGGGGTAGAGCATTTGACTTCAAATCAAGAGGTCCCTGA<br>TTCAAATCCAGGTGCCCCCT |
| 822 | GGGCGTATAGCTCAGGGGTAGAGCATTTGACTTCAGATCAAGAGGTCCCCAG<br>TTCAAATCTGGGTGCCCCCT |
| 823 | GGGGGTATAGCTCACAGGTAGAGCATTTGACTTCAGATCAAGAGGTCCCCGG<br>TTCAAATCTGGGTGCCCCCT |
| 824 | GGGCGTATAGCTCAGGGGTAGAGCATTTGACTTCAGATCAAGAGGTCCCCAG<br>TTCAAATCTGGGTGCCCA |
| 825 | GGGGGTATAGCTCACAGGTAGAGCATTTGACTTCAGATCAAGAGGTCCCCGG<br>TTCAAATCCGGTTACTCCCT |
| 826 | GGGGGTAGGGCTCAGGGATAGAGCATTTGACTTCAGATCAAGAGGTCCCCGG<br>TTCGAATCTAGGTGCCCCCT |
| 827 | GGTATATCTCAGGGGGCAGAGCATTTGACTTCAGATCAAGAGGTCCCCGGTT<br>GAAATCCGGGTGCT |
| 828 | GGGGGTATAGCTCAGGGGTAGAGCACTTGACTTCAGATCAAGAGGTCCCTGG<br>TTCAAATCCAGGTGCCCCCT |
| 829 | GGGGGTATAGCTCAGTGGTAGAGCATTTGACTTCAGATCAAGAGGTCCCTGG<br>TTCAAATCCGGGTGCCCCCT |
| 830 | GGGGGTATAGCTCAGTGGGTAGAGCATTTGACTTCAGATCAAGAGGTCCCCG<br>GTTCAAATCCGGGTGCCCCCT |
| 831 | GGGGGTGTAGCTCAGTGGTAGAGCATTTGACTTCAGATCAAGAGGTCCCTGG<br>TTCAAATCCAGGTGCCCCCT |
| 832 | GGGGGTATAGCTCAGGGGTAGAGCATTTGACTTCAGATCAAGAGGTCCCCGG<br>TTCAAATCCGGGTGCCCCCT |
| 833 | GGGGGTATAGCTCAGGGGTAGAGCATTTGACTTCAGATCAAGAGGTCCCTGG<br>TTCAAATCCAGGTGCCCCCT |
| 834 | GACCTCGTGGCGCAATGGTAGCGCGTCTGACTTCAGATCAGAAGGTTGCGTG<br>TTCAAATCACGTCGGGGTCA |
| 835 | GACCTCGTGGCACAATGGTAGCACGTCTGACTTCAGATCAGAAGGTTGCGTG<br>TTCAAATCACGTCGGGGTCA |
| 836 | GAAGCGGTGGCTCAATGGTAGAGCTTTCGACTTCAATTAAATCTTGGAAATT<br>CCACGGAATAAGATTGCAATCGAAGGGTTGCAGGTTCAATTCCTGTCCGTTT<br>CA |
| 837 | GAAGCGGTGGCTCAATGGTAGAGCTTTCGACTTCAAATCGAAGGGTTGCAGG<br>TTCAATTCCTGTCCGTTTCA |
| 838 | GGCCTCATGGTGCAACAGTAGTGTGTCTGACTTCAGATCAGAAGGTTGTATG<br>TTCAAATCACATAGGGGTCA |
| 839 | GACCTCGTGGTGAAATGGTAGCATGTTTGACTTCAAATCAGGAGGTTGTGTG<br>TTCAAGTCACATCAGGGTCA |
| 840 | GACCTTGTGGCGCAATGGTAGCATGTTTGACTTCAAATCAGGAGGTTGTGTG<br>TTCAAGTCACATCAGGGTCA |
| 841 | GACCTCGTGGCGCAACGGTAGCGCGTCTGACTTCAGATCAGAAGGCTGCGTG<br>TTCGAATCACGCCGGGGTCA |

TABLE 3-continued

| SEQ ID NO | Suppressor tRNA Sequence |
| --- | --- |
| 842 | GACCTTGTGGCTCAATGGTAGCGCATCTGACTTCAGATCAGGAGGTTGCACG<br>TTCAAATCATGCCGGGGTCA |
| 843 | GACCTTGTGGCGCAACGGTAGCGCGTCTGACTTCAGATCAGAAGGTTGCGTG<br>TTCAAATCACGTCGGGGTCA |
| 844 | GACCTCGTGGCGCAACGGTAGCGCGTCTGACTTCAGATCAGAAGGTTGCGTA<br>TTCAAATCACGTCGGGGTCA |
| 845 | GACCTCGTGGCGCAACGGCAGCGCGTCTGACTTCACATTAGAAGGTTGCGTG<br>TTCAAATCACGTCGGGGTCA |
| 846 | GACCTCATGGCGCAACGGTAGCGCGTCTGACTTCAGATCAGAAGGTTGCGTG<br>TTCAAATCACATCGGGGTCA |
| 847 | GACCTCGTGGTGCAACGGTAGCGCGTATGATTTCAGATCAGAAGGTTGCGTG<br>TTCAAATCACGTCGGGGTCA |
| 848 | GACCTCGTAGCGCAACGGTAGCGCGTCTGACTTCAGATCAGAAGGTTGCGTG<br>TTCAAATCACGTCGGGGTCA |
| 849 | AGGGGTATAGCTCAATTGGCAGAGCGTCGGTCTTCAAAACCGAAGGTTGTAG<br>GTTCGATTCCTACTGCCCCTGCCA |
| 850 | GACCTCATGGCGCAACGGTAGCGCGTCTGACTTCAGATCAGAAGGTTGCGTG<br>TTCAAATCACGTCGGGGTCA |
| 851 | GACCTCGTGGCGCAACGGTAGCGCGTCTAACTTCAGATCAGAAGGTTGCGTG<br>TTCAAATCACGTCGGGGTCA |
| 852 | ACGGGAGTAGCTCAGTTGGTAGAGCACCGGTCTTCAAAACCGGGTGTCGGGA<br>GTTCGAGCCTCTCCTCCCGTG |
| 853 | GACCTCGTGGCGCAACGGTAGCGCGTCTGACTTCAGATCAGAAGGTTGCATG<br>TTCAAATCACGTCGGGGTCA |
| 854 | GACTCCGTGGCGCAACGGTAGCGCGTCCGACTTCAGATCGGAAGGTTGCGTG<br>TTCAAATCACGTCGGGGTCA |
| 855 | GACTCCGTGGCGCAACGGTAGCGCGTCTGACTTCAGATCAGAAGGTTGCGTG<br>TTCAAATCACGTCGGGGTCA |
| 856 | GGCCTCGTGGCGCAACGGTAGCGCGTCTGACTCCAGATCAGAAGGTTGCGTG<br>TTCAAATCACGTCGGGGTCA |
| 857 | GGCCTCGTGGCGCAACGGTAGCACGTCTGACTCCAGATCAGAAGGTTGCGTG<br>TTCAAATCACGTCGGGGTCA |
| 858 | CGGCCTCGTGGCGCAACGGTAGCACGTCTGACTTCAGATCAGAAGGTTGCGT<br>GTTCAAATCACGTCGGGGTCA |
| 859 | GGCCTCGTCGCGCAACGGTAGCGCGTCTGACTCCAGATCAGAAGGTTGCGTG<br>TTCAAATCACGTCGGGGTCA |
| 860 | GGCCTCGTCGCGCAACGGTAGCGCGTCTGACTTCAGATCAGAAGGTTGCGTG<br>TTCAAATCACGTCGGGGTCA |
| 861 | GGCCTCGTCGCGCAACGGTAGCACGTCTGACTCCAGATCAGAAGGTTGCGTG<br>TTCAAATCACGTCGGGGTCA |
| 862 | GGCCTCGTCGCGCAACGGTAGCACGTCTGACTTCAGATCAGAAGGTTGCGTG<br>TTCAAATCACGTCGGGGTCA |

In certain embodiments, the tRNA comprises, consists essentially of, or consists of a nucleotide sequence shown in any one of TABLEs 8-10. In certain embodiments, the tRNA comprises, consists essentially of, or consists of a nucleotide sequence having 80%, 85%, 86%, 87%, 88%, 89%, 90%, 91%, 92%, 93%, 94%, 95%, 96%, 97%, 98%, or 99% sequence identity to a nucleotide sequence in any one of TABLEs 8-10.

In certain embodiments, the tRNA comprises, consists essentially of, or consists of the nucleotide sequence of SEQ ID NO: 6. In certain embodiments, the tRNA comprises, consists essentially of, or consists of the nucleotide sequence of SEQ ID NO: 7. In certain embodiments, the tRNA comprises, consists essentially of, or consists of the nucleotide sequence of SEQ ID NO: 8. In certain embodiments, the tRNA comprises, consists essentially of, or consists of the nucleotide sequence of SEQ ID NO: 9. In certain embodiments, the tRNA comprises, consists essentially of, or consists of the nucleotide sequence of SEQ ID NO: 11. In certain embodiments, the tRNA comprises, consists essentially of, or consists of the nucleotide sequence of SEQ ID NO: 16. In certain embodiments, the tRNA comprises, consists essentially of, or consists of the nucleotide sequence of SEQ ID NO: 17. In certain embodiments, the tRNA comprises, consists essentially of, or consists of the nucleotide sequence of SEQ ID NO: 18. In certain embodiments, the tRNA comprises, consists essentially of, or consists of the nucleotide sequence of SEQ ID NO: 19. In certain embodiments, the tRNA comprises, consists essentially of, or consists of the nucleotide sequence of SEQ ID NO: 20. In certain embodiments, the tRNA comprises, consists essentially of, or consists of the nucleotide sequence of SEQ ID NO: 21. In certain embodiments, the tRNA comprises, consists essentially of, or consists of the nucleotide sequence of SEQ ID NO: 22. In certain embodiments, the tRNA comprises, consists essentially of, or consists of the nucleotide sequence of SEQ ID NO: 35. In certain embodiments, the tRNA comprises, consists essentially of, or consists of the nucleotide sequence of SEQ ID NO: 36. In certain embodiments, the tRNA comprises, consists essentially of, or consists of the nucleotide sequence of SEQ ID NO: 37. In certain embodiments, the tRNA comprises, consists essentially of, or consists of the nucleotide sequence of SEQ ID NO: 38. In certain embodiments, the tRNA comprises, consists essentially of, or consists of the nucleotide sequence of SEQ ID NO: 39. In certain embodiments, the tRNA comprises, consists essentially of, or consists of the nucleotide sequence of SEQ ID NO: 40. In certain embodiments, the tRNA comprises, consists essentially of, or consists of the nucleotide sequence of SEQ ID NO: 44. In certain embodiments, the tRNA comprises, consists essentially of, or consists of the nucleotide sequence of SEQ ID NO: 45. In certain embodiments, the tRNA comprises, consists essentially of, or consists of the nucleotide sequence of SEQ ID NO: 178. In certain embodiments, the tRNA comprises, consists essentially of, or consists of the nucleotide sequence of SEQ ID NO: 179. In certain embodiments, the tRNA comprises, consists essentially of, or consists of the nucleotide sequence of SEQ ID NO: 180. In certain embodiments, the tRNA comprises, consists essentially of, or consists of the nucleotide sequence of SEQ ID NO: 181. In certain embodiments, the tRNA comprises, consists essentially of, or consists of the nucleotide sequence of SEQ ID NO: 182. In certain embodiments, the tRNA comprises, consists essentially of, or consists of the nucleotide sequence of SEQ ID NO: 186. In certain embodiments, the tRNA comprises, consists essentially of, or consists of the nucleotide sequence of SEQ ID NO: 187.

In certain embodiments, the tRNA may comprise one or more mutations (e.g., nucleotide substitutions, deletions, or insertions) relative to a reference tRNA sequence (e.g., a tRNA disclosed herein). In certain embodiments, the tRNA may comprise, consist, or consist essentially of, a single mutation, or a combination of 2, 3, 4, 5, 6, 7, 8, 9, 10, 11, 12, 13, 14, 15 or more than 15 mutations. It is contemplated that the tRNA may comprise, consist, or consist essentially 1-15, 1-10, 1-7, 1-6, 1-5, 1-4, 1-3, 1-2, 2-15, 2-10, 2-7, 2-6, 2-5, 2-4, 2-3, 3-15, 3-10, 3-7, 3-6, 3-5, or 3-4 mutations.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul (1993) J. Mol. Evol. 36, 290-300; Altschul et al., (1997) Nucleic Acids Res. 25:3389-3402) are tailored for sequence similarity searching. For a discussion of basic issues in searching sequence databases see Altschul et al. (1994) Nature Genetics 6:119-129. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=–3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

It is contemplated that a tRNA may comprise on or more modifications. Exemplary modified tRNAs include: acylated tRNA; alkylated tRNA; a tRNA containing one or more bases other than adenine, cytosine, guanine, or uracil; a tRNA covalently modified by the attachment of a specific ligand or antigenic, fluorescent, affinity, reactive, spectral, or other probe moiety; a tRNA containing one or more ribose moieties that are methylated or otherwise modified; aa-tRNAs that are aminoacylated with an amino acid other than the 20 natural amino acids, including non-natural amino acids that function as a carrier for reagents, specific ligands, or as an antigenic, fluorescent, reactive, affinity, spectral, or other probe; or any combination of these compositions. Exemplary modified tRNA molecules are described in Soll et al. (1995) "tRNA: Structure, Biosynthesis, and Function," ASM Press; El Yacoubi et al. (2012) Annu. Rev. Genet. 46:69-95; Grosjean et al. (1998) "Modification and Editing of RNA." ASM Press; Hendrickson et al. (2004) Annu. Rev. Biochem. 73:147-176, 2004; Ibba et al. (2000) Annu. Rev. Biochem. 69:617-650; Johnson et al. (1995) Cold Spring Harbor Symp. Quant. Biol. 60:71-82; Johnson et al. (1982) J. Mol. Biol. 156:113-140; Crowley et al. (1994) Cell 78:61-71; Beier et al. (2001) Nucleic Acids Res. 29:4767-4782; Tones et al. (2014) Trends Mol. Med. 20:306-314; Bjork et al. (1987) Annu. Rev. Biochem. 56:263-287; Schaffrath et al. (2017) RNA Biol. 14(9):1209-1222; and Johansson et al. (2008) Mol. Cell. Biol. 28(10):3301-12.

Figure 1:
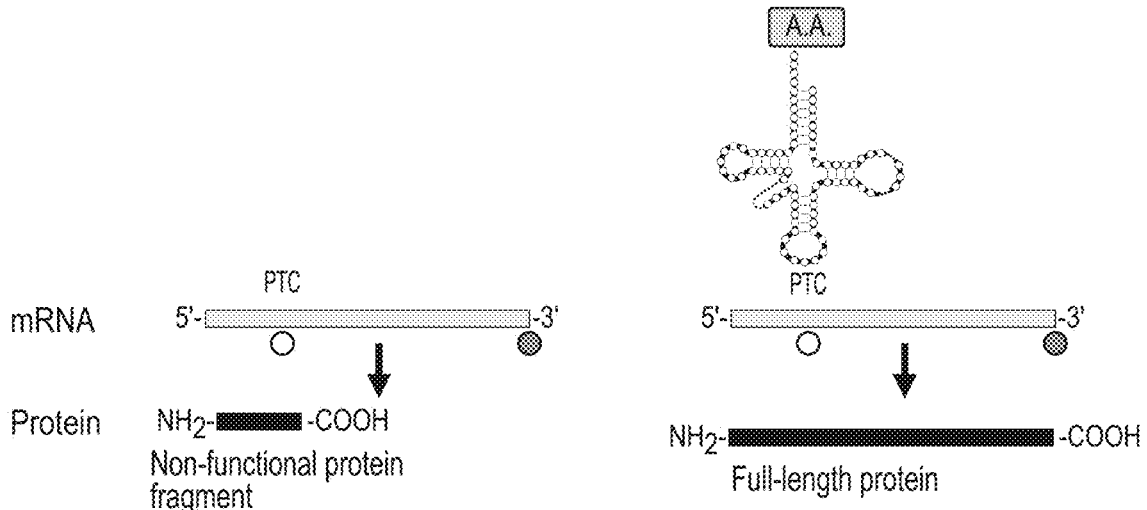
FIG. 1 is a schematic representation of a transcript (e.g., an SCN1A transcript) containing a premature termination codon (PTC) which leads to a truncated protein product (e.g., a protein product in a subject with Dravet syndrome). Native termination codons are indicated as shaded circles, and premature termination codons are indicated as unshaded circles. Expression of a suppressor tRNA (e.g., an anticodon modified arginine tRNA) charged with its cognate amino acid (A.A.) allows read-through of the PTC and facilitates expression of the full-length protein.
Figure 2A:
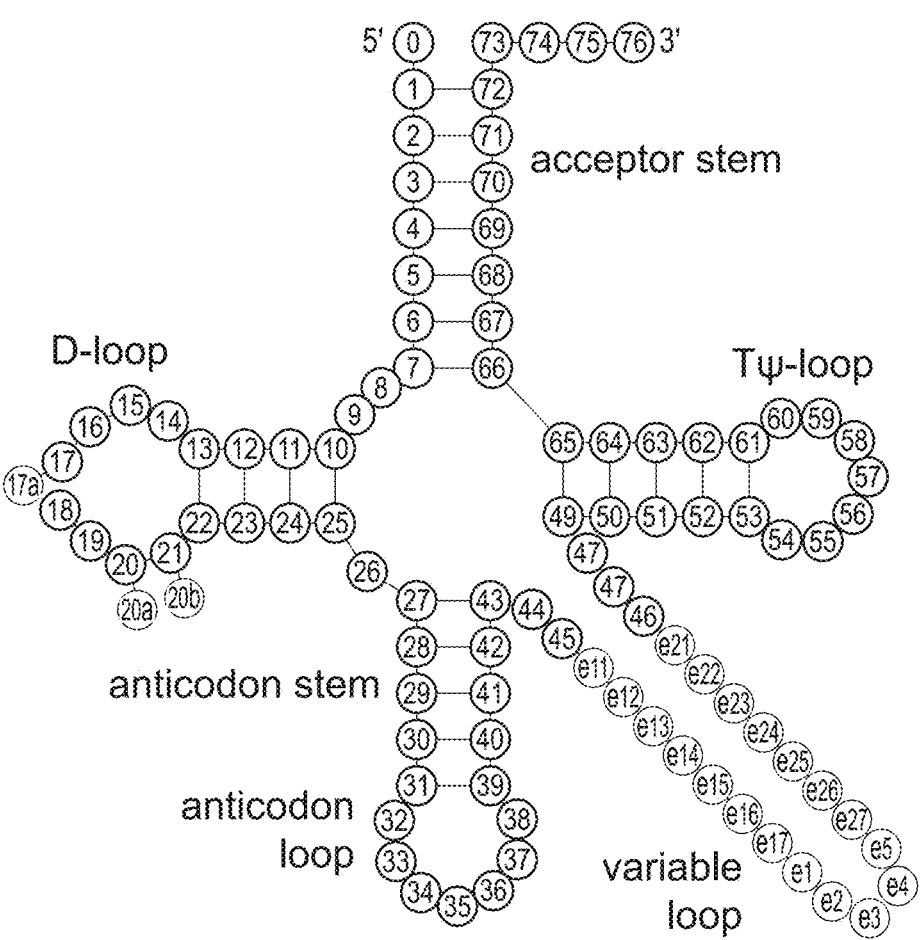
FIG. 2A is a consensus tRNA secondary structure. The numbering of the residues is based on the tRNA numbering system described in Steinberg et al. (1993) NUCLEIC ACIDS RES. 21:3011-15.

In certain embodiments, a tRNA comprises a naturally occurring nucleotide modification. Naturally occurring tRNAs contain a wide variety of post-transcriptionally modified nucleotides, which are described, for example, in Machnicka et al. (2014) RNA BIOLOGY 11(12): 1619-1629, and include one or more of the residues as shown in FIG. 2B. In certain embodiments, the tRNA comprises one or more of the residues selected from the group consisting of: 2'-O-methylguanosine or G at position 0; pseudouridine or U at position 1; 2'-O-methyladenosine, A, 2'-O-methyluridine, U, 2'-O-methylcytidine, C, 2'-O-methylguanosine, or G at position 4; N2-methylguanosine or G at position 6; N2-methylguanosine or G at position 7; 1-methyladenosine, A, 1-methylguanosine, G, or a modified G at position 9; N2-methylguanosine or G at position 10; N4-acetylcytidine or C at position 12; pseudouridine, U, 2'-O-methylcytidine, or C at position 13; 1-methyladenosine, A, or a modified A at position 14; dihydrouridine (D) or U at position 16; D or U at position 17; 2'-O-methylguanosine or G at position 18; 3-(3-amino-3-carboxypropyl)uridine, D, or U at position 20; 3-(3-amino-3-carboxypropyl)uridine, D, pseudouridine, U, or a modified U at position 20a; D, pseudouridine, or U at position 20b; pseudouridine or U at position 25; pseudouridine, U, N2,N2-dimethylguanosine, N2-methylguanosine, G, or a modified G at position 26; pseudouridine, U, N2,N2-dimethylguanosine, or G at position 27; pseudouridine or U at position 28; pseudouridine or U at position 30; pseudouridine or U at position 31; 2'-O-methylpseudouridine, 2'-O-methyluridine, pseudouridine, U, 2'-O-methylcytidine, 3-methylcytidine, C, or a modified C at position 32; inosine, A, 2-thiouridine, 2'-O-methyluridine, 5-(carboxyhydroxymethyl)uridine methyl ester, 5-carbamoylmethyluridine, 5-carboxymethylaminomethyl-2'-O-methyluridine, 5-methoxycarbonylmethyl-2-thiouridine, 5-methoxycarbonylmethyluridine, pseudouridine, U, a modified U, 2'-O-methylcytidine, 5-formyl-2'-O-methylcytidine, 5-methylcytidine, C, a modified C, queuosine, mannosyl-queuosine, galactosyl-queuosine, 2'-O-methylguanosine, or G at position 34; pseudouridine or U at position 35; pseudouridine, U, or a modified U at position 36; 1-methylinosine, 2-methylthio-N6-threonylcarbamoyladenosine, N6-isopentenyladenosine, N6-methyl-N6-threonylcarbamoyladenosine, N6-threonylcarbamoyladenosine, A, a modified A, 1-methylguanosine, peroxywybutosine, wybutosine, G, or a modified G at position 37; pseudouridine, U, 5-methylcytidine, C, or a modified C at position 38; 1-methylpseudouridine, 2'-O-methylpseudouridine, 2'-O-methyluridine, pseudouridine, U, 2'-O-methylguanosine, or G at position 39; pseudouridine, U, 5-methylcytidine, or C at position 40; 2'-O-methyluridine, U, or a modified U at position 44; pseudouridine or U at position e 11; pseudouridine or U at position e12; pseudouridine or U at position e14; 3-methylcytidine or C at position e2; 7-methylguanosine or G at position 46; D, U, or a modified U at position 47; D, U, 5-methylcytidine, C, or a modified C at position 48; A, a modified A, 5-methylcytidine, C, or a modified C at position 49; pseudouridine, U, 5-methylcytidine, or C at position 50; 5,2'-O-dimethyluridine, 5-methyluridine, pseudouridine, or U at position 54; pseudouridine or U at position 55; 1-methyladenosine, A, or a modified A at position 58; 2'-O-ribosyladenosine (phosphate), A, 2'-O-ribosylguanosine (phosphate), G, or a modified G at position 64; pseudouridine or U at position 65; pseudouridine, U, N2-methylguanosine, or G at position 67; pseudouridine or U at position 68; and, pseudouridine, U, 5-methylcytidine, or C at position 72. A, C, G, and U, refer to unmodified adenine, cytosine, guanine, and uracil, respectively. The numbering of the residues is based on the tRNA numbering system described in Steinberg et al., (1993) NUCLEIC ACIDS RES. 21:3011-15.

In certain embodiments, the tRNA comprises one or more nucleotide modifications selected from 5-methyl uridine, 5-carbamoylmethyluridine, 5-carbamoyl-methyl-2-O-methyluridine, 5-methoxy-carbonylmethyluridine, 5-methoxycarbonylmethyl-2-thiouridine, pseudouridine, dihydrouridine, 1-methyladenosine, and inosine.

II. Methods of Making tRNAs

It is contemplated the tRNA molecules (e.g., suppressor tRNAs) useful in the practice of the invention can be produced by methods known in the art, including extracellular production by synthetic chemical methods, intracellular production by recombinant DNA methods, or purification from natural sources.

For example, DNA molecules encoding tRNAs can be synthesized chemically or by recombinant DNA methodologies. For example, the sequences of the tRNAs can be synthesized or cloned from libraries by conventional hybridization techniques or polymerase chain reaction (PCR) techniques, using the appropriate synthetic nucleic acid primers. The resulting DNA molecules encoding the tRNAs can be ligated to other appropriate nucleotide sequences, including, for example, expression control sequences to produce conventional gene expression constructs (i.e., expression vectors) encoding the tRNAs. Production of defined gene constructs is within routine skill in the art. Nucleic acids encoding desired tRNAs can be incorporated (ligated) into expression vectors, such as the expression vectors described in the following section, which can be introduced into host cells through conventional transfection or transformation techniques. Exemplary host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the tRNAs. Specific expression and purification conditions will vary depending upon the expression system employed.

Alternatively, tRNAs can be chemically synthesized or purified from natural sources by methods known in art. When a tRNA is aminoacylated prior to introduction into the cell or administration to the subject, the tRNA may be aminoacylated with a desired amino acid by any method known in the art, including chemical or enzymatic aminoacylation.

III. Expression Vectors

The tRNAs of interest may be expressed in a cell of interest by incorporating a gene encoding a tRNA of interest into an appropriate expression vector. As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide of interest.

In certain embodiments, the expression vector is a viral vector. The term "virus" is used herein to refer to an obligate intracellular parasite having no protein-synthesizing or energy-generating mechanism. Exemplary viral vectors include retroviral vectors (e.g., lentiviral vectors), adenoviral vectors, adeno-associated viral vectors, herpesviruses vectors, epstein-barr virus (EBV) vectors, polyomavirus vectors (e.g., simian vacuolating virus 40 (SV40) vectors), poxvirus vectors, and pseudotype virus vectors.

The virus may be a RNA virus (having a genome that is composed of RNA) or a DNA virus (having a genome composed of DNA). In certain embodiments, the viral vector is a DNA virus vector. Exemplary DNA viruses include parvoviruses (e.g., adeno-associated viruses), adenoviruses, asfarviruses, herpesviruses (e.g., herpes simplex virus 1 and 2 (HSV-1 and HSV-2), epstein-barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). In certain embodiments, the viral vector is a RNA virus vector. Exemplary RNA viruses include bunyaviruses (e.g., hantavirus), coronaviruses, flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses.

In certain embodiments, the expression vector comprises a regulatory sequence or promoter operably linked to the nucleotide sequence encoding the tRNA. The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

tRNA genes preferably have strong promoters that are active in a variety of cell types. The promoters for eukaryotic tRNA genes typically are present within the structural sequences encoding the tRNA molecule itself. Although there are elements which regulate transcriptional activity within the 5' upstream region, the length of an active transcriptional unit may be considerably less than 500 base pairs.

Additional exemplary promoters which may be employed include, but are not limited to, the retroviral LTR, the SV40 promoter, the human cytomegalovirus (CMV) promoter, the U6 promoter, or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

In certain embodiments, an expression vector comprises a tRNA coding sequence that encodes a tRNA that comprises, consists essentially of, or consists of a nucleotide sequence shown in TABLE 2 or TABLE 3. In certain embodiments, an expression vector comprises a tRNA coding sequence that encodes a tRNA that comprises, consists essentially of, or consists of a nucleotide sequence having 80%, 85%, 86%, 87%, 88%, 89%, 90%, 91%, 92%, 93%, 94%, 95%, 96%, 97%, 98%, or 99% to a nucleotide sequence shown in TABLE 2 or TABLE 3.

In certain embodiments, in addition to a tRNA coding sequence, the expression vector comprises a nucleotide sequence corresponding to a genomic DNA sequence flanking a wild-type tRNA gene (i.e., a DNA sequence from the same genome as a wild-type tRNA gene and which is 5' or 3' to the wild-type tRNA gene in the genome, e.g., immediately 5' or 3' to the wild-type tRNA gene in the genome). In certain embodiments, in addition to a tRNA coding sequence, the expression vector comprises a nucleotide sequence corresponding to an exogenous promoter.

In certain embodiments, the expression vector comprises a nucleotide sequence shown in TABLE 4. In certain embodiments, the expression vector comprises a nucleotide sequence having 80%, 85%, 86%, 87%, 88%, 89%, 90%, 91%, 92%, 93%, 94%, 95%, 96%, 97%, 98%, or 99% sequence identity to a nucleotide sequence shown in TABLE 4. In certain embodiments, in the expression vector, the nucleotide sequence set forth in TABLE 4 is operably linked to the nucleotide sequence encoding the tRNA. In certain embodiments, in the expression vector, the nucleotide sequence set forth in TABLE 4 is 5' or 3' (e.g., immediately 5' or immediately 3) to the nucleotide sequence encoding the tRNA. In certain embodiments, the expression vector comprises a nucleotide sequence selected from SEQ ID NOs: 869-888, or a nucleotide sequence having 80%, 85%, 86%, 87%, 88%, 89%, 90%, 91%, 92%, 93%, 94%, 95%, 96%, 97%, 98%, or 99% sequence identity to a sequence selected from SEQ ID NOs: 869-888.

In certain embodiments, the expression vector is an expression vector described in Example 8 or Example 9 herein.

TABLE 4

| SEQ ID NO | Location (Relative to tRNA) | Nucleotide Sequence |
|---|---|---|
| 26 | 5' | CTACCCAGAGGCAGGCGGGAGACTCCCCCGAGCGTCCAATAAGAGC GCCGCCAATGGAGCCGCCCGCCCGCGGGGGTGCAGAGGGACTTCCG GGTGAGGTCCTCCGCTACTTCCCTCCCCACGGAAAAGATAGACCAG TCTGACGCGAGCCTGAAGGCGGCTACACGCTTTAAGCTAAGTAAAG GCACCTTCTCGCTGGC |

TABLE 4-continued

| SEQ ID NO | Location (Relative to tRNA) | Nucleotide Sequence |
|---|---|---|
| 27 | 3' | ACTTGTATGTTGTTTTTATCTGTCAGTTTGTTAATCCCAAGATTCC CTTTGGAAATAAAGCGAAATTGACCGTAGTGGTTATGACCAACTTC TAGTCTAAACTTAATTCTTGGAACTCAAGGATCTGAGCAAACAACT GTCAGGGTGACACATTGCTTAAACGGTGACAGCGGTCGAGAGCCTT GTCCCGGATGGAGAGT |
| 32 | 3' | ACTTGTATGTTGTTTTTATCTGTCAGTTTGTTAATCCCAAGATTCC CTTTGGAAATAAAGCGAAATTGACCGTAGTGGTTATGACCAACTTC TAGTCTAAACTT |
| 33 | 5' | GAGGGCCTATTTCCCATGATTCCTTCATATTTGCATATACGATACA AGGCTGTTAGAGAGATAATTAGAATTAATTTGACTGTAAACACAAA GATATTAGTACAAAATACGTGACGTAGAAAGTAATAATTTCTTGGG TAGTTTGCAGTTTTAAAATTATGTTTTAAAATGGACTATCATATGC TTACCGTAACTTGAAAGTATTTCGATTTCTTGGCTTTATATATCTT GTGGAAAGGACGGGCGGAGGAAGGCACCTTCTCGCTGGC |
| 34 | 3' | ACTTGTATGTTGTTTTTATCTGTCAGTTTGTTAATCCCAAGATTCC |
| 173 | 5' | GATCACCGGAAGAGGTGACAGACACCTCGGGGCCCATGAACGTTTG GAATTCGTAAGGACATGAGAATCTCGGTGGTTCCGTGTCTGCCCGC CATCGCGGCCACCGGCCACGGGCCCAAGCCAAGTGTAGCGAAGCTT AGAAAAGGTTGCCCAACGTCATGTGGCTTGAGAAGGCTGCCGGGCG CCTTAAGCCGCCAGCA |
| 174 | 3' | CACTGAACCTTTTTTTGGCCTTAGAATCCCTGTTTTGGGGCCTGCA GGAAGTAGCAACCAACCCGAGCCTCCGCAGGGAATGCACTGACCTG TAGAATGGACGTTCAGCTTCCCTCCCTGTGTCTCAACACGATTACA TTTCAGGAACAGCCTGGGCTGGGAGGCACTGCGCACGCGCGCCGAG TCGGGCGGAAAAATAA |
| 869 | 5' | CCAAAACATCTTTTACTGTAGTATCTACTTACCATACTACCCAAGA ATGGCACACTGCTCACATCTTCAAAAGCTTAAACCAAGAGCACTAC ACAGGTGC |
| 870 | 5' | TGTGTGTCGGGGCCGGTACCCTGCTTCCGGTTCCCGCACGCATTCC CGGATTGCAGTGCGGACCCCTTCTGTAAGCGCGCGATAAAGCGCGG TTTTGGAA |
| 871 | 5' | TCATGTCATATAAGTAGAACCATACAATATATATATAAAATCCAGG TTAATAGCCAATCTTACAACATTTCTCATATTTTTTGCAGTTGCTA AGCCATGG |
| 872 | 5' | ACATTACAATACATATCAACATATCACCATAATTAAATTGCAAGTC TTCGTCAAAAGCAAGCCTTAAAGGAGTATCCCAAAAACACATTTTC CCCAGAAG |
| 873 | 5' | AGACCTTTAGAGCGTGGTTAAACCCATATGTTGGGATTTATGCTGC TTTTATGGTAGCAATACCCTATATTAAGATTTGAAGTAGACCCGGA AAGTTAGT |
| 874 | 5' | GTTCATGAAAGAATAAATAAATGTTTAAAAAAAAAAAAAAACTGAGG TAAATTTCTATATTCTTTCATAAAAGCAGTTTAAAGACGAACGTTT TTCGAGGT |
| 875 | 5' | GCTGGGTCTCGGTGACACTGACGACGGGAGGCGCGGTCGGAAGAGC GCGGGGCCGTCGCCTCTGGCTTAACATAGCAGATGCGCTGAGACTC CAACAGGT |
| 876 | 5' | CAGTGGCGGCGAAAACTCTCTGCGTTCTGGAGGGAGGGTGCGGGCA GGAGGAGGTAGAGGATGCCTTGTAAGCGGAGCAAAAACAAGGTTCA ACGTCTGC |
| 877 | 5' | CAAATCACTTGCCTCTCGGCGCGAGACCGCGATGCGCGGGGGCGGG AGCGTGATGATGGCATCGCGTAAGGAGAGGGTGTGAGAAGCCGGAT CCTGTGGT |
| 878 | 5' | CCCTGTGTCCGAAGAGGTCTGCGTTGCGACTTACGTGGTAGTGCTT GGAAGGTGCGGAGTAGATGAGAGATAAGTGAATGTGGACAAACCTG TCACGTAG |
| 879 | 5' | GAGCGGAGCTCAGAGGGTGCGCGCTCCGCCCTTTCGCGGGCCTGGC ATGAGCGCAGTGGTTGTTACACTAAAGTGTCTCCGCCTGTCGAATA TTCTCGTG |

TABLE 4-continued

| SEQ ID NO | Location (Relative to tRNA) | Nucleotide Sequence |
|---|---|---|
| 880 | 5' | GTGTCACTGGTTTCAAATCAACCTCAATTTTTTTGGAGACGTGAGT GCTGAGCATTTTTTCTTCAGTGAAGTGACTTGGCAGCCAAAATCGC CAACGCCC |
| 881 | 5' | TCCTGGCATGTCCCGCCCAAGTCCCTTAGCCCCGCTCCCCAACCCT GCCCCATTCCCACTCTAGTACCCGTAAGCTACAAGACGCCGCCGTT CGTCGGGT |
| 882 | 5' | TGCTCAGTCGTCCTGCCGGGCGGGCCCTGAGGTTGCAAGGGACGGA GGAAGTTTCGTGCGTGCGCCCTTCCTATAGCGCCCAGTAGAACTGA CAGTACCT |
| 883 | 5' | TCCTCGGATTACGCATGCTCAGTGCAATCTTCGGTTGCCTGGACTA GCGCTCCGGTTTTTCTGTGCTGAACCTCAGGGGACGCCGACACACG TACACGTC |
| 884 | 5' | GATAATTTCCTGAAAGAAAAGATCAATTCGATGTTACCAAATCTGG GATATCCAGAAAAATTTTCTTCTTCTCCTAGGAGAAAAACTATCAA ATGTCAGG |
| 885 | 5' | TCTCTCACGGCAAACTGTTGCAGACTGTAGAGACGCTATGCCAAGA ATCTTTTACTTAAAAGCAGGAATAGATTCAATAGGCAACTTCACTG CACATGTA |
| 886 | 5' | CAACCTCCCCTTCTCAAGGAGCAGGTGGATTGGTCCCGAGCTAGCT GGTGGGCGGAGGTGACGTTTTTATAAGTTGCTCAAGAGACGGTAAC AACCGACG |
| 887 | 5' | GTGGAACTTCCACTGAATTACTCTTTTCGCATGTAAGATCACTGAA CCGTGATAATCATTGATCCTATTTGTAGAACTGTATGAAACAGTTC CCTAAGGA |
| 888 | 5' | TCGCTCAACAGGCGGCCAGGGTGCGAGCAGTGAAGCTGCGGCACGC CGGAGCGTTTAATGGCCATCAAATTGGCCTCTCTAGGAGGTAGCTG CAGCCGGA |
| 895 | 5' | AAAGGCACCTTCTCGCTGGC |
| 896 | 3' | ACTTGTATGTTGTTTTT |
| 897 | 5' | TCTCGCTGGC |
| 900 | 5' | AGCGCTCCGGTTTTTCTGTGCTGAACCTCAGGGGACGCCGACACAC GTACACGTC |

Adeno-Associated Virus (AAV) Vectors

In certain embodiments, an expression vector is an adeno-associated virus (AAV) vector. AAV is a small, nonenveloped icosahedral virus of the genus Dependoparvovirus and family Parvovirus. AAV has a single-stranded linear DNA genome of approximately 4.7 kb. AAV is capable of infecting both dividing and quiescent cells of several tissue types, with different AAV serotypes exhibiting different tissue tropism.

AAV includes numerous serologically distinguishable types including serotypes AAV-1 to AAV-12, as well as more than 100 serotypes from nonhuman primates (See, e.g., Srivastava (2008) J. CELL BIOCHEM., 105(1): 17-24, and Gao et al. (2004) J. VIROL., 78(12), 6381-6388). The serotype of the AAV vector used in the present invention can be selected by a skilled person in the art based on the efficiency of delivery, tissue tropism, and immunogenicity. For example, AAV-1, AAV-2, AAV-4, AAV-5, AAV-8, and AAV-9 can be used for delivery to the central nervous system; AAV-1, AAV-8, and AAV-9 can be used for delivery to the heart; AAV-2 can be used for delivery to the kidney; AAV-7, AAV-8, and AAV-9 can be used for delivery to the liver; AAV-4, AAV-5, AAV-6, AAV-9 can be used for delivery to the lung, AAV-8 can be used for delivery to the pancreas, AAV-2, AAV-5, and AAV-8 can be used for delivery to the photoreceptor cells; AAV-1, AAV-2, AAV-4, AAV-5, and AAV-8 can be used for delivery to the retinal pigment epithelium; AAV-1, AAV-6, AAV-7, AAV-8, and AAV-9 can be used for delivery to the skeletal muscle. In certain embodiments, the AAV capsid protein comprises a sequence as disclosed in U.S. Pat. No. 7,198,951, such as, but not limited to, AAV-9 (SEQ ID NOs: 1-3 of U.S. Pat. No. 7,198,951), AAV-2 (SEQ ID NO: 4 of U.S. Pat. No. 7,198,951), AAV-1 (SEQ ID NO: 5 of U.S. Pat. No. 7,198,951), AAV-3 (SEQ ID NO: 6 of U.S. Pat. No. 7,198,951), and AAV-8 (SEQ ID NO: 7 of U.S. Pat. No. 7,198,951). AAV serotypes identified from rhesus monkeys, e.g., rh.8, rh.10, rh.39, rh.43, and rh.74, are also contemplated in the instant invention. Besides the natural AAV serotypes, modified AAV capsids have been developed for improving efficiency of delivery, tissue tropism, and immunogenicity. Exemplary natural and modified AAV capsids are disclosed in U.S. Pat. Nos. 7,906,111, 9,493,788, and 7,198,951, and PCT Publication No. WO2017189964A2.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous gene of interest. Accordingly, in certain embodiments, the AAV vector comprises a genome comprising an expression cassette for an exogenous gene flanked by a 5' ITR and a 3' ITR. The ITRs may be derived from the same serotype as the capsid or a derivative thereof. Alternatively, the ITRs may be of a different serotype from the capsid, thereby generating a pseudotyped AAV. In certain embodiments, the ITRs are derived from AAV-2. In certain embodiments, the ITRs are derived from AAV-5. At least one of the ITRs may be modified to mutate or delete the terminal resolution site, thereby allowing production of a self-complementary AAV vector.

The rep and cap proteins can be provided in trans, for example, on a plasmid, to produce an AAV vector. A host cell line permissive of AAV replication must express the rep and cap genes, the ITR-flanked expression cassette, and helper functions provided by a helper virus, for example adenoviral genes Ela, Elb55K, E2a, E4orf6, and VA (Weitzman et al., Adeno-associated virus biology. Adeno-Associated Virus: Methods and Protocols, pp. 1-23, 2011). Methods for generating and purifying AAV vectors have been described in detail (See e.g., Mueller et al., (2012) CURRENT PROTOCOLS IN MICROBIOLOGY, 14D.1.1-14D.1.21, Production and Discovery of Novel Recombinant Adeno-Associated Viral Vectors). Numerous cell types are suitable for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, and 8,163,543, U.S. Patent Publication No. 20020081721, and PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the present invention. Similarly, it is contemplated that any adenoviral type may be used, and a person of skill in the art will be able to identify AAV and adenoviral types suitable for the production of their desired recombinant AAV vector (rAAV). AAV particles may be purified, for example by affinity chromatography, iodixonal gradient, or CsCl gradient.

AAV vectors may have single-stranded genomes that are 4.7 kb in size, or are larger or smaller than 4.7 kb, including oversized genomes that are as large as 5.2 kb, or as small as 3.0 kb. Thus, where the exogenous gene of interest to be expressed from the AAV vector is small, the AAV genome may comprise a stuffer sequence. Further, vector genomes may be substantially self-complementary thereby allowing for rapid expression in the cell. In certain embodiments, the genome of a self-complementary AAV vector comprises from 5' to 3': a 5' ITR; a first nucleic acid sequence comprising a promoter and/or enhancer operably linked to a coding sequence of a gene of interest; a modified ITR that does not have a functional terminal resolution site; a second nucleic acid sequence complementary or substantially complementary to the first nucleic acid sequence; and a 3' ITR. AAV vectors containing genomes of all types are suitable for use in the method of the present invention.

Non-limiting examples of AAV vectors include pAAV-MCS (Agilent Technologies), pAAVK-EF1α-MCS (System Bio Catalog #AAV502A-1), pAAVK-EF1α-MCS1-CMV-MCS2 (System Bio Catalog #AAV503A-1), pAAV-Zs-Greenl (Clontech Catalog #6231), pAAV-MCS2 (Addgene Plasmid #46954), AAV-Stuffer (Addgene Plasmid #106248), pAAVscCBPIGpluc (Addgene Plasmid #35645), AAVSl-_Puro_PGK1_3×FLAG_Twin_Strep (Addgene Plasmid #68375), pAAV-RAM-d2TTA::TRE-MCS-WPRE-pA (Addgene Plasmid #63931), pAAV-UbC (Addgene Plasmid #62806), pAAVS1-P-MCS (Addgene Plasmid #80488), pAAV-Gateway (Addgene Plasmid #32671), pAAV-Puro-_siKD (Addgene Plasmid #86695), pAAVS1-Nst-MCS (Addgene Plasmid #80487), pAAVS1-Nst-CAG-DEST (Addgene Plasmid #80489), pAAVS1-P-CAG-DEST (Addgene Plasmid #80490), pAAVf-EnhCB-lacZnls (Addgene Plasmid #35642), and pAAVS1-shRNA (Addgene Plasmid #82697). These vectors can be modified to be suitable for therapeutic use. For example, an exogenous gene of interest can be inserted in a multiple cloning site, and a selection marker (e.g., puro or a gene encoding a fluorescent protein) can be deleted or replaced with another (same or different) exogenous gene of interest. Further examples of AAV vectors are disclosed in U.S. Pat. Nos. 5,871,982, 6,270,996, 7,238,526, 6,943,019, 6,953,690, 9,150,882, and 8,298,818, U.S. Patent Publication No. 2009/0087413, and PCT Publication Nos. WO2017075335A1, WO2017075338A2, and WO2017201258A1.

In certain embodiments, the expression vector is an AAV vector capable of targeting the nervous system, e.g., the central nervous system, in a subject, e.g., a human subject. Exemplary AAV vectors that can target the nervous system include the AAV9 variants AAV-PHP.B (See, e.g., Deverman et al. (2016) NAT. BIOTECHNOL. 34(2):204-209), AAV-AS (See, e.g., Choudhury et al. (2016) MOL. THER. 24:726-35), and AAV-PHP.eB (See, e.g., Chan et al. (2017) NAT. NEUROSCI. 20:1172-79). Additional exemplary AAV-based strategies for targeting the nervous system are described in Bedrook et al. (2018) ANNU REV NEUROSCI. 41:323-348. In certain embodiments, the AAV vector is an AAV-PHP.eB vector.

Lentivirus Vectors

In certain embodiments, the viral vector can be a retroviral vector. Examples of retroviral vectors include moloney murine leukemia virus vectors, spleen necrosis virus vectors, and vectors derived from retroviruses such as rous sarcoma virus, harvey sarcoma virus, avian leukosis virus, human immunodeficiency virus, myeloproliferative sarcoma virus, and mammary tumor virus. Retroviral vectors are useful as agents to mediate retroviral-mediated gene transfer into eukaryotic cells.

In certain embodiments, the retroviral vector is a lentiviral vector. Exemplary lentiviral vectors include vectors derived from human immunodeficiency virus-1 (HIV-1), human immunodeficiency virus-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), and caprine arthritis encephalitis virus (CAEV).

Retroviral vectors typically are constructed such that the majority of sequences coding for the structural genes of the virus are deleted and replaced by the gene(s) of interest. Often, the structural genes (i.e., gag, pol, and env), are removed from the retroviral backbone using genetic engineering techniques known in the art. Accordingly, a minimum retroviral vector comprises from 5' to 3': a 5' long terminal repeat (LTR), a packaging signal, an optional exogenous promoter and/or enhancer, an exogenous gene of interest, and a 3' LTR. If no exogenous promoter is provided, gene expression is driven by the 5' LTR, which is a weak promoter and requires the presence of Tat to activate expression. The structural genes can be provided in separate vectors for manufacture of the lentivirus, rendering the produced virions replication-defective. Specifically, with respect to lentivirus, the packaging system may comprise a single packaging vector encoding the Gag, Pol, Rev, and Tat genes, and a third, separate vector encoding the envelope protein Env (usually VSV-G due to its wide infectivity). To improve the safety of the packaging system, the packaging vector can be split, expressing Rev from one vector, Gag and Pol from another vector. Tat can also be eliminated from the packaging system by using a retroviral vector comprising a chimeric 5' LTR, wherein the U3 region of the 5' LTR is replaced with a heterologous regulatory element.

The genes can be incorporated into the proviral backbone in several general ways. The most straightforward constructions are ones in which the structural genes of the retrovirus are replaced by a single gene that is transcribed under the control of the viral regulatory sequences within the LTR. Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Accordingly, the new gene(s) are flanked by 5' and 3' LTRs, which serve to promote transcription and polyadenylation of the virion RNAs, respectively. The term "long terminal repeat" or "LTR" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals, and sequences needed for replication and integration of the viral genome. The U3 region contains the enhancer and promoter elements. The U5 region is the sequence between the primer binding site and the R region and contains the polyadenylation sequence. The R (repeat) region is flanked by the U3 and U5 regions. In certain embodiments, the R region comprises a trans-activation response (TAR) genetic element, which interacts with the trans-activator (tat) genetic element to enhance viral replication. This element is not required in embodiments wherein the U3 region of the 5' LTR is replaced by a heterologous promoter.

In certain embodiments, the retroviral vector comprises a modified 5' LTR and/or 3' LTR. Modifications of the 3' LTR are often made to improve the safety of lentiviral or retroviral systems by rendering viruses replication-defective. In specific embodiments, the retroviral vector is a self-inactivating (SIN) vector. As used herein, a SIN retroviral vector refers to a replication-defective retroviral vector in which the 3' LTR U3 region has been modified (e.g., by deletion or substitution) to prevent viral transcription beyond the first round of viral replication. This is because the 3' LTR U3 region is used as a template for the 5' LTR U3 region during viral replication and, thus, the viral transcript cannot be made without the U3 enhancer-promoter. In a further embodiment, the 3' LTR is modified such that the U5 region is replaced, for example, with an ideal polyadenylation sequence. It should be noted that modifications to the LTRs such as modifications to the 3' LTR, the 5' LTR, or both 3' and 5' LTRs, are also contemplated to be useful in the practice of the invention.

In certain embodiments, the U3 region of the 5' LTR is replaced with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus, because there is no complete U3 sequence in the virus production system.

Adjacent the 5' LTR are sequences necessary for reverse transcription of the genome (the tRNA primer binding site) and for efficient packaging of viral RNA into particles (the Psi site). As used herein, the term "packaging signal" or "packaging sequence" refers to sequences located within the retroviral genome which are required for encapsidation of retroviral RNA strands during viral particle formation (see e.g., Clever et al., 1995 J. VIROLOGY, 69(4):2101-09). The packaging signal may be a minimal packaging signal (also referred to as the psi [Ψ] sequence) needed for encapsidation of the viral genome.

In certain embodiments, the retroviral vector (e.g., lentiviral vector) further comprises a FLAP. As used herein, the term "FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou et al. (2000) CELL, 101:173. During reverse transcription, central initiation of the plus-strand DNA at the cPPT and central termination at the CTS lead to the formation of a three-stranded DNA structure: a central DNA flap. While not wishing to be bound by any theory, the DNA flap may act as a cis-active determinant of lentiviral genome nuclear import and/or may increase the titer of the virus. In particular embodiments, the retroviral vector backbones comprise one or more FLAP elements upstream or downstream of the heterologous genes of interest in the vectors. For example, in particular embodiments, a transfer plasmid includes a FLAP element. In one embodiment, a vector of the invention comprises a FLAP element isolated from HIV-1.

In certain embodiments, the retroviral vector (e.g., lentiviral vector) further comprises an export element. In one embodiment, retroviral vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) RRE (see e.g., Cullen et al., (1991) J. VIROL. 65: 1053; and Cullen et al., (1991) CELL 58: 423) and the hepatitis B virus post-transcriptional regulatory element (HPRE). Generally, the RNA export element is placed within the 3' UTR of a gene, and can be inserted as one or multiple copies.

In certain embodiments, the retroviral vector (e.g., lentiviral vector) further comprises a posttranscriptional regulatory element. A variety of posttranscriptional regulatory elements can increase expression of a heterologous nucleic acid, e.g., woodchuck hepatitis virus posttranscriptional regulatory element (WPRE; see Zufferey et al., (1999) J. VIROL., 73:2886); the posttranscriptional regulatory element present in hepatitis B virus (HPRE) (Huang et al., MOL. CELL. BIOL., 5:3864); and the like (Liu et al., (1995), GENES DEV., 9:1766). The posttranscriptional regulatory element is generally positioned at the 3' end the heterologous nucleic acid sequence. This configuration results in synthesis of an mRNA transcript whose 5' portion comprises the heterologous nucleic acid coding sequences and whose 3' portion comprises the posttranscriptional regulatory element sequence. In certain embodiments, vectors of the invention lack or do not comprise a posttranscriptional regulatory element such as a WPRE or HPRE, because in some instances these elements increase the risk of cellular transformation and/or do not substantially or significantly increase the amount of mRNA transcript or increase mRNA stability. Therefore, in certain embodiments, vectors of the invention lack or do not comprise a WPRE or HPRE as an added safety measure.

Elements directing the efficient termination and polyadenylation of the heterologous nucleic acid transcripts increase heterologous gene expression. Transcription termination signals are generally found downstream of the polyadenylation signal. Accordingly, in certain embodiments, the retroviral vector (e.g., lentiviral vector) further comprises a polyadenylation signal. The term "polyadenylation signal" or "polyadenylation sequence" as used herein denotes a DNA sequence which directs both the termination and polyadenylation of the nascent RNA transcript by RNA polymerase H. Efficient polyadenylation of the recombinant transcript is desirable as transcripts lacking a polyadenylation signal are unstable and are rapidly degraded. Illustrative examples of polyadenylation signals that can be used in a vector of the invention, includes an ideal polyadenylation sequence (e.g., AATAAA, ATTAAA AGTAAA), a bovine growth hormone polyadenylation sequence (BGHpA), a rabbit β-globin polyadenylation sequence (rOgpA), or another suitable heterologous or endogenous polyadenylation sequence known in the art.

In certain embodiments, a retroviral vector further comprises an insulator element. Insulator elements may contribute to protecting retrovirus-expressed sequences, e.g., therapeutic genes, from integration site effects, which may be mediated by cis-acting elements present in genomic DNA and lead to deregulated expression of transferred sequences (i.e., position effect; see, e.g., Burgess-Beusse et al., (2002) PROC. NATL. ACAD. SCI., USA, 99:16433; and Zhan et al., 2001, HUM. GENET., 109:471). In certain embodiments, the retroviral vector comprises an insulator element in one or both LTRs or elsewhere in the region of the vector that integrates into the cellular genome. Suitable insulators for use in the invention include, but are not limited to, the chicken β-globin insulator (see Chung et al., (1993). CELL 74:505; Chung et al., (1997) PROC. NATL. ACAD. SCI., USA 94:575; and Bell et al., 1999. CELL 98:387). Examples of insulator elements include, but are not limited to, an insulator from a β-globin locus, such as chicken HS4.

Non-limiting examples of lentiviral vectors include pLVX-EFlalpha-AcGFP1-C1 (Clontech Catalog #631984), pLVX-EFlalpha-IRES-mCherry (Clontech Catalog #631987), pLVX-Puro (Clontech Catalog #632159), pLVX-IRES-Puro (Clontech Catalog #632186), pLenti6IV5-

DEST™ (Thermo Fisher), pLenti6.21V5-DEST™ (Thermo Fisher), pLKO.1 (Plasmid #10878 at Addgene), pLKO.3G (Plasmid #14748 at Addgene), pSico (Plasmid #11578 at Addgene), pUM1-EGFP (Plasmid #19319 at Addgene), FUGW (Plasmid #14883 at Addgene), pLVTHM (Plasmid #12247 at Addgene), pLVUT-tTR-KRAB (Plasmid #11651 at Addgene), pLL3.7 (Plasmid #11795 at Addgene), pLB (Plasmid #11619 at Addgene), pWPXL (Plasmid #12257 at Addgene), pWPI (Plasmid #12254 at Addgene), EF.CMV.RFP (Plasmid #17619 at Addgene), pLenti CMV Puro DEST (Plasmid #17452 at Addgene), pLenti-puro (Plasmid #39481 at Addgene), pULTRA (Plasmid #24129 at Addgene), pLX301 (Plasmid #25895 at Addgene), pHIV-EGFP (Plasmid #21373 at Addgene), pLV-mCherry (Plasmid #36084 at Addgene), pLionll (Plasmid #1730 at Addgene), pInducer10-mir-RUP-PheS (Plasmid #44011 at Addgene). These vectors can be modified to be suitable for therapeutic use. For example, a selection marker (e.g., puro, EGFP, or mCherry) can be deleted or replaced with a second exogenous gene of interest. Further examples of lentiviral vectors are disclosed in U.S. Pat. Nos. 7,629,153, 7,198,950, 8,329,462, 6,863,884, 6,682,907, 7,745,179, 7,250,299, 5,994,136, 6,287,814, 6,013,516, 6,797,512, 6,544,771, 5,834,256, 6,958,226, 6,207,455, 6,531,123, and 6,352,694, and PCT Publication No. WO2017/091786.

Adenoviral Vectors

In certain embodiments, the viral vector can be an adenoviral vector. Adenoviruses are medium-sized (90-100 nm), non-enveloped (naked), icosahedral viruses composed of a nucleocapsid and a double-stranded linear DNA genome. The term "adenovirus" refers to any virus in the genus Adenoviridae including, but not limited to, human, bovine, ovine, equine, canine, porcine, murine, and simian adenovirus subgenera. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

A human adenovirus can be used as the source of the adenoviral genome for the adenoviral vector. For instance, an adenovirus can be of subgroup A (e.g., serotypes 12, 18, and 31), subgroup B (e.g., serotypes 3, 7, 1 1, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serogroup or serotype. Adenoviral serotypes 1 through 51 are available from the American Type Culture Collection (ATCC, Manassas, Virginia). Non-group C adenoviral vectors, methods of producing non-group C adenoviral vectors, and methods of using non-group C adenoviral vectors are disclosed in, for example, U.S. Pat. Nos. 5,801,030, 5,837, 511, and 5,849,561, and PCT Publication Nos. WO1997/ 012986 and WO1998/053087.

Non-human adenovirus (e.g., ape, simian, avian, canine, ovine, or bovine adenoviruses) can be used to generate the adenoviral vector (i.e., as a source of the adenoviral genome for the adenoviral vector). For example, the adenoviral vector can be based on a simian adenovirus, including both new world and old world monkeys (see, e.g., Virus Taxonomy: VHIth Report of the International Committee on Taxonomy of Viruses (2005)). A phylogeny analysis of adenoviruses that infect primates is disclosed in, e.g., Roy et al. (2009) PLoS PATHOG. 5(7): e1000503. A gorilla adenovirus can be used as the source of the adenoviral genome for the adenoviral vector. Gorilla adenoviruses and adenoviral vectors are described in, e.g., PCT Publication Nos. WO2013/052799, WO2013/052811, and WO2013/052832. The adenoviral vector can also comprise a combination of subtypes and thereby be a "chimeric" adenoviral vector.

The adenoviral vector can be replication-competent, conditionally replication-competent, or replication-deficient. A replication-competent adenoviral vector can replicate in typical host cells, i.e., cells typically capable of being infected by an adenovirus. A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., a promoter. Conditionally-replicating adenoviral vectors are further described in U.S. Pat. No. 5,998,205. A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

Preferably, the adenoviral vector is replication-deficient, such that the replication-deficient adenoviral vector requires complementation of at least one replication-essential gene function of one or more regions of the adenoviral genome for propagation (e.g., to form adenoviral vector particles). The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See, e.g., Morsy et al. (1998) PROC. NATL. ACAD. SCI. USA 95: 965-976, Chen et al. (1997) PROC. NATL. ACAD. SCI. USA 94: 1645-1650, and Kochanek et al. (1999) Hum. GENE THER. 10(15):2451-9. Examples of replication-deficient adenoviral vectors are disclosed in U.S. Pat. Nos. 5,837,511, 5,851,806, 5,994,106, 6,127,175, 6,482,616, and 7,195,896, and PCT Publication Nos. WO1994/028152, WO1995/002697, WO1995/016772, WO1995/034671, WO1996/022378, WO1997/012986, WO1997/021826, and WO2003/022311.

The replication-deficient adenoviral vector of the invention can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al. (1977) J. GEN. VIROL. 36: 59-72), PER.C6 cells (described in, e.g., PCT Publication No. WO1997/000326, and U.S. Pat. Nos. 5,994,128 and 6,033,908), and 293-ORF6 cells (described in, e.g., PCT Publication No. WO1995/034671 and Brough et al. (1997) J. VIROL. 71: 9206-9213). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Publication No. 2008/0233650). Additional suitable complementing cells are described in, for example, U.S. Pat. Nos. 6,677,156 and 6,682,929, and PCT Publication No. WO2003/020879. Formulations for adenoviral vector-containing compositions are further described in, for example, U.S. Pat. Nos. 6,225,289, and 6,514,943, and PCT Publication No. WO2000/034444.

Additional exemplary adenoviral vectors, and/or methods for making or propagating adenoviral vectors are described in U.S. Pat. Nos. 5,559,099, 5,837,511, 5,846,782, 5,851, 806, 5,994,106, 5,994,128, 5,965,541, 5,981,225, 6,040,174, 6,020,191, 6,083,716, 6,113,913, 6,303,362, 7,067,310, and 9,073,980.

Commercially available adenoviral vector systems include the ViraPower™ Adenoviral Expression System available from Thermo Fisher Scientific, the AdEasy™ adenoviral vector system available from Agilent Technologies, and the Adeno-X™ Expression System 3 available from Takara Bio USA, Inc.

Viral Vector Production

Methods for producing viral vectors are known in the art. Typically, a virus of interest is produced in a suitable host cell line using conventional techniques including culturing a transfected or infected host cell under suitable conditions so as to allow the production of infectious viral particles. Nucleic acids encoding viral genes and/or tRNAs can be incorporated into plasmids and introduced into host cells through conventional transfection or transformation techniques. Exemplary suitable host cells for production of disclosed viruses include human cell lines such as HeLa, Hela-S3, HEK293, 911, A549, HER96, or PER-C6 cells. Specific production and purification conditions will vary depending upon the virus and the production system employed.

In certain embodiments, producer cells may be directly administered to a subject, however, in other embodiments, following production, infectious viral particles are recovered from the culture and optionally purified. Typical purification steps may include plaque purification, centrifugation, e.g., cesium chloride gradient centrifugation, clarification, enzymatic treatment, e.g., benzonase or protease treatment, chromatographic steps, e.g., ion exchange chromatography or filtration steps.

IV. Pharmaceutical Compositions

For therapeutic use, a tRNA and/or expression vector preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (See *Remington's Pharmaceutical Sciences,* 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1: 10-29). In certain embodiments, the composition does not comprise (or is substantially free of, for example, the composition comprises less than 5%, 4%, 3%, 2%, 1%, 0.5% or 0.1% of) a nanoparticle or an aminolipid delivery compound, e.g., as described in U.S. Patent Publication No. 2017/0354672. In certain embodiments, the tRNA or expression vector introduced into the cell or administered to the subject is not conjugated to or associated with another moiety, e.g., a carrier particle, e.g., an aminolipid particle. As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxybutyric acid. Sustained release compositions may also include liposomes that can be prepared by any of several methods known in the art.

Pharmaceutical compositions containing a tRNA and/or expression vector disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a tRNA and/or expression vector is administered intrathecally. In certain embodiments, a tRNA and/or expression vector is administered by injection. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

In general, any method of delivering a nucleic acid molecule can be adapted for use with a tRNA (see e.g., Akhtar et al. (1992) TRENDS CELL. BIOL. 2(5):139-144 and PCT Publication No. WO94/02595). The tRNA can be modified or alternatively delivered using a drug delivery system to prevent the rapid degradation of the tRNA by endo- and exo-nucleases in vivo. tRNA molecules can be modified by chemical conjugation to lipophilic groups such as cholesterol to enhance cellular uptake and prevent degradation. tRNA molecules can also be conjugated to or otherwise associated with an aptamer. A tRNA can also be delivered using drug delivery systems such as a nanoparticle, a dendrimer, a polymer, liposomes, or a cationic delivery system. Positively charged cationic delivery systems facilitate binding of a tRNA molecule (negatively charged) and also enhance interactions at the negatively charged cell membrane to permit efficient uptake of a tRNA by the cell. Cationic lipids, dendrimers, or polymers can either be bound to the RNA, e.g., tRNA, or induced to form a vesicle or micelle (see e.g., Kim et al. (2008) JOURNAL OF CONTROLLED RELEASE 129(2):107-116) that encases the RNA. Methods for making and administering cationic-RNA complexes are well within the abilities of one skilled in the art (see, e.g., Sorensen et al. (2003) J. MOL. BIOL 327:761-766; Verma et al. (2003) CLIN. CANCER RES. 9:1291-1300; Arnold et al. (2007) J. HYPERTENS. 25:197-205). Some non-limiting examples of drug delivery systems useful for systemic delivery of RNAs, e.g., tRNAs include DOTAP (Sorensen et al. (2003) supra; Verma et al. (2003), supra), Oligofectamine, solid nucleic acid lipid particles (Zimmermann et al. (2006) NATURE 441:111-114), cardiolipin (Chien et al. (2005) CANCER GENE THER. 12:321-328; Pal et al. (2005) INT J. ONCOL. 26:1087-1091), polyethyleneimine (Bonnet et al. (2008) PHARM. RES. 25(12):2972-82; Aigner (2006) J. BIOMED. BIOTECHNOL. 71659), Arg-Gly-Asp (RGD) peptides (Liu (2006) MOL. PHARM. 3:472-487), and polyamidoamines (Tomalia et al. (2007) BIOCHEM. SOC. TRANS. 35:61-67; Yoo et al. (1999) PHARM. RES. 16:1799-1804). In certain embodiments, a tRNA forms a complex with cyclodextrin for systemic administration. Methods for administration and pharmaceutical compositions of RNAs and cyclodextrins can be found in U.S. Pat. No. 7,427,605.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In a preferred embodiment, the pharmaceutical composition is administered subcutaneously and in an even more preferred embodiment intravenously. Preparations for parenteral administration include sterile aqueous or non-aqueous solutions, suspensions, and emulsions.

Generally, a therapeutically effective amount of active component, for example, a tRNA and/or expression vector, is in the range of 0.1 mg/kg to 100 mg/kg, e.g., 1 mg/kg to 100 mg/kg, 1 mg/kg to 10 mg/kg. In certain embodiments, a therapeutically effective amount of a viral expression vector is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life, and the disease being treated. Exemplary dosing frequencies are once per day, once per week and once every two weeks. A preferred route of administration is parenteral, e.g., intravenous infusion. In certain embodiments, a polypeptide and/or multimeric protein is lyophilized, and then reconstituted in buffered saline, at the time of administration.

In certain embodiments, the tRNA or expression vector is not conjugated to or associated with another moiety, e.g., a carrier particle, e.g., an aminolipid particle. In certain embodiments, the tRNA or expression vector is introduced into the cell or administered to subject in a dosage form lacking a nanoparticle. In certain embodiments, the tRNA or expression vector is introduced into the cell or administered to subject in a dosage form lacking an aminolipid delivery compound, e.g., as described in U.S. Patent Publication No. 2017/0354672.

V. Therapeutic Uses

The compositions and methods disclosed herein can be used to treat a premature termination codon (PTC)-mediated disorder in a subject. As used herein, the term "PTC-mediated disorder" refers to a disorder that is mediated, enhanced, exacerbated, or otherwise facilitated by or associated with a PTC in a gene.

The invention provides a method of treating a PTC-mediated disorder in a subject in need thereof. The method comprises administering to the subject an effective amount of a tRNA and/or expression vector, e.g., a tRNA and/or expression vector disclosed herein, either alone or in a combination with another therapeutic agent to treat the PTC-mediated disorder in the subject.

In certain embodiments, the premature termination codon-mediated disorder is a disorder listed in TABLE 5 below, and/or the gene with a premature termination codon is a gene listed in the corresponding row of TABLE 5 below.

TABLE 5

| Gene | Disorder |
| --- | --- |
| SCN1A | Dravet Syndrome; Genetic Epilepsy with Febrile Seizures (GEFS) |
| KCNQ2 | Benign Familial Infantile Epilepsy (BFIE); Early Infantile Epileptic Encephalopathy (EIEE) |
| SCN2A | Benign Familial Infantile Epilepsy (BFIE); Early Infantile Epileptic Encephalopathy (EIEE) |
| CDKL5 | Early Infantile Epileptic Encephalopathy (EIEE); Lennox-Gastaut Syndrome; CDKL5 deficiency disorder |
| MECP2 | Rett Syndrome; PPM-X Syndrome |
| STXBP1 | Early Infantile Epileptic Encephalopathy (EIEE); Ohtahara Syndrome; Dravet Syndrome |
| SCN8A | Benign Familial Infantile Epilepsy (BFIE); Early Infantile Epileptic Encephalopathy (EIEE) |
| CACNA1A | Episodic Ataxia; Hemiplegic Migraine |
| SLC2A1 | Iditiopathic Generalized Epilepsy |
| FOXG1 | FOXG1 Syndrome |
| PCDH19 | Early Infantile Epileptic Encephalopathy (EIEE) |
| GRIN2B | Early Infantile Epileptic Encephalopathy (EIEE) |
| DEPDC5 | Familial Focal Epilepsy with Variable Foci (FFEVF) |
| GRIN2A | Early Infantile Epileptic Encephalopathy (EIEE); Lennox-Gastaut Syndrome |
| CHD2 | Childhood-onset epileptic encephalopathy |
| SCN9A | Congenital insensitivity to pain, etc |
| SYNGAP1 | SYNGAP1-related intellectual disability |
| ALDH7A1 | Pyridoxine-dependent epilepsy |
| GRIN1 | Early Infantile Epileptic Encephalopathy (EIEE); Lennox-Gastaut Syndrome |
| TBC1D24 | Early Infantile Epileptic Encephalopathy (EIEE); Familial Infantile Myoclonic Epilepsy (FIME) |
| SLC6A1 | Myoclonic Astatic Epilepsy |
| DNM1 | Early Infantile Epileptic Encephalopathy (EIEE) |
| ARX | Early Infantile Epileptic Encephalopathy (EIEE); X-linked Intellectual Disability |
| KCNB1 | Early Infantile Epileptic Encephalopathy (EIEE) |
| KCNA1 | Partial Epilepsy and Episodic Ataxia |
| GABRG2 | Genetic Epilepsy with Febrile Seizures (GEFS); Early Infantile Epileptic Encephalopathy (EIEE); Febrile seizures |
| WWOX | Early Infantile Epileptic Encephalopathy (EIEE) |
| GABRB3 | Early Infantile Epileptic Encephalopathy (EIEE); Lennox-Gastaut Syndrome |
| SZT2 | Early Infantile Epileptic Encephalopathy (EIEE) |
| LGI1 | Autosomal Dominant Partial Epilepsy with Auditory Features (ADPEAF) |
| PNPO | PNPO-Deficiency |
| SCN1B | Genetic Epilepsy with Febrile Seizures (GEFS); Early Infantile Epileptic Encephalopathy (EIEE) |
| UBA5 | Early Infantile Epileptic Encephalopathy (EIEE) |
| KCTD7 | Progressive Myoclonus Epilepsy |

TABLE 5-continued

| Gene | Disorder |
| --- | --- |
| SCARB2 | Action Myoclonus - Renal Failure (AMRF); Progressive Myoclonic Epilepsy |
| SLC13A5 | Early Infantile Epileptic Encephalopathy (EIEE) |
| CSTB | Progressive Myoclonic Epilepsy |
| EPM2A | Progressive Myoclonic Epilepsy |
| PRRT2 | Benign Familial Infantile Seizures (BFIS) |
| NHLRC1 | Progressive Myoclonic Epilepsy |
| SLC25A22 | Early Infantile Epileptic Encephalopathy (EIEE) |
| PRRT2 | Benign Familial Infantile Seizures (BFIS) |
| ALG13 | Early Infantile Epileptic Encephalopathy (EIEE) |

In certain embodiments, the premature termination codon-mediated disorder is a disorder listed in TABLE 6 below, and/or the gene with a premature termination codon is a gene listed in the corresponding row of TABLE 6 below.

TABLE 6

| Gene | Disorder |
| --- | --- |
| β-globin | β-thalassemia |
| CHM | Choroideremia |
| CFTR | Cystic Fibrosis |
| dystrophin | Duchenne Muscular Dystrophy |
| α-L-iduronidase | Hurler Syndrome |
| KIF1A | KIF1A |
| FBN1 | Marfan Syndrome |
| ARSB | Maroteaux-Lamy Syndrome |
| SMPD1 | Niemann Pick Disease |
| NAGLU | Sanfilippo Syndrome |
| DHCR7 | Smith-Lemli-Opitz Syndrome |
| SCN5A | Brugada Syndrome |
| KCNH2 (hERG) | Long QT Syndrome type 2 |
| KCNQ1 | Long QT Syndrome type 1 |
| TTN | Dilated Cardiomyopathy |
| MYBPC3 | Familial Hypertrophic Cardiomyopathy |
| LMNA | Dilated Cardiomyopathy (sometimes Emery-Dreifuss Muscular Dystrophy) |
| PKP2 | Familial Arrythmogenic Right Ventricular Dysplasia |
| PLN | Familial Isolated Dilated Cardiomyopathy |
| TSC1/2 | Tuberous Sclerosis |
| LDLR | Familial Hypercholesterolemia |
| SMN1 | Spinal Muscular Atrophy |

In certain embodiments, the PTC-mediated disorder is an epilepsy (e.g., Dravet syndrome), wherein the method reduces seizure frequency, seizure severity, and/or cognitive impairment in the subject. For example, in certain embodiments, the method reduces seizure frequency in the subject by at least 10%, 20%, 30%, 40%, 50%, 60%, 70%, 80%, 90% or 100% over the period of, e.g., a day, a week, or a month. In certain embodiments, the method reduces seizure frequency by 50% over the period of, e.g., a day, a week, or a month.

In certain embodiments, the PTC-mediated disorder is Dravet and/or the gene with a premature termination codon is SCN1A. In certain embodiments, a premature termination codon in the SCN1A gene is caused by a mutation, or a combination of mutations, selected from c.5745C>G, c.5713G>T, c.5701C>T, c.5677C>T, c.5641C>T, c.5629C>T, c.5623C>T, c.5503A>T, c.5473G>T, c.5437G>T, c.5428C>T, c.5403G>A, c.5402G>A, c.5383G>T, c.5371G>T, c.5049T>G, c.4921G>T, c.4900C>T, c.4873C>T, c.4779del, c.4778G>A, c.4774G>T, c.4761T>G, c.4648G>T, c.4540C>T, c.4516A>T, c.4514C>A, c.4508T>G, c.4488C>G, c.4471G>T, c.4300A>T, c.4269G>A, c.4268G>A, c.4233T>A, c.4222G>T, c.4191G>A, c.4190G>A, c.4186C>T, c.4159A>T, c.4155C>A, c.3964del, c.3952C>T, c.3825G>A, c.3824G>A, c.3819G>A, c.3818G>A, c.3795T>A, c.3789T>G, c.3779G>A, c.3750C>G, c.3724G>T, c.3700C>T, c.3697C>T, c.3657dup, c.3624G>A, c.3604C>T, c.3582G>A, c.3578G>A, c.3574C>T, c.3463C>T, c.3454del, c.3424G>T, c.3422C>A, c.3406G>T, c.3328G>T, c.3273C>A, c.3262G>T, c.3073C>T, c.3060T>A, c.2844T>A, c.2749C>T, c.2695C>T, c.2645T>A, c.2560C>T, c.2551C>T, c.2546C>A, c.2462G>A, c.2298del, c.2228G>A, c.2181G>A, c.2180G>A, c.2101C>T, c.2038A>T, c.1958T>A, c.1837C>T, c.1834C>T, c.1804G>T, c.1795G>T, c.1738C>T, c.1702C>T, c.1660C>T, c.1624C>T, c.1516C>T, c.1378C>T, c.1363C>T, c.1354A>T, c.1348C>T, c.1345G>T, c.1344dup, c.1306G>T, c.1278C>A, c.1278C>G, c.1151G>A, c.1129C>T, c.1118T>A, c.942del, c.75 1del, c.644T>A, c.327C>G, c.249C>A, c.121A>T, c.4846_4850 dup, c.4787_4788del, c.4578_4612dup, c.4211_4212del, c.4125_4130delinsATAATCATACTGATTGCCTA AAACTAAT, c.3690_3693del, c.3338_3339del, c.1247_1248insGTAGA, c.825_826 insGTATA, and c.278_279dup. In certain embodiments, a premature termination codon in the SCN1A gene is caused by a mutation, or a combination of mutations, selected from c.58G>T, c.575G>A, c.664C>T, c.962C>G, c.1095dupT, c.1129C>T, c.1315C>T, c.1348C>T, c.1366G>T, c.1492A>T, c.1537G>T, c.1624C>T, c.1738C>T, c.1804G>T, c.1837C>T, c.2134C>T, c.2370T>A, c.2495G>A, c.2593C>T, c.2635delC, c.2904C>A, c.3295G>T, c.3311C>A, c.3452C>G, c.3637C>T, c.3656G>A, c.3733C>T, c.3783C>A, c.3829C>T, c.3985C>T, c.4359T>G, c.4547C>A, c.4573C>T, c.4721C>G, c.4954G>T, c.5641G>T, c.5656C>T, and c.5734C>T. In certain embodiments, a premature termination codon in the SCN1A gene is caused by a mutation selected from c.664C>T, c.1129C>T, c.1492A>T, c.1624C>T, c.1738C>T, c.1837C>T, c.2134C>T, c.2593C>T, c.3637C>T, c.3733C>T, c.3985C>T, c.4573C>T, c.5656C>T, and c.5734C>T. In certain embodiments, a premature termination codon in the SCN1A gene is caused by a mutation selected from c.1738C>T and c.3985C>T.

In certain embodiments, a premature termination codon in the SCN1A gene is caused by a mutation set forth in TABLE 7, or a combination of mutations set forth in TABLE 7.

TABLE 7

| Mutation (coding DNA) | Mutation (Protein) | Suppressor Class |
| --- | --- | --- |
| c.664C > T | Arg222Ter | Arg > TGA |
| c.3637C > T | Arg1213Ter | Arg > TGA |
| c.3733C > T | Arg1245Ter | Arg > TGA |
| c.2134C > T | Arg712Ter | Arg > TGA |
| c.1837C > T | Arg613Ter | Arg > TGA |
| c.4188C > A | Cys1396Ter | Cys > TGA |
| c.2877T > A | Cys959Ter | Cys > TGA |
| c.3183T > A | Cys1061Ter | Cys > TGA |
| c.3607C > T | Gln1203Ter | Gln > TAA |
| c.2782C > T | Gln928Ter | Gln > TAA |
| c.3829C > T | Gln1277Ter | Gln > TAA |
| c.2893C > T | Gln965Ter | Gln > TAA |
| c.3106C > T | Gln1036Ter | Gln > TAG |
| c.3496C > T | Gln1166Ter | Gln > TAG |
| c.5662C > T | Gln1888Ter | Gln > TAG |
| c.5461C > T | Gln1821Ter | Gln > TAG |

TABLE 7-continued

| Mutation (coding DNA) | Mutation (Protein) | Suppressor Class |
|---|---|---|
| c.3730C > T | Gln1244Ter | Gln > TAG |
| c.5506G > T | Glu1836Ter | Glu > TAA |
| c.5470G > T | Glu1824Ter | Glu > TAA |
| c.3757G > T | Glu1253Ter | Glu > TAA |
| c.3439G > T | Glu1147Ter | Glu > TAA |
| c.1345G > T | Glu449Ter | Glu > TAA |
| c.5404G > T | Glu1802Ter | Glu > TAG |
| c.1804G > T | Glu602Ter | Glu > TAG |
| c.5416G > T | Glu1806Ter | Glu > TAG |
| c.1795G > T | Glu599Ter | Glu > TAG |
| c.1549G > T | Glu517Ter | Glu > TAG |
| c.4255G > T | Gly1419Ter | Gly > TGA |
| c.4954G > T | Gly1652Ter | Gly > TGA |
| c.4807G > T | Gly1603Ter | Gly > TGA |
| c.487G > T | Gly163Ter | Gly > TGA |
| c.1843G > T | Gly615Ter | Gly > TGA |
| c.539T > A | Leu180Ter | Leu > TAA |
| c.2678T > A | Leu893Ter | Leu > TAA |
| c.644T > A | Leu215Ter | Leu > TAG |
| c.1958T > A | Leu653Ter | Leu > TAG |
| c.1118T > A | Leu373Ter | Leu > TAG |
| c.4541T > G | Leu1514Ter | Leu > TGA |
| c.2627T > G | Leu876Ter | Leu > TGA |
| c.4549A > T | Lys1517Ter | Lys > TAA |
| c.5536A > T | Lys1846Ter | Lys > TAA |
| c.121A > T | Lys41Ter | Lys > TAA |
| c.4192A > T | Lys1398Ter | Lys > TAA |
| c.1354A > T | Lys452Ter | Lys > TAA |
| c.2071A > T | Lys691Ter | Lys > TAG |
| c.3455C > A | Ser1152Ter | Ser > TAA |
| c.2579C > A | Ser860Ter | Ser > TAA |
| c.1883C > A | Ser628Ter | Ser > TAA |
| c.4547C > A | Ser1516Ter | Ser > TAG |
| c.2213G > A | Trp738Ter | Trp > TAG |
| c.3611G > A | Trp1204Ter | Trp > TAG |
| c.4811G > A | Trp1604Ter | Trp > TAG |
| c.4223G > A | Trp1408Ter | Trp > TAG |
| c.5435G > A | Trp1812Ter | Trp > TAG |
| c.3615G > A | Trp1205Ter | Trp > TGA |
| c.4224G > A | Trp1408Ter | Trp > TGA |
| c.4302G > A | Trp1434Ter | Trp > TGA |
| c.3858G > A | Trp1286Ter | Trp > TGA |
| c.5436G > A | Trp1812Ter | Trp > TGA |
| c.3762T > A | Tyr1254Ter | Tyr > TAA |
| c.3828T > A | Tyr1276Ter | Tyr > TAA |
| c.4266T > A | Tyr1422Ter | Tyr > TAA |
| c.3306C > A | Tyr1102Ter | Tyr > TAA |
| c.249C > A | Tyr83Ter | Tyr > TAA |
| c.5082T > G | Tyr1694Ter | Tyr > TAG |
| c.4794T > G | Tyr1598Ter | Tyr > TAG |
| c.4521C > G | Tyr1507Ter | Tyr > TAG |
| c.3822T > G | Tyr1274Ter | Tyr > TAG |
| c.5778C > G | Tyr1926Ter | Tyr > TAG |

Additional exemplary mutations, including exemplary mutations causing a premature termination codon in a gene, e.g., the SCN1A gene, can be found in ClinVar (available on the world wide web at ncbi.nlm.nih.gov/clinvar/), "A catalog of SCN1A variants" Lossin et al. (2009) BRAIN DEV. 2009 31(2):114-30, the SCN1A Registry (available on the world wide web at scnla.net/scnla-registry/), the SCN1A Mutation Database (available on the world wide web at gzneurosci-.com/scnladatabase), and the Leiden Open Variation Database (LOVD v. 3.0; available on the world wide web at databases.lovd.nl/shared/genes/SCN1A). Unless indicated otherwise, any SCN1A mutations described herein are relative to SCN1a isoform 1 (NCBI reference sequence NM_001165963, SEQ ID NO: 863).

In another aspect, the invention provides a method of treating Dravet syndrome in a subject in need thereof wherein the subject has a SCN1A gene with a mutation set forth in a row TABLE 7, the method comprising administering to the subject an effective amount of a suppressor tRNA of the suppressor class indicated in the same row of TABLE 7 as the mutation, or an expression vector comprising a nucleotide sequence encoding the tRNA. "Suppressor Class" as used in TABLE 7 (e.g., Arg>TGA) refers to the endogenous tRNA type from which the suppressor tRNA is derived (e.g., an arginine tRNA) and the termination codon recognized by the suppressor tRNA (e.g., TGA). Exemplary Arg>TGA suppressor tRNAs include tRNAs comprising a nucleotide sequence selected from SEQ ID NOs: 6-9, 11, 16-18, 19-22, and 35. Exemplary Gln>TAA suppressor tRNAs include tRNAs comprising a nucleotide sequence selected from SEQ ID NOs: 36-40, 44, and 45. Exemplary Gln>TAG suppressor tRNAs include tRNAs comprising a nucleotide sequence selected from SEQ ID NOs: 178-182, 186, and 187.

For example, in certain embodiments, the subject has a SCN1A gene with a premature termination codon selected from c.664C>T, c.3637C>T, c.3733C>T, c.2134C>T, and c.1837C>T, and the method comprises administering to the subject an effective amount of a suppressor tRNA comprising a nucleotide sequence selected from SEQ ID NOs: 6-9, 11, 16-18, 19-22, and 35. In certain embodiments, the subject has a SCN1A gene with a premature termination codon selected from c.3607C>T, c.2782C>T, c.3829C>T, and c.2893C>T, and the method comprises administering to the subject an effective amount of a suppressor tRNA comprising a nucleotide sequence selected from SEQ ID NOs: 36-40, 44, and 45. In certain embodiments, the subject has a SCN1A gene with a premature termination codon selected from c.3106C>T, c.3496C>T, c.5662C>T, c.5461C>T, and c.3730C>T, and the method comprises administering to the subject an effective amount of a suppressor tRNA comprising a nucleotide sequence selected from SEQ ID NOs: 178-182, 186, and 187.

In certain embodiments, wherein the gene is a SCN1A gene, the SCN1A gene product produced with the tRNA is a functional SCN1A gene product. In certain embodiments, the functional SCN1A gene product has greater activity than the truncated SCN1A gene product, e.g., greater voltage-gated sodium channel activity. In certain embodiments, the method increases voltage-gated sodium channel activity in a cell, tissue, or subject by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, or about 1000% relative to a cell, tissue, or subject without the tRNA. In certain embodiments, the method increases voltage-gated sodium channel activity in a cell, tissue, or subject by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject without the tRNA. Voltage-gated sodium channel activity may be measured by any method known in the art, for example, as described in Kalume et al. (2007) J. Neurosci. 27(41):11065-74, Yu et al. (2007) Nat. Neurosci. 9(9): 1142-9, and Han et al. (2012) Nature 489(7416): 385-390.

In certain embodiments, the functional SCN1A gene product is the Na$_v$1.1 protein. In certain embodiments, the functional SCN1A gene product comprises, consists essentially of, or consists of the amino acid sequence of any one of the following amino acid sequences, or an amino acid sequence having 80%, 85%, 86%, 87%, 88%, 89%, 90%, 91%, 92%, 93%, 94%, 95%, 96%, 97%, 98%, or 99% sequence identity to any one of the following amino acid sequences (each corresponding to different isoforms of SCN1A):

(SEQ ID NO: 863)

```
MEQTVLVPPGPDSENFFTRESLAAIERRIAEEKAKNPKPDKKDDDENGPKPNSDLEAGKNLPFI

YGDIPPEMVSEPLEDLDPYYINKKTFIVLNKGKAIFRESATSALYILTPENPLRKIAIKILVHS

LFSMLIMCTILTNCVFMTMSNPPDWTKNVEYTFTGIYTFESLIKIIARGFCLEDFTELRDPWNW

LDFTVITFAYVTEFVDLGNVSALRTFRVLRALKTISVIPGLKTIVGALIQSVKKLSDVMILTVF

CLSVFALIGLQLEMGNLRNKCIQWPPTNASLEEHSIEKNITVNYNGTLINETVFEFDWKSYIQD

SRYHYFLEGFLDALLCGNSSDAGQCPEGYMCVKAGRNPNYGYTSFDTFSWAFLSLFRLMTQDFW

ENLYQLTLRAAGKTYMIFFVLVIFLGSFYLINLILAVVAMAYEEQNQATLEEAEQKEAEFQQMI

EQLKKQQEAAQQAATATASEHSREPSAAGRLSDSSSEASKLSSKSAKERRNRRKKRKQKEQSGG

EEKDEDEFQKSESEDSIRRKGFRFSIEGNRLTYEKRYSSPHQSLLSIRGSLFSPRRNSRTSLFS

FRGRAKDVGSENDFADDEHSTFEDNESRRDSLFVPRRHGERRNSNLSQTSRSSRMLAVFPANGK

MHSTVDCNGVVSLVGGPSVPTSPVGQLLPEVIIDKPATDDNGTTTETEMRKRRSSSFHVSMDFL

EDPSQRQRAMSIASILTNTVEELEESRQKCPPCWYKFSNIFLIWDCSPYWLKVKHVVNLVVMDP

FVDLAITICIVLNTLFMAMEHYPMTDHFNNVLTVGNLVFTGIFTAEMELKIIAMDPYYYFQEGW

NIFDGFIVTLSLVELGLANVEGLSVLRSFRLLRVFKLAKSWPTLNMLIKIIGNSVGALGNLTLV

LAIIVFIFAVVGMQLFGKSYKDCVCKIASDCQLPRWHMNDFFHSFLIVFRVLCGEWIETMWDCM

EVAGQAMCLTVFMMVMVIGNLVVLNLFLALLLSSFSADNLAATDDDNEMNNLQIAVDRMHKGVA

YVKRKIYEFIQQSFIRKQKILDEIKPLDDLNNKKDSCMSNHTAEIGKDLDYLKDVNGTTSGIGT

GSSVEKYIIDESDYMSFINNPSLTVTVPIAVGESDFENLNTEDFSSESDLEESKEKLNESSSSS

EGSTVDIGAPVEEQPVVEPEETLEPEACFTEGCVQRFKCCQINVEEGRGKQWWNLRRTCFRIVE

HNWFETFIVEMILLSSGALAFEDIYIDQRKTIKTMLEYADKVFTYIFILEMLLKWVAYGYQTYF

TNAWCWLDFLIVDVSLVSLTANALGYSELGAIKSLRTLRALRPLRALSRFEGMRVVVNALLGAI

PSIMNVLLVCLIFWLIFSIMGVNLFAGKFYHCINTTTGDRFDIEDVNNHTDCLKLIERNETARW

KNVKVNFDNVGFGYLSLLQVATFKGWMDIMYAAVDSRNVELQPKYEESLYMYLYFVIFIIFGSF

FTLNLFIGVIIDNFNQQKKKFGGQDIFMTEEQKKYYNAMKKLGSKKPQKPIPRPGNKFQGMVFD

FVTRQVFDISIMILICLNMVTMMVETDDQSEYVTTILSRINLVFIVLFTGECVLKLISLRHYYF

TIGWNIFDFVVVILSIVGMFLAELIEKYFVSPTLERVIRLARIGRILRLIKGAKGIRTLLFALM

MSLPALFNIGLLLFLVMFIYAIFGMSNFAYVKREVGIDDMENFETFGNSMICLFQITTSAGWDG

LLAPILNSKPPDCDPNKVNPGSSVKGDCGNPSVGIFFFVSYIIISELVVVNMYIAVILENFSVA

TEESAEPLSEDDFEMFYEVWEKFDPDATQFMEFEKLSQFAAALEPPLNLPQPNKLQLIAMDLPM

VSGDRIHCLDILFAFTKRVLGESGEMDALRIQMEERFMASNPSKVSYQPITTTLKRKQEEVSAV

IIQRAYRRHLLKRTVKQASFTYNKNKIKGGANLLIKEDMIIDRINENSITEKTDLTMSTAACPP

SYDRVTKPIVEKHEQEGKDEKAKGK;
```

-continued (SEQ ID NO: 864)
MEQTVLVPPGPDSFNFFTRESLAAIERRIAEEKAKNPKPDKKDDDENGPKPNSDLEAGKNLPFI

YGDIPPEMVSEPLEDLDPYYINKKTFIVLNKGKAIFRFSATSALYILTPFNPLRKIAIKILVHS

LFSMLIMCTILTNCVFMTMSNPPDWTKNVEYTFTGIYTFESLIKIIARGFCLEDFTELRDPWNW

LDFTVITFAYVTEFVDLGNVSALRTFRVLRALKTISVIPGLKTIVGALIQSVKKLSDVMILTVF

CLSVFALIGLQLFMGNLRNKCIQWPPTNASLEEHSIEKNITVNYNGTLINETVFEFDWKSYIQD

SRYHYFLEGFLDALLCGNSSDAGQCPEGYMCVKAGRNPNYGYTSFDTFSWAFLSLFRLMTQDFW

ENLYQLTLRAAGKTYMIFFVLVIFLGSFYLINLILAVVAMAYEEQNQATLEEAEQKEAEFQQMI

EQLKKQQEAAQQAATATASEHSREPSAAGRLSDSSSEASKLSSKSAKERRNRRKKRKQKEQSGG

EEKDEDEFQKSESEDSIRRKGFRFSIEGNRLTYEKRYSSPHQSLLSIRGSLFSPRRNSRTSLFS

FRGRAKDVGSENDFADDEHSTFEDNESRRDSLFVPRRHGERRNSNLSQTSRSSRMLAVFPANGK

MHSTVDCNGVVSLVGGPSVPTSPVGQLLPEGTTTETEMRKRRSSSFHVSMDFLEDPSQRQRAMS

IASILTNTVEELEESRQKCPPCWYKFSNIFLIWDCSPYWLKVKHVVNLVVMDPFVDLAITICIV

LNTLFMAMEHYPMTDHFNNVLTVGNLVFTGIFTAEMELKIIAMDPYYYFQEGWNIFDGFIVTLS

LVELGLANVEGLSVLRSFRLLRVFKLAKSWPTLNMLIKIIGNSVGALGNLTLVLAIIVFIFAVV

GMQLFGKSYKDCVCKIASDCQLPRWHMNDFFHSFLIVFRVLCGEWIETMWDCMEVAGQAMCLTV

FMMVMVIGNLVVLNLFLALLLSSFSADNLAATDDDNEMNNLQIAVDRMHKGVAYVKRKIYEFIQ

QSFIRKQKILDEIKPLDDLNNKKDSCMSNHTAEIGKDLDYLKDVNGTTSGIGTGSSVEKYIIDE

SDYMSFINNPSLTVTVPIAVGESDFENLNTEDFSSESDLEESKEKLNESSSSSEGSTVDIGAPV

EEQPVVEPEETLEPEACFTEGCVQRFKCCQINVEEGRGKQWWNLRRTCFRIVEHNWFETFIVFM

ILLSSGALAFEDIYIDQRKTIKTMLEYADKVETYIFILEMLLKWVAYGYQTYFTNAWCWLDFLI

VDVSLVSLTANALGYSELGAIKSLRTLRALRPLRALSRFEGMRVVVNALLGAIPSIMNVLLVCL

IFWLIFSIMGVNLFAGKFYHCINTTTGDRFDIEDVNNHTDCLKLIERNETARWKNVKVNFDNVG

FGYLSLLQVATFKGWMDIMYAAVDSRNVELQPKYEESLYMYLYFVIFIIFGSFFTLNLFIGVII

DNFNQQKKKFGGQDIFMTEEQKKYYNAMKKLGSKKPQKPIPRPGNKFQGMVEDEVTRQVFDISI

MILICLNMVTMMVETDDQSEYVTTILSRINLVFIVLFTGECVLKLISLRHYYFTIGWNIFDFVV

VILSIVGMFLAELIEKYFVSPTLERVIRLARIGRILRLIKGAKGIRTLLFALMMSLPALENIGL

LLFLVMFIYAIFGMSNFAYVKREVGIDDMFNFETFGNSMICLFQITTSAGWDGLLAPILNSKPP

DCDPNKVNPGSSVKGDCGNPSVGIFFFVSYIIISFLVVVNMYIAVILENFSVATEESAEPLSED

DFEMFYEVWEKFDPDATQFMEFEKLSQFAAALEPPLNLPQPNKLQLIAMDLPMVSGDRIHCLDI

LFAFTKRVLGESGEMDALRIQMEERFMASNPSKVSYQPITTTLKRKQEEVSAVIIQRAYRRHLL

KRTVKQASFTYNKNKIKGGANLLIKEDMIIDRINENSITEKTDLTMSTAACPPSYDRVTKPIVE

KHEQEGKDEKAKGK;

(SEQ ID NO: 865)
MEQTVLVPPGPDSFNFFTRESLAAIERRIAEEKAKNPKPDKKDDDENGPKPNSDLEAGKNLPFI

YGDIPPEMVSEPLEDLDPYYINKKTFIVLNKGKAIFRFSATSALYILTPENPLRKIAIKILVHS

LFSMLIMCTILTNCVFMTMSNPPDWTKNVEYTFTGIYTFESLIKIIARGFCLEDFTFLRDPWNW

LDFTVITFAYVTEFVDLGNVSALRTFRVLRALKTISVIPGLKTIVGALIQSVKKLSDVMILTVF

CLSVFALIGLQLFMGNLRNKCIQWPPTNASLEEHSIEKNITVNYNGTLINETVFEFDWKSYIQD

SRYHYFLEGELDALLCGNSSDAGQCPEGYMCVKAGRNPNYGYTSFDTFSWAFLSLFRLMTQDFW

ENLYQLTLRAAGKTYMIFFVLVIFLGSFYLINLILAVVAMAYEEQNQATLEEAEQKEAEFQQMI

EQLKKQQEAAQQAATATASEHSREPSAAGRLSDSSSEASKLSSKSAKERRNRRKKRKQKEQSGG

-continued

EEKDEDEFQKSESEDSIRRKGFRFSIEGNRLTYEKRYSSPHQSLLSIRGSLFSPRRNSRTSLFS

FRGRAKDVGSENDFADDEHSTFEDNESRRDSLFVPRRHGERRNSNLSQTSRSSRMLAVFPANGK

MHSTVDCNGVVSLGTTTETEMRKRRSSSFHVSMDFLEDPSQRQRAMSIASILTNTVEELEESRQ

KCPPCWYKFSNIFLIWDCSPYWLKVKHVVNLVVMDPFVDLAITICIVLNTLFMAMEHYPMTDHF

NNVLTVGNLVFTGIFTAEMELKIIAMDPYYYFQEGWNIFDGFIVTLSLVELGLANVEGLSVLRS

FRLLRVEKLAKSWPTLNMLIKIIGNSVGALGNLTLVLAIIVFIFAVVGMQLFGKSYKDCVCKIA

SDCQLPRWHMNDFFHSFLIVERVLCGEWIETMWDCMEVAGQAMCLTVFMMVMVIGNLVVLNLFL

ALLLSSFSADNLAATDDDNEMNNLQIAVDRMHKGVAYVKRKIYEFIQQSFIRKQKILDEIKPLD

DLNNKKDSCMSNHTAEIGKDLDYLKDVNGTTSGIGTGSSVEKYIIDESDYMSFINNPSLTVTVP

IAVGESDFENLNTEDESSESDLEESKEKLNESSSSSEGSTVDIGAPVEEQPVVEPEETLEPEAC

FTEGCVQRFKCCQINVEEGRGKQWWNLRRTCFRIVEHNWFETFIVEMILLSSGALAFEDIYIDQ

RKTIKTMLEYADKVFTYIFILEMLLKWVAYGYQTYFTNAWCWLDFLIVDVSLVSLTANALGYSE

LGAIKSLRTLRALRPLRALSRFEGMRVVVNALLGAIPSIMNVLLVCLIFWLIFSIMGVNLFAGK

FYHCINTTTGDRFDIEDVNNHTDCLKLIERNETARWKNVKVNFDNVGFGYLSLLQVATFKGWMD

IMYAAVDSRNVELQPKYEESLYMYLYFVIFIIFGSFFTLNLFIGVIIDNFNQQKKKFGGQDIFM

TEEQKKYYNAMKKLGSKKPQKPIPRPGNKFQGMVFDFVTRQVFDISIMILICLNMVTMMVETDD

QSEYVTTILSRINLVFIVLFTGECVLKLISLRHYYFTIGWNIFDFVVVILSIVGMFLAELIEKY

FVSPTLERVIRLARIGRILRLIKGAKGIRTLLFALMMSLPALFNIGLLLFLVMFIYAIFGMSNF

AYVKREVGIDDMENFETEGNSMICLFQITTSAGWDGLLAPILNSKPPDCDPNKVNPGSSVKGDC

GNPSVGIFFFVSYIIISFLVVVNMYIAVILENFSVATEESAEPLSEDDFEMFYEVWEKEDPDAT

QFMEFEKLSQFAAALEPPLNLPQPNKLQLIAMDLPMVSGDRIHCLDILFAFTKRVLGESGEMDA

LRIQMEERFMASNPSKVSYQPITTTLKRKQEEVSAVIIQRAYRRHLLKRTVKQASFTYNKNKIK

GGANLLIKEDMIIDRINENSITEKTDLTMSTAACPPSYDRVTKPIVEKHEQEGKDEKAKGK;

(SEQ ID NO: 866)
MEQTVLVPPGPDSENFFTRESLAAIERRIAEEKAKNPKPDKKDDDENGPKPNSDLEAGKNLPFI

YGDIPPEMVSEPLEDLDPYYINKKTFIVLNKGKAIFRFSATSALYILTPENPLRKIAIKILVHS

LFSMLIMCTILTNCVFMTMSNPPDWTKNVEYTFTGIYTFESLIKIIARGFCLEDFTFLRDPWNW

LDFTVITFAYVTEFVDLGNVSALRTFRVLRALKTISVIPGLKTIVGALIQSVKKLSDVMILTVF

CLSVFALIGLQLFMGNLRNKCIQWPPTNASLEEHSIEKNITVNYNGTLINETVFEFDWKSYIQD

SRYHYFLEGFLDALLCGNSSDAGQCPEGYMCVKAGRNPNYGYTSFDTFSWAFLSLFRLMTQDFW

ENLYQLTLRAAGKTYMIFFVLVIFLGSFYLINLILAVVAMAYEEQNQATLEEAEQKEAEFQQMI

EQLKKQQEAAQAATATASEHSREPSAAGRLSDSSSEASKLSSKSAKERRNRRKKRKQKEQSGGE

EKDEDEFQKSESEDSIRRKGFRFSIEGNRLTYEKRYSSPHQSLLSIRGSLFSPRRNSRTSLFSF

RGRAKDVGSENDFADDEHSTFEDNESRRDSLFVPRRHGERRNSNLSQTSRSSRMLAVFPANGKM

HSTVDCNGVVSLVGGPSVPTSPVGQLLPEGTTTETEMRKRRSSSFHVSMDFLEDPSQRQRAMSI

ASILTNTVEELEESRQKCPPCWYKFSNIFLIWDCSPYWLKVKHVVNLVVMDPFVDLAITICIVL

NTLFMAMEHYPMTDHFNNVLTVGNLVFTGIFTAEMFLKIIAMDPYYYFQEGWNIFDGFIVTLSL

VELGLANVEGLSVLRSFRLLRVFKLAKSWPTLNMLIKIIGNSVGALGNLTLVLAIIVFIFAVVG

MQLFGKSYKDCVCKIASDCQLPRWHMNDFFHSFLIVFRVLCGEWIETMWDCMEVAGQAMCLTVF

MMVMVIGNLVVLNLFLALLLSSFSADNLAATDDDNEMNNLQIAVDRMHKGVAYVKRKIYEFIQQ

SFIRKQKILDEIKPLDDLNNKKDSCMSNHTAEIGKDLDYLKDVNGTTSGIGTGSSVEKYIIDES

-continued

DYMSFINNPSLTVTVPIAVGESDFENLNTEDFSSESDLEESKEKLNESSSSSEGSTVDIGAPVE

EQPVVEPEETLEPEACFTEGCVQRFKCCQINVEEGRGKQWWNLRRTCFRIVEHNWFETFIVFMI

LLSSSGALAFEDIYIDQRKTIKTMLEYADKVETYIFILEMLLKWVAYGYQTYFTNAWCWLDFLIV

DVSLVSLTANALGYSELGAIKSLRTLRALRPLRALSRFEGMRVVVNALLGAIPSIMNVLLVCLI

FWLIFSIMGVNLFAGKFYHCINTTTGDRFDIEDVNNHTDCLKLIERNETARWKNVKVNFDNVGF

GYLSLLQVATFKGWMDIMYAAVDSRNVELQPKYEESLYMYLYFVIFIIFGSFFTLNLFIGVIID

NFNQQKKKFGGQDIFMTEEQKKYYNAMKKLGSKKPQKPIPRPGNKFQGMVFDFVTRQVFDISIM

ILICLNMVTMMVETDDQSEYVTTILSRINLVFIVLFTGECVLKLISLRHYYFTIGWNIFDFVVV

ILSIVGMFLAELIEKYFVSPTLFRVIRLARIGRILRLIKGAKGIRTLLFALMMSLPALFNIGLL

LFLVMFIYAIFGMSNFAYVKREVGIDDMFNFETFGNSMICLFQITTSAGWDGLLAPILNSKPPD

CDPNKVNPGSSVKGDCGNPSVGIFFFVSYIIISFLVVVNMYIAVILENFSVATEESAEPLSEDD

FEMFYEVWEKFDPDATQFMEFEKLSQFAAALEPPLNLPQPNKLQLIAMDLPMVSGDRIHCLDIL

FAFTKRVLGESGEMDALRIQMEERFMASNPSKVSYQPITTTLKRKQEEVSAVIIQRAYRRHLLK

RTVKQASFTYNKNKIKGGANLLIKEDMIIDRINENSITEKTDLTMSTAACPPSYDRVTKPIVEK

HEQEGKDEKAKGK;

(SEQ ID NO: 867)
MEQTVLVPPGPDSFNFFTRESLAAIERRIAEEKAKNPKPDKKDDDENGPKPNSDLEAGKNLPFI

YGDIPPEMVSEPLEDLDPYYINKKTFIVLNKGKAIFRFSATSALYILTPFNPLRKIAIKILVHS

LFSMLIMCTILTNCVFMTMSNPPDWTKNVEYTFTGIYTFESLIKIIARGFCLEDFTFLRDPWNW

LDFTVITFAYVTEFVDLGNVSALRTFRVLRALKTISVIPGLKTIVGALIQSVKKLSDVMILTVF

CLSVFALIGLQLFMGNLRNKCIQWPPTNASLEEHSIEKNITVNYNGTLINETVFEFDWKSYIQD

SRYHYFLEGFLDALLCGNSSDAGQCPEGYMCVKAGRNPNYGYTSFDTFSWAFLSLFRLMTQDFW

ENLYQLTLRAAGKTYMIFFVLVIFLGSFYLINLILAVVAMAYEEQNQATLEEAEQKEAEFQQMI

EQLKKQQEAAQAATATASEHSREPSAAGRLSDSSSEASKLSSKSAKERRNRRKKRKQKEQSGGE

EKDEDEFQKSESEDSIRRKGFRFSIEGNRLTYEKRYSSPHQSLLSIRGSLFSPRRNSRTSLFSF

RGRAKDVGSENDFADDEHSTFEDNESRRDSLFVPRRHGERRNSNLSQTSRSSRMLAVFPANGKM

HSTVDCNGVVSLGTTTETEMRKRRSSSFHVSMDFLEDPSQRQRAMSIASILTNTVEELEESRQK

CPPCWYKFSNIFLIWDCSPYWLKVKHVVNLVVMDPFVDLAITICIVLNTLFMAMEHYPMTDHFN

NVLTVGNLVFTGIFTAEMELKIIAMDPYYYFQEGWNIFDGFIVTLSLVELGLANVEGLSVLRSF

RLLRVFKLAKSWPTLNMLIKIIGNSVGALGNLTLVLAIIVFIFAVVGMQLFGKSYKDCVCKIAS

DCQLPRWHMNDFFHSFLIVFRVLCGEWIETMWDCMEVAGQAMCLTVFMMVMVIGNLVVLNLFLA

LLLSSFSADNLAATDDDNEMNNLQIAVDRMHKGVAYVKRKIYEFIQQSFIRKQKILDEIKPLDD

LNNKKDSCMSNHTAEIGKDLDYLKDVNGTTSGIGTGSSVEKYIIDESDYMSFINNPSLTVTVPI

AVGESDFENLNTEDFSSESDLEESKEKLNESSSSSEGSTVDIGAPVEEQPVVEPEETLEPEACF

TEGCVQRFKCCQINVEEGRGKQWWNLRRTCFRIVEHNWFETFIVEMILLSSSGALAFEDIYIDQR

KTIKTMLEYADKVETYIFILEMLLKWVAYGYQTYFTNAWCWLDELIVDVSLVSLTANALGYSEL

GAIKSLRTLRALRPLRALSRFEGMRVVVNALLGAIPSIMNVLLVCLIFWLIFSIMGVNLFAGKF

YHCINTTTGDRFDIEDVNNHTDCLKLIERNETARWKNVKVNFDNVGFGYLSLLQVATFKGWMDI

MYAAVDSRNVELQPKYEESLYMYLYFVIFIIFGSFFTLNLFIGVIIDNENQQKKKEGGQDIFMT

EEQKKYYNAMKKLGSKKPQKPIPRPGNKFQGMVFDFVTRQVFDISIMILICLNMVTMMVETDDQ

SEYVTTILSRINLVFIVLFTGECVLKLISLRHYYFTIGWNIFDFVVVILSIVGMFLAELIEKYF

-continued

VSPTLFRVIRLARIGRILRLIKGAKGIRTLLFALMMSLPALFNIGLLLFLVMFIYAIFGMSNFA

YVKREVGIDDMFNFETFGNSMICLFQITTSAGWDGLLAPILNSKPPDCDPNKVNPGSSVKGDCG

NPSVGIFFFVSYIIISFLVVVNMYIAVILENFSVATEESAEPLSEDDFEMFYEVWEKFDPDATQ

FMEFEKLSQFAAALEPPLNLPQPNKLQLIAMDLPMVSGDRIHCLDILFAFTKRVLGESGEMDAL

RIQMEERFMASNPSKVSYQPITTTLKRKQEEVSAVIIQRAYRRHLLKRTVKQASFTYNKNKIKG

GANLLIKEDMIIDRINENSITEKTDLTMSTAACPPSYDRVTKPIVEKHEQEGKDEKAKGK;
or (SEQ ID NO: 868)
MFLKIIAMDPYYYFQEGWNIFDGFIVTLSLVELGLANVEGLSVLRSFRLLRVFKLAKSWPTLNM

LIKIIGNSVGALGNLTLVLAIIVFIFAVVGMQLFGKSYKDCVCKIASDCQLPRWHMNDFFHSFL

IVFRVLCGEWIETMWDCMEVAGQAMCLTVFMMVMVIGNLVVLNLFLALLLSSFSADNLAATDDD

NEMNNLQIAVDRMHKGVAYVKRKIYEFIQQSFIRKQKILDEIKPLDDLNNKKDSCMSNHTAEIG

KDLDYLKDVNGTTSGIGTGSSVEKYIIDESDYMSFINNPSLTVTVPIAVGESDFENLNTEDFSS

ESDLEESKEKLNESSSSSEGSTVDIGAPVEEQPVVEPEETLEPEACFTEGCVQRFKCCQINVEE

GRGKQWWNLRRTCFRIVEHNWFETFIVEMILLSSGALAFEDIYIDQRKTIKTMLEYADKVFTYI

FILEMLLKWVAYGYQTYFTNAWCWLDFLIVDVSLVSLTANALGYSELGAIKSLRTLRALRPLRA

LSRFEGMRVVVNALLGAIPSIMNVLLVCLIFWLIFSIMGVNLFAGKFYHCINTTTGDRFDIEDV

NNHTDCLKLIERNETARWKNVKVNFDNVGFGYLSLLQVATFKGWMDIMYAAVDSRNVELQPKYE

ESLYMYLYFVIFIIFGSFFTLNLFIGVIIDNFNQQKKKFGGQDIEMTEEQKKYYNAMKKLGSKK

PQKPIPRPGNKFQGMVFDFVTRQVEDISIMILICLNMVTMMVETDDQSEYVTTILSRINLVFIV

LFTGECVLKLISLRHYYFTIGWNIFDFVVVILSIVGMFLAELIEKYFVSPTLFRVIRLARIGRI

LRLIKGAKGIRTLLFALMMSLPALFNIGLLLFLVMFIYAIFGMSNFAYVKREVGIDDMENFETF

GNSMICLFQITTSAGWDGLLAPILNSKPPDCDPNKVNPGSSVKGDCGNPSVGIFFFVSYIIISF

LVVVNMYIAVILENFSVATEESAEPLSEDDFEMFYEVWEKFDPDATQFMEFEKLSQFAAALEPP

LNLPQPNKLQLIAMDLPMVSGDRIHCLDILFAFTKRVLGESGEMDALRIQMEERFMASNPSKVS

YQPITTTLKRKQEEVSAVIIQRAYRRHLLKRTVKQASFTYNKNKIKGGANLLIKEDMIIDRINE

NSITEKTDLTMSTAACPPSYDRVTKPIVEKHEQEGKDEKAKGK.

The term "effective amount" as used herein refers to the amount of an active agent (e.g., tRNA or expression vector according to the present invention or a secondary active agent in a combination therapy) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive.

The delivery can be such that an effect of the first treatment delivered is still detectable when the second is delivered.

In certain embodiments, a method or composition described herein is administered in combination with one or more additional therapeutic agents, e.g., DIACOMIT® (stiripentol), EPIODOLEX® (cannabidiol), a ketogenic diet, ONFI® (clobazam), TOPAMAX® (topiramate), fenfluramine, or valproic acid. For example, during the treatment of Dravet Syndrome, a method or composition described herein is administered in combination with one or more additional therapeutic agents, e.g., DIACOMIT® (stiripentol), EPIODOLEX® (cannabidiol), a ketogenic diet, ONFI® (clobazam), TOPAMAX® (topiramate), fenfluramine, or valproic acid.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/ or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1

This Example describes arginine aminoacylated suppressor tRNAs that facilitate read-through of a premature termination codon (PTC).

Suppressor tRNAs were generated from endogenous mouse arginine-tRNAs by converting their normal anticodons to TCA anticodons that recognize TGA termination codons (referred to as $Arg_{TCA}$ suppressor tRNAs). Five of the endogenous arginine-tRNAs contained introns that must be spliced out in order to produce mature tRNAs; corresponding $Arg_{TCA}$ suppressor tRNAs with and without these intronic sequences were generated. Suppressor tRNA sequences are shown in TABLE 8.

TABLE 8

| SEQ ID NO | Suppressor tRNA ID Number | Suppressor tRNA Name | Suppressor tRNA Sequence (anticodon lowercase) |
|---|---|---|---|
| 1 | 089 | tRNA-Arg-ACG-1-1-TCA-SUP | GGGCCAGTGGCGCAATGGATAACG CGTCTGACTtcaGATCAGAAGATTC CAGGTTCGACTCCTGGCTGGCTCG |
| 2 | 090 | tRNA-Arg-ACG-2-1-TCA-SUP | GGGCCAGTGGCGCAATGGATAACG CGTCTGACTtcaGATCAGAAGATTG TAGGTTCGACTCCTACCTGGCTCG |
| 3 | 101 | tRNA-Arg-ACG-3-1-TCA-SUP | GGGCCAGTGGCGCAATGGATAACG CGTCTGACTtcaGATCAGAAGATTC TAGGTTCGACTCCTGGCTGGCTCG |

TABLE 8-continued

| SEQ ID NO | Suppressor tRNA ID Number | Suppressor tRNA Name | Suppressor tRNA Sequence (anticodon lowercase) |
|---|---|---|---|
| 4 | 102 | tRNA-Arg-CCG-1-1-TCA-SUP | GGCCGCGTGGCCTAATGGATAAGG CGTCTGATTtcaGATCAGAAGATTG AGGGTTCGAGTCCCTTCGTGGTCG |
| 5 | 103 | tRNA-Arg-CCG-2-1-TCA-SUP | GGCCGCGTGGCCTAATGGATAAGG CGTCTGATTtcaGATCAGAAGATTG GGGGTTCGAGTCCCTTCGTGGTCG |
| 6 | 104 | tRNA-Arg-CCG-3-1-TCA-SUP | GACCCAGTGGCCTAATGGATAAGG CATCAGCCTtcaGAGCTGGGGATTG TGGGTTCGAGTCCCATCTGGGTCG |
| 7 | 105 | tRNA-Arg-CCT-1-1-TCA-SUP | GCCCCAGTGGCCTAATGGATAAGG CACTGGCCTtcaAAGCCAGGGATTG TGGGTTCGAGTCCCACCTGGGGTA |
| 8 | 106 | tRNA-Arg-CCT-2-1-TCA-SUP | GCCCCAGTGGCCTAATGGATAAGG CACTGGCCTtcaAAGCCAGGGATTG TGGGTTCGAGTCCCACCTGGGGTG |
| 9 | 107 | tRNA-Arg-CCT-3-1-TCA-SUP | GCCCCGGTGGCCTAATGGATAAGGC ATTGGCCTtcaAAGCCAGGGATTGTG GGTTCGAGTCCCACCCGGGGTA |
| 10 | 108 | tRNA-Arg-CCT-4-1-TCA-SUP | GCCCCAGTGGCCTAATGGATAAGGC ATTGGCCTtcaAAGCCAGGGATTGTG GGTTCGAGTCCCATCTGGGGTG |
| 11 | 001 | tRNA-Arg-TCG-1-1-TCA-SUP | GGCCGCGTGGCCTAATGGATAAGGC GTCTGACTtcaGATCAGAAGATTGCA GGTTCGAGTCCTGCCGCGGTCG |
| 12 | 109 | tRNA-Arg-TCG-2-1-TCA-SUP | GACCGCGTGGCCTAATGGATAAGGC GTCTGACTtcaGATCAGAAGATTGAG GGTTCGAGTCCCTTCGTGGTCG |
| 13 | 110 | tRNA-Arg-TCG-3-1-TCA-SUP | GACCACGTGGCCTAATGGATAAGGC GTCTGACTtcaGATCAGAAGATTGAG GGTTCGAATCCCTTCGTGGTTG |
| 14 | 111 | tRNA-Arg-TCG-4-1-TCA-SUP | GACCACGTGGCCTAACGGATAAGGC GTCTGACTtcaGATCAGAAGATTGAG GGTTCGAATCCCTTCGTGGTTA |
| 15 | 112 | tRNA-Arg-TCT-1-1-TCA-SUP_contains intron | GGCTCTGTGGCGCAATGGATAGCGC ATTGGACTtcaAGTGACGAGAAAGCG ATTCAAAGGTTGTGGGTTCGAATCCC ACCAGAGTCG |
| 16 | 113 | tRNA-Arg-TCT-1-1-TCA-SUP_no intron | GGCTCTGTGGCGCAATGGATAGCGC ATTGGACTtcaAATTCAAAGGTTGTG GGTTCGAATCCCACCAGAGTCG |
| 17 | 114 | tRNA-Arg-TCT-2-1-TCA-SUP_contains intron | GGCTCCGTGGCGCAATGGATAGCGC ATTGGACTtcaAGAGGCTGAAGGCAT TCAAAGGTTCCGGGTTCGAGTCCCGG CGGAGTCG |
| 18 | 115 | tRNA-Arg-TCT-2-1-TCA-SUP_no intron | GGCTCCGTGGCGCAATGGATAGCGC ATTGGACTtcaAATTCAAAGGTTCCG GGTTCGAGTCCCGGCGGAGTCG |
| 19 | 116 | tRNA-Arg-TCT-3-1-TCA-SUP_contains intron | GGCTCTGTGGCGCAATGGATAGCGC ATTGGACTtcaAGCATGATTGAGAGA TTCAAAGGTTGCGGGTTCGAGTCCCG CCAGAGTCG |
| 20 | 117 | tRNA-Arg-TCT-3-1-TCA-SUP_no intron | GGCTCTGTGGCGCAATGGATAGCGC ATTGGACTtcaAATTCAAAGGTTGCG GGTTCGAGTCCCGCCAGAGTCG |
| 21 | 118 | tRNA-Arg-TCT-4-1-TCA-SUP_contains intron | GGCTCTGTGGCGCAATGGATAGCGC ATTGGACTtcaAGACAAATGGAGGCA TTCAAAGGTTGTGGGTTCGAGTCCCA CCAGAGTCG |

TABLE 8-continued

| SEQ ID NO | Suppressor tRNA ID Number | Suppressor tRNA Name | Suppressor tRNA Sequence (anticodon lowercase) |
|---|---|---|---|
| 22 | 119 | tRNA-Arg-TCT-4-1-TCA-SUP_no intron | GGCTCTGTGGCGCAATGGATAGCGC ATTGGACTtcaAATTCAAAGGTTGTG GGTTCGAGTCCCACCAGAGTCG |
| 23 | 120 | tRNA-Arg-TCT-5-1-TCA-SUP | GTCTCTGTGGCGCAATGGACGAGCG CGCTGGACTtcaAATCCAGAGGTTCT GGGTTCGAGTCCCGGCAGAGATG |
| 24 | 121 | tRNA-Arg-TCT-6-1-TCA-SUP_contains intron | GGCTCTGTGGAGCAATGGATAGCAC ATTGGACTtcaAGCATGACCGAGAGA TTCAAAGGTTGCGGGTTCGAGTCCCA CCAGAGTTG |
| 25 | 122 | tRNA-Arg-TCT-6-1-TCA-SUP_no intron | GGCTCTGTGGAGCAATGGATAGCAC ATTGGACTtcaAATTCAAAGGTTGCG GGTTCGAGTCCCACCAGAGTTG |
| 35 | 179 | tRNA-Arg-TCT-5-1-TCA-SUP_T51C | GTCTCTGTGGCGCAATGGACGAGCG CGCTGGACTtcaAATCCAGAGGTTCC GGGTTCGAGTCCCGGCAGAGATG |

In this Example, all mature tRNA sequences (as predicted by GtRNAdb; http://gtrnadb.ucsc.edu) were expressed in the context of upstream and downstream genomic flanking sequences (±200 bps) from tRNA-Arg-TCG-1-1—a highly expressed arginine-tRNA, i.e., the tRNA sequences were expressed with a 5' flanking sequence of SEQ ID NO: 26 and a 3' flanking sequence of SEQ ID NO: 27. All mature tRNA sequences including upstream and downstream genomic flanking sequences were generated in a pGL4 vector backbone.

Figure 3:
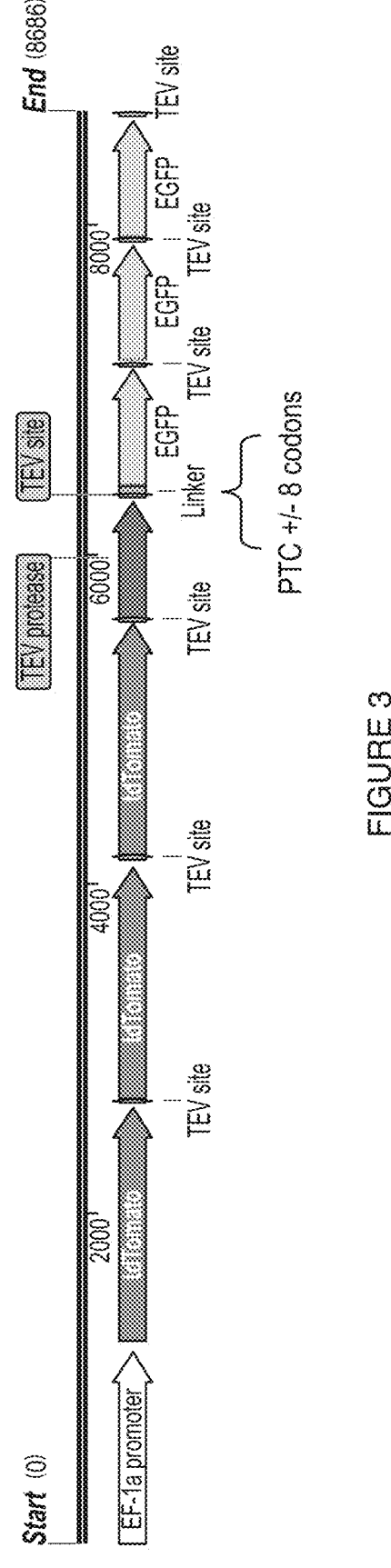
FIG. 3 is a schematic representation of a dual fluorescent reporter construct which contains three copies of a red fluorescent protein (tdTomato), a TEV protease, a 51 bp linker region comprising a PTC+/−8 flanking codons, and three copies of a green fluorescent protein (EGFP). Expression is driven by a promoter for elongation factor EF-1a located upstream of the first copy of tdTomato. All copies of tdTomato, EGFP, and the TEV protease are separated from one another by TEV protease cleavage sites (Glu-Asn-Leu-Tyr-Phe-Gln-(Gly/Ser)).

The Arg$_{TCA}$ suppressors were tested for PTC readthrough activity by flow cytometry in cell lines containing dual fluorescent readthrough reporters. These reporters include three copies of a red fluorescent protein (tdTomato), TEV protease, a linker region containing a PTC, and three copies of a green fluorescent protein (EGFP). A schematic of a reporter construct is shown in FIG. 3. In the absence of any PTC readthrough as a result of a suppressor tRNA, translation will be terminated by the PTC within the linker region, and only tdTomato will be expressed (and therefore only red fluorescence detected). PTC readthrough activity as a result of a suppressor tRNA will allow translation to proceed through the PTC in the linker region, and for both tdTomato and EGFP to be expressed (and therefore both red and green fluorescence detected). Accordingly, readthrough can be assessed by quantifying the percentage of viable cells expressing both the red and green fluorescent reporters above background (double positive %).

To screen for suppressor tRNAs with readthrough activity at PTCs relevant to Dravet syndrome, linker regions were generated containing the PTC and eight flanking codons on either side of the PTC from the SCN1A transcript of two patients with nonsense mutations in the SCN1A gene: subject N and subject S.

The linker region derived from the subject N SCN1A transcript is as follows, and the reporter including this linker region is referred to as the subject N-PTC reporter:

(SEQ ID NO: 28)
CTGAGACCTCTAAGAGCCTTATCTtgaTTTGAAGGGATGAGGGTGGTTGT
G.

A corresponding linker with a wild-type Arg codon in place of the PTC was used as a control, and had the following sequence:

(SEQ ID NO: 193)
CTGAGACCTCTAAGAGCCTTATCTcgaTTTGAAGGGATGAGGGTGGTTGT
G.

The linker region derived from the subject S SCN1A transcript is as follows, and the reporter including this linker region is referred to as the subject S-PTC reporter:

(SEQ ID NO: 29)
ACAAGCCTTTTCAGCTTTAGAGGGtgaGCAAAGGATGTGGGATCTGAGAA
C.

A corresponding linker with a wild-type Arg codon in place of the PTC was used as a control, and had the following sequence:

(SEQ ID NO: 194)
ACAAGCCTTTTCAGCTTTAGAGGGcgaGCAAAGGATGTGGGATCTGAGAA
C.

An additional 51 base pair linker region was derived from a mouse model of Dravet syndrome caused by an R1407X nonsense mutation in SCN1A (Ogiwara et al., 2007, Neurobiology of Disease). The linker region derived from the SCN1A R1407X transcript is as follows, and the reporter including this linker region is referred to as R1407X-PTC reporter:

(SEQ ID NO: 30)
CTAATAGAAAGAAATGAGACCGCCtgaTGGAAAAATGTGAAAGTAAACTT
T.

A corresponding linker with a wild-type Arg codon in place of the PTC was used as a control, and had the following sequence:

(SEQ ID NO: 195)
CTAATAGAAAGAAATGAGACCGCCcggTGGAAAAATGTGAAAGTAAACTT

T.

Figure 5:
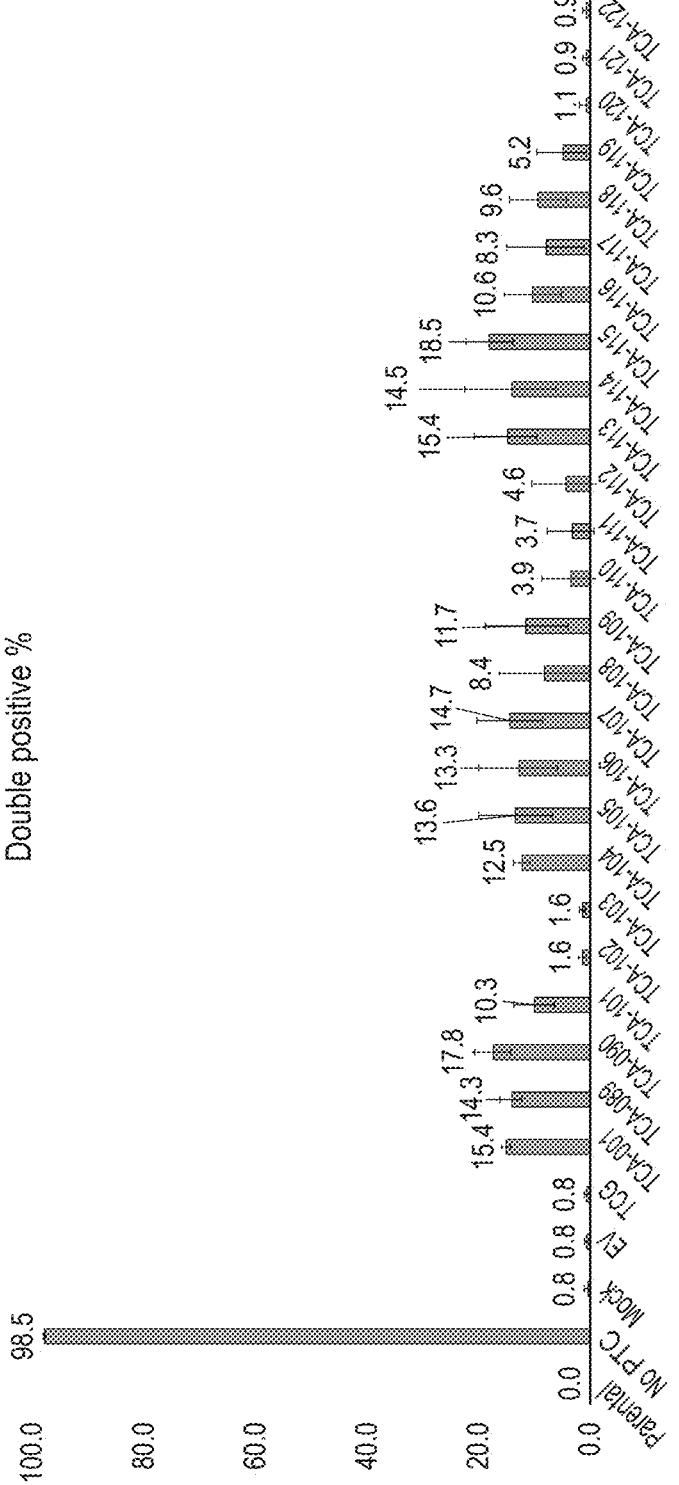
FIG. 5 is a graph depicting readthrough activity of $Arg_{TCA}$ suppressor tRNAs in a Flp-In-3T3 cell line stably expressing a dual fluorescent reporter with the R1407X-PTC linker region (SEQ ID NO: 30), which is derived from a clinically relevant SCN1A nonsense mutation linked to Dravet syndrome. Cells were transfected with the indicated $Arg_{TCA}$ suppressor tRNAs (SEQ ID NOs: 1-25) and readthrough activity was measured by flow cytometry in three independent experiments at 24 hours post transfection. "Parental" indicates the original 3T3 cell line without a fluorescent reporter, "no PTC" indicates an 3T3 cell line stably expressing a dual fluorescent reporter with a version of the R1407X-PTC linker region that lacks a PTC (SEQ ID NO: 195), "Mock" indicates mock-transfected cells, "EV" (empty vector) indicates cells transfected with an expression construct that does not contain a tRNA or an EGFP reporter, "TCG" indicates cells transfected with an expression construct that contained a wild-type Arg-tRNA with a TCG anticodon. Readthrough activity is presented as the percentage of viable cells that that express both tdTomato and EGFP above background ("double positive %"). Error bars represent the standard deviation of the data.
Figure 6:
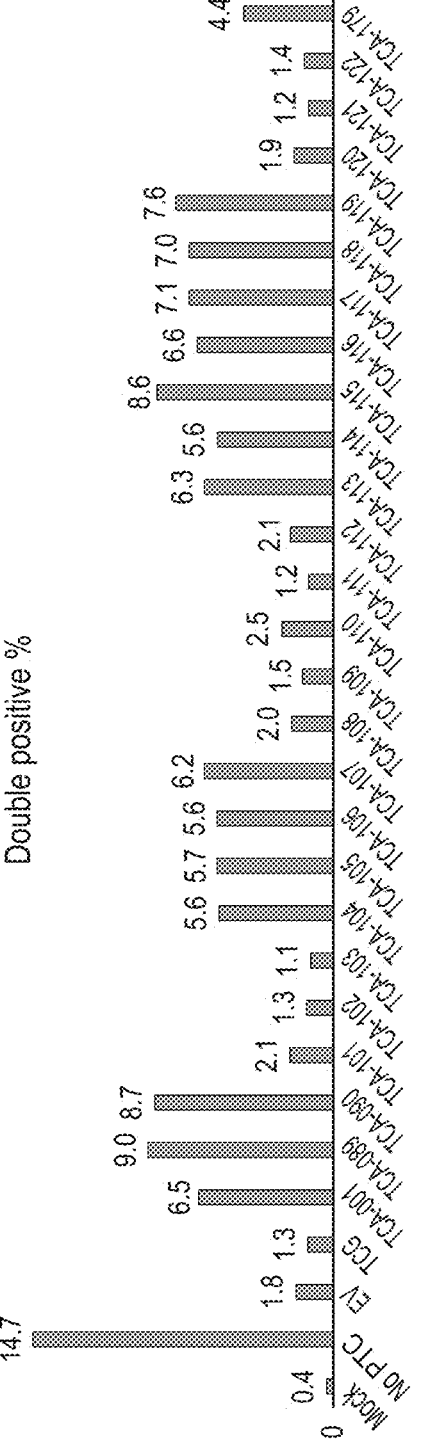
FIG. 6 is a graph depicting readthrough activity of $Arg_{TCA}$ suppressor tRNAs in Flp-In-3T3 cells transiently transfected with a dual fluorescent reporter with the subject N-PTC linker region (SEQ ID NO: 28), which is derived from a clinically relevant SCN1A nonsense mutation linked to Dravet syndrome. Cells were co-transfected with the indicated $Arg_{TCA}$ suppressor tRNAs (SEQ ID NOs: 1-25 and 35) and readthrough activity was measured by flow cytometry. "Mock" indicates mock-transfected cells, "no PTC" indicates cells transfected with a dual fluorescent reporter with a version of the subject N-PTC linker region that lacks a PTC (SEQ ID NO: 193), "EV" (empty vector) indicates cells co-transfected with an expression construct that does not contain a tRNA, "TCG" indicates cells co-transfected with an expression construct that contains a wild-type Arg-tRNA with a TCG anticodon. Readthrough activity was measured by flow cytometry and is presented as the percentage of viable cells that that express both tdTomato and EGFP above background ("double positive %").

Arg$_{TCA}$ suppressors were tested in multiple assay contexts, including (i) a human Flp-In-293 cell line stably expressing the subject S-PTC reporter and transiently transfected with a plasmid encoding an Arg$_{TCA}$ suppressor (results shown in FIG. 4), (ii) a murine Flp-In-3T3 cell line stably expressing the R1407X-PTC reporter and transiently transfected with a plasmid encoding an Arg$_{TCA}$ suppressor (results shown in FIG. 5), and (iii) Flp-In-293 cells transiently co-transfected with plasmids encoding the subject N-PTC reporter and an Arg$_{TCA}$ suppressor tRNA (results shown in FIG. 6). Transfections were done using the Lipofectamine 3000 Transfection Reagent according to the manufacturer's protocol.

Figure 8A:
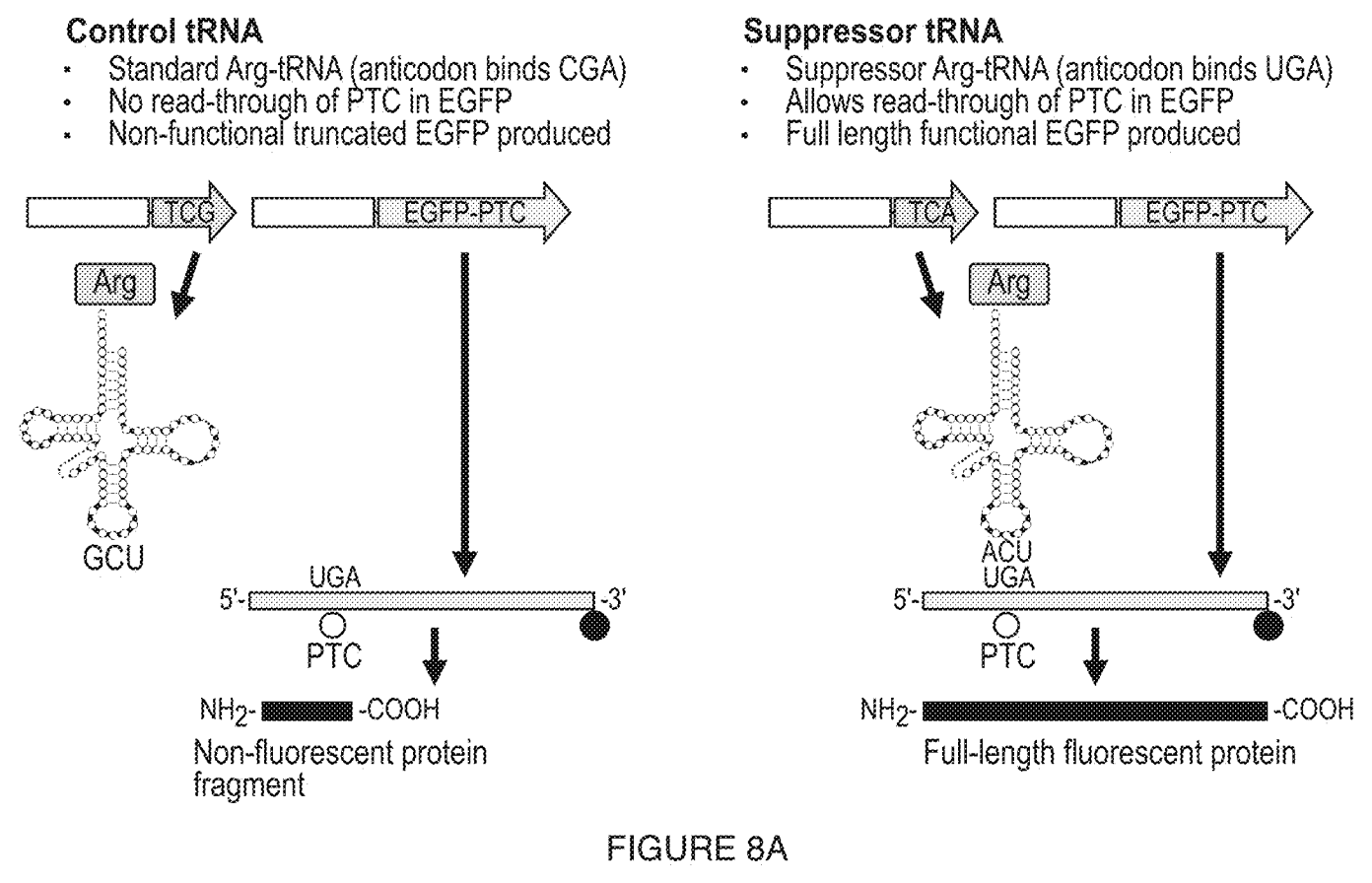

An additional reporter construct was generated including EGFP with a nuclear localization signal (NLS) and containing an arginine-to-TGA mutation (R96X) within the EGFP open reading frame that abolishes fluorescence in the absence of PTC readthrough. The general experimental approach is shown in FIG. 8A. EGFP expression was driven by the CMV early enhancer/chicken 13 actin (CAG) promoter. The reporter construct is referred to as CAG:NLS-EGFP (R96X-TGA) and its sequence is as follows:

(SEQ ID NO: 31)
CGTTACATAACTTACGGTAAATGGCCCGCCTGGCTGACCGCCCAACGACC

CCCGCCCATTGACGTCAATAATGACGTATGTTCCCATAGTAACGCCAATA

GGGACTTTCCATTGACGTCAATGGGTGGAGTATTTACGGTAAACTGCCCA

CTTGGCAGTACATCAAGTGTATCATATGCCAAGTACGCCCCCTATTGACG

TCAATGACGGTAAATGGCCCGCCTGGCATTATGCCCAGTACATGACCTTA

TGGGACTTTCCTACTTGGCAGTACATCTACGTATTAGTCATCGCTATTAC

CATGGTCGAGGTGAGCCCCACGTTCTGCTTCACTCTCCCCATCTCCCCCC

CCTCCCCACCCCCAATTTTGTATTTATTTATTTTTTAATTATTTTGTGCA

GCGATGGGGGCGGGGGGGGGGGGGGGGCGCGCGCCAGGCGGGGCGGGGCG

GGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGG

CGGCCCTATAAAAAGCGAAGCGCGCGGCGGGCGGGAGTCGCTGCGCGCTG

CCTTCGCCCCGTGCCCCGCTCCGCCGCCGCCTCGCGCCGCCCGCCCCGGC

TCTGACTGACCGCGTTACTCCCACAGGTGAGCGGGCGGGACGGCCCTTCT

CCTCCGGGCTGTAATTAGCGCTTGGTTTAATGACGGCTTGTTTCTTTTCT

GTGGCTGCGTGAAAGCCTTGAGGGGCTCCGGGAGCGCCGGCAGGAAGGAA

ATGGGCGGGGAGGGCCTTCGTGCGTCGCCGCGCCGCCGTCCCCTTCTCCC

TCTCCAGCCTCGGGGCTGTCCGCGGGGGACGGCTGCCTTCGGGGGGGAC

GGGGCAGGGCGGGGTTCGGCTTCTGGCGTGTGACCGGCGGCTCTAGAGCC

TCTGCTAACCATGTTCATGCCTTCTTCTTTTTCCTACAGCTCCTGGGCAA

-continued
CGTGCTGGTTATTGTGCTGTCTCATCATTTTGGCAAAGAATTGCGGCCCA

ACGGTACCGGATCCACCGGCCGCCACCATGGGAAGCCCAAAGAAGAAGCG

TAAGGTAATGGTGAGCAAGGGCGAGGAGCTGTTCACCGGGGTGGTGCCCA

TCCTGGTCGAGCTGGACGGCGACGTAAACGGCCACAAGTTCAGCGTGTCC

GGCGAGGGCGAGGGCGATGCCACCTACGGCAAGCTGACCCTGAAGTTCAT

CTGCACCACCGGCAAGCTGCCCGTGCCCTGGCCCACCCTCGTGACCACCC

TGACCTACGGCGTGCAGTGCTTCAGCCGCTACCCCGACCACATGAAGCAG

CACGACTTCTTCAAGTCCGCCATGCCCGAAGGCTACGTCCAGGAGTGAAC

CATCTTCTTCAAGGACGACGGCAACTACAAGACCCGCGCCGAGGTGAAGT

TCGAGGGCGACACCCTGGTGAACCGCATCGAGCTGAAGGGCATCGACTTC

AAGGAGGACGGCAACATCCTGGGGCACAAGCTGGAGTACAACTACAACAG

CCACAACGTCTATATCATGGCCGACAAGCAGAAGAACGGCATCAAGGTGA

ACTTCAAGATCCGCCACAACATCGAGGACGGCAGCGTGCAGCTCGCCGAC

CACTACCAGCAGAACACCCCCATCGGCGACGGCCCCGTGCTGCTGCCCGA

CAACCACTACCTGAGCACCCAGTCCGCCCTGAGCAAAGACCCCAACGAGA

AGCGCGATCACATGGTCCTGCTGGAGTTCGTGACCGCCGCCGGGATCACT

CTCGGCATGGACGAGCTGTACAAGGGAAGCCCCAAGAAAAAGCGGAAGGT

GTAA.

Figure 7:
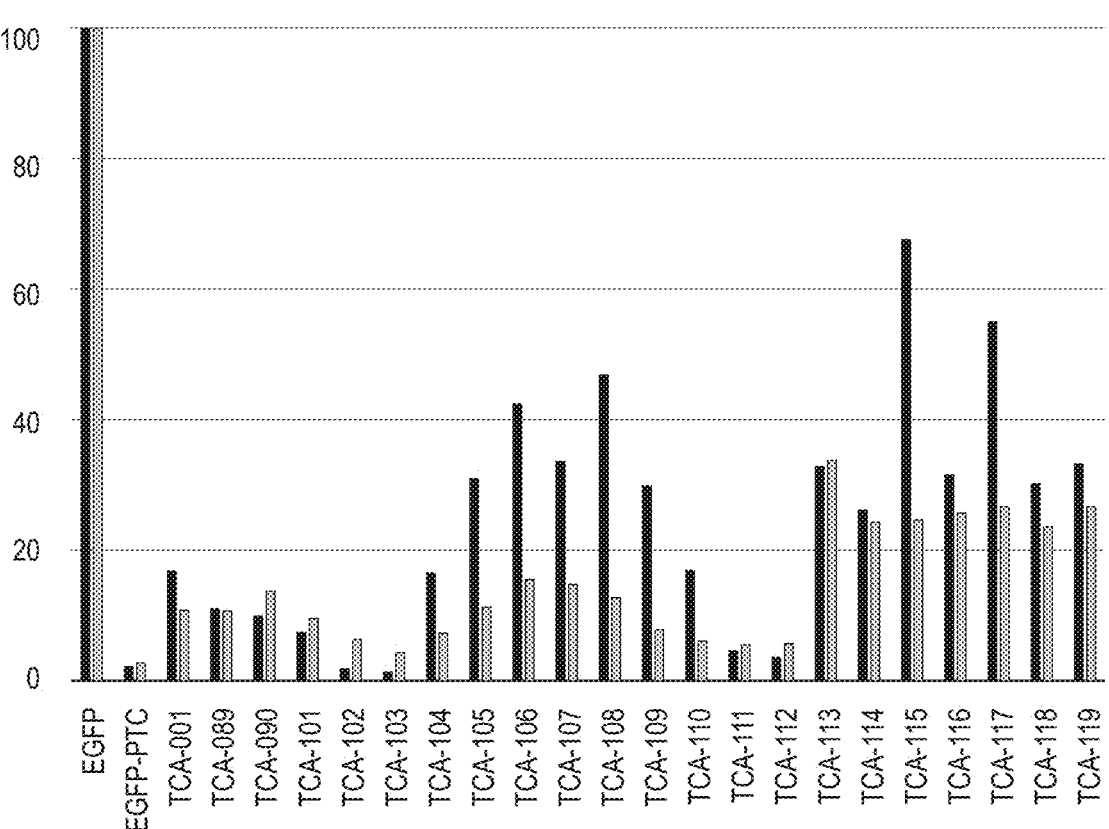
FIG. 7 is a graph depicting readthrough activity of the indicated $Arg_{TCA}$ suppressor tRNAs (as measured by percent positive GFP cells) in Neuro-2a (N2a) and Flp-In-293 (293) cells. Cells were co-transfected with an expression construct containing an EGFP-R96X-TGA reporter (SEQ ID NO: 31) and an expression construct containing the indicated ArgicA suppressor tRNA (SEQ ID NOs: 1-22). "EGFP" indicates cells transfected with a version of the EGFP reporter that lacks a PTC, "EGFP-PTC" indicates cells transfected with the EGFP-R96X-TGA reporter alone. EGFP expression was analyzed by flow cytometry at ~24 hours post transfection in 293 cells and ~48 hours post transfection in N2a cells. Readthrough activity is presented as the percentage of viable cells that express EGFP above background ("% GFP+") with all values normalized to cells expressing EGFP lacking a PTC.

The activity of the Arg$_{TCA}$ suppressors was assessed in HEK293 cells and murine Neuro-2a cells (a neural crest-derived cell line extensively used to study neuronal differentiation) transiently co-transfected with a plasmid encoding the Arg$_{TCA}$ suppressor tRNA and a plasmid encoding the CAG:NLS-EGFP (R96X-TGA) reporter. Transfections were done using the Lipofectamine 3000 Transfection Reagent according to the manufacturer's protocol. Co-transfections were done using equal amounts of the indicated suppressor plasmid and the CAG:NLS-EGFP (R96X-TGA) reporter plasmid. EGFP expression was analyzed by flow cytometry at ~24 hours post transfection in 293 cells and ~48 hours post transfection in Neuro-2a cells. The results are shown in FIG. 7.

In general, the relative readthrough activity of Arg$_{TCA}$ suppressor tRNAs remained consistent across multiple assay formats. The following suppressors reliably showed readthrough activity above baseline: TCA-001 (SEQ ID NO: 11), TCA-89 (SEQ ID NO: 1), TCA-90 (SEQ ID NO: 2), TCA-105 (SEQ ID NO: 7), TCA-106 (SEQ ID NO: 8), TCA-107 (SEQ ID NO: 9), TCA-113 (SEQ ID NO: 16), TCA-114 (SEQ ID NO: 17), TCA-115 (SEQ ID NO: 18), TCA-116 (SEQ ID NO: 19), TCA-117 (SEQ ID NO: 20), TCA-118 (SEQ ID NO: 21), and TCA-119 (SEQ ID NO: 22).

Together, these results demonstrate that the described suppressor tRNAs can facilitate expression of transcripts, e.g., SCN1A transcripts, containing premature termination codons associated with disorders, e.g., Dravet syndrome.

Example 2

This Example describes the impact of expression vector features on the read-through of a premature termination codon (PTC) by arginine aminoacylated suppressor tRNAs.

Figure 8B:
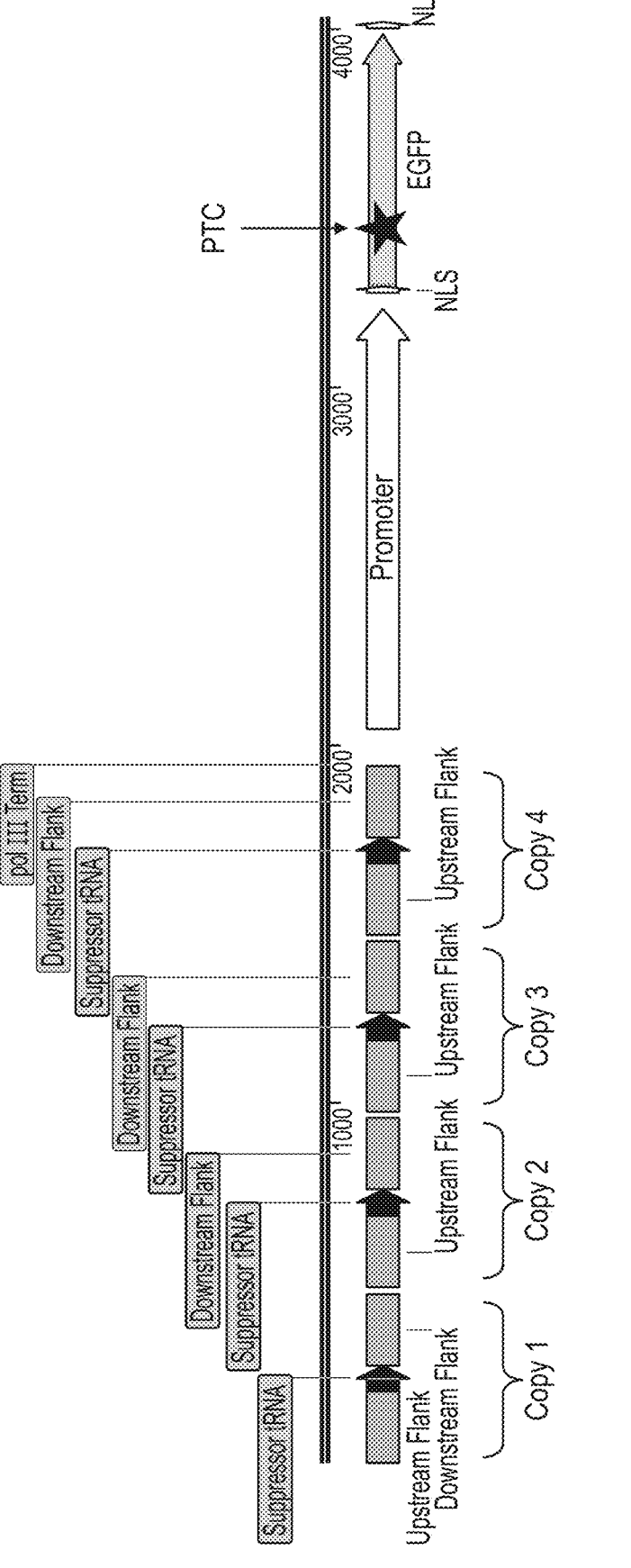
FIG. 8B is a schematic representation of an exemplary reporter construct which contains EGFP with a PTC and 4 copies of a suppressor tRNA.

Expression constructs containing both Arg$_{TCA}$ suppressor tRNAs and EGFP (R96X-TGA) reporters on the same plasmid were generated in a pGL4 vector backbone. These constructs included 1, 2, 3 or 4 copies of Arg$_{TCA}$ suppressor tRNAs 113 (SEQ ID NO: 16), 115 (SEQ ID NO: 18), and 001 (SEQ ID NO: 11) (as described in Example 1 and shown in TABLE 8). Each copy of the tRNA sequences was expressed in the context of either (i) 200 bps upstream genomic flanking sequences from tRNA-Arg-TCG-1-1 (SEQ ID NO: 26) and 200 bps of downstream genomic flanking sequence from tRNA-Arg-TCG-1-1 (SEQ ID NO: 27), (ii) 200 bps upstream genomic flanking sequences from tRNA-Arg-TCG-1-1 (SEQ ID NO: 26) and 104 bps of downstream genomic flanking sequence from tRNA-Arg-TCG-1-1 (SEQ ID NO: 32), or (iii) an upstream U6 promoter including 19 bps of upstream flanking genomic sequence from tRNA-Arg-TCG-1-1 (SEQ ID NO: 33) and 46 bps of downstream flanking genomic sequence from tRNA-Arg-TCG-1-1 (SEQ ID NO: 34). The general experimental approach is shown in FIG. 8A and a schematic of an exemplary reporter construct containing 4 copies of the suppressor tRNA is shown in FIG. 8B. Reporter constructs were either a CAG:NLS-EGFP (R96X-TGA) reporter construct (as described in Example 1) or an EF1a:NLS-EGFP (R96X-TGA) reporter construct in which the CAG promoter was replaced with an elongation factor-1 alpha (EF1a) promoter, whose sequence is as follows:

```
                              (SEQ ID NO: 177)
GGCTCCGGTGCCCGTCAGTGGGCAGAGCGCACATCGCCCACAGTCCCCGA

GAAGTTGGGGGGAGGGGTCGGCAATTGAACCGGTGCCTAGAGAAGGTGGC

GCGGGGTAAACTGGGAAAGTGATGTCGTGTACTGGCTCCGCCTTTTTCCC

GAGGGTGGGGGAGAACCGTATATAAGTGCACTAGTCGCCGTGAACGTTCT

TTTTCGCAACGGGTTTGCCGCCAGAACACAGGTAAGTGCCGTGTGTGGTT

CCCGCGGGCCTGGCCTCTTTACGGGTTATGGCCCTTGCGTGCCTTGAATT

ACTTCCACCTGGCTGCAGTACGTGATTCTTGATCCCGAGCTTCGGGTTGG

AAGTGGGTGGGAGAGTTCGTGGCCTTGCGCTTAAGGAGCCCCTTCGCCTC

GTGCTTGAGTTGTGGCCTGGCCTGGGCGCTGGGGCCGCCGCGTGCGAATC

TGGTGGCACCTTCGCGCCTGTCTCGCTGCTTTCGATAAGTCTCTAGCCAT

TTAAAATTTTTGATGACCTGCTGCGACGCTTTTTTTCTGGCAAGATAGTC

TTGTAAATGCGGGCCAAGATCAGCACACTGGTATTTCGGTTTTTGGGGCC

GCGGGCGGCGACGGGGCCCGTGCGTCCCAGCGCACATGTTCGGCGAGGCG

GGGCCTGCGAGCGCGGCCACCGAGAATCGGACGGGGGTAGTCTCAAGCTG

CCCGGCCTGCTCTGGTGCCTGGCCTCGCGCCGCCGTGTATCGCCCCGCCC

TGGGCGGCAAGGCTGGCCCGGTCGGCACCAGTTGCGTGAGCGGAAAGATG

GCCGCTTCCCGGCCCTGCTGCAGGGAGCACAAAATGGAGGACGCGGCGCT

CGGGAGAGCGGGCGGGTGAGTCACCCACACAAAGGAAAAGGGCCTTTCCG

TCCTCAGCCGTCGCTTCATGTGACTCCACGGAGTACCGGGCGCCGTCCAG

GCACCTCGATTAGTTCTCCAGCTTTTGGAGTACGTCGTCTTTAGGTTGGG

GGGAGGGGTTTTATGCGATGGAGTTTCCCCACACTGAGTGGGTGGAGACT

GAAGTTAGGCCAGCTTGGCACTTGATGTAATTCTCCTTGGAATTTGCCCT

TTTTGAGTTTGGATCTTGGTTCATTCTCAAGCCTCAGACAGTGGTTCAAA

GTTTTTTTCTTCCATTTCAGGTGTCGTGAGGTACCGGATCCACCGGCCGC
```

-continued

```
CACCATGGGAAGCCCAAAGAAGAAGCGTAAGGTAATGGTGAGCAAGGGCG

AGGAGCTGTTCACCGGGGTGGTGCCCATCCTGGTCGAGCTGGACGGCGAC

GTAAACGGCCACAAGTTCAGCGTGTCCGGCGAGGGCGAGGGCGATGCCAC

CTACGGCAAGCTGACCCTGAAGTTCATCTGCACCACCGGCAAGCTGCCCG

TGCCCTGGCCCACCCTCGTGACCACCCTGACCTACGGCGTGCAGTGCTTC

AGCCGCTACCCCGACCACATGAAGCAGCACGACTTCTTCAAGTCCGCCAT

GCCCGAAGGCTACGTCCAGGAGTGAACCATCTTCTTCAAGGACGACGGCA

ACTACAAGACCCGCGCCGAGGTGAAGTTCGAGGGCGACACCCTGGTGAAC

CGCATCGAGCTGAAGGGCATCGACTTCAAGGAGGACGGCAACATCCTGGG

GCACAAGCTGGAGTACAACTACAACAGCCACAACGTCTATATCATGGCCG

ACAAGCAGAAGAACGGCATCAAGGTGAACTTCAAGATCCGCCACAACATC

GAGGACGGCAGCGTGCAGCTCGCCGACCACTACCAGCAGAACACCCCCAT

CGGCGACGGCCCCGTGCTGCTGCCCGACAACCACTACCTGAGCACCCAGT

CCGCCCTGAGCAAAGACCCCAACGAGAAGCGCGATCACATGGTCCTGCTG

GAGTTCGTGACCGCCGCCGGGATCACTCTCGGCATGGACGAGCTGTACAA

GGGAAGCCCCAAGAAAAAGCGGAAGGTGTAA.
```

Neuro-2a cells or HEK293 (Flpin-293) cells were transfected with these constructs and readthrough was assayed by fluorescent imaging or flow cytometry ~24 hours or 48 hours post transfection. Transfections were done using the Lipofectamine 3000 Transfection Reagent according to the manufacturer's protocol.

The results are shown FIGS. 9-10 (fluorescent images) and FIGS. 11-17 (quantification of fluorescent signal as measured by flow cytometry). Improved readthrough upon increased copy number was seen for the 001 and 113 suppressors. Together, the results show that increasing the copy number of the suppressor tRNA modules in reporter constructs often results in enhanced readthrough activity. Additionally, U6-containing constructs exhibited PTC readthrough activity, although generally not as much as was seen for equivalent suppressor tRNAs expressed in the flanking genomic context.

Example 3

This example describes the design of a functional arginine aminoacylated suppressor tRNA that facilitates read-through of a premature termination codon (PTC) in a transcript.

Figure 4:
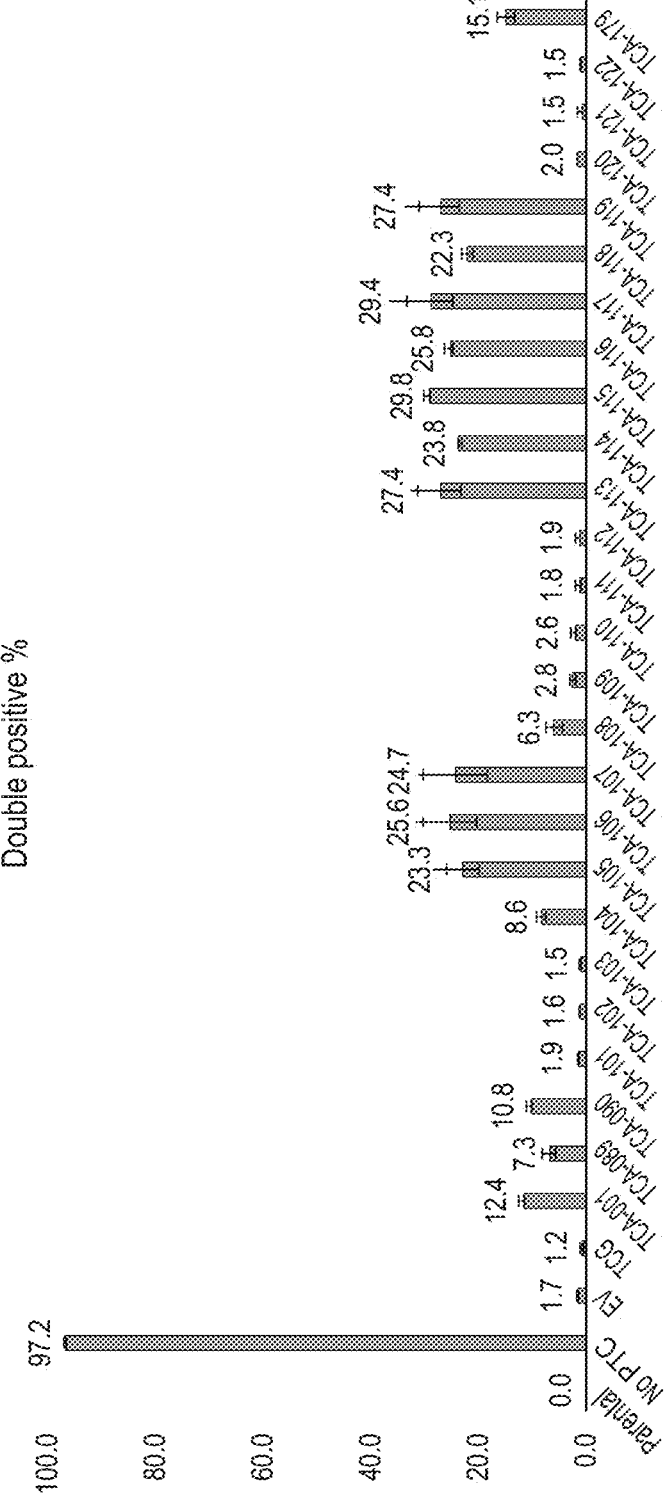
FIG. 4 is a graph depicting readthrough activity of $Arg_{TCA}$ suppressor tRNAs in a Flp-In-293 cell line stably expressing a dual fluorescent reporter with the subject S-PTC linker region (SEQ ID NO: 29), which is derived from a clinically relevant SCN1A nonsense mutation linked to Dravet syndrome. Cells were transfected with the indicated $Arg_{TCA}$ suppressor tRNAs (SEQ ID NOs: 1-25 and 35) and read-through activity was measured by flow cytometry in two independent experiments at 24 hours post-transfection. "Parental" indicates the original Flp-In-293 cell line without a fluorescent reporter, "no PTC" indicates a Flp-In-293 cell line stably expressing a dual fluorescent reporter with a version of the subject S-PTC linker region that lacks a PTC (SEQ ID NO: 194), "EV" (empty vector) indicates cells transfected with an expression construct that does not contain a tRNA, "TCG" indicates cells transfected with an expression construct that contains a wild-type Arg-tRNA with a TCG anticodon. Readthrough activity is presented as the percentage of viable cells that that express both tdTomato and EGFP above background ("Double positive %"). Error bars represent the standard deviation of the data.

C57BL/6J mice have a naturally occurring C-to-T mutation in the T-loop (position 51) of Arg-TCT-5-1 that has been shown to affect pre-tRNA processing and function (Ryuta Ishimura et al., *Science*, 2014). Arg$_{TCA}$ suppressor 120 (as described in Example 1 and shown in TABLE 8) contains a T at position 51. A modified suppressor tRNA was generated that included a substitution of C for Tat position 51 of Arg$_{TCA}$ suppressor 120 (referred to as Arg$_{TCA}$ suppressor 179 and having a nucleotide sequence of SEQ ID NO: 35). Arg$_{TCA}$ suppressors 120 and 179 were tested by transfection into a Flp-In-293 cell line stably expressing the subject S-PTC Reporter and by co-transfection with a plasmid encoding the subject N-PTC reporter into Flp-In-3T3 cells. Transfections were done using the Lipofectamine 3000 Transfection Reagent according to the manufacturer's protocol. Results are shown in FIG. 4 and FIG. 6. While Arg$_{TCA}$ suppressor 120 was non-functional, Arg$_{TCA}$ suppressor 179, containing only a single substitution, showed PTC read-through activity.

Example 4

This Example describes glutamine aminoacylated suppressor tRNAs that facilitate read-through of a premature termination codon (PTC).

Suppressor tRNAs were generated from endogenous mouse glutamine-tRNAs by converting their normal anticodons to TTA or CTA anticodons (referred to as Gln$_{TTA}$ or Gln$_{CTA}$ suppressor tRNAs, respectively). Suppressor tRNA sequences are shown in TABLE 9.

TABLE 9

| SEQ ID NO | Suppressor tRNA ID Number | Suppressor tRNA Name | Suppressor tRNA Sequence (anticodon lowercase) |
|---|---|---|---|
| 36 | 002 | tRNA-Gln-TTG-1-1-TTA-SUP | GGTCCCATGGTGTAATGGTTAGCAC TCTGGACTttaAATCCAGCGATCCG AGTTCAAATCTCGGTGGGACCT |
| 37 | 155 | tRNA-Gln-CTG-1-1-TTA-SUP | GGTTCCATGGTGTAATGGTTAGCAC TCTGGACTttaAATCCAGCGACCCG AGTTCAAATCTCGGTGGGACCT |
| 38 | 156 | tRNA-Gln-CTG-2-1-TTA-SUP | GGTTCCATGGTGTAATGGTTAGCAC TCTGGACTttaAATCCAGCGATCCG AGTTCAAATCTCGGTGGAACCT |
| 39 | 157 | tRNA-Gln-CTG-3-1-TTA-SUP | GGTTCCATGGTGTAATGGTTAGCAC TCTGGACTttaAATCCAGCGATCCG AGTTCAAATCTCGGTGGGACCT |
| 40 | 158 | tRNA-Gln-CTG-4-1-TTA-SUP | GGTTCCATGGTGTAATGGTGAGCAC TCTGGACTttaAATCCAGCGATCCG AGTTCAAATCTCGGTGGGACCT |
| 41 | 159 | tRNA-Gln-CTG-5-1-TTA-SUP | GGTTCCATGGTGTAATGGCTAGCAC TCTGGACTttaAATCCAGCGATCCG AGTTCAAATCTCGGTGGGATTT |
| 42 | 160 | tRNA-Gln-CTG-6-1-TTA-SUP | GGTTCCATGGTGTAATGGTTAGCAC TCTGGACTttaAATCCAGCCATACA AGTTCAAATCTCAGTGGAACCT |
| 43 | 161 | tRNA-Gln-CTG-7-1-TTA-SUP | GGTTCCTTGGTGTAAGATGAGC ACTCTGGATTttaAATCCAGCG ATCAGAGTTCAAATCTCGGTGG GACCT |
| 44 | 162 | tRNA-Gln-TTG-2-1-TTA-SUP | GGTCCCATGGTGTAATGGTTAG CACTCTGGACTttaAATCCAGC AATCTGAGTTCAAATCTCGGTG GGACCT |
| 45 | 163 | tRNA-Gln-TTG-3-1-TTA-SUP | GGCCCCATGGTGTAATGGTTAG CACTCTGGACTttaAATCCAGC GATCCGAGTTCAAATCTCGGTG GGACCT |
| 46 | 164 | tRNA-Gln-TTG-4-1-TTA-SUP | GGTCTCATGGTGTAATGGTTAG CACACTGGACTttaAGTCCAGC AATCCGAGTTCGAGTCTTGGTG AGACCA |
| 47 | 165 | tRNA-Gln-TTG-5-1-TTA-SUP | GGACCCATGGTGTAATGGTTAG CACTCTGGACTttaAATCCAGC AATCCAAGTTCAAATCTCGGTG GGACCT |
| 48 | 166 | tRNA-Gln-TTG-6-1-TTA-SUP | GTTTCCATGGTGTAATGGTTGG CACTCTGGACTttaAATCCAGC AATCCAAGTTCAAGTCTCTGTG GGACCT |
| 178 | 196 | tRNA-Gln-CTG-1-1-CTA-SUP | GGTCCCATGGTGTAATGGTTAG CACTCTGGACTctaAATCCAGC GATCCGAGTTCAAATCTCGGTG GGACCT |

TABLE 9-continued

| SEQ ID NO | Suppressor tRNA ID Number | Suppressor tRNA Name | Suppressor tRNA Sequence (anticodon lowercase) |
|---|---|---|---|
| 179 | 189 | tRNA-Gln-CTG-2-1-CTA-SUP | GGTTCCATGGTGTAATGGTTAG CACTCTGGACTctaAATCCAGC GACCCGAGTTCAAATCTCGGTG GGACCT |
| 180 | 190 | tRNA-Gln-CTG-3-1-CTA-SUP | GGTTCCATGGTGTAATGGTTAG CACTCTGGACTctaAATCCAGC GATCCGAGTTCAAATCTCGGTG GAACCT |
| 181 | 191 | tRNA-Gln-CTG-4-1-CTA-SUP | GGTTCCATGGTGTAATGGTTAG CACTCTGGACTctaAATCCAGC GATCCGAGTTCAAATCTCGGTG GGACCT |
| 182 | 192 | tRNA-Gln-CTG-5-1-CTA-SUP | GGTTCCATGGTGTAATGGTGAG CACTCTGGACTctaAATCCAGC GATCCGAGTTCAAATCTCGGTG GGACCT |
| 183 | 193 | tRNA-Gln-CTG-6-1-CTA-SUP | GGTTCCATGGTGTAATGGCTAG CACTCTGGACTctaAATCCAGC GATCCGAGTTCAAATCTCGGTG GGATTT |
| 184 | 194 | tRNA-Gln-CTG-7-1-CTA-SUP | GGTTCCATGGTGTAATGGTTAG CACTCTGGACTctaAATCCAGC CATACAAGTTCAAATCTCAGTG GAACCT |
| 185 | 195 | tRNA-Gln-TTG-1-1-CTA-SUP | GGTTCCTTGGTGTAAGATGAGC ACTCTGGATTctaAATCCAGCG ATCAGAGTTCAAATCTCGGTGG GACCT |
| 186 | 197 | tRNA-Gln-TTG-2-1-CTA-SUP | GGTCCCATGGTGTAATGGTTAG CACTCTGGACTctaAATCCAGC AATCTGAGTTCAAATCTCGGTG GGACCT |
| 187 | 198 | tRNA-Gln-TTG-3-1-CTA-SUP | GGCCCCATGGTGTAATGGTTAG CACTCTGGACTctaAATCCAGC GATCCGAGTTCAAATCTCGGTG GGACCT |
| 188 | 199 | tRNA-Gln-TTG-4-1-CTA-SUP | GGTCTCATGGTGTAATGGTTAG CACACTGGACTctaAGTCCAGC AATCCGAGTTCGAGTCTTGGTG AGACCA |
| 189 | 200 | tRNA-Gln-TTG-5-1-CTA-SUP | GGACCCATGGTGTAATGGTTAG CACTCTGGACTctaAATCCAGC AATCCAAGTTCAAATCTCGGTG GGACCT |
| 190 | 201 | tRNA-Gln-TTG-6-1-CTA-SUP | GTTTCCATGGTGTAATGGTTGG CACTCTGGACTctaAATCCAGC AATCCAAGTTCAAGTCTCTGTG GGACCT |

In this Example, all mature tRNA sequences were expressed in the context of upstream and downstream genomic flanking sequences (±200 bps) from tRNA-Gln-TTG-1-1— a highly expressed glutamine-tRNA, i.e., the tRNA sequences were expressed with a 5' flanking sequence of SEQ ID NO: 173 and a 3' flanking sequence of SEQ ID NO: 174. All mature tRNA sequences including upstream and downstream genomic flanking sequences were generated in a pGL4 vector backbone.

The Gln$_{TTA}$ suppressors were tested for PTC readthrough activity by flow cytometry in two independently derived Flp-In-293 cell lines containing an integrated fluorescent readthrough reporter. Results are shown in FIG. 18. The reporters included three copies of a red fluorescent protein (tdTomato), TEV protease, a linker region containing a PTC, and three copies of a green fluorescent protein (EGFP). A schematic of the reporter construct is shown in FIG. 3. In the absence of any PTC readthrough as a result of a suppressor tRNA, translation will be terminated by the PTC within the linker region, and only tdTomato will be expressed (and therefore only red fluorescence detected). PTC readthrough activity as a result of a suppressor tRNA will allow translation to proceed through the PTC in the linker region, and for both tdTomato and EGFP to be expressed (and therefore both red and green fluorescence detected). Accordingly, readthrough was assessed with flow cytometry by quantifying the percentage of viable cells expressing both the red and green fluorescent reporters above background (double positive %). The linker was derived from a mouse Dmd$^{mdx}$ transcript, and had the following sequence:

(SEQ ID NO: 192)
CTGCAAAGTTCTTTGAAAGAGCAAtaaAATGGCTTCAACTATCTGAGTGA

C.

A corresponding linker with a wild-type Gln codon in place of the PTC was used as a control, and had the following sequence:

(SEQ ID NO: 191)
CTGCAAAGTTCTTTGAAAGAGCAACAAAATGGCTTCAACTATCTGAGTGA

C.

An additional reporter construct was generated in a pGL4 vector backbone including EGFP with a nuclear localization signal (NLS) and containing a glutamine-to-TAA mutation (Q69X) that abolishes fluorescence in the absence of PTC readthrough. EGFP expression was driven by the CMV early enhancer/chicken β actin (CAG) promoter. The reporter construct is referred to as CAG:NLS-EGFP (Q69X-TAA) and its sequence is as follows:

(SEQ ID NO: 175)
CGTTACATAACTTACGGTAAATGGCCCGCCTGGCTGACCGCCCAACGACC

CCCGCCCATTGACGTCAATAATGACGTATGTTCCCATAGTAACGCCAATA

GGGACTTTCCATTGACGTCAATGGGTGGAGTATTTACGGTAAACTGCCCA

CTTGGCAGTACATCAAGTGTATCATATGCCAAGTACGCCCCCTATTGACG

TCAATGACGGTAAATGGCCCGCCTGGCATTATGCCCAGTACATGACCTTA

TGGGACTTTCCTACTTGGCAGTACATCTACGTATTAGTCATCGCTATTAC

CATGGTCGAGGTGAGCCCCACGTTCTGCTTCACTCTCCCCATCTCCCCCC

CCTCCCCACCCCCAATTTTGTATTTATTTATTTTTTAATTATTTTGTGCA

GCGATGGGGGCGGGGGGGGGGGGGGGGCGCGCGCCAGGCGGGGCGGGGCG

GGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGG

CGGCCCTATAAAAAGCGAAGCGCGCGGCGGGCGGGAGTCGCTGCGCGCTG

CCTTCGCCCCGTGCCCCGCTCCGCCGCCGCCTCGCGCCGCCGCCCCGGC

TCTGACTGACCGCGTTACTCCCACAGGTGAGCGGGCGGGACGGCCCTTCT

CCTCCGGGCTGTAATTAGCGCTTGGTTTAATGACGGCTTGTTTCTTTTCT

GTGGCTGCGTGAAAGCCTTGAGGGGCTCCGGGAGCGCCGGCAGGAAGGAA

ATGGGGGGGGAGGGCCTTCGTGCGTCGCCGCGCCGCCGTCCCCTTCTCCC

TCTCCAGCCTCGGGGCTGTCCGCGGGGGGACGGCTGCCTTCGGGGGGGAC

GGGGCAGGGCGGGGTTCGGCTTCTGGCGTGTGACCGGCGGCTCTAGAGCC

TCTGCTAACCATGTTCATGCCTTCTTCTTTTTCCTACAGCTCCTGGGCAA

CGTGCTGGTTATTGTGCTGTCTCATCATTTTGGCAAAGAATTGCGGCCCA

ACGGTACCGGATCCACCGGCCGCCACCATGGGAAGCCCAAAGAAGAAGCG

-continued
TAAGGTAATGGTGAGCAAGGGCGAGGAGCTGTTCACCGGGGTGGTGCCCA

TCCTGGTCGAGCTGGACGGCGACGTAAACGGCCACAAGTTCAGCGTGTCC

GGCGAGGGCGAGGGCGATGCCACCTACGGCAAGCTGACCCTGAAGTTCAT

CTGCACCACCGGCAAGCTGCCCGTGCCCTGGCCCACCCTCGTGACCACCC

TGACCTACGGCGTGTAATGCTTCAGCCGCTACCCCGACCACATGAAGCAG

CACGACTTCTTCAAGTCCGCCATGCCCGAAGGCTACGTCCAGGAGCGCAC

CATCTTCTTCAAGGACGACGGCAACTACAAGACCCGCGCCGAGGTGAAGT

TCGAGGGCGACACCCTGGTGAACCGCATCGAGCTGAAGGGCATCGACTTC

AAGGAGGACGGCAACATCCTGGGGCACAAGCTGGAGTACAACTACAACAG

CCACAACGTCTATATCATGGCCGACAAGCAGAAGAACGGCATCAAGGTGA

ACTTCAAGATCCGCCACAACATCGAGGACGGCAGCGTGCAGCTCGCCGAC

CACTACCAGCAGAACACCCCCATCGGCGACGGCCCCGTGCTGCTGCCCGA

CAACCACTACCTGAGCACCCAGTCCGCCCTGAGCAAAGACCCCAACGAGA

AGCGCGATCACATGGTCCTGCTGGAGTTCGTGACCGCCGCCGGGATCACT

CTCGGCATGGACGAGCTGTACAAGGGAAGCCCCAAGAAAAAGCGGAAGGT

GTAA.

The activity of the Gln$_{TT4}$ suppressors was assessed by flow cytometry in Neuro-2a cells transiently co-transfected with plasmids encoding a Gln$_{TT4}$ suppressor tRNA and the CAG:NLS-EGFP (Q69X-TAA) reporter. Transfections were done using the Lipofectamine 3000 Transfection Reagent according to the manufacturer's protocol. The results are shown in FIG. 19.

An additional reporter construct was generated in a pGL4 vector backbone including EGFP with a nuclear localization signal (NLS) and containing a glutamine-to-TAG mutation (Q69X) that abolishes fluorescence in the absence of PTC readthrough. EGFP expression is driven by the CMV early enhancer/chicken β actin (CAG) promoter. The reporter construct is referred to as CAG:NLS-EGFP (Q69X-TAG) and its sequence is as follows:

(SEQ ID NO: 176)
CGTTACATAACTTACGGTAAATGGCCCGCCTGGCTGACCGCCCAACGACC

CCCGCCCATTGACGTCAATAATGACGTATGTTCCCATAGTAACGCCAATA

GGGACTTTCCATTGACGTCAATGGGTGGAGTATTTACGGTAAACTGCCCA

CTTGGCAGTACATCAAGTGTATCATATGCCAAGTACGCCCCCTATTGACG

TCAATGACGGTAAATGGCCCGCCTGGCATTATGCCCAGTACATGACCTTA

TGGGACTTTCCTACTTGGCAGTACATCTACGTATTAGTCATCGCTATTAC

CATGGTCGAGGTGAGCCCCACGTTCTGCTTCACTCTCCCCATCTCCCCCC

CCTCCCCACCCCCAATTTTGTATTTATTTATTTTTTAATTATTTTGTGCA

GCGATGGGGGCGGGGGGGGGGGGGGGGCGCGCGCCAGGCGGGGCGGGGCG

GGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGG

CGGCCCTATAAAAAGCGAAGCGCGCGGCGGGCGGGAGTCGCTGCGCGCTG

CCTTCGCCCCGTGCCCCGCTCCGCCGCCGCCTCGCGCCGCCGCCCCGGC

-continued

```
TCTGACTGACCGCGTTACTCCCACAGGTGAGCGGGCGGGACGGCCCTTCT

CCTCCGGGCTGTAATTAGCGCTTGGTTTAATGACGGCTTGTTTCTTTTCT

GTGGCTGCGTGAAAGCCTTGAGGGGCTCCGGGAGCGCCGGCAGGAAGGAA

ATGGGCGGGGAGGGCCTTCGTGCGTCGCCGCGCCGCCGTCCCCTTCTCCC

TCTCCAGCCTCGGGGCTGTCCGCGGGGGGACGGCTGCCTTCGGGGGGGAC

GGGGCAGGGCGGGGTTCGGCTTCTGGCGTGTGACCGGCGGCTCTAGAGCC

TCTGCTAACCATGTTCATGCCTTCTTCTTTTTCCTACAGCTCCTGGGCAA

CGTGCTGGTTATTGTGCTGTCTCATCATTTTGGCAAAGAATTGCGGCCCA

ACGGTACCGGATCCACCGGCCGCCACCATGGGAAGCCCAAAGAAGAAGCG

TAAGGTAATGGTGAGCAAGGGCGAGGAGCTGTTCACCGGGGTGGTGCCCA

TCCTGGTCGAGCTGGACGGCGACGTAAACGGCCACAAGTTCAGCGTGTCC

GGCGAGGGCGAGGGCGATGCCACCTACGGCAAGCTGACCCTGAAGTTCAT

CTGCACCACCGGCAAGCTGCCCGTGCCCTGGCCCACCCTCGTGACCACCC

TGACCTACGGCGTGTAGTGCTTCAGCCGCTACCCCGACCACATGAAGCAG

CACGACTTCTTCAAGTCCGCCATGCCCGAAGGCTACGTCCAGGAGCGCAC

CATCTTCTTCAAGGACGACGGCAACTACAAGACCCGCGCCGAGGTGAAGT

TCGAGGGCGACACCCTGGTGAACCGCATCGAGCTGAAGGGCATCGACTTC

AAGGAGGACGGCAACATCCTGGGGCACAAGCTGGAGTACAACTACAACAG

CCACAACGTCTATATCATGGCCGACAAGCAGAAGAACGGCATCAAGGTGA

ACTTCAAGATCCGCCACAACATCGAGGACGGCAGCGTGCAGCTCGCCGAC

CACTACCAGCAGAACACCCCCATCGGCGACGGCCCCGTGCTGCTGCCCGA

CAACCACTACCTGAGCACCCAGTCCGCCCTGAGCAAAGACCCCAACGAGA

AGCGCGATCACATGGTCCTGCTGGAGTTCGTGACCGCCGCCGGGATCACT

CTCGGCATGGACGAGCTGTACAAGGGAAGCCCCAAGAAAAAGCGGAAGGT

GTAA.
```

The activity of the $Gln_{CTA}$ suppressors was assessed in Neuro-2a cells transiently co-transfected with plasmids encoding a $Gln_{CTA}$ suppressor tRNA and the CAG:NLS-EGFP (Q69X-TAG) reporter. The results are shown in FIG. 20.

Together, these results demonstrate that the described suppressor tRNAs can facilitate expression of transcripts containing premature termination codons associated with disorders.

Example 5

This Example describes readthrough activity of disclosed suppressor tRNAs and small molecule nonsense suppression therapies.

Disclosed suppressor tRNAs were tested alongside non-sense suppression drugs translarna (ataluren), gentamicin, and G418 (geneticin). PTC readthrough activity was measured in Neuro-2a cells ~48 hours after transfection with an expression construct containing a CAG:NLS-EGFP (R96X-TGA) reporter (as described in Example 1) and either (i) including an $Arg_{TCA}$ suppressor tRNA at the indicated copy number on the same construct, or (ii) treated with ataluren, (iii) treated with gentamicin, or (iv) treated with G418. Transfections were performed using the Lipofectamine 3000 Transfection Reagent according to the manufacturer's protocol. For all experimental conditions, cell culture medium was replaced with fresh medium ~6 hours after transfection and the indicated drugs at the indicated concentrations were added at this point. PTC readthrough activity was measured as the percentage of EGFP positive cells. A reporter containing wildtype EGFP without a PTC was used as a control. Cell viability in cells receiving the same set of treatments was assessed by flow cytometry following staining with 7-Amino Actinomycin D (7-AAD; Thermo Fisher Scientific #006993-50), a membrane impermeant dye that is generally excluded from viable cells, which was used according to the manufacturer's protocol. The results are shown in FIGS. 21-23. Together, the results demonstrate that the $Arg_{TCA}$ suppressor tRNA #115 (SEQ ID NO: 18) produces far greater readthrough than any of the nonsense suppression drugs. Additionally, the results show that, unlike for any of the nonsense suppression drugs, treatment with the $Arg_{TCA}$ suppressor tRNA is not accompanied by a decrease in cell viability.

Example 6

This Example describes aminoacylated suppressor tRNAs that facilitate read-through of a premature termination codon (PTC).

Suppressor tRNAs are generated from endogenous mouse tRNAs by converting their normal anticodons to anticodons that recognize premature termination codons (PTCs). Suppressor tRNA sequences are shown in TABLE 10.

TABLE 10

| SEQ ID NO | Suppressor tRNA Name | Suppressor tRNA Sequence |
|---|---|---|
| 49 | pre-tRNA-Leu-CAA->cta--1-1 | GTCAGGATGGCCGAGTGGTCTAAGGCGCCAGACTctaGCTATGGCTTCCTCGCTCTGAGGGTTCTGGTCTCCCCTGGAGGCGTGGGTTCGAATCCCACTTCTGACA |
| 50 | pre-tRNA-Leu-CAA->cta--2-1 | GTCAGGATGGCCGAGTGGTCTAAGGCGCCAGACTctaGCTTAGCTTCCCTGTCTGGGGATTCTGGTCTCCGTATGGAGGCGTGGGTTCGAATCCCACTTCTGACA |

TABLE 10-continued

| SEQ ID NO | Suppressor tRNA Name | Suppressor tRNA Sequence |
|---|---|---|
| 51 | pre-tRNA-Leu-CAA->cta--3-1 | GTCAGGATGGCCGAGTGGTCTAAGGC GCCAGACTctaGGTGACAAGCCTTAC CTACGGGTGTTCTGGTCTCCGAATGG AGGCGTGGGTTCGAATCCCACTTCTG ACA |
| 52 | pre-tRNA-Leu-CAA->cta--4-1 | GTCAGGATGGCCGAGTGGTCTAAGGC GCCAGACTctaGCGTTCGCTTCCTCT ACTGAGGGTTCTGGTCTCCGTGTGGA GGCGTGGGTTCGAATCCCACTTCTGA CA |
| 53 | pre-tRNA-Leu-CAA->tca--1-1 | GTCAGGATGGCCGAGTGGTCTAAGGC GCCAGACTtcaGCTATGGCTTCCTCG CTCTGAGGGTTCTGGTCTCCCCTGGA GGCGTGGGTTCGAATCCCACTTCTGA CA |
| 54 | pre-tRNA-Leu-CAA->tca--2-1 | GTCAGGATGGCCGAGTGGTCTAAGGC GCCAGACTtcaGCTTAGCTTCCCTGT CTGGGGATTCTGGTCTCCGTATGGAG GCGTGGGTTCGAATCCCACTTCTGAC A |
| 55 | pre-tRNA-Leu-CAA->tca--3-1 | GTCAGGATGGCCGAGTGGTCTAAGGC GCCAGACTtcaGGTGACAAGCCTTAC CTACGGGTGTTCTGGTCTCCGAATGG AGGCGTGGGTTCGAATCCCACTTCTG ACA |
| 56 | pre-tRNA-Leu-CAA->tca--4-1 | GTCAGGATGGCCGAGTGGTCTAAGGC GCCAGACTtcaGCGTTCGCTTCCTCT ACTGAGGGTTCTGGTCTCCGTGTGGA GGCGTGGGTTCGAATCCCACTTCTGA CA |
| 57 | pre-tRNA-Leu-CAA->tta--1-1 | GTCAGGATGGCCGAGTGGTCTAAGGC GCCAGACTttaGCTATGGCTTCCTCG CTCTGAGGGTTCTGGTCTCCCCTGGA GGCGTGGGTTCGAATCCCACTTCTGA CA |
| 58 | pre-tRNA-Leu-CAA->tta--2-1 | GTCAGGATGGCCGAGTGGTCTAAGGC GCCAGACTttaGCTTAGCTTCCCTGT CTGGGGATTCTGGTCTCCGTATGGAG GCGTGGGTTCGAATCCCACTTCTGAC A |
| 59 | pre-tRNA-Leu-CAA->tta--3-1 | GTCAGGATGGCCGAGTGGTCTAAGGC GCCAGACTttaGGTGACAAGCCTTAC CTACGGGTGTTCTGGTCTCCGAATGG AGGCGTGGGTTCGAATCCCACTTCTG ACA |
| 60 | pre-tRNA-Leu-CAA->tta--4-1 | GTCAGGATGGCCGAGTGGTCTAAGGC GCCAGACTttaGCGTTCGCTTCCTCT ACTGAGGGTTCTGGTCTCCGTGTGGA GGCGTGGGTTCGAATCCCACTTCTGA CA |
| 61 | pre-tRNA-Tyr-GTA->cta--1-1 | CCTTCGATAGCTCAGTTGGTAGAGCG GAGGACTctaGAGTTACTAGAATAGT GATCCTTAGGTCGCTGGTTCGAATCC GGCTCGAAGGA |
| 62 | pre-tRNA-Tyr-GTA->cta--2-1 | CCTTCGATAGCTCAGTTGGTAGAGCG GAGGACTctaGTCAGTACAATATGGT AATCCTTAGGTCGCTGGTTCGATTCC GGCTCGAAGGA |
| 63 | pre-tRNA-Tyr-GTA->cta--3-1 | CCTTCGATAGCTCAGCTGGTAGAGCG GAGGACTctaGGCTTGTGGCTGTGGA CATCCTTAGGTCGCTGGTTCGATTCC GGCTCGAAGGA |

TABLE 10-continued

| SEQ ID NO | Suppressor tRNA Name | Suppressor tRNA Sequence |
|---|---|---|
| 64 | pre-tRNA-Tyr-GTA->cta--4-1 | CCTTCGATAGCTCAGCTGGTAGAGCG GAGGACTctaGCTAACTCCCCGTTAG AAGACATCCTTAGGTCGCTGGTTCGA CTCCGGCTCGAAGGA |
| 65 | pre-tRNA-Tyr-GTA->cta--5-1 | CTTTCGATAGTTCAGTTGGTAGAGCG GAGGACTctaGAGTATTAACGTTGGT GATCCTTAGGTCGCTGGTTCGAGTCC GGCTCGAAGGA |
| 66 | pre-tRNA-Tyr-GTA->tta--1-1 | CCTTCGATAGCTCAGTTGGTAGAGCG GAGGACTttaGAGTTACTAGAATAGT GATCCTTAGGTCGCTGGTTCGAATCC GGCTCGAAGGA |
| 67 | pre-tRNA-Tyr-GTA->tta--2-1 | CCTTCGATAGCTCAGTTGGTAGAGCG GAGGACTttaGTCAGTACAATATGGT AATCCTTAGGTCGCTGGTTCGATTCC GGCTCGAAGGA |
| 68 | pre-tRNA-Tyr-GTA->tta--3-1 | CCTTCGATAGCTCAGCTGGTAGAGCG GAGGACTttaGGCTTGTGGCTGTGGA CATCCTTAGGTCGCTGGTTCGATTCC GGCTCGAAGGA |
| 69 | pre-tRNA-Tyr-GTA->tta--4-1 | CCTTCGATAGCTCAGCTGGTAGAGCG GAGGACTttaGCTAACTCCCCGTTAG AAGACATCCTTAGGTCGCTGGTTCGA CTCCGGCTCGAAGGA |
| 70 | pre-tRNA-Tyr-GTA->tta--5-1 | CTTTCGATAGTTCAGTTGGTAGAGCG GAGGACTttaGAGTATTAACGTTGGT GATCCTTAGGTCGCTGGTTCGAGTCC GGCTCGAAGGA |
| 71 | tRNA-Cys-GCA->tca--1-1 | GGGGGTATAGCTCAGTGGTAGAGCAT TTGACTtcaGATCAAGAGGTCCCTGG TTCAAATCCAGGTGCCCCCT |
| 72 | tRNA-Cys-GCA->tca--10-1 | GGGGGTATAGCTCAGGGGTAGAGCAT TTGACTtcaGATCAAGAGGTCCCTGG TTCAAATCCAGATGCCCCCT |
| 73 | tRNA-Cys-GCA->tca--11-1 | GGGGGTATAGCTCAGGGGTAGAGTAT TTGGCTtcaGATCAAGAGGTCCCTGG TTCAAATCCAGGTGCCCCCT |
| 74 | tRNA-Cys-GCA->tca--12-1 | GGGGGTATAGCTCAGGGGTAGAGCAT TTGACTtcaGATCAAGAGGTCCTTGG TTCAAATCCAGGTGTCCCCT |
| 75 | tRNA-Cys-GCA->tca--13-1 | GGGGGTATAGCTCAGAGGTAGAGCAT TTGACTtcaGATCAAGAGATCTCTGG TTCAAATCCAGGTGCCCCCT |
| 76 | tRNA-Cys-GCA->tca--14-1 | GGGGGTATAGCTCAGGGGTAGAGCAT TTGACTtcaGATCAAGAGGTCCCTAG TTCAAATCCAGGTGCCCCCT |
| 77 | tRNA-Cys-GCA->tca--15-1 | GGTGGTATAGCTCAGGGGTAGAGCAT TTGACTtcaGATCAAGAGATCCCTGG TTCGAATCCAGGTGCCCCCT |
| 78 | tRNA-Cys-GCA->tca--16-1 | GGGGGTATAACTCAGGGGTAGAGCAT TTGACTtcaGATCAAGAGGTCCCTGG TTCAAATCCAGGTGCCCCCT |
| 79 | tRNA-Cys-GCA->tca--17-1 | TGGGGTATAGCTCAGGGGTAGAGCAT TTGACTtcaGATCAAGAGGTCCCTGG TTCAAATCCAGGTGCCCCCT |
| 80 | tRNA-Cys-GCA->tca--18-1 | GGGGGTATAGCTCAGAGGAAGAGCAT TTGACTtcaGATCAAGAGGTCCCTGA TTCAAATCCAGGTGCCCCCT |

TABLE 10-continued

| SEQ ID NO | Suppressor tRNA Name | Suppressor tRNA Sequence |
|---|---|---|
| 81 | tRNA-Cys-GCA->tca--19-1 | GGGGGTAAAGCTCAGGGGTAGAGCAT TTGACTtcaGATTAAGAGGTCCCTGG TTCAAATCCAGGTACCCCCT |
| 82 | tRNA-Cys-GCA->tca--2-1 | GGGGGTATAGCTCAGTGGTAGAGCAT TTGACTtcaGATCAAGAGGTCCCTGG TTCAAATCCGGGTGCCCCCT |
| 83 | tRNA-Cys-GCA->tca--21-1 | GGGGTTATAGCTCAGGTGTAGAGCAT TTGACTtcaGATCAAGAGGTCCCTGG TTCAAATCCAGGTGCCCCCT |
| 84 | tRNA-Cys-GCA->tca--24-1 | GGGGGTATAGCTCAGGGGTAGAGCAT TTGACTtcaGATCACGAGGTCCCTGG TTCAAATCGAGGTGCCCCCT |
| 85 | tRNA-Cys-GCA->tca--25-1 | GGGGGTATAGCTCAGGGGTGGAGCAT TTGACTtcaGATCAAGGGGTCCCTGT TTCAAATCCAGGTGCCCCCT |
| 86 | tRNA-Cys-GCA->tca--3-1 | GGGGGTATAGCTCAGTGGTAGAGCAT TTGACTtcaGATCAAGAGGTCCCGG TTCAAATCCGGGTGCCCCCT |
| 87 | tRNA-Cys-GCA->tca--4-1 | GGGGGTATAGCTCAGGGGTAGAGCAT TTGACTtcaGATCAAGAGGTCCCTGG TTCAAATCCAGGTGCCCCCT |
| 88 | tRNA-Cys-GCA->tca--5-1 | GGGGGTATAGCTCAGGGGTAGAGCAT TTGACTtcaGATCAAGAGGTCCCTGG TTCAAATCCGGGTGCCCCCT |
| 89 | tRNA-Cys-GCA->tca--6-1 | GGGGGTATAGCTCAGGGGTAGAGCAT TTGACTtcaGATCAAGAGGTCCCTGG TTCAAATCCAGGTACCCCCT |
| 90 | tRNA-Cys-GCA->tca--7-1 | GGGGGTATAGCTCAGGGGTAGAGCAT TTGACTtcaGATCAAGAGGTCCCGG TTCAAATCCGGGTGCCCCCT |
| 91 | tRNA-Cys-GCA->tca--8-1 | GGGGGCATAGCTCAGGGGTAGAGCAT TTGACTtcaGATCAAGAGGTCCCGG TTCAAATCCGGGTGCTCCCT |
| 92 | tRNA-Cys-GCA->tca--9-1 | GGGGGTATAGCTCAGGGGTAGAGCAT TTGACTtcaGATTAAGAGGTCCCTGG TTCAAATCCAGGTGCCCCCT |
| 93 | tRNA-Glu-CTC->cta--1-1 | TCCCTGGTGGTCTAGTGGTTAGGATT CGGCGCTctaACCGCCGCGGCCCGGG TTCGATTCCCGGTCAGGGAA |
| 94 | tRNA-Glu-CTC->cta--2-1 | TCCCTGGTGGTCTAGTGGTTAGGATT TGGCGCTctaACCGCCGCGGCCTGGG TTCGATTCCCGGTCAGGGAA |
| 95 | tRNA-Glu-CTC->cta--5-1 | TCCCTGGTGGTCTAGTGGTTAGGCTT TGGTGCTctaACCTCCATGGCCCAGG TTTGATTCCTGGTCAGGGAA |
| 96 | tRNA-Glu-CTC->tta--1-1 | TCCCTGGTGGTCTAGTGGTTAGGATT CGGCGCTttaACCGCCGCGGCCCGGG TTCGATTCCCGGTCAGGGAA |
| 97 | tRNA-Glu-CTC->tta--2-1 | TCCCTGGTGGTCTAGTGGTTAGGATT TGGCGCTttaACCGCCGCGGCCTGGG TTCGATTCCCGGTCAGGGAA |
| 98 | tRNA-Glu-CTC->tta--5-1 | TCCCTGGTGGTCTAGTGGTTAGGCTT TGGTGCTttaACCTCCATGGCCCAGG TTTGATTCCTGGTCAGGGAA |
| 99 | tRNA-Glu-TTC->cta--1-1 | TCCCACATGGTCTAGCGGTTAGGATT CCTGGTTctaACCCAGGCGGCCCGGG TTCGACTCCCGGTGTGGGAA |

TABLE 10-continued

| SEQ ID NO | Suppressor tRNA Name | Suppressor tRNA Sequence |
|---|---|---|
| 100 | tRNA-Glu-TTC->cta--2-1 | TCCCATATGGTCTAGCGGTTAGGATT CCTGGTTctaACCCAGGCGGCCCGGG TTCGACTCCCGGTATGGGAA |
| 101 | tRNA-Glu-TTC->cta--3-1 | TCCCTGGTGGTCTAGTGGCTAGGATT CGGCGCTctaACCGCCGCGGCCCGGG TTCGATTCCCGGTCAGGGAA |
| 102 | tRNA-Glu-TTC->tta--1-1 | TCCCACATGGTCTAGCGGTTAGGATT CCTGGTTttaACCCAGGCGGCCCGGG TTCGACTCCCGGTGTGGGAA |
| 103 | tRNA-Glu-TTC->tta--2-1 | TCCCATATGGTCTAGCGGTTAGGATT CCTGGTTttaACCCAGGCGGCCCGGG TTCGACTCCCGGTATGGGAA |
| 104 | tRNA-Glu-TTC->tta--3-1 | TCCCTGGTGGTCTAGTGGCTAGGATT CGGCGCTttaACCGCCGCGGCCCGGG TTCGATTCCCGGTCAGGGAA |
| 105 | tRNA-Gly-ACC->tca--1-1 | GTTTCCGTAGTGTAGTGGTTAGCGCG TTCGCCTtcaAAAGCGAAAGGTCCCC GGTTCGAAACCGGGCGGAAACA |
| 106 | tRNA-Gly-CCC->tca--1-1 | GCGCCGCTGGTGTAGTGGTATCATGC AAGATTtcaATTCTTGCGACCCGGGT TCGATTCCCGGGCGGCGCA |
| 107 | tRNA-Gly-CCC->tca--2-1 | GCATTGGTAGTTCAATGGTAGAATTC TCGCCTtcaACGCGGGTGACCCGGGT TCGATTCCCGGCCAATGCA |
| 108 | RNA-Gly-CCC->tca--3-1 | GCATTGGTGGTTCAATGGTAGAATTC TCGCCTtcaACGCGGGTGACCCGGGT TCGATTCCCGGCCAATGCA |
| 109 | tRNA-Gly-CCC->tca--4-1 | GCATTGGTGGTTCAATGGTAGAATTC TCGCCTtcaACTCGGGTGACCCGGGT TCGATTCCCGGCCAATGCA |
| 110 | tRNA-Gly-GCC->tca--1-1 | GCATGGGTGGTTCAGTGGTAGAATTC TCGCCTtcaACGCGGGAGGCCCGGGT TCGATTCCCGGCCCATGCA |
| 111 | tRNA-Gly-GCC->tca--2-1 | GCATTGGTGGTTCAGTGGTAGAATTC TCGCCTtcaACGCGGGAGGCCCGGGT TCGATTCCCGGCCAATGCA |
| 112 | tRNA-Gly-GCC->tca--3-1 | GCATTGGTGGTTCAGTGGTAGAATTC TCGCCTtcaACGCGGGAGGCCCGGGT TTGATTCCCGGCCAATGCA |
| 113 | tRNA-Gly-GCC->tca--4-1 | GCATTGGTGGTTCAGTGGTAGAATTC TCGCCTtcaACGCGGGAGGCCCGGGT TCGGTTCCCGGCCAATGCA |
| 114 | tRNA-Gly-TCC->tca--1-1 | GCGTTGGTGGTATAGTGGTGAGCATA GCTGCCTtcaAAGCAGTTGACCCGGG TTCGATTCCCGGCCAACGCA |
| 115 | tRNA-Leu-AAG->cta--1-1 | GGTAGCGTGGCCGAGCGGTCTAAGGC GCTGGATTctaGCTCCAGTCTCTTCG GGGGCGTGGGTTCGAATCCCACCGCT GCCA |
| 116 | tRNA-Leu-AAG->cta--2-1 | GGTAGTGTGGCCGAGCGGTCTAAGGC GCTGGATTctaGCTCCAGTCTCTTCG GGGGCGTGGGTTCGAATCCCACCGCT GCCA |
| 117 | tRNA-Leu-AAG->cta--3-1 | GGTAGTGTGGCCGAGCGGTCTAAGGC GCTGGATTctaGCTCCAGTCTCTTCG GGGGCGTGGGTTCGAATCCCACCACT GCCA |

TABLE 10-continued

| SEQ ID NO | Suppressor tRNA Name | Suppressor tRNA Sequence |
|---|---|---|
| 118 | tRNA-Leu-AAG->tca--1-1 | GGTAGCGTGGCCGAGCGGTCTAAGGC GCTGGATTtcaGCTCCAGTCTCTTCG GGGGCGTGGGTTCGAATCCCACCGCT GCCA |
| 119 | tRNA-Leu-AAG->tca--2-1 | GGTAGTGTGGCCGAGCGGTCTAAGGC GCTGGATTtcaGCTCCAGTCTCTTCG GGGGCGTGGGTTCGAATCCCACCGCT GCCA |
| 120 | tRNA-Leu-AAG->tca--3-1 | GGTAGTGTGGCCGAGCGGTCTAAGGC GCTGGATTtcaGCTCCAGTCTCTTCG GGGGCGTGGGTTCGAATCCCACCACT GCCA |
| 121 | tRNA-Leu-AAG->tta--1-1 | GGTAGCGTGGCCGAGCGGTCTAAGGC GCTGGATTttaGCTCCAGTCTCTTCG GGGGCGTGGGTTCGAATCCCACCGCT GCCA |
| 122 | tRNA-Leu-AAG->tta--2-1 | GGTAGTGTGGCCGAGCGGTCTAAGGC GCTGGATTttaGCTCCAGTCTCTTCG GGGGCGTGGGTTCGAATCCCACCGCT GCCA |
| 123 | tRNA-Leu-AAG->tta--3-1 | GGTAGTGTGGCCGAGCGGTCTAAGGC GCTGGATTttaGCTCCAGTCTCTTCG GGGGCGTGGGTTCGAATCCCACCACT GCCA |
| 124 | tRNA-Leu-CAA->cta--1-1 | GTCAGGATGGCCGAGTGGTCTAAGGC GCCAGACTctaGTTCTGGTCTCCCCT GGAGGCGTGGGTTCGAATCCCACTTC TGACA |
| 125 | tRNA-Leu-CAA->cta--2-1 | GTCAGGATGGCCGAGTGGTCTAAGGC GCCAGACTctaGTTCTGGTCTCCGTA TGGAGGCGTGGGTTCGAATCCCACTT CTGACA |
| 126 | tRNA-Leu-CAA->cta--3-1 | GTCAGGATGGCCGAGTGGTCTAAGGC GCCAGACTctaGTTCTGGTCTCCGAA TGGAGGCGTGGGTTCGAATCCCACTT CTGACA |
| 127 | tRNA-Leu-CAA->cta--4-1 | GTCAGGATGGCCGAGTGGTCTAAGGC GCCAGACTctaGTTCTGGTCTCCGTG TGGAGGCGTGGGTTCGAATCCCACTT CTGACA |
| 128 | tRNA-Leu-CAA->tca--1-1 | GTCAGGATGGCCGAGTGGTCTAAGGC GCCAGACTtcaGTTCTGGTCTCCCCT GGAGGCGTGGGTTCGAATCCCACTTC TGACA |
| 129 | tRNA-Leu-CAA->tca--2-1 | GTCAGGATGGCCGAGTGGTCTAAGGC GCCAGACTtcaGTTCTGGTCTCCGTA TGGAGGCGTGGGTTCGAATCCCACTT CTGACA |
| 130 | tRNA-Leu-CAA->tca--3-1 | GTCAGGATGGCCGAGTGGTCTAAGGC GCCAGACTtcaGTTCTGGTCTCCGAA TGGAGGCGTGGGTTCGAATCCCACTT CTGACA |
| 131 | tRNA-Leu-CAA->tca--4-1 | GTCAGGATGGCCGAGTGGTCTAAGGC GCCAGACTtcaGTTCTGGTCTCCGTG TGGAGGCGTGGGTTCGAATCCCACTT CTGACA |
| 132 | tRNA-Leu-CAA->tta--1-1 | GTCAGGATGGCCGAGTGGTCTAAGGC GCCAGACTttaGTTCTGGTCTCCCCT GGAGGCGTGGGTTCGAATCCCACTTC TGACA |

TABLE 10-continued

| SEQ ID NO | Suppressor tRNA Name | Suppressor tRNA Sequence |
|---|---|---|
| 133 | tRNA-Leu-CAA->tta--2-1 | GTCAGGATGGCCGAGTGGTCTAAGGC GCCAGACTttaGTTCTGGTCTCCGTA TGGAGGCGTGGGTTCGAATCCCACTT CTGACA |
| 134 | tRNA-Leu-CAA->tta--3-1 | GTCAGGATGGCCGAGTGGTCTAAGGC GCCAGACTttaGTTCTGGTCTCCGAA TGGAGGCGTGGGTTCGAATCCCACTT CTGACA |
| 135 | tRNA-Leu-CAA->tta--4-1 | GTCAGGATGGCCGAGTGGTCTAAGGC GCCAGACTttaGTTCTGGTCTCCGTG TGGAGGCGTGGGTTCGAATCCCACTT CTGACA |
| 136 | tRNA-Leu-CAG->cta--1-1 | GTCAGGATGGCCGAGCGGTCTAAGGC GCTGCGTTctaGTCGCAGTCTCCCCT GGAGGCGTGGGTTCGAATCCCACTCC TGACA |
| 137 | tRNA-Leu-CAG->cta--2-1 | GTCAGGATGGCCGAGCGGTCTAAGGC GCTGCGTTctaGTCGCAGTCTCCCCT GGAGGCGTGGGTTCGAATCCCACTTC TGACA |
| 138 | tRNA-Leu-CAG->cta--3-1 | GTCAGGATGGCCGAGTGGTCTAAGGA GCTGTGTTctaGTCGCAGTCTCCCCT GGAGGCGTGGGTTCGAATCCCACTCC TGACA |
| 139 | tRNA-Leu-CAG->cta--4-1 | GTCAGGATGGCCGAGCAGTCTAAGGC ACTGCGTTctaGTCGCAGTCTCCCCT GGAGGCGTGGATTCGAATCCCACTCC TGACA |
| 140 | tRNA-Leu-CAG->tca--1-1 | GTCAGGATGGCCGAGCGGTCTAAGGC GCTGCGTTtcaGTCGCAGTCTCCCCT GGAGGCGTGGGTTCGAATCCCACTCC TGACA |
| 141 | tRNA-Leu-CAG->tca--2-1 | GTCAGGATGGCCGAGCGGTCTAAGGC GCTGCGTTtcaGTCGCAGTCTCCCCT GGAGGCGTGGGTTCGAATCCCACTTC TGACA |
| 142 | tRNA-Leu-CAG->tca--3-1 | GTCAGGATGGCCGAGTGGTCTAAGGA GCTGTGTTtcaGTCGCAGTCTCCCCT GGAGGCGTGGGTTCGAATCCCACTCC TGACA |
| 143 | tRNA-Leu-CAG->tca--4-1 | GTCAGGATGGCCGAGCAGTCTAAGGC ACTGCGTTtcaGTCGCAGTCTCCCCT GGAGGCGTGGATTCGAATCCCACTCC TGACA |
| 144 | tRNA-Leu-CAG->tta--1-1 | GTCAGGATGGCCGAGCGGTCTAAGGC GCTGCGTTttaGTCGCAGTCTCCCCT GGAGGCGTGGGTTCGAATCCCACTCC TGACA |
| 145 | tRNA-Leu-CAG->tta--2-1 | GTCAGGATGGCCGAGCGGTCTAAGGC GCTGCGTTttaGTCGCAGTCTCCCCT GGAGGCGTGGGTTCGAATCCCACTTC TGACA |
| 146 | tRNA-Leu-CAG->tta--3-1 | GTCAGGATGGCCGAGTGGTCTAAGGA GCTGTGTTttaGTCGCAGTCTCCCCT GGAGGCGTGGGTTCGAATCCCACTCC TGACA |
| 147 | tRNA-Leu-CAG->tta--4-1 | GTCAGGATGGCCGAGCAGTCTAAGGC ACTGCGTTttaGTCGCAGTCTCCCCT GGAGGCGTGGATTCGAATCCCACTCC TGACA |

TABLE 10-continued

| SEQ ID NO | Suppressor tRNA Name | Suppressor tRNA Sequence |
|---|---|---|
| 148 | tRNA-Leu-TAA->cta--1-1 | ACCAGAATGGCCGAGTGGTTAAGGCG TTGGACTctaGATCCAATGGATTTAT ATCCGCGTGGGTTCGAACCCCACTTC TGGTA |
| 149 | tRNA-Leu-TAA->cta--2-1 | ACCAGGATGGCCGAGTGGTTAAGGCG TTGGACTctaGATCCAATGGACATAT GTCTGCGTGGGTTCGAACCCCACTCC TGGTA |
| 150 | tRNA-Leu-TAA->cta--3-1 | ACTGGGATGGCTGAGTGGTTAAGGCG TTGGACTctaGATCCAATGGGCGGTT GCCTGCGTGGGTTCGAACCCCACTCC CAGTA |
| 151 | tRNA-Leu-TAA->cta--4-1 | GATGGGATGGCTGAGAGGTTAAGGCT TTGGACTctaGATCCAATGGGCAGAT GCCTGCGTGGGTTTGAACCCCACTCC CAATA |
| 152 | tRNA-Leu-TAA->tca--1-1 | ACCAGAATGGCCGAGTGGTTAAGGCG TTGGACTtcaGATCCAATGGATTTAT ATCCGCGTGGGTTCGAACCCCACTTC TGGTA |
| 153 | tRNA-Leu-TAA->tca--2-1 | ACCAGGATGGCCGAGTGGTTAAGGCG TTGGACTtcaGATCCAATGGACATAT GTCTGCGTGGGTTCGAACCCCACTCC TGGTA |
| 154 | tRNA-Leu-TAA->tca--3-1 | ACTGGGATGGCTGAGTGGTTAAGGCG TTGGACTtcaGATCCAATGGGCGGTT GCCTGCGTGGGTTCGAACCCCACTCC CAGTA |
| 155 | tRNA-Leu-TAA->tca--4-1 | GATGGGATGGCTGAGAGGTTAAGGCT TTGGACTtcaGATCCAATGGGCAGAT GCCTGCGTGGGTTTGAACCCCACTCC CAATA |
| 156 | tRNA-Leu-TAA->tta--1-1 | ACCAGAATGGCCGAGTGGTTAAGGCG TTGGACTttaGATCCAATGGATTTAT ATCCGCGTGGGTTCGAACCCCACTTC TGGTA |
| 157 | tRNA-Leu-TAA->tta--2-1 | ACCAGGATGGCCGAGTGGTTAAGGCG TTGGACTttaGATCCAATGGACATAT GTCTGCGTGGGTTCGAACCCCACTCC TGGTA |
| 158 | tRNA-Leu-TAA->tta--3-1 | ACTGGGATGGCTGAGTGGTTAAGGCG TTGGACTttaGATCCAATGGGCGGTT GCCTGCGTGGGTTCGAACCCCACTCC CAGTA |
| 159 | tRNA-Leu-TAA->tta--4-1 | GATGGGATGGCTGAGAGGTTAAGGCT TTGGACTttaGATCCAATGGGCAGAT GCCTGCGTGGGTTTGAACCCCACTCC CAATA |
| 160 | tRNA-Leu-TAG->cta--1-1 | GGTAGCGTGGCCGAGCGGTCTAAGGC GCTGGATTctaGCTCCAGTCTCTTCG GAGGCGTGGGTTCGAATCCCACCGCT GCCA |
| 161 | tRNA-Leu-TAG->cta--2-1 | GGTAGTGTGGCCGAGCGGTCTAAGGC GCTGGATTctaGCTCCAGTCTCTTCG GAGGCGTGGGTTCGAATCCCACCACT GCCA |
| 162 | tRNA-Leu-TAG->cta--3-1 | GGTAGCGTGGCCGAGTGGTCTAAGGC GCTGGATTctaGCTCCAGTCATTTCG ATGGCGTGGGTTCGAATCCCACCGCT GCCA |

TABLE 10-continued

| SEQ ID NO | Suppressor tRNA Name | Suppressor tRNA Sequence |
|---|---|---|
| 163 | tRNA-Leu-TAG->tca--1-1 | GGTAGCGTGGCCGAGCGGTCTAAGGC GCTGGATTtcaGCTCCAGTCTCTTCG GAGGCGTGGGTTCGAATCCCACCGCT GCCA |
| 164 | tRNA-Leu-TAG->tca--2-1 | GGTAGTGTGGCCGAGCGGTCTAAGGC GCTGGATTtcaGCTCCAGTCTCTTCG GAGGCGTGGGTTCGAATCCCACCACT GCCA |
| 165 | tRNA-Leu-TAG->tca--3-1 | GGTAGCGTGGCCGAGTGGTCTAAGGC GCTGGATTtcaGCTCCAGTCATTTCG ATGGCGTGGGTTCGAATCCCACCGCT GCCA |
| 166 | tRNA-Leu-TAG->tta--1-1 | GGTAGCGTGGCCGAGCGGTCTAAGGC GCTGGATTttaGCTCCAGTCTCTTCG GAGGCGTGGGTTCGAATCCCACCGCT GCCA |
| 167 | tRNA-Leu-TAG->tta--2-1 | GGTAGTGTGGCCGAGCGGTCTAAGGC GCTGGATTttaGCTCCAGTCTCTTCG GAGGCGTGGGTTCGAATCCCACCACT GCCA |
| 168 | tRNA-Leu-TAG->tta--3-1 | GGTAGCGTGGCCGAGTGGTCTAAGGC GCTGGATTttaGCTCCAGTCATTTCG ATGGCGTGGGTTCGAATCCCACCGCT GCCA |
| 169 | tRNA-Lys-CTT->cta--1-1 | GCCCAGCTAGCTCAGTTGGTAGAGCG TGGGACTctaAATCCTAGGGTCGTGG GTTCGAACCCCACGTTGGGCG |
| 170 | tRNA-Lys-CTT->cta--12-1 | GCCCAGCTAGCTCAGTCTGTAGAGCA TGAGACTctaAGTCTCAGGGTCATGG GTTGGAGCCCCATGTTGTGCA |
| 171 | tRNA-Lys-CTT->cta--13-1 | GCCTAGCTAGTTCAGTCGGTAGAGCA TGAGACTctaAATCTCAGGTTCATGA GTTTGAGCCCCATGTTGGTTTGGCA |
| 172 | tRNA-Lys-CTT->cta--14-1 | CCCCGGCTAGCTCAGTCAGTAGAGCT TGAGAATctaAATCTCAGGGTCGTGG GTTGGAGCCCCACGTTGGGCG |
| 196 | tRNA-Lys-CTT->cta--2-1 | GCCCGGCTAGCTCAGTCGGTAGAGCA TGGGACTctaAATCCCAGGGTCGTGG GTTCGAGCCCCACGTTGGGCG |
| 197 | tRNA-Lys-CTT->cta--3-1 | GCCCGGCTAGCTCAGTCGGTAGAGCA TGAGACTctaAATCTCAGGGTCGTGG GTTCGAGCCCCACGTTGGGCG |
| 198 | tRNA-Lys-CTT->cta--4-1 | GCCCAGCTAGCTCAGTCTGTAGAGCA TGAGACTctaAATCTCAGGGTCGTGA GTTCGAGCCCCACGTTGGGTG |
| 199 | tRNA-Lys-CTT->cta--5-1 | GCCCAGATAGCTCAGTGGGTAGAGCA TGAGACTctaAATCTCAGGGTCATGG GTTCATGCCCCATGTTGGGTA |
| 200 | tRNA-Lys-CTT->cta--6-1 | GTCCTGCTGGCTCAGTCGGTACAGCA TGGGACTctaAATCCCAGGGTCGTGG GTTCGAGCTCCACGTTGGGTA |
| 201 | tRNA-Lys-CTT->cta--7-1 | GCCTGGCTAGCTCAGTCCATAGAGCA TGGGACTctaAATCCCAGGGTCATGG GTTCGAGCCCCATATTAGGCA |
| 202 | tRNA-Lys-CTT->cta--8-1 | GCCCAGCTAGCTTAGTTGGTAGAGCA TGAGACTctaAATCTCAGAGTCATGG GTTCAGGCCTCATGTTTGGCA |

TABLE 10-continued

| SEQ ID NO | Suppressor tRNA Name | Suppressor tRNA Sequence |
|---|---|---|
| 203 | RNA-Lys-CTT->cta--9-1 | AACCTGGCTAGGTCAGTTGGTAGATC<br>ATGAGACTctaAATCTCAGGGTCATG<br>GGTTCAAGCCCCATGTTGGTTT |
| 204 | tRNA-Lys-CTT->tta--1-1 | GCCCAGCTAGCTCAGTTGGTAGAGCG<br>TGGGACTttaAATCCTAGGGTCGTGG<br>GTTCGAACCCCACGTTGGGCG |
| 205 | tRNA-Lys-CTT->tta--12-1 | GCCCAGCTAGCTCAGTCTGTAGAGCA<br>TGAGACTttaAGTCTCAGGGTCATGG<br>GTTGGAGCCCCATGTTGTGCA |
| 206 | tRNA-Lys-CTT->tta--13-1 | GCCTAGCTAGTTCAGTCGGTAGAGCA<br>TGAGACTttaAATCTCAGGTTCATGA<br>GTTTGAGCCCCATGTTGGTTTGGCA |
| 207 | tRNA-Lys-CTT->tta--14-1 | CCCCGGCTAGCTCAGTCAGTAGAGCT<br>TGAGAATttaAATCTCAGGGTCGTGG<br>GTTGGAGCCCCACGTTGGGCG |
| 208 | tRNA-Lys-CTT->tta--2-1 | GCCCGGCTAGCTCAGTCGGTAGAGCA<br>TGGGACTttaAATCCCAGGGTCGTGG<br>GTTCGAGCCCCACGTTGGGCG |
| 209 | tRNA-Lys-CTT->tta--3-1 | GCCCGGCTAGCTCAGTCGGTAGAGCA<br>TGAGACTttaAATCTCAGGGTCGTGG<br>GTTCGAGCCCCACGTTGGGCG |
| 210 | tRNA-Lys-CTT->tta--4-1 | GCCCAGCTAGCTCAGTCTGTAGAGCA<br>TGAGACTttaAATCTCAGGGTCGTGA<br>GTTCGAGCCCCACGTTGGGTG |
| 211 | tRNA-Lys-CTT->tta--5-1 | GCCCAGATAGCTCAGTGGGTAGAGCA<br>TGAGACTttaAATCTCAGGGTCATGG<br>GTTCATGCCCCATGTTGGGTA |
| 212 | tRNA-Lys-CTT->tta--6-1 | GTCCTGCTGGCTCAGTCGGTACAGCA<br>TGGGACTttaAATCCCAGGGTCGTGG<br>GTTCGAGCTCCACGTTGGGTA |
| 213 | tRNA-Lys-CTT->tta--7-1 | GCCTGGCTAGCTCAGTCCATAGAGCA<br>TGGGACTttaAATCCCAGGGTCATGG<br>GTTCGAGCCCCATATTAGGCA |
| 214 | tRNA-Lys-CTT->tta--8-1 | GCCCAGCTAGCTTAGTTGGTAGAGCA<br>TGAGACTttaAATCTCAGAGTCATGG<br>GTTCAGGCCTCATGTTTGGCA |
| 215 | tRNA-Lys-CTT->tta--9-1 | AACCTGGCTAGGTCAGTTGGTAGATC<br>ATGAGACTttaAATCTCAGGGTCATG<br>GGTTCAAGCCCCATGTTGGTTT |
| 216 | tRNA-Lys-TTT->cta--1-1 | GCCCGGATAGCTCAGTCGGTAGAGCA<br>TCAGACTctaAATCTGAGGGTCCAGG<br>GTTCAAGTCCCTGTTCGGGCG |
| 217 | tRNA-Lys-TTT->cta--2-1 | GCCTGGATAGCTCAGTCGGTAGAGCA<br>TCAGACTctaAATCTGAGGGTCCAGG<br>GTTCAAGTCCCTGTTCAGGCG |
| 218 | tRNA-Lys-TTT->cta--3-1 | GCCTGGATAGCTCAATTGGTAGAGCA<br>TCAGACTctaAATCTGAGGGTTCAGG<br>GTTCAAGTCCCTGTTCAGGCG |
| 219 | tRNA-Lys-TTT->cta--4-1 | GCCCAGCCAGCTCAGTAGGTAGAGTA<br>TGAGACTctaAATCTCAGGGTGGTGG<br>GTTCGAGCCCCATGTTGGGGG |
| 220 | tRNA-Lys-TTT->cta--5-1 | TGTGGTGTAGCTCAGTCGGTAGAGCA<br>TCAGACTctaAATCTGAGGGTCCAGG<br>GTTCAGGTCCCTGTTCGGGTGCCAAA<br>A |

TABLE 10-continued

| SEQ ID NO | Suppressor tRNA Name | Suppressor tRNA Sequence |
|---|---|---|
| 221 | tRNA-Lys-TTT->tta--1-1 | GCCCGGATAGCTCAGTCGGTAGAGCA TCAGACTttaAATCTGAGGGTCCAGG GTTCAAGTCCCTGTTCGGGCG |
| 222 | tRNA-Lys-TTT->tta--2-1 | GCCTGGATAGCTCAGTCGGTAGAGCA TCAGACTttaAATCTGAGGGTCCAGG GTTCAAGTCCCTGTTCAGGCG |
| 223 | tRNA-Lys-TTT->tta--3-1 | GCCTGGATAGCTCAATTGGTAGAGCA TCAGACTttaAATCTGAGGGTTCAGG GTTCAAGTCCCTGTTCAGGCG |
| 224 | tRNA-Lys-TTT->tta--4-1 | GCCCAGCCAGCTCAGTAGGTAGAGTA TGAGACTttaAATCTCAGGGTGGTGG GTTCGAGCCCCATGTTGGGGG |
| 225 | tRNA-Lys-TTT->tta--5-1 | TGTGGTGTAGCTCAGTCGGTAGAGCA TCAGACTttaAATCTGAGGGTCCAGG GTTCAGGTCCCTGTTCGGGTGCCAAA A |
| 226 | tRNA-Ser-AGA->cta--1-1 | GTAGTCGTGGCCGAGTGGTTAAGGCG ATGGACTctaAATCCATTGGGGTTTC CCCGCGCAGGTTCGAATCCTGCCGAC TACG |
| 227 | tRNA-Ser-AGA->cta--2-1 | GTAGTCGTGGCCGAGTGGTTAAGGCG ATGGACTctaAATCCATTGGGGTCTC CCCGCGCAGGTTCGAATCCTGCCGAC TACG |
| 228 | tRNA-Ser-AGA->cta--3-1 | GTAGTCGTGGCCAAGTGAGTAAGGCA ATGGACTctaAATCCATTGGGGTCTC CCAGCACAGGTTCAAATCCTGCTGAC TATG |
| 229 | tRNA-Ser-AGA->tca--1-1 | GTAGTCGTGGCCGAGTGGTTAAGGCG ATGGACTtcaAATCCATTGGGGTTTC CCCGCGCAGGTTCGAATCCTGCCGAC TACG |
| 230 | tRNA-Ser-AGA->tca--2-1 | GTAGTCGTGGCCGAGTGGTTAAGGCG ATGGACTtcaAATCCATTGGGGTCTC CCCGCGCAGGTTCGAATCCTGCCGAC TACG |
| 231 | tRNA-Ser-AGA->tca--3-1 | GTAGTCGTGGCCAAGTGAGTAAGGCA ATGGACTtcaAATCCATTGGGGTCTC CCAGCACAGGTTCAAATCCTGCTGAC TATG |
| 232 | tRNA-Ser-AGA->tta--1-1 | GTAGTCGTGGCCGAGTGGTTAAGGCG ATGGACTttaAATCCATTGGGGTTTC CCCGCGCAGGTTCGAATCCTGCCGAC TACG |
| 233 | tRNA-Ser-AGA->tta--2-1 | GTAGTCGTGGCCGAGTGGTTAAGGCG ATGGACTttaAATCCATTGGGGTCTC CCCGCGCAGGTTCGAATCCTGCCGAC TACG |
| 234 | tRNA-Ser-AGA->tta--3-1 | GTAGTCGTGGCCAAGTGAGTAAGGCA ATGGACTttaAATCCATTGGGGTCTC CCAGCACAGGTTCAAATCCTGCTGAC TATG |
| 235 | tRNA-Ser-CGA->cta--1-1 | GCTGTGATGGCCGAGTGGTTAAGGCG TTGGACTctaAATCCAATGGGGTCTC CCCGCGCAGGTTCGAATCCTGCTCAC AGCG |
| 236 | tRNA-Ser-CGA->cta--2-1 | GTCACGGTGGCCGAGTGGTTAAGGCG TTGGACTctaAATCCAATGGGGTTTC CCCGCACAGGTTCGAATCCTGTTCGT GACG |

TABLE 10-continued

| SEQ ID NO | Suppressor tRNA Name | Suppressor tRNA Sequence |
|---|---|---|
| 237 | tRNA-Ser-CGA->cta--3-1 | GCTGTGATGGCCGAGTGGTTAAGGCG TTGGACTctaAATCCAATGGGTTCTT CCCGCGCAGGTTCAAATCCTGCTCAC AGCG |
| 238 | tRNA-Ser-CGA->tca--1-1 | GCTGTGATGGCCGAGTGGTTAAGGCG TTGGACTtcaAATCCAATGGGGTCTC CCCGCGCAGGTTCGAATCCTGCTCAC AGCG |
| 239 | tRNA-Ser-CGA->tca--2-1 | GTCACGGTGGCCGAGTGGTTAAGGCG TTGGACTtcaAATCCAATGGGGTTTC CCCGCACAGGTTCGAATCCTGTTCGT GACG |
| 240 | tRNA-Ser-CGA->tca--3-1 | GCTGTGATGGCCGAGTGGTTAAGGCG TTGGACTtcaAATCCAATGGGTTCTT CCCGCGCAGGTTCAAATCCTGCTCAC AGCG |
| 241 | tRNA-Ser-CGA->tta--1-1 | GCTGTGATGGCCGAGTGGTTAAGGCG TTGGACTttaAATCCAATGGGGTCTC CCCGCGCAGGTTCGAATCCTGCTCAC AGCG |
| 242 | tRNA-Ser-CGA->tta--2-1 | GTCACGGTGGCCGAGTGGTTAAGGCG TTGGACTttaAATCCAATGGGGTTTC CCCGCACAGGTTCGAATCCTGTTCGT GACG |
| 243 | tRNA-Ser-CGA->tta--3-1 | GCTGTGATGGCCGAGTGGTTAAGGCG TTGGACTttaAATCCAATGGGTTCTT CCCGCGCAGGTTCAAATCCTGCTCAC AGCG |
| 244 | tRNA-Ser-GCT->cta--1-1 | GACGAGGTGGCCGAGTGGTTAAGGCG ATGGACTctaAATCCATTGTGCTCTG CACGCGTGGGTTCGAATCCCACCTTC GTCG |
| 245 | tRNA-Ser-GCT->cta--2-1 | GACGAGGTGGCCGAGTGGTTAAGGCG ATGGACTctaAATCCATTGTGCTCTG CACGCATGGGTTCGAATCCCATCCTC GTCG |
| 246 | tRNA-Ser-GCT->cta--3-1 | GACGAGGTGGCCGAGTGGTTAAGGCG ATGGACTctaAATCCATTGTGCTTTG CACGCGTGGGTTCGAATCCCATCCTC GTCG |
| 247 | tRNA-Ser-GCT->cta--4-1 | GACGAGGTGGCCGAGTGGTTAAGGCG ATGGACTctaAATCCATTGTGCTCTG CACGCGTGGGTTCGAATCCCATCCTC GTCG |
| 248 | tRNA-Ser-GCT->cta--5-1 | GATGAGGTGGCCGAGTGGTTAAGGCG ATGGACTctaAATCCATTGTGCTCTG CACGCATGGGTTCGAATCCCATCCTC ATCG |
| 249 | tRNA-Ser-GCT->tca--1-1 | GACGAGGTGGCCGAGTGGTTAAGGCG ATGGACTtcaAATCCATTGTGCTCTG CACGCGTGGGTTCGAATCCCACCTTC GTCG |
| 250 | tRNA-Ser-GCT->tca--2-1 | GACGAGGTGGCCGAGTGGTTAAGGCG ATGGACTtcaAATCCATTGTGCTCTG CACGCATGGGTTCGAATCCCATCCTC GTCG |
| 251 | tRNA-Ser-GCT->tca--3-1 | GACGAGGTGGCCGAGTGGTTAAGGCG ATGGACTtcaAATCCATTGTGCTTTG CACGCGTGGGTTCGAATCCCATCCTC GTCG |

TABLE 10-continued

| SEQ ID NO | Suppressor tRNA Name | Suppressor tRNA Sequence |
|---|---|---|
| 252 | tRNA-Ser-GCT->tca--4-1 | GACGAGGTGGCCGAGTGGTTAAGGCG ATGGACTtcaAATCCATTGTGCTCTG CACGCGTGGGTTCGAATCCCATCCTC GTCG |
| 253 | tRNA-Ser-GCT->tca--5-1 | GATGAGGTGGCCGAGTGGTTAAGGCG ATGGACTtcaAATCCATTGTGCTCTG CACGCATGGGTTCGAATCCCATCCTC ATCG |
| 254 | tRNA-Ser-GCT->tta--1-1 | GACGAGGTGGCCGAGTGGTTAAGGCG ATGGACTttaAATCCATTGTGCTCTG CACGCGTGGGTTCGAATCCCACCTTC GTCG |
| 255 | tRNA-Ser-GCT->tta--2-1 | GACGAGGTGGCCGAGTGGTTAAGGCG ATGGACTttaAATCCATTGTGCTCTG CACGCATGGGTTCGAATCCCATCCTC GTCG |
| 256 | tRNA-Ser-GCT->tta--3-1 | GACGAGGTGGCCGAGTGGTTAAGGCG ATGGACTttaAATCCATTGTGCTTTG CACGCGTGGGTTCGAATCCCATCCTC GTCG |
| 257 | tRNA-Ser-GCT->tta--4-1 | GACGAGGTGGCCGAGTGGTTAAGGCG ATGGACTttaAATCCATTGTGCTCTG CACGCGTGGGTTCGAATCCCATCCTC GTCG |
| 258 | tRNA-Ser-GCT->tta--5-1 | GATGAGGTGGCCGAGTGGTTAAGGCG ATGGACTttaAATCCATTGTGCTCTG CACGCATGGGTTCGAATCCCATCCTC ATCG |
| 259 | tRNA-Ser-GGA->cta--1-1 | GCTGAAATAGCTCAGTTGGGAGAGCA TTAGACTctaGATCTAAAGGTCCCTG GTTTGATCCCGGGTTTCGGCA |
| 260 | tRNA-Ser-GGA->tca--1-1 | GCTGAAATAGCTCAGTTGGGAGAGCA TTAGACTtcaGATCTAAAGGTCCCTG GTTTGATCCCGGGTTTCGGCA |
| 261 | tRNA-Ser-GGA->tta--1-1 | GCTGAAATAGCTCAGTTGGGAGAGCA TTAGACTttaGATCTAAAGGTCCCTG GTTTGATCCCGGGTTTCGGCA |
| 262 | tRNA-Ser-TGA->cta--1-1 | GCAGCGATGGCCGAGTGGTTAAGGCG TTGGACTctaAATCCAATGGGGTCTC CCCGCGCAGGTTCGAACCCTGCTCGC TGCG |
| 263 | tRNA-Ser-TGA->tca--1-1 | GCAGCGATGGCCGAGTGGTTAAGGCG TTGGACTtcaAATCCAATGGGGTCTC CCCGCGCAGGTTCGAACCCTGCTCGC TGCG |
| 264 | tRNA-Ser-TGA->tta--1-1 | GCAGCGATGGCCGAGTGGTTAAGGCG TTGGACTttaAATCCAATGGGGTCTC CCCGCGCAGGTTCGAACCCTGCTCGC TGCG |
| 265 | RNA-Trp-CCA->cta--1-1 | GACCTCGTGGCGCAATGGTAGCGCGT CTGACTctaGATCAGAAGGTTGCGTG TTCAAATCACGTCGGGGTCA |
| 266 | tRNA-Trp-CCA->cta--2-1 | GACCTCGTGGCGCAACGGTAGCGCGT CTGACTctaGATCAGAAGGCTGCGTG TTCGAATCACGTCGGGGTCA |
| 267 | tRNA-Trp-CCA->cta--3-1 | GGCCTCGTGGCGCAACGGTAGCGCGT CTGACTctaGATCAGAAGGTTGCGTG TTCAAATCACGTCGGGGTCA |

TABLE 10-continued

| SEQ ID NO | Suppressor tRNA Name | Suppressor tRNA Sequence |
|---|---|---|
| 268 | tRNA-Trp-CCA->cta--4-1 | GACCTCGTGGCGCAACGGTAGCGCGT CTGACTctaGATCAGAAGGTTGCGTG TTCAAATCACGTCGGGGTCA |
| 269 | tRNA-Trp-CCA->cta--5-1 | GACCTCGTGGCGCAATGGTAGCGCGT CTGACTctaGATCAGAAGGTTGCGTG TTCAAGTCACGTCGGGGTCA |
| 270 | tRNA-Trp-CCA->cta--6-1 | GACCTCGTGGCACAATGGTAGCACGT CTGACTctaGATCAGAAGGTTGCGTG TTCAAATCACGTCGGGGTCA |
| 271 | tRNA-Trp-CCA->tca--1-1 | GACCTCGTGGCGCAATGGTAGCGCGT CTGACTtcaGATCAGAAGGTTGCGTG TTCAAATCACGTCGGGGTCA |
| 272 | tRNA-Trp-CCA->tca--2-1 | GACCTCGTGGCGCAACGGTAGCGCGT CTGACTtcaGATCAGAAGGCTGCGTG TTCGAATCACGTCGGGGTCA |
| 273 | tRNA-Trp-CCA->tca--3-1 | GGCCTCGTGGCGCAACGGTAGCGCGT CTGACTtcaGATCAGAAGGTTGCGTG TTCAAATCACGTCGGGGTCA |
| 274 | tRNA-Trp-CCA->tca--4-1 | GACCTCGTGGCGCAACGGTAGCGCGT CTGACTtcaGATCAGAAGGTTGCGTG TTCAAATCACGTCGGGGTCA |
| 275 | tRNA-Trp-CCA->tca--5-1 | GACCTCGTGGCGCAATGGTAGCGCGT CTGACTtcaGATCAGAAGGTTGCGTG TTCAAGTCACGTCGGGGTCA |
| 276 | tRNA-Trp-CCA->tca--6-1 | GACCTCGTGGCACAATGGTAGCACGT CTGACTtcaGATCAGAAGGTTGCGTG TTCAAATCACGTCGGGGTCA |
| 277 | tRNA-Tyr-GTA->cta--1-1 | CCTTCGATAGCTCAGTTGGTAGAGCG GAGGACTctaGATCCTTAGGTCGCTG GTTCGAATCCGGCTCGAAGGA |
| 278 | tRNA-Tyr-GTA->cta--2-1 | CCTTCGATAGCTCAGTTGGTAGAGCG GAGGACTctaGATCCTTAGGTCGCTG GTTCGATTCCGGCTCGAAGGA |
| 279 | tRNA-Tyr-GTA->cta--3-1 | CCTTCGATAGCTCAGCTGGTAGAGCG GAGGACTctaGATCCTTAGGTCGCTG GTTCGATTCCGGCTCGAAGGA |
| 280 | tRNA-Tyr-GTA->cta--4-1 | CCTTCGATAGCTCAGCTGGTAGAGCG GAGGACTctaGATCCTTAGGTCGCTG GTTCGACTCCGGCTCGAAGGA |
| 281 | tRNA-Tyr-GTA->cta--5-1 | CTTTCGATAGTTCAGTTGGTAGAGCG GAGGACTctaGATCCTTAGGTCGCTG GTTCGAGTCCGGCTCGAAGGA |
| 282 | tRNA-Tyr-GTA->tta--1-1 | CCTTCGATAGCTCAGTTGGTAGAGCG GAGGACTttaGATCCTTAGGTCGCTG GTTCGAATCCGGCTCGAAGGA |
| 283 | tRNA-Tyr-GTA->tta--2-1 | CCTTCGATAGCTCAGTTGGTAGAGCG GAGGACTttaGATCCTTAGGTCGCTG GTTCGATTCCGGCTCGAAGGA |
| 284 | tRNA-Tyr-GTA->tta--3-1 | CCTTCGATAGCTCAGCTGGTAGAGCG GAGGACTttaGATCCTTAGGTCGCTG GTTCGATTCCGGCTCGAAGGA |
| 285 | tRNA-Tyr-GTA->tta--4-1 | CCTTCGATAGCTCAGCTGGTAGAGCG GAGGACTttaGATCCTTAGGTCGCTG GTTCGACTCCGGCTCGAAGGA |

TABLE 10-continued

| SEQ ID NO | Suppressor tRNA Name | Suppressor tRNA Sequence |
|---|---|---|
| 286 | tRNA-Tyr-GTA->tta--5-1 | CTTTCGATAGTTCAGTTGGTAGAGCG GAGGACTttaGATCCTTAGGTCGCTG GTTCGAGTCCGGCTCGAAGGA |

The suppressor tRNAs are tested for PTC readthrough activity by flow cytometry in cell lines containing dual fluorescent readthrough reporters. These reporters include three copies of a red fluorescent protein (tdTomato), TEV protease, a linker region containing a PTC, and three copies of a green fluorescent protein (EGFP). A schematic of a reporter construct is shown in FIG. 3. In the absence of any PTC readthrough as a result of a suppressor tRNA, translation will be terminated by the PTC within the linker region, and only tdTomato will be expressed (and therefore only red fluorescence detected). PTC readthrough activity as a result of a suppressor tRNA will allow translation to proceed through the PTC in the linker region, and for both tdTomato and EGFP to be expressed (and therefore both red and green fluorescence detected). Accordingly, readthrough can be assessed by quantifying the percentage of viable cells expressing both the red and green fluorescent reporters above background (double positive %).

Example 7

This Example describes glutamine aminoacylated suppressor tRNAs that facilitate read-through of a premature termination codon (PTC).

In this Example, all mature tRNA sequences were expressed in the context of upstream and downstream genomic flanking sequences (±200 bps) from tRNA-Gln-TTG-1-1—a highly expressed glutamine-tRNA, i.e., the tRNA sequences were expressed with a 5' flanking sequence of SEQ ID NO: 173 and a 3' flanking sequence of SEQ ID NO: 174. All mature tRNA sequences including upstream and downstream genomic flanking sequences were generated in a pGL4 vector backbone.

The Gln$_{CTA}$ suppressor tRNAs were tested for PTC readthrough activity by flow cytometry in Flp-In-293 cells that either contain an integrated dual fluorescent readthrough reporter or were transiently co-transfected with an expression construct containing a dual fluorescent readthrough reporter. The reporters included three copies of a red fluorescent protein (tdTomato), TEV protease, a linker region containing a PTC, and three copies of a green fluorescent protein (EGFP). A schematic of the reporter construct is shown in FIG. 3. In the absence of any PTC readthrough as a result of a suppressor tRNA, translation will be terminated by the PTC within the linker region, and only tdTomato will be expressed (and therefore only red fluorescence detected). PTC readthrough activity as a result of a suppressor tRNA allows translation to proceed through the PTC in the linker region, and for both tdTomato and EGFP to be expressed (and therefore both red and green fluorescence to be detected). Accordingly, readthrough was assessed with flow cytometry by quantifying the percentage of viable cells expressing both the red and green fluorescent reporters above background (double positive %). To screen for suppressor tRNAs with readthrough activity at PTCs relevant to Dravet syndrome, linker regions were generated containing the PTC and eight flanking codons on either side of the PTC from the SCN1A transcript of three patients with Gln(Q)-to-TAG nonsense mutations in SCN1A: patient 3 (W1397X), patient 4 (51505X), and patient 5 (Q1810X).

The linker region derived from the patient 3 SCN1A transcript is as follows, and the reporter including this linker region is referred to as the patient3-Gln-TAG (W1397X) reporter:

(SEQ ID NO: 889)
ATAGAAAGAAATGAGACTGCTCGAtagAAAAATGTG

AAAGTAAACTTTGAT.

A corresponding linker with a wild-type Trp(W) codon in place of the PTC was used as a control, and had the following sequence:

(SEQ ID NO: 890)
ATAGAAAGAAATGAGACTGCTCGATGGAAAAATGT

GAAAGTAAACTTTGAT.

The linker region derived from the patient 4 SCN1A transcript is as follows, and the reporter including this linker region is referred to as the patient4-Gln-TAG (51505X) reporter:

(SEQ ID NO: 891)
TATAATGCAATGAAAAAATTAGGAtagAAAAAACCG

CAAAAGCCTATACCT.

A corresponding linker with a wild-type Ser(S) codon in place of the PTC was used as a control, and had the following sequence:

(SEQ ID NO: 892)
TATAATGCAATGAAAAAATTAGGATCGAAAAAACCG

CAAAAGCCTATACCT.

The linker region derived from the patient 5 SCN1A transcript is as follows, and the reporter including this linker region is referred to as the patient5-Gln-TAG (Q1810X) reporter:

(SEQ ID NO: 893)
GAGAAGTTTGATCCCGATGCAACTtagTTCATGGAA

TTTGAAAAATTATCT.

A corresponding linker with a wild-type Gln codon in place of the PTC was used as a control, and had the following sequence:

(SEQ ID NO: 894)

GAGAAGTTTGATCCCGATGCAACTCAGTTCATGGAAT

TTGAAAAATTATCT.

The Gln_{CTA} suppressor tRNAs (SEQ ID NOs: 178-190) were tested for PTC readthrough activity by flow cytometry in multiple assay contexts, including (i) human Flp-In-293 cells transiently co-transfected with the patient3-Gln-TAG (W1397X) reporter, the patient4-Gln-TAG (S1505X) reporter, or the patient5-Gln-TAG (Q1810X) reporter (results are shown in FIG. 24 and (ii) a human Flp-In-293 cell line cell line stably expressing the patient3-Gln-TAG (W1397X) reporter and transiently transfected with a plasmid encoding a Gln_{CTA} suppressor tRNA (results are shown in FIG. 25). Transfections were done using the Lipofectamine 3000 Transfection Reagent according to the manufacturer's protocol.

Together, these results demonstrate that the described suppressor tRNAs can facilitate expression of transcripts, e.g., SCN1A transcripts, containing premature termination codons associated with disorders, e.g., Dravet syndrome.

Example 8

This Example describes the impact of the nucleotide sequence flanking a suppressor tRNA on the read-through of a premature termination codon (PTC) by the suppressor tRNA.

Expression vectors were generated that encoded an EGFP-R96X-TGA reporter (SEQ ID NO: 31, as described in Example 1) and a single copy of the Arg_{TCA} suppressor tRNA #115 (tRNA-Arg-TCT-2-1-TCA-SUP_no intron, SEQ ID NO: 18, as described in Example 1). The expression vectors included sequences immediately 5' and 3' to the tRNA coding sequence that were in each instance derived from the genomic DNA that is 5' and 3' to the mouse tRNA-Arg-TCG-1-1 gene but were of varying length. Details of the expression vectors are shown in TABLE 11.

TABLE 11

| Name | 5' to tRNA coding sequence | tRNA coding sequence | 3' to tRNA coding sequence |
|---|---|---|---|
| Flank300 | 200 nt 5' to the mouse tRNA-Arg-TCG-1-1 gene (SEQ ID NO: 26) | TCA-115 (SEQ ID NO: 18) | 104 nt 3' to the mouse tRNA-Arg-TCG-1-1 gene (SEQ ID NO: 32) |
| Flank20 | 20 nt 5' to the mouse tRNA-Arg-TCG-1-1 gene (SEQ ID NO: 895) | TCA-115 (SEQ ID NO: 18) | 17 nt 3' to the mouse tRNA-Arg-TCG-1-1 gene (SEQ ID NO: 896) |
| Flank10 | 10 nt 5' to the mouse tRNA-Arg-TCG-1-1 gene (SEQ ID NO: 897) | TCA-115 (SEQ ID NO: 18) | 17 nt 3' to the mouse tRNA-Arg-TCG-1-1 gene (SEQ ID NO: 896) |

TABLE 11-continued

| Name | 5' to tRNA coding sequence | tRNA coding sequence | 3' to tRNA coding sequence |
|---|---|---|---|
| Flank0 | Random sequence | TCA-115 (SEQ ID NO: 18) | 17 nt 3' to the mouse tRNA-Arg-TCG-1-1 gene (SEQ ID NO: 896) |

The expression vectors in TABLE 11 were tested for PTC readthrough activity by flow cytometry in Neuro-2a cells. Transfections were performed using the Lipofectamine 3000 Transfection Reagent according to the manufacturer's protocol. The results are shown in FIGS. 26A and 26B and demonstrate that, although the Arg_{TCA} suppressor tRNA #115, exhibits activity even with a random 5' leader sequence, using a 5' leader sequence from an endogenous tRNA gene can increase suppressor tRNA activity.

Example 9

This Example describes the impact of the nucleotide sequence flanking a suppressor tRNA on the read-through of a premature termination codon (PTC) by the suppressor tRNA.

A library of expression vectors was generated that included (i) one of 20 unique 100 nt leader sequences (a sequence immediately 5' to the tRNA coding sequence) derived from the human genomic DNA that is immediately 5' to an endogenous tRNA gene in combination with (ii) a nucleotide sequence encoding TCA-115 (tRNA-Arg-TCT-2-1-TCA-SUP_no intron, SEQ ID NO: 18, as described in Example 1) or TTA-163 (tRNA-Gln-TTG-3-1-TTA-SUP, SEQ ID NO: 45, as described in Example 4). A schematic illustrating the design of the expression vector constructs in the library is depicted in FIG. 27. The 20 unique 100 nt leader sequences included sequences derived from the highest abundance tRNAs in human HEK293 cells and include leader sequences derived from Arg-TCT-1-1 (SEQ ID NO: 875), Tyr-GTA-5-1 (SEQ ID NO: 883), Ser-GCT-3-1 (SEQ ID NO: 878), Arg-TCG-1-1 (SEQ ID NO: 886), Arg-TCG-3-1 (SEQ ID NO: 888), Ser-TGA-1-1 (SEQ ID NO: 879), Arg-TCG-5-1 (SEQ ID NO: 871), Lys-TTT-6-1 (SEQ ID NO: 887), Asn-GTT-1-1 (SEQ ID NO: 880), Arg-CCG-2-1 (SEQ ID NO: 877), Ala-AGC-4-1 (SEQ ID NO: 874), Leu-TAA-1-1 (SEQ ID NO: 876), Ser-CGA-4-1 (SEQ ID NO: 870), Ser-TGA-4-1 (SEQ ID NO: 869), Ser-GCT-2-1 (SEQ ID NO: 872), Arg-TCT-2-1 (SEQ ID NO: 881), Thr-TGT-1-1 (SEQ ID NO: 885), Ile-AAT-4-1 (SEQ ID NO: 873), Val-CAC-2-1 (SEQ ID NO: 884), or Asn-GTT-3-1 (SEQ ID NO: 882) genes.

The leader sequences in combination with the Arg_{TCA} suppressor tRNA #115 (SEQ ID NO: 18) or the Gln_{TTA} suppressor tRNA #163 (SEQ ID NO: 45) were tested for PTC readthrough activity by flow cytometry in cell lines co-transfected with an EGFP-R96X-TGA reporter (SEQ ID NO: 31) for Arg_{TCA} constructs or an EGFP-Q69X-TAA reporter (SEQ ID NO: 175) for Gln_{TTA} constructs. The results are shown in FIGS. 28-32 and indicate that (i) the activity of suppressor tRNAs is influenced by the leader sequence, and (ii) suppressor tRNAs (including suppressor tRNAs of different classes) when combined with the identified leader sequences showed high readthrough activity.

Example 10

This Example describes readthrough activity of certain suppressor tRNAs disclosed herein and small molecule nonsense suppression therapies.

The suppressor tRNAs were tested alongside nonsense suppression drugs translarna (ataluren), gentamicin, and G418 (geneticin). PTC readthrough activity was measured in Neuro-2a cells ~48 hours after transfection with an expression construct containing a CAG:NLS-EGFP (Q69X-TAA) reporter (as described in Example 4, SEQ ID NO: 175) and either (i) including a Gln suppressor tRNA (either #002, tRNA-Gln-TTG-1-1-TTA-SUP, SEQ ID NO: 36, or #196, tRNA-Gln-TTG-1-1-CTA-SUP, SEQ ID NO: 178, both as described in Example 4) at the indicated copy number on the same construct, or (ii) treated with ataluren, (iii) treated with gentamicin, or (iv) treated with G418. Transfections were performed using the Lipofectamine 3000 Transfection Reagent according to the manufacturer's protocol. For all experimental conditions, cell culture medium was replaced with fresh medium ~6 hours after transfection and the indicated drugs at the indicated concentrations were added at this point. PTC readthrough activity was measured as the percentage of EGFP positive cells as measured by flow cytometry. A reporter containing wildtype EGFP without a PTC was used as a control. Cell viability in cells receiving the same set of treatments was assessed by flow cytometry following staining with 7-Amino Actinomycin D (7-AAD; Thermo Fisher Scientific #006993-50), a membrane impermeant dye that is generally excluded from viable cells, which was used according to the manufacturer's protocol. Results are shown in FIGS. 33-34 for the $Gln_{TTA}$ suppressor tRNA #002 (SEQ ID NO: 36) and FIGS. 35-36 for the $Gln_{CTA}$ suppressor tRNA #196 (SEQ ID NO: 178). Together, the results demonstrate that the suppressor tRNAs produce greater readthrough than any of the nonsense suppression drugs. Additionally, the results show that, unlike for any of the nonsense suppression drugs, treatment with the suppressor tRNAs is not accompanied by a decrease in cell viability.

Example 11

This Example describes rescue of full-length SCN1a protein expression by certain suppressor tRNAs disclosed herein.

Flp-In-293 cells were (i) transfected with an expression construct containing mouse SCN1A with an Arg(R)-to-TGA PTC (R1407X) and a 3×FLAG tag peptide (DYKDHD-G-DYKDHD-I-DYKDDDDK) at the C-terminus (SEQ ID NO: 899) and (ii) either co-transfected with an expression construct containing the $Arg_{TCA}$ suppressor tRNA #115 (tRNA-Arg-TCT-2-1-TCA-SUP_no intron, SEQ ID NO: 18), or treated with G418, gentamicin, or ataluren. An expression construct containing wild-type mouse SCN1A and a 3×FLAG tag peptide at the C-terminus (SEQ ID NO: 898) was used as a control. SEQ ID NOs: 898 and 899 are as follows:

```
                                (SEQ ID NO: 898)
ATGGAGCAAACAGTGCTTGTACCACCAGGACCTGACAGCTTCAAC

TTCTTCACCAGAGAATCCCTTGCAGCTATTGAAAGGCGCATTGCA

GAAGAGAAGGCTAAGAATCCCAAGCCAGACAAAAAGATGATGAT

GAAAATGGCCCAAAGCCAAACAGTGACTTGGAAGCTGGGAAGAAC

CTTCCATTTATCTATGGAGACATTCCTCCAGAGATGGTGTCGGAG

CCTCTGGAGGACCTGGACCCCTACTATATCAATAAGAAGACTTTT
```

```
ATAGTATTGAATAAAGGGAAGGCCATCTTCCGGTTCAGTGCCACC

TCCGCCCTGTACATTTTAACACCCTTCAATCCTCTTAGGAAAATA

GCTATTAAGATTTTGGTACACTCATTATTCAGCATGTTAATCATG

TGCACTATTTTGACAAACTGTGTATTTATGACAATGAGTAACCCT

CCCGACTGGACAAAGAATGTGGAGTACACCTTCACAGGAATATAT

ACTTTTGAATCACTAATAAAAATTATTGCAAGGGGCTTCTGTTTA

GAAGATTTTACTTTCCTTCGCGACCCATGGAACTGGCTGGACTTC

ACTGTCATTACATTCGCATATGTGACGGAGTTTGTGGACCTGGGC

AATGTCTCAGCATTGAGAACATTCAGAGTTCTTCGAGCATTGAAA

ACTATTTCAGTCATTCCAGGCCTGAAGACCATCGTGGGGGCCCTG

ATCCAGTCGGTGAAGAAGCTGTCTGACGTCATGATACTCACTGTG

TTCTGTCTCAGTGTGTTCGCACTCATCGGGTTGCAGCTCTTCATG

GGCAACCTGAGGAATAAATGTGTACAGTGGCCTCCCACCAACGCT

TCCCTTGAGGAACATAGCATAGAGAAGAATATAACTATGGATTAC

AATGGCACACTTGTAAATGAAACCGTGTTCGAGTTTGACTGGAAA

TCATACATTCAAGACTCAAGATATCATTATTTCCTGGAGGGTGTT

TTAGATGCACTGCTGTGTGGAAATAGCTCTGATGCAGGCCAATGT

CCAGAAGGATATATGTGTGTAAAAGCTGGTAGAAACCCTAATTAT

GGTTACACAAGCTTTGATACCTTCAGTTGGGCATTTTTGTCCCTG

TTTCGACTGATGACTCAGGACTTCTGGGAAAATCTATACCAACTG

ACATTGCGTGCTGCTGGCAAAACCTACATGATATTTTTTGTGCTG

GTCATTTTCTTGGGCTCATTCTACCTGATAAACTTGATCCTGGCT

GTGGTGGCCATGGCCTATGAGGAGCAGAATCAGGCCACACTGGAG

GAGGCTGAACAGAAAGAGGCAGAATTTCAGCAGATGTTGGAGCAA

CTTAAGAAGCAGCAAGAGGCTGCACAGCAGGCAGCGGCTACAACA

GCCTCAGAACATTCCAGGGAGCCCAGTGCAGCAGGCAGGCTCTCA

GATAGCTCTTCAGAAGCCTCTAAGTTGAGTTCGAAGAGTGCTAAA

GAAAGACGAAATCGGAGGAAAAAAAGGAAACAGAAAGAGCAGTCT

GGAGGAGAAGAGAAAGATGATGATGAATTCCACAAGTCTGAGTCT

GAAGACAGCATCAGGAGGAAGGGGTTTCGCTTCTCCATAGAAGGG

AATAGACTGACATATGAAAAGAGGTACTCTTCCCCGCATCAGTCT

CTGTTAAGCATTCGTGGTTCCCTGTTCTCCCCAAGACGCAATAGC

AGAACAAGTCTTTTCAGCTTTAGAGGGCGAGCCAAGGATGTGGGG

TCTGAGAATGACTTTGCTGATGATGAACACAGCACCTTTGAGGAT

AATGAGAGCCGTAGAGACTCACTGTTCGTTCCCCGAAGACACGGA

GAGCGACGCAACAGTAACCTGAGCCAGACCAGCAGGTCCTCCCGA

ATGCTGGCGGTGTTTCCAGCCAATGGGAAGATGCACAGCACGGTG

GATTGCAATGGTGTGGTTTCCTTGGTTGGTGGACCCTCAGTTCCC

ACATCGCCAGTTGGACAGCTTCTGCCAGAGGGAACAACCACTGAA

ACTGAGATGAGAAAGAGGAGGTCGAGCTCTTTCCATGTTTCCATG

GACTTTCTAGAAGATCCTTCCCAGAGGCAAAGGGCAATGAGCATA
```

-continued

GCCAGCATCTTAACAAATACAGTAGAAGAACTAGAAGAATCCAGG

CAGAAATGTCCACCCTGTTGGTATAAATTTTCCAACATATTCTTA

ATTTGGGACTGTTCTCCATATTGGCTGAAAGTTAAACATATTGTC

AACCTGGTGGTGATGGACCCATTTGTTGATCTGGCCATTACCATC

TGCATTGTGTTAAATACGCTCTTCATGGCTATGGAGCACTACCCC

ATGACTGAACATTTCAACCATGTTCTTACAGTGGGAAACTTGGTC

TTCACTGGGATTTTCACAGCAGAAATGTTCCTGAAAATCATCGCA

ATGGATCCTTACTATTACTTCCAAGAAGGCTGGAATATCTTTGAT

GGTTTCATTGTGACACTCAGCCTGGTAGAACTTGGCCTTGCCAAT

GTGGAAGGATTGTCAGTTCTCCGTTCATTTCGACTGCTCCGAGTG

TTCAAGTTGGCAAAGTCTTGGCCCACACTGAATATGCTCATTAAG

ATCATTGGTAACTCGGTGGGAGCACTGGGCAACCTGACTCTGGTG

TTGGCCATCATTGTCTTTATTTTTGCCGTGGTTGGCATGCAGCTG

TTTGGAAAAAGTTACAAAGATTGTGTCTGCAAAATTGCCACTGAC

TGCAAACTCCCACGTTGGCACATGAACGACTTCTTCCACTCGTTC

CTGATCGTGTTCCGCGTGCTGTGTGGGGAGTGGATAGAGACCATG

TGGGACTGCATGGAGGTGGCAGGACAAGCTATGTGCCTTACTGTC

TTCATGATGGTCATGGTGATTGGGAACCTTGTGGTCTTGAACCTC

TTTCTGGCCTTGCTTCTGAGCTCATTTAGTGCAGACAACCTTGCA

GCCACTGATGATGACAATGAGATGAACAACCTGCAGATTGCTGTG

GACAGGATGCACAAAGGAATAGCTTATGTAAAAAGAAAAATATAT

GAATTCATTCAACAATCCTTTGTTAAGAAACAGAAGATTCTAGAT

GAAATTAAGCCACTTGATGATCTAAACAACAGAAAAGACAATTGT

ATCTCTAACCACACAACAGAAATTGGGAAAGATCTGGACTGTCTG

AAAGATGTGAATGGAACCACAAGTGGCATAGGGACGGGCAGCAGT

GTGGAGAAGTACATCATTGATGAGAGTGATTATATGTCATTCATA

AACAACCCCAGCCTCACTGTGACTGTGCCCATTGCTGTGGGAGAG

TCTGACTTTGAGAACTTAAACACAGAAGACTTTAGCAGTGAATCA

GATCTAGAAGAAAGCAAAGAGAAACTCAACGAAAGCAGTAGCTCC

TCAGAGGGAAGCACAGTAGACATTGGGGCGCCTGCAGAGGAACAG

CCTGTCATTGAACCAGAAGAAACCCTTGAGCCCGAAGCTTGCTTC

ACTGAAGGCTGTGTCCAGAGATTCAAGTGCTGTCAAATCAGCGTG

GAAGAAGGAAGAGGGAAACAGTGGTGGAACCTACGGAGGACGTGC

TTCCGAATAGTTGAACACAACTGGTTTGAGACCTTCATTGTGTTC

ATGATTCTCCTGAGTAGTGGTGCCCTGGCCTTTGAGGATATATAT

ATTGATCAGCGAAAGACGATCAAAACCATGCTGGAGTATGCTGAC

AAAGTCTTCACTTACATTTTCATCCTGGAGATGCTCCTCAAATGG

GTGGCCTATGGCTATCAAACATACTTCACCAATGCCTGGTGTTGG

CTAGACTTCTTAATTGTTGATGTTTCATTGGTCAGTTTAACAGCA

AATGCCTTGGGTTACTCTGAACTCGGGGCCATCAAATCCCTAAGG

-continued

ACACTAAGAGCTCTGAGACCCCTAAGAGCCTTATCACGATTTGAA

GGGATGAGGGTGGTTGTGAATGCCCTGTTAGGAGCAATTCCATCC

ATCATGAATGTGCTTCTGGTTTGCCTTATATTCTGGCTAATTTTC

AGCATCATGGGCGTAAATTTGTTTGCTGGCAAATTCTACCACTGT

GTTAACACCACAACTGGTGACATATTTGAGATCAGCGAAGTCAAT

AATCATTCTGATTGCCTAAAACTAATAGAAAGAAATGAGACCGCC

CGGTGGAAAAATGTGAAAGTAAACTTTGATAATGTAGGATTTGGG

TATCTTTCTTTGCTTCAAGTTGCCACATTTAAGGGCTGGATGGAT

ATCATGTATGCTGCAGTTGATTCCAGAAATGTTGAACTACAGCCT

AAGTATGAGGAAAGCCTGTACATGTATTTGTACTTCGTCATCTTC

ATCATCTTCGGGTCCTTCTTTACCCTGAACCTGTTTATTGGTGTC

ATTATCGACAATTTCAACCAGCAAAAGAAGAAGTTTGGAGGTCAA

GACATCTTTATGACAGAAGAACAGAAGAAATACTATAATGCAATG

AAGAAATTAGGATCAAAAAAGCCACAAAAGCCTATCCCTCGACCT

GGAAACAAATTTCAAGGAATGGTTTTTGACTTTGTAACCAGACAA

GTGTTTGATATCAGCATCATGATCCTCATCTGTCTGAACATGGTG

ACCATGATGGTGGAAACGGATGACCAGAGCGATTATGTGACAAGC

ATTTTGTCACGCATCAACCTGGTGTTCATCGTCCTGTTCACCGGC

GAGTGTGTGCTCAAGCTCATCTCGCTCCGCCATTATTATTTCACC

ATTGGATGGAACATTTTCGATTTTGTGGTGGTCATCCTCTCCATT

GTAGGGATGTTTCTTGCGGAGCTAATAGAAAAGTATTTTGTGTCT

CCTACCCTGTTCCGAGTCATCCGCCTGGCCAGGATTGGACGAATC

CTACGCCTGATCAAAGGTGCCAAGGGGATCCGCACGCTGCTCTTT

GCTCTGATGATGTCCCTTCCTGCGCTGTTTAACATCGGCCTCCTG

CTTTTTTCTCGTCATGTTCATCTACGCCATCTTTGGGATGTCCAAC

TTTGCCTATGTTAAGAGGGAAGTTGGGATTGATGACATGTTCAAC

TTTGAGACCTTCGGCAACAGCATGATCTGCCTGTTCCAAATCACC

ACCTCTGCGGGCTGGGATGGACTGCTGGCCCCCATCCTCAACAGC

AAACCCCCTGACTGTGACCCTAATAAAGTTAACCCTGGAAGCTCG

GTGAAGGGAGACTGTGGGAACCCATCTGTGGGGATTTTCTTTTTT

GTCAGCTACATCATCATATCCTTCCTGGTTGTGGTGAACATGTAC

ATTGCTGTCATCCTGGAGAACTTCAGCGTTGCCACAGAAGAAAGT

GCAGAGCCTCTGAGTGAGGACGACTTTGAGATGTTCTACGAGGTC

TGGGAGAAGTTCGACCCTGACGCCACCCAGTTCATGGAATTTGAA

AAATTATCTCAGTTTGCAGCTGCTCTAGAACCCCCTCTCAATTTG

CCACAACCAAACAAACTTCAGCTCATTGCCATGGACCTGCCCATG

GTGAGTGGAGACCGCATCCACTGCCTGGACATCTTATTTGCTTTT

ACAAAGCGGGTGTTGGGTGAGAGTGGAGAGATGGATGCTCTTCGA

ATCCAGATGGAAGAGCGGTTCATGGCTTCCAACCCCTCCAAGGTC

TCTTATCAGCCCATCACTACTACATTAAAACGCAAACAAGAGGAG

GTGTCAGCTGTTATCATTCAGCGAGCTTATAGGCGCCACCTTTTG

-continued

AAGCGAACAGTAAAACAAGCTTCATTCACATACAATAAGAACAAA

CTCAAAGGTGGGGCTAATCTTCTTGTAAAAGAAGACATGCTCATT

GACAGAATAAACGAAAACTCTATTACGGAGAAAACTGACCTGACA

ATGTCCACAGCAGCTTGTCCGCCCTCCTACGATCGGGTGACAAAG

CCAATCGTGGAGAAACACGAGCAGGAAGGGAAGGATGAAAAAGCC

AAAGGGAAAGACTACAAAGACCATGACGGTGATTATAAAGATCAT

GACATCGATTACAAGGATGACGATGACAAGTAA;
and (SEQ ID NO: 899)

ATGGAGCAAACAGTGCTTGTACCACCAGGACCTGACAGCTTCAAC

TTCTTCACCAGAGAATCCCTTGCAGCTATTGAAAGGCGCATTGCA

GAAGAGAAGGCTAAGAATCCCAAGCCAGACAAAAAAGATGATGAT

GAAAATGGCCCAAAGCCAAACAGTGACTTGGAAGCTGGGAAGAAC

CTTCCATTTATCTATGGAGACATTCCTCCAGAGATGGTGTCGGAG

CCTCTGGAGGACCTGGACCCCTACTATATCAATAAGAAGACTTTT

ATAGTATTGAATAAAGGGAAGGCCATCTTCCGGTTCAGTGCCACC

TCCGCCCTGTACATTTTAACACCCTTCAATCCTCTTAGGAAAATA

GCTATTAAGATTTTGGTACACTCATTATTCAGCATGTTAATCATG

TGCACTATTTTGACAAACTGTGTATTTATGACAATGAGTAACCCT

CCCGACTGGACAAAGAATGTGGAGTACACCTTCACAGGAATATAT

ACTTTTGAATCACTAATAAAAATTATTGCAAGGGGCTTCTGTTTA

GAAGATTTTACTTTCCTTCGCGACCCATGGAACTGGCTGGACTTC

ACTGTCATTACATTCGCATATGTGACGGAGTTTGTGGACCTGGGC

AATGTCTCAGCATTGAGAACATTCAGAGTTCTTCGAGCATTGAAA

ACTATTTCAGTCATTCCAGGCCTGAAGACCATCGTGGGGCCCTG

ATCCAGTCGGTGAAGAAGCTGTCTGACGTCATGATACTCACTGTG

TTCTGTCTCAGTGTGTTCGCACTCATCGGGTTGCAGCTCTTCATG

GGCAACCTGAGGAATAAATGTGTACAGTGGCCTCCCACCAACGCT

TCCCTTGAGGAACATAGCATAGAGAAGAATATAACTATGGATTAC

AATGGCACACTTGTAAATGAAACCGTGTTCGAGTTTGACTGGAAA

TCATACATTCAAGACTCAAGATATCATTATTTCCTGGAGGGTGTT

TTAGATGCACTGCTGTGTGGAAATAGCTCTGATGCAGGCCAATGT

CCAGAAGGATATATGTGTGTAAAAGCTGGTAGAAACCCTAATTAT

GGTTACACAAGCTTTGATACCTTCAGTTGGGCATTTTTGTCCCTG

TTTCGACTGATGACTCAGGACTTCTGGGAAAATCTATACCAACTG

ACATTGCGTGCTGCTGGCAAAACCTACATGATATTTTTGTGCTG

GTCATTTTCTTGGGCTCATTCTACCTGATAAACTTGATCCTGGCT

GTGGTGGCCATGGCCTATGAGGAGCAGAATCAGGCCACACTGGAG

GAGGCTGAACAGAAAGAGGCAGAATTTCAGCAGATGTTGGAGCAA

CTTAAGAAGCAGCAAGAGGCTGCACAGCAGGCAGCGGCTACAACA

GCCTCAGAACATTCCAGGGAGCCCAGTGCAGCAGGCAGGCTCTCA

-continued

GATAGCTCTTCAGAAGCCTCTAAGTTGAGTTCGAAGAGTGCTAAA

GAAAGACGAAATCGGAGGAAAAAAAGGAAACAGAAAGAGCAGTCT

GGAGGAGAAGAGAAAGATGATGATGAATTCCACAAGTCTGAGTCT

GAAGACAGCATCAGGAGGAAGGGGTTTCGCTTCTCCATAGAAGGG

AATAGACTGACATATGAAAAGAGGTACTCTTCCCCGCATCAGTCT

CTGTTAAGCATTCGTGGTTCCCTGTTCTCCCCAAGACGCAATAGC

AGAACAAGTCTTTTCAGCTTTAGAGGGCGAGCCAAGGATGTGGGG

TCTGAGAATGACTTTGCTGATGATGAACACAGCACCTTTGAGGAT

AATGAGAGCCGTAGAGACTCACTGTTCGTTCCCCGAAGACACGGA

GAGCGACGCAACAGTAACCTGAGCCAGACCAGCAGGTCCTCCCGA

ATGCTGGCGGTGTTTCCAGCCAATGGGAAGATGCACAGCACGGTG

GATTGCAATGGTGTGGTTTCCTTGGTTGGTGGACCCTCAGTTCCC

ACATCGCCAGTTGGACAGCTTCTGCCAGAGGGAACAACCACTGAA

ACTGAGATGAGAAAGAGGAGGTCGAGCTCTTTCCATGTTTCCATG

GACTTTCTAGAAGATCCTTCCCAGAGGCAAAGGGCAATGAGCATA

GCCAGCATCTTAACAAATACAGTAGAAGAACTAGAAGAATCCAGG

CAGAAATGTCCACCCTGTTGGTATAAATTTTCCAACATATTCTTA

ATTTGGGACTGTTCTCCATATTGGCTGAAAGTTAAACATATTGTC

AACCTGGTGGTGATGGACCCATTTGTTGATCTGGCCATTACCATC

TGCATTGTGTTAAATACGCTCTTCATGGCTATGGAGCACTACCCC

ATGACTGAACATTTCAACCATGTTCTTACAGTGGGAAACTTGGTC

TTCACTGGGATTTTCACAGCAGAAATGTTCCTGAAAATCATCGCA

ATGGATCCTTACTATTACTTCCAAGAAGGCTGGAATATCTTTGAT

GGTTTCATTGTGACACTCAGCCTGGTAGAACTTGGCCTTGCCAAT

GTGGAAGGATTGTCAGTTCTCCGTTCATTTCGACTGCTCCGAGTG

TTCAAGTTGGCAAAGTCTTGGCCCACACTGAATATGCTCATTAAG

ATCATTGGTAACTCGGTGGGAGCACTGGGCAACCTGACTCTGGTG

TTGGCCATCATTGTCTTTATTTTTGCCGTGGTTGGCATGCAGCTG

TTTGGAAAAAGTTACAAAGATTGTGTCTGCAAAATTGCCACTGAC

TGCAAACTCCCACGTTGGCACATGAACGACTTCTTCCACTCGTTC

CTGATCGTGTTCCGCGTGCTGTGTGGGGAGTGGATAGAGACCATG

TGGGACTGCATGGAGGTGGCAGGACAAGCTATGTGCCTTACTGTC

TTCATGATGGTCATGGTGATTGGGAACCTTGTGGTCTTGAACCTC

TTTCTGGCCTTGCTTCTGAGCTCATTTAGTGCAGACAACCTTGCA

GCCACTGATGATGACAATGAGTGAACAACCTGCAGATTGCTGTG

GACAGGATGCACAAAGGAATAGCTTATGTAAAAAGAAAAATATAT

GAATTCATTCAACAATCCTTTGTTAAGAAACAGAAGATTCTAGAT

GAAATTAAGCCACTTGATGATCTAAACAACAGAAAAGACAATTGT

ATCTCTAACCACACAACAGAAATTGGGAAAGATCTGGACTGTCTG

AAAGATGTGAATGGAACCACAAGTGGCATAGGGACGGGCAGCAGT

GTGGAGAAGTACATCATTGATGAGAGTGATTATATGTCATTCATA

-continued

```
AACAACCCCAGCCTCACTGTGACTGTGCCCATTGCTGTGGGAGAG

TCTGACTTTGAGAACTTAAACACAGAAGACTTTAGCAGTGAATCA

GATCTAGAAGAAAGCAAAGAGAAACTCAACGAAAGCAGTAGCTCC

TCAGAGGGAAGCACAGTAGACATTGGGGCGCCTGCAGAGGAACAG

CCTGTCATTGAACCAGAAGAAACCCTTGAGCCCGAAGCTTGCTTC

ACTGAAGGCTGTGTCCAGAGATTCAAGTGCTGTCAAATCAGCGTG

GAAGAAGGAAGAGGGAAACAGTGGTGGAACCTACGGAGGACGTGC

TTCCGAATAGTTGAACACAACTGGTTTGAGACCTTCATTGTGTTC

ATGATTCTCCTGAGTAGTGGTGCCCTGGCCTTTGAGGATATATAT

ATTGATCAGCGAAAGACGATCAAAACCATGCTGGAGTATGCTGAC

AAAGTCTTCACTTACATTTTCATCCTGGAGATGCTCCTCAAATGG

GTGGCCTATGGCTATCAAACATACTTCACCAATGCCTGGTGTTGG

CTAGACTTCTTAATTGTTGATGTTTCATTGGTCAGTTTAACAGCA

AATGCCTTGGGTTACTCTGAACTCGGGGCCATCAAATCCCTAAGG

ACACTAAGAGCTCTGAGACCCCTAAGAGCCTTATCACGATTTGAA

GGGATGAGGGTGGTTGTGAATGCCCTGTTAGGAGCAATTCCATCC

ATCATGAATGTGCTTCTGGTTTGCCTTATATTCTGGCTAATTTTC

AGCATCATGGGCGTAAATTTGTTTGCTGGCAAATTCTACCACTGT

GTTAACACCACAACTGGTGACATATTTGAGATCAGCGAAGTCAAT

AATCATTCTGATTGCCTAAAACTAATAGAAAGAAATGAGACCGCC

TGATGGAAAAATGTGAAAGTAAACTTTGATAATGTAGGATTTGGG

TATCTTTCTTTGCTTCAAGTTGCCACATTTAAGGGCTGGATGGAT

ATCATGTATGCTGCAGTTGATTCCAGAAATGTTGAACTACAGCCT

AAGTATGAGGAAAGCCTGTACATGTATTTGTACTTCGTCATCTTC

ATCATCTTCGGGTCCTTCTTTACCCTGAACCTGTTTATTGGTGTC

ATTATCGACAATTTCAACCAGCAAAAGAAGAAGTTTGGAGGTCAA

GACATCTTTATGACAGAAGAACAGAAGAAATACTATAATGCAATG

AAGAAATTAGGATCAAAAAAGCCACAAAAGCCTATCCCTCGACCT

GGAAACAAATTTCAAGGAATGGTTTTTGACTTTGTAACCAGACAA

GTGTTTGATATCAGCATCATGATCCTCATCTGTCTGAACATGGTG

ACCATGATGGTGGAAACGGATGACCAGAGCGATTATGTGACAAGC

ATTTTGTCACGCATCAACCTGGTGTTCATCGTCCTGTTCACCGGC

GAGTGTGTGCTCAAGCTCATCTCGCTCCGCCATTATTATTTCACC

ATTGGATGGAACATTTTCGATTTTGTGGTGGTCATCCTCTCCATT

GTAGGGATGTTTCTTGCGGAGCTAATAGAAAAGTATTTTGTGTCT

CCTACCCTGTTCCGAGTCATCCGCCTGGCCAGGATTGGACGAATC

CTACGCCTGATCAAAGGTGCCAAGGGGATCCGCACGCTGCTCTTT

GCTCTGATGATGTCCCTTCCTGCGCTGTTTAACATCGGCCTCCTG

CTTTTTCTCGTCATGTTCATCTACGCCATCTTTGGGATGTCCAAC

TTTGCCTATGTTAAGAGGGAAGTTGGGATTGATGACATGTTCAAC
```

-continued

```
TTTGAGACCTTCGGCAACAGCATGATCTGCCTGTTCCAAATCACC

ACCTCTGCGGGCTGGGATGGACTGCTGGCCCCCATCCTCAACAGC

AAACCCCCTGACTGTGACCCTAATAAAGTTAACCCTGGAAGCTCG

GTGAAGGGAGACTGTGGGAACCCATCTGTGGGGATTTTCTTTTTT

GTCAGCTACATCATCATATCCTTCCTGGTTGTGGTGAACATGTAC

ATTGCTGTCATCCTGGAGAACTTCAGCGTTGCCACAGAAGAAAGT

GCAGAGCCTCTGAGTGAGGACGACTTTGAGATGTTCTACGAGGTC

TGGGAGAAGTTCGACCCTGACGCCACCCAGTTCATGGAATTTGAA

AAATTATCTCAGTTTGCAGCTGCTCTAGAACCCCCTCTCAATTTG

CCACAACCAAACAAACTTCAGCTCATTGCCATGGACCTGCCCATG

GTGAGTGGAGACCGCATCCACTGCCTGGACATCTTATTTGCTTTT

ACAAAGCGGGTGTTGGGTGAGAGTGGAGAGATGGATGCTCTTCGA

ATCCAGATGGAAGAGCGGTTCATGGCTTCCAACCCCTCCAAGGTC

TCTTATCAGCCCATCACTACTACATTAAAACGCAAACAAGAGGAG

GTGTCAGCTGTTATCATTCAGCGAGCTTATAGGCGCCACCTTTTG

AAGCGAACAGTAAAACAAGCTTCATTCACATACAATAAGAACAAA

CTCAAAGGTGGGGCTAATCTTCTTGTAAAAGAAGACATGCTCATT

GACAGAATAAACGAAAACTCTATTACGGAGAAAACTGACCTGACA

ATGTCCACAGCAGCTTGTCCGCCCTCCTACGATCGGGTGACAAAG

CCAATCGTGGAGAAACACGAGCAGGAAGGGAAGGATGAAAAAGCC

AAAGGGAAAGACTACAAAGACCATGACGGTGATTATAAAGATCAT

GACATCGATTACAAGGATGACGATGACAAGTAA.
```

SCN1A was detected by Western blot as follows. Protein was isolated at 24 hours post transfection in RIPA Lysis and Extraction Buffer (Thermo Fisher Scientific #89900) containing Halt Protease Inhibitor Cocktail (Thermo Fisher Scientific #87786) according to the manufacturer's protocol. Protein concentrations were determined using the Pierce BCA Protein Assay Kit (Thermo Fisher Scientific #23225). 30 μg of protein was separated on either NuPAGE 4-12% Bis-Tris (Thermo Fisher Scientific #NP0322BOX) or NuPAGE 3-8%, Tris-Acetate (Thermo Fisher Scientific #EA0375BOX) protein gels at 150V for 1.5 hours and transferred to PVDF membranes at 30V overnight followed by 250 mA for 30 min at 4° C. Blots were blocked in SuperBlock T20 Blocking Buffer (Thermo Fisher Scientific #37536) at room temperature for 1 hour, incubated with the primary anti-FLAG M2 antibody (Sigma, F1804-200UG, 1:1000) in TBST overnight at 4° C., washed 3 times with TBST, and incubated with the Goat anti-Mouse IgG (H+L) Secondary Antibody, HRP secondary antibody (Thermo Fisher Scientific #31431, 1:30,000) at room temperature for 1 hour. The blots were developed by applying the Super-Signal West Femto Maximum Sensitivity Substrate (Thermo Fisher Scientific #34094) and signals were detected by the iBright Imaging system. The results are shown in FIG. 37 and demonstrate that the $Arg_{TCA}$ suppressor tRNA #115, but not the small molecules drugs, was able to rescue full-length SCN1A protein expression.

Flp-In-293 cells were also co-transfected with (i) an expression construct containing mouse SCN1A with an Arg(R)-to-TGA PTC (R1407X) and a 3×FLAG tag peptide at the C-terminus (SEQ ID NO: 899) and (ii) an expression construct containing the $Arg_{TCA}$ suppressor tRNA #104 (tRNA-Arg-CCG-3-1-TCA-SUP, SEQ ID NO: 6), the $Arg_{TCA}$ suppressor tRNA #106 (tRNA-Arg-CCT-2-1-TCA-SUP, SEQ ID NO: 8), or the $Arg_{TCA}$ suppressor tRNA #115 (tRNA-Arg-TCT-2-1-TCA-SUP_no intron, SEQ ID NO: 18). SCN1A expression was measured by Western blot using an anti-FLAG antibody as described above in this Example. The results are shown in FIG. 38 and demonstrate that each suppressor tRNA tested rescued full-length SCN1A protein expression.

Flp-In-293 cells were also co-transfected with (i) an expression construct containing mouse SCN1A with an Arg(R)-to-TGA PTC (R1407X) and a 3×FLAG tag peptide at the C-terminus (SEQ ID NO: 899) and (ii) an expression construct containing the $Arg_{TCA}$ suppressor tRNA #115 (tRNA-Arg-TCT-2-1-TCA-SUP_no intron, SEQ ID NO: 18) at a range of doses (13 ng per well, 40 ng per well, 113 ng per well, or 400 ng per well; 6-well cell culture plate). SCN1A expression was measured by Western blot using an anti-FLAG antibody as described above in this Example. The results are shown in FIG. 39 and demonstrate that tRNA 115 was able to rescue full-length SCN1A protein expression over a broad dose range.

Example 12

This Example describes readthrough activity of disclosed suppressor tRNAs delivered by adeno-associated virus (AAV) vectors.

Constructs that were packaged into AAV-PHP.eB capsids are depicted in FIG. 40. Construct 262 contains wild-type EGFP driven by an EF1a promoter. Construct 269 contains EGFP-R96X-TGA driven by an EF1a promoter (SEQ ID NO: 177) and two copies of the $Arg_{TCA}$ suppressor tRNA #115 (tRNA-Arg-TCT-2-1-TCA-SUP_no intron, SEQ ID NO: 18, as described in Example 1) in the context of 55 bps upstream flanking genomic DNA from tRNA-Tyr-GTA-5-1 (SEQ ID NO: 900). Both constructs contain 5' and 3' ITR sequences from AAV2, which provide cis-acting elements for AAV replication and packaging. AAV-PHP.eB containing construct 262 and construct 269 was produced by Vigene Biosciences.

Prior to AAV transduction, 293 cells (Agilent #240073) were pre-transfected with an expression construct containing the LY6A gene (CCDS ID 27540.1) driven by the CMV early enhancer/chicken β actin (CAG) promoter, which is required for robust transduction by AAV-PHP.eB. For pre-transfection, cells were transiently transfected with the LY6A expression construct using lipofectamine 3000 Transfection Reagent according to the manufacturer's protocol. At ~24 hours post-transfection the media was exchanged for fresh media and the cells were allowed to recover for another 24 hours prior to viral transduction. The cells were then transduced at an MOI of 1E5 vg/cell. Results are depicted in FIG. 41. AAV delivered $Arg_{TCA}$ suppressor tRNA #115 resulted in ~13.2% PTC readthrough based on GFP intensity. The suppressor tRNA shows comparable readthrough activity when delivered by AAV or transient transfection.

Example 13

This Example describes ribosome profiling experiments that demonstrate that disclosed suppressor tRNAs do not cause a significant amount of off-target native stop codon read-through.

In order to determine whether suppressor tRNAs cause readthrough of native stop codons, ribosome profiling was used to quantify the number of ribosomes found in the 3' UTR of mRNAs from (i) cells transfected with an expression construct containing a suppressor tRNA relative to (ii) cells transfected with an expression construct that lacks a suppressor tRNA. Ribosomes typically terminate translation upon encountering a stop codon, so if suppressor tRNAs cause increased readthrough of native stop codons, this will be indicated by an increase in the density of ribosomes found in the 3' UTR of mRNAs in cells expressing a suppressor tRNA, especially in the 3' UTR mRNAs containing a native stop codon that is recognized by the expressed suppressor tRNA.

Neuro-2a cells were transfected with either (i) an expression construct containing an EGFP-R96X-TGA reporter (SEQ ID NO: 177) and the $Arg_{TCA}$ suppressor tRNA #001 (SEQ ID NO: 11) on the same construct or (ii) an expression construct lacking a suppressor tRNA and containing a wild-type version of the EGFP reporter. Expression of EGFP is depicted in FIG. 42. At ~48 hours post transfection, cells were subjected to ribosome footprint profiling as follows. Cells were lysed in the lysis buffer (10 mM Tris-HCl pH7.5, 5 mM MgCl2, 100 mM KCl, 1% Triton X-100, 1 mM DTT, 50 µg/mL Emetine (Sigma #324693), and 500 U/mL RNA-sin (Promega #N2615)) and cell lysates were sheared ten times with a 25-gauge needle followed by centrifugation at 20,000 g for 10 minutes at 4° C. The supernatants were digested with micrococcal nuclease (MNase; 120 units/OD A260 lysates; New England Biolabs #M02475) at room temperature for 30 minutes prior to adding 5 uL SuperAse-IN (Thermo Fisher Scientific #AM2694) to stop the reaction. MNase-treated extracts were loaded to a 15-45% sucrose gradient and separated by density in a SW 41Ti swinging-bucket rotor (Beckman Coulter #331362) at 41,000 rpm at 4° C. for 2:26 hours. After fractionation and collection of fractions containing monosomes, ribosome protected mRNA fragments were precipitated from the sucrose overnight at ~20° C. with 1.25 mL of 95% ethanol. mRNA fragments were re-suspended with 10 mM Tris-HCl, pH 8.0, and separated on a 15% denaturing polyacrylamide gel (TBE-urea gel; Thermo Fisher Scientific #EC68852BOX). RNA fragments with sizes ranging from 26 to 34 nt were excised from the gel and isolated to generate the ribosome-protected fragment library. After 3' linker ligation, rRNA depletion with the Ribo-Zero reagents in the TruSeq Stranded Total RNA Library Prep Gold Kit (Illumina #20020598), reverse transcription, circularization, and PCR amplification with indexing primers, the PCR products were separated on an 8% nondenaturing polyacrylamide gel (Thermo Fisher Scientific #EC62152BOX). The barcoded cDNA libraries were extracted from the gel and sequenced by the NextSeq 550 Sequencing System with the single read run type. Following sequencing, raw reads were trimmed of adapters using Trimmomatic then depleted for non-coding RNA by aligning against Ensembl's mouse mm10 ncRNA reference using bowtie2. Remaining reads were aligned against UCSC's mm10 mouse reference assembly, again using bowtie2. Multi-mapping reads were discarded. The resulting final set of aligned reads was quantified using the RiboProfiling package in R and custom Python scripting. Python was used to generate plots examining 3' UTR occupancy and fold change for each gene with 20 or more uniquely mapping reads, and the distributions for genes with each native stop codon were compared using the 2 sample Kolmogorov-Smirnov test. The results are depicted in FIG. 43.

Together, these results demonstrate that suppressor tRNAs can facilitate expression of transcripts, e.g., EGFP-R96X-TGA, containing premature termination codons while not causing a significant amount of off-target native stop codon read-through in the expressing cells.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein

What is claimed is:

1. A tRNA comprising the nucleotide sequence of SEQ ID NO: 20, 19, 21, or 2, wherein each thymine in SEQ ID NO: 20, 19, 21, or 2 is replaced by uracil.

2. An expression vector comprising a nucleotide sequence encoding the tRNA of claim 1.

3. The expression vector of claim 2, wherein the expression vector comprises:

(a) 1, 2, 3, 4, or more than 4 copy numbers of the nucleotide sequence encoding the tRNA; and/or (b) the nucleotide sequence set forth in any one of SEQ ID NOs: 869-888 that is immediately 5' to the nucleotide sequence encoding the tRNA.

4. The expression vector of claim 2, wherein the expression vector is a viral vector.

5. The expression vector of claim 4, wherein the viral vector:

(a) is a DNA virus vector; and/or (b) is an adeno-associated virus (AAV) vector.

6. A pharmaceutical composition comprising a nucleic acid encoding the tRNA of claim 1 and a pharmaceutically acceptable excipient.

7. The pharmaceutical composition of claim 6, wherein the composition does not comprise an aminolipid particle, an aminolipid delivery compound, or a nanoparticle.

8. A method of expressing in a mammalian cell a functional gene product encoded by a gene containing a premature termination codon, the method comprising introducing into the cell an effective amount of a nucleic acid encoding the tRNA of claim 1, wherein expression of the tRNA permits an arginine amino acid to be incorporated into the gene product at a position that would otherwise result in a truncated gene product caused by the premature termination codon, and wherein the premature termination codon is TGA.

9. The method of claim 8, wherein the cell contains:

(a) less truncated gene product than a cell without the tRNA; and/or (b) a greater amount of functional gene product than a cell without the tRNA.

10. The method of claim 8, wherein the gene is a dystrophin gene or an SCN1A gene.

11. A method of increasing in a cell voltage-gated sodium channel activity encoded by a SCN1A gene containing a premature termination codon, the method comprising introducing into the cell an effective amount of a nucleic acid encoding the tRNA of claim 1, wherein expression of the tRNA permits an arginine amino acid to be incorporated into the SCN1A gene product at a position that would otherwise result in a truncated SCN1A gene product caused by the premature termination codon, and wherein the premature termination codon is TGA.

12. The method of claim 8, wherein:

(a) the cell is a human cell; and/or (b) the tRNA becomes aminoacylated in the cell.

13. A method of treating a premature termination codon-mediated disorder in a subject in need thereof, wherein the subject has a gene with a premature termination codon and the premature termination codon is TGA, the method comprising administering to the subject an effective amount of a nucleic acid encoding the tRNA of claim 1, thereby to treat the disorder in the subject.

14. The method of claim 13, wherein the disorder is Duchenne Muscular Dystrophy or Dravet syndrome.

15. The method of claim 13, wherein the subject is a human.

16. The tRNA of claim 1, comprising the nucleotide sequence of SEQ ID NO: 20.

17. The tRNA of claim 1, comprising the nucleotide sequence of SEQ ID NO: 19.

18. The tRNA of claim 1, comprising the nucleotide sequence of SEQ ID NO: 21.

19. The tRNA of claim 1, comprising the nucleotide sequence of SEQ ID NO: 2.

\* \* \* \* \*